US011813308B2

(12) United States Patent
Hruska et al.

(10) Patent No.: US 11,813,308 B2
(45) Date of Patent: *Nov. 14, 2023

(54) TREATMENT OF CARDIOVASCULAR DISEASE USING ACTRII LIGAND TRAPS

(71) Applicants: CELGENE CORPORATION, Summit, NJ (US); WASHINGTON UNIVERSITY, St. Louis, MO (US)

(72) Inventors: Keith Hruska, Creve Coeur, MO (US); Yifu Fang, St. Louis, MO (US); William Smith, Woodstock, NY (US); Nianhang Chen, Basking Ridge, NJ (US)

(73) Assignees: Celgene Corporation, Missouri (MO); Washington University, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/517,782

(22) PCT Filed: Oct. 8, 2015

(86) PCT No.: PCT/US2015/054674
§ 371 (c)(1),
(2) Date: Apr. 7, 2017

(87) PCT Pub. No.: WO2016/069234
PCT Pub. Date: May 6, 2016

(65) Prior Publication Data
US 2017/0304397 A1 Oct. 26, 2017

Related U.S. Application Data

(60) Provisional application No. 62/062,021, filed on Oct. 9, 2014, provisional application No. 62/078,321, filed on Nov. 11, 2014, provisional application No. 62/103,515, filed on Jan. 14, 2015, provisional application No. 62/167,052, filed on May 27, 2015, provisional application No. 62/170,015, filed on Jun. 2, 2015.

(51) Int. Cl.
| *A61K 38/17* | (2006.01) |
| *A61K 38/00* | (2006.01) |
| *C07K 14/71* | (2006.01) |
| *A61P 9/10* | (2006.01) |
| *A61P 9/00* | (2006.01) |
| *A61P 19/10* | (2006.01) |

(52) U.S. Cl.
CPC .............. *A61K 38/179* (2013.01); *A61P 9/00* (2018.01); *A61P 9/10* (2018.01); *A61P 19/10* (2018.01); *C07K 14/71* (2013.01); *A61K 38/00* (2013.01); *C07K 2319/30* (2013.01)

(58) Field of Classification Search
None
See application file for complete search history.

(56) References Cited

U.S. PATENT DOCUMENTS

| 4,973,577 A | 11/1990 | Vale, Jr. et al. |
| 5,118,667 A | 6/1992 | Adams et al. |
| 5,658,876 A | 8/1997 | Crowley et al. |
| 5,703,043 A | 12/1997 | Celeste et al. |
| 5,760,010 A | 6/1998 | Klein |
| 5,808,007 A | 9/1998 | Lee et al. |
| 5,824,637 A | 10/1998 | Crowley et al. |
| 5,847,078 A | 12/1998 | Eto et al. |
| 5,885,794 A | 3/1999 | Mathews et al. |
| 6,004,780 A | 12/1999 | Soppet et al. |
| 6,093,547 A | 7/2000 | Jin et al. |
| 6,132,988 A | 10/2000 | Sugino et al. |
| 6,162,896 A | 12/2000 | Mathews et al. |

(Continued)

FOREIGN PATENT DOCUMENTS

| EP | 1 416 273 A1 | 11/1992 |
| EP | 1174149 A1 | 1/2002 |

(Continued)

OTHER PUBLICATIONS

Fang et al., 2014, Kidney International 85(1): 142-150.*

(Continued)

*Primary Examiner* — Elizabeth C. Kemmerer
(74) *Attorney, Agent, or Firm* — Jones Day

(57) ABSTRACT

Provided herein are methods of treating diseases associated with vascular calcification and/or cardiovascular disease in a subject by using the level of a biomarker, in particular, snail homolog 1 (Snai1), phosphosmad2, phosphosmad3, urinary protein, dickkopf homolog 1 (Dkk1), collagen type 1 alpha 1 (Col1a1), activin (e.g., free activin), runt-related transcription factor 2 (Runx2), alkaline phosphatase (Alp), bone-specific alkaline phosphatase (BSAP), C-terminal type 1 collagen telopeptide (CTX), osterix, Klotho, alpha-smooth muscle actin (alpha-SMA), myocardin (MYOCD), activin receptor type 2A (ActRIIA), axis inhibition protein 2 (Axin2), and/or smooth muscle protein 22-alpha (Sm22-alpha), as an indicator(s) of responsiveness of the subject to the treatment, efficacy of the treatment, or appropriate dosage for the treatment with an activin type II receptor signaling inhibitor. Provided herein are methods of bone resorption in a subject by using the level of a biomarker, in particular, snail homolog 1 (Snai1), phosphosmad2, phosphosmad3, urinary protein, dickkopf homolog 1 (Dkk1), collagen type 1 alpha 1 (Col1a1), activin (e.g., free activin), runt-related transcription factor 2 (Runx2), alkaline phosphatase (Alp), bone-specific alkaline phosphatase (BSAP), c-terminal telopeptide (CTX), osterix, Klotho, alpha-smooth muscle actin (alpha-SMA), myocardin (MYOCD), activin receptor type 2A (ActRIIA), axis inhibition protein 2 (Axin2), and/or smooth muscle protein 22-alpha (Sm22-alpha), as an indicator(s) of responsiveness of the subject to the treatment, efficacy of the treatment, or appropriate dosage for the treatment with an activin type II receptor signaling inhibitor.

26 Claims, 57 Drawing Sheets
Specification includes a Sequence Listing.

(56) References Cited

U.S. PATENT DOCUMENTS

| | | |
|---|---|---|
| 6,287,816 B1 | 9/2001 | Rosen et al. |
| 6,440,930 B1 | 8/2002 | Rinella, Jr. |
| 6,451,334 B2 | 9/2002 | Perrine |
| 6,537,966 B1 | 3/2003 | Duan et al. |
| 6,548,634 B1 | 4/2003 | Ballinger et al. |
| 6,599,876 B2 | 7/2003 | Kojima |
| 6,605,699 B1 | 8/2003 | Ni et al. |
| 6,632,180 B1 | 10/2003 | Laragh |
| 6,656,475 B1 | 12/2003 | Lee et al. |
| 6,656,708 B1 | 12/2003 | Yu et al. |
| 6,692,925 B1 | 2/2004 | Miyazono et al. |
| 6,696,260 B1 | 2/2004 | Lee et al. |
| 6,777,205 B1 | 8/2004 | Carcagno et al. |
| 6,835,544 B2 | 12/2004 | Mathews et al. |
| 6,891,082 B2 | 5/2005 | Lee et al. |
| 7,192,717 B2 | 3/2007 | Hill et al. |
| 7,202,210 B2 | 4/2007 | Wolfman et al. |
| 7,261,893 B2 | 8/2007 | Veldman et al. |
| 7,320,789 B2 | 1/2008 | Dunham et al. |
| 7,560,441 B2 | 7/2009 | Wolfman et al. |
| 7,612,041 B2 | 11/2009 | Knopf et al. |
| 7,709,605 B2 | 5/2010 | Knopf et al. |
| 7,842,663 B2 | 11/2010 | Knopf et al. |
| 7,893,213 B2 | 2/2011 | Mathews et al. |
| 7,919,296 B2 | 4/2011 | Wang |
| 7,951,771 B2 | 5/2011 | Knopf et al. |
| 7,960,343 B2 | 6/2011 | Knopf et al. |
| 7,988,973 B2 | 8/2011 | Sherman |
| 8,007,809 B2 | 8/2011 | Sherman |
| 8,058,229 B2 | 11/2011 | Seehra et al. |
| 8,067,360 B2 | 11/2011 | Knopf et al. |
| 8,128,933 B2 | 3/2012 | Knopf et al. |
| 8,138,142 B2 | 3/2012 | Seehra et al. |
| 8,173,601 B2 | 5/2012 | Knopf |
| 8,178,488 B2 | 5/2012 | Knopf et al. |
| 8,216,997 B2 | 7/2012 | Seehra et al. |
| 8,252,900 B2 | 8/2012 | Knopf et al. |
| 8,293,881 B2 | 10/2012 | Seehra et al. |
| 8,343,933 B2 | 1/2013 | Knopf et al. |
| 8,361,957 B2 | 1/2013 | Seehra et al. |
| 8,367,611 B2 | 2/2013 | Knopf et al. |
| 8,388,968 B2 | 3/2013 | Berger et al. |
| 8,629,109 B2 | 1/2014 | Knopf et al. |
| 8,637,611 B2 | 1/2014 | Dershem |
| 8,703,694 B2 | 4/2014 | Knopf et al. |
| 8,703,927 B2 | 4/2014 | Seehra et al. |
| 8,710,016 B2 | 4/2014 | Seehra et al. |
| 8,765,663 B2 | 7/2014 | Seehra et al. |
| 8,895,016 B2 | 11/2014 | Sherman et al. |
| 9,138,459 B2 | 9/2015 | Knopf et al. |
| 9,163,075 B2 | 10/2015 | Knopf et al. |
| 9,181,533 B2 | 11/2015 | Seerah et al. |
| 9,353,356 B2 | 5/2016 | Knopf et al. |
| 9,399,669 B2 | 7/2016 | Knopf et al. |
| 9,439,945 B2 | 9/2016 | Seehra et al. |
| 9,505,813 B2 | 11/2016 | Seerah et al. |
| 9,526,759 B2 | 12/2016 | Knopf et al. |
| 9,572,865 B2 | 2/2017 | Knopf et al. |
| 9,617,319 B2 | 4/2017 | Seehra et al. |
| 9,745,559 B2 | 8/2017 | Seerah et al. |
| 9,790,284 B2 | 10/2017 | Knopf et al. |
| 9,850,298 B2 | 12/2017 | Attie |
| 9,919,030 B2 | 3/2018 | Sherman et al. |
| 9,932,379 B2 | 4/2018 | Seehra et al. |
| 10,071,135 B2 | 9/2018 | Knopf et al. |
| 10,093,707 B2 | 10/2018 | Sherman et al. |
| 10,131,700 B2 | 11/2018 | Seehra et al. |
| 10,195,249 B2 * | 2/2019 | Sung .................. A61K 38/179 |
| 10,259,861 B2 | 4/2019 | Knopf et al. |
| 10,358,633 B2 | 7/2019 | Seehra et al. |
| 10,377,996 B2 | 8/2019 | Seehra et al. |
| 10,487,144 B2 | 11/2019 | Attie et al. |
| 10,548,976 B2 | 2/2020 | Cappellini et al. |
| 10,550,170 B2 | 2/2020 | Sherman et al. |
| 10,689,427 B2 | 6/2020 | Seehra et al. |
| 10,695,405 B2 | 6/2020 | Kumar et al. |
| 10,722,558 B2 | 7/2020 | Kumar et al. |
| 10,889,626 B2 | 1/2021 | Seehra et al. |
| 10,889,882 B2 | 1/2021 | Kadali et al. |
| 10,968,282 B2 | 4/2021 | Knopf et al. |
| 11,066,654 B2 | 7/2021 | Seehra et al. |
| 11,471,510 B2 | 10/2022 | Attie et al. |
| 2001/0039036 A1 | 11/2001 | Mathews et al. |
| 2003/0082233 A1 | 5/2003 | Lyons et al. |
| 2003/0083251 A1 | 5/2003 | Westenfelder |
| 2003/0118556 A1 | 6/2003 | Kaspar et al. |
| 2003/0133939 A1 | 7/2003 | Ledbetter et al. |
| 2003/0144203 A1 | 7/2003 | Bowen |
| 2003/0215913 A1 | 11/2003 | Alvarez et al. |
| 2003/0224397 A1 | 12/2003 | Lowman et al. |
| 2004/0033511 A1 | 2/2004 | Pfizenmaier et al. |
| 2004/0121008 A1 | 6/2004 | Shiraishi et al. |
| 2004/0132675 A1 | 7/2004 | Kuo et al. |
| 2004/0138129 A1 | 7/2004 | MacLeod |
| 2004/0197828 A1 | 10/2004 | Gaddy |
| 2004/0209805 A1 | 10/2004 | Phillips et al. |
| 2004/0223966 A1 | 11/2004 | Wolfman et al. |
| 2005/0106148 A1 | 5/2005 | Kay et al. |
| 2005/0197292 A1 | 9/2005 | Smithson et al. |
| 2005/0239070 A1 | 10/2005 | Von Knebel-Doeberitz et al. |
| 2005/0244867 A1 | 11/2005 | Soppet et al. |
| 2005/0257278 A1 | 11/2005 | Lee et al. |
| 2006/0068468 A1 | 3/2006 | Knopf et al. |
| 2006/0172347 A1 | 8/2006 | Mellor et al. |
| 2006/0208106 A1 | 9/2006 | Boehland et al. |
| 2006/0210657 A1 | 9/2006 | Chou |
| 2007/0048830 A1 | 3/2007 | Gilbert et al. |
| 2007/0149455 A1 | 6/2007 | Wolfman et al. |
| 2007/0172956 A1 | 7/2007 | Magari et al. |
| 2007/0184052 A1 | 8/2007 | Lin et al. |
| 2007/0249022 A1 | 10/2007 | Knopf et al. |
| 2007/0275895 A1 | 11/2007 | Duan et al. |
| 2007/0292885 A1 | 12/2007 | Bejanin et al. |
| 2008/0021104 A1 | 1/2008 | Tarallo |
| 2008/0075692 A1 | 3/2008 | Perrine |
| 2008/0089897 A1 | 4/2008 | Wolfman |
| 2008/0102065 A1 | 5/2008 | Borges et al. |
| 2008/0139590 A1 | 6/2008 | Qian et al. |
| 2009/0005308 A1 | 1/2009 | Knopf et al. |
| 2009/0017019 A1 | 1/2009 | Shields et al. |
| 2009/0047281 A1 | 2/2009 | Sherman |
| 2009/0074768 A1 | 3/2009 | Knopf et al. |
| 2009/0087433 A1 | 4/2009 | Wolfman et al. |
| 2009/0098113 A1 | 4/2009 | Knopf et al. |
| 2009/0099086 A1 | 4/2009 | Knopf et al. |
| 2009/0118188 A1 | 5/2009 | Knopf et al. |
| 2009/0142333 A1 | 6/2009 | Knopf et al. |
| 2009/0148436 A1 | 6/2009 | LaVallie et al. |
| 2009/0163417 A1 | 6/2009 | Sherman |
| 2010/0008918 A1 | 1/2010 | Sherman et al. |
| 2010/0015144 A1 | 1/2010 | Sherman et al. |
| 2010/0028331 A1 * | 2/2010 | Sherman ................ C07K 14/71 |
| | | 424/130.1 |
| 2010/0028332 A1 | 2/2010 | Sherman et al. |
| 2010/0068215 A1 | 3/2010 | Seehra et al. |
| 2010/0111852 A1 | 5/2010 | Yoshida |
| 2010/0113932 A1 | 5/2010 | Antich et al. |
| 2010/0160220 A1 | 6/2010 | Cao |
| 2010/0183624 A1 | 7/2010 | Seehra et al. |
| 2010/0272734 A1 | 10/2010 | Berger et al. |
| 2010/0316644 A1 | 12/2010 | Seehra et al. |
| 2011/0038831 A1 | 2/2011 | Seehra et al. |
| 2011/0053930 A1 | 3/2011 | Yu et al. |
| 2011/0070233 A1 | 3/2011 | Seehra et al. |
| 2011/0092670 A1 | 4/2011 | Knopf et al. |
| 2011/0129469 A1 | 6/2011 | Koncarevic et al. |
| 2011/0135638 A1 | 6/2011 | Seehra et al. |
| 2011/0218147 A1 | 9/2011 | Knopf et al. |
| 2011/0294734 A1 | 12/2011 | Garreta et al. |
| 2012/0003218 A1 | 1/2012 | Sherman et al. |
| 2012/0015877 A1 | 1/2012 | Seehra et al. |
| 2012/0052067 A1 | 3/2012 | Sherman |

(56) References Cited

U.S. PATENT DOCUMENTS

| | | |
|---|---|---|
| 2012/0148588 A1 | 6/2012 | Knopf et al. |
| 2012/0156204 A1 | 6/2012 | Seehra et al. |
| 2012/0237521 A1 | 9/2012 | Berger et al. |
| 2013/0004489 A1 | 1/2013 | Knopf et al. |
| 2013/0065299 A1 | 3/2013 | Knopf et al. |
| 2013/0071393 A1 | 3/2013 | Seehra et al. |
| 2013/0177559 A1 | 7/2013 | Seehra et al. |
| 2013/0184210 A1 | 7/2013 | Knopf et al. |
| 2013/0195862 A1 | 8/2013 | Knopf et al. |
| 2013/0243743 A1 | 9/2013 | Seehra et al. |
| 2013/0244324 A1 | 9/2013 | Seehra et al. |
| 2014/0056902 A1 | 2/2014 | Shimizu et al. |
| 2014/0079700 A1 | 3/2014 | Knopf et al. |
| 2014/0314759 A1 | 10/2014 | Seehra et al. |
| 2015/0183845 A1 | 7/2015 | Sherman et al. |
| 2015/0266950 A1 | 9/2015 | Sung et al. |
| 2015/0276766 A1 | 10/2015 | Sung et al. |
| 2015/0283209 A1 | 10/2015 | Sung et al. |
| 2015/0361163 A1 | 12/2015 | Kumar et al. |
| 2016/0039922 A1 | 2/2016 | Attie |
| 2016/0108379 A1 | 4/2016 | Knopf et al. |
| 2016/0120939 A1 | 5/2016 | Knopf et al. |
| 2016/0264681 A1 | 9/2016 | Seehra et al. |
| 2016/0279197 A1 | 9/2016 | Sherman et al. |
| 2016/0279203 A1 | 9/2016 | Sherman et al. |
| 2016/0289286 A1 | 10/2016 | Attie et al. |
| 2016/0318983 A1 | 11/2016 | Koncarevic et al. |
| 2016/0319254 A1 | 11/2016 | Knopf et al. |
| 2016/0326228 A1 | 11/2016 | Seerah et al. |
| 2017/0058016 A1 | 3/2017 | Knopf et al. |
| 2017/0137791 A1 | 5/2017 | Seerah et al. |
| 2017/0145074 A1 | 5/2017 | Knopf et al. |
| 2017/0190784 A1 | 7/2017 | Knopf et al. |
| 2017/0204382 A1 | 7/2017 | Seerah et al. |
| 2017/0274077 A1 | 9/2017 | Kumar et al. |
| 2017/0291935 A1 | 10/2017 | Sherman et al. |
| 2017/0304397 A1 | 10/2017 | Hruska et al. |
| 2017/0320925 A1 | 11/2017 | Seehra et al. |
| 2017/0327800 A1 | 11/2017 | Seerah et al. |
| 2017/0360887 A1 | 12/2017 | Attie et al. |
| 2018/0009872 A1 | 1/2018 | Sherman et al. |
| 2018/0037622 A1 | 2/2018 | Seerah et al. |
| 2018/0050085 A1 | 2/2018 | Kumar et al. |
| 2018/0050089 A1 | 2/2018 | Kumar et al. |
| 2018/0080012 A1 | 3/2018 | Seehra et al. |
| 2018/0125928 A1 | 5/2018 | Attie et al. |
| 2018/0161426 A1 | 6/2018 | Cappellini et al. |
| 2018/0162954 A1 | 6/2018 | Knopf et al. |
| 2018/0194828 A1 | 7/2018 | Seehra et al. |
| 2018/0194834 A1 | 7/2018 | Attie et al. |
| 2018/0214471 A1 * | 8/2018 | Heo .................. A61K 36/815 |
| 2019/0049469 A1 | 2/2019 | Sung et al. |
| 2019/0062392 A1 | 2/2019 | Koncarevic et al. |
| 2019/0192625 A1 | 6/2019 | Knopf et al. |
| 2019/0225664 A1 | 7/2019 | Sherman et al. |
| 2019/0233486 A1 | 8/2019 | Attie et al. |
| 2019/0262423 A1 | 8/2019 | Sung et al. |
| 2019/0263876 A1 | 8/2019 | Seehra et al. |
| 2019/0352619 A1 | 11/2019 | Knopf et al. |
| 2020/0031903 A1 | 1/2020 | Sherman |
| 2020/0071381 A1 | 3/2020 | Knopf et al. |
| 2020/0071383 A1 | 3/2020 | Sherman et al. |
| 2020/0101134 A1 | 4/2020 | Gale et al. |
| 2020/0101157 A1 | 4/2020 | Cappellini et al. |
| 2020/0109193 A1 | 4/2020 | Attie et al. |
| 2020/0148788 A1 | 5/2020 | Knopf et al. |
| 2020/0157512 A1 | 5/2020 | Seehra et al. |
| 2020/0165583 A1 | 5/2020 | Seehra et al. |
| 2020/0181217 A1 | 6/2020 | Seehra et al. |
| 2020/0181218 A1 | 6/2020 | Seehra et al. |
| 2020/0199186 A1 | 6/2020 | Seehra et al. |
| 2020/0199546 A1 | 6/2020 | Seehra et al. |
| 2020/0199547 A1 | 6/2020 | Seehra et al. |
| 2020/0199548 A1 | 6/2020 | Seehra et al. |
| 2020/0208124 A1 | 7/2020 | Seehra et al. |
| 2020/0255495 A1 | 8/2020 | Sherman et al. |
| 2020/0360475 A1 | 11/2020 | Sherman et al. |
| 2020/0384080 A1 | 12/2020 | Kumar et al. |
| 2020/0390860 A1 | 12/2020 | Kumar et al. |
| 2020/0397865 A1 | 12/2020 | Kumar et al. |
| 2020/0405814 A1 | 12/2020 | Kumar et al. |
| 2021/0023174 A1 | 1/2021 | Kumar et al. |
| 2021/0038689 A1 | 2/2021 | Sherman et al. |
| 2021/0115105 A1 | 4/2021 | Seehra et al. |
| 2021/0188955 A1 | 6/2021 | Kumar et al. |
| 2021/0207107 A1 | 7/2021 | Seehra et al. |
| 2021/0230239 A1 | 7/2021 | Attie et al. |
| 2021/0253658 A1 | 8/2021 | Seehra et al. |
| 2021/0261682 A1 | 8/2021 | Knopf et al. |
| 2021/0269494 A1 | 9/2021 | Koncarevic et al. |
| 2021/0299216 A1 | 9/2021 | Kumar et al. |
| 2021/0299220 A1 | 9/2021 | Kumar et al. |
| 2021/0322514 A1 | 10/2021 | Kumar et al. |
| 2021/0346464 A1 | 11/2021 | Laadem et al. |
| 2021/0355181 A1 | 11/2021 | Sherman et al. |
| 2021/0355191 A1 | 11/2021 | Sherman |
| 2022/0017639 A1 | 1/2022 | Knopf et al. |
| 2022/0041670 A1 | 2/2022 | Seehra et al. |
| 2022/0098559 A1 | 3/2022 | Seehra et al. |
| 2022/0118049 A1 | 4/2022 | Sherman et al. |
| 2022/0169996 A1 | 6/2022 | Seehra et al. |
| 2022/0281951 A1 | 9/2022 | Knopf et al. |

FOREIGN PATENT DOCUMENTS

| | | |
|---|---|---|
| EP | 1 362 062 | 5/2005 |
| EP | 1 884 235 | 2/2008 |
| JP | 2007/99764 | 4/2007 |
| JP | 2009-512710 A | 3/2009 |
| RU | 2421126 | 6/2011 |
| WO | WO 1992/004913 A1 | 4/1992 |
| WO | WO 1992/020793 A1 | 11/1992 |
| WO | WO 1993/000432 A1 | 1/1993 |
| WO | WO 1994/015965 A1 | 7/1994 |
| WO | WO 1994/026893 A1 | 11/1994 |
| WO | WO 1995/010611 A1 | 4/1995 |
| WO | WO 1995/029685 A1 | 11/1995 |
| WO | WO 1997/023613 A2 | 7/1997 |
| WO | WO 1998/018926 A1 | 5/1998 |
| WO | WO 1999/006559 A1 | 2/1999 |
| WO | WO 2000/018932 A2 | 4/2000 |
| WO | WO 2000/043781 A2 | 7/2000 |
| WO | WO 2000/062809 | 10/2000 |
| WO | WO 2001/002863 | 1/2001 |
| WO | WO 2001/036001 | 5/2001 |
| WO | WO 2001/043763 A1 | 6/2001 |
| WO | WO 2002/010214 A2 | 2/2002 |
| WO | WO 2002/022680 A2 | 3/2002 |
| WO | WO 2002/032925 | 4/2002 |
| WO | WO 2002/036152 A1 | 5/2002 |
| WO | WO 2002/040501 A2 | 5/2002 |
| WO | WO 2002/043759 A2 | 6/2002 |
| WO | WO 2002/074340 A1 | 9/2002 |
| WO | WO 2002/085306 A2 | 10/2002 |
| WO | WO 2002/088171 | 11/2002 |
| WO | WO 2002/094852 A2 | 11/2002 |
| WO | WO 2003/006057 A1 | 1/2003 |
| WO | WO 2003/053219 A2 | 7/2003 |
| WO | WO 2003/072808 A1 | 9/2003 |
| WO | WO 2003/087162 A2 | 10/2003 |
| WO | WO 2004/016639 A1 | 2/2004 |
| WO | WO 2004/039948 | 5/2004 |
| WO | WO 2004/069237 A1 | 8/2004 |
| WO | WO 2004/086953 A2 | 10/2004 |
| WO | WO 2004/092199 | 10/2004 |
| WO | WO 2004/108157 A2 | 12/2004 |
| WO | WO 2005/003158 A2 | 1/2005 |
| WO | WO 2005/009460 A2 | 2/2005 |
| WO | WO 2005/014650 A2 | 2/2005 |
| WO | WO 2005/025601 | 3/2005 |
| WO | WO 2005/028517 A2 | 3/2005 |
| WO | WO 2005/037989 | 4/2005 |

(56) References Cited

FOREIGN PATENT DOCUMENTS

| | | |
|---|---|---|
| WO | WO 2005/053795 A2 | 6/2005 |
| WO | WO 2005/070967 A2 | 8/2005 |
| WO | WO 2005/094871 A2 | 10/2005 |
| WO | WO 2005/097825 A2 | 10/2005 |
| WO | WO 2005/113590 A2 | 12/2005 |
| WO | WO 2006/002387 A2 | 1/2006 |
| WO | WO 2006/012627 A2 | 2/2006 |
| WO | WO 2006/020884 | 2/2006 |
| WO | WO 2006/039400 A2 | 4/2006 |
| WO | WO 2006/055689 | 5/2006 |
| WO | WO 2006/083183 A1 | 8/2006 |
| WO | WO 2006/088972 | 8/2006 |
| WO | WO 2006/115274 A1 | 11/2006 |
| WO | WO 2007/038703 A2 | 4/2007 |
| WO | WO 2007/053775 A1 | 5/2007 |
| WO | WO 2007/062188 | 5/2007 |
| WO | WO 2007/067616 A2 | 6/2007 |
| WO | WO 2007/071023 | 6/2007 |
| WO | WO 2007/075702 | 7/2007 |
| WO | WO 2007/076127 A2 | 7/2007 |
| WO | WO 2007/087505 | 8/2007 |
| WO | WO 2007047969 A2 | 8/2007 |
| WO | WO 2007/101060 | 9/2007 |
| WO | WO 2008/015383 A2 | 2/2008 |
| WO | WO 2008/031061 | 3/2008 |
| WO | WO 2008/060139 | 5/2008 |
| WO | WO 2008/072723 A1 | 6/2008 |
| WO | WO 2008/073292 A2 | 6/2008 |
| WO | WO 2008/076437 A2 | 6/2008 |
| WO | WO 2008/094708 A2 | 8/2008 |
| WO | WO 2008/097541 A2 | 8/2008 |
| WO | WO 2008/100384 A2 | 8/2008 |
| WO | WO 2008/109167 A2 | 9/2008 |
| WO | WO 2008/151078 A1 | 12/2008 |
| WO | WO 2009/009059 A1 | 1/2009 |
| WO | WO 2009/019504 A1 | 2/2009 |
| WO | WO 2009/019505 A2 | 2/2009 |
| WO | WO 2009/021747 | 2/2009 |
| WO | WO 2009/025651 A1 | 2/2009 |
| WO | WO 2009/058346 | 5/2009 |
| WO | WO 2009/070243 | 6/2009 |
| WO | WO 2009/137075 A1 | 11/2009 |
| WO | WO 2009/137613 A2 | 11/2009 |
| WO | WO 2009/158015 A2 | 12/2009 |
| WO | WO 2009/158025 A2 | 12/2009 |
| WO | WO 2009/158033 A2 | 12/2009 |
| WO | WO 2010/019261 A1 | 2/2010 |
| WO | WO 2010/062383 | 6/2010 |
| WO | WO 2010/083034 A1 | 7/2010 |
| WO | WO 2010/144452 | 12/2010 |
| WO | WO 2010/151426 | 12/2010 |
| WO | WO 2011/020045 | 2/2011 |
| WO | WO 2011/031901 A1 | 3/2011 |
| WO | WO 2012/027065 | 3/2012 |
| WO | WO 2013/059347 | 4/2013 |
| WO | WO 2014/066487 | 1/2014 |
| WO | WO 2014/066486 | 5/2014 |
| WO | WO 2014/071158 A1 * | 5/2014 |
| WO | WO 2014/071158 | 8/2014 |
| WO | WO 2015/161220 | 10/2015 |
| WO | WO 2015/192111 | 12/2015 |
| WO | WO 2016/069234 | 5/2016 |
| WO | WO 2016/090077 | 6/2016 |
| WO | WO 2016/090188 | 6/2016 |
| WO | WO 2016/183280 | 11/2016 |
| WO | WO 2016/187378 | 11/2016 |
| WO | WO 2017/079591 | 5/2017 |
| WO | WO 2017/091706 | 6/2017 |
| WO | WO 2018/022762 | 2/2018 |
| WO | WO 2018/067874 | 4/2018 |
| WO | WO 2018/231905 | 12/2018 |
| WO | WO 2020/092523 | 5/2020 |
| WO | WO 2021/211418 | 10/2021 |
| WO | WO 2021/231851 | 11/2021 |

OTHER PUBLICATIONS

Goodman et al., 2000, N. Engl. J. Med. 342(20): 1478-83.*
Wannamethee et al. (2013, Arterioscler. Thromb. Vasc. Biol. 33:1070-1076).*
Rodan, 1998, PNAS USA 95:13361-13362.*
Zhou et al. (2010, PNAS USA 107:12919-12924).*
Kim et al. (2011, J. Korean Med. Sci. 26:1178-1184).*
Sardiwal et al. (2013, Am. J. Kidney Dis. 62(4):810-822).*
Claes et al. (2013, J. Clin. Endocrinol. Metab. 98(8):3221-3228).*
Chen et al. (May 2013, PLoS ONE 8(5):e64558 doi:10.1371/journal.pone.0064558).*
Alexopoulos et al. (2010, Int. J. Cardiol. 139:142-149).*
Huk et al. (2013, Arteriosclerosis, Thrombosis, and Vascular Biology 33(2):285-293).*
Hao et al. (1999, J. Mol. Cell. Cardiol. 31:667-678).*
Lei et al. (2011, J. Pharmacol. Sci. 117(2):98-105).*
Steitz et al. (2001, Circ Res 89(12): 1147-1154).*
Abaza et al., "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin", Journal of Protein Chemistry, 11(5):433-444 (1992).
Abbiotec: ACTR-IIA Antibody: Catalog No. 251303 (http://www.abbiotec.com) Jun. 3, 2010.
Acceleron Pharma Presents Positive Phase 1 Results Demonstrating ACE-011 Increases Markers of Bone Formation, Acceleron Pharma, pp. 1-2, retrieved from the Internet, www.acceleronpharma.com/contents/news/press-releases/detail.jsp/q/news-id/47> (2007).
Acta Cryst.,"The CCP4 suite: programs for protein crystallography: Collaborative Computational Project, No. 4," D50: 760-763 (1994). (Abstract only).
Akel et al., "Neutralization of Autocrine Transforming Growth Factor—in Human Cord Blood CD34$^+$CD38$^-$Lin$^-$ Cells Promotes Stem-Cell-Factor-Mediated Erythropoietin-Independent Early Erythroid Progenitor Development and Reduces Terminal Differentiation." Stem Cells, 21:557-567 (2003).
Akpan et al., "The effects of a soluble activin type IIB receptor on obesity and insulin sensitivity," International Journal of Obesity, 33(11):1265-1273 (2009).
"Anti-human Activin RIIA Antibody," R&D Systems, Catalog No. AF340 (Feb. 14, 2006).
Allendorph, G.P., et al., "Structure of the ternary signaling complex of a TGF-β0 superfamily member," PNAS, 103(20):7643-7648 (2006).
Anonymous "Iron and Thalassemia," Accessed on the Internet Apr. 3, 2014 at <sickle.bwh.harvard.edu/thaliron.html>. Published Apr. 25, 1997.
Anonymous "Learning about Thalassemia" <http://www.genome.gov/10001221> Accessed on Internet Jul. 9, 2013, Published Jun. 28, 2010.
Anti-ActRIIA Antibodies: Commercial Monoclonal Antibodies Against Human ActRIIA (2010).
Antibodies for ACVR2A: http://www.genecards.org/cgi-bin/carddisp.pl?gene=Acvr2a (Jun. 8, 2010).
Attie et al., "A Single Ascending-Dose Study of Muscle Regulator Ace-031 in Healthy volunteers," Muscle & Nerve, pp. 1-8 (2012).
Banks et al., "The Value of Mammalian Models for Duchenne Muscular Dystrophy in Developing Therapeutic Strategies," Current Topics in Developmental Biology, 84:431-453 (2008).
Benny Klimek et al., "Acute inhibition of myostatin-family proteins preserves skeletal muscle in mouse models of cancer cachexia," Biochemical and Biophysical Research Communications, 391:1548-1554 (2010).
Berenson, "Multiple Myeloma," Multiple Myeloma: Plasma Cell Disorders: Merck Manual Professional, pp. 1-5, Jul. 2008.
Bhatia et al., "Protein Glycosylation: Implications for In Vivo Functions and Therapeutic Applications". Advances in Biochemical Engineering/Biotechnology, vol. 64: 155-201 (1998).
Binkert et al., "Cloning, sequence analysis and expression of a cDNA encoding a novel insulin-like growth factor binding protein (IGFBP-2)," The EMBO Journal, 8(9):2497-2502 (1989).

(56) References Cited

OTHER PUBLICATIONS

Bodey et al., "Failure of Cancer Vaccines: The Significant Limitations of this Approach to Immunotherapy," Anticancer Research, 20:2665-2676 (2000).
Bogdanovich et al., "Functional improvement of dystrophic muscle by myostatin blockade," Nature, 420:418-421 (2002).
Bork, "Powers and Pitfalls in Sequence Analysis: The 70% Hurdle," Genome Research, 10:398-400 (2000).
Bowie et al., "Deciphering the Message in Protein Sequences: Tolerance to Amino Acid Substitutions," Science, 247:1306-1310 (1990).
Broxmeyer et al., "Selective and indirect modulation of human multipotential and erythroid hematopoietic progenitor cell proliferation by recombinant human activin and inhibin," Proc. Natl. Acad. Sci. USA, 85:9052-9056 (1988).
Burdette et al., "Activin A mediates growth inhibition and cell cycle arrest through Smads in human breast cancer cells." Cancer Research, 65(17):7968-7975; (2005).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell Biol., 111:2129-2138 (1990).
Cadena et al., "Administration of a Soluble Activin Type IIB Receptor Promotes Skeletal Muscle Growth Independent of Fiber Type," Journal of Applied Physiology, 109:635-642 (2010).
Caricasole et al., "Human Growth-Differentiation Factor 3 (HGDF3): Developmental Regulation in Human Teratocarcinoma Cell Lines and Expression in Primary Testicular Germ Cell Tumours," Oncogene, 16:95-103 (1998).
Cannon and Nedergaard, "Neither fat nor flesh," Nature, vol. 454(7207): 947-948 (2008).
Carrancio et al. "An activin receptor IIA ligand trap promotes erythropoiesis resulting in a rapid induction of red blood cells and haemoglobin," British Journal of Haematology, vol. 165: 870-882 (2014).
Casset et al., "A Peptide mimetic of an anti-CD4 monoclonal antibody by rational design," Biochemical and Biophysical Research Communications, vol. 307:198-205 (2003).
CDR Definitions from Handbook of Therapeutic Antibodies, (2007).
Centrella et al., "Activin-A Binding and Biochemical Effects in Osteoblast-Enriched Cultures from Fetal-Rat Parietal Bone," Molecular and Cellular Biology, 11(1):250-58 (1991).
Chamberlain et al., "Innovations and strategies for the development of anticancer vaccines," Expert Opinion on Pharmacotherapy, 1(4):603-614 (2000).
Chamow and Ashkenzi, "Immunoadhesins: Principles and Applications," TIBTECH, 14: 52-60 (1996).
Chang, "Exploring the Effects of Luteinizing Hormone-Releasing Hormone Agonist Therapy on Bone Health: Implications in the Management of Prostate Cancer," Urology, vol. 52: 29-35 (2003).
Chapman et al., "Effect of intron A from human cytomegalovirus (Towne) immediate-early gene on heterologous expression in mammalian cells," Nucleic Acids Research, 19(14):3979-3986 (1991).
Chantry et al., "Inhibiting Activin-A Signaling Stimulates Bone Formation and Prevents Cancer-Induced Bone Destruction in Vivo," Journal of Bone and Mineral Research, 25(12): 2357-2370 (2010).
Chardès et al., "Efficient amplification and direct sequencing of mouse variable regions from any immunoglobulin gene family," FEBS Lett. vol. 452(3): 386-394 (1999).
Chavez-Tapia et al., "Insulin sensitizers in treatment of nonalcoholic fatty liver disease: Systematic review," World Journal of Gastroenterology, vol. 12(48): 7826-7831 (2006).
Chen et al., "Selection and Analysis of an Optimized Anti-VEGF Antibody: Crystal Structure of an Affinity-matured Fab in Complex with Antigen," J. Mol. Biol., vol. 293: 865-881 (1999).
Chen et al. "Regulation of Cell Proliferation, Apoptosis, and Carcinogenesis by Activin," Exp. Biol. Med., 227(2):75-87 (2002).

Cirillo et al., "Hematocrit, blood pressure, and hypertension. The Gubbio Population Study," Hypertension, 20(3):319-326 (1992).
Coerver et al., "Activin Signaling through Activin Receptor Type II Causes the Cachexia-Like Symptoms in Inhibin-Deficent Mice," Molecular Endocrinology, 10(5):534-543 (1996).
Collins, "Multidisciplinary Symposium: Haematological Malignancies," Cancer Imaging 5:S119-S126 (2005).
Colman, "Effects of amino acid sequence changes on antibody-antigen interactions," Research of Immunology, 145(1):33-36 (1994).
Crisan et al., "A Reservoir of Brown Adipocyte Progenitors in Human Skeletal Muscle," Stem Cells, vol. 26(9): 2425-2433 (2008).
Daluiski et al., "Bone Morphogenetic Protein-3 is a Negative Regulator of Bone Density," Nature Genetics, 27:84-88 (2001).
Database Geneseq [Online], "Variable heavy chain of anti-human Fas ligand antibody NOK-4," retrieved from EBI accession No. GSP:AAW00829; Database accession No. AAW00829; abstract, sequence (1997).
Database Geneseq [Online]; "Monoclonal antibody 10D4 HMGB1 Vkappa domain," retrieved from EBI accession No. GSP:ADY85028, Database accession No. GSP:ADY85028; abstract, sequence (2005).
Deal, "Potential New Drug Targets for Osteoporosis," Nature Clinical Practice, 5(1):20-27 (2009).
Deconinck et al., "Pathophysiology of Duchenne Muscular Dystrophy: Current Hypotheses," Pediatr. Neurol., 36:1-7 (2007).
Del Re et al., "Reconstitution and Analysis of Soluble Inhibin and Activin Receptor Complexes in a Cell-free System," The Journal of Biological Chemistry, 279(51):53126-53135 (2004).
Delogu et al., "DNA vaccine combinations expressing either tissue plasminogen activator signal sequence fusion proteins or ubiquitin-conjugated antigens induce sustained protective immunity in a mouse model of pulmonary tuberculosis," Infection and Immunity, 70(1):292-302 (2002).
Depaolo et al., "Passive Immunoneutralization with a Monoclonal Antibody Reveals a Role For Endogenous Activin-B in Mediating FSH Hypersecretion during Estrus and Following Ovariectomy of Hypophysectomized, Pituitary-Grafted Rats," Endocrinology, 130(3):1741-1743 (1992).
Donald et al., "SDR: a database of predicted specificity-determining residues in proteins," Nucleic Acids Research, vol. 37: D191-D194 (2009).
Donaldson et al., GenBank: BAA06548.1: activin typell A receptor precursor [Homo sapiens] (1992).
Donaldson et al., "Activin and inhibin binding to the soluble extracellular domain of activin receptor II", Endocrinology 140(4):1760-1766 (1999).
Donaldson et al., "Molecular Cloning and Binding Properties of the Human Type II Activin Receptor", Biochemical and Biophysical Research Communications, 184(1):310-316 (1992).
Dussiot et al., "An activin receptor IIA ligand trap corrects ineffective erythropoiesis in B-thalassemia," Nature Medicine, vol. 20: 398-407 (2014).
Ear et al., "RAP-011 Efficiently Rescues Erthropoiesis in Zebrafish Models of Diamond Blackfan Anemia," 55 ASH Annual Meeting and Exposition. Abstract #3702 (2013).
Eijken, "The Activin A-Follistatin System: Potent Regulator of Human Extracellular Matrix Mineralization," The FASEB Journal, 21:2949-2960 (2007).
Elliot et al., "Enhancement of therapeutic protein in vivo activities through glycoengineering," Nature Biotechnology, vol. 21: 414-421 (2003).
Fafioffe et al.,"Activin and inhibin receptor gene expression in the ewe pituitary throughout the oestrous cycle," Journal of Endocrinology, 182:55-68 (2004).
Fajardo et al., "Treatment with a Soluble Receptor for Activin Improves Bone Mass and Structure in the Axial and Appendicular Skeleton of Female Cynomolgus Macaques (Macaca fascicularis)," Bone, 46:64-71 (2010).
Fan et al., "Preclinical evaluation of Hematide, a novel erythropoiesis stimulating agent, for the treatment of anemia," Experimental Hematology 34:1303-1311 (2006).
Farmer, "Brown Fat and Skeletal Muscle: Unlikely Cousins?," Cell, vol. 134(5): 726-727 (2008).

(56) References Cited

OTHER PUBLICATIONS

Ferguson et al., "The role of effectors of the activin signalling pathway, activin receptors IIA and IIB, and Smad2, in patterning of tooth development," Development, vol. 128: 4605-4613 (2001).
Foucar, Myelodysplastic/ Myeloproliferative Neoplasms, Am J Clin Pathol, vol. 132: 281-289 (2009).
Fournier et al., "Blockade of the activin receptor IIb activates functional brown adipogenesis and thermogenesis by inducing mitochondrial oxidative metabolism," Mol. Cell. Biol. vol. 32(14): 2871-2879 (2012).
Frankel et al., "Characterization of diphtheria fusion proteins targeted to the human interleukin-3 receptor," Protein Engineering, vol. 13(8): 575-581 (2000).
Frigon, et al., "Regulation of Globin Gene Expression in Human K562 Cells by Recombinant Activin A," Blood, 79(3):765-772 (1992).
Fuller et al., "Activin A Is an Essential Cofactor for Osteoclast Induction," Biochemical and Biophysical Research Communications, 268:2-7 (2000).
Funaba et al., "Expression and Localization of Activin Receptors During Endochondral Bone Development," European Journal of Endocrinology, 144:63-71 (2001).
Gaddy-Kurten et al., "Inhibin Suppresses and Activin Stimulates Osteoblastogenesis and Osteoclastogenesis in Murine Bone Marrow Cultures," Endocrinology, 143(1):74-83 (2002).
Gamer et al., "BMP-3 is a Novel Inhibitor of Both Activin and BMP-4 Signaling in Xenopus Embryos," Developmental Biology, 285:156-168 (2005).
Ge et al., "GDF11 Forms a Bone Morphogenetic Protein 1-Activated Latent Complex That Can Modulate Nerve Growth Factor-Induced Differentiation of PC12 Cells", Molecular and Cellular Biology, 25(14):5846-5858 (2005).
GenBank NM_001106, *Homo sapiens* activin A receptor, type IIb (ACVR2B), mRNA, http://www.ncbi.nlm.nih.gov/entrez/viewer.fcgi?db=nucleotide&val=116734707 (Downloaded on Jan. 29, 2007).
Gilbert et al., "Prolonged dystrophin expression and functional correction of mdx mouse muscle following gene transfer with a helper-dependent (gutted) adenovirus-encoding murine dystrophin," Human Molecular Genetics, 12(11)1287-1299 (2003).
Gilchrist et al., "Antagonists of the Receptor-G Protein Interface Block Gi-coupled Signal Transduction," The Journal of Biological Chemistry, 273(24):14912-14919 (1998).
Gonzalez-Cadavid et al., "Organization of the human myostatin gene and expression in healthy men and HIV-infected men with muscle wasting," PNAS, 95:14938-14943 (1998).
Gray et al., "Identification of a binding site on the type II activin receptor for activin and inhibin", The Journal of Biological Chemistry, 275(5):3206-3212(2000).
Greenspan et al., "Defining epitopes: It's not as easy as it seems," Nature Biotechnology, 17:936-937 (1999).
Greenwald et al., "Characterization of the Extracellular Ligand-Binding Domain of the Type II Activin Receptor," Biochemistry, 37(47):16711-16718 (1998).
Greenwald et al., "The BMP7/ActRII Extracellular Domain Complex Provides New Insights into the Cooperative Nature of Receptor Assembly," Molecular Cell, 11:605-617 (2003).
Greenwald et al., "Three-finger toxin fold for the extracellular ligand-binding domain of the type II activin receptor serine kinase," Nature Structural Biology, 6(1):18-22 (1999).
Gregoriadis et al., "Polysialic acids: potential in drug delivery," FEBS, 315(3):271-276 (1993).
Guo et al., Protein Tolerance to Random Amino Acid Change. Proc. Natl. Acad. Sci. USA, 101(25):9205-9210 (Jun. 22, 2004). Epub Jun. 14, 2004.
Gupta et al., "Transforming Growth Factor-beta Superfamily: Evaluation as Breast Cancer Biomarkers and Preventive Agents," Current Cancer Drug Targets, 4:165-182 (2004).
Gura, "Cancer Models: Systems for Identifying New Drugs Are Often Faulty," Science, 278(5340):1041-1042 (1997).

Haidar et al., "Paraspinal extramedullary hematopoiesis in patients with thalassemia intermedia," Eur Spine J., vol. 19: 871-878 (2010).
Hamrick et al., "Bone Mineral Content and Density in the Humerus of Adult Myostatin-Deficient Mice," Calcified Tissue International, 71:63-68 (2002).
Hamrick, "Increased Bone Mineral Density in the Femora of GDF8 Knockout Mice," The Anatomical Record, Part A 272A:388-391 (2003).
Hamrick, et al., "Femoral Morphology and Cross-sectional Geometry of Adult Myostatin-deficient Mice," Bone, 27(3):343-349 (2000).
Harousseau et al., "Multiple Myeloma," American Society of Hematology, pp. 237-256 (2004).
Harrison, et al., "An Activin Mutant with Disrupted ALK4 Binding Blocks Signaling via Type II Receptors," The Journal of Biological Chemistry, 279(27):28036-28044 (2004).
Harrison, et al., "Antagonists of activin signaling: mechanisms and potential biological applications," Trends in Endocrinology and Metabolism, 16(2):73-78 (2005).
Hashimoto et al., "Functional Regulation of Osteoblastic Cells by the Interaction of Activin-A with Follistatin," The Journal of Biological Chemistry, 267(7):4999-5004 (1992).
Hemmati-Brivanlou, et al., "A truncated activin receptor inhibits mesoderm induction and formation of axial structures in Xenopus embryos," Nature, 359:609-614 (1992).
Herbert et al., The Dictionary of Immunology, Academic Press, 3rd Edition, London, pp. 58-59 (1985).
Hilden et al., "Expression of Type II Activin Receptor Genes During Differentiation of Human K562 Cells and cDNA Cloning of the Human Type IIB Activin Receptor," Blood, 83(8):2163-2170 (1994).
Hill et al., "Regulation of Myostatin in Vivo by Growth and Differentiation Factor-Associated Serum Protein-1: A Novel Protein with Protease Inhibitor and Follistatin Domains," Molecular Endocrinology, 17(6):1144-1154 (2003).
Holm et al., "Functional mapping and single chain construction of the anti-cytokeratin 8 monoclonal antibody TS1," Molecular Immunology, vol. 44(6): 1075-1084 (2007).
"Human Activin RIIA Antibody," R&D Systems, Tools for Cell Biology Research, Catalog No. MAB340 (Mar. 22, 2011).
Hsieh et al., "HIF-prolyl hydroxylase inhibition results in endogenous erythropoietin induction, erythrocytosis, and modest fetal hemoglobin expression in rhesus macaques," Blood, 110(6):2140-2147 (2007).
Ikenoue et al., "Inhibitory Effects of Activin-A on Osteoblast Differentiation During Cultures of Fetal Rat Calvarial Cells," Journal of Cellular Biochemistry, 75:206-214 (1999).
Ito et al., "Presence of activin signal transduction in normal ovarian cells and epithelial ovarian carcinoma," British Journal of Cancer, vol. 82(8): 1415-1420 (2000).
"The Illustrated Guide to Bone Marrow Diagnosis Second Edition," Ed. By G. Kumar. Originally published 2003.
Kaiser, "First Pass at Cancer Genome Reveals Complex Landscape," Science, 313:1370 (2006).
Kanemitsu, "Clinical application of subforms of creatine kinase MM and macro creatine kinases," Journal of Chromatography, vol. 526: 423-438 (1990).
Kaspar, et al., "Retrograde Viral Delivery of IGF-1 Prolongs Survival in a Mouse ALS Model," Science, 301:839-842 (2003).
Kim, et al., "ACE-011, a Soluble Activin Receptor Type IIa IgG-Fc Fusion Protein, Increases Hemoglobin and Hematocrit Levels in Postmenopausal Healthy Women," Blood, 112(11) (2008).
Knight, "Roles of Inhibins, Activins, and Follistatin in the Female Reproductive System," Frontiers in Neuroendocrinology, 17:476-509 (1996).
Koncarevic et al., "A Soluble Activin Receptor Type IIB Prevents the Effects of Androgen Deprivation on Body Composition and Bone Health," Endocrinology, vol. 151(9); 4289-4300 (2010).
Kos et al., "Activin type II receptors in embryonic dorsal root ganglion neurons of the chicken," J. Neurobiol., vol. 47(2): 93-108 (2001).
Kosaki et al., "Left-Right Axis Malformations Associated With Mutations in ACVR2B, the Gene for Human Activin Receptor Type IIB," American Journal of Medical Genetics, 82:70-76 (1999).
Koseki et al., "Role of TGF-beta Family in Osteoclastogenesis Induced by RANKL," Cellular Signaling, 14:31-36 (2002).

(56) References Cited

OTHER PUBLICATIONS

Krag et al., "Heregulin ameliorates the dystrophic phenotype in mdx mice," PNAS, 101(38):13856-13860 (2004).
Krneta et al., "Dissociation of Angiogenesis and Tumorigenesis in Follistatin- and Activin-Expressing Tumors," Cancer Research, 66(11):5686-5695 (2006).
Krystal et al., "Transforming Growth Factor 1 Is an Inducer of Erythroid Differentiation". J. Exp. Med. vol. 180 pp. 851-860 (1994).
Kubanek, "Introduction: The Role of the Microenvironment and Cytokines on the Modulation of Erythropoiesis," Annals New York Academy of Sciences, pp. 257-258 (1994).
Kumar et al., "Regulation of FSHbeta and GnRH Receptor Gene Expression in Activin Receptor II Knockout Male Mice," Mol. Cell. Endocrinol., 212:19-27 (2003).
Kunihro et al., "Regulation of Muscle Mass and Hepatic Steatosis by Follistatin-derived Myostatin Inhibitors," Making Muscle in the Embryo and Adult: a joint meeting of Frontiers in Myogenesis and Skeletal Muscle Stem and Satellite Cells, New York, NY, p. 45 (Abstract) (1990).
Kuntz, "Structure-Based Strategies for Drug Design and Discovery," Science, 257:1078-1082 (1992). (Abstract only).
Lazar, "How Now, Brown Fat?" Science, vol. 321(5892): 1048-1049 (2008).
Kwiatkowski et al., "Iron chelation therapy in sickle-cell disease and other transfusion-dependent anemias," Hematol Oncol Clin N Am., vol. 18: 1355-1377 (2004).
Lazar et al., "Transforming Growth Factor α: Mutation of Aspartic Acid 47 and Leucine 48 Results in Different Biological Activities," Molecular and Cellular Biology, 8(3):1247-1252 (1988).
Lebrun et al, "Activin and Inhibin Have Antagonistic Effects on Ligand-Dependent Heteromerization of the Type I and Type II Activin Receptors and Human Erythroid Differentiation," Molecular and Cellular Biology, 17(3):1682-1691 (1997).
Lee et al., "Regulation of Muscle Growth by Multiple Ligands Signaling Through Activin Type II Receptors," PNAS 102(50):18117-18122 (2005).
Lee, et al., "Regulation of Myostatin Activity and Muscle Growth," PNAS, 98(16):9306-9311 (2001).
Leto et al., "Activin A Circulating Levels in Patients with Bone Metastasis from Breast or Prostate Cancer," Clin Exp Metastasis, 23:117-122 (2006).
Li et al., "Prevention of cachexia-like syndrome development and reduction of tumor progression in inhibin-deficient mice following administration of a chimeric activin receptor type II-murine Fc protein," Molecular Human Reproduction, 13(9):675-683 (2007).
Lifespan Biosciences, Activin Receptor Type 2A (ACVR2A) Mouse anti-Human Monoclonal Antibody—LS-C33835—LifeSpan Biosciences, (2010).
Liu et al., "Characterization of isoforms of activin receptor-interacting protein 2 that augment activin signaling," Journal of Endocrinology, vol. 189: 409-421 (2006).
Lotinun et al., "A Soluble Activin Receptor Type IIA Fusion Protein (ACE-011) Increases Bone Mass Via a Dual Anabolic-Antiresorptive Effect in Cynomolgus Monkeys," Bone, 46:1082-1088 (2010).
Lu et al., "Simian Immunodeficiency Virus DNA Vaccine Trial in Macaques," Journal of Virology, 70(6):3978-3991 (1996).
Ludlow et al., "Development of a new antibody to the human inhibin/activin βB subunit and its application to improved inhibin B ELISAs," J. Immunol. Methods, 329:102-111 (2008).
Ma, "Animal Models of Disease," Modern Drug Discovery, 30-36 (2004).
Maccallum et al., "Antibody-antigen Interactions: Contact Analysis and Binding site Topography," J. Mol. Biol, vol. 262: 732-745 (1996).
Maclennan et al., "Multiple Myeloma," BMJ, vol. 308:1033-1036 (1994).
Maguer-Satta et al, "A Novel Role for Fibronectin Type 1 Domain in the Regulation of Human Hematopoietic Cell Adhesiveness Through Binding to Follistatin Domains of FLRG and Follistatin," Experimental Cell Research, 312(4):434-442 (2006).
Maguer-Satta et al, "Regulation of human erythropoiesis by activin A, BMP2, and BMP4, members of the TGFβ family," Experimental Cell Research, 282:110-120 (2003).
Maguer-Satta et al., "FLRG, Member of the Follistatin Family, a New Player in Hematopoiesis," Molecular and Cellular Endocrinology, 225:109-118 (2004).
Marri et al, Human Biochemistry, Moscow, "Mir", vol. 1: 34-35 (1993).
Mathews et al., "Expression Cloning of an Activin Receptor, a Predicted Transmembrane Serine Kinase," Cell, 65(6):973-982 (1991).
Matzuk et al., "Cloning of the human activin receptor cDNA reveals high evolutionary conservation," Biochim Biophys Acta, 1130(1):105-108 (1992).
Matzuk et al., "Different phenotypes for mice deficient in either activins or activin receptor type II," Nature, 374:356-360 (1995).
Mccarthy et al., Monoclonal antibodies that recognize the type-2 activin receptor, ACTR2, Hybridoma, vol. 13(3): 199-203 (1994).
Mcnally, "Powerful Genes—Myostatin Regulation of Human Muscle Mass," N. Engl. J. Med., 350(26):2642-2644 (2004).
Mcpherron, et al., "GDF-3 and GDF-9: Two New Members of the Transforming Growth Factor-Beta Superfamily Containing a Novel Pattern of Cysteines," Journal of Biological Chemistry, 268(5):3444-3449 (1993).
Mcpherron, et al., "Regulation of Skeletal Muscle Mass in Mice by a New TGF-beta Superfamily Member," Nature, 387:83-90 (1997).
Mcpherron and Lee, "Suppression of body fat accumulation in myostatin-deficient mice," The Journal of Clinical Investigation, vol. 109(5): 595-601 (2002).
Mcpherson et al., "Growth inhibitory response to activin A and B by human prostate tumour cell lines LNCaP and DU145", Journal of Endocrinology, 154:535-545 (1997).
Menstruation: Absent Periods (Amenorrhea), Website downloaded on Jun. 14, 2010, <http://adam.about.com/reports/000101_2.htm?p=1> (11 pages).
Merck Manual. Iron-Utilization Anemias (Sideroblastic Anemias), pp. 1150-1151 (1992).
Merck Manuals Online Medical Library (online). Iron Deficiency Anemia, Jun. 10, 2008. Downloaded from the internet on Jan. 5, 2010. <http://web.archive.org/web/20080610070221/http://www.merck.com/mmpe/sec11/ch130/ch130d.html> pp. 1-4.
Merck Manuals Online Medical Library (online). Anemia of Chronic Disease, Jun. 10, 2008. Downloaded from the internet on Jan. 5, 2010. <http://web.archive.org/web/20080610070226/http://www.merck.com/mmpe/sec11/ch130/ch130d.html> pp. 1-2.
The Merck Manual of Diagnosis and Therapy, 17th Edition. myelodysplastic Syndrome, pp. 865 and 963-955 (1999).
Meriggiola et al., "Follistatin Decreases Activin-Stimulated FSH Secretion with No Effect On GnRH-Stimulated FSH Secretion in Prepubertal Male Monkeys," Endocrinology, 134(4):1967-1970 (1994).
Monoclonal Anti-human Activin RII Antibody, R&D Systems, Catalog No. MAB3391 (Feb. 18, 2009).
The website downloaded Oct. 28, 2014 from the Multiple Myeloma Research Foundation, themmrf.org/multiple-myeloma/symptoms/bone-lesions/, 2 pages total.
Mickle et al., "Genotype-Phenotype Relationships in Cystic Fibrosis," Med. Clin. North Am., 84(3):597-607 (2000).
Miller et al., "Ligand Binding to Proteins: The Binding Landscape Model," Protein Science, 6:2166-2179 (1997).
Miura et al., "Utrophin upregulation for treating Duchenne or Becker muscular dystrophy: how close are we?," Trends in Molecular Medicine, 12(3):122-129 (2006).
Moore et al., "Molecular Basis of Bone Morphogenetic Protein-15 Signaling in Granulosa Cells*," The Journal of Biological Chemistry, vol. 278(1): 304-310 (2003).
Morrison et al., "A soluble activin type IIB receptor improves function in a mouse model of amyotrophic lateral sclerosis," Experimental Neurology vol. 217: 258-268 (2009).
Mosekilde et al., "Emerging Anabolic Treatments in Osteoporosis," Current Drug Safety, 6:62-74 (2011).

(56) References Cited

OTHER PUBLICATIONS

Murase et al., "Possible Involvement of Protein Kinases and Smad2 Signaling Pathways on Osteoclast Differentiation Enhanced by Activin A," Journal of Cellular Physiology, 188:236-242 (2001).
Murata et al., "Anti-activin A Antibody (IgY) Specifically Neutralizes Various Activin A Activities," Proceedings of the Society for Experimental Biology & Medicine, 211(1):100-107 (1996).
Nagamine et al., "Immunohistochemical Detection of Activin A, Follistatin, and Activin Receptors during Fracture Healing in the Rat," Journal of Orthopaedic Research, 16:314-321 (1998).
Nakamura et al, "Effect of Erythroid Differentiation Factor on Maintenance of Human Hematopoietic Cells in Co-cultures with Allogenic Stromal Cells," Biochemical and Biophysical Research Communications, 194(3):1103-1110 (1993).
Nemeth, "Hepcidin in Beta-thalassemia," Annals of the New York Academy of Sciences, vol. 1202: 31-35. Published Aug. 2, 2010.
Ngo et al., "Computational Complexity, Protein Structure Prediction, and the Levinthal Paradox," The Protein Folding Problem and Tertiary Structure Prediction, Merz et al., eds., Birkhauser, Boston, 433 and 492-495 (1994).
"NIH website downloaded May 28, 2014 from: web.archive.org/web/20030409091558/http://www.cc.nih.gov/ccc/patient_ education/pepubs/subq.pdf; Patient Information Publications: Giving a Subcutaneous Injection ( 6 pages total)".
Ogawa et al., "Bovine Bone Activin Enhances Bone Morphogenetic Protein-Induced Ectopic Bone Formation," The Journal of Biological Chemistry, 267(20):14233-14237 (1992).
Oh et al., "Activin type IIA and IIB receptors mediate Gdf1 1 signaling in axial vertebral patterning," Genes & Development, 16:2749-2754 (2002).
Oue et al., "Effect of Local Injection of Activin A on Bone Formation in Newborn Rats," Bone, 15(3):361-366 (1994).
Padlan et al., "Identification of specificity-determining residues in antibodies," The FASEB Journal, vol. 9: 133-139 (1995).
Paulson, "Targeting a new regulator of erythropoiesis to alleviate anemia," Nature Medicine, News and Views, vol. 20(4) (2 pages) (2014).
Pakula and Sauer, "Genetic analysis of protein stability and function," Annu. Rev. Genet., vol. 23: 289-310 (1989).
Patel et al., "The function of Myostatin and strategies of Myostatin blockade—new hope for therapies aimed at promoting growth of skeletal muscle," Neuromuscular Disorders, 15:117-126 (2005).
Paul, Fundamental Immunology, 3rd edition, Raven Press, New York, 1003: 292-295 (1999).
Pearsall et al., An investigative pharmacology study of a GDF-8 (myostatin) inhibitor, ACE-031, in the common Marmoset (*Callithrix jacchus*), Database Biosis, Biosciences Information Service, Accession No. PREV201200750016; Faseb Journal, vol. 22, Experimental Biology Annual Meeting, San Diego, CA Apr. 5-9, 2008 (Abstract).
Pearsall et al., "A Soluble Activin Receptor Type IIA (ACTRIIA) Acts As a Novel Bone Anabolic Agent," The Official Journal of the European Calcified Tissue Society, 34th Europena Symposium on Calcified Tissues, May (2007).
Pearsall et al., "Treatment with a Soluble Activin Type II Receptor Reverses Bone Loss in Ovariectomized Mice," Journal of Bone and Mineral Research 2006 Abstracts, 21(1):s1-s530 (2006).
Pearsall et al., "A soluble activin Type IIA receptor induces bone formation and improves skeletal integrity", PNAS, 105(19):7082-7087 (2008).
Perrien et al., "Inhibin A Is an Endocrine Stimulator of Bone Mass and Strength," Endocrinology, 148(4):1654-1665 (2007).
Phillips, "The challenge of gene therapy and DNA delivery," J. Pharm. Pharmacology, 53:1169-1174 (2001).
Pirollo et al., "Targeted Delivery of Small Interfering RNA: Approaching Effective Cancer Therapies," Cancer Res., 68(5):1247-1250 (2008).
Qi et al., "Blockade of type transforming growth factor signaling prevents liver fibrosis and dysfunction in the rat," PNAS, 96:2345-2349 (1999).
Raju, "Glycosylation in the Fc domain of IgG increases resistance to proteolytic cleavage by papain," Biochemical and Biophysical Research Communications, 341:797-803 (2006).
Rebbapragada et al., "Myostatin Signals Through a Transforming Growth Fact beta-Like Signaling Pathway To Block Adipogenesis," Molecular and Cellular Biology, 23(20):7230-7242 (2003).
"Recombinant Human Activin RIIB/Fc Chimera," R&D Systems 339-RB/CF (Aug. 27, 2003).
"Recombinant Human Activin RIIA/Fc Chimera," R&D Systems 340-R2 (Aug. 27, 2003).
Reis et al., "Activin, Inhibin and the Human Breast," Molecular and Cellular Edocrinology, 225:77-82 (2004).
Risbridger et al., "Activins and Inhibins in Endocrine and Other Tumors," Endocrine Reviews, 22(6):836-858 (2001).
Robinson et al., "Inhibins and Activins Regulate Mammary Epithelial Cell Differentiation Through Mesenchymal-epithelial Interactions," Development, 124:2701-2708 (1997).
Rodriquez et al., "Enhanced Osteoclastogenesis Causes Osteopenia in Twisted Gastrulation-Deficient Mice Through Increased BMP Signaling," J. Bone Miner. Res., 24(11):1917-1926 (2009).
Rosenzweig et al., "Cloning and characterization of a human type II receptor for bone morphogenetic proteins," PNAS, 92:7632-7636 (1995).
Ruckle et al., "Single-Dose, Randomized, Double-Blind, Placebo-Controlled Study of ACE-011 (ActRIIA-IgG1) in Postmenopausal Women," Journal of Bone and Mineral Research, vol. 24(4), pp. 744-752 (2009).
Ruzek et al. "Minimal Effects on Immune Parameters Following Chronic Anti-TGF-□ Monoclonal Antibody Administration to Normal Mice", Immunopharmacology and Immunotoxicology, 25(2):235-257 (2003).
Sakai et al., "Activin Enhances Osteoclast-Like Cell Formation in Vitro," Biochemical and Biophysical Research Communications, 195(1):39-46 (1993).
Sakai et al., "Activin Increases Bone Mass and Mechanical Strength of Lumbar Vertebrae in Aged Ovariectomized Rats," Bone, 27(1):91-96 (2000).
Sakai et al., "Activin release from bone coupled to bone resorption in organ culture of neonatal mouse calvaria," Bone, 26(3):235-240 (2000).
Sakai et al., "Involvement of Activin in the Regulation of Bone Metabolism," Molecular and Cellular Endocrinology, 180:183-188 (2001).
Sakai et al., "Local Administration of Activin Promotes Fracture Healing in the Rat Fibula Fracture Model," Bone, 25(2):191-196 (1999).
Sakai et al., "The Measurement of Activin/EDF in Mouse Serum: Evidence for Extragonadal Production", Biochecmical and Biophysical Research Communications, 188(2):921-926 (1992).
Sakai et al., "Osteogenic Activity of Activin in Young Normal Rats and Young Adult and Aged Rats after Ovarlectomy," Bone 23:(Suppl.) 467 (1998).
Sako et al., "Characterization of the Ligand Binding Functionality of the Extracellular Domain of Activin Receptor Type IIB," The Journal of Biological Chemistry, 285(27):21037-21048 (2010).
Satoh et al., "Hemodynamic changes by recombinant erythropoietin therapy in hemodialyzed patients," Hypertension, 15(3):262-266 (1990).
Schmelzer et al., "Purification and Characterization of Recombinant Human Activin B," Biochimica et Biophysica Acta, 1039(2):135-141 (1990).
Schuelke et al., "Myostatin Mutation Associated with Gross Muscle Hypertrophy in a Child," New England Journal of Medicine, 350(26):2682-2688 (2004).
Seale et al., "PRDM16 controls a brown fat/skeletal muscle switch," Nature, vol. 454(7207): 961-967 (2008).
Shao et al., "Effect of Activin A on Globin Gene Expression in Purified Human Erythroid Progenitors," Blood, 79(3):773-781 (1992).
Shao et al., "Efficient synthesis of globoside and isoglboside tetrasaccharides by using beta (1→3) N-acetylgalactosaminyltransferase/UDP-N-acetylglucosamine C4 epimerase fusion protein," Chem Commun.: 1422-1423 (2003).

(56) References Cited

OTHER PUBLICATIONS

Shapiro et al., "Side Effects of Adjuvant Treatment of Breast Cancer," New England Journal of Medicine, vol. 344: 1997-2008 (2001).
Shav-Tal et al., "The Role of Activin A in Regulation of Hemopoiesis," Stem Cells, 20:493-500 (2002).
Shi et al., "Energy Balance, Myostatin, and GILZ: Factors Regulating Adipocyte Differentiation in Belly and Bone," PPAR Research, pp. 1-12 (2007).
Shiozaki et al, "Activin A: A Commitment Factor in Erythroid Differentiation," Biochemical and Biophysical Research Communications, 242:631-635 (1998).
Shiozaki et al., "Evidence for the participation of endogenous activin A/erythroid differentiation factor in the regulation of erythropoiesis," Proc. Natl. Acad. Sci. USA, 89:1553-1556 (1992).
Shiozaki et al., "In Vivo Treatment With Erythroid Differentiation Factor (EDF / Activin A) Increases Erythroid Precursors (CFU-E and BFU-E) in Mice," Biochemical and Biophysical Research Communications, 165(3):1155-1161 (1989).
Shoji et al., "Identification and Characterization of a PDZ Protein That Interacts with Activin Type II Receptors," The Journal of Biological Chemistry, vol. 275(8): 5485-5492 (2000).
Shuto et al., "Osteoblasts Express Types I and II Activin Receptors During Early Intramembranous and Endochondral Bone Formation," Journal of Bone Mineral Research, 12(3):403-411 (1997).
Smith et al., "The analysis of doxorubicin resistance in human breast cancer cells using antibody microarrays," Mol. Cancer Therapy, vol. 5: 2115-2120 (2006).
Smith et al., The Status, Quality, and Expansion of the NIH Full-Length cDNA Project: The Mammalian Gene Collection (MGC), Genome Res., vol. 14(10b),: 2127-2127 (2004).
Song et al., "The Type II Activin Receptors Are Essential for Egg Cylinder Growth, Gastrulation, and Rostral Head Development in Mice," Development Biology, 213:157-169 (1999).
Pearsall et al., 2007, "The use of a soluble activin receptor type IIa as a novel anabolic agent for treatment of bone loss." Osteoporos Int., 18(Suppl 1):152.
Sun et al., "FSH Directly Regulates Bone Mass," Cell, 125:247-260 (2006).
Suragani et al., "4236 ACE-536, a Modified Type II Activin Receptor Increases Red Blood Cells in Vivo by Promoting Maturation of Late Stage Erythroblasts," 52nd ASH Annual Meeting and Expositions, Orange County Convention Center, Orlando, FL Dec. 4-7, 2010. (abstract).
Suragani et al., "Transforming growth factor-β superfamily ligand trap ACE-536 corrects anemia by promoting late-stage erythropoiesis," Letters, Nature Medicine, Advance Online Publication (44 pages) (2014).
Swanson et al., "Use of Biosensors to Monitor the Immune Response," Biologics, vol. 109: 71-78 (2000).
Swanson, "New Technologies for the Detection of Antibodies to Therapeutic Proteins," Immunogenicity of Therapeutics Biological Products, vol. 112: 127-133 (2003).
Tanno and Miller, "Iron Loading and Overloading due to Ineffective Erythropoiesis," Advances in Hematology, Article ID 358283, Chapter 2 (Abstract) (2010).
Thompson et al., "Structures of an ActRIIB: activin A complex reveal a novel binding mode for TGF-beta ligand: receptor interactions", EMBO 22(7):1555-1566 (2003).
Thompson et al., "Beta A versus beta B: is it merely a matter of express?," Molecular and Cellular Endocrinology, 225:9-17 (2004).
Thorpe and Swanson, "Current methods for Detecting Antibodies against Erythropoietin and Other Recombinant Proteins," Clinical and Diagnostic Laboratory Immunology, vol. 12(1): 28-39 (2005).
Tinsley et al., "Expression of full-length utrophin prevents muscular dystrophy in mdx mice," Nature Medicine, 4(12):1441-1444 (1998).
Tisdale, "Cachexia in Cancer Patients," Nat. Rev. Cancer, 2:862-871 (2002).
Tokuriki et al., "Stability effects of mutations and protein evolvability," Current Opinion in Structural Biology, 19:596-604 (2009).

Trivedi et al., "Investigational Anabolic Therapies for Osteoporosis," Expert Opin. Investig. Drugs, 19(8):995-1005 (2010).
Truksa et al., "Bone morphogenetic proteins 2, 4, and 9 stimulate murine hepcidin 1 expression independently of Hfe, transferrin receptor 2 (Tfr2), and IL-6," PNAS, vol. 103(27): 10289-10293 (2006).
Tseng et al., "New role of bone morphogenetic protein 7 in brown adipogenesis and energy expenditure," Nature: International Weekly Journal of Science (and Supplementary Information), vol. 454(7207): 1000-1004 (2008).
Tsuchida et al., "Activin isoforms signal through type I receptor serine/threonine kinase ALK7," Molecular and Cellular Endocrinology, 220:59-65 (2004).
Tu et al., "Genetic Disruption of Myostatin Reduces the Development of Proatherogenic Dyslipidemia and Atherogenic Lesions in Ldlr Null Mice," Diabetes, 58:1739-1748 (2009).
Type 2 Diabetes, PubMed Health, Diseases and Conditions, U.S. National Library of Medicine, Bethesda, MD (online), Jun. 28, 2011 [retrieved on Jun. 6, 2012). Retrieved from the Internet:<URL:http://www.ncbi.nlm.nih.gov/pubmedhealth/PMH0001356/>.
Ukkola et al., "Adiponectin: A Link Between Excess Adiposity and Associated Comorbidities?", Journal of Molecular Medicine, 80(11):696-702 (2002).
Utzschneider et al., Review: The Role of Insulin Resistance in Nonalcoholic Fatty Liver Disease, J. Clin. Endocrinol. Metab., 91(12):4753-4761 (Dec. 2006), Epub Sep. 12, 2006.
US Biological Technical Data Sheet for A0856-10A, accessed on Feb. 20, 2013.
US Biological, Activin Receptor Type IIA (RIIA) A0856-05E www.usbio.net/technicalsheet.php?item=A0856-05E dated Jun. 8, 2010.
Vajdos et al., "Comprehensive Functional Maps of the Antigen-binding Site of an Anti-ErbB2 Antibody Obtained with Shotgun Scanning mutagenesis," J. Mol. Biol., vol. 320(2): 415-428 (2002).
Vallet et al., "Activin A promotes multiple myeloma-induced osteolysis and is a promising target for myeloma bone disease," PNAS, 107(11):5124-5129 (2010).
Vidal et al., "Making sense of antisense," European Journal of Cancer, 41:2812-2818 (2005).
Wagner et al., "A Phase I/II trial of MYO-029 in Adult Subjects with Muscular Dystrophy," Ann. Neurol., 63:561-571 (2008).
Wagner et al., "Loss of Myostatin Attenuates Severity of Muscular Dystrophy in mdx Mice," Ann. Neurol., 52:832-836 (2002).
Wagner et al., "Muscle regeneration in the prolonged absence of myostatin," PNAS, 102(7):2519-2524 (2005).
Walsh et al., "Myostatin: a modulator of skeletal-muscle stems cells," Biochemical Society Transactions, 33(Pt.6):1513-1517 (2005).
Wang et al., "A Single Amino Acid Determines Lysophospholipid Specificity of the $S1P_1(EDG1)$ and $LPA_1$ (EDG2) Phospholipid Growth Factor Receptors," The Journal of Biological Chemistry, 276(52):49213-49220 (2001).
Wang et al., "GDF-3 is an adipogenic cytokine under high fat dietary condition," Biochemical and Biophysical Research Comm., 321(4):1024-1031 (2004).
Ware, "How I use hydroxyurea to treat young patients with sickle cell anemia," Blood, vol. 115(26): 5300-5311 (2010).
Ward, "An update on disordered iron metabolism and iron overload," Hematology, vol. 15(5): 311-317 (2010).
Weber et al., A slient H-bond can by mutationally activated for high-affinity interaction of BMP-2 and activin type IIB receptor, BMC Structural Biology, 7(6):1-20 (2007).
Wells, "Additivity of Mutational Effects in Proteins," Biochemistry, 29(37):8509-8517 (1990).
Welt et al., "Activin: an endocrine or panacrine agent?," European Journal of Endocrinology 139:469-471 (1998).
Wiater et al., "Inhibin is an Antagonist of Bone Morphogenetic Protein Signaling," The Journal of Biological Chemistry, 278(10):7934-7941 (2003).
Wolfman et al., "Activation of latent myostatin by the BMP-1/tolloid family of metalloproteinases," PNAS, 100(26):15842-15846 (2003).

(56) References Cited

OTHER PUBLICATIONS

Wong et al., "Validation parameters for a novel biosensor assay which simultaneously measures serum concentrations of a humanized monoclonal antibody and detects induced antibodies," Journal of Immunological Methods, vol. 209: 1-15 (1997).

Yamato et al., "Induction of apoptosis in Myeloma Cells with Activin A," Japanese Journal of Clinical Hematology; 37th Annual Meeting, Symposium 3, Apoptosis in Blood Disorders, 37:7, pp. 564-567, (2012). (translated).

Yokota et al., "Isolation and characterization of a mouse cDNA clone that expresses mast-cell growth-factor activity in monkey cells," Proc. Natl. Acad. Sci. USA, 81:1070-1074 (1984).

Yu et al., "Specific roles of activin/inhibin in human erythropoiesis in vitro." Annals New York Academy of Sciences, 20(10):1243-1246 (1991).

Yu et al., "Importance of FSH-releasing protein and inhibin in erythrodifferentiation," Nature, 330:765-767 (1987).

Zatz et al., "Serum creatine-kinase (CK) and pyruvate-kinase (PK) activities in Duchenne (DMD) as compared with Becker (BMD) muscular dystrophy," Journal of the Neurological Sciences, vol. 102: 190-196 (1991).

Zhang et al., Effects of Activin A on the Activities of the Mouse Peritoneal Macrophages, Cellular & Molecular Immunology, vol. 2(1): 63-67 (2005).

Zhao et al., "Transgenic expression of myostatin propeptide prevents diet-induced obesity and insulin resistance," Biochemical and Biophysical Research Communications, 337:248-255 (2005).

Fang et al., "Early chronic kidney disease-mineral bone disorder stimulates vascular calcification." Kidney International (Jan. 2014), vol. 85, No. 1, pp. 142-150.

International Search Report dated Feb. 11, 2016 for International Patent Application No. PCT/US2015/054674.

Written Opinion of the International Searching Authority dated Feb. 11, 2016 for International Patent Application No. PCT/US2015/054674.

Boydstun II. Chronic Kidney Disease in Adolescents. Adolesc. Med. Clin. 2005, 16(1):185-99.

Goodman et al., 2000, "Coronary-artery calcification in young adults with end-stage renal disease who are undergoing dialysis." N. Engl. J. Med., 342(20):1478-83.

Milliner et al., 1990, "Soft tissue calcification in pediatric patients with end-stage renal disease." Kidney Int. 38(5):931-6.

Agapova et al., 2016, "Ligand trap for the activin type IIA receptor protects against vascular disease and renal fibrosis in mice with chronic kidney disease." Kidney Int., 89(6),1231-1243.

Sugatani et al., 2017, "Ligand trap of the activin receptor type IIA inhibits osteoclast stimulation of bone remodeling in diabetic mice with chronic kidney disease." Kidney Int., 91(1):86-95.

Smith et al., 2015, "Long-term effects of 3 dose levels of Sotatercept compared with placebo for correction of anemia in hemodialysis subjects: interim analysis of ACE-011-REN-001", ERA EDTA Abstract FP661; https://www.abstracts2view.com/era_archive/view.php?nu=ERA15L1_971&terms=.

Fang et al., 2014, "Treatment of the CKD-MBD with a Ligand Trap for the Activin Receptor Type 2A." Journal of the American Society of Nephrology, Abstract Supplement, Kidney Week 2014; Abstract FR-PO816.

Hruska et al., 2014, "Chronic Kidney Disease (CKD) Stimulates Activin and Endothelial to Mesenchymal Transition (EnMT), which Causes Vascular Calcification and Is Inhibited by an Activin Ligand Trap." Journal of the American Society of Nephrology, Abstract Supplement, Kidney Week 2014; Abstract SA-OR063.

Malluche et al., 2014, "Sotatercept: Initial Signal-Seeking Quantitative Computed Tomography Results for Bone Mass in Hemodialysis Subjects Treated With Escalating Doses: Interim Analysis of ACE-011-REN-001." Journal of the American Society of Nephrology, Abstract Supplement, Kidney Week 2014; Abstract TH-PO602.

Malluche et al., 2015, "The role of activin signaling in the pathogenesis of renal osteodystrophy of ckd-mbd", ERA EDTA Abstract FP406; https://www.abstracts2view.com/era_archive/view.php?nu=ERA15L1_2789&terms=.

Smith et al., 2015, "Quantitative computed tomography results for bone mass and abdominal aortic vascular calcification in hemodialysis subjects treated with escalating dose levels of Sotatercept: interim analysis of ACE-011-REN-001", ERA EDTA Abstract FP661; https://www.abstracts2view.com/era_archive/view.php?nu=ERA15L1_971&terms=.

Extended Search Report dated Sep. 3, 2018 for European Pat. App. No. 15855379.2.

Abe et al., 2004, "Activin receptor signaling", Growth Factors (Chur, Switzerland), 22:105-110.

Adrago et al., 2004, "A simple vascular calcification score predicts cardiovascular risk in haemodialysis patients", Nephrol Dial Transplant, 19:1480-1488.

Agatston et al., 1990, "Quantification of coronary artery calcium using ultrafast computed tomography", J Am Coll Cardiol, 15:827-832.

Akimoto et al., 2012, "Characteristics of urinary and serum soluble klotho protein in patients with different degrees of chronic kidney disease", BMC Nephrology, Biomed Central, London, 13(1):155.

Al-Aly et al., 2007, "Aortic Msx2-Wnt calcification cascade is regulated by TNF-alpha-dependent signals in diabetic Ldlr-/- mice", Ateriosclerosis, Thrombosis, and Vascular Biology, 27:2589-2596.

Antsiferova et al., 2012, "The bright and the dark sides of activin in wound healing and cancer", J of Cell Science, 125:3929-3937.

Arbustini et al., 2002, "Plaque composition in plexogenic and thromboembolic pulmonary hypertension: the critical role of thrombotic material in pultaceous core formation", Heart, 88(2):177-182.

Attisano et al., 1992, "Novel activin receptors: distinct genes and alternative mRNA splicing generate a repertoire of serine/threonine kinase receptors", Cell 68: 97-108.

Baber et al., 2013, "Risk for recurrent coronary heart disease and all-cause mortality among individuals with chronic kidney disease compared with diabetes mellitus, metabolic syndrome, and cigarette smokers", Am Heart J, 166:373-380.

Balint et al, 1993, "Antibody engineering by parsimonious mutagenesis", Gene 137(1):109-118.

Blacher et al., 2001, "Arterial calcifications, arterial stiffness, and cardiovascular risk in end-stage renal disease", Hypertension, 38:938-948.

Burrill et al., 2007, "Multidetector computed tomographic angiography of the cardiovascular system", Postgrad Med J, 83(985):698-704.

Brown et al, 1992, "The promoter for the procyclic acidic repetitive protein (PARP) genes of Trypanosoma brucei shares features with RNA polymerase I promoters," Mol. Cell Biol. 12(6):2644-2652.

Camoretti-Mercado et al., 1998, "Expression and cytogenetic localization of the human SM22 gene (TAGLN)", Genomics, 49:452-457.

Cao et al., 2005, "Osterix, a transcription factor for osteoblast differentiation, mediates antitumor in activity murine osteosarcoma", Cancer Research, 65(4):1124-1128.

Chamorro et al., 2005, "FGF-20 and DKK1 are transcriptional targets of beta-catenin and FGF-20 is implicated in cancer and development", the EMBO Journal, 24:73-84.

Chang-Yeol and Whitman, 2001, "Nodal signals to SMADs through Cripto-dependent and Cripto-independent mechanisms," Mol. Cell 7: 949-957.

Cooley et al., 2014, "TGF-β signaling mediates endothelial-to-mesenchymal transition (EndMT) during vein graft remodeling", Science Translational Medicine, 6(227):227ra234.

Cunningham et al., 1989, "High-resolution epitope mapping of hGH-receptor interactions by alanine-scanning mutagenesis", Science, 244(4908):1081-1085.

Dalal et al., 2011, "Relationship of serum fibroblast growth factor 23 with cardiovascular disease in older community-dwelling women", European Journal of Endocrinology; 165:797-803.

Davies et al., 2003, "BMP-7 is an efficacious treatment of vascular calcification in a murine model of atherosclerosis and chronic renal failure", J Am Soc Nephrol, 14:1559-1567.

(56) References Cited

OTHER PUBLICATIONS

Davies et al., 2005, "Low turnover osteodystrophy and vascular calcification are amenable to skeletal anabolism in an animal model of chronic kidney disease and the metabolic syndrome", J Am Soc Nephrol, 16:917-928.
Dhingra et al., 2007, "Relations of serum phosphorus and calcium levels to the incidence of cardiovascular disease in the community", Arch Intern Med, 167:879-885.
Drueke TB, 2008, "Is parathyroid hormone measurement useful for the diagnosis of renal bone disease?", 73(6):674-676.
Edge et al., 1981, "Deglycosylation of glycoproteins by trifluoromethanesulfonic acid", Anal Biochem, 118(1):131.
Faul et al. 2011, "FGF23 induces left ventricular hypertrophy", J Clin Invest, 121:4393-4408.
Gonzalez-Sancho, J.M., 2004, "The Wnt antagonist DICKKOPF-1 gene is a downstream target of beta-catenin/TCF and is downregulated in human colon cancer", Oncogene; 24:1098-1103.
Gregory et al., 2004, "An Alizarin red-based assay of mineralization by adherent cells in culture: comparison with cetylpyridinium chloride extraction", Analytical Biochem., 329:77-84.
Grodberg et al., 1993, "Alanine scanning mutagenesis of human erythropoietin identifies four amino acids which are critical for biological activity", Eur J Biochem, 218(2):597-601.
Guerra et al., 2018, "Lack of GDF11 does not ameliorate erythropoiesis in beta-thalassemia and does not prevent the activity of the trap-ligand RAP-536", Blood, 132:165.
Gutierrez et al., 2008, "Fibroblast growth factor 23 and mortality among patients undergoing hemodialysis", New England Journal of Medicine, 359:584-592.
Herberth et al., 2009, "The five most commonly used intact parathyroid hormone assays are useful for screening but not for diagnosing bone turnover abnormalities in CKD-5 patients", Clin Nephrol, 72(1):5-14.
Hino et al, 2004, "Bone morphogenetic protein-3 family members and their biological functions", Front Biosci, 9:1520-1529.
Hochuli et al., 1987, "New metal chelate adsorbent selective for proteins and peptides containing neighbouring histidine residues", J. Chromatography, 411:177.
Hu et al., 2011, "Klotho deficiency causes vascular calcification in chronic kidney disease", J Am Soc Nephrol, 22:124-136.
Ike et al., 1983, "Solid phase synthesis of polynucleotides. VIII. Synthesis of mixed oligodeoxyribonucleotides by the phosphotriester solid phase method", Nucleic Acid Res, 11(2):477.
Itakura et al., 1984, "Synthesis and use of synthetic oligonucleotides", Annu Rev Biochem, 53:323.
Itakura et al., 1984, "Expression in *Escherichia coli* of a chemically synthesized gene for the hormone somatostatin", Science, 198:1056.
Jankert et al., 1991, "Rapid and efficient purification of native histidine-tagged protein expressed by recombinant vaccinia virus", PNAS USA, 88(20):8972.
Koni et al., 2001, "Conditional vascular cell adhesion molecule 1 deletion in mice: impaired lymphocyte migration to bone marrow", J of Experimental Medicine, 193:741-754.
Korkko et al., 1998, "Analysis of the COL1A1 and COL1A2 genes by PCR amplification and scanning by conformation-sensitive gel electrophoresis identifies only COL1A1 mutations in 15 patients with osteogenesis imperfecta type I: identification of common sequences of null-allele mutations", American Journal of Human Genetics, 62(1):98-110.
Kawakami et al., 2013, "Wnt signalling in kidney diseases: dual roles in renal injury and repair", J Pathol, 229:221-231.
Kozbar et al., 1983, "The production of monoclonal antibodies from human lymphocytes", Immunology Today, 4(3):72.
Kubo et al., 1999, "Osteoporosis influences the late period of fracture healing in a rat model prepared by ovariectomy and low calcium diet", Steroid Biochemistry & Molecular Biology, 68:197-202.
Lehmann et al., 2008, "Bone histomorphometry and biochemical markers of bone turnover in subjects with chronic kidney disease Stages 3-5", Clin Nephrology, 70(4):296-305.
Leonard et al., 2009, "A structural approach to skeletal fragility in chronic kidney disease", Semin. Nephrol., 29:133-143.
Lim et al. 2012, "Vascular Klotho deficiency potentiates the development of human artery calcification and mediates resistance to fibroblast growth factor 23", Circulation, 125:2243-2255.
Madura et al., 1993, "N-recognin/Ubc2 interactions in the N-end rule pathway", J. Biol. Chem., 268:12046-12054.
Mao et al., 2001, "Low-density lipoprotein receptor-related protein-5 binds to Axin and regulates the canonical Wnt signaling pathway", Mol Cell, 7:801-809.
Mathew et al., 2008, "The mechanism of phosphorus as a cardiovascular risk factor in CKD", J Am Soc Nephrol, 19:1092-1105.
Matsumara et al., 1998, "Identification of the human klotho gene and its two transcripts encoding membrane and secreted klotho protein", Biochem Biophys Res Commun, 242:626-630.
Medici et al., 2008, "Snail and Slug promote epithelial-mesenchymal transition through beta-catenin-T-cell factor-4-dependent expression of transforming growth factor-beta3", Molecular Biology of the Cell, 19(11):4875-4887.
Merx et al., 2005, "Myocardial stiffness, cardiac remodeling, and diastolic dysfunction in calcification-prone fetuin-A-deficient mice", Journal of the American Society of Nephrology, 16:3357-3364.
Myers et al., 1986, "Fine structure genetic analysis of a beta-globin promoter", Science, 232:613.
Moe et al., 2006, "Definition, evaluation, and classification of renal osteodystrophy: a position statement from Kidney Disease: Improving Global Outcomes (KDIGO)", Kidney International, 69:1945-1953.
Moore-Morris et al., 2014, "Resident fibroblast lineages mediate pressure overload-induced cardiac fibrosis", J of Clinical Investigation, 124:2921-2934.
Moran et al., 2008, "Left ventricular hypertrophy in mild and moderate reduction in kidney function determined using cardiac magnetic resonance imaging and cystatin C: the multi-ethnic study of atherosclerosis (MESA)", American Journal of Kidney Diseases, 52:839-848.
Nagashima et al., 1993, "Alanine-scanning mutagenesis of the epidermal growth factor-like domains of human thrombomodulin identifies critical residues for its cofactor activity", J. Biol. Chem., 268:2888-2892.
Niehrs et al., 2006, "Function and biological roles of the Dickkopf family of Wnt modulators", Oncogene, 25:7469-7481.
Niida et al., 2004, "DKK1, a negative regulator of Wnt signaling, is a target of the beta-catenin/TCF pathway", Oncogene, 23:8520-8526.
Okuno and Inaba, 2009, "Biochemical markers of bone turnover. New aspect. Dialysis and bone metabolic marker", Clinical Calcium, 19(8):1084-1091 (English abstract only).
Oliveira et al., 2013, "Disturbances of Wnt/β-catenin pathway and energy metabolism in early CKD: effect of phosphate binders", Nephrology Dialysis Transplantation, 28:2510-2517.
Park et al., 2012, "Associations between kidney function and subclinical cardiac abnormalities in CKD", Journal of the American Society of Nephrology, 23:1725-1734.
Pereira et al., 2009, "Patterns of FGF-23, DMP1, and MEPE expression in patients with chronic kidney disease", Bone 45:1161-1168.
Reya et al., 2003, "A role for Wnt signalling in self-renewal of haematopoietic stem cells", Nature, 423:409-414.
Rheault et al., 2004, "Mouse model of X-linked Alport syndrome", J of the Amer Soc of Nephrol, 15:1466-1474.
Rinkevich et al., 2014, "In vivo clonal analysis reveals lineage-restricted progenitor characteristics in mammalian kidney development, maintenance, and regeneration", Cell Reports, 7:1270-1283.
Roberts et al., 1992, "Directed evolution of a protein: selection of potent neutrophil elastase inhibitors displayed on M13 fusion phage", PNAS USA, 89(6):2429-2433.
Rosen et al., 2000, "Serum CTX: a new marker of bone resorption that shows treatment effect more often than other markers because of low coefficient of variability and large changes with bisphosphonate therapy", Calcif Tissue Int., 66(2):100-103.

(56) References Cited

OTHER PUBLICATIONS

Ruf et al., 1994, "Mutational mapping of functional residues in tissue factor: identification of factor VII recognition determinants in both structural modules of the predicted cytokine receptor homology domain", Biochemistry, 33(6):1565-1572.
Sabbagh et al., 2012, "Repression of osteocyte Wnt/β-catenin signaling is an early event in the progression of renal osteodystrophy", J. Bone Mineral Research, 27:1757-1772.
Schmermund et al., 2000, "Assessment of coronary calcification by electron-beam computed tomography in symptomatic patients with normal, abnormal or equivocal exercise stress test", Eur Heart J, 21(20):1674-1682.
Sharpe et al., 1999, "Inhibin B levels in plasma of the male rat from birth to adulthood: effect of experimental manipulation of Sertoli cell number", J of Anthology, 20:94-101.
Sharma et al., 2010, "Cardiac risk stratification: role of the coronary calcium score", Vasc Health Risk Management, 6:603-611.
Simone et al, 1998, "Activin regulates betaA-subunit and activin receptor messenger ribonucleic acid and cellular proliferation in activin-responsive testicular tumor cells", Endocrinology, 139:1147-1155.
Stoller et al., 2008, "Cre reporter mouse expressing a nuclear localized fusion of GFP and beta-galactosidase reveals new derivatives of Pax3-expressing precursors", Genesis (New York, Ny 2000) 46:200-204.
Surendran et al., 2002, "A role for Wnt-4 in renal fibrosis", Am J Physiol Renal Physiol, 282:F431-F441.
Surendran et al., 2005, "Wnt-dependent beta-catenin signaling is activated after unilateral ureteral obstruction, and recombinant secreted frizzled-related protein 4 alters the progression of renal fibrosis", J Am Soc Nephrol, 16:2373-2384.
Terada et al., 2003, "Expression and function of the developmental gene Wnt-4 during experimental acute renal failure in rats", Journal of the American Society of Nephrology, 14:1223-1233.
Thambiah et al., 2012, "Circulating sclerostin and Dickkopf-1 (DKK!) in predialsyis chronic kidney disease (CKD): Relationship with bone density and arterial stiffness", Calcified Tissue International, 90(6):473-480.
Toth et al., 2007, "Simultaneous visualization of multiple antigens with tyramide signal amplification using antibodies from the same speciesHistoChem & Cytochem", 55:545-554.
Towler et al., 1998, "Diet-induced diabetes activates an osteogenic gene regulatory program in the aortas of low density lipoprotein receptor-deficient mice", J of Biological Chemistry, 273:30427-30434.
Townsend et al., 2015, "Arterial stiffness and chronic kidney disease: lessons from the Chronic Renal Insufficiency Cohort study", Current Opinion in Nephrology and Hypertension, 24:47-53.
Vidal and Legrain, 1999, "Yeast forward and reverse 'n'-hybrid systems", Nucleic Acids Res., 27(4):919-929.
Wagenseil et al., 2005, "Reduced vessel elasticity alters cardiovascular structure and function in newborn mice", Circulation Research, 104:1217-1224.
Wagenseil et al., 2005, "Effects of elastin haploinsufficiency on the mechanical behavior of mouse arteries", AJP Heart and Circulatory Physiology, 289:H1209-H1217.
Wang et al., 1994, "Single amino acid insertions probe the alpha subunit of the *Escherichia coli* F1F0-ATP synthase", J. Biol. Chem., 269(4):3095-3099.
Yamada et al., 2008, "Utility of serum tartrate-resistant acid phosphatase (TRACP5b) as a bone resorption marker in patients with chronic kidney disease: independence from renal dysfunction", Clin. Endocrinolo. (Oxf)., 69(2):189-96.
Yamashita et al., 1995, "Osteogenic protein-1 binds to activin type II receptors and induces certain activin-like effects." J. Cell Biol. 130:217-226.
Zeisberg et al., 2007, "Endothelial-to-mesenchymal transition contributes to cardiac fibrosis", Nat Med, 13:952-961.
Boutet et al., 2006, "Snail activation disrupts tissue homeostasis and induces fibrosis in the adult kidney", Embo J, 25(23):5603-5613.
Casalena et al., 2012, "Transforming growth factor-β, bioenergetics, and mitochondria in renal disease", Semin Nephrol., 32(3):295-303.
Claes et al., 2013, "Sclerostin: another vascular calcification inhibitor?", J. Clin. Endocrinol. Metab., 98(8):3221-3228.
Dong et al., 2010, "Blockade of the Ras-extracellular signal-regulated kinase 1/2 pathway is involved in smooth muscle 22 alpha-mediated suppression of vascular smooth muscle cell proliferation and neointima hyperplasia", Arterioscler Throm Vase Biol, 30(4):683-691.
Fang et al., 2014, "CKD-induced wingless/integration1 inhibitors and phosphorus cause the CKD-mineral and bone disorder", J Am Soc Nephrol, 25(8):1760-1773.
Huang et al., 2008, "Myocardin regulates expression of contractile genes in smooth muscle cells and is required for closure of the ductus arteriosus in mice", J Clin Invest, 118(2):515-525.
Kim et al., 2011, "A novel biomarker of coronary atherosclerosis: serum DKK1 concentration correlates with coronary artery calcification and atherosclerotic plaques", J. Korean Med. Sci., vol. 26:1178-1184.
Lan et al., 2012, "Smads as therapeutic targets for chronic kidney disease", Kidney Res Clin Prac, 31(1):4-11.
Lang et al., 2013, "Vascular calcification—is aldosterone a culprit?", Nephrol Dial Transplant, 28(5):1080-1084.
Mang et al., 2013, "ActA and ActRIIA expression in Smads signaling pathway in ischemia brain injury", Journal of Apoplexy and Nervous Diseases, 30(1): 15-17 (English abstract).
Ning et al., 2011, "Expression Pattern of Activin Receptor IIA in Atherosclerotic Plaque of ApoE-/-Mice", Medical Recapitulate, 17(10):1573-1575 (English abstract).
Sardiwal et al., 2013, "Bone alkaline phosphatase in CKD-Mineral bone disorder", Am. J. Kidney Dis., 62(4):810-822.
Sarnak et al., 2003, "Kidney disease as a risk factor for development of cardiovascular disease: a statement from the American Heart Association Councils on Kidney in Cardiovascular Disease, High Blood Pressure Research, Clinical Cardiology, and Epidemiology and Prevention", Circulation, 108(17):2154-2169.
Valenta et al., 2003, "HMG box transcription factor TCF-4's interaction with CtBP1 controls the expression of the Wnt target Axin2/Conductin in human embryonic kidney cells", Nucleic Acids Res., 31(9):2369-2380.
Zhang et al., 2012, "Therapeutical effect of atorvastatin on artheroscleros mediated by ActRIIA", Journal of Jilin University: Med Ed, 38(1):54-57 (English abstract).
Zheng et al., 2012, "A pilot trial assessing urinary gene expression profiling with an mRNA array for diabetic nephropathy", PLoS One, 7(5): e34824.
Chaykovska et al., 2013, "Effects of telmisartan and linagliptin when used in combination on blood pressure and oxidative stress in rats with 2-kidney-1-clip hypertension", J Hypertens, 31(11):2290-2298.
Lu et al., 2014, "Vascular calcification and renal bone disorders", Scientific World Journal.
Przedlacki et al., 2002, "Cross-linked C-terminal telopeptide of type I collagen in serum before and after treatment with alfacalcidol and calcium carbonate in early and moderate chronic renal failure", Neprhon, 92(2):304-308.
Stein et al., 2001, "Effects of statins on biomarkers of bone metabolism: a randomised trial", Nutr Metab Cardiovasc Disc, 11(2):84-87.
Wang et al., 2008, "Radial artery calcification in end-stage renal disease patients is associated with deposition of osteopontin and diminished expression of alpha-smooth muscle actin" Nephrology, 13(5):367-375.
Mathew et al., 2007, "Reversal of the adynamic bone disorder and decreased vascular calcification in chronic kidney disease by sevelamer carbonate therapy", J Am Soc Nephrol, 18:122-130.
Ohnuki et al., 2012, "Expression of transcription factor Snail and tubulointerstital fibrosis in progressive nephropathy," Journal of Nephrology, 25(2):233-239.

* cited by examiner

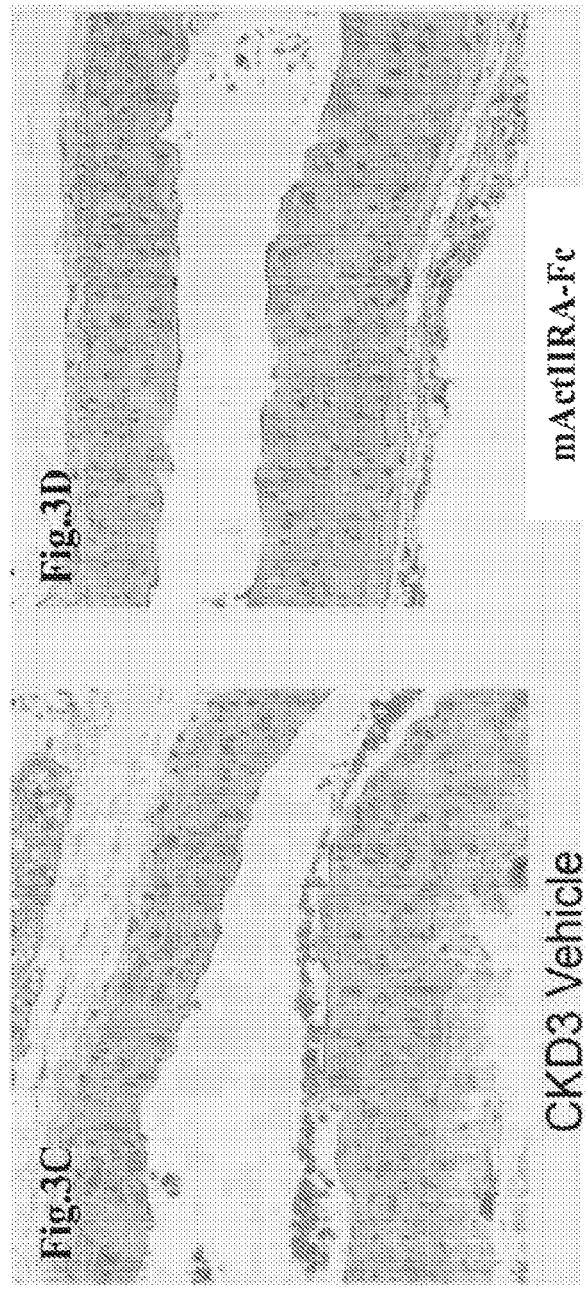

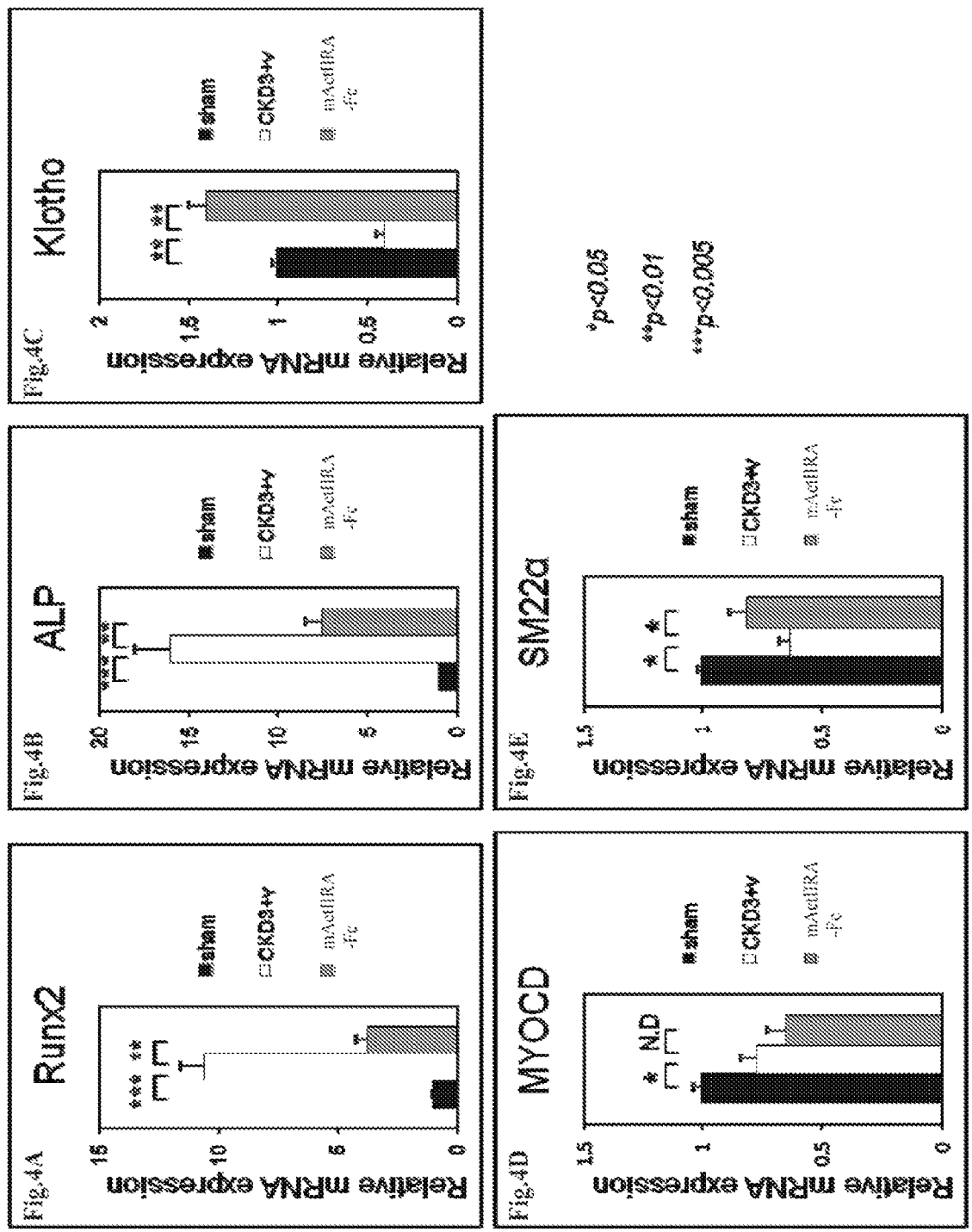

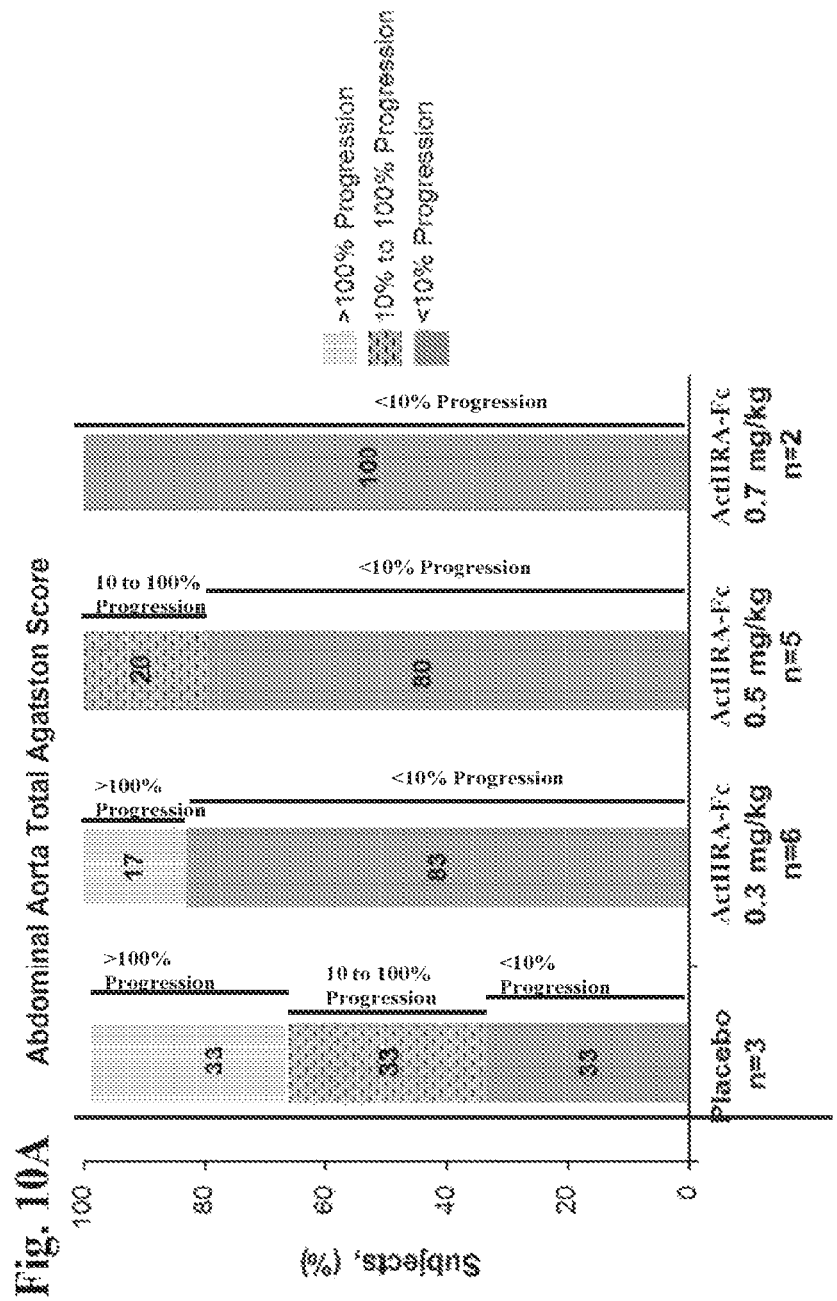

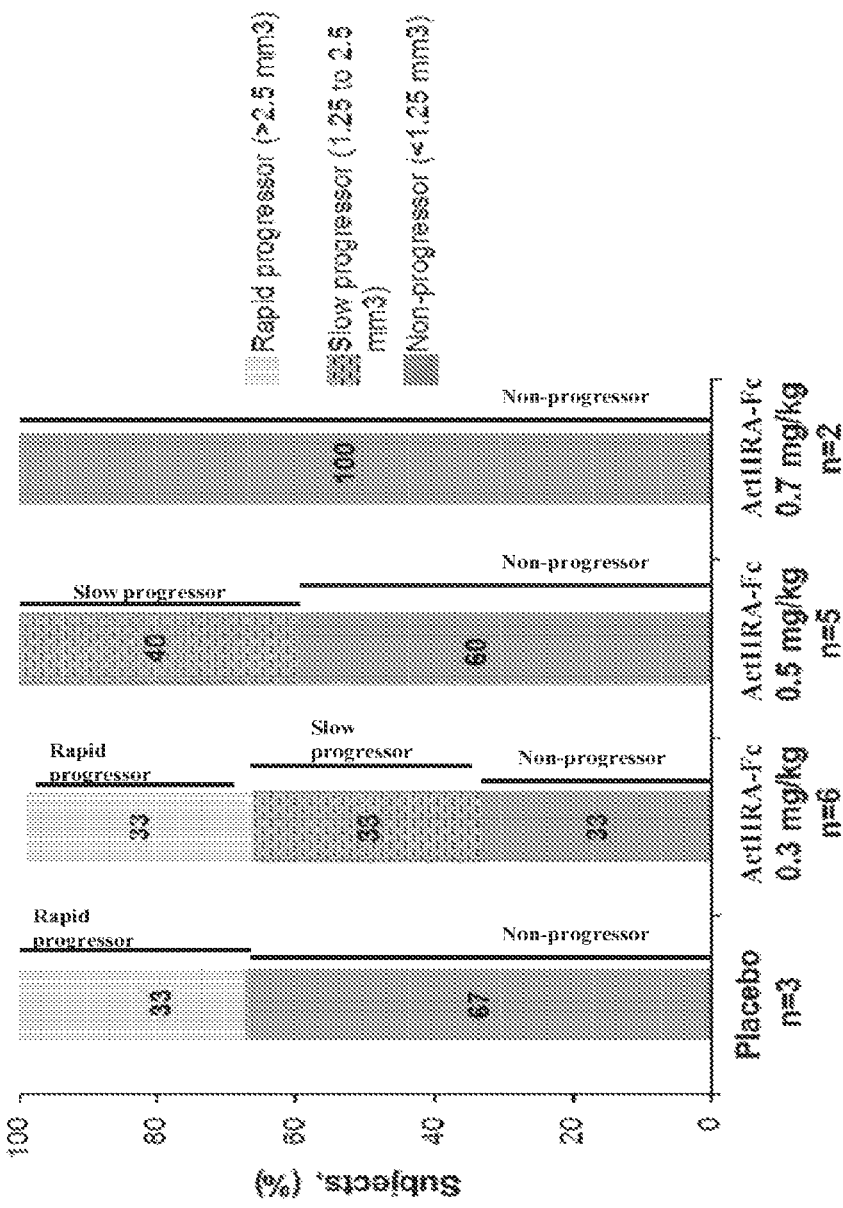

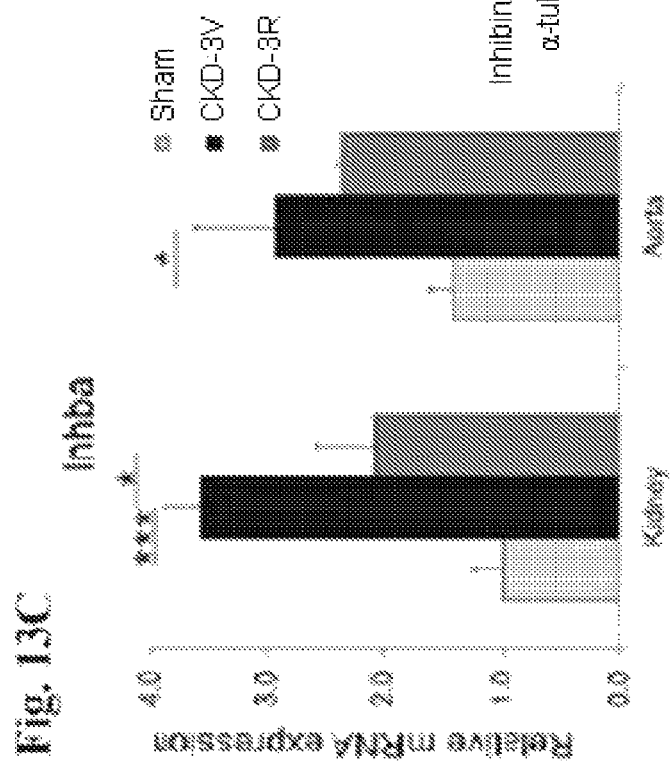
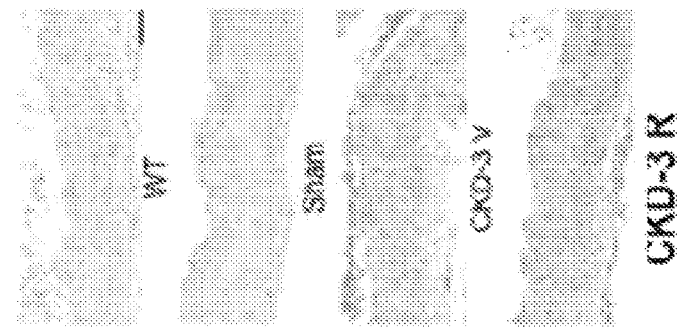

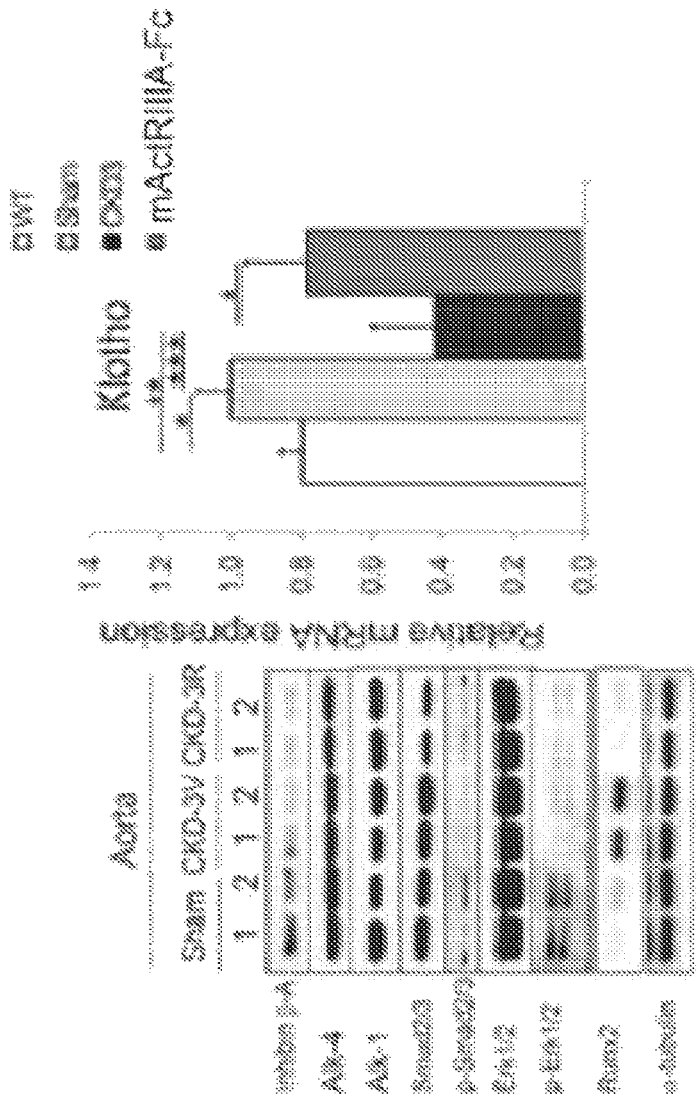

1=sham; 2=CKD-3 V; 3=CKD-3R

Fig. 26 A
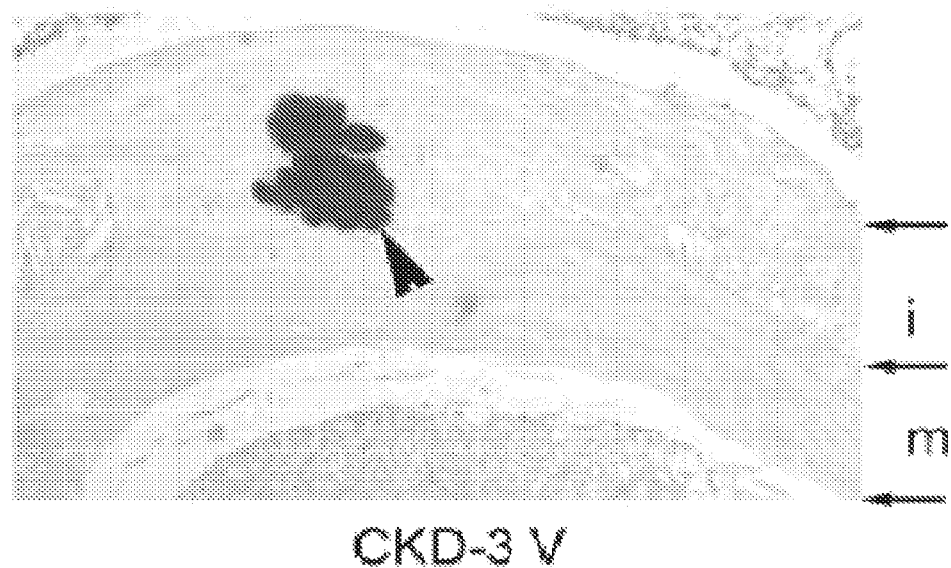
CKD-3 V
CKD-3 RAP-011
Fig. 26 B

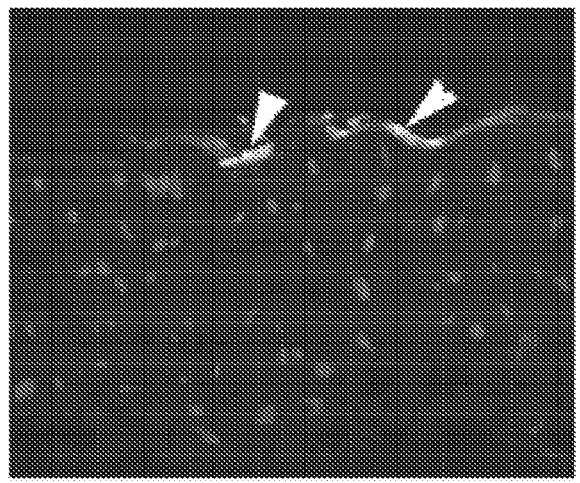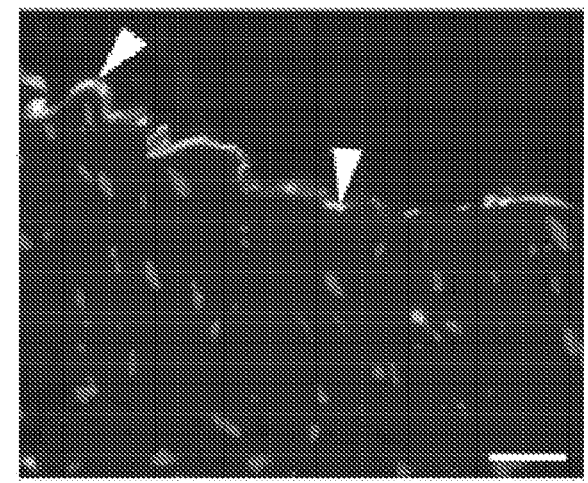
Fig. 28A  Fig. 28B
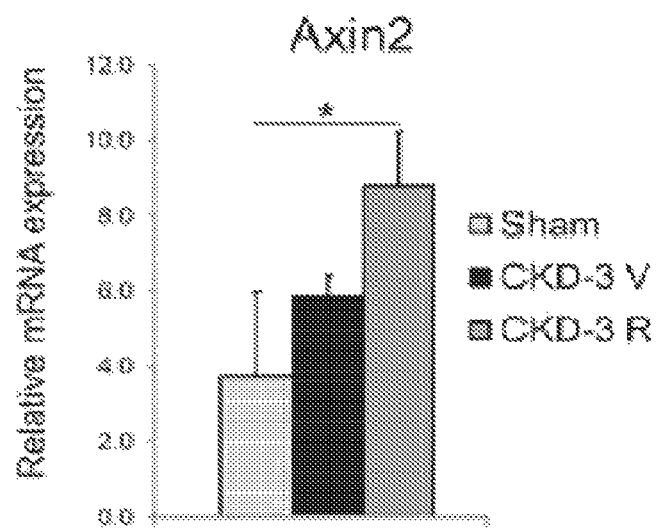
Fig. 28C

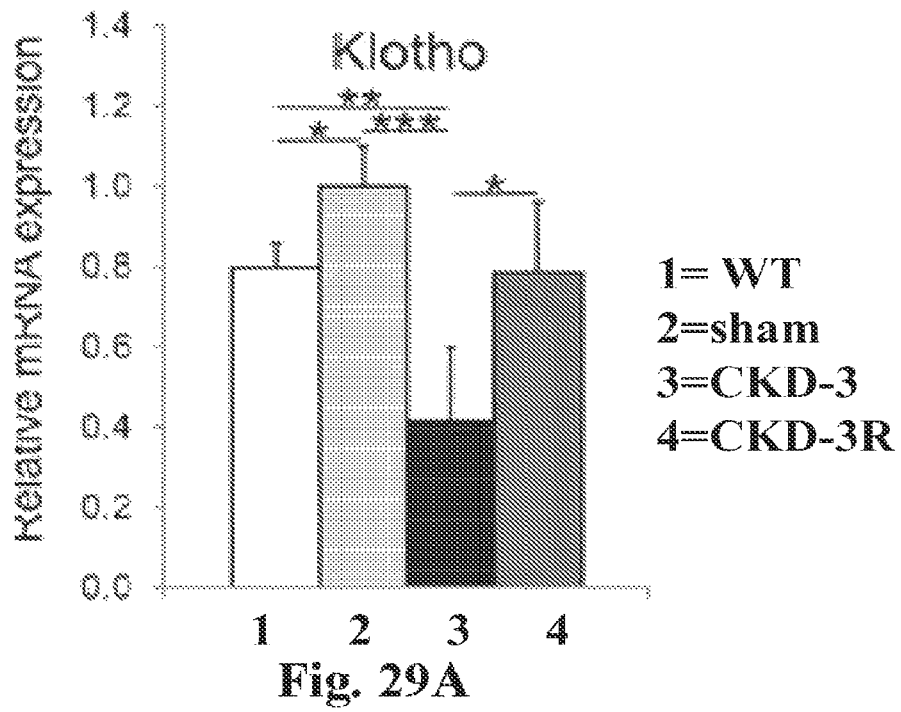
Fig. 29A
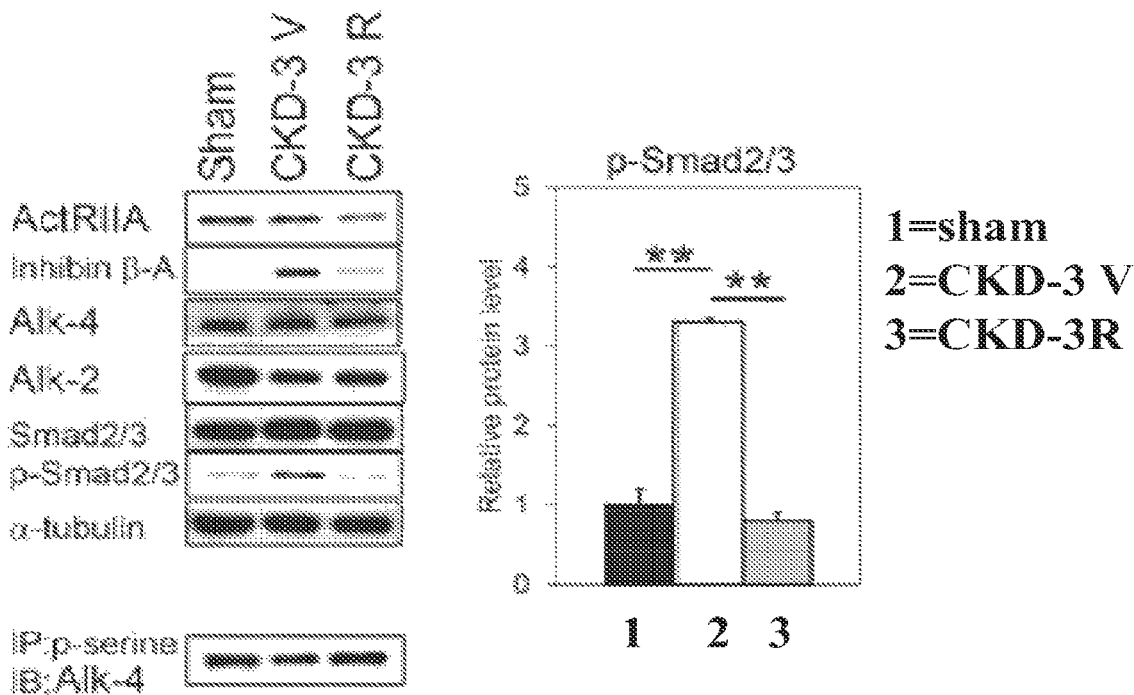
Fig. 29B
Fig. 29C

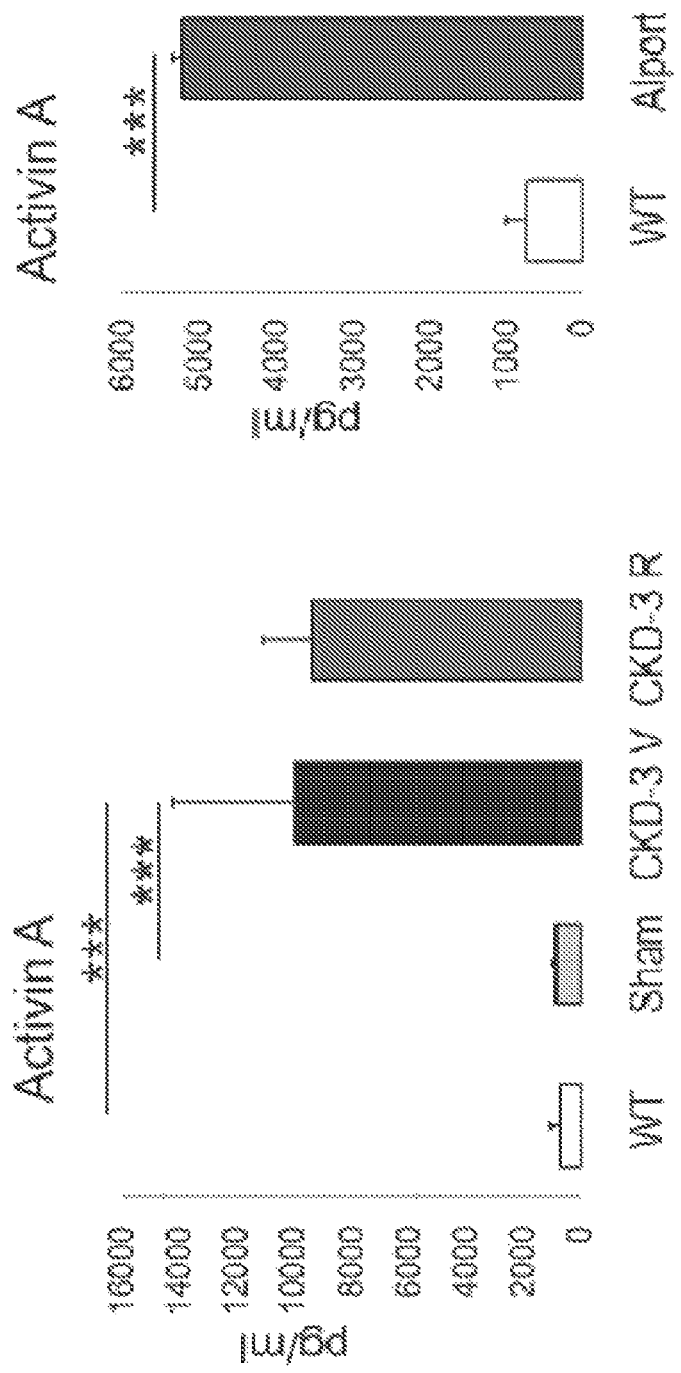

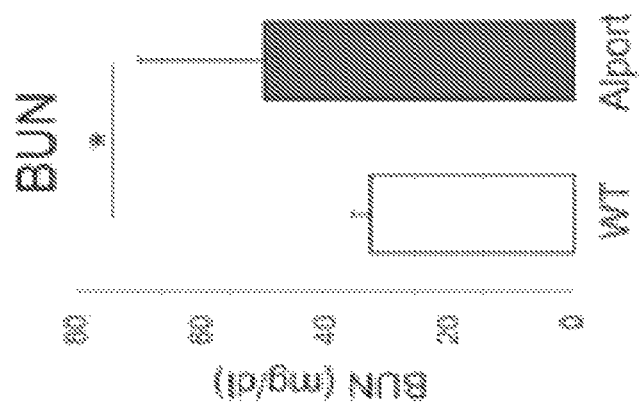
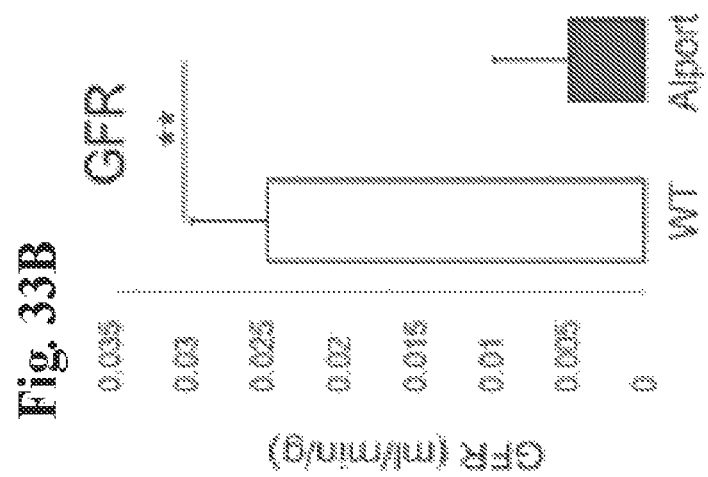
Fig. 33B

TREATMENT OF CARDIOVASCULAR DISEASE USING ACTRII LIGAND TRAPS

CROSS-REFERENCES TO RELATED APPLICATIONS

This application is a national stage of International Patent Application No. PCT/US2015/054674, filed Oct. 8, 2015, which claims the benefit of priority of U.S. Provisional Patent Application No. 62/062,021, filed Oct. 9, 2014; U.S. Provisional Patent Application No. 62/078,321, filed Nov. 11, 2014; U.S. Provisional Patent Application No. 62/103,515, filed Jan. 14, 2015; U.S. Provisional Patent Application No. 62/167,052, filed May 27, 2015; and U.S. Provisional Patent Application No. 62/170,015, filed Jun. 2, 2015, the entire contents of each of which are incorporated herein by reference and for all purposes.

GOVERNMENT LICENSE RIGHTS

This invention was made with government support under grant numbers DK070790 and DK089137 awarded by National Institutes of Health. The government has certain rights in the invention.

SEQUENCE LISTING

The present application incorporates by reference a Sequence Listing submitted as file name 12827_934_999_SeqListing.txt, of size 206 kilobytes, which was created on Feb. 14, 2018. The Sequence Listing is incorporated herein by reference in its entirety and for all purposes.

FIELD

Provided herein are methods of treating and/or preventing cardiovascular disease, vascular calcification, cardiovascular disease associated with and/or resulting from vascular calcification, and/or cardiovascular disease associated with and/or resulting from renal disease in a subject, comprising administering to the subject an activin type II receptor signaling inhibitor (ActRII signaling inhibitor, e.g., an activin ligand trap). More specifically, provided herein are methods for selecting subjects for the treatment of cardiovascular disease, vascular calcification, elevated levels of arterial stiffness, left ventricular hypertrophy, cardiovascular disease associated with and/or resulting from vascular calcification, cardiovascular disease associated with and/or resulting from elevated levels of arterial stiffness, cardiovascular disease associated with and/or resulting from left ventricular hypertrophy, and/or cardiovascular disease associated with and/or resulting from renal disease, by using the level and/or activity of one or more biomarkers, in particular, snail homolog 1 (Snai1), phosphosmad2, phosphosmad3, urinary protein, dickkopf homolog 1 (Dkk1), collagen type 1 alpha 1 (Col1a1), activin (e.g., free activin), runt-related transcription factor 2 (Runx2), alkaline phosphatase (Alp), bone-specific alkaline phosphatase (BSAP), Osterix, C-terminal type 1 collagen telopeptide (CTX), Klotho, alpha-smooth muscle action (alpha-SMA), myocardin (MYOCD), axis inhibition protein 2 (Axin2), and/or smooth muscle protein 22-alpha (Sm22-alpha), as an indicator(s) of responsiveness of a subject to the treatment, efficacy of the treatment, or appropriate dosage for the treatment with an activin type II receptor (ActRII) signaling inhibitor. Provided herein are methods of reducing bone resorption in a subject, comprising administering to the subject an ActRII signaling inhibitor. More specifically, provided herein are methods for selecting subjects for the reduction of bone resorption, by using the level and/or activity of one or more biomarkers, in particular, Snai1, phosphosmad2, phosphosmad3, urinary protein, Dkk1, col1a1, activin (e.g., free activin), Runx2, Alp, BSAP, Osterix, CTX, Klotho, alpha-SMA, MYOCD, and/or Sm22-alpha, as an indicator(s) of responsiveness of a subject to the treatment, efficacy of the treatment, or appropriate dosage for the treatment with an ActRII signaling inhibitor.

BACKGROUND

A common complication of renal disease involving anemia is vascular calcification, which leads, in many cases, to cardiovascular disease. In renal subjects, atherosclerosis and the resulting cardiovascular disease can result in significant mortality apart from mortality associated with renal disease per se. As such, there is a continued need for the discovery and development of new drugs and treatment and/or prevention methods for cardiovascular disease in renal subjects. Additionally, because renal subjects frequently suffer from anemia, it would be beneficial to treat the anemia and the attendant cardiovascular disease with a single therapeutic, a capability not possessed by currently-used erythropoiesis-stimulating agents (ESAs) such as erythropoictin.

Two related type II receptors, ActRIIA and ActRIIB, have been identified as the type II receptors for activins (Mathews and Vale, 1991, Cell 65:973-982; Attisano et al., 1992, Cell 68: 97-108). Besides activins. ActRIIA and ActRIIB can biochemically interact with several other TGF-beta family proteins, including BMP7, Nodal, GDF8, and GDF11 (Yamashita et al., 1995, J. Cell Biol. 130:217-226; Lee and McPherron, 2001, Proc. Natl. Acad. Sci. 98:9306-9311; Yeo and Whitman, 2001, Mol. Cell 7: 949-957; Oh et al., 2002, Genes Dev. 16:2749-54). ALK4 is the primary type I receptor for activins, particularly for activin A, and ALK-7 may serve as a receptor for activins as well, particularly for activin B.

An activin ligand trap, consisting of a humanized fusion-protein consisting of the extracellular domain of activin-receptor type IIA (ActRIIA) and the human IgG1 Fc (referred to herein as ActRIIA-hFc or "Sotatercept"; SEQ ID NO: 7), is currently being evaluated in phase II clinical trials for treatment of subjects with anemia and bone disorders associated with end-stage renal disease (ESRD) as well as for those subjects with beta-thalassemia. In healthy postmenopausal women, ActRIIA-hFc was shown to significantly increase hematocrit (Hct) and hemoglobin (Hgb) as well as bone mineral density.

SUMMARY

Provided herein are methods for treating and/or preventing vascular calcification in a subject, comprising administering to the subject a pharmaceutically effective dose of an activin receptor type II (ActRII) signaling inhibitor (e.g., an activin ligand trap), wherein the subject has: (a) elevated levels of Runx2 as compared to levels of Runx2 in a reference population; (b) elevated levels of Alp as compared to levels of Alp in a reference population; (c) elevated levels of Snai1 as compared to levels of Snai1 in a reference population; (d) elevated levels of phosphosmad2 as compared to levels of phosphosmad2 in a reference population; (e) elevated levels of Dkk1 as compared to levels of Dkk1 in a reference population; (f) elevated levels of col1a1 as compared to levels of col1a1 in a reference population; (g)

elevated levels of activin (e.g., free activin) as compared to levels of activin in a reference population; (h) elevated levels of BSAP as compared to levels of BSAP in a reference population; (i) elevated levels of Osterix as compared to levels of Osterix in a reference population; (j) elevated levels of CTX as compared to levels of CTX in a reference population; (k) decreased levels of Klotho as compared to levels of Klotho in a reference population; (l) decreased levels of alpha-SMA as compared to levels of alpha-SMA in a reference population; (m) decreased levels of MYOCD as compared to levels of MYOCD in a reference population; (n) decreased levels of Sm22-alpha as compared to levels of Sm22-alpha in a reference population; (o) elevated levels of phosphosmad3 as compared to levels of phosphosmad3 in a reference population; (p) elevated levels of urinary protein as compared to levels of urinary protein in a reference population; and/or (q) decreased levels of activin receptor type 2A (ActRIIA) as compared to levels of ActRIIA in a reference population. See, e.g., Section 8.6 for a description of the reference population.

Provided herein are methods for treating and/or preventing cardiovascular disease in a subject, comprising administering to the subject a pharmaceutically effective dose of an activin receptor type II (ActRII) signaling inhibitor (e.g., an activin ligand trap), wherein the subject has: (a) elevated levels of Runx2 as compared to levels of Runx2 in a reference population; (b) elevated levels of Alp as compared to levels of Alp in a reference population; (c) elevated levels of Snai1 as compared to levels of Snai1 in a reference population; (d) elevated levels of phosphosmad2 as compared to levels of phosphosmad2 in a reference population; (e) elevated levels of Dkk1 as compared to levels of Dkk1 in a reference population; (f) elevated levels of col1a1 as compared to levels of col1a1 in a reference population; (g) elevated levels of activin (e.g., free activin) as compared to levels of activin in a reference population; (h) elevated levels of BSAP as compared to levels of BSAP in a reference population; (i) elevated levels of Osterix as compared to levels of Osterix in a reference population; (j) elevated levels of CTX as compared to levels of CTX in a reference population; (k) decreased levels of Klotho as compared to levels of Klotho in a reference population; (l) decreased levels of alpha-SMA as compared to levels of alpha-SMA in a reference population; (m) decreased levels of MYOCD as compared to levels of MYOCD in a reference population; (n) decreased levels of Sm22-alpha as compared to levels of Sm22-alpha in a reference population; (o) elevated levels of phosphosmad3 as compared to levels of phosphosmad3 in a reference population; (p) elevated levels of urinary protein as compared to levels of urinary protein in a reference population; and/or (q) decreased levels of ActRIIA as compared to levels of ActRIIA in a reference population.

Provided herein are methods for treating and/or preventing cardiovascular disease in a subject, comprising administering to the subject a pharmaceutically effective dose of an activin receptor type II (ActRII) signaling inhibitor (e.g., an activin ligand trap), wherein the subject has: (a) elevated levels of Runx2 as compared to levels of Runx2 in a reference population; (b) elevated levels of Alp as compared to levels of Alp in a reference population; (c) elevated levels of Snai1 as compared to levels of Snai1 in a reference population; (d) elevated levels of phosphosmad2 as compared to levels of phosphosmad2 in a reference population; (e) elevated levels of Dkk1 as compared to levels of Dkk1 in a reference population; (f) elevated levels of col1a1 as compared to levels of col1a1 in a reference population: (g) elevated levels of activin (e.g., free activin) as compared to levels of activin in a reference population; (h) elevated levels of BSAP as compared to levels of BSAP in a reference population: (i) elevated levels of Osterix as compared to levels of Osterix in a reference population; (j) elevated levels of CTX as compared to levels of CTX in a reference population; (k) decreased levels of Klotho as compared to levels of Klotho in a reference population; (l) decreased levels of alpha-SMA as compared to levels of alpha-SMA in a reference population; (m) decreased levels of MYOCD as compared to levels of MYOCD in a reference population: (n) decreased levels of Sm22-alpha as compared to levels of Sm22-alpha in a reference population; (o) elevated levels of phosphosmad3 as compared to levels of phosphosmad3 in a reference population; (p) elevated levels of urinary protein as compared to levels of urinary protein in a reference population; and/or (q) decreased levels of ActRIIA as compared to levels of ActRIIA in a reference population, and wherein the cardiovascular disease is associated with and/or results from vascular calcification.

Provided herein are methods for treating and/or preventing cardiovascular disease in a subject, comprising administering to the subject a pharmaceutically effective dose of an activin receptor type II (ActRII) signaling inhibitor (e.g., an activin ligand trap), wherein the subject has: (a) elevated levels of Runx2 as compared to levels of Runx2 in a reference population; (b) elevated levels of Alp as compared to levels of Alp in a reference population; (c) elevated levels of Snai1 as compared to levels of Snai1 in a reference population; (d) elevated levels of phosphosmad2 as compared to levels of phosphosmad2 in a reference population; (e) elevated levels of Dkk1 as compared to levels of Dkk1 in a reference population; (f) elevated levels of col1a1 as compared to levels of col1a1 in a reference population; (g) elevated levels of activin (e.g., free activin) as compared to levels of activin in a reference population; (h) elevated levels of BSAP as compared to levels of BSAP in a reference population; (i) elevated levels of Osterix as compared to levels of Osterix in a reference population; (j) elevated levels of CTX as compared to levels of CTX in a reference population; (k) decreased levels of Klotho as compared to levels of Klotho in a reference population; (l) decreased levels of alpha-SMA as compared to levels of alpha-SMA in a reference population; (m) decreased levels of MYOCD as compared to levels of MYOCD in a reference population: (n) decreased levels of Sm22-alpha as compared to levels of Sm22-alpha in a reference population; (o) elevated levels of phosphosmad3 as compared to levels of phosphosmad3 in a reference population; (p) elevated levels of urinary protein as compared to levels of urinary protein in a reference population; and/or (q) decreased levels of ActRIIA as compared to levels of ActRIIA in a reference population, and wherein the cardiovascular disease is associated with and/or results from renal disease.

Provided herein are methods for reducing bone resorption in a subject, comprising administering to the subject a pharmaceutically effective dose of an activin receptor type II (ActRII) signaling inhibitor (e.g., an activin ligand trap), wherein the subject has: (a) elevated levels of Runx2 as compared to levels of Runx2 in a reference population; (b) elevated levels of Alp as compared to levels of Alp in a reference population; (c) elevated levels of Snai1 as compared to levels of Snai1 in a reference population: (d) elevated levels of phosphosmad2 as compared to levels of phosphosmad2 in a reference population; (e) elevated levels of Dkk1 as compared to levels of Dkk1 in a reference population; (f) elevated levels of col1a1 as compared to levels of col1a1 in a reference population; (g) elevated levels of activin (e.g., free activin) as compared to levels of activin in a reference population; (h) elevated levels of BSAP as compared to levels of BSAP in a reference population; (i) elevated levels of Osterix as compared to levels of Osterix in a reference population; (j) elevated levels of CTX as compared to levels of CTX in a reference population; (k) decreased levels of Klotho as compared to levels of Klotho in a reference population; (l) decreased levels of alpha-SMA as compared to levels of alpha-SMA in a reference population; (m) decreased levels of MYOCD as compared to levels of MYOCD in a reference population; (n) decreased levels of Sm22-alpha as compared to levels of Sm22-alpha in a reference population; (o) elevated levels of phosphosmad3 as compared to levels of phosphosmad3 in a reference population; (p) elevated levels of urinary protein as compared to levels of urinary protein in a reference population; and/or (q) decreased levels of ActRIIA as compared to levels of ActRIIA in a reference population.

Provided herein are methods for treating and/or preventing arterial stiffness in a subject, comprising administering to the subject a pharmaceutically effective dose of an activin receptor type II (ActRII) signaling inhibitor (e.g., an activin ligand trap), wherein the subject has: (a) elevated levels of Runx2 as compared to levels of Runx2 in a reference population; (b) elevated levels of Alp as compared to levels of Alp in a reference population; (c) elevated levels of Snai1 as compared to levels of Snai1 in a reference population; (d) elevated levels of phosphosmad2 as compared to levels of phosphosmad2 in a reference population; (e) elevated levels of Dkk1 as compared to levels of Dkk1 in a reference population; (f) elevated levels of col1a1 as compared to levels of col1a1 in a reference population; (g) elevated levels of activin (e.g., free activin) as compared to levels of activin in a reference population; (h) elevated levels of BSAP as compared to levels of BSAP in a reference population; (i) elevated levels of Osterix as compared to levels of Osterix in a reference population: (j) elevated levels of CTX as compared to levels of CTX in a reference population; (k) decreased levels of Klotho as compared to levels of Klotho in a reference population; (l) decreased levels of alpha-SMA as compared to levels of alpha-SMA in a reference population; (m) decreased levels of MYOCD as compared to levels of MYOCD in a reference population; (n) decreased levels of Sm22-alpha as compared to levels of Sm22-alpha in a reference population; (o) elevated levels of phosphosmad3 as compared to levels of phosphosmad3 in a reference population; (p) elevated levels of urinary protein as compared to levels of urinary protein in a reference population; and/or (q) decreased levels of ActRIIA as compared to levels of ActRIIA in a reference population.

Provided herein are methods for treating and/or preventing left ventricular hypertrophy in a subject, comprising administering to the subject a pharmaceutically effective dose of an activin receptor type II (ActRII) signaling inhibitor (e.g., an activin ligand trap), wherein the subject has: (a) elevated levels of Runx2 as compared to levels of Runx2 in a reference population; (b) elevated levels of Alp as compared to levels of Alp in a reference population: (c) elevated levels of Snai1 as compared to levels of Snai1 in a reference population; (d) elevated levels of phosphosmad2 as compared to phosphosmad2 in a reference population; (e) elevated levels of Dkk1 as compared to levels of Dkk1 in a reference population; (f) elevated levels of col1a1 as compared to levels of col1a1 in a reference population; (g) elevated levels of activin (e.g., free activin) as compared to levels of activin in a reference population; (h) elevated levels of BSAP as compared to levels of BSAP in a reference population: (i) elevated levels of Osterix as compared to levels of Osterix in a reference population; (j) elevated levels of CTX as compared to levels of CTX in a reference population; (k) decreased levels of Klotho as compared to levels of Klotho in a reference population; (l) decreased levels of alpha-SMA as compared to levels of alpha-SMA in a reference population; (m) decreased levels of MYOCD as compared to levels of MYOCD in a reference population; (n) decreased levels of Sm22-alpha as compared to levels of Sm22-alpha in a reference population; (o) elevated levels of phosphosmad3 as compared to levels of phosphosmad3 in a reference population; (p) elevated levels of urinary protein as compared to levels of urinary protein in a reference population: and/or (q) decreased levels of ActRIIA as compared to levels of ActRIIA in a reference population.

In certain embodiments, the pharmaceutically effective dose of the ActRII signaling inhibitor is about 15 mg, about 30 mg, about 45 mg, about 60 mg, about 75 mg, about 90 mg, or about 1 g, or about 0.1 mg/kg, about 0.13 mg/kg, about 0.2 mg/kg, about 0.26 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, or about 1.5 mg/kg. In certain embodiments, the pharmaceutically effective dose of the ActRII signaling inhibitor is about 0.1 mg/kg. In certain embodiments, the pharmaceutically effective dose of the ActRII signaling inhibitor is about 0.3 mg/kg. In certain embodiments, the pharmaceutically effective dose of the ActRII signaling inhibitor is about 0.5 mg/kg. In certain embodiments, the pharmaceutically effective dose of the ActRII signaling inhibitor is about 0.7 mg/kg.

In certain embodiments, the pharmaceutically effective dose is administered via injection. In certain embodiments, the pharmaceutically effective dose is administered (i) once every 28 days; or (ii) once every 42 days. In certain embodiments, the pharmaceutically effective dose is administered once every 14 days. In certain embodiments, the pharmaceutically effective dose is administered once every 21 days. In certain embodiments, the pharmaceutically effective dose is administered continuously and/or indefinitely.

In certain embodiments, the elevated levels of Snai1, phosphosmad2, Dkk1, col1a1, activin (e.g., free activin), Runx2, Alp, BSAP, CTX, phosphosmad3, urinary protein and/or Osterix, are about 10%, 20%, 25%, 30%, 40%, 50%, 60%, 70%, 75%, 80% 90%, 100%, 200%, or 500% greater than the levels of Snai1, phosphosmad2, Dkk1, col1a1, activin (e.g., free activin), Runx2, Alp, BSAP, CTX, phosphosmad3, urinary protein, and/or Osterix, respectively, in the reference population.

In certain embodiments, the elevated levels of Snai1, phosphosmad2, Dkk1, col1a1, activin (e.g., free activin), Runx2, Alp, BSAP, CTX, phosphosmad3, urinary protein, and/or Osterix are equal to or about 10%, 20%, 25%, 30%, 40%, 50%, 60%, 70%, 75%, 80%, 90%, 100%, 200%, or 500% greater than the levels of Snai1, phosphosmad2, Dkk1, col1a1, activin (e.g., free activin), Runx2, Alp, BSAP, CTX, phosphosmad3, urinary protein, and/or Osterix, respectively, in the top 10%, top 5%, top 4%, top 3%, top 2%, or top 1% in the reference population.

In certain embodiments, the decreased levels of Klotho, alpha-SMA, MYOCD, ActRIIA, Axin2, and/or Sm22-alpha are about 10%, 20%, 25%, 30%, 40%, 50%, 60%, 70%, 75%, 80%, 90%, or 100% less than the levels of Klotho, alpha-SMA, MYOCD, ActRIIA, Axin2, and/or Sm22-alpha, respectively, in the reference population.

In certain embodiments, the decreased levels of Klotho, alpha-SMA, MYOCD, ActRIIA, Axin2, and/or Sm22-alpha are equal to or about 10%, 20%, 25%, 30%, 40%, 50%, 60%, 70%, 75%, 80%, 90%, or 100% less than the levels of Klotho, alpha-SMA, MYOCD, ActRIIA, Axin2, and/or Sm22-alpha, respectively, in the bottom 10%, bottom 5%, bottom 4%, bottom 3%, bottom 2%, or bottom 1% in the reference population.

Provided herein are methods for treating and/or preventing vascular calcification in a subject, wherein the method comprises: (a) administering to the subject an initial dose of an ActRII signaling inhibitor to the subject; (b) taking a first measurement of the level of Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha in the subject; (c) after a period of time, taking a second measurement of the level of Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha in the subject; and (d) administering to the subject an adjusted dose of the activin receptor type II signaling inhibitor. In certain embodiments, the adjusted dose is based on the detected change between the first measurement and the second measurement. In certain embodiments, the dose is adjusted as described in Section 8.3.4.

Provided herein are methods for treating and/or preventing cardiovascular disease in a subject, wherein the method comprises: (a) administering to the subject an initial dose of an ActRII signaling inhibitor to the subject; (b) taking a first measurement of the level of Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha in the subject; (c) after a period of time, taking a second measurement of the level of Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha in the subject; and (d) administering to the subject an adjusted dose of the activin receptor type II signaling inhibitor. In certain embodiments, the adjusted dose is based on the detected change between the first measurement and the second measurement. In certain embodiments, the dose is adjusted as described in Section 8.3.4.

Provided herein are methods for treating and/or preventing cardiovascular disease in a subject, wherein the method comprises: (a) administering to the subject an initial dose of an ActRII signaling inhibitor to the subject; (b) taking a first measurement of the level of Snai1, phosphosmad2, Dkk1, col1a1, activin (e.g., free activin), Runx2. Alp, BSAP, CTX, Osterix, Klotho, alpha-SMA, MYOCD, phosphosmad3, urinary protein, ActRIIA, Axin2, and/or Sm22-alpha in the subject; (c) after a period of time, taking a second measurement of the level of Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha in the subject; and (d) administering to the subject an adjusted dose of the activin receptor type II signaling inhibitor; and wherein the cardiovascular disease is associated with and/or results from vascular calcification. In certain embodiments, the adjusted dose is based on the detected change between the first measurement and the second measurement. In certain embodiments, the dose is adjusted as described in Section 8.3.4.

Provided herein are methods for treating and/or preventing cardiovascular disease in a subject, wherein the method comprises: (a) administering to the subject an initial dose of an ActRII signaling inhibitor to the subject; (b) taking a first measurement of the level of Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha in the subject; (c) after a period of time, taking a second measurement of the level of Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha in the subject; and (d) administering to the subject an adjusted dose of the activin receptor type II signaling inhibitor; and wherein the cardiovascular disease is associated with and/or results from renal disease. In certain embodiments, the adjusted dose is based on the detected change between the first measurement and the second measurement. In certain embodiments, the dose is adjusted as described in Section 8.3.4.

Provided herein are methods for reducing bone resorption in a subject, wherein the method comprises: (a) administering to the subject an initial dose of an ActRII signaling inhibitor to the subject; (b) taking a first measurement of the level of Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha in the subject; (c) after a period of time, taking a second measurement of the level of Snai1, phosphosmad2, Dkk1, col1a1, activin (e.g., free activin), Runx2. Alp, BSAP, CTX, Osterix, Klotho, alpha-SMA, MYOCD, phosphosmad3, urinary protein, ActRIIA, Axin2, and/or Sm22-alpha in the subject; and (d) administering to the subject an adjusted dose of the activin receptor type II signaling inhibitor. In certain embodiments, the bone resorption is assessed as described in Section 8.6. In certain embodiments, the adjusted dose is based on the detected change between the first measurement and the second measurement. In certain embodiments, the dose is adjusted as described in Section 8.3.4.

Provided herein are methods for treating and/or preventing arterial stiffness in a subject, wherein the method comprises: (a) administering to the subject an initial dose of an ActRII signaling inhibitor to the subject; (b) taking a first measurement of the level of Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha in the subject; (c) after a period of time, taking a second measurement of the level of Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha in the subject; and (d) administering to the subject an adjusted dose of the activin receptor type II signaling inhibitor. In certain embodiments, the arterial stiffness is assessed as described in Section 8.6. In certain embodiments, the adjusted dose is based on the detected change between the first measurement and the second measurement. In certain embodiments, the dose is adjusted as described in Section 8.3.4.

Provided herein are methods for treating and/or preventing left ventricular hypertrophy in a subject, wherein the method comprises: (a) administering to the subject an initial dose of an ActRII signaling inhibitor to the subject; (b) taking a first measurement of the level of Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha in the subject; (c) after a period of time, taking a second measurement of the level of Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha in the subject; and (d) administering to the subject an adjusted dose of the activin receptor type II signaling inhibitor. In certain embodiments, the adjusted dose is based on the detected change between the first measurement and the second measurement. In certain embodiments, the dose is adjusted as described in Section 8.3.4.

In certain embodiments, the initial dose of the ActRII signaling inhibitor is about 15 mg, about 30 mg, about 45 mg, about 60 mg, about 75 mg, about 90 mg, or about 1 g or about 0.1 mg/kg, about 0.13 mg/kg, about 0.2 mg/kg, about 0.26 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, or about 1.5 mg/kg. In certain embodiments, the initial dose of the ActRII signaling inhibitor is about 0.1 mg/kg. In certain embodiments, the initial dose of the ActRII signaling inhibitor is about 0.3 mg/kg. In certain embodiments, the initial dose of the ActRII signaling inhibitor is about 0.5 mg/kg. In certain embodiments, the initial dose of the ActRII signaling inhibitor is about 0.7 mg/kg.

In certain embodiments, the initial dose is administered via injection. In certain embodiments, the initial dose is administered (i) once every 28 days; or (ii) once every 42 days. In certain embodiments, the initial dose is administered once every 14 days. In certain embodiments, the initial dose is administered once every 21 days.

In certain embodiments, the adjusted dose of the ActRII signaling inhibitor is greater than the initial dose if: (a) the level of Runx2 is elevated as compared to the level of Runx2 in a reference population; (b) the level of Alp is elevated as compared to the level of Alp in a reference population; (c) the level of Snai1 is elevated as compared to the level of Snai1 in a reference population; (d) the level of phosphosmad2 is elevated as compared to the level of phosphosmad2 in a reference population; (e) the level of Dkk1 is elevated as compared to the level of Dkk1 in a reference population; (f) the level of Col1a1 is elevated as compared to the level of Col1a1 in a reference population; (g) the level of activin is elevated as compared to the level of activin in a reference population: (h) the level of BSAP is elevated as compared to the level of BSAP in a reference population; (i) the level of CTX is elevated as compared to the level of CTX in a reference population; (j) the level of Osterix is elevated as compared to the level of Osterix in a reference population; (k) the level of Klotho is decreased as compared to the level Klotho in a reference population; (l) the level of alpha-SMA is decreased as compared to the level of alpha-SMA in a reference population; (m) the level of MYOCD is decreased as compared to the level of MYOCD in a reference population; (n) the level of Sm22-alpha is decreased as compared to the level of Sm22-alpha in a reference population; (o) the level of phosphosmad3 is elevated as compared to the level of phosphosmad3 in a reference population; (p) the level of urinary protein is elevated as compared to the level of urinary protein in a reference population; (q) the level of ActRIIA is decreased as compared to the level ActRIIA in a reference population; and/or (r) the level of Axin2 is decreased as compared to the level Axin2 in a reference population.

In certain embodiments, the adjusted dose is about 2.5 mg, about 5 mg, about 10 mg, about 15 mg, about 20 mg, or about 35 mg greater than the initial dose, or about 0.05 mg/kg, about 0.1 mg/kg, about 0.15 mg/kg, about 0.25 mg/kg, about 0.3 mg/kg, about 0.35 mg/kg, about 0.4 mg/kg, or about 0.5 mg/kg greater than the initial dose. In certain embodiments, the adjusted dose is administered more frequently than the initial dose. In certain embodiments, the adjusted dose is administered every 5, 10, 15, 20, 25, 28, 30, 35, or 40 days.

In certain embodiments, the adjusted dose of the ActRII signaling inhibitor is less than the initial dose if: (a) the level of Runx2 is decreased as compared to the level of Runx2 in a reference population; (b) the level of Alp is decreased as compared to the level of Alp in a reference population; (c) the level of BSAP is decreased as compared to the level of BSAP in a reference population; (d) the level of Snai1 is decreased as compared to the level of Snai1 in a reference population; (e) the level of phosphosmad2 is decreased as compared to the level of phosphosmad2 in a reference population; (f) the level of Dkk1 is decreased as compared to the level of Dkk1 in a reference population; (g) the level of col1a1 is decreased as compared to the level of col1a1 in a reference population; (h) the level of activin (e.g., free activin) is decreased as compared to the level of activin (e.g., free activin) in a reference population; (i) the level of CTX is decreased as compared to the level of CTX in a reference population; (j) the level of Osterix is decreased as compared to the level of Osterix in a reference population; (k) the level of Klotho is elevated as compared to the level of Klotho in a reference population; (l) the level of alpha-SMA is elevated as compared to the level of alpha-SMA in a reference population; (m) the level of MYOCD is elevated as compared to the level of MYOCD in a reference population; (n) the level of Sm22-alpha is elevated as compared to the level of Sm22-alpha in a reference population; (o) the level of phosphosmad3 is decreased as compared to level of phosphosmad3 in a reference population; (p) the level of urinary protein is decreased as compared to level of urinary protein in a reference population; (q) the level of ActRIIA is elevated as compared to level of ActRIIA in a reference population; and/or (r) the level of Axin2 is elevated as compared to level of Axin2 in a reference population.

In certain embodiments, the adjusted dose is about 2.5 mg, about 5 mg, about 10 mg, about 15 mg, about 20 mg, or about 35 mg less than the initial dose, or about 0.05 mg/kg, about 0.1 mg/kg, about 0.15 mg/kg, about 0.25 mg/kg, about 0.3 mg/kg, about 0.35 mg/kg, about 0.4 mg/kg, or about 0.5 mg/kg less than the initial dose. In certain embodiments, the adjusted dose is administered less frequently than the initial dose. In certain embodiments, the adjusted dose is administered every 30, 35, 40, 42, 50, 60, 70, 80, or 90 days. In certain embodiments, the adjusted dose is administered continuously and/or indefinitely.

In certain embodiments, the first measurement is taken prior to the commencement of the treatment. In certain embodiments, the first measurement is taken immediately after commencement of the treatment or within at most 1 day, 2 days, 3 days, 4 days, 5 days, 6 days, or 1 week, 2 weeks, 3 weeks, 4 weeks, or 2 months thereof. In certain embodiments, the second measurement is taken immediately after commencement of the treatment or within at most 1 day, 2 days, 3 days, 4 days, 5 days, 6 days, or 1 week, 2 weeks, 1 month, 2 months, 3 months, 4 months, 5 months, 6 months, 7 months, 8 months, 9 months, 10 months, 11 months, or 12 months thereof.

In certain embodiments, (a) the elevated levels of Snail, phosphosmad2, Dkk1, col1a1, activin (e.g., free activin), Runx2, Alp, BSAP, CTX, phosphosmad3, urinary protein, and/or Osterix are about 10%, 20%, 25%, 30%, 40%, 50%, 60%, 70%, 75%, 80% 90%, 100%, 200%, or 500% greater than the levels of Snail, phosphosmad2, Dkk1, col1a1, activin (e.g., free activin), Runx2, Alp, BSAP, CTX, phosphosmad3, urinary protein, and/or Osterix, respectively, in the reference population; and/or (b) the decreased levels of Klotho, alpha-SMA, MYOCD, ActRIIA, Axin2, and/or Sm22-alpha are about 10%, 20%, 25%, 30%, 40%, 50%, 60%, 70%, 75%, 80% 90%, or 100% less than the levels of Klotho, alpha-SMA, MYOCD, ActRIIA, Axin2, and/or Sm22-alpha, respectively, in a reference population.

In certain embodiments, (a) the elevated levels of Snail, phosphosmad2, Dkk1, col1a1, activin (e.g., free activin), Runx2, Alp, BSAP, CTX, phosphosmad3, urinary protein, and/or Osterix are equal to or about 10%, 20%, 25%, 30%, 40%, 50%, 60%, 70%, 75%, 80%, 90%, 100%, 200%, or 500% greater than the levels of Snail, phosphosmad2, Dkk1, col1a1, activin (e.g., free activin), Runx2, Alp, BSAP, CTX, phosphosmad3, urinary protein, and/or Osterix, respectively, in the top 10%, top 5%, top 4%, top 3%, top 2%, or top 1% in the reference population; and/or (b) the decreased levels of Klotho, alpha-SMA, MYOCD, ActRIIA, Axin2, and/or Sm22-alpha are equal to or about 10%, 20%, 25%, 30%, 40%, 50%, 60%, 70%, 75%, 80%, 90%, or 100% less than the levels of Klotho, alpha-SMA, MYOCD, ActRIIA, Axin2, and/or Sm22-alpha, respectively, in the bottom 10%, bottom 5%, bottom 4%, bottom 3%, bottom 2%, or bottom 1% in the reference population.

In certain embodiments, (a) the elevated levels of Klotho, alpha-SMA, MYOCD, ActRIIA, Axin2, and/or Sm22-alpha are about 10%, 20%, 25%, 30%, 40%, 50%, 60%, 70%, 75%, 80% 90%, 100%, 200%, or 500% greater than the levels of Klotho, alpha-SMA, MYOCD, ActRIIA, Axin2, and/or Sm22-alpha, respectively, in the reference population; and/or (b) the decreased levels of Snail, phosphosmad2, Dkk1, col1a1, activin (e.g., free activin). Runx2, Alp, BSAP, CTX, phosphosmad3, urinary protein, and/or Osterix are about 10%, 20%, 25%, 30%, 40%, 50%, 60%, 70%, 75%, 80% 90%, or 100% less than the levels of Snail, phosphosmad2, Dkk1, col1a1, activin (e.g., free activin), Runx2. Alp, BSAP, CTX, phosphosmad3, urinary protein, and/or Osterix, respectively, in a reference population.

In certain embodiments, (a) the elevated levels of Klotho, alpha-SMA, MYOCD, ActRIIA, Axin2, and/or Sm22-alpha are equal to or about 10%, 20%, 25%, 30%, 40%, 50%, 60%, 70%, 75%, 80%, 90%, 100%, 200%, or 500% greater than the levels of Klotho, alpha-SMA, MYOCD, ActRIIA, Axin2, and/or Sm22-alpha, respectively, in the top 10%, top 5%, top 4%, top 3%, top 2%, or top 1% in the reference population; and/or (b) the decreased levels of Snail, phosphosmad2, Dkk1, col1a1, activin (e.g., free activin), Runx2, Alp, BSAP, CTX, phosphosmad3, urinary protein, and/or Osterix are equal to or about 10%, 20%, 25%, 30%, 40%, 50%, 60%, 70%, 75%, 80%0, 90%, or 100% less than the levels of Snail, phosphosmad2, Dkk1, col1a1, activin (e.g., free activin), Runx2, Alp, BSAP, CTX, phosphosmad3, urinary protein, and/or Osterix, respectively, in the bottom 10%, bottom 5%, bottom 4%, bottom 3%, bottom 2%, or bottom 1% in the reference population.

In certain embodiments, the level of Snail, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha is the protein level of Snail, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha, respectively. In certain embodiments, the protein level is determined by enzyme-linked immunosorbant assay (ELISA). In certain embodiments, the ELISA is performed with (a) Runx2-specific antibody SC-390715 (Santa Cruz) to determine Runx2 levels; (b) Alp-specific antibody SC-98652 (Santa Cruz) to determine Alp levels; (c) Snail-specific antibody sc-393172 (Santa Cruz) to determine Snail levels; (d) phosphosmad2-specific antibody sc-101801 (Santa Cruz) to determine phosphosmad2 levels; (e) Dkk1-specific antibody sc-374574 (Santa Cruz) to determine Dkk1 levels; (f) Col1a1-specific antibody sc-8784 (Santa Cruz) to determine col1a1 levels; (g) activin-specific antibody A1594 (Sigma Aldrich) to determine activin levels; (h) BSAP-specific antibody SC-98652 (Santa Cruz) to determine BSAP levels; (i) CTX-specific antibody ABIN1173415 (Antibodies Online) to determine CTX levels; (j) Osterix-specific antibody SC-22538 (Santa Cruz) to determine Osterix levels; (k) Klotho-specific antibody SC-22218 (Santa Cruz) to determine Klotho levels; (l) alpha-SMA-specific antibody SC-53142 (Santa Cruz) to determine alpha-SMA levels; (m) MYOCD-specific antibody SC-21561 (Santa Cruz) to determine MYOCD levels; (n) Sm22-alpha-specific antibody SC-271719 (Santa Cruz) to determine Sm22-alpha levels; (o) phosphosmad3-specific antibody sc-11769 (Santa Cruz) to determine phosphosmad3 levels; and/or (p) ActRIIA-specific antibody ab 135634 (Abcam) to determine ActRIIA levels.

In certain embodiments, the level of Snail, Dkk1, col1a1, activin, Runx2, Alp, BSAP, CTX, Osterix, Klotho, alpha-SMA, MYOCD, phosphosmad3, phosphosmad3, urinary protein, ActRIIA, Axin2, and/or Sm22-alpha is the mRNA level of Snail, Dkk1, col1a1, activin, Runx2, Alp, BSAP, CTX, Osterix, Klotho, alpha-SMA, MYOCD, phosphosmad3, phosphosmad3, urinary protein, ActRIIA, Axin2, and/or Sm22-alpha, respectively. In certain embodiments, the mRNA level is determined by quantitative reverse transcription polymerase chain reaction (qRT-PCR). In certain embodiments, the qRT-PCR is performed with (a) Runx2-specific primers (SEQ ID NOS: 48 and 49) to determine Runx2 levels; (b) Alp-specific primers (SEQ ID NOS: 50 and 51) to determine Alp levels; (c) Snail-specific primers (SEQ ID NOS: 78 and 79) to determine Snail levels; (d) Dkk1-specific primers (SEQ ID NOS: 80 and 81) to determine Dkk1 levels; (e) col1a1-specific primers (SEQ ID NOS: 82 and 83) to determine col1a1 levels; (f) activin-specific primers (SEQ ID NOS: 84 and 85) to determine activin levels; (g) Osterix-specific primers (SEQ ID NOS: 52 and 53) to determine Osterix levels; (h) Klotho-specific primers (SEQ ID NOS: 54 and 55) to determine Klotho levels; and/or (i) Sm22-alpha-specific primers (SEQ ID NOS: 56 and 57) to determine Sm22-alpha levels.

In certain embodiments, the Snail, phosphosmad2, Dkk1, col1a1, activin (e.g., free activin), Runx2, Alp, BSAP, CTX, Osterix, Klotho, Sm22-alpha, MYOCD, phosphosmad3, urinary protein, ActRIIA, Axin2. ActRIIA, Axin2, and/or alpha-SMA levels are in a tissue. In certain embodiments, the tissue is aorta. In certain embodiments, the tissue is kidney. In certain embodiments, the tissue is bone. In certain embodiments, the tissue is serum. In a preferred embodiment, the Runx2, Dkk1, Alp, osterix, sm22-alpha, Klotho, alpha-SMA, MYOCD, ActRIIA, Axin2, levels and/or activity are in aorta. In a preferred embodiment, the phosphosmad3, urinary protein, phosphosmad2, ActRIIA, Axin2, and col1a1 levels and/or activity are in kidney. In a preferred embodiment, the activin levels and/or activity are in serum.

In certain embodiments, the Snai1, phosphosmad2, Dkk1, col1a1, activin (e.g., free activin), Runx2, Alp, BSAP, CTX, Osterix, Klotho, Sm22-alpha, MYOCD, ActRIIA, Axin2, and/or alpha-SMA levels are in aorta.

In certain embodiments, the vascular calcification is calcific atherosclerosis, calcific medial vasculopathy (also known as Mönckeberg's medial calcific sclerosis), medial calcification, elastocalcinosis, calcific uremic arterolopathy, calcific aortic valvular stenosis, or portal vein calcification.

In certain embodiments, the cardiovascular disease is a disease associated with vascular calcification such as atherosclerosis, hyperlipidemia, osteoporosis, hypertension, inflammation, type 2 diabetes mellitus, end-stage renal disease, required amputation, pseudoxanthoma elasticum, congenital bicuspid valve, rheumatic heart disease, portal hypertension, or liver disease.

In certain embodiments, the cardiovascular disease is secondary to chronic kidney disease. In certain embodiments, the chronic kidney disease is stage 3, 4, or 5 chronic kidney disease. In certain embodiments, the chronic kidney disease is chronic kidney disease mineral and bone disease.

In certain embodiments, the subject has high turnover bone disease, e.g., high-turnover renal osteodystrophy (ROD).

Also provided herein is a method of treating high-turnover bone disease, e.g., high-turnover ROD, comprising administering to a pharmaceutically effective amount of an ActRII signaling inhibitor to a subject.

In certain embodiments, the ActRII signaling inhibitor is a polypeptide comprising an amino acid sequence selected from the group consisting of: (a) 90% identical to SEQ ID NO:2; (b) 95% identical to SEQ ID NO:2; (c) 98% identical to SEQ ID NO:2; (d) SEQ ID NO:2; (e) 90% identical to SEQ ID NO:3; (f) 95% identical to SEQ ID NO:3; (g) 98% identical to SEQ ID NO:3; (h) SEQ ID NO:3; (i) 90% identical to SEQ ID NO:6; (j) 95% identical to SEQ ID NO:6; (k) 98% identical to SEQ ID NO:6; (l) SEQ ID NO:6; (m) 90% identical to SEQ ID NO:7; (n) 95% identical to SEQ ID NO:7; (o) 98% identical to SEQ ID NO:7; (p) SEQ ID NO:7; (q) 90% identical to SEQ ID NO: 12; (r) 95% identical to SEQ ID NO:12; (s) 98% identical to SEQ ID NO:12; (t) SEQ ID NO:12; (u) 90% identical to SEQ ID NO: 17; (v) 95% identical to SEQ ID NO: 17; (w) 98% identical to SEQ ID NO: 17; (x) SEQ ID NO: 17; (y) 90% identical to SEQ ID NO:20; (z) 95% identical to SEQ ID NO:20; (aa) 98% identical to SEQ ID NO:20; (bb) SEQ ID NO:20; (cc) 90% identical to SEQ ID NO:21; (dd) 95% identical to SEQ ID NO:21; (ee) 98% identical to SEQ ID NO:21; and (ff) SEQ ID NO:21. In certain embodiments, the ActRII signaling inhibitor is a polypeptide comprising the amino acid sequence of SEQ ID NO:7. In certain embodiments, the ActRII signaling inhibitor is a humanized fusion-protein consisting of the extracellular domain of ActRIIA and the human IgG1 Fc domain.

In certain embodiments, the ActRII signaling inhibitor is Sotatercept (SEQ ID NO: 7; see, e.g., Section 9). Sotatercept is an activin ligand trap that is useful in the methods described herein (see Section 8).

In certain embodiments, the subject is human.

BRIEF DESCRIPTION OF THE FIGURES

FIG. 3A depicts the level of ACTRII in wildtype mouse aorta. FIG. 3B depicts the level of ACTRII in sham-treated mouse aorta. FIG. 3C depicts the increased level of ACTRII in mouse aorta of a CKD-3 model as compared to FIG. 3A and/or FIG. 3B. FIG. 3D depicts the decreased level of ACTRII in mouse aorta of a CKD-3 model treated mActRIIA-Fc as compared to FIG. 3C.

FIG. 4A depicts the mRNA levels of Runx2 in a mouse model of chronic kidney disease in the presence (CKD3+ActRII-Fc) and absence (CKD3+v) of treatment with an inhibitor of ActRII signaling. FIG. 4B depicts the mRNA levels of Alp in a mouse model of chronic kidney disease in the presence (CKD3+ActRII-Fc) and absence (CKD3+v) of treatment with an inhibitor of ActRII signaling. FIG. 4C depicts the mRNA levels of Klotho in a mouse model of chronic kidney disease in the presence (CKD3+ActRII-Fc) and absence (CKD3+v) of treatment with an inhibitor of ActRII signaling. FIG. 4D depicts the mRNA levels of myocardin (MYOCD) in a mouse model of chronic kidney disease in the presence (CKD3+ActRII-Fc) and absence (CKD3+v) of treatment with an inhibitor of ActRII signaling. FIG. 4E depicts the mRNA levels of Sm22-alpha (SM22α) in a mouse model of chronic kidney disease in the presence (CKD3+ActRII-Fc) and absence (CKD3+v) of treatment with an inhibitor of ActRII signaling.

FIG. 10A depicts the percentage of subjects in each treatment category for change in the total Agatston score. FIG. 10B depicts the percentage of subjects in each treatment category for change in the square root transformed total volume score.

FIG. 12A and FIG. 12B utilize A model of vascular calcification with ablative CKD as described in Section 9.4.1.1 was utilized to produce decreased kidney function similar to human CKD stage 3, referred to as CKD-3 (CKD-3 V for vehicle treated) with a 70% reduction in GFR compared to WT C57B6 mice (WT) estimated by inulin clearances and BUN.

FIG. 13 demonstrates that CKD increases Activin in the circulation and the kidney and aortic ActRIIA expression. "WT"=wildtype; "sham"=mice sham treated; "CKD-3 V"=mice treated with vehicle; "CKD-3 R"=mice treated with mActRIIA-Fc. FIG. 13C demonstrates inhibin betaA expression in mouse kidney and aorta (activin-A is formed of homodimers of the inhibin betaA gene). FIG. 13D demonstrates protein levels for inhibin betaA in kidney homogenates. 1, 2, and 3, refer to individual samples. FIG. 13E depicts immunohistochemistry of aortic ActRIIA. ActRIIA expression was detected in the aortas of wild type (WT) and sham operated ldlr−/− high fat fed mice (Sham), which was stimulated in CKD-3 mice treated with vehicle (CKD-3 V) or mActRIIA-Fc (CKD-3 mActRIIA-Fc). Scale bar is 20 µm.

FIG. 14 demonstrates CKD stimulated endothelial to mesenchymal transition.

FIG. 15 depicts the effects of mActRIIA-Fc on vascular calcification in ldlr−/− high fat fed mice with CKD-3.

FIG. 16 demonstrates the effects of decreased ActRIIA signaling on CKD stimulated cardiac disease.

FIG. 17 B depicts ascending aortas from wild-type (WT—28 wks.), sham-operated (Sham—28 wks.), CKD-3 (28 wks.), and CKD-3 treated with Dkk1 monoclonal antibody (Dkk1 mab—28 wks.) mice. For FIG. 17, black represents WT or sham-operated mice, while open or grey represents CKD-3 mice. Values are presented as mean±standard deviation. N=5-6 mice for carotid arteries, 3-6 for ascending aortas.

FIG. 18 demonstrates ActRIIA signaling in kidney and aorta. FIG. 18A depicts activin signaling determined by westerns of kidney (left) and aortic (right) homogenates from sham, CKD-3 vehicle-(CKD-3 V) and mActRIIA-Fc-treated (CKD-3 R) mice. Activin levels were increased in kidney homogenates but not in aortic homogenates, the Alk4 (AcvR1B) and Alk2 (AcvR1) type 1 receptors were present in kidney homogenates, but CKD-3 did not increase Alk4 phosphorylation. Alk4 and Alk1 (AcvRL1) were present in aortic homogenates. CKD-3 increased smad2/3 phosphorylation in kidneys but not aortas, and increased kidney Col1A1 levels. mActRIIA-Fc treatment decreased kidney phosphosmad2/3 and Col1A1 levels. In aortas, not only was there no effect of CKD-3 on phosphosmad2/3 levels, there was no effect on phosphoErk 1/2 levels. Runx2 levels were increased by CKD-3 and normalized by mActRIIA-Fc. FIG. 18B depicts a decrease of Klotho mRNA expression in kidney of CKD-3 mice and its correction by mActRIIA-Fc-treatment.

FIG. 28A depicts immunofluorescence microscopy of beta-catenin expression in the aortas of wild-type mice. FIG. 28B depicts immunofluorescence microscopy of beta-catenin expression in the aortas of a CKD mouse. There was no immunofluorescence for beta-catenin in the vascular smooth muscle cells. There was beta-catenin expression in the endothelium of aortas from CKD mice. Arrow heads, beta-catenin and CD31 colocalization in endothelial cells. Scale bar 20 μm. FIG. 28C depicts aortic Axin2 mRNA expression levels.

FIG. 29A depicts the effects of mActRIIA-Fc treatment on renal klotho mRNA levels and demonstrates CKD-3 decreased klotho gene expression levels in kidney homogenates, and mActRIIA-Fc treatment significantly increased them compared to CKD-3V. *p<0.05, p<0.01, *p<0.005. FIG. 29B depicts the analysis of ActRIIA signaling by westerns of kidney homogenates from sham, CKD-3 vehicle, and mActRIIA-Fc treated mice. All of the immunoblots are representative of homogenates from 3 or 4 kidneys. ActRIIA levels were not affected by CKD-3 or mActRIIA-Fc. Activin A (inhibin β-A) levels were increased in kidney homogenates of CKD-3 mice (quantitation is shown in FIG. 30A-B) and decreased by mActRIIA-Fc. The Alk4 (AcvR1B) and Alk2 (AcvR1) type 1 receptors were present in kidney homogenates, but CKD-3 V or CKD-3 R did not significantly affect Alk4 phosphorylation. CKD-3 increased renal smad2/3 phosphorylation and mActRIIA-Fc treatment decreased kidney phosphosmad2/3. FIG. 29C depicts immunoblot quantitation of FIG. 29B), *p<0.01.

FIG. 31A depicts induction of circulating activin-A by CKD in atherosclerotic ldlr−/− high fat fed CKD-3 mice. FIG. 31B depicts induction of circulating activin-A by CKD in Alport's syndrome mice as described herein.

FIG. 33A and FIG. 33B depict chronic kidney disease in mice analogous to human stage 3 kidney disease. CKD was staged in the mouse models in a manner analogous to the staging of human CKD. The model of vascular calcification with ablative CKD as described in methods (Section 9.10.1) was used to produce decreased kidney function similar to human CKD stage 3, referred to as CKD-3 (CKD-3 V for vehicle treated) with a 70% reduction in GFR compared to WT C57B6 mice (WT) estimated by inulin clearances and BUN. Treatment of CKD-3 mice with mActRIIA-Fc (CKD-3 R), 10 mg/kg twice weekly subcutaneously, had no effect on inulin clearance or BUN.

DETAILED DESCRIPTION

Overview

Figure 1A:
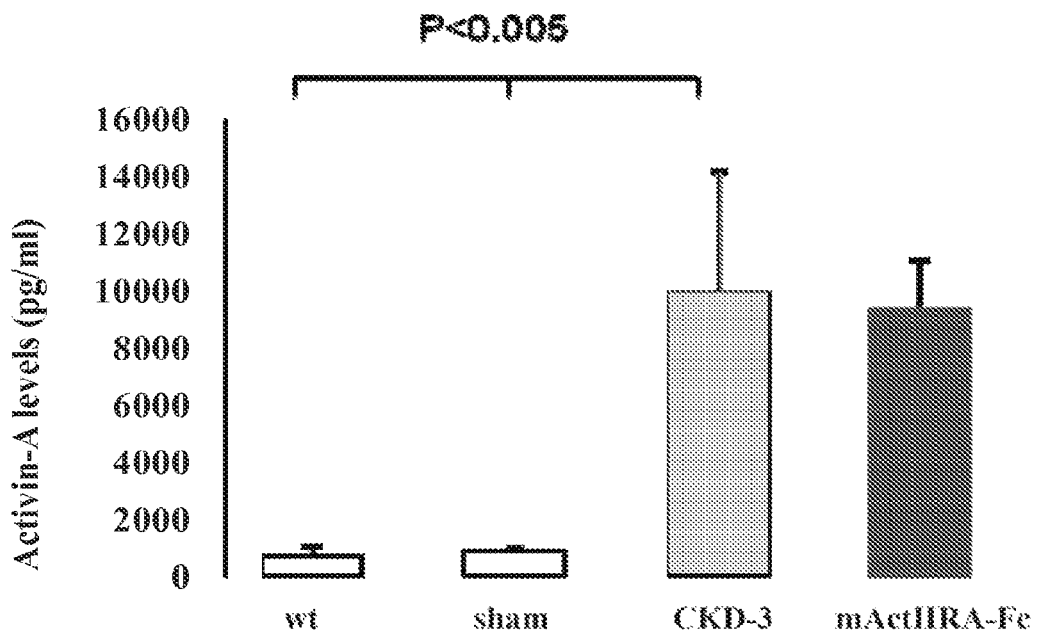
FIG. 1A depicts increased Activin-A levels (pg/ml) in the interstitial fibrosis model of kidney disease (CKD-3) as compared to wild-type and sham models.

Provided herein, in one aspect, is a method for the treatment and/or prevention of cardiovascular disease, vascular calcification, cardiovascular disease associated with and/or resulting from vascular calcification, and/or cardiovascular disease associated with and/or resulting from renal disease, elevated levels of arterial stiffness (e.g., as indicated by decreased vascular compliance), and/or left ventricular hypertrophy (LVH), including cardiovascular disease associated with and/or resulting from elevated levels of arterial stiffness and/or LVH, wherein the method comprises administering an inhibitor of ActRII signaling (e.g., an activin ligand trap) to a subject in need of treatment and/or prevention thereof. In certain embodiments, the subject is a renal subject. The inhibitor of ActRII signaling can be an inhibitor of ActRIIA signaling and/or ActRIIB signaling.

In particular, provided herein are methods of treating and/or preventing cardiovascular disease, vascular calcification, cardiovascular disease associated with and/or resulting from vascular calcification, cardiovascular disease associated with and/or resulting from renal disease, elevated levels of arterial stiffness, and/or left ventricular hypertrophy (LVH) by using the level and/or activity of Snai1, phosphosmad2, Dkk1, col1a1, activin (e.g., free activin), Runx2, Alp. BSAP, CTX, Osterix, Klotho, alpha-SMA, MYOCD, phosphosmad3, urinary protein, ActRIIA. Axin2, and/or Sm22-alpha, as an indicator of the patient population, as an indicator of responsiveness of a subject to the treatment and/or prevention with an ActRII signaling inhibitor, as an indicator of efficacy of the treatment with an ActRII signaling inhibitor, or as an indicator of appropriate dosage for the treatment with an ActRII signaling inhibitor. The levels and/or activity of Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha can also be utilized to identify diseases and/or conditions for treatment and/or prevention with an ActRII signaling inhibitor. An ActRII signaling inhibitor used in the methods described herein can be an inhibitor of ActRIIA signaling and/or ActRIIB signaling, such as any of the inhibitors described herein or known in the art. In a preferred embodiment, an ActRII signaling inhibitor is a humanized fusion-protein consisting of the extracellular domain of ActRIIA and the human IgG1 Fc domain ("ActRIIA-Fc," e.g., SEQ ID NO:7).

The methods provided herein are based, in part, on the discovery that the levels of Snai1, phosphosmad2, Dkk1, col1a1, activin (e.g., free activin), Runx2, Alp, BSAP, CTX, phosphosmad3, urinary protein, and Osterix are elevated, and the levels of Klotho, alpha-SMA, MYOCD, ActRIIA, and Sm22-alpha are decreased in a mouse model of chronic kidney disease-induced vascular calcification as compared to a wildtype mouse. Further, without being limited by theory, ligand trapping by mActRIIA-Fc reduces vascular calcification in a chronic kidney disease mouse model (ldlr−/− mice, high fat diet). As shown in the Examples presented herein (See Section 9), treatment of chronic kidney disease mice with mActRIIA-Fc reduced vascular calcification, reduced aortic calcium levels, reduced phosphosmad3 levels, reduced urinary protein levels, reduced phosphosmad2 levels, reduced Dkk1 levels, reduced Runx2 levels, reduced Alp levels, reduced BSAP levels, reduced CTX levels, and reduced Osterix levels, and elevated Klotho levels, elevated alpha-SMA levels, elevated Axin2 levels and elevated Sm22-alpha levels. Furthermore, the methods provided herein are based, in part, on the discovery that the decrease in vascular calcification in chronic kidney disease mice upon treatment with mActRIIA-Fc is correlated with a decrease in Dkk1, phosphosmad2, Runx2, Alp, BSAP, CTX, phosphosmad3, urinary protein, and/or Osterix levels, and an increase in Klotho, alpha-SMA, Axin2, and/or Sm22-alpha levels (See Examples, Section 9). Taken together, the data presented herein indicate that Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha levels can identify which subjects may respond to ActRIIA-Fc and/or can be used to monitor clinical response to an ActRII signaling inhibitor and/or select target patient populations. The data presented herein also indicate that ActRIIA-Fc (e.g., mActRIIA-Fc, or ActRIIA-hFc such as SEQ ID NO:7) is useful in treating vascular calcification associated with chronic kidney disease. Additionally, the data presented herein also indicate that ActRIIA-Fc (e.g., mActRIIA-Fc, or ActRIIA-hFc such as SEQ ID NO:7) is useful in treating diseases associated with elevated levels of Snai1, phosphosmad2, Dkk1, col1a1, activin (e.g., free activin) Runx2, Alp, BSAP, CTX, phosphosmad3, urinary protein, and/or Osterix, or diseases associated with decreased levels of Klotho, alpha-SMA, MYOCD, ActRIIA, and/or Sm22-alpha. Finally, the data presented herein also indicate that ActRIIA-Fc (e.g., mActRIIA-Fc, or hActRIIA-hFc such as SEQ ID NO:7) is useful in decreasing calcium deposits in aortic atheroma, reducing aortic calcium levels, reversing the CKD-induced increase in heart weight, and decreasing renal fibrosis, and accordingly, is useful in treating cardiovascular disease.

The findings described herein, illustrated in the Examples (See Section 9), indicate that detection of the levels and/or activity of Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, or Sm22-alpha can be used (i) as a marker (e.g., serum biomarker) of the extent of vascular calcification in a subject, (ii) as a marker to measure the subject's response to an ActRII signaling inhibitor (such as ActRIIA-Fc), or (iii) to evaluate the pharmacodynamic effects of an ActRII signaling inhibitor (such as ActRIIA-Fc) in a subject following treatment, wherein the subject is a subject with cardiovascular disease, vascular calcification, cardiovascular disease associated with and/or resulting from vascular calcification, and/or cardiovascular disease associated with and/or resulting from renal disease. Thus, in certain embodiments, Snai1, phosphosmad2, Dkk1, col1a1, activin (e.g., free activin). Runx2, Alp. BSAP, CTX, Osterix, Klotho, alpha-SMA, MYOCD, phosphosmad3, urinary protein, Axin2, and/or Sm22-alpha can be used in the methods described herein as an indicator of efficacy of ActRIIA-Fc (e.g., ActRIIA-hFc such as SEQ ID NO:7) treatment and/or as an indicator of absence of response to the treatment with ActRIIA-Fc (e.g., ActRIIA-hFc such as SEQ ID NO:7). In addition, as described herein, Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha can be used as a reliable molecular marker to evaluate time-course treatment efficacy of ActRIIA-Fc (e.g., ActRIIA-hFc such as SEQ ID NO:7). Further, in a specific embodiment, provided herein is a method which comprises detection of the level and/or activity of Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha in the blood (e.g., detecting abnormal expression in a disease associated with impaired vascular smooth muscle cell function), and administration of an ActRII signaling inhibitor, such as ActRIIA-Fc, in a dose dependent on the level and/or activity of Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha.

In certain embodiments, the ActRII signaling inhibitor is Sotatercept (SEQ ID NO: 7; see, e.g., Section 9). Sotatercept is an activin ligand trap that is useful in the methods described herein (see Section 8).

Abbreviations

As used herein, "Snai1" or "Snai1" refer to snail homolog 1. See, for example, Twigg and Wilkie, 1999, Hum Genet. 105(4):320-326 GenBank™ accession number NM_005985.3 provides an exemplary human Snai1 nucleic acid sequence. GenBank™ accession number NP_005976.2 provides an exemplary human Snai1 amino acid sequence.

As used herein, "phosphosmad3" refers to phosphorylated mothers against decapentaplegic homolog 3. See, for example, Matsuzaki, 2013, Cytokine Growth Factor Rev, 24(4):385-399. GenBank™ accession number NM_005902.3 provides an exemplary human phosphosmad3 nucleic acid sequence. GenBank™ accession number NP_005893.1 provides an exemplary human phosphosmad3 amino acid sequence.

As used herein, "phosphosmad2" refers to phosphorylated mothers against decapentaplegic homolog 2. See, for example, Matsuzaki, 2013, Cytokine Growth Factor Rev, 24(4):385-399. GenBank™ accession number NM_001003652.3 provides an exemplary human phosphosmad2 nucleic acid sequence. GenBank™ accession number NP_001003652.1 provides an exemplary human phosphosmad2 amino acid sequence.

As used herein, "Dkk1" refers to dickkopf-related protein 1. See, for example. Fang, Y., et al., 2014. J Am Soc Nephrol 25:1760-1763. GenBank™ accession number NM_012242.2 provides an exemplary human Dkk1 nucleic acid sequence. GenBank™ accession number NP_036374.1 provides an exemplary human Dkk1 amino acid sequence.

As used herein, "col1a1" refers to collagen type 1, alpha 1. See, for example, Korkko et al., 1998, Am. J. Hum. Genet., 62:98-110. GenBank™ accession number XM_005257059.2 provides an exemplary human col1a1 nucleic acid sequence. GenBank™ accession number XP_005257116.2 provides an exemplary human col1a1 amino acid sequence.

As used herein, "Runx2" refers to runt-related transcription factor 2. See, for example, Komori, 2010, Adv Exp Med Biol, 658:43-49. GenBank™ accession number NM_001145920.2 provides an exemplary human Runx2 nucleic acid sequence. GenBank™ accession number NP_001139392.1 provides an exemplary human Runx2 amino acid sequence.

As used herein, "Alp" or "Alp1" refers to alkaline phosphatase. As used herein, "BSAP" refers to bone-specific alkaline phosphatase. See, for example, Martins et al., 2013, Bone, 56(2):390-397. GenBank™ accession number NM_000478.4 provides an exemplary human Alp nucleic acid sequence. GenBank™ accession number NP_000469.3 provides an exemplary human Alp amino acid sequence.

As used herein, "CTX" refers to C-terminal telopeptides type I collagen. See, for example, Rosen et al, 2000, Calcif Tissue Int. 66(2): 100-103.

As used herein, "Osterix" refers to Osterix, also known as the Sp7 transcription factor. See, for example, Cao et al., 2005, Cancer Res. 65(4):1124-1128. GenBank™ accession number NM_001173467.2 provides an exemplary human Osterix nucleic acid sequence. GenBank™ accession number NP_001166938.1 provides an exemplary human Osterix amino acid sequence.

As used herein, "Klotho" refers to Klotho. See, for example, Matsumura et al. 1998, Biochem Biophys Res Commun, 242:626-630. GenBank™ accession number NM_004795.3 provides an exemplary human Klotho nucleic acid sequence. GenBank™ accession number NP_004786.2 provides an exemplary human Klotho amino acid sequence.

As used herein, "alpha-SMA" or "αSMA" or "α-SMA" refers to alpha smooth muscle actin. See, for example, Nowak et al., 1999, Nat. Genet. 23:208-212. GenBank™ accession number NM_001100.3 provides an exemplary human alpha-SMA nucleic acid sequence. GenBank™ accession number NP_001091.1 provides an exemplary human alpha-SMA amino acid sequence.

As used herein, "MYOCD" refers to myocardin. See, for example, Imamura et al., 2010, Gene, 464:1-10. GenBank™ accession number NM 001146312.2 provides an exemplary human MYOCD nucleic acid sequence. GenBank™ accession number NP_001139784.1 provides an exemplary human MYOCD amino acid sequence.

As used herein, "Sm22-alpha" or "Sm22a" or "Sm22-α" refers to smooth muscle protein 22 alpha, also known as "transgelin", "Tagln", or "Tagln1". See, for example, Camoretti-Mercado, 1998, Genomics, 49:452-457. GenBank™ accession number NM_001001522.1 provides an exemplary human Sm22-alpha nucleic acid sequence. GenBank™ accession number NP_001001522.1 provides an exemplary human Sm22-alpha amino acid sequence.

As used herein, "ActRII" refers to activin receptor type II. As used herein, "ActRIIA" refers to activin receptor type IIA. See, for example, Mathews and Vale, 1991, Cell 65:973-982. GenBank™ accession number NM_001278579.1 provides an exemplary human ActRIIA nucleic acid sequence. GenBank™ accession number NP_001265508.1 provides an exemplary human ActRIIA amino acid sequence. As used herein, "ActRIIB" refers to activin receptor type IIB. See, for example, Attisano et al., 1992, Cell 68: 97-108. GenBank™ accession number NM_001106.3 provides an exemplary human ActRIIB nucleic acid sequence. GenBank™ accession number NP_001097.2 provides an exemplary human ActRIIB amino acid sequence.

As used herein, "Axin2" refers to axis inhibitor 2. GenBank™ accession number NM_004655.3 provides an exemplary human Axin2 nucleic acid sequence. GenBank™ accession number NP_004646.3 provides an exemplary human amino acid sequence.

As used herein, "mActRIIA-Fc" or "ActRIIA-mFc" refers to a mouse activin type IIA receptor-IgG1 fusion protein. See, for example, U.S. Pat. No. 8,173,601. As used herein, "mActRIIB-Fc" or "ActRIIB-mFc" refers to a mouse activin type 11B receptor-IgG1 fusion protein. See, for example, U.S. Pat. No. 8,173,601. As used herein, "hActRIIA-Fc" or "ActRIIA-hFc" refers to a human activin type IIA receptor-IgG1 fusion protein. See, for example, U.S. Pat. No. 8,173, 601. As used herein, "hActRIIB-Fc" or "ActRIIB-hFc" refers to a human activin type IIB receptor-IgG1 fusion protein. See, for example, U.S. Pat. No. 8,173,601.

As used herein, "LVH" refers to left ventricular hypertrophy.

Methods of Treatment and/or Prevention
Cardiovascular Disease and/or Vascular Calcification In certain embodiments, provided herein are methods for treating and/or preventing cardiovascular disease, vascular calcification, cardiovascular disease associated with and/or resulting from vascular calcification, cardiovascular disease associated with and/or resulting from elevated levels of arterial stiffness, elevated levels of arterial stiffness, left ventricular hypertrophy, cardiovascular disease associated with and/or resulting from left ventricular hypertrophy, and/or cardiovascular disease associated with and/or resulting from renal disease in a subject, comprising administering to the subject a pharmaceutically effective dose of an ActRII signaling inhibitor (e.g., an activin ligand trap). In certain embodiments, the subject is a renal subject. In certain other embodiments, the subject has been diagnosed as having chronic kidney disease-mineral bone disorder. In certain other embodiments, the subject has not been diagnosed as having chronic kidney disease-mineral bone disorder.

In certain embodiments, the subject has elevated levels and/or activity of Runx2 as compared to levels and/or activity of Runx2 in a reference population, elevated levels and/or activity of Alp as compared to levels and/or activity of Alp in a reference population, elevated levels and/or activity of Snail as compared to levels and/or activity of Snail in a reference population, elevated levels and/or activity of phosphosmad2 as compared to levels and/or activity of phosphosmad2 in a reference population, elevated levels and/or activity of phosphosmad3 as compared to levels and/or activity of phosphosmad3 in a reference population, elevated levels and/or activity of urinary protein as compared to levels and/or activity of urinary protein in a reference population, elevated levels and/or activity of Dkk1 as compared to levels and/or activity of Dkk1 in a reference population, elevated levels and/or activity of activin (e.g., free activin) as compared to levels and/or activity of activin (e.g., free activin) in a reference population, elevated levels and/or activity of col1a1 as compared to levels and/or activity of col1a1 in a reference population, elevated levels and/or activity of BSAP as compared to levels and/or activity of BSAP in a reference population, elevated levels and/or activity of CTX as compared to levels and/or activity of CTX in a reference population, elevated levels and/or activity of Osterix as compared to levels and/or activity of Osterix in a reference population, decreased levels and/or activity of Klotho as compared to levels and/or activity of Klotho in a reference population, decreased levels and/or activity of alpha-SMA as compared to levels and/or activity of alpha-SMA in a reference population, decreased levels and/or activity of MYOCD as compared to levels and/or activity of MYOCD in a reference population, decreased levels and/or activity of Sm22-alpha as compared to levels and/or activity of Sm22-alpha in a reference population; and/or decreased levels and/or activity of ActRIIA as compared to levels and/or activity of ActRIIA in a reference population.

In certain embodiments, the subject has elevated levels and/or activity of Runx2 as compared to prior levels and/or activity of Runx2 in the subject, elevated levels and/or activity of Alp as compared to prior levels and/or activity of Alp in the subject, elevated levels and/or activity of Snail as compared to prior levels and/or activity of Snail in the subject, elevated levels and/or activity of phosphosmad2 as compared to prior levels and/or activity of phosphosmad2 in the subject, elevated levels and/or activity of phosphosmad3 as compared to prior levels and/or activity of phosphosmad3 in the subject, elevated levels and/or activity of urinary protein as compared to prior levels and/or activity of urinary protein in the subject, elevated levels and/or activity of Dkk1 as compared to prior levels and/or activity of Dkk1 in the subject, elevated levels and/or activity of activin (e.g., free activin) as compared to prior levels and/or activity of activin (e.g., free activin) in the subject, elevated levels and/or activity of col1a1 as compared to prior levels and/or activity of col1a1 in the subject, elevated levels and/or activity of BSAP as compared to prior levels and/or activity of BSAP in the subject, elevated levels and/or activity of CTX as compared to prior levels and/or activity of CTX in the subject, elevated levels and/or activity of Osterix as compared to prior levels and/or activity of Osterix in the subject, decreased levels and/or activity of Klotho as compared to prior levels and/or activity of Klotho in the subject, decreased levels and/or activity of alpha-SMA as compared to prior levels and/or activity of alpha-SMA in the subject, decreased levels and/or activity of MYOCD as compared to prior levels and/or activity of MYOCD in the subject, decreased levels and/or activity of ActRIIA as compared to prior levels and/or activity of ActRIIA in the subject, and/or decreased levels and/or activity of Sm22-alpha as compared to prior levels and/or activity of Sm22-alpha in the subject. In certain embodiments, the prior levels and/or activity of Runx2 in the subject, the prior levels and/or activity of Alp in the subject, the prior levels and/or activity of Snail in the subject, the prior levels and/or activity of phosphosmad2 in the subject, the prior levels and/or activity of phosphosmad3 in the subject, the prior levels and/or activity of urinary protein in the subject, the prior levels and/or activity of Dkk1 in the subject, the prior levels and/or activity of activin (e.g., free activin) in the subject, the prior levels and/or activity of col1a1 in the subject, the prior levels and/or activity of BSAP in the subject, the prior levels and/or activity of CTX in the subject, the prior levels and/or activity of Osterix in the subject, the prior levels and/or activity of Klotho in the subject, the prior levels and/or activity of alpha-SMA in the subject, the prior levels and/or activity of MYOCD in the subject, the prior levels and/or activity of ActRIIA in the subject, and/or the prior levels and/or activity of Sm22-alpha in the subject are the respective levels 1, 2, 3, 4, 5, 6, 8, 10, 12, 18, 24, or 48 months before the onset of symptoms or the diagnosis of (i) cardiovascular disease; (ii) vascular calcification; (iii) cardiovascular disease associated with and/or resulting from vascular calcification; (iv) cardiovascular disease associated with and/or resulting from renal disease; (v) elevated levels of arterial stiffness; and/or left ventricular hypertrophy (LVH).

In certain embodiments, the subject is treated in accordance with the methods as described in 8.3.4. In certain embodiments, the vascular calcification in the subject is analyzed by measuring Agatston scores as described in Section 8.6.

In certain embodiments, a subject to be treated with the methods provided herein has the levels and/or activity of Snail, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha as described in Section 8.6. Thus, in certain specific embodiments, a method provided herein comprises (i) selecting a subject based on the levels and/or activity of Snail, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, and/or Sm22-alpha as described in Section 8.6; and (ii) administering a pharmaceutically effective dose of an ActRII signaling inhibitor (e.g., an activin ligand trap). In a specific embodiment, the subject has cardiovascular disease. In a specific embodiment, the subject has vascular calcification. In a specific embodiment, the subject has cardiovascular disease associated with and/or resulting from vascular calcification. In a specific embodiment, the subject has cardiovascular disease associated with and/or resulting from renal disease. In a specific embodiment, the subject has renal disease. In certain other embodiments, the subject has been diagnosed as having chronic kidney disease-mineral bone disorder. In certain other embodiments, the subject has not been diagnosed as having chronic kidney disease-mineral bone disorder. In certain embodiments, the vascular calcification in the subject is analyzed by measuring Agatston scores as described in Section 8.6. In specific embodiments, the subject has been diagnosed with elevated levels of arterial stiffness. In a specific embodiment, the subject has been diagnosed with LVH. In a specific embodiment, the subject has cardiovascular disease associated with and/or resulting from elevated levels of arterial stiffness. In a specific embodiment, the subject has cardiovascular disease associated with and/or resulting from LVH.

In certain embodiments, the levels and/or activity of Snail, phosphosmad2, Dkk1, col1a1, activin (e.g., free activin), Runx2, Alp, BSAP, CTX, Osterix, Klotho, alpha- SMA, MYOCD, phosphosmad3, urinary protein, ActRIIA, Axin2, and/or Sm22-alpha are determined as described in Section 8.6. In certain embodiments, the level and/or activity of Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha are the protein level and/or activity of Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha, respectively. In certain embodiments, the level and/or activity of Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha are the mRNA level and/or activity of Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha, respectively. In certain embodiments, the Snai1, phosphosmad2, Dkk1, col1a1, activin (e.g., free activin), Runx2, Alp, BSAP, CTX, Osterix, Klotho, Sm22-alpha, MYOCD, and/or ActRIIA, Axin2, alpha-SMA levels are in a tissue. In certain embodiments, the tissue is aorta. In certain embodiments, the tissue is kidney. In certain embodiments, the tissue is bone. In certain embodiments, the tissue is serum. In a preferred embodiment, the Runx2, Dkk1, Alp, osterix, sm22-alpha, Klotho, alpha-SMA, MYOCD, ActRIIA, Axin2 levels and/or activity are in aorta. In a preferred embodiment, the phosphosmad2, phosphosmad3, urinary protein, ActRIIA, Axin2, and col1a1 levels and/or activity are in kidney. In a preferred embodiment, the activin levels and/or activity are in serum. In certain embodiments, the levels of activin are elevated in the subject with respect to a reference population. In certain embodiments, the levels of follistatin in the subject are about equal to the levels of follistatin in a reference population.

In certain embodiments, the reference population is a population as described in Section 8.6. In certain embodiments, the subject is a subject as described in Section 8.4.

In certain embodiments, the ActRII signaling inhibitor is ActRIIA-Fc such as ActRIIA-hFc (e.g., SEQ ID NO:7). In certain embodiments, the ActRII signaling inhibitor is an ActRII signaling inhibitor as described in Section 8.5.

In certain embodiments, the pharmaceutically effective dose is a dose as described in Section 8.7. In certain embodiments, the pharmaceutically effective dose is an initial dose. In certain embodiments, the pharmaceutically effectively dose is administered at a frequency as described in Section 8.7. In certain embodiments, the pharmaceutically effective dose is administered as described in Section 8.7.

In certain embodiments, the methods provided herein are utilized in combination with a second pharmaceutically active agent, as described in Section 8.8.

In certain embodiments, "treat," "treatment," or "treating," in the context of cardiovascular disease or chronic kidney disease, includes amelioration of at least one symptom of cardiovascular disease or chronic kidney disease, respectively.

As will be recognized by one of skill in the art, levels and/or activity of one or more of Runx2, Alp, Snai1, phosphosmad2, Dkk1, col1a1, activin, BSAP, CTX, osterix, Klotho, alpha-SMA, MYOCD, ActRIIA, Axin2, Sm22-alpha, phosphosmad3, and urinary protein can be compared respectively to the level and/or activity in a corresponding reference population. Thus, in certain embodiments, the level and/or activity one of Runx2, Alp, Snai1, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein is compared to its level and/or activity in a corresponding reference population. In certain embodiments, the level and/or activity of two of Runx2, Alp, Snai1, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein is compared to its level and/or activity in a corresponding reference population. In certain embodiments, the level and/or activity of three of Runx2, Alp, Snai1, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein is compared to its level and/or activity in a corresponding reference population. In certain embodiments, the level and/or activity of three of Runx2, Alp, Snai1, phosphosmad2, Dkk1, col1a1, activin. BSAP, CTX, osterix. Klotho, alpha-SMA, MYOCD. Sm22-alpha, phosphosmad3, ActRIIA, Axin2, and urinary protein is compared to its level and/or activity in a corresponding reference population. In certain embodiments, the level and/or activity of four of Runx2, Alp, Snai1, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein is compared to its level and/or activity in a corresponding reference population. In certain embodiments, the level and/or activity of five of Runx2, Alp, Snai1, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein is compared to its level and/or activity in a corresponding reference population. In certain embodiments, the level and/or activity of six of Runx2, Alp, Snai1, phosphosmad2. Dkk1, col1a1, activin, BSAP, CTX, osterix, Klotho, alpha-SMA, MYOCD, Sm22-alpha, phosphosmad3. ActRIIA, Axin2, and urinary protein is compared to its level and/or activity in a corresponding reference population. In certain embodiments, the level and/or activity of seven of Runx2, Alp, Snai1, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein is compared to its level and/or activity in a corresponding reference population. In certain embodiments, the level and/or activity of eight of Runx2, Alp, Snai1, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein is compared to its level and/or activity in a corresponding reference population. In certain embodiments, the level and/or activity of nine of Runx2, Alp, Snai1, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein is compared to its level and/or activity in a corresponding reference population. In certain embodiments, the level and/or activity of ten of Runx2, Alp, Snai1, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein is compared to its level and/or activity in a corresponding reference population. In certain embodiments, the level and/or activity of eleven of Runx2, Alp, Snai1, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein is compared to its level and/or activity in a corresponding reference population. In certain embodiments, the level and/or activity of twelve of Runx2, Alp, Snai1, phosphosmad2, Dkk1, col1a1, activin, BSAP, CTX, osterix, Klotho, alpha-SMA, MYOCD, Sm22-alpha, phosphosmad3. ActRIIA, Axin2, and urinary protein is compared to its level and/or activity in a corresponding reference population. In certain embodiments, the level and/or activity of thirteen of Runx2, Alp, Snai1, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein is compared to its level and/or activity in a corresponding reference population. In certain embodiments, the level and/or activity of fourteen of Runx2, Alp, Snai1, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein is compared to its level and/or activity in a corresponding reference population. In certain embodiments, the level and/or activity of fifteen of Runx2, Alp, Snai1, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein is compared to its level and/or activity in a corresponding reference population. In certain embodiments, the level and/or activity of sixteen of Runx2, Alp, Snai1, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein is compared to its level and/or activity in a corresponding reference population. In certain embodiments, the level and/or activity of seventeen of Runx2, Alp, Snai1, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein is compared to its level and/or activity in a corresponding reference population. In certain embodiments, the level and/or activity of each of Runx2, Alp, Snai1, phosphosmad2, Dkk11, col1a1, activin, BSAP, CTX, osterix, Klotho, alpha-SMA, MYOCD, Sm22-alpha, phosphosmad3, ActRIIA, Axin2, and urinary protein is compared to its level and/or activity in a corresponding reference population.

Diseases Associated with Snai1, Phosphosmad2, Dkk1, Col1A1, Activin (e.g., Free Activin), Runx2, Alp, BSAP, CTX, Osterix, Klotho, Alpha-SMA, Myocd, Phosphosmad3, Urinary Protein, ActRIIA, Axin2, and/or Sm22-Alpha In certain embodiments, provided herein are methods for treating and/or preventing one or more diseases associated with Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha, comprising administering to the subject a pharmaceutically effective dose of an ActRII signaling inhibitor (e.g., an activin ligand trap).

In certain embodiments, the subject is a subject as described in Section 8.4.

In certain embodiments, the ActRII signaling inhibitor is ActRIIA-Fc such as ActRIIA-hFc (e.g., SEQ ID NO:7). In certain embodiments, the ActRII signaling inhibitor is an ActRII signaling inhibitor as described in Section 8.5.

In certain embodiments, the pharmaceutically effective dose is a dose as described in Section 8.7. In certain embodiments, the pharmaceutically effective dose is an initial dose. In certain embodiments, the pharmaceutically effectively dose is administered at a frequency as described in Section 8.7. In certain embodiments, the pharmaceutically effective dose is administered as described in Section 8.7. In certain embodiments, the pharmaceutically effective dose is adjusted depending on the level and/or activity of certain biomarkers as described herein.

In certain embodiments, the methods provided herein are utilized in combination with a second pharmaceutically active agent, as described in Section 8.8.

Chronic Kidney Disease-Mineral/Bone Disorder

In certain embodiments, provided herein are methods for treating chronic kidney disease-mineral bone disorder in a subject, comprising administering to the subject a pharmaceutically effective dose of an ActRII signaling inhibitor (e.g., an activin ligand trap). In certain embodiments, provided herein are methods for reducing bone resorption in a subject, comprising administering to the subject a pharmaceutically effective dose of an ActRII signaling inhibitor. In certain embodiments, the subject has cardiovascular disease. In certain embodiments, the subject has vascular calcification. In certain embodiments, the subject has cardiovascular disease associated with and/or resulting from vascular calcification. In certain embodiments, the subject has cardiovascular disease associated with and/or resulting from renal disease. In certain embodiments, the subject is a renal subject. In certain other embodiments, the subject has been diagnosed as having chronic kidney disease-mineral bone disorder. In certain other embodiments, the subject has not been diagnosed as having chronic kidney disease-mineral bone disorder.

In certain embodiments, the subject has elevated levels and/or activity of Runx2 as compared to levels and/or activity of Runx2 in a reference population, elevated levels and/or activity of Alp as compared to levels and/or activity of Alp in a reference population, elevated levels and/or activity of Snai1 as compared to levels and/or activity of Snai1 in a reference population, elevated levels and/or activity of phosphosmad2 as compared to levels and/or activity of phosphosmad2 in a reference population, elevated levels and/or activity of phosphosmad3 as compared to levels and/or activity of phosphosmad3 in a reference population, elevated levels and/or activity of urinary protein as compared to levels and/or activity of urinary protein in a reference population, elevated levels and/or activity of Dkk1 as compared to levels and/or activity of Dkk1 in a reference population, elevated levels and/or activity of col1a1 as compared to levels and/or activity of col1a1 in a reference population, elevated levels and/or activity of activin (e.g., free activin) as compared to levels and/or activity of activin (e.g., free activin) in a reference population, elevated levels and/or activity of BSAP as compared to levels and/or activity of BSAP in a reference population, elevated levels and/or activity of CTX as compared to levels and/or activity of CTX in a reference population, elevated levels and/or activity of Osterix as compared to levels and/or activity of Osterix in a reference population, decreased levels and/or activity of Klotho as compared to levels and/or activity of Klotho in a reference population, decreased levels and/or activity of alpha-SMA as compared to levels and/or activity of alpha-SMA in a reference population, decreased levels and/or activity of MYOCD as compared to levels and/or activity of MYOCD in a reference population, decreased levels and/or activity of ActRIIA as compared to levels and/or activity of ActRIIA in a reference population, and/or decreased levels and/or activity of Sm22-alpha as compared to levels and/or activity of Sm22-alpha in a reference population. In certain embodiments, the Snai1, phosphosmad2, Dkk1, col1a1, activin (e.g., free activin), Runx2, Alp, BSAP, CTX, Osterix, Klotho, Sm22-alpha, MYOCD, phosphosmad3, urinary protein, ActRIIA, and/or alpha-SMA levels are in a tissue. In certain embodiments, the tissue is aorta. In certain embodiments, the tissue is kidney. In certain embodiments, the tissue is bone. In certain embodiments, the tissue is serum. In a preferred embodiment, the Runx2, Dkk1, Alp, osterix, sm22-alpha, Klotho, alpha-SMA, MYOCD, and/or ActRIIA levels and/or activity are in aorta. In a preferred embodiment, the phosphosmad2, phosphosmad3, urinary protein, and col1a1, and/or ActRIIA levels and/or activity are in kidney. In a preferred embodiment, the activin levels and/or activity are in serum. In certain embodiments, the Snail, phosphosmad2, Dkk1, col1a1, activin (e.g., free activin), Runx2, Alp, BSAP, CTX, Osterix, Klotho, Sm22-alpha, MYOCD, ActRIIA, and/or alpha-SMA levels are in aorta.

In certain embodiments, the subject has elevated levels and/or activity of Runx2 as compared to prior levels and/or activity of Runx2 in the subject, elevated levels and/or activity of Alp as compared to prior levels and/or activity of Alp in the subject, elevated levels and/or activity of Snail as compared to prior levels and/or activity of Snail in the subject, elevated levels and/or activity of phosphosmad2 as compared to prior levels and/or activity of phosphosmad2 in the subject, elevated levels and/or activity of phosphosmad3 as compared to prior levels and/or activity of phosphosmad3 in the subject, elevated levels and/or activity of urinary protein as compared to prior levels and/or activity of urinary protein in the subject, elevated levels and/or activity of Dkk1 as compared to prior levels and/or activity of Dkk1 in the subject, elevated levels and/or activity of activin (e.g., free activin) as compared to prior levels and/or activity of activin (e.g., free activin) in the subject, elevated levels and/or activity of col1a1 as compared to prior levels and/or activity of col1a1 in the subject, elevated levels and/or activity of BSAP as compared to prior levels and/or activity of BSAP in the subject, elevated levels and/or activity of CTX as compared to prior levels and/or activity of CTX in the subject, elevated levels and/or activity of Osterix as compared to prior levels and/or activity of Osterix in the subject, decreased levels and/or activity of Klotho as compared to prior levels and/or activity of Klotho in the subject, decreased levels and/or activity of alpha-SMA as compared to prior levels and/or activity of alpha-SMA in the subject, decreased levels and/or activity of MYOCD as compared to prior levels and/or activity of MYOCD in the subject, decreased levels and/or activity of ActRIIA as compared to prior levels and/or activity of ActRIIA in the subject, and/or decreased levels and/or activity of Sm22-alpha as compared to prior levels and/or activity of Sm22-alpha in the subject. In certain embodiments, the prior levels and/or activity of Runx2 in the subject, the prior levels and/or activity of Alp in the subject, the prior levels and/or activity of Snail in the subject, the prior levels and/or activity of phosphosmad2 in the subject, the prior levels and/or activity of phosphosmad3 in the subject, the prior levels and/or activity of urinary protein in the subject, the prior levels and/or activity of Dkk1 in the subject, the prior levels and/or activity of activin (e.g., free activin) in the subject, the prior levels and/or activity of col1a1 in the subject, the prior levels and/or activity of BSAP in the subject, the prior levels and/or activity of CTX in the subject, the prior levels and/or activity of Osterix in the subject, the prior levels and/or activity of Klotho in the subject, the prior levels and/or activity of alpha-SMA in the subject, the prior levels and/or activity of MYOCD in the subject, the prior levels and/or activity of ActRIIA in the subject, and/or the prior levels and/or activity of Sm22-alpha in the subject are the respective levels 1, 2, 3, 4, 5, 6, 8, 10, 12, 18, 24, or 48 months before the onset of symptoms or the diagnosis of CKD-MBD.

In certain embodiments, the subject is treated in accordance with the methods as described in Section 8.3.4. In certain embodiments, the vascular calcification in the subject is analyzed by measuring Agatston scores as described in Section 8.6.

In certain embodiments, a subject to be treated with the methods provided herein has the levels and/or activity of Snail, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha as described in Section 8.6. Thus, in certain specific embodiments, a method provided herein comprises (i) selecting a subject based on the levels and/or activity of Snail, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, and/or Sm22-alpha as described in Section 8.6; and (ii) administering a pharmaceutically effective dose of an ActRII signaling inhibitor (e.g., an activin ligand trap). In a specific embodiment, the subject has cardiovascular disease. In a specific embodiment, the subject has vascular calcification. In a specific embodiment, the subject has cardiovascular disease associated with and/or resulting from vascular calcification. In a specific embodiment, the subject has cardiovascular disease associated with and/or resulting from renal disease. In a specific embodiment, the subject has renal disease. In certain other embodiments, the subject has been diagnosed as having chronic kidney disease-mineral bone disorder. In certain other embodiments, the subject has not been diagnosed as having chronic kidney disease-mineral bone disorder. In a specific embodiment, the subject has elevated levels of arterial stiffness. In a specific embodiment, the subject has cardiovascular disease associated with and/or resulting from elevated levels of arterial stiffness. In a specific embodiment, the subject has LVH. In a specific embodiment, the subject has cardiovascular disease associated with and/or resulting from LVH.

In certain embodiments, the levels and/or activity of Snail, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha are determined as described in Section 8.6. In certain embodiments, the elevated levels of Snail, phosphosmad2, Dkk1, col1a1, activin (e.g., free activin), Runx2, Alp, BSAP, CTX, phosphosmad3, urinary protein, and/or Osterix are as described in Section 8.6. In certain embodiments, the decreased levels of Klotho, alpha-SMA, MYOCD, ActRIIA, and/or Sm22-alpha are as described in Section 8.6. In certain embodiments, the Snail, phosphosmad2, Dkk1, col1a1, activin (e.g., free activin), Runx2, Alp, BSAP, (TX, Osterix, Klotho, Sm22-alpha, MYOCD, phosphosmad3, urinary protein, ActRIIA, and/or alpha-SMA levels are in a tissue. In certain embodiments, the tissue is aorta. In certain embodiments, the tissue is kidney. In certain embodiments, the tissue is bone. In certain embodiments, the tissue is serum. In a preferred embodiment, the Runx2, Dkk1, Alp, osterix, sm22-alpha, Klotho, alpha-SMA, ActRIIA, Axin2, and MYOCD levels and/or activity are in aorta. In a preferred embodiment, the phosphosmad2, phosphosmad3, urinary protein, ActRIIA, and col1a1 levels and/or activity are in kidney. In a preferred embodiment, the activin levels and/or activity are in serum. In certain embodiments, the level and/or activity of Snail, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, and/or Sm22-alpha are the protein level and/or activity of Snail, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, and/or Sm22-alpha, respectively. In certain embodiments, the level and/or activity of Snail, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, and/or Sm22-alpha are the mRNA level and/or activity of Snail, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, and/or Sm22-alpha, respectively. In certain embodiments, the levels of activin are elevated in the subject with respect to a reference population. In certain embodiments, the levels of follistatin in the subject are about equal to the levels of follistatin in a reference population.

In certain embodiments, the reference population is a population as described in Section 8.6. In certain embodiments, the subject is a subject as described in Section 8.4.

In certain embodiments, the ActRII signaling inhibitor is ActRIIA-Fc such as ActRIIA-hFc (e.g., SEQ ID NO:7). In certain embodiments, the ActRII signaling inhibitor is an ActRII signaling inhibitor as described in Sections 8.5.

In certain embodiments, the pharmaceutically effective dose is a dose as described in Section 8.7. In certain embodiments, the pharmaceutically effective dose is an initial dose. In certain embodiments, the pharmaceutically effectively dose is administered at a frequency as described in Section 8.7. In certain embodiments, the pharmaceutically effective dose is administered as described in Section 8.7.

In certain embodiments, the methods provided herein are utilized in combination with a second pharmaceutically active agent, as described in Section 8.8.

In certain embodiments, provided herein are methods for treating end-stage kidney disease in a subject, comprising administering to the subject a pharmaceutically effective dose of an ActRII signaling inhibitor (e.g., an activin ligand trap), wherein the subject is on hemodialysis, and wherein the subject has previously been administered an erythropoietin-stimulating agent. In certain embodiments, provided herein are methods for treating end-stage kidney disease in a subject, comprising subcutaneously administering to the subject 0.13 mg/kg of an ActRII signaling inhibitor (e.g., an activin ligand trap) at an interval of once every 14 days, wherein the subject is on hemodialysis, and wherein the subject has previously been administered an erythropoietin-stimulating agent. In certain embodiments, provided herein are methods for treating end-stage kidney disease in a subject, comprising subcutaneously administering to the subject 0.26 mg/kg of an ActRII signaling inhibitor (e.g., an activin ligand trap) at an interval of once every 14 days, wherein the subject is on hemodialysis, and wherein the subject has previously been administered an erythropoietin-stimulating agent. In certain embodiments, provided herein are methods for treating end-stage kidney disease in a subject, comprising subcutaneously administering to the subject 0.3 mg/kg of an ActRII signaling inhibitor (e.g., an activin ligand trap) at an interval of once every 28 days, wherein the subject is on hemodialysis, and wherein the subject has previously been administered an erythropoictin-stimulating agent. In certain embodiments, provided herein are methods for treating end-stage kidney disease in a subject, comprising subcutaneously administering to the subject 0.5 mg/kg of an ActRII signaling inhibitor (e.g., an activin ligand trap) at an interval of once every 28 days, wherein the subject is on hemodialysis, and wherein the subject has previously been administered an erythropoietin-stimulating agent. In certain embodiments, provided herein are methods for treating end-stage kidney disease in a subject, comprising subcutaneously administering to the subject 0.7 mg/kg of an ActRII signaling inhibitor (e.g., an activin ligand trap) at an interval of once every 28 days, wherein the subject is on hemodialysis, and wherein the subject has previously been administered an erythropoietin-stimulating agent. In certain embodiments, provided herein are methods for treating end-stage kidney disease in a subject, comprising intravenously administering to the subject 0.1 mg/kg of an ActRII signaling inhibitor (e.g., an activin ligand trap) at an interval of once every 14 days, wherein the subject is on hemodialysis, and wherein the subject has previously been administered an erythropoietin-stimulating agent. In certain embodiments, provided herein are methods for treating end-stage kidney disease in a subject, comprising subcutaneously administering to the subject 0.2 mg/kg of an ActRII signaling inhibitor (e.g., an activin ligand trap) at an interval of once every 14 days, wherein the subject is on hemodialysis, and wherein the subject has previously been administered an erythropoietin-stimulating agent. In certain embodiments, the ActRII signaling inhibitor is ActRIIA-hFc (SEQ ID NO:7).

Adjusted Dosing

In certain embodiments, the levels and/or activity of Snail, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha may be further used (i) to evaluate appropriate dosing for a subject, wherein the subject is a candidate to be treated or is being treated with an ActRII signaling inhibitor (e.g., an activin ligand trap); (ii) to evaluate whether to adjust the dosage of the ActRII signaling inhibitor during treatment; and/or (iii) to evaluate an appropriate maintenance dose of the ActRII signaling inhibitor. If the Snail, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha level and/or activity is greater than or less than the level and/or activity in a reference population, dosing with an ActRII signaling inhibitor may be initiated, increased, reduced, delayed or terminated depending on the level and/or activity of Snail, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha, respectively. In certain embodiments, provided herein are methods for treating and/or preventing cardiovascular disease, vascular calcification, cardiovascular disease associated with and/or resulting from vascular calcification, cardiovascular disease associated with and/or resulting from renal disease, CKD-MBD, elevated levels of arterial stiffness, LVH, cardiovascular disease associated with and/or resulting from elevated levels of arterial stiffness, and/or cardiovascular disease associated with and/or resulting from LVH, in a subject comprising (i) administering to the subject an initial dose of an ActRII signaling inhibitor; (ii) taking a first measurement of the level and/or activity of Snail, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha in the subject; (iii) after a period of time, taking a second measurement of the level and/or activity of Snail, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha in the subject; and (iv) administering to the subject an adjusted dose of the ActRII signaling inhibitor. In certain embodiments, the ActRII signaling inhibitor is ActRIIA-Fc such as ActRIIA-hFc (e.g., SEQ ID NO:7). In certain embodiments, the ActRII signaling inhibitor is an ActRII signaling inhibitor as described in Section 8.5. In certain other embodiments, the subject has been diagnosed as having chronic kidney disease-mineral bone disorder. In certain other embodiments, the subject has not been diagnosed as having chronic kidney disease-mineral bone disorder. In certain embodiments, the vascular calcification in the subject is analyzed by measuring Agatston scores as described in Section 8.6.6. In certain embodiments, the adjusted dose is based on the detected change between the first measurement and the second measurement.

In certain embodiments, the levels and/or activity of Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha are determined as described in Section 8.6. In certain embodiments, the level and/or activity of Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha are the protein level and/or activity of Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, and/or Sm22-alpha, respectively. In certain embodiments, the level and/or activity of Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha are the mRNA level and/or activity of Snai1, phosphosmad2, Dkk1, col1a1, activin (e.g., free activin), Runx2, Alp, BSAP, CTX, Osterix, Klotho, alpha-SMA, MYOCD, phosphosmad3, urinary protein, ActRIIA, Axin2, and/or Sm22-alpha, respectively. In certain embodiments, the Snai1, phosphosmad2, Dkk1, col1a1, activin (e.g., free activin), Runx2, Alp, BSAP, CTX, Osterix, Klotho, Sm22-alpha, MYOCD, phosphosmad3, urinary protein, ActRIIA, Axin2, and/or alpha-SMA levels are in a tissue. In certain embodiments, the tissue is aorta. In certain embodiments, the tissue is kidney. In certain embodiments, the tissue is bone. In certain embodiments, the tissue is serum. In a preferred embodiment, the Runx2, Dkk1, Alp, osterix, sm22-alpha, Klotho, alpha-SMA, MYOCD, ActRIIA, or Axin2 levels and/or activity are in aorta. In a preferred embodiment, the phosphosmad2, phosphosmad3, urinary protein, ActRIIA, Axin2, and col1a1 levels and/or activity are in kidney. In a preferred embodiment, the activin levels and/or activity are in serum. In certain embodiments, the levels of activin are elevated in the subject with respect to a reference population. In certain embodiments, the levels of follistatin are normal in the subject with respect to a reference population. In certain embodiments, the vascular calcification in the subject is analyzed by measuring Agatston scores as described in Section 8.6.

In certain embodiments, the reference population is a population as described in Section 8.6. In certain embodiments, the subject is a subject as described in Section 8.4.

In certain embodiments, the initial dose is a dose as described in Section 8.7. In certain embodiments, the initial dose is administered at a frequency as described in Section 8.7. In certain embodiments, the initial dose is administered as described in Section 8.7.

In certain embodiments, the first measurement and/or the second measurement is taken as described in Section 8.6. In certain embodiments, the first measurement is taken prior to the commencement of the treatment. In certain embodiments, the first measurement is taken after the commencement of the treatment or within at most 1 day, 2 days, 3 days, 4 days, 5 days, 6 days, or 1 week, 2 weeks, 3 weeks, 4 weeks, or two months thereof. In certain embodiments, the second measurement is taken immediately after commencement of the treatment or within at most 1 day, 2 days, 3 days, 4 days, 5 days, 6 days, or 1 week, 2 weeks, 1 month, 2 months, 3 months, 4 months, 5 months, 6 months, 7 months, 8 months, 9 months, 10 months, 11 months, or 12 months thereof.

In certain embodiments, the adjusted dose of the ActRII signaling inhibitor is greater than the initial dose if the level and/or activity of Runx2 is elevated as compared to the level and/or activity of Runx2 in a reference population, the level and/or activity of Alp is elevated as compared to the level and/or activity of Alp in a reference population, the level and/or activity of Snai1 is elevated as compared to the level and/or activity of Snai1 in a reference population, the level and/or activity of phosphosmad2 is elevated as compared to the level and/or activity of phosphosmad2 in a reference population, the level and/or activity of phosphosmad3 is elevated as compared to the level and/or activity of phosphosmad3 in a reference population, the level and/or activity of urinary protein is elevated as compared to the level and/or activity of urinary protein in a reference population, the level and/or activity of Dkk1 is elevated as compared to the level and/or activity of Dkk1 in a reference population, the level and/or activity of col1a1 is elevated as compared to the level and/or activity of col1a1 in a reference population, the level and/or activity of activin (e.g., free activin) is elevated as compared to the level and/or activity of activin (e.g., free activin) in a reference population, the level and/or activity of BSAP is elevated as compared to the level and/or activity of BSAP in a reference population, the level and/or activity of CTX is elevated as compared to the level and/or activity of CTX in a reference population, the level and/or activity of Osterix is elevated as compared to the level and/or activity of Osterix in a reference population, the level and/or activity of Klotho is decreased as compared to the level and/or activity of Klotho in a reference population, the level and/or activity of alpha-SMA is decreased as compared to the level and/or activity of alpha-SMA in a reference population, the level and/or activity of MYOCD is decreased as compared to the level and/or activity of MYOCD in a reference population, the level and/or activity of ActRIIA is decreased as compared to the level and/or activity of ActRIIA in a reference population, the level and/or activity of Axin2 is decreased as compared to the level and/or activity of Axin2 in a reference population, and/or the level and/or activity of Sm22-alpha is decreased as compared to the level and/or activity of Sm22-alpha in a reference population. In certain embodiments, the elevated levels of Snai1, phosphosmad2, Dkk1, col1a1, activin (e.g., free activin), Runx2, Alp, BSAP, CTX, phosphosmad3, urinary protein, and/or Osterix are as described in Section 8.6. In certain embodiments, the decreased levels of Klotho, alpha-SMA, ALP, ActRIIA, Axin2, and/or Sm22-alpha are as described in Section 8.6. In certain embodiments, the Snai1, phosphosmad2, Dkk1, col1a1, activin (e.g., free activin), Runx2, Alp, BSAP, CTX, Osterix, Klotho, Sm22-alpha, MYOCD, phosphosmad3, urinary protein, ActRIIA, Axin2, and/or alpha-SMA levels are in a tissue. In certain embodiments, the tissue is aorta. In certain embodiments, the tissue is kidney. In certain embodiments, the tissue is bone. In certain embodiments, the tissue is serum. In a preferred embodiment, the Runx2, Dkk1, Alp, osterix, sm22-alpha, Klotho, alpha-SMA, ActRIIA, Axin2, and MYOCD levels and/or activity are in aorta. In a preferred embodiment, the phosphosmad2, phosphosmad3, urinary protein, ActRIIA, Axin2, and col1a1 levels and/or activity are in kidney. In a preferred embodiment, the activin levels and/or activity are in serum.

In certain embodiments, the adjusted dose is a dose as described in Section 8.7. In certain embodiments, the adjusted dose is administered at a frequency as described in Section 8.7. In certain embodiments, the adjusted dose is administered as described in Section 8.7.

In certain embodiments, the subject has elevated levels and/or activity of Runx2 as compared to prior levels and/or activity of Runx2 in the subject, elevated levels and/or activity of Alp as compared to prior levels and/or activity of Alp in the subject, elevated levels and/or activity of Snail as compared to prior levels and/or activity of Snail in the subject, elevated levels and/or activity of phosphosmad2 as compared to prior levels and/or activity of phosphosmad2 in the subject, elevated levels and/or activity of phosphosmad3 as compared to prior levels and/or activity of phosphosmad3 in the subject, elevated levels and/or activity of urinary protein as compared to prior levels and/or activity of urinary protein in the subject, elevated levels and/or activity of Dkk1 as compared to prior levels and/or activity of Dkk1 in the subject, elevated levels and/or activity of activin (e.g., free activin) as compared to prior levels and/or activity of activin (e.g., free activin) in the subject, elevated levels and/or activity of col1a1 as compared to prior levels and/or activity of col1a1 in the subject, elevated levels and/or activity of BSAP as compared to prior levels and/or activity of BSAP in the subject, elevated levels and/or activity of CTX as compared to prior levels and/or activity of CTX in the subject, elevated levels and/or activity of Osterix as compared to prior levels and/or activity of Osterix in the subject, decreased levels and/or activity of Klotho as compared to prior levels and/or activity of Klotho in the subject, decreased levels and/or activity of alpha-SMA as compared to prior levels and/or activity of alpha-SMA in the subject, decreased levels and/or activity of MYOCD as compared to prior levels and/or activity of MYOCD in the subject, decreased levels and/or activity of ActRIIA as compared to prior levels and/or activity of ActRIIA in the subject, decreased levels and/or activity of Axin2 as compared to prior levels and/or activity of Axin2 in the subject, and/or decreased levels and/or activity of Sm22-alpha as compared to prior levels and/or activity of Sm22-alpha in the subject. In certain embodiments, the prior levels and/or activity of Runx2 in the subject, the prior levels and/or activity of Alp in the subject, the prior levels and/or activity of Snail in the subject, the prior levels and/or activity of phosphosmad2 in the subject, the prior levels and/or activity of phosphosmad3 in the subject, the prior levels and/or activity of urinary protein in the subject, the prior levels and/or activity of Dkk1 in the subject, the prior levels and/or activity of activin (e.g., free activin) in the subject, the prior levels and/or activity of col1a1 in the subject, the prior levels and/or activity of BSAP in the subject, the prior levels and/or activity of CTX in the subject, the prior levels and/or activity of Osterix in the subject, the prior levels and/or activity of Klotho in the subject, the prior levels and/or activity of alpha-SMA in the subject, the prior levels and/or activity of MYOCD in the subject, the prior levels and/or activity of ActRIIA in the subject, the prior levels and/or activity of ActRIIA in the subject, the prior levels and/or activity of Axin2 in the subject, the prior levels and/or activity of Axin2 in the subject, and/or the prior levels and/or activity of Sm22-alpha in the subject are the respective levels 1, 2, 3, 4, 5, 6, 8, 10, 12, 18, 24, or 48 months before the onset of symptoms or the diagnosis of (i) cardiovascular disease; (ii) vascular calcification; (iii) cardiovascular disease associated with and/or resulting from vascular calcification; (iv) cardiovascular disease associated with and/or resulting from renal disease; (v) CKD-MBD; (vi) elevated levels of arterial stiffness; (vii) LVH; (viii) cardiovascular disease associated with and/or resulting from elevated levels of arterial stiffness; and/or (ix) cardiovascular disease associated with and/or resulting from LVH.

In certain embodiments, the adjusted dose of the ActRII signaling inhibitor (e.g., an activin ligand trap) is less than the initial dose if the level and/or activity of Runx2 is decreased as compared to the level and/or activity of Runx2 in a reference population, the level and/or activity of Alp is decreased as compared to the level and/or activity of Alp in a reference population, the level and/or activity of Snail is decreased as compared to the level and/or activity of Snail in a reference population, the level and/or activity of phosphosmad2 is decreased as compared to the level and/or activity of phosphosmad2 in a reference population, the level and/or activity of phosphosmad3 is decreased as compared to the level and/or activity of phosphosmad3 in a reference population, the level and/or activity of urinary protein is decreased as compared to the level and/or activity of urinary protein in a reference population, the level and/or activity of Dkk1 is decreased as compared to the level and/or activity of Dkk1 in a reference population, the level and/or activity of col1a1 is decreased as compared to the level and/or activity of col1a1 in a reference population, the level and/or activity of activin (e.g., free activin) is decreased as compared to the level and/or activity of activin (e.g., free activin) in a reference population, the level and/or activity of BSAP is decreased as compared to the level and/or activity of BSAP in a reference population, the level and/or activity of CTX is decreased as compared to the level and/or activity of CTX in a reference population, the level and/or activity of Osterix is decreased as compared to the level and/or activity of Osterix in a reference population, the level and/or activity of Klotho is elevated as compared to the level and/or activity of Klotho in a reference population, the level and/or activity of alpha-SMA is elevated as compared to the level and/or activity of alpha-SMA in a reference population, the level and/or activity of MYOCD is elevated as compared to the level and/or activity of MYOCD in a reference population, the level and/or activity of ActRIIA is elevated as compared to the level and/or activity of ActRIIA in a reference population, the level and/or activity of Axin2 is elevated as compared to the level and/or activity of Axin2 in a reference population, and/or the level and/or activity of Sm22-alpha is elevated as compared to the level and/or activity of Sm22-alpha in a reference population. In certain embodiments, the elevated levels of Klotho, alpha-SMA, MYOCD, ActRIIA, Axin2, and/or Sm22-alpha are as described in Section 8.6. In certain embodiments, the decreased levels of Snail, phosphosmad2, Dkk1, col1a1, activin (e.g., free activin), Runx2, Alp, BSAP, CTX, phosphosmad3, urinary protein, and/or Osterix are as described in Section 8.6. In certain embodiments, the Snail, phosphosmad2, Dkk1, col1a1, activin (e.g., free activin), Runx2, Alp, BSAP, CTX, Osterix, Klotho, Sm22-alpha, MYOCD, phosphosmad3, urinary protein, ActRIIA. Axin2, and/or alpha-SMA levels are in a tissue. In certain embodiments, the tissue is aorta. In certain embodiments, the tissue is kidney. In certain embodiments, the tissue is bone. In certain embodiments, the tissue is serum. In a preferred embodiment, the Runx2, Dkk1, Alp, osterix, sm22-alpha, Klotho, alpha-SMA, ActRIIA, Axin2, and MYOCD levels and/or activity are in aorta. In a preferred embodiment, the phosphosmad2, phosphosmad3, urinary protein. ActRIIA, Axin2, and col1a1 levels and/or activity are in kidney. In a preferred embodiment, the activin levels and/or activity are in serum.

In certain embodiments, the Snai1, phosphosmad2, Dkk1, col1a1, activin (e.g., free activin), Runx2, Alp, BSAP, CTX, Osterix, Klotho, Sm22-alpha, MYOCD, ActRIIA, Axin2, and/or alpha-SMA levels are in aorta.

In certain embodiments, the reference population is a population as described in Section 8.6. In certain embodiments, the adjusted dose is a dose as described in Section 8.7. In certain embodiments, the adjusted dose is administered at a frequency as described in Section 8.7. In certain embodiments, the adjusted dose is administered as described in Section 8.7

In certain embodiments, the methods provided herein are utilized in combination with a second pharmaceutically active agent, as described in Section 8.8.

As will be recognized by one of skill in the art, levels and/or activity of one or more of Runx2, Alp, Snai1, phosphosmad2, Dkk1, col1a1, activin, BSAP, CTX, osterix, Klotho, alpha-SMA, MYOCD, ActRIIA, Axin2, Sm22-alpha, phosphosmad3, and urinary protein can be compared independently and respectively to the level and/or activity in a corresponding reference population, such as described above in Section 8.3.1.

Patient Populations

The subjects treated in accordance with the methods described herein can be any mammals such as rodents and primates, and in a preferred embodiment, humans. In certain embodiments, the methods described herein can be used to treat cardiovascular disease, vascular calcification, cardiovascular disease associated with and/or resulting from vascular calcification, cardiovascular disease associated with and/or resulting from renal disease, high-turnover ROD, elevated levels of arterial stiffness, cardiovascular disease associated with and/or resulting from elevated levels of arterial stiffness, LVH, and/or cardiovascular disease associated with and/or resulting from LVH; or to monitor and/or decrease vascular calcification, arterial (e.g., vascular) stiffness, LVH, aortic calcium levels, endothelial to mesenchymal transition, and/or bone formation, and/or to increase bone mineral density and/or vascular smooth muscle cell function, in any mammals such as rodents and primates, and in a preferred embodiment, in human subjects.

In certain embodiments, the subject treated in accordance with the methods described herein has elevated levels of activin as compared to the levels of activin in a reference population. In certain embodiments, the activin levels are the kidney, plasma, or aortic activin levels. In certain embodiments, the activin is activin A. In certain embodiments, the subject treated in accordance with the methods described herein has about equal levels of follistatin as compared to the levels of follistatin in a reference population. In certain embodiments, the subject treated in accordance with the methods described herein does not have elevated levels of follistatin as compared to the levels of follistatin in a reference population. In certain embodiments, the subject treated in accordance with the methods described herein does not have decreased levels of follistatin as compared to the levels of follistatin in a reference population. In certain embodiments, the subject treated in accordance with the methods described herein has about equal levels of follistatin-like 3 as compared to the levels of follistatin-like 3 in a reference population. In certain embodiments, the subject treated in accordance with the methods described herein does not have elevated levels of follistatin-like 3 as compared to the levels of follistatin-like 3 in a reference population. In certain embodiments, the subject treated in accordance with the methods described herein does not have decreased levels of follistatin-like 3 as compared to the levels of follistatin-like 3 in a reference population. In certain embodiments, the subject treated in accordance with the methods described herein has about equal levels of inhibin as compared to the levels of inhibin in a reference population. In certain embodiments, the subject treated in accordance with the methods described herein does not have elevated levels of inhibin as compared to the levels of inhibin in a reference population. In certain embodiments, the subject treated in accordance with the methods described herein does not have decreased levels of inhibin as compared to the levels of inhibin in a reference population. In certain embodiments, the level of free activin in a subject is determined by the stoichiometry of inhibin, follistatin, and follistatin-like 3 levels to activin levels. Accordingly, in certain embodiments, the subject treated in accordance with the methods described herein has an increased level of free activin.

In certain embodiments, the subject treated in accordance with the methods described herein does not have an increase in phosphoerk 1/2 as compared to a reference population as described in Section 8.6. In certain embodiments, the phosphoerk 1/2 is aortic phosphoerk 1/2.

In certain embodiments, the subject treated in accordance with the methods described herein has increased endothelial to mesenchymal transition (EnMT) as compared to EnMT in a reference population. In certain embodiments, the subject treated in accordance with the methods described herein has increased expression of transcription factors associated with EnMT, such as, for example, Snai1. In certain embodiments, the increased EnMT in the subject results in increased osteoblastic transition in the subject as compared to the osteoblastic transition in a reference population. In certain embodiments, the increased EnMT in the subject results in increased vascular stiffness in the subject as compared to the vascular stiffness in a reference population. In certain embodiments, the increased EnMT in the subject results in increased vascular calcification in the subject as compared to the vascular calcification in a reference population. In certain embodiments, the increased EnMT in the subject results in decreased vascular smooth muscle function in the subject as compared to the vascular smooth muscle function in a reference population. In certain embodiments, the increased EnMT in the subject results in increased LVH in the subject as compared to the LVH in a reference population.

In certain embodiments, the subject treated in accordance with the methods provided herein has renal fibrosis. In certain embodiments, the subject treated in accordance with the methods provided herein has glomerulosclerosis.

In certain embodiments, the subject treated in accordance with the methods described herein has elevated levels and/or activity of Snai1, phosphosmad2, Dkk1, col1a1, activin (e.g., free activin), Runx2, Alp, BSAP, CTX, phosphosmad3, urinary protein, and/or Osterix, and/or decreased levels and/or activity of Klotho, alpha-SMA, MYOCD, ActRIIA, and/or Sm22-alpha, as compared to the levels of Snai1, phosphosmad2, Dkk1, col1a1, activin (e.g., free activin), Runx2, Alp, BSAP, CTX, phosphosmad3, urinary protein, Osterix, Klotho, alpha-SMA, MYOCD, ActRIIA, and/or Sm22-alpha, respectively, in a reference population. In certain embodiments, the subject treated in accordance with the methods described herein has (i) vascular calcification; and (ii) elevated levels and/or activity of Snai1, phosphosmad2, phosphosmad3, urinary protein, Dkk1, col1a1, activin (e.g., free activin), Runx2, Alp, BSAP, CTX, and/or Osterix, and/or decreased levels and/or activity of Klotho, alpha-SMA, MYOCD, ActRIIA, and/or Sm22-alpha, as compared to the levels of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha, respectively, in a reference population. In certain embodiments, the subject treated in accordance with the methods described herein has (i) cardiovascular disease; and (ii) elevated levels and/or activity of Snai1, phosphosmad2, phosphosmad3, urinary protein, Dkk1, col1a1, activin (e.g., free activin), Runx2, Alp, BSAP, CTX, and/or Osterix, and/or decreased levels and/or activity of Klotho, alpha-SMA, MYOCD, ActRIIA, and/or Sm22-alpha, as compared to the levels of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, and/or Sm22-alpha, respectively, in a reference population. In certain embodiments, the subject treated in accordance with the methods described herein has (i) cardiovascular disease associated with and/or resulting from vascular calcification, and (ii) elevated levels and/or activity of Snai1, phosphosmad2, phosphosmad3, urinary protein, Dkk1, col1a1, activin (e.g., free activin), Runx2, Alp, BSAP, CTX, and/or Osterix, and/or decreased levels and/or activity of Klotho, alpha-SMA, MYOCD, ActRIIA, and/or Sm22-alpha, as compared to the levels of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, and/or Sm22-alpha, respectively, in a reference population. In certain embodiments, the subject treated in accordance with the methods described herein has (i) cardiovascular disease associated with and/or resulting from renal disease; and (ii) elevated levels and/or activity of Snai1, phosphosmad2, phosphosmad3, urinary protein, Dkk1, col1a1, activin (e.g., free activin), Runx2, Alp, BSAP, CTX, and/or Osterix, and/or decreased levels and/or activity of Klotho, alpha-SMA, MYOCD, ActRIIA, and/or Sm22-alpha, as compared to the levels of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha, respectively, in a reference population. In certain embodiments, the subject treated in accordance with the methods described herein has (i) CKD-MBD; and (ii) elevated levels and/or activity of Snai1, phosphosmad2, phosphosmad3, urinary protein. Dkk1, col1a1, activin (e.g., free activin), Runx2, Alp, BSAP, CTX, and/or Osterix, and/or decreased levels and/or activity of Klotho, alpha-SMA, MYOCD, ActRIIA, and/or Sm22-alpha, as compared to the levels of Snai1, phosphosmad2, phosphosmad3, urinary protein, Dkk1, col1a1, activin (e.g., free activin). Runx2, Alp, BSAP, CTX, Osterix, Klotho, alpha-SMA, MYOCD, ActRIIA, and/or Sm22-alpha, respectively, in a reference population. In certain embodiments, the subject treated in accordance with the methods described herein has (i) elevated levels of arterial stiffness; and (ii) elevated levels and/or activity of Snai1, phosphosmad2, phosphosmad3, urinary protein, Dkk1, col1a1, activin (e.g., free activin). Runx2, Alp, BSAP, CTX, and/or Osterix, and/or decreased levels and/or activity of Klotho, alpha-SMA, MYOCD, ActRIIA, and/or Sm22-alpha, as compared to the levels of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, and/or Sm22-alpha, respectively, in a reference population. In certain embodiments, the subject treated in accordance with the methods described herein has (i) cardiovascular disease associated with and/or resulting from elevated levels of arterial stiffness; and (ii) elevated levels and/or activity of Snai1, phosphosmad2, phosphosmad3, urinary protein, Dkk1, col1a1, activin (e.g., free activin), Runx2, Alp, BSAP, CTX, and/or Osterix, and/or decreased levels and/or activity of Klotho, alpha-SMA, MYOCD, ActRIIA, and/or Sm22-alpha, as compared to the levels of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, and/or Sm22-alpha, respectively, in a reference population. In certain embodiments, the subject treated in accordance with the methods described herein has (i) LVH; and (ii) elevated levels and/or activity of Snai1, phosphosmad2, phosphosmad3, urinary protein, Dkk1, col1a1, activin (e.g., free activin), Runx2, Alp, BSAP, CTX, and/or Osterix, and/or decreased levels and/or activity of Klotho, alpha-SMA, MYOCD, ActRIIA, and/or Sm22-alpha, as compared to the levels of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, and/or Sm22-alpha, respectively, in a reference population. In certain embodiments, the subject treated in accordance with the methods described herein has (i) cardiovascular disease associated with and/or resulting from LVH; and (ii) elevated levels and/or activity of Snai1, phosphosmad2, phosphosmad3, urinary protein, Dkk1, col1a1, activin (e.g., free activin), Runx2, Alp, BSAP, CTX, and/or Osterix, and/or decreased levels and/or activity of Klotho, alpha-SMA, MYOCD, ActRIIA, and/or Sm22-alpha, as compared to the levels of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, and/or Sm22-alpha, respectively, in a reference population.

In certain embodiments, the subject treated in accordance with the methods described herein has elevated levels and/or activity of Snai1, phosphosmad2, phosphosmad3, urinary protein, Dkk1, col1a1, activin (e.g., free activin), Runx2, Alp, BSAP, CTX, and/or Osterix, and/or decreased levels and/or activity of Klotho, alpha-SMA, MYOCD, ActRIIA, and/or Sm22-alpha, as compared to prior levels of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, and/or Sm22-alpha, respectively, in the subject 1, 2, 3, 4, 5, 6, 8, 10, 12, 18, 24, or 48 months before the onset of symptoms or the diagnosis of (i) cardiovascular disease; (ii) vascular calcification; (iii) cardiovascular disease associated with and/or resulting from vascular calcification; (iv) cardiovascular disease associated with and/or resulting from renal disease; (v) CKD-MBD; (vi) elevated levels of arterial stiffness; (vii) LVH; (viii) cardiovascular disease associated with and/or resulting from elevated levels of arterial stiffness; and/or (ix) cardiovascular disease associated with and/or resulting from LVH.

In certain other embodiments, the subject has been diagnosed as having chronic kidney disease-mineral bone disorder. In certain other embodiments, the subject has not been diagnosed as having chronic kidney disease-mineral bone disorder. In certain embodiments, the reference population is a population as described in Section 8.6. In certain embodiments, the elevated levels of Snai1, phosphosmad2, phosphosmad3, urinary protein, Dkk1, col1a1, activin (e.g., free activin), Runx2, Alp, BSAP, CTX, and/or Osterix are as described in Section 8.6. In certain embodiments, the decreased levels of Klotho, alpha-SMA, MYOCD, ActRIIA, and/or Sm22-alpha are as described in Section 8.6.

In certain embodiments, the subject treated in accordance with the methods provided herein has a disease associated with elevated Snai1 levels. In certain embodiments, the subject treated in accordance with the methods provided herein has a disease associated with elevated phosphosmad2 levels. In certain embodiments, the subject treated in accordance with the methods provided herein has a disease associated with elevated phosphosmad3 levels. In certain embodiments, the subject treated in accordance with the methods provided herein has a disease associated with elevated urinary protein levels. In certain embodiments, the subject treated in accordance with the methods provided herein has a disease associated with elevated Dkk1 levels. In certain embodiments, the subject treated in accordance with the methods provided herein has a disease associated with elevated Col1a1 levels. In certain embodiments, the subject treated in accordance with the methods provided herein has a disease associated with elevated Runx2 levels. In certain embodiments, the subject treated in accordance with the methods provided herein has a disease associated with elevated Alp levels. In certain embodiments, the subject treated in accordance with the methods provided herein has a disease associated with elevated BSAP levels. In certain embodiments, the subject treated in accordance with the methods provided herein has a disease associated with elevated CTX levels. In certain embodiments, the subject treated in accordance with the methods provided herein has a disease associated with elevated Osterix levels. In certain embodiments, the subject treated in accordance with the methods provided herein has a disease associated with elevated ActRIIA levels. In certain embodiments, the subject treated in accordance with the methods provided herein has a disease associated with decreased Klotho levels. In certain embodiments, the subject treated in accordance with the methods provided herein has a disease associated with decreased alpha-SMA levels. In certain embodiments, the subject treated in accordance with the methods provided herein has a disease associated with decreased MYOCD levels. In certain embodiments, the subject treated in accordance with the methods provided herein has a disease associated with decreased Sm22-alpha levels. In certain embodiments, the subject treated in accordance with the methods provided herein has a disease associated with decreased ActRIIA levels.

In certain embodiments, the subject treated in accordance with the methods provided herein has cardiovascular disease. In certain embodiments, the subject treated in accordance with the methods provided herein has vascular calcification. In certain embodiments, the subject treated in accordance with the methods provided herein has a cardiovascular disease associated with and/or resulting from vascular calcification. In certain embodiments, the vascular calcification is determined as described in Section 8.6. In certain embodiments, the vascular calcification is determined by Agatston score. In certain embodiments, the vascular calcification is calcific atherosclerosis, calcific medial vasculopathy (also known as Mönckeberg's medial calcific sclerosis), medial calcification, elastocalcinosis, calcific uremic arteriolopathy, calcific aortic valvular stenosis, and/or portal vein calcification. In certain embodiments, the disease associated with calcific atherosclerosis is atherosclerosis, hyperlipidemia, osteoporosis, hypertension, inflammation, type 2 diabetes mellitus, end-stage renal disease, required amputation, pseudoxanthoma elasticum, end-stage renal disease, hyperlipidemia, congenital bicuspid valve, rheumatic heart disease, and/or liver disease. In certain embodiments, the subject treated in accordance with the methods provided herein has CKD-induced increased heart weight. In certain embodiments, the subject has cardiac hypertrophy. In certain embodiments, the subject has myocyte hypertrophy. In certain embodiments, the subject has increased arterial and/or vascular stiffness. In certain embodiments, the subject has LVH.

In certain embodiments, the subject treated in accordance with the methods described herein has an undesirably high level of aortic calcium, vascular calcification, elevated levels of arterial stiffness, and/or osteoblast numbers as compared to a reference population as described in Section 8.6. In certain embodiments, the subject treated in accordance with the methods described herein is at risk for developing undesirably high level of aortic calcium, vascular calcification, elevated levels of arterial stiffness, and/or osteoblast numbers, such as a subject with chronic kidney disease as compared to a reference population as described in Section 8.6. In certain embodiments, the subject treated in accordance with the methods provided herein has calcium deposits in aortic atheromas as compared to a reference population as described in Section 8.6. In certain embodiments, the subject treated in accordance with the methods provided herein has elevated levels of arterial stiffness in the form of aortic stiffness as compared to a reference population as described in Section 8.6. In certain embodiments, the subject treated in accordance with the methods provided herein has a level of elevated levels of arterial stiffness that increases hypertension as compared to a reference population as described in Section 8.6.

In certain embodiments, the subject treated in accordance with the methods provided herein has cardiovascular disease is associated with and/or results from renal disease. In certain embodiments, the renal disease is chronic kidney disease. In certain embodiments, the subject treated in accordance with the methods provided herein has chronic kidney disease. In certain embodiments, the subject has cardiovascular disease secondary to chronic kidney disease. In certain embodiments, the chronic kidney disease has reached stage 3, stage 4, stage 5, or stage 5D. In a specific embodiment, the kidney disease is end-stage kidney disease. In certain embodiments, the subject has a glomerular filtration rate of less than 60 ml/min/1.73 m$^2$ in adults or less than 89 ml/min/1.73 m$^2$ in pediatric subjects. See, Moe et al., 2006, Kidney International 69:1945-1953. In certain embodiments, the subject is an adult, wherein the subject has a glomerular filtration rate of less than 50 ml/min/1.73 m$^2$, 40 ml/min/1.73 m$^2$, 30 ml/min/1.73 m$^2$, 20 ml/min/1.73 m$^2$, or less than 10 ml/min/1.73 m$^2$. In certain embodiments, the subject is a pediatric subject, wherein the pediatric subject has a glomerular filtration rate of less than 80 ml/min/1.73 m$^2$, 70 ml/min/1.73 m$^2$, 60 ml/min/1.73 m$^2$, 50 ml/min/1.73 m$^2$, 40 ml/min/1.73 m$^2$, 30 ml/min/1.73 m$^2$, 20 ml/min/1.73 m$^2$, or less than 10 ml/min/1.73 m$^2$. Without being bound by theory, a glomerular filtration rate of less than 60 ml/min/1.73 m$^2$ in adult subjects and less than 89 ml/min/1.73 m$^2$ in pediatric subjects results in detectable abnormalities in calcium levels, phosphorus levels, PTH levels, and vitamin D metabolism; and abnormal levels of these markers result in bone disease. In certain embodiments, the subject has reduced inulin clearance as compared to a reference population, such as a reference population as described in Section 8.6. In certain embodiments, the subject has reduced blood urea nitrogen levels as compared to a reference population, such as a reference population as described in Section 8.6. In certain embodiments, the subject is hyperphosphatemic. In certain embodiments, the subject has renal fibrosis.

In certain embodiments, the subject has Alport's syndrome. In certain embodiments, the subject has one or more somatic mutations in the COL4A5 gene associated with Alport's syndrome.

In certain embodiments, the subject treated in accordance with the methods provided herein has a bone pathology associated with chronic kidney disease, i.e., CKD-Mineral/Bone Disorder (CKD-MBD). See Moe et al., 2006, Kidney International 69:1945-1953. In certain embodiments, the subject has decreased trabecular bone volume as compared to trabecular bone volume in a reference population, such as a reference population as described in Section 8.6. In certain embodiments, the subject has decreased trabecular thickness as compared to trabecular thickness in a reference population, such as a reference population as described in Section 8.6. In certain embodiments, the subject has increased erosion surface to bone surface ratio as compared to erosion surface to bone surface ratio in a reference population, such as a reference population as described in Section 8.6. In certain embodiments, the subject has increased osteoclast levels as compared to osteoclast levels in a reference population, such as a reference population as described in Section 8.6. In certain embodiments, the subject has increased osteoblast surface to bone surface ratio as compared to osteoblast surface to bone surface ratio in a reference population, such as a reference population as described in Section 8.6. In certain embodiments, the subject has increased osteoblast levels as compared to osteoblast levels in a reference population, such as a reference population as described in Section 8.6. In certain embodiments, the subject has reduced bone formation rate as compared to bone formation rate in a reference population, such as a reference population as described in Section 8.6. In certain embodiments, the CKD-MBD consists of renal osteodystrophy and vascular calcification. In certain embodiments, the CKD-MBD consists of renal osteodystrophy. In certain embodiments, the CKD-MBD is low-turnover CKD-MBD. In certain embodiments, the CKD-MBD consists of elevated levels of arterial stiffness and/or LVH. Low-turnover CKD-MBD can be diagnosed by the histological features set forth in Table 1 below. See National Kidney Foundation, Kidney Disease Outcomes Quality Initiative Guidelines at the website of the National Kidney Foundation. In certain embodiments, the subject has high-turnover ROD.

TABLE 1

Histological Features of Low-Turnover CKD-MBD

| Feature | Adynamic | Osteomalacia |
|---|---|---|
| Bone Formation | | |
| Trabecular bone volume | Normal, low | Variable Low, normal or high |
| Osteoid volume | Normal, low | High-very high |
| Osteoid seam thickness | Normal, low | High-very high |
| Number of osteoblasts | Low | Low |
| Bone formation rate | Low-very low | Low-very low |
| Mineralization lag time | Normal | Prolonged |
| Bone Resorption | | |
| Eroded bone perimeter | Normal, low | Variable Often low, may be high |
| Number of osteoclasts | Low | Low, may be normal or high |
| Marrow fibrosis | Absent | Absent |

In certain embodiments, the subject is undergoing hemodialysis.

In certain embodiments, the subject treated in accordance with the methods described herein has end-stage renal disease. In certain embodiments, the subject treated in accordance with the methods described herein undergoes dialysis.

In certain embodiments, the subject treated in accordance with the methods described herein has increased bone resorption as compared to bone resorption in a reference population. In certain embodiments, the increased bone resorption is determined by the levels of CTX. In certain embodiments, the levels of CTX are determined as described in Section 8.6. In certain embodiments, the bone resorption is assessed as described in Section 8.6.

In certain embodiments, the subject treated in accordance with the methods described here can be of any age. In certain embodiments, the subject treated in accordance with the methods described herein is less than 18 years old. In a specific embodiment, the subject treated in accordance with the methods described herein is less than 13 years old. In another specific embodiment, the subject treated in accordance with the methods described herein is less than 12, less than 11, less than 10, less than 9, less than 8, less than 7, less than 6, or less than 5 years old. In another specific embodiment, the subject treated in accordance with the methods described herein is 1-3 years old, 3-5 years old, 5-7 years old, 7-9 years old, 9-11 years old, 11-13 years old, 13-15 years old, 15-20 years old, 20-25 years old, 25-30 years old, or greater than 30 years old. In another specific embodiment, the subject treated in accordance with the methods described herein is 30-35 years old, 35-40 years old, 40-45 years old, 45-50 years old, 50-55 years old, 55-60 years old, or greater than 60 years old. In another specific embodiment, the subject treated in accordance with the methods described herein is 60-65 years old, 65-70 years old, 70-75 years old, 75-80 years old, or greater than 80 years old.

In certain embodiments, a subject treated in accordance with the methods provided herein has end-stage kidney disease. In certain embodiments, a subject treated in accordance with the methods provided herein is on hemodialysis. In certain embodiments, a subject treated in accordance with the methods provided herein has previously been administered an erythropoietin-stimulating agent. In certain embodiments, a subject treated in accordance with the methods provided herein has end-stage kidney disease, is on hemodialysis, and has previously been administered an erythropoietin-stimulating agent.

As will be recognized by one of skill in the art, levels and/or activity of one or more of Runx2, Alp, Snail, phosphosmad2, Dkk1, col1a1, activin, BSAP, CTX, osterix, Klotho, alpha-SMA, MYOCD, ActRIIA, Axin2, Sm22-alpha, phosphosmad3, and urinary protein can be compared independently and respectively to the level and/or activity in a corresponding reference population, such as described above in Section 8.3.1.

Inhibitors of ActRII Signaling

The ActRII signaling inhibitors described in this section and known in the art can be used in the methods provided herein. In certain embodiments, the ActRII signaling inhibitors described in this section can be used in the methods provided herein (See, Section 8.3).

Inhibitors of ActRII signaling receptors encompassed herein include ActRIIA signaling inhibitors and ActRIIB signaling inhibitors (see below). In certain embodiments, an ActRII signaling inhibitor is specific to ActRIIA signaling. In other embodiments, an ActRII signaling inhibitor is specific to ActRIIB signaling. In certain embodiments, an ActRII signaling inhibitor preferentially inhibits ActRIIA signaling. In other embodiments, an ActRII signaling inhibitor preferentially inhibits ActRIIB signaling. In certain embodiments, an ActRII signaling inhibitor inhibits both ActRIIA signaling and ActRIIB signaling.

In certain embodiments, inhibitors of ActRII signaling can be polypeptides comprising activin-binding domains of ActRII. Without being bound by theory, such activin-binding domain comprising polypeptides sequester activin and thereby prevent activin signaling. These activin-binding domain comprising polypeptides may comprise all or a portion of the extracellular domain of an ActRII (i.e., all or a portion of the extracellular domain of ActRIIA or all or a portion of the extracellular domain of ActRIIB). In specific embodiments, the extracellular domain of an ActRII is soluble.

In certain embodiments, the activin-binding domain comprising polypeptides are linked to an Fc portion of an antibody (e.g., a conjugate comprising an activin-binding domain comprising polypeptide of an ActRII receptor and an Fc portion of an antibody is generated). Without being bound by theory, the antibody portion confers increased stability on the conjugate. In certain embodiments, the activin-binding domain is linked to an Fc portion of an antibody via a linker, e.g., a peptide linker.

The inhibitors of ActRII signaling used in the compositions and methods described herein comprise molecules that inhibit ActRIIA signaling and/or ActRIIB signaling, directly or indirectly, either extracellularly or intracellularly. In some embodiments, the inhibitors of ActRIIA signaling and/or ActRIIB signaling used in the compositions and methods described herein inhibit ActRIIA signaling and/or ActRIIB signaling via interactions with the receptor(s) itself. In other embodiments, the inhibitors of ActRIIA signaling and/or ActRIIB signaling used in the compositions and methods described herein inhibit ActRIIA signaling and/or ActRIIB signaling via interactions with an ActRIIA and/or ActRIIB ligand, e.g., Activin.

Inhibitors of ActRIIA Signaling

As used herein, the term "ActRIIA" refers to a family of activin receptor type IIA (ActRIIA) proteins from any species and variants derived from such ActRIIA proteins by mutagenesis or other modification. Reference to ActRIIA herein is understood to be a reference to any one of the currently identified forms. Members of the ActRIIA family are generally transmembrane proteins, composed of a ligand-binding extracellular domain with a cysteine-rich region, a transmembrane domain, and a cytoplasmic domain with predicted serine/threonine kinase activity.

ActRIIA signaling inhibitors to be used in the compositions and methods described herein include, without limitation, activin-binding soluble ActRIIA polypeptides; antibodies that bind to activin (particularly the activin A or B subunits, also referred to as $\beta_A$ or $\beta_B$) and disrupt ActRIIA binding; antibodies that bind to ActRIIA and disrupt activin binding; non-antibody proteins selected for activin or ActRIIA binding (see e.g., WO/2002/088171, WO/2006/055689, WO/2002/032925, WO/2005/037989, US 2003/0133939, and US 2005/0238646, each of which is incorporated herein by reference in its entirety, for examples of such proteins and methods for design and selection of same); and randomized peptides selected for activin or ActRIIA binding, which can be conjugated to an Fc domain.

In certain embodiments, two or more different proteins (or other moieties) with activin or ActRIIA binding activity, especially activin binders that block the type I (e.g., a soluble type I activin receptor) and type II (e.g., a soluble type II activin receptor) binding sites, respectively, may be linked together to create a bifunctional or multifunctional binding molecule that inhibits ActRIIA signaling and thus can be used in the compositions and methods described herein. In certain embodiments, Activin-ActRIIA signaling axis antagonists that inhibit ActRIIA signaling include nucleic acid aptamers, small molecules and other agents are used in the compositions and methods described herein include.

ActRIIA Signaling Inhibitors Comprising ActRIIA Polypeptides

The term "ActRIIA polypeptide" includes polypeptides comprising any naturally occurring polypeptide of an ActRIIA family member as well as any variants thereof (including mutants, fragments, fusions, and peptidomimetic forms) that retain a useful activity. For example, ActRIIA polypeptides include polypeptides derived from the sequence of any known ActRIIA having a sequence at least about 80% identical to the sequence of an ActRIIA polypeptide, and optionally at least 85%, 90%, 95%, 97%, 98%, 99% or greater identity. For example, an ActRIIA polypeptide may bind to and inhibit the function of an ActRIIA protein and/or activin. An ActRIIB polypeptide may be selected for its ability to promote bone growth and bone mineralization. Examples of ActRIIA polypeptides include human ActRIIA precursor polypeptide (SEQ ID NO: 1) and soluble human ActRIIA polypeptides (e.g., SEQ ID NOS: 2, 3, 7 and 12). With respect to the ActRIIA precursor polypeptide whose amino acid sequence is depicted at SEQ ID NO: 1, the signal peptide of the human ActRIIA precursor polypeptide located at amino acid positions 1 to 20; the extracellular domain is located at amino acid positions 21 to 135 and the N-linked glycosylation sites of the human ActRIIA precursor polypeptide (SEQ ID NO: 1) are located at amino acid positions 43 and 56 of SEQ ID NO: 1. The nucleic acid sequence encoding the human ActRIIB precursor polypeptide of SEQ ID NO: 1 is disclosed as SEQ ID NO:4 (nucleotides 164-1705 of Genbank entry NM_001616). The nucleic acid sequence encoding the soluble human ActRIIA polypeptide of SEQ ID NO:2 is disclosed as SEQ ID NO:5. See Table 21 for a description of the sequences.

In specific embodiments, the ActRIIA polypeptides used in the compositions and methods described herein are soluble ActRIIA polypeptides. An extracellular domain of an ActRIIA protein can bind to activin and is generally soluble, and thus can be termed a soluble, activin-binding ActRIIA polypeptide. Thus, as used herein, the term "soluble ActRIIA polypeptide" generally refers to polypeptides comprising an extracellular domain of an ActRIIA protein, including any naturally occurring extracellular domain of an ActRIIA protein as well as any variants thereof (including mutants, fragments and peptidomimetic forms). Soluble ActRIIA polypeptides can bind to activin; however, the wild type ActRIIA protein does not exhibit significant selectivity in binding to activin versus GDF8/1. Native or altered ActRIIA proteins may be given added specificity for activin by coupling them with a second, activin-selective binding agent. Examples of soluble, activin-binding ActRIIA polypeptides include the soluble polypeptides illustrated in SEQ ID NOS: 2, 3, 7, 12 and 13. Other examples of soluble, activin-binding ActRIIA polypeptides comprise a signal sequence in addition to the extracellular domain of an ActRIIA protein, for example, the honey bee mellitin leader sequence (SEQ ID NO: 8), the tissue plasminogen activator (TPA) leader (SEQ ID NO: 9) or the native ActRIIA leader (SEQ ID NO: 10). The ActRIIA-hFc polypeptide illustrated in SEQ ID NO: 13 uses a TPA leader.

In certain embodiments, the inhibitors of ActRIIA signaling used in the compositions and methods described herein comprise a conjugate/fusion protein comprising an activin-binding domain of ActRIIA linked to an Fc portion of an antibody. In certain embodiments, the activin-binding domain is linked to an Fc portion of an antibody via a linker, e.g., a peptide linker. Optionally, the Fe domain has one or more mutations at residues such as Asp-265, lysine 322, and Asn-434. In certain cases, the mutant Fe domain having one or more of these mutations (e.g., an Asp-265 mutation) has a reduced ability to bind to the Fcy receptor relative to a wild-type Fc domain. In other cases, the mutant Fc domain having one or more of these mutations (e.g., an Asn-434 mutation) has an increased ability to bind to the MHC class I-related Fc-receptor (FcRN) relative to a wild-type Fe domain. Exemplary fusion proteins comprising a soluble extracellular domain of ActRIIA fused to an Fc domain are set forth in SEQ ID NOs: 6, 7, 12, and 13.

In a specific embodiment, the ActRIIA signaling inhibitors used in the compositions and methods described herein comprise the extracellular domain of ActRIIA, or a portion thereof, linked to an Fc portion of an antibody, wherein said ActRIIA signaling inhibitor comprises an amino acid sequence that is at least 75% identical to an amino acid sequence selected from SEQ ID NOs: 6, 7, 12, and 13. In another specific embodiment, the ActRIIA signaling inhibitors used in the compositions and methods described herein comprise the extracellular domain of ActRIIA, or a portion thereof, linked to an Fe portion of an antibody, wherein said ActRIIA signaling inhibitor comprises an amino acid sequence that is at least 80%, 85%, 90%, 95%, 96%, 97%, 98%, or 99% identical to an amino acid sequence selected from SEQ ID NOs: 6, 7, 12, and 13.

In certain embodiments, the inhibitors of ActRIIA signaling used in the compositions and methods described herein comprise a truncated form of an extracellular domain of ActRIIA. The truncation can be at the carboxy terminus and/or the amino terminus of the ActRIIA polypeptide. In certain embodiments, the truncation can be 1, 2, 3, 4, 5, 6, 7, 8, 9, 10, 11, 12, 13, 14, 15, 16, 17, 18, 19, 20, 21, 22, 23, 24, or 25 amino acids long relative to the mature ActRIIB polypeptide extracellular domain. In certain embodiments, the truncation can be 1, 2, 3, 4, 5, 6, 7, 8, 9, 10, 11, 12, 13, 14, 15, 16, 17, 18, 19, 20, 21, 22, 23, 24, or 25 N-terminal amino acids of the mature ActRIIA polypeptide extracellular domain. In certain embodiments, the truncation can be 1, 2, 3, 4, 5, 6, 7, 8, 9, 10, 11, 12, 13, 14, 15, 16, 17, 18, 19, 20, 21, 22, 23, 24, or 25 C-terminal amino acids of the mature ActRIIA polypeptide extracellular domain. For example, truncated forms of ActRIIA include polypeptides with amino acids 20-119; 20-128; 20-129; 20-130; 20-131; 20-132; 20-133; 20-134; 20-131; 21-131; 22-131; 23-131; 24-131; and 25-131, wherein the amino acid positions refer to the amino acid positions in SEQ ID NO: 1.

In certain embodiments, the inhibitors of ActRIIA signaling used in the compositions and methods described herein comprise an extracellular domain of ActRIIA with one or more amino acid substitutions. In certain embodiments, the inhibitors of ActRIIA signaling used in the compositions and methods described herein comprise a truncated form of an ActRIIA extracellular domain that also carries an amino acid substitution.

In a specific embodiment, the ActRIIA signaling inhibitor to be used in the compositions and methods described herein is a fusion protein between the extracellular domain of the human ActRIIA receptor and the Fc portion of IgG1. In another specific embodiment, the ActRIIA signaling inhibitor to be used in the compositions and methods described herein is a fusion protein between a truncated extracellular domain of the human ActRIIA receptor and the Fc portion of IgG1. In another specific embodiment, the ActRIIA signaling inhibitor to be used in the compositions and methods described herein is a fusion protein between a truncated extracellular domain of the human ActRIIA receptor and the Fc portion of IgG1, wherein the truncated extracellular domain of the human ActRIIA receptor possesses one or more amino acid substitutions.

Functionally active fragments of ActRIIA polypeptides can be obtained, for example, by screening polypeptides recombinantly produced from the corresponding fragment of the nucleic acid encoding an ActRIIA polypeptide. In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function as antagonists (inhibitors) of ActRIIA protein or signaling mediated by activin.

In addition, functionally active variants of ActRIIA polypeptides can be obtained, for example, by screening libraries of modified polypeptides recombinantly produced from the corresponding mutagenized nucleic acids encoding an ActRIIA polypeptide. The variants can be produced and tested to identify those that can function as antagonists (inhibitors) of ActRIIA protein or signaling mediated by activin. In certain embodiments, a functional variant of the ActRIIA polypeptides comprises an amino acid sequence that is at least 75% identical to an amino acid sequence selected from SEQ ID NOs: 2 or 3. In certain cases, the functional variant has an amino acid sequence at least 80%, 85%, 90%, 95%, 97%, 98%, 99% or 100% identical to an amino acid sequence selected from SEQ ID NOs: 2 or 3.

Functional variants may be generated, for example, by modifying the structure of an ActRIIA polypeptide for such purposes as enhancing therapeutic efficacy, or stability (e.g., ex vivo shelf life and resistance to proteolytic degradation in vivo). Such modified ActRIIA polypeptides when selected to retain activin binding, can be considered functional equivalents of the naturally-occurring ActRIIA polypeptides. Modified ActRIIA polypeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of an ActRIIA polypeptide results in a functional homolog can be readily determined by assessing the ability of the variant ActRIIA polypeptide to produce a response in cells in a fashion similar to the wild-type ActRIIA polypeptide.

In certain embodiments, the ActRIIA signaling inhibitor to be used in the compositions and methods described herein provided herein may comprise an ActRIIA polypeptide having one or more specific mutations that can alter the glycosylation of the polypeptide. Such mutations may introduce or eliminate one or more glycosylation sites, such as O-linked or N-linked glycosylation sites. Asparagine-linked glycosylation recognition sites generally comprise a tripeptide sequence, asparagine-X-threonine (or asparagines-X-serine) (where "X" is any amino acid) which is specifically recognized by appropriate cellular glycosylation enzymes. The alteration may also be made by the addition of, or substitution by, one or more serine or threonine residues to the sequence of the wild-type ActRIIA polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on an ActRIIA polypeptide is by chemical or enzymatic coupling of glycosides to the ActRIIA polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on an ActRIIA polypeptide may be accomplished chemically and/or enzymatically. Chemical deglycosylation may involve, for example, exposure of the ActRIIA polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on ActRIIA polypeptides can be achieved by the use of a variety of endo- and exo-glycosidases as described by Thotakura et al. (1987) Meth. Enzymol. 138:350. The sequence of an ActRIIA polypeptide may be adjusted, as appropriate, depending on the type of expression system used, as mammalian, yeast, insect and plant cells may all introduce differing glycosylation patterns that can be affected by the amino acid sequence of the peptide. In general, ActRIIA proteins for use in humans can be expressed in a mammalian cell line that provides proper glycosylation, such as HEK293 or CHO cell lines, although other expression systems, such as other mammalian expression cell lines, yeast cell lines with engineered glycosylation enzymes and insect cells, are expected to be useful as well.

Further provided herein are methods of generating mutants, particularly sets of combinatorial mutants of an ActRIIA polypeptide, as well as truncation mutants; pools of combinatorial mutants are especially useful for identifying functional variant sequences. The purpose of screening such combinatorial libraries may be to generate, for example, ActRIIA polypeptide variants which can act as either agonists or antagonist, or alternatively, which possess novel activities all together. A variety of screening assays are provided below, and such assays may be used to evaluate variants. For example, an ActRIIA polypeptide variant may be screened for ability to bind to an ActRIIA ligand, to prevent binding of an ActRIIA ligand to an ActRIIA polypeptide or to interfere with signaling caused by an ActRIIA ligand.

Combinatorially-derived variants can be generated which have a selective or generally increased potency relative to a naturally occurring ActRIIA polypeptide. Likewise, mutagenesis can give rise to variants which have intracellular half-lives dramatically different than the corresponding a wild-type ActRIIA polypeptide. For example, the altered protein can be rendered either more stable or less stable to proteolytic degradation or other cellular processes which result in destruction of, or otherwise inactivation of a native ActRIIA polypeptide. Such variants, and the genes which encode them, can be utilized to alter ActRIIA polypeptide levels by modulating the half-life of the ActRIIA polypeptides. For instance, a short half-life can give rise to more transient biological effects and can allow tighter control of recombinant ActRIIA polypeptide levels within the subject. In an Fc fusion protein, mutations may be made in the linker (if any) and/or the Fc portion to alter the half-life of the protein.

A combinatorial library may be produced by way of a degenerate library of genes encoding a library of polypeptides which each include at least a portion of potential ActRIIA polypeptide sequences. For instance, a mixture of synthetic oligonucleotides can be enzymatically ligated into gene sequences such that the degenerate set of potential ActRIIA polypeptide nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate vector for expression. The synthesis of degenerate oligonucleotides is well known in the art (see, for example, Narang, S A (1983) Tetrahedron 39:3; Itakura et al., (1981) Recombinant DNA, Proc. 3rd Cleveland Sympos. Macromolecules, ed. AG Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, ActRIIA polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of ActRIIA polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of ActRIIA polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include activin binding assays and activin-mediated cell signaling assays.

In certain embodiments, ActRIIA polypeptides used in the inhibitors of the methods and compositions described herein may further comprise post-translational modifications in addition to any that are naturally present in the ActRIIA polypeptides. Such modifications may include, but are not limited to, acetylation, carboxylation, glycosylation, phosphorylation, lipidation, and acylation. As a result, the modified ActRIIA polypeptides may contain non-amino acid elements, such as polyethylene glycols, lipids, poly- or mono-saccharide, and phosphates. Effects of such non-amino acid elements on the functionality of an ActRIIA polypeptide may be tested by any method known to the skilled artisan. When an ActRIIA polypeptide is produced in cells by cleaving a nascent form of the ActRIIA polypeptide, post-translational processing may also be important for correct folding and/or function of the protein. Different cells (such as CHO, HeLa, MDCK, 293, WI38, NIH-3T3 or HEK293) have specific cellular machinery and characteristic mechanisms for such post-translational activities and may be chosen to ensure the correct modification and processing of the ActRIIA polypeptides.

In certain aspects, functional variants or modified forms of the ActRIIA polypeptides used in the inhibitors of the methods and compositions described herein include fusion proteins having at least a portion of the ActRIIA polypeptides and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS$_6$) fusion partners. As another example, a fusion domain may be selected so as to facilitate detection of the ActRIIA polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus hemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, an ActRIIA polypeptide is fused with a domain that stabilizes the ActRIIA polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, such as further stimulation of bone growth or muscle growth, as desired).

It is understood that different elements of the fusion proteins may be arranged in any manner that is consistent with the desired functionality. For example, an ActRIIA polypeptide may be placed C-terminal to a heterologous domain, or, alternatively, a heterologous domain may be placed C-terminal to an ActRIIA polypeptide. The ActRIIA polypeptide domain and the heterologous domain need not be adjacent in a fusion protein, and additional domains or amino acid sequences may be included C- or N-terminal to either domain or between the domains.

In certain embodiments, the ActRIIA polypeptides used in the inhibitors of the methods and compositions described herein may contain one or more modifications that are capable of stabilizing the ActRIIA polypeptides. For example, such modifications may enhance the in vitro half life of the ActRIIA polypeptides, enhance circulatory half life of the ActRIIA polypeptides or reduce proteolytic degradation of the ActRIIA polypeptides. Such stabilizing modifications may include, but are not limited to, fusion proteins (including, for example, fusion proteins comprising an ActRIIA polypeptide and a stabilizer domain), modifications of a glycosylation site (including, for example, addition of a glycosylation site to an ActRIIA polypeptide), and modifications of carbohydrate moiety (including, for example, removal of carbohydrate moieties from an ActRIIA polypeptide). In the case of fusion proteins, an ActRIIA polypeptide is fused to a stabilizer domain such as an IgG molecule (e.g., an Fe domain). As used herein, the term "stabilizer domain" not only refers to a fusion domain (e.g., Fc) as in the case of fusion proteins, but also includes nonproteinaceous modifications such as a carbohydrate moiety, or nonproteinaceous polymer, such as polyethylene glycol.

In certain embodiments, isolated and/or purified forms of ActRIIA polypeptides, which are isolated from, or otherwise substantially free of, other proteins can be used with the methods and compositions described herein. ActRIIA polypeptides can generally be produced by expression from recombinant nucleic acids.

In certain aspects, the ActRIIA polypeptides used in the compositions and methods described herein are generated using isolated and/or recombinant nucleic acids encoding any of the ActRIIA polypeptides (e.g., soluble ActRIIA polypeptides), including fragments, functional variants and fusion proteins disclosed herein. For example, SEQ ID NO: 4 encodes the naturally occurring human ActRIIA precursor polypeptide, while SEQ ID NO: 5 encodes the processed extracellular domain of ActRIIA. Such nucleic acids may be single-stranded or double stranded. Such nucleic acids may be DNA or RNA molecules. These nucleic acids may be used, for example, in methods for making ActRIIA polypeptides or as direct therapeutic agents (e.g., in a gene therapy approach).

In certain aspects, nucleic acids encoding ActRIIA polypeptides may include nucleic acids that are variants of SEQ ID NO: 4 or 5. Variant nucleotide sequences include sequences that differ by one or more nucleotide substitutions, additions or deletions, such as allelic variants.

In certain embodiments, isolated or recombinant nucleic acid sequences encoding ActRIIA polypeptides may be least 80%, 85%, 90%, 95%, 97%, 98%, 99% or 100% identical to SEQ ID NO: 4 or 5. One of ordinary skill in the art will appreciate that nucleic acid sequences complementary to SEQ ID NO: 4 or 5, and variants of SEQ ID NO: 4 or 5 may be used in the production of ActRIIA polypeptides suitable for use in the methods and compositions described herein. In further embodiments, such nucleic acid sequences can be isolated, recombinant, and/or fused to a heterologous nucleotide sequence, or be from a DNA library.

In other embodiments, nucleic acids used in the production of ActRIIA polypeptides suitable for use in the methods and compositions described herein may include nucleotide sequences that hybridize under highly stringent conditions to the nucleotide sequence designated in SEQ ID NO: 4 or 5, complement sequence of SEQ ID NO: 4 or 5, or fragments thereof. One of ordinary skill in the art will understand that appropriate stringency conditions which promote DNA hybridization can be varied. For example, one can perform the hybridization at 6.0 times sodium chloride/sodium citrate (SSC) at about 45 degree Celsius, followed by a wash of 2.0 times SSC at 50 degree Celsius. For example, the salt concentration in the wash step can be selected from a low stringency of about 2.0 times SSC at 50 degree Celsius to a high stringency of about 0.2 times SSC at 50 degree Celsius. In addition, the temperature in the wash step can be increased from low stringency conditions at room temperature, about 22 degree Celsius, to high stringency conditions at about 65 degree Celsius. Both temperature and salt may be varied, or temperature or salt concentration may be held constant while the other variable is changed. In one embodiment, nucleic acids which hybridize under low stringency conditions of 6 times SSC at room temperature followed by a wash at 2 times SSC at room temperature can be used with the methods and compositions described herein.

Isolated nucleic acids which differ from the nucleic acids as set forth in SEQ ID NOs: 4 or 5 due to degeneracy in the genetic code also can be used in the production of ActRIIA polypeptides suitable for use in the methods and compositions described herein. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation.

In certain embodiments, the recombinant nucleic acids may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated herein. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects, the a nucleic acid used in the production of ActRIIA polypeptides suitable for use in the methods and compositions described herein can be provided in an expression vector comprising a nucleotide sequence encoding an ActRIIA polypeptide and operably linked to at least one regulatory sequence. Regulatory sequences are art-recognized and are selected to direct expression of the ActRIIA polypeptide. Accordingly, the term regulatory sequence includes promoters, enhancers, and other expression control elements. Exemplary regulatory sequences are described in Goeddel; Gene Expression Technology: Methods in Enzymology, Academic Press, San Diego, Calif. (1990). For instance, any of a wide variety of expression control sequences that control the expression of a DNA sequence when operatively linked to it may be used in these vectors to express DNA sequences encoding an ActRIIA polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast .alpha.-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid used in the production of ActRIIA polypeptides suitable for use in the methods and compositions described herein can be produced by ligating the cloned gene, or a portion thereof, into a vector suitable for expression in either prokaryotic cells, eukaryotic cells (yeast, avian, insect or mammalian), or both. Expression vehicles for production of a recombinant ActRIIA polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as E. coli.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see Molecular Cloning A Laboratory Manual, 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the .beta.-gal containing pBlueBac III).

Vectors can be designed for production of the subject ActRIIA polypeptides in CHO cells, such as a Pcmv-Script vector (Stratagene, La Jolla, Calif.). pcDNA4 vectors (Invitrogen, Carlsbad, Calif.) and pCI-neo vectors (Promega, Madison, Wis.). As will be apparent, the subject gene constructs can be used to cause expression of the subject ActRIIA polypeptides in cells propagated in culture, e.g., to produce proteins, including fusion proteins or variant proteins, for purification.

Host cells transfected with a recombinant gene including a coding sequence (e.g., SEQ ID NO: 4 or 5) for one or more of the subject ActRIIA polypeptides can be used in the production of ActRIIA polypeptides suitable for use in the methods and compositions described herein. The host cell may be any prokaryotic or eukaryotic cell. For example, an ActRIIA polypeptide provided herein may be expressed in bacterial cells such as E. coli, insect cells (e.g., using a baculovirus expression system), yeast, or mammalian cells. Other suitable host cells are known to those skilled in the art.

Accordingly, provided herein are methods of producing the ActRIIA polypeptides. For example, a host cell transfected with an expression vector encoding an ActRIIA polypeptide can be cultured under appropriate conditions to allow expression of the ActRIIA polypeptide to occur. The ActRIIA polypeptide may be secreted and isolated from a mixture of cells and medium containing the ActRIIA polypeptide. Alternatively, the ActRIIA polypeptide may be retained cytoplasmically or in a membrane fraction and the cells harvested, lysed and the protein isolated. A cell culture includes host cells, media and other byproducts. Suitable media for cell culture are well known in the art. The subject ActRIIA polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the ActRIIA polypeptides and affinity purification with an agent that binds to a domain fused to the ActRIIA polypeptide (e.g., a protein A column may be used to purify an ActRIIA-Fc fusion). In a preferred embodiment, the ActRIIA polypeptide is a fusion protein containing a domain which facilitates its purification. In one embodiment, purification is achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. As demonstrated herein, ActRIIA-hFc protein was purified to a purity of >98% as determined by size exclusion chromatography and >95% as determined by SDS PAGE. This level of purity was sufficient to achieve desirable effects on bone in mice and an acceptable safety profile in mice, rats and non-human primates.

In another embodiment, a fusion gene coding for a purification leader sequence, such as a poly-(His)/enterokinase cleavage site sequence at the N-terminus of the desired portion of a recombinant ActRIIA polypeptide, can allow purification of the expressed fusion protein by affinity chromatography using a $Ni^{2+}$ metal resin. The purification leader sequence can then be subsequently removed by treatment with enterokinase to provide the purified ActRIIA polypeptide (e.g., see Hochuli et al., (1987) J. Chromatography 411:177; and Janknecht et al., PNAS USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al., John Wiley & Sons: 1992).

ActRIIA-Fc fusion protein can be expressed in stably transfected CHO-DUKX B1 1 cells from a pAID4 vector (SV40 ori/enhancer, CMV promoter), using a tissue plasminogen leader sequence of SEQ ID NO:9. The Fc portion is a human IgG1 Fc sequence, as shown in SEQ ID NO:7. In certain embodiments, upon expression, the protein contained has, on average, between about 1.5 and 2.5 moles of sialic acid per molecule of ActRIIA-Fc fusion protein.

In certain embodiments, the long serum half-life of an ActRIIA-Fc fusion can be 25-32 days in human subjects. Additionally, the CHO cell expressed material can have a higher affinity for activin B ligand than that reported for an ActRIIA-hFc fusion protein expressed in human 293 cells (del Re et al., J Biol Chem. 2004 Dec. 17; 279(51):53126-35). Additionally, without being bound by theory, the use of the TPA leader sequence provided greater production than other leader sequences and, unlike ActRIIA-Fc expressed with a native leader, may provide a highly pure N-terminal sequence. Use of the native leader sequence may result in two major species of ActRIIA-Fc, each having a different N-terminal sequence.

Inhibitors of ActRIIB Signaling

As used herein, the term "ActRIIB" refers to a family of activin receptor type IIB (ActRIIB) proteins from any species and variants derived from such ActRIIB proteins by mutagenesis or other modification. Reference to ActRIIB herein is understood to be a reference to any one of the currently identified forms of the receptor. Members of the ActRIIB family are generally transmembrane proteins, composed of a ligand-binding extracellular domain with a cysteine-rich region, a transmembrane domain, and a cytoplasmic domain with predicted serine/threonine kinase activity.

ActRIIB signaling inhibitors to be used in the compositions and methods described herein include, without limitation, activin-binding soluble ActRIIB polypeptides; antibodies that bind to activin (particularly the activin A or B subunits, also referred to as $\beta_A$ or $\beta_B$) and disrupt ActRIIB binding; antibodies that bind to ActRIIB and disrupt activin binding; non-antibody proteins selected for activin or ActRIIB binding; and randomized peptides selected for activin or ActRIIB binding, which can be conjugated to an Fc domain.

In certain embodiments, two or more different proteins (or other moieties) with activin or ActRIIB binding activity, especially activin binders that block the type I (e.g., a soluble type I activin receptor) and type II (e.g., a soluble type II activin receptor) binding sites, respectively, may be linked together to create a bifunctional or multi functional binding molecule that inhibits ActRIIB and thus can be used in the compositions and methods described herein include. In certain embodiments, Activin-ActRIIB signaling axis antagonists that inhibit ActRIIB include nucleic acid aptamers, small molecules and other agents are used in the compositions and methods described herein include.

ActRIIB Signaling Inhibitors Comprising ActRIIB Polypeptides

As used herein, the term "ActRIIB polypeptide" refers to polypeptides comprising any naturally occurring polypeptide of an ActRIIB family member as well as any variants thereof (including mutants, fragments, fusions, and peptidomimetic forms) that retain a useful activity. For example, ActRIIB polypeptides include polypeptides derived from the sequence of any known ActRIIB receptor having a sequence at least about 80% identical to the sequence of an ActRIIB polypeptide, and optionally at least 85%, 90%, 95%, 96%, 97%, 98%, 99% or greater identity. For example, an ActRIIB polypeptide may bind to and inhibit the function of an ActRIIB protein and/or activin. An example of an ActRIIB polypeptide includes the human ActRIIB precursor polypeptide (SEQ ID NO: 16 or SEQ ID NO:28). With respect to the ActRIIB precursor polypeptide whose amino acid sequence is depicted as SEQ ID NO:16 or SEQ ID NO:28 (i.e., the human ActRIIB precursor polypeptide), the signal peptide of the ActRIIB precursor polypeptide is located at amino acids 1 to 18; the extracellular domain is located at amino acids 19 to 134 and the potential N-linked glycosylation sites are located at amino acid positions 42 and 65. The nucleic acid sequence encoding the human ActRIIB precursor polypeptide of SEQ ID NO: 16 is disclosed as SEQ ID NO: 19 (SEQ ID NO: 19 provides an alanine at the codon corresponding to amino acid position 64, but could be readily modified by one of skill in the art using methods known in the art to provide an arginine at the codon corresponding to amino acid position 64 instead). See Table 21 for a description of the sequences.

The numbering of amino acids for all of the ActRIIB-related polypeptides described herein is based on the amino acid numbering for SEQ ID NO: 16 and SEQ ID NO:28 (which only differ in the amino acid expressed at position 64), unless specifically designated otherwise. For example, if an ActRIIB polypeptide is described as having a substitution/mutation at amino acid position 79, then it is to be understood that position 79 refers to the $79^{th}$ amino acid in SEQ ID NO: 16 or SEQ ID NO:28, from which the ActRIIB polypeptide is derived. Likewise, if an ActRIIB polypeptide is described as having an alanine or an arginine at amino acid position 64, then it is to be understood that position 64 refers to the $64^{th}$ amino acid in SEQ ID NO: 16 or SEQ ID NO:28, from which the ActRIIB polypeptide is derived.

In certain embodiments, the inhibitors of ActRIIB signaling used in the compositions and methods described herein comprise polypeptides comprising an activin-binding domain of ActRIIB. In some embodiments, the activin-binding domains of ActRIIB comprise the extracellular domain of ActRIIB, or a portion thereof: In specific embodiments, the extracellular domain or portion thereof of ActRIIB is soluble. Illustrative modified forms of ActRIIB polypeptides are disclosed in U.S. Patent Application Publication Nos. 20090005308 and 20100068215, the disclosures of which are incorporated herein by reference in their entireties.

In specific embodiments, the ActRIIB polypeptides used in the compositions and methods described herein are soluble ActRIIB polypeptides. The term "soluble ActRIIB polypeptide" generally refers to polypeptides comprising an extracellular domain of an ActRIIB protein, including any naturally occurring extracellular domain of an ActRIIB protein as well as any variants thereof (including mutants, fragments and peptidomimetic forms). Soluble ActRIIB polypeptides can bind to activin; however, the wild type ActRIIB protein does not exhibit significant selectivity in binding to activin versus GDF8/11. In certain embodiments, altered forms of ActRIIB with different binding properties can be used in the methods provided herein. Such altered forms are disclosed, e.g., in international patent application publication Nos. WO 2006/012627 and WO 2010/019261, the disclosures of which are incorporated herein by reference in their entireties. Native or altered ActRIIB proteins may be given added specificity for activin by coupling them with a second, activin-selective binding agent. Exemplary soluble ActRIIB polypeptides include the extracellular domain of a human ActRIIB polypeptide (e.g., SEQ ID NOs: 17, 18, 23, 26, 27, 29, 30, 31, 32, 33, 36, 37, 42, and 43).

An Fc fusion protein having the ActRIIB extracellular sequence disclosed by Hilden et al. (Blood, 1994, 83(8): 2163-70), which has an alanine at the position corresponding to amino acid 64 of the ActRIIB precursor amino acid sequence, i.e., SEQ ID NO: 16 (herein referred to as "A64"), has been demonstrated to possess a relatively low affinity for activin and GDF-11. By contrast, an Fc fusion protein with an arginine at position 64 of the ActRIIB precursor amino acid sequence (herein referred to as "R64") has an affinity for activin and GDF-11 in the low nanomolar to high picomolar range (see, e.g., U.S. Patent Application Publication No. 20100068215, the disclosure of which is herein incorporated in its entirety). An ActRIIB precursor amino acid sequence with an arginine at position 64 is presented in SEQ ID NO:28. As such, in certain embodiments, the ActRIIB polypeptides used in accordance with the compositions and methods described herein may comprise either (i) an alanine at the position corresponding to amino acid 64 of the ActRIIB precursor amino acid sequence, i.e., SEQ ID NO: 16; or (ii) an arginine at position 64 of the ActRIIB precursor amino acid sequence, i.e., SEQ ID NO: 28. In other embodiments, the ActRIIB polypeptides used in accordance with the compositions and methods described herein may comprise an amino acid that is not alanine or arginine at the position corresponding to amino acid 64 of the ActRIIB precursor amino acid sequence, i.e., SEQ ID NO: 16 or SEQ ID NO:28.

It has been shown that a deletion of the proline knot at the C-terminus of the extracellular domain of ActRIIB reduces the affinity of the receptor for activin (see, e.g., Attisano et al., Cell, 1992, 68(1):97-108). An ActRIIB-Fc fusion protein containing amino acids 20-119 of SEQ ID NO: 28 (i.e., SEQ ID NO:32), "ActRIIB(20-119)-Fc" has reduced binding to GDF-11 and activin relative to an ActRIIB-Fc fusion protein containing amino acids 20-134 of SEQ ID NO: 28 (i.e., SEQ ID NO:31), "ActRIIB(20-134)-Fc", which includes the proline knot region and the complete juxtamembrane domain. However, an ActRIIB-Fc fusion protein containing amino acids 20-129 of SEQ ID NO: 28, "ActRIIB(20-129)-Fc" retains similar but somewhat reduced activity relative to the non-truncated extracellular domain of ActRIIB, even though the proline knot region is disrupted. Thus, ActRIIB polypeptides comprising extracellular domains that stop at amino acid 134, 133, 132, 131, 130 and 129 of SEQ ID NO: 28 (or SEQ ID NO: 16) are all expected to be active, but constructs stopping at amino acid 134 or 133 may be most active. Similarly, mutations at any of residues 129-134 are not expected to alter ligand binding affinity by large margins, as indicated by the fact that mutations of P129 and P130 of SEQ ID NO: 28 do not substantially decrease ligand binding. Therefore, the ActRIIB polypeptides used in accordance with the methods and compositions described herein may end as early as amino acid 109 (i.e., the final cysteine) of SEQ ID NO:28 (or SEQ ID NO:16), however, forms ending at or between amino acid positions 109 and 119 of SEQ ID NO:28 (or SEQ ID NO: 16) are expected to have reduced ligand binding ability.

Amino acid 29 of SEQ ID NO:16 and SEQ ID NO:28 represents the initial cysteine in the ActRIIB precursor sequence. It is expected that an ActRIIB polypeptide beginning at amino acid 29 of the N-terminus of SEQ ID NO:16 or SEQ ID NO:28, or before these amino acid positions, will retain ligand binding activity. An alanine to asparagine mutation at position 24 of SEQ ID NO: 16 or SEQ ID NO:28 introduces an N-linked glycosylation sequence without substantially affecting ligand binding. This confirms that mutations in the region between the signal cleavage peptide and the cysteine cross-linked region, corresponding to amino acids 20-29 of SEQ ID NO:16 or SEQ ID NO:28, are well tolerated. In particular, ActRIIB polypeptides beginning at amino acid position 20, 21, 22, 23 and 24 of SEQ ID NO: 16 or SEQ ID NO:28 will retain activity, and ActRIIB polypeptides beginning at amino acid positions 25, 26, 27, 28 and 29 of SEQ ID NO: 16 or SEQ ID NO:28 are also expected to retain activity. An ActRIIB polypeptide beginning at amino acid position 22, 23, 24 or 25 of SEQ ID NO:16 or SEQ ID NO:28 will have the most activity.

Taken together, the active portions (i.e., ActRIIB polypeptides) of the ActRIIB precursor protein (i.e., SEQ ID NO: 16 or SEQ ID NO:28) to be used in accordance with the methods and compositions described herein will generally comprise amino acids 29-109 of SEQ ID NO: 16 or SEQ ID NO:28, and such ActRIIB polypeptides may, for example, begin at a residue corresponding to any one of amino acids 19-29 of SEQ ID NO:16 or SEQ ID NO:28 and end at a position corresponding to any one of amino acids 109-134 of SEQ ID NO: 16 or SEQ ID NO:28. Specific examples of ActRIIB polypeptides encompassed herein include those that begin at an amino acid position from 19-29, 20-29 or 21-29 of SEQ ID NO: 16 or SEQ ID NO:28 and end at an amino acid position from 119-134, 119-133 or 129-134, 129-133 of SEQ ID NO:16 or SEQ ID NO:28. Other specific examples of ActRIIB polypeptides encompassed herein include those that begin at an amino acid position from 20-24 (or 21-24, or 22-25) of SEQ ID NO: 16 or SEQ ID NO:28 and end at an amino acid position from 109-134 (or 109-133), 119-134 (or 119-133) or 129-134 (or 129-133) of SEQ ID NO:16 or SEQ ID NO:28. Variant ActRIIB polypeptides falling within these ranges are also contemplated, particularly those having at least 80%, 85%, 90%, 91%, 92%, 93%, 94%, 95%, 96%, 97%, 98%, or 99% sequence identity or sequence homology to the corresponding portion of SEQ ID NO: 16 or SEQ ID NO:28.

In certain embodiments, the inhibitors of ActRIIB signaling used in the compositions and methods described herein comprise a truncated form of an extracellular domain of ActRIIB. The truncation can be at the carboxy terminus and/or the amino terminus of the ActRIIB polypeptide. In certain embodiments, the truncation can be 1, 2, 3, 4, 5, 6, 7, 8, 9, 10, 11, 12, 13, 14, 15, 16, 17, 18, 19, 20, 21, 22, 23, 24, or 25 amino acids long relative to the mature ActRIIB polypeptide extracellular domain. In certain embodiments, the truncation can be 1, 2, 3, 4, 5, 6, 7, 8, 9, 10, 11, 12, 13, 14, 15, 16, 17, 18, 19, 20, 21, 22, 23, 24, or 25 N-terminal amino acids of the mature ActRIIB polypeptide extracellular domain. In certain embodiments, the truncation can be 1, 2, 3, 4, 5, 6, 7, 8, 9, 10, 11, 12, 13, 14, 15, 16, 17, 18, 19, 20, 21, 22, 23, 24, or 25 C-terminal amino acids of the mature ActRIIB polypeptide extracellular domain. For example, truncated forms of ActRIIB include polypeptides with amino acids 20-119; 20-128; 20-129; 20-130: 20-131; 20-132; 20-133; 20-134; 20-131: 21-131; 22-131: 23-131; 24-131; and 25-131, wherein the amino acid positions refer to the amino acid positions in SEQ ID NO:16 or SEQ ID NO:28.

Additional exemplary truncated forms of ActRIIB include (i) polypeptides beginning at amino acids at any of amino acids 21-29 of SEQ ID NO: 16 or SEQ ID NO:28 (optionally beginning at 22-25 of SEQ ID NO: 16 or SEQ ID NO:28) and ending at any of amino acids 109-134 of SEQ ID NO:16 or SEQ ID NO:28; (ii) polypeptides beginning at any of amino acids 20-29 of SEQ ID NO: 16 or SEQ ID NO:28 (optionally beginning at 22-25 of SEQ ID NO: 16 or SEQ ID NO:28) and ending at any of amino acids 109-133 of SEQ ID NO: 16 or SEQ ID NO:28; (iii) polypeptides beginning at any of amino acids 20-24 of SEQ ID NO:16 or SEQ ID NO:28 (optionally beginning at 22-25 of SEQ ID NO:16 or SEQ ID NO:28) and ending at any of amino acids 109-133 of SEQ ID NO:16 or SEQ ID NO:28; (iv) polypeptides beginning at any of amino acids 21-24 of SEQ ID NO: 16 or SEQ ID NO:28 and ending at any of amino acids 109-134 of SEQ ID NO:16 or SEQ ID NO:28; (v) polypeptides beginning at any of amino acids 20-24 of SEQ ID NO: 16 or SEQ ID NO:28 and ending at any of amino acids 118-133 of SEQ ID NO:16 or SEQ ID NO:28; (vi) polypeptides beginning at any of amino acids 21-24 of SEQ ID NO: 16 or SEQ ID NO:28 and ending at any of amino acids 118-134 of SEQ ID NO: 16 or SEQ ID NO:28; (vii) polypeptides beginning at any of amino acids 20-24 of SEQ ID NO: 16 or SEQ ID NO:28 and ending at any of amino acids 128-133 of SEQ ID NO:16 or SEQ ID NO:28; (viii) polypeptides beginning at any of amino acids 20-24 of SEQ ID NO: 16 or SEQ ID NO:28 and ending at any of amino acids 128-133 of SEQ ID NO:16 or SEQ ID NO:28; (ix) polypeptides beginning at any of amino acids 21-29 of SEQ ID NO:16 or SEQ ID NO:28 and ending at any of amino acids 118-134 of SEQ ID NO:16 or SEQ ID NO:28; (x) polypeptides beginning at any of amino acids 20-29 of SEQ ID NO:16 or SEQ ID NO:28 and ending at any of amino acids 118-133 of SEQ ID NO:16 or SEQ ID NO:28; (xi) polypeptides beginning at any of amino acids 21-29 of SEQ ID NO:16 or SEQ ID NO:28 and ending at any of amino acids 128-134 of SEQ ID NO:16 or SEQ ID NO:28; and (xii) polypeptides beginning at any of amino acids 20-29 of SEQ ID NO: 16 or SEQ ID NO:28 and ending at any of amino acids 128-133 of SEQ ID NO: 16 or SEQ ID NO:28. In a specific embodiment, an ActRIIB polypeptides comprises, consists essentially of, or consists of, an amino acid sequence beginning at amino acid position 25 of SEQ ID NO: 16 or SEQ ID NO:28 and ending at amino acid position 131 of SEQ ID NO:16 or SEQ ID NO:28. In another specific embodiment, an ActRIIB polypeptide consists of, or consists essentially of, the amino acid sequence of SEQ ID NO:17, 18, 23, 26, 27, 29, 30, 31, 32, 33, 36, 37, 42, or 43.

Any of the ActRIIB polypeptides used in the compositions and methods described herein may be produced as a homodimer. Any of the ActRIIB polypeptides used in the compositions and methods described herein may be formulated as a fusion protein having a heterologous portion that comprises a constant region from an IgG heavy chain, such as an Fc domain. Any of the ActRIIB polypeptides used in the compositions and methods described herein may comprise an acidic amino acid at the position corresponding to position 79 of SEQ ID NO: 16 or SEQ ID NO:28, optionally in combination with one or more additional amino acid substitutions, deletions or insertions relative to SEQ ID NO: 16 or SEQ ID NO:28.

In specific embodiments, the inhibitors of ActRIIB signaling used in the compositions and methods described herein comprise an extracellular domain of ActRIIB with one or more amino acid substitutions/mutations. Such an amino acid substitution/mutation can be, for example, an exchange from the leucine at amino acid position 79 of SEQ ID NO: 16 or SEQ ID NO:28 to an acidic amino acid, such as aspartic acid or glutamic acid. For example, position L79 of SEQ ID NO: 16 or SEQ ID NO:28 may be altered in ActRIIB extracellular domain polypeptides to confer altered activin-myostatin (GDF-11) binding properties. L79A and L79P mutations reduce GDF-1 binding to a greater extent than activin binding. L79E and L79D mutations retain GDF-11 binding, while demonstrating greatly reduced activin binding.

In certain embodiments, the inhibitors of ActRIIB signaling used in the compositions and methods described herein comprise a truncated form of an ActRIIB extracellular domain that also carries an amino acid substitution, e.g., an exchange from the leucine at amino acid position 79 of SEQ ID NO: 16 or SEQ ID NO:28 to an acidic amino acid, such as aspartic acid or glutamic acid. In a specific embodiment, the truncated form of an extracellular domain of ActRIIB polypeptide that also carries an amino acid substitution used in the compositions and methods described herein is SEQ ID NO:23. Forms of ActRIIB that are truncated and/or carry one or more amino acid substitutions can be linked to an Fc domain of an antibody as discussed above.

Functionally active fragments of ActRIIB polypeptides can be obtained, for example, by screening polypeptides recombinantly produced from the corresponding fragment of the nucleic acid encoding an ActRIIB polypeptide. In addition, fragments can be chemically synthesized using techniques known in the art such as conventional Merrifield solid phase f-Moc or t-Boc chemistry. As will be recognized by one of skill in the art, other techniques, including for example various resins and solution phase systems for peptide synthesis can be used to synthesize peptidyl fragments described herein. The fragments can be produced (recombinantly or by chemical synthesis) and tested to identify those peptidyl fragments that can function as antagonists (inhibitors) of ActRIIB protein or signaling mediated by activin.

In addition, functionally active variants of ActRIIB polypeptides can be obtained, for example, by screening libraries of modified polypeptides recombinantly produced from the corresponding mutagenized nucleic acids encoding an ActRIIB polypeptide. The variants can be produced and tested to identify those that can function as antagonists (inhibitors) of ActRIIB protein or signaling mediated by activin. In certain embodiments, a functional variant of the ActRIIB polypeptides comprises an amino acid sequence that is at least 75% identical to an amino acid sequence selected from SEQ ID NO: 17, 18, 23, 26, 27, 29, 30, 31, 32, 33, 36, 37, 42, and 43. In certain embodiments, the functional variant has an amino acid sequence at least 80%, 850/0, 90%, 95%, 96%, 97%, 98%, or 99% identical to an amino acid sequence selected from SEQ ID NO:17, 18, 23, 26, 27, 29, 30, 31, 32, 33, 36, 37, 42, and 43.

Functional variants may be generated, for example, by modifying the structure of an ActRIIB polypeptide for such purposes as enhancing therapeutic efficacy, or stability (e.g., ex vivo shelf life and resistance to proteolytic degradation in vivo). Such modified ActRIIB polypeptides when selected to retain activin binding, are considered functional equivalents of the naturally-occurring ActRIIB polypeptides. Modified ActRIIB polypeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of an ActRIIB polypeptide results in a functional homolog can be readily determined by assessing the ability of the variant ActRIIB polypeptide to produce a response in cells in a fashion similar to the wild-type ActRIIB polypeptide.

ActRIIB polypeptide mutants, particularly sets of combinatorial mutants of an ActRIIB polypeptide, as well as truncation mutants; pools of combinatorial mutants are especially useful for identifying functional variant sequences can be used in the methods and compositions described herein. The purpose of screening such combinatorial libraries may be to generate, for example, ActRIIB polypeptide variants which can act as either agonists or antagonist, or alternatively, which possess novel activities all together.

It has been demonstrated that the ligand binding pocket of ActRIIB is defined by residues Y31, N33, N35, L38 through T41, E47, E50, Q53 through K55, L57, H58, Y60, S62, K74, W78 through N83, Y85, R87, A92, and E94 through F101 of SEQ ID NO: 16 or SEQ ID NO:28. At these positions, it is expected that conservative mutations will be tolerated, although a K74A mutation is well-tolerated, as are R40A, K55A, F82A and mutations at position L79. R40 is a K in *Xenopus*, indicating that basic amino acids at this position will be tolerated. Q53 is R in bovine ActRIIB and K in *Xenopus* ActRIIB, and therefore amino acids including R, K, Q, N and H will be tolerated at this position. Thus, a general formula for an ActRIIB polypeptide for use in the methods and compositions described herein is one that comprises amino acids 29-109 of SEQ ID NO: 16 or SEQ ID NO:28, but optionally beginning at an amino acid position ranging from 20-24 or 22-25 of SEQ ID NO: 16 or SEQ ID NO:28 and ending at an amino acid position ranging from 129-134 of SEQ ID NO: 16 or SEQ ID NO:28, and comprising no more than 1, 2, 5, or 15 conservative amino acid changes in the ligand binding pocket, and zero, one or more non-conservative alterations at amino acid positions 40, 53, 55, 74, 79 and/or 82 of SEQ ID NO: 16 or SEQ ID NO:28 in the ligand binding pocket. Such an ActRIIB polypeptide may retain greater than 80%, 90%, 95% or 99% sequence identity or sequence homology to the sequence of amino acids 29-109 of SEQ ID NO:16 or SEQ ID NO:28. Sites outside the binding pocket, at which variability may be particularly well tolerated, include the amino and carboxy termini of the extracellular domain of ActRIIB, and positions 42-46 and 65-73. An asparagine to alanine alteration at position 65 of SEQ ID NO: 16 or SEQ ID NO:28 (N65A) actually improves ligand binding in the A64 background, and is thus expected to have no detrimental effect on ligand binding in the R64 background. This change probably eliminates glycosylation at N65 in the A64 background, thus demonstrating that a significant change in this region is likely to be tolerated. While an R64A change is poorly tolerated, R64K is well-tolerated, and thus another basic residue, such as H may be tolerated at position 64.

As a specific example of an ActRIIB polypeptide with a mutation in the ligand binding domain, the positively-charged amino acid residue Asp (D80) of the ligand-binding domain of ActRIIB can be mutated to a different amino acid residue such that the variant ActRIIB polypeptide preferentially binds to GDF8, but not activin. In a specific embodiment, the D80 residue is changed to an amino acid residue selected from the group consisting of: an uncharged amino acid residue, a negative amino acid residue, and a hydrophobic amino acid residue. As a further specific example, the hydrophobic residue L79 can be altered to the acidic amino acids aspartic acid or glutamic acid to greatly reduce activin binding while retaining GDF11 binding. As will be recognized by one of skill in the art, most of the described mutations, variants or modifications may be made at the nucleic acid level or, in some cases, by post translational modification or chemical synthesis. Such techniques are well known in the art.

In specific embodiments, the inhibitors of ActRIIB signaling used in the compositions and methods described herein comprise a conjugate/fusion protein comprising an extracellular domain (e.g., an activin-binding domain) of an ActRIIB receptor linked to an Fc portion of an antibody. Such conjugate/fusion proteins may comprise any of the ActRIIB polypeptides disclosed herein (e.g., any of SEQ ID NOS:17, 18, 23, 26, 27, 29, 30, 31, 32, 33, 36, 37, 42, or 43), any ActRIIB polypeptides known in the art, or any ActRIIB polypeptides generated using methods known in the art and/or provided herein.

In certain embodiments, the extracellular domain is linked to an Fc portion of an antibody via a linker, e.g., a peptide linker. Exemplary linkers include short polypeptide sequences such as 2-10, 2-5, 2-4, 2-3 amino acid residues (e.g., glycine residues), such as, for example, a Gly-Gly-Gly linker. In a specific embodiment, the linker comprises the amino acid sequence Gly-Gly-Gly (GGG). In another specific embodiment, the linker comprises the amino acid sequence Thr-Gly-Gly-Gly (TGGG). Optionally, the Fc domain has one or more mutations at residues such as Asp-265, lysine 322, and Asn-434. In certain cases, the mutant Fc domain having one or more of these mutations (e.g., an Asp-265 mutation) has a reduced ability to bind to the Fcγ receptor relative to a wild-type Fc domain. In other cases, the mutant Fc domain having one or more of these mutations (e.g., an Asn-434 mutation) has an increased ability to bind to the MHC class I-related Fc-receptor (FcRN) relative to a wild-type Fc domain. Exemplary fusion proteins comprising a soluble extracellular domain of ActRIIB fused to an Fc domain are set forth in SEQ ID NOs:20, 21, 24, 25, 34, 35, 38, 39, 40, 41, 44, 46, and 47.

In a specific embodiment, the ActRIIB signaling inhibitors used in the compositions and methods described herein comprise the extracellular domain of ActRIIB, or a portion thereof, linked to an Fc portion of an antibody, wherein said ActRIIB signaling inhibitor comprises an amino acid sequence that is at least 75% identical to an amino acid sequence selected from SEQ ID NOs:20, 21, 24, 25, 34, 35, 38, 39, 40, 41, 44, 46, and 47. In another specific embodiment, the ActRIIB signaling inhibitors used in the compositions and methods described herein comprise the extracellular domain of ActRIIB, or a portion thereof, linked to an Fc portion of an antibody, wherein said ActRIIB signaling inhibitor comprises an amino acid sequence that is at least 80%, 85%, 90%, 95%, 96%, 97%, 98%, or 99% identical to an amino acid sequence selected from SEQ ID NOS:20, 21, 24, 25, 34, 35, 38, 39, 40, 41, 44, 46, and 47.

In a specific embodiment, the ActRIIB signaling inhibitor to be used in the compositions and methods described herein is a fusion protein between the extracellular domain of the human ActRIIB receptor and the Fc portion of IgG1. In another specific embodiment, the ActRIIB signaling inhibitor to be used in the compositions and methods described herein is a fusion protein between a truncated extracellular domain of the human ActRIIB receptor and the Fc portion of IgG1. In another specific embodiment, the ActRIIB signaling inhibitor to be used in the compositions and methods described herein is a fusion protein between a truncated extracellular domain of the human ActRIIB receptor and the Fc portion of IgG1, wherein the truncated extracellular domain of the human ActRIIB receptor possesses an amino acid substitution at the amino acid position corresponding to amino acid 79 of SEQ ID NO: 16 or SEQ ID NO:28. In one embodiment, the amino acid substitution at the amino acid position corresponding to amino acid 79 of SEQ ID NO: 16 or SEQ ID NO:28 is substitution of Leucine for Aspartic Acid (i.e., an L79D mutation).

In a specific embodiment, the ActRIIB signaling inhibitor to be used in the compositions and methods described herein is SEQ ID NO:24 or 25, which represents a fusion protein between the extracellular domain of the human ActRIIB receptor and the Fc portion of IgG1, wherein said ActRIIB extracellular domain comprises amino acids 25-131 of SEQ ID NO:28 with an L79D mutation. The nucleic acid sequence encoding the ActRIIB-Fc fusion protein of SEQ ID NO:24 is presented in SEQ ID NO:45.

In another specific embodiment, the ActRIIB signaling inhibitor to be used in the compositions and methods described herein is SEQ ID NO:34 or 35, which represents a fusion protein between the extracellular domain of the human ActRIIB receptor and the Fc portion of IgG1, wherein said ActRIIB extracellular domain comprises amino acids 25-131 of SEQ ID NO:16 with an L79D mutation.

Asparagine-linked glycosylation recognition sites generally comprise a tripeptide sequence, asparagine-X-threonine (or asparagine-X-serine) (where "X" is any amino acid) which is specifically recognized by appropriate cellular glycosylation enzymes. The alteration may also be made by the addition of, or substitution by, one or more serine or threonine residues to the sequence of the wild-type ActRIIB polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on an ActRIIB polypeptide is by chemical or enzymatic coupling of glycosides to the ActRIIB polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in International Patent Application No. WO 87/05330 published Sep. 11, 1987, and in Aplin and Wriston (1981) CRC Crit. Rev. Biochem., pp. 259-306, incorporated by reference herein. Removal of one or more carbohydrate moieties present on an ActRIIB polypeptide may be accomplished chemically and/or enzymatically. Chemical deglycosylation may involve, for example, exposure of the ActRIIB polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on ActRIIB polypeptides can be achieved by the use of a variety of endo- and exo-glycosidases as described by Thotakura et al. (1987) Meth. Enzymol. 138:350. The sequence of an ActRIIB polypeptide may be adjusted, as appropriate, depending on the type of expression system used, as mammalian, yeast, insect and plant cells may all introduce differing glycosylation patterns that can be affected by the amino acid sequence of the peptide. In general, ActRIIB proteins for use in humans will be expressed in a mammalian cell line that provides proper glycosylation, such as HEK293 or CHO cell lines, although other expression systems, such as other mammalian expression cell lines, yeast cell lines with engineered glycosylation enzymes and insect cells, are expected to be useful as well.

In specific embodiments, mutated ActRIIB polypeptides comprising the addition of a further N-linked glycosylation site (N—X—S/T) that increases the serum half-life of an ActRIIB-Fc fusion protein, relative to the ActRIIB(R64)-Fc form can be used in the methods and compositions described herein. In a specific embodiment, introduction of an asparagine at position 24 of SEQ ID NO: 16 or SEQ ID NO:28 (A24N) results in the creation of an NXT sequence that confers a longer half-life. Other NX(T/S) sequences can be found at 42-44 (NQS) and 65-67 (NSS), although the latter may not be efficiently glycosylated with the R at position 64 (i.e., in R64 polypeptides). N—X—S/T sequences may be generally introduced at positions outside the ligand binding pocket of ActRIIB, which is detailed above. Particularly suitable sites for the introduction of non-endogenous N—X—S/T sequences include amino acids 20-29, 20-24, 22-25, 109-134, 120-134 or 129-134 of SEQ ID NO:16 or SEQ ID NO:28. N—X—S/T sequences may also be introduced into the linker between the ActRIIB sequence and the Fc or other fusion component. Such a site may be introduced with minimal effort by introducing an N in the correct position with respect to a pre-existing S or T, or by introducing an S or T at a position corresponding to a pre-existing N. Thus, desirable alterations that would create an N-linked glycosylation site are: A24N, R64N, S67N (possibly combined with an N65A alteration), E106N, R112N, G120N, E123N, P129N, A132N, R112S and R112T (with all amino acid positions corresponding to the positions they can be found in SEQ ID NO:16 or SEQ ID NO:28). Any S that is predicted to be glycosylated may be altered to a T without creating an immunogenic site, because of the protection afforded by the glycosylation. Likewise, any T that is predicted to be glycosylated may be altered to an S. Thus the alterations S67T and S44T are encompassed herein. Likewise, in an A24N variant, an S26T alteration may be used. Accordingly, an ActRIIB polypeptide may include one or more additional, non-endogenous N-linked glycosylation consensus sequences.

A variety of screening assays may be used to evaluate ActRIIB polypeptide variants. For example, an ActRIIB polypeptide variant may be screened for ability to bind to an ActRIIB ligand, to prevent binding of an ActRIIB ligand to an ActRIIB polypeptide or to interfere with signaling caused by an ActRIIB ligand. The activity of an ActRIIB polypeptide or its variants may also be tested in a cell-based or in vivo assay.

Combinatorially-derived variants can be generated which have a selective or generally increased potency relative to a naturally occurring ActRIIB polypeptide. Likewise, mutagenesis can give rise to variants which have intracellular half-lives dramatically different than the corresponding wild-type ActRIIB polypeptide. For example, the altered protein can be rendered either more stable or less stable to proteolytic degradation or other cellular processes which result in destruction of, or otherwise inactivation of a native ActRIIB polypeptide. Such variants, and the genes which encode them, can be utilized to alter ActRIIB polypeptide levels by modulating the half-life of the ActRIIB polypeptides. For instance, a short half-life can give rise to more transient biological effects and can allow tighter control of recombinant ActRIIB polypeptide levels within the subject. In an Fc fusion protein, mutations may be made in the linker (if any) and/or the Fc portion to alter the half-life of the protein.

A combinatorial library may be produced by way of a degenerate library of genes encoding a library of polypeptides which each include at least a portion of potential ActRIIB polypeptide sequences. For instance, a mixture of synthetic oligonucleotides can be enzymatically ligated into gene sequences such that the degenerate set of potential ActRIIB polypeptide nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate vector for expression. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. AG Walton, Amsterdam; Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, ActRIIB polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of ActRIIB polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of ActRIIB polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include activin binding assays and activin-mediated cell signaling assays.

In certain embodiments, ActRIIB polypeptides used in the methods and compositions described herein may further comprise post-translational modifications in addition to any that are naturally present in the ActRIIB polypeptides. Such modifications include, but are not limited to, acetylation, carboxylation, glycosylation, phosphorylation, lipidation, and acylation. As a result, the modified ActRIIB polypeptides may contain non-amino acid elements, such as polyethylene glycols, lipids, poly- or mono-saccharide, and phosphates. Effects of such non-amino acid elements on the functionality of an ActRIIB polypeptide may be tested by any method known to the skilled artisan. When an ActRIIB polypeptide is produced in cells by cleaving a nascent form of the ActRIIB polypeptide, post-translational processing may also be important for correct folding and/or function of the protein. Different cells (such as CHO, HeLa, MDCK, 293, W138, NIH-3T3 or HEK293) have specific cellular machinery and characteristic mechanisms for such post-translational activities and may be chosen to ensure the correct modification and processing of the ActRIIB polypeptides.

In certain aspects, functional variants or modified forms of the ActRIIB polypeptides include fusion proteins having at least a portion of the ActRIIB polypeptides and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS6) fusion partners. As another example, a fusion domain may be selected so as to facilitate detection of the ActRIIB polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus hemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, an ActRIIB polypeptide is fused with a domain that stabilizes the ActRIIB polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, such as further stimulation of bone growth or muscle growth, as desired).

It is understood that different elements of the fusion proteins may be arranged in any manner that is consistent with the desired functionality. For example, an ActRIIB polypeptide may be placed C-terminal to a heterologous domain, or, alternatively, a heterologous domain may be placed C-terminal to an ActRIIB polypeptide. The ActRIIB polypeptide domain and the heterologous domain need not be adjacent in a fusion protein, and additional domains or amino acid sequences may be included C- or N-terminal to either domain or between the domains.

In certain embodiments, the ActRIIB polypeptides used in the methods and compositions described herein contain one or more modifications that are capable of stabilizing the ActRIIB polypeptides. For example, such modifications enhance the in vitro half life of the ActRIIB polypeptides, enhance circulatory half life of the ActRIIB polypeptides or reduce proteolytic degradation of the ActRIIB polypeptides. Such stabilizing modifications include, but are not limited to, fusion proteins (including, for example, fusion proteins comprising an ActRIIB polypeptide and a stabilizer domain), modifications of a glycosylation site (including, for example, addition of a glycosylation site to an ActRIIB polypeptide), and modifications of carbohydrate moiety (including, for example, removal of carbohydrate moieties from an ActRIIB polypeptide). In the case of fusion proteins, an ActRIIB polypeptide is fused to a stabilizer domain such as an IgG molecule (e.g., an Fc domain). As used herein, the term "stabilizer domain" not only refers to a fusion domain (e.g., Fc) as in the case of fusion proteins, but also includes nonproteinaceous modifications such as a carbohydrate moiety, or nonproteinaceous polymer, such as polyethylene glycol.

In certain embodiments, the methods and compositions described herein use isolated or purified ActRIIB polypeptides, i.e., ActRIIB polypeptides which are isolated from, or otherwise substantially free of, other proteins can be used with the methods and compositions described herein. ActRIIB polypeptides will generally be produced by expression from recombinant nucleic acids.

In certain aspects, the ActRIIB polypeptides used in the methods and compositions described herein are encoded by isolated and/or recombinant nucleic acids, including fragments, functional variants and fusion proteins disclosed herein. For example, SEQ ID NO: 19 encodes the naturally occurring human ActRIIB precursor polypeptide. The subject nucleic acids may be single-stranded or double stranded. Such nucleic acids may be DNA or RNA molecules. These nucleic acids may be used, for example, in methods for making ActRIIB polypeptides or as direct therapeutic agents (e.g., in a gene therapy approach).

In certain aspects, the nucleic acids that can be used to produce ActRIIB polypeptides suitable for use in the methods and compositions described herein are further understood to include nucleic acids that are variants of SEQ ID NO: 19 as well as variants of those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43). Variant nucleotide sequences include sequences that differ by one or more nucleotide substitutions, additions or deletions, such as allelic variants.

In certain embodiments, the isolated or recombinant nucleic acid sequences that can be used to produce ActRIIB polypeptides suitable for use in the methods and compositions described herein are at least 80%, 85%, 90%, 95%, 97%, 98%, 99% or 100% identical to SEQ ID NO: 19 or those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43). One of ordinary skill in the art will appreciate that nucleic acid sequences complementary to SEQ ID NO: 19 or those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43), and variants of SEQ ID NO: 19 or those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43) can be used with the methods and compositions described herein. In further embodiments, the nucleic acid sequences can be isolated, recombinant, and/or fused with a heterologous nucleotide sequence, or in a DNA library.

In other embodiments, nucleic acids that can be used to produce ActRIIB polypeptides suitable for use in the methods and compositions described herein include nucleotide sequences that hybridize under highly stringent conditions to the nucleotide sequence designated in SEQ ID NO: 19 or those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43), complement sequence of SEQ ID NO: 19 or those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43), or fragments thereof. One of ordinary skill in the art will understand that appropriate stringency conditions which promote DNA hybridization can be varied. For example, one can perform the hybridization at 6.0 times sodium chloride/sodium citrate (SSC) at about 45 degree Celsius, followed by a wash of 2.0 times SSC at 50 degree Celsius. For example, the salt concentration in the wash step can be selected from a low stringency of about 2.0 times SSC at 50 degree Celsius to a high stringency of about 0.2 times SSC at 50 degree Celsius. In addition, the temperature in the wash step can be increased from low stringency conditions at room temperature, about 22 degree Celsius, to high stringency conditions at about 65 degree Celsius. Both temperature and salt may be varied, or temperature or salt concentration may be held constant while the other variable is changed. In one embodiment, nucleic acids which hybridize under low stringency conditions of 6 times SSC at room temperature followed by a wash at 2 times SSC at room temperature can be used with the methods and compositions described herein.

Isolated nucleic acids which differ from the nucleic acids as set forth in SEQ ID NO: 19 or those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43) due to degeneracy in the genetic code can also be used to produce ActRIIB polypeptides suitable for use in the methods and compositions described herein. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms can be used with the methods and compositions described herein.

In certain embodiments, the recombinant nucleic acids that can be used to produce ActRIIB polypeptides suitable for use in the methods and compositions described herein may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art can be used with the methods and compositions described herein. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects, the nucleic acids that can be used to produce ActRIIB polypeptides suitable for use in the methods and compositions described herein are provided in an expression vector comprising a nucleotide sequence encoding an ActRIIB polypeptide and operably linked to at least one regulatory sequence. Regulatory sequences are art-recognized and are selected to direct expression of the ActRIIB polypeptide. Accordingly, the term regulatory sequence includes promoters, enhancers, and other expression control elements. Exemplary regulatory sequences are described in Goeddel; Gene Expression Technology: Methods in Enzymology, Academic Press, San Diego, Calif. (1990). For instance, any of a wide variety of expression control sequences that control the expression of a DNA sequence when operatively linked to it may be used in these vectors to express DNA sequences encoding an ActRIIB polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast .alpha.-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid can be produced by ligating the cloned gene, or a portion thereof, into a vector suitable for expression in either prokaryotic cells, eukaryotic cells (yeast, avian, insect or mammalian), or both. Expression vehicles for production of a recombinant ActRIIB polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as E. coli.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see Molecular Cloning A Laboratory Manual, 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the .beta.-gal containing pBlueBac III).

In one embodiment, a vector can be designed for production of the ActRIIB polypeptides used in the methods and compositions described herein in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject ActRIIB polypeptides in cells propagated in culture, e.g., to produce proteins, including fusion proteins or variant proteins, for purification.

Host cells transfected with a recombinant gene including a coding sequence (e.g., SEQ ID NO: 19 or those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43)) for one or more of the subject ActRIIB polypeptides can be used to produce ActRIIB polypeptides suitable for use in the methods and compositions described herein. The host cell may be any prokaryotic or eukaryotic cell. For example, an ActRIIB polypeptide may be expressed in bacterial cells such as E. coli, insect cells (e.g., using a baculovirus expression system), yeast, or mammalian cells. Other suitable host cells are known to those skilled in the art.

Accordingly, provided herein are methods of producing the ActRIIB polypeptides used in the methods and compositions described herein. For example, a host cell transfected with an expression vector encoding an ActRIIB polypeptide can be cultured under appropriate conditions to allow expression of the ActRIIB polypeptide to occur. The ActRIIB polypeptide may be secreted and isolated from a mixture of cells and medium containing the ActRIIB polypeptide. Alternatively, the ActRIIB polypeptide may be retained cytoplasmically or in a membrane fraction and the cells harvested, lysed and the protein isolated. A cell culture includes host cells, media and other byproducts. Suitable media for cell culture are well known in the art. The subject ActRIIB polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the ActRIIB polypeptides and affinity purification with an agent that binds to a domain fused to the ActRIIB polypeptide (e.g., a protein A column may be used to purify an ActRIIB-Fc fusion). In a preferred embodiment, the ActRIIB polypeptide is a fusion protein containing a domain which facilitates its purification. In a preferred embodiment, purification is achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. As demonstrated herein, ActRIIB-hFc protein was purified to a purity of >98% as determined by size exclusion chromatography and >95% as determined by SDS PAGE. This level of purity was sufficient to achieve desirable effects on bone in mice and an acceptable safety profile in mice, rats and non-human primates.

In another embodiment, a fusion gene coding for a purification leader sequence, such as a poly-(His)/enterokinase cleavage site sequence at the N-terminus of the desired portion of the recombinant ActRIIB polypeptide, can allow purification of the expressed fusion protein by affinity chromatography using a Ni2+ metal resin. The purification leader sequence can then be subsequently removed by treatment with enterokinase to provide the purified ActRIIB polypeptide (e.g., see Hochuli et al., (1987) J. Chromatography 411:177; and Janknecht et al., PNAS USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al., John Wiley & Sons: 1992).

ActRIIB-Fc fusion protein can be expressed in stably transfected CHO-DUKX BI 1 cells from a pAID4 vector (SV40 ori/enhancer, CMV promoter), using a tissue plasminogen leader sequence of SEQ ID NO:8. The Fc portion can comprise a human IgG1 Fc sequence, as shown in SEQ ID NO:7. In certain embodiments, upon expression, the protein contained has, on average, between about 1.5 and 2.5 moles of sialic acid per molecule of ActRIIB-Fc fusion protein.

In certain embodiments, the long serum half-life of an ActRIIB-Fc fusion can be 25-32 days in human subjects. Additionally, the CHO cell expressed material can have a higher affinity for activin B ligand than that reported for an ActRIIB-hFc fusion protein expressed in human 293 cells (del Re et al., J Biol Chem. 2004 Dec. 17; 279(51):53126-35). Additionally, without being bound by theory, the use of the TPA leader sequence provided greater production than other leader sequences and, unlike ActRIIB-Fc expressed with a native leader, may provide a highly pure N-terminal sequence. Use of the native leader sequence may result in two major species of ActRIIB-Fc, each having a different N-terminal sequence.

Other ActRII Receptor Signaling Inhibitors

In certain embodiments, the inhibitors of ActRII signaling used in the compositions and methods described herein are nucleic acid compounds.

Examples of categories of nucleic acid compounds that inhibit ActRII receptors include antisense nucleic acids, siRNA or RNAi constructs and catalytic nucleic acid constructs. A nucleic acid compound may be single- or double-stranded. A double-stranded compound may also include regions of overhang or non-complementarity, where one or the other of the strands is single-stranded. A single-stranded compound may include regions of self-complementarity, meaning that the compound may form a so-called "hairpin" or "stem-loop" structure, with a region of double helical structure.

In certain embodiments, the nucleic acid compounds that inhibit ActRII receptors may comprise a nucleotide sequence that is complementary to a region consisting of no more than 1000, no more than 500, no more than 250, no more than 100 or no more than 50, 35, 30, 25, 22, 20 or 18 nucleotides of the full-length ActRII receptor nucleic acid sequence or activin nucleic acid sequence (e.g., the nucleic acid sequence of an activin A or activin B subunit, also referred to as $\beta_A$ or $\beta_B$). In specific embodiments, the region of complementarity will be at least 8 nucleotides, and optionally at least 10 or at least 15 nucleotides, and optionally between 15 and 25 nucleotides. A region of complementarity may fall within an intron, a coding sequence or a noncoding sequence of the target transcript, such as the coding sequence portion. Generally, a nucleic acid compound that inhibits an ActRII receptor will have a length of about 8 to about 500 nucleotides or base pairs in length, and optionally the length will be about 14 to about 50 nucleotides. A nucleic acid compound that inhibits an ActRII receptor may be a DNA (particularly for use as an antisense), an RNA, or an RNA:DNA hybrid. Any one strand may include a mixture of DNA and RNA, as well as modified forms that cannot readily be classified as either DNA or RNA. Likewise, a double stranded nucleic acid compound may be DNA:DNA, DNA:RNA, or RNA:RNA, and any one strand may also include a mixture of DNA and RNA, as well as modified forms that cannot readily be classified as either DNA or RNA.

The nucleic acid compounds that inhibit an ActRII receptor may include any of a variety of modifications, including one or more modifications to the backbone (the sugar-phosphate portion in a natural nucleic acid, including internucleotide linkages) or the base portion (the purine or pyrimidine portion of a natural nucleic acid). In certain embodiments, an antisense nucleic acid compound will have a length of about 15 to about 30 nucleotides and will often contain one or more modifications to improve certain characteristics, such as stability in the serum, stability in a cell, or stability in a place where the compound is likely to be delivered, such as, e.g., the stomach in the case of orally delivered compounds and the lung for inhaled compounds. In the case of an RNAi construct, the strand complementary to the target transcript will generally be RNA or modifications thereof. The other strand may be RNA, DNA, or any other variation. The duplex portion of double stranded or single stranded "hairpin" RNAi construct may, in certain embodiments, have a length of 18 to 40 nucleotides in length and optionally about 21 to 23 nucleotides in length, so long as it serves as a Dicer substrate. Catalytic or enzymatic nucleic acids may be ribozymes or DNA enzymes and may also contain modified forms. In certain embodiments, nucleic acid compounds that inhibit ActRII receptors may inhibit expression of their target by about 50%, 60%, 70%, 75%, 80%, 85%, 90%, 95%, 99%, or more under physiological conditions and at a concentration where a nonsense or sense control has little or no effect. Concentrations for testing the effect of nucleic acid compounds include 1, 5, 10 micromolar, or more.

In other embodiments, the inhibitors of ActRII signaling used in the compositions and methods described herein are antibodies. Such antibodies include antibodies that bind to activin (particularly the activin A or B subunits, also referred to as $\beta A$ or $\beta B$) and disrupt ActRII receptor binding; and antibodies that bind to ActRII receptor polypeptides (e.g., a soluble ActRIIA or soluble ActRIIB polypeptide) and disrupt activin binding.

By using immunogens derived from an ActRII receptor polypeptide or an activin polypeptide, anti-protein/anti-peptide antisera or monoclonal antibodies can be made by standard protocols (see, for example, Antibodies: A Laboratory Manual ed. by Harlow and Lane (Cold Spring Harbor Press: 1988)). A mammal, such as a mouse, a hamster or rabbit can be immunized with an immunogenic form of the ActRII receptor polypeptide, an antigenic fragment which is capable of eliciting an antibody response, or a fusion protein. Techniques for conferring immunogenicity on a protein or peptide include conjugation to carriers or other techniques well known in the art. An immunogenic portion of an ActRII receptor or activin polypeptide can be administered in the presence of adjuvant. The progress of immunization can be monitored by detection of antibody titers in plasma or serum. Standard ELISA or other immunoassays can be used with the immunogen as antigen to assess the levels of antibodies.

Following immunization of an animal with an antigenic preparation of an ActRII receptor polypeptide, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with an ActRII receptor polypeptide and monoclonal antibodies isolated from a culture comprising such hybridoma cells.

The term "antibody" as used herein is intended to include fragments thereof which are also specifically reactive with a subject polypeptide. Antibodies can be fragmented using conventional techniques and the fragments screened for utility in the same manner as described above for whole antibodies. For example, F(ab)2 fragments can be generated by treating antibody with pepsin. The resulting F(ab)2 fragment can be treated to reduce disulfide bridges to produce Fab fragments. An antibody is further intended to include bispecific, single-chain, chimeric, humanized and fully human molecules having affinity for an ActRII receptor or activin polypeptide conferred by at least one CDR region of the antibody. An antibody may further comprise a label attached thereto and able to be detected (e.g., the label can be a radioisotope, fluorescent compound, enzyme or enzyme co-factor).

In certain embodiments, the antibody is a recombinant antibody, which term encompasses any antibody generated in part by techniques of molecular biology, including CDR-grafted or chimeric antibodies, human or other antibodies assembled from library-selected antibody domains, single chain antibodies and single domain antibodies (e.g., human $V_H$ proteins or camelid $V_{HH}$ proteins). In certain embodiments, an antibody can be a monoclonal antibody. For example, a method for generating a monoclonal antibody that binds specifically to an ActRII receptor polypeptide or activin polypeptide may comprise administering to a mouse an amount of an immunogenic composition comprising the antigen polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monoclonal antibody that binds specifically to the antigen. Once obtained, a hybridoma can be propagated in a cell culture, optionally in culture conditions where the hybridoma-derived cells produce the monoclonal antibody that binds specifically to the antigen. The monoclonal antibody may be purified from the cell culture.

The adjective "specifically reactive with" as used in reference to an antibody is intended to mean, as is generally understood in the art, that the antibody is sufficiently selective between the antigen of interest (e.g., an ActRII receptor polypeptide) and other antigens that are not of interest that the antibody is useful for, at minimum, detecting the presence of the antigen of interest in a particular type of biological sample. In certain methods employing the antibody, such as therapeutic applications, a higher degree of specificity in binding may be desirable. Monoclonal antibodies generally have a greater tendency (as compared to polyclonal antibodies) to discriminate effectively between the desired antigens and cross-reacting polypeptides. One characteristic that influences the specificity of an antibody: antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ or less. Given the extraordinarily tight binding between activin and an ActRII receptor, it is expected that a neutralizing anti-activin or anti-ActRII receptor antibody would generally have a dissociation constant of $10^{-10}$ or less.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interaction between antibodies and antigens to identify particularly desirable antibodies. Such techniques include ELISAs, surface plasmon resonance binding assays (e.g., the Biacore™ binding assay, Biacore AB, Uppsala, Sweden), sandwich assays (e.g., the paramagnetic bead system of IGEN International, Inc., Gaithersburg, Md.), Western blots, immunoprecipitation assays, and immunohistochemistry.

In certain embodiments, ActRII signaling inhibitors to be used in the compositions and methods described herein include alternative forms of activin, particularly those with alterations in the type I receptor binding domain can bind to type II receptors and fail to form an active ternary complex. In certain embodiments, nucleic acids, such as antisense molecules, siRNAs or ribozymes that inhibit activin A, B, C or E, or, particularly, ActRII receptor expression, can be used in the compositions and methods described herein. In certain embodiments, the ActRII signaling inhibitors to be used in the compositions and methods described herein exhibit selectivity for inhibiting GDF11-mediated signaling versus other members of the TGF-beta family, particularly with respect to GDF8 and activin.

In other embodiments, the inhibitors of ActRII signaling used in the compositions and methods described herein are non-antibody proteins with ActRII receptor antagonist activity, including inhibin (i.e., inhibin alpha subunit), follistatin (e.g., follistatin-288 and follistatin-315), Cerberus, follistatin related protein ("FSRP"), endoglin, activin C, alpha(2)-macroglobulin, and an M108A (methionine to alanine change at position 108) mutant activin A.

In a specific embodiment, the ActRII signaling inhibitor to be used in the compositions and methods described herein is a follistatin polypeptide that antagonizes activin bioactivity and/or binds to activin. The term "follistatin polypeptide" includes polypeptides comprising any naturally occurring polypeptide of follistatin as well as any variants thereof (including mutants, fragments, fusions, and peptidomimetic forms) that retain a useful activity, and further includes any functional monomer or multimer of follistatin. Variants of follistatin polypeptides that retain activin binding properties can be identified based on previous studies involving follistatin and activin interactions. For example, WO2008/030367, which is included by reference herein in its entirety, discloses specific follistatin domains ("FSDs") that are shown to be important for activin binding. Follistatin polypeptides include polypeptides derived from the sequence of any known follistatin having a sequence at least about 80% identical to the sequence of a follistatin polypeptide, and optionally at least 85%, 90%, 95%, 96%, 97%, 98%, 99& or greater identity. Examples of follistatin polypeptides include the mature follistatin polypeptide or shorter isoforms or other variants of the human follistatin precursor polypeptide as described, for example, in WO2005/025601, which is included by reference herein in its entirety.

In a specific embodiment, the ActRII signaling inhibitor to be used in the compositions and methods described herein is a follistatin-like related gene (FLRG) that antagonizes activin bioactivity and/or binds to activin. The term "FLRG polypeptide" includes polypeptides comprising any naturally occurring polypeptide of FLRG as well as any variants thereof (including mutants, fragments, fusions, and peptidomimetic forms) that retain a useful activity. Variants of FLRG polypeptides that retain activin binding properties can be identified using routine methods to assay FLRG and activin interactions. See, for example, U.S. Pat. No. 6,537,966, which is included by reference herein in its entirety. FLRG polypeptides include polypeptides derived from the sequence of any known FLRG having a sequence at least about 80% identical to the sequence of an FLRG polypeptide, and optionally at least 85%, 90%, 95%, 96%, 97%, 98%, 99% or greater identity.

In certain embodiments, functional variants or modified forms of the follistatin polypeptides and FLRG polypeptides include fusion proteins having at least a portion of the follistatin polypeptides or FLRG polypeptides and one or more fusion domains, such as, for example, domains that facilitate isolation, detection, stabilization or multimerization of the polypeptide. Suitable fusion domains are discussed in detail above with reference to the ActRIIA and ActRIIB polypeptides. In one embodiment, an ActRII signaling inhibitor is a fusion protein comprising an activin binding portion of a follistatin polypeptide fused to an Fc domain. In another embodiment, an ActRII signaling inhibitor is a fusion protein comprising an activin binding portion of an FLRG polypeptide fused to an Fe domain.

Assays

Various ActRII polypeptide variants, or soluble ActRII polypeptide variants, may be tested for their ability to inhibit ActRII. In addition, compounds can be tested for their ability to inhibit ActRII. Once inhibitors of ActRII signaling activity are confirmed, these compounds can be used with the methods provided herein. ActRII can be ActRIIA or ActRIIB. The assays below are described for ActRIIA but can be performed analogously for ActRIIB.

Assessing Snai1, Phosphosmad2, Phosphosmad3, Urinary Protein, Dkk1, Col1a1, Activin (e.g., Free Activin), Runx2, Alp, BSAP, CTX, Osterix, Klotho, Alpha-SMA, MYOCD, ActRIIA, Axin2, and/or Sm22-Alpha Level and/or Activity The level and/or the activity of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha can be determined by any method known in the art or described herein. For example, the level of Snai1, urinary protein, Dkk1, col1a1, activin, Runx2, Alp, BSAP, CTX, Osterix, Klotho, alpha-SMA, MYOCD, ActRIIA, Axin2, and/or Sm22-alpha in a tissue sample can be determined by assessing (e.g., quantifying) transcribed RNA of Snai1, urinary protein, Dkk1, col1a1, activin, Runx2, Osterix, Alp, BSAP, CTX, Klotho, alpha-SMA, MYOCD, ActRIIA, Axin2, and/or Sm22-alpha, respectively, in the sample using, e.g., Northern blotting, PCR analysis, real time PCR analysis, or any other technique known in the art or described herein. It will be recognized by one of skill in the art, levels and/or activity of one or more of Runx2, Alp, Snai1, phosphosmad2, Dkk1, col1a1, activin, BSAP, CTX, osterix, Klotho, alpha-SMA, MYOCD, ActRIIA, Axin2, Sm22-alpha, phosphosmad3, and urinary protein can be compared independently and respectively to the level and/or activity in a corresponding reference population, such as described above in Section 8.3.1. In one embodiment, the level of Snai1, urinary protein, Dkk1, col1a1, activin, Runx2, Alp, BSAP, CTX, Osterix, Klotho, alpha-SMA, MYOCD, ActRIIA, Axin2, and/or Sm22-alpha in a tissue sample can be determined by assessing (e.g., quantifying) mRNA of Snai1, urinary protein, Dkk1, col1a1, activin, Runx2, Alp, BSAP, CTX, Osterix, Klotho, alpha-SMA, MYOCD, ActRIIA, Axin2, and/or Sm22-alpha, respectively, in the sample. In a specific embodiment, the mRNA level of Snai1, urinary protein, Dkk1, col1a1, activin, Runx2, Alp, BSAP, CTX, Osterix, Klotho, alpha-SMA, MYOCD, ActRIIA, Axin2, and/or Sm22-alpha is determined by quantitative reverse transcriptase polymerase chain reaction (qRT-PCR). In a specific embodiment, the nucleic acid sequence of the Runx2 mRNA comprises the nucleic acid sequence of SEQ ID NO: 58. In a specific embodiment, the nucleic acid sequence of the Alp mRNA comprises the nucleic acid sequence of SEQ ID NO: 59. In a specific embodiment, the nucleic acid sequence of the Snai1 mRNA comprises the nucleic acid sequence of SEQ ID NO: 74. In a specific embodiment, the nucleic acid sequence of the Dkk1 mRNA comprises the nucleic acid sequence of SEQ ID NO: 75. In a specific embodiment, the nucleic acid sequence of the col1a1 mRNA comprises the nucleic acid sequence of SEQ ID NO: 76. In a specific embodiment, the nucleic acid sequence of the activin mRNA comprises the nucleic acid sequence of SEQ ID NO: 77. In a specific embodiment, the nucleic acid sequence of the Osterix mRNA comprises the nucleic acid sequence of SEQ ID NO: 60. In a specific embodiment, the nucleic acid sequence of the Klotho mRNA comprises the nucleic acid sequence of SEQ ID NO: 61. In a specific embodiment, the nucleic acid sequence of the alpha-SMA mRNA comprises the nucleic acid sequence of SEQ ID NO: 70. In a specific embodiment, the nucleic acid sequence of the MYOCD mRNA comprises the nucleic acid sequence of SEQ ID NO: 71. In a specific embodiment, the nucleic acid sequence of the Sm22-alpha mRNA comprises the nucleic acid sequence of SEQ ID NO: 62. In a specific embodiment, the qRT-PCR is performed with Runx2-specific primers (SEQ ID NOS: 48 and 49) to determine Runx2 levels. In a specific embodiment, the qRT-PCR is performed with Alp-specific primers (SEQ ID NOS: 50 and 51) to determine Alp levels. In a specific embodiment, the qRT-PCR is performed with Snai1-specific primers (SEQ ID NOS: 78 and 79) to determine Snai1 levels. In a specific embodiment, the qRT-PCR is performed with Dkk1-specific primers (SEQ ID NOS: 80 and 81) to determine Dkk1 levels. In a specific embodiment, the qRT-PCR is performed with col1a1-specific primers (SEQ ID NOS: 82 and 83) to determine col1a1 levels. In a specific embodiment, the qRT-PCR is performed with activin-specific primers (SEQ ID NOS: 84 and 85) to determine activin levels. In a specific embodiment, the qRT-PCR is performed with Osterix-specific primers (SEQ ID NOS: 52 and 53) to determine Osterix levels. In a specific embodiment, the qRT-PCR is performed with Klotho-specific primers (SEQ ID NOS: 54 and 55) to determine Klotho levels. In a specific embodiment, the qRT-PCR is performed with Sm22-alpha-specific primers (SEQ ID NOS: 56 and 57) to determine Sm22-alpha levels.

The level of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha in a tissue sample can also be determined by assessing (e.g., quantifying) the level of protein expression of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha, respectively, in the sample using, e.g., immunohistochemical analysis, Western blotting, ELISA, immunoprecipitation, flow cytometry analysis, or any other technique known in the art or described herein. In a specific embodiment, the amino acid sequence of the Runx2 protein comprises the amino acid sequence of SEQ ID NO: 63. In a specific embodiment, the amino acid sequence of the Alp protein comprises the amino acid sequence of SEQ ID NO: 64. In a specific embodiment, the amino acid sequence of the Snai1 protein comprises the amino acid sequence of SEQ ID NO: 86. In a specific embodiment, the amino acid sequence of the Dkk1 protein comprises the amino acid sequence of SEQ ID NO: 87. In a specific embodiment, the amino acid sequence of the col1a1 protein comprises the amino acid sequence of SEQ ID NO: 88. In a specific embodiment, the amino acid sequence of the activin (e.g., free activin) protein comprises the amino acid sequence of SEQ ID NO: 89. In a specific embodiment, the amino acid sequence of the BSAP protein comprises the amino acid sequence of SEQ ID NO: 72. In a specific embodiment, the amino acid sequence of the Osterix protein comprises the amino acid sequence of SEQ ID NO: 65. In a specific embodiment, the amino acid sequence of the Klotho protein comprises the amino acid sequence of SEQ ID NO: 66. In a specific embodiment, the amino acid sequence of the alpha-SMA protein comprises the amino acid sequence of SEQ ID NO: 68. In a specific embodiment, the amino acid sequence of the MYOCD comprises the amino acid sequence of SEQ ID NO: 69. In a specific embodiment, the amino acid sequence of the Sm22-alpha protein comprises the amino acid sequence of SEQ ID NO: 67. In a specific embodiment, the amino acid sequence of the ActRIIA protein comprises the amino acid sequence of SEQ ID NO: 1. In a specific embodiment, the amino acid sequence of the ActRIIA protein comprises the amino acid sequence of SEQ ID NO: 2. In a specific embodiment, the amino acid sequence of the ActRIIA protein comprises the amino acid sequence of SEQ ID NO: 3. In a specific embodiment, the amino acid sequence of the ActRIIA protein comprises the amino acid sequence of SEQ ID NO: 4. In a specific embodiment, the amino acid sequence of the ActRIIA protein comprises the amino acid sequence of SEQ ID NO: 5. In a specific embodiment, the amino acid sequence of the Axin2 protein comprises the amino acid sequence of SEQ ID NO: 87. In particular embodiments, the level and/or activity of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha is determined by western blot. In a particular embodiment, the activity of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha is determined by western blot analysis of a protein modulated by Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, or SM22-alpha. In particular embodiments, the level of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha is determined by a method capable of quantifying the amount of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha, respectively, present in a tissue sample of a subject (e.g., in human serum), and/or capable of detecting the correction of the level of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha, respectively, following treatment with an ActRII signaling inhibitor. In one embodiment, the level of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha in a tissue sample is determined by assessing (e.g., quantifying) protein expression of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha, respectively, in the sample using ELISA. For example, Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha can be identified and quantified in the human serum using ELISA method. The ELISA method for use in determining the level of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha in a tissue sample can comprise coating of ELISA plates with the tissue sample (e.g., human serum), and detecting Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha, respectively, in the tissue sample (e.g., human serum) that bind to Snai1-, phosphosmad2-, phosphosmad3-, urinary protein-, Dkk1-, col1a1-, activin-(e.g., free activin), Runx2-, Alp-, BSAP-, CTX-, Osterix-, Klotho-, alpha-SMA-, MYOCD-, ActRIIA-, Axin2-, and/or Sm22-alpha-specific antibodies, respectively. In some embodiments, the method for use in determining the level and/or activity of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha as described herein (e.g., ELISA) is capable of detecting from 100 pg/ml of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha. In a specific embodiment, the ELISA is performed with Runx2-specific antibody SC-390715 (Santa Cruz) to determine Runx2 levels. In a specific embodiment, the ELISA is performed with Alp-specific antibody SC-98652 (Santa Cruz) to determine Alp levels. In a specific embodiment, the ELISA is performed with Snai1-specific antibody sc-393172 (Santa Cruz) to determine Snai1 levels. In a specific embodiment, the ELISA is performed with phosphosmad2-specific antibody sc-101801 (Santa Cruz) to determine phosphosmad2 levels. In a specific embodiment, the ELISA is performed with phosphosmad3-specific antibody sc-130218 (Santa Cruz) to determine phosphosmad3 levels. In a specific embodiment, the ELISA is performed with Dkk1-specific antibody sc-374574 (Santa Cruz) to determine Dkk1 levels. In a specific embodiment, the ELISA is performed with col1a1-specific antibody sc-8784 (Santa Cruz) to determine col1a1 levels. In a specific embodiment, the ELISA is performed with activin-specific antibody A1594 (Sigma Aldrich) to determine activin (e.g., free activin) levels. In a specific embodiment, the ELISA is performed with BSAP-specific antibody SC-98652 (Santa Cruz) to determine BSAP levels. In a specific embodiment, the ELISA is performed with CTX-specific antibody ABIN1173415 (Antibodies Online) to determine CTX levels. In a specific embodiment, the ELISA is performed with Osterix-specific antibody SC-22538 (Santa Cruz) to determine Osterix levels. In a specific embodiment, the ELISA is performed with Klotho-specific antibody SC-22218 (Santa Cruz) to determine Klotho levels. In a specific embodiment, the ELISA is performed with alpha-SMA-specific antibody SC-53142 (Santa Cruz) to determine alpha-SMA levels. In a specific embodiment, the ELISA is performed with MYOCD-specific antibody SC-21561 (Santa Cruz) to determine MYOCD levels. In a specific embodiment, the ELISA is performed with Sm22-alpha-specific antibody SC-271719 (Santa Cruz) to determine Sm22-alpha levels. In a specific embodiment, the ELISA is performed with ActRIIA-specific antibody ab 135634 (Abcam) to determine ActRIIA levels.

The levels of one or more of Runx2, Alp, Snai1, phosphosmad2, Dkk1, col1a1, activin, BSAP, CTX, osterix, Klotho, alpha-SMA, MYOCD, ActRIIA, Axin2, Sm22-alpha, phosphosmad3, and urinary protein described in the Elisa assays described herein can be compared independently and respectively to the level and/or activity in a corresponding reference population, such as described above in Section 8.3.1.

Antibodies for use in assays that measure the levels of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha in a sample (e.g., in a tissue sample, e.g., a sample of aorta, blood, serum, plasma, liver, spleen, and/or bone marrow) are known in the art or could be readily developed using approaches known to those of skill in the art. Examples of monoclonal antibodies that can be used in assays that measure the levels of Runx2 in a sample include antibodies from LifeSpan Biosciences Inc., Seattle, Wash., with catalog numbers LS-B4293, LS-B4294, LS-B4296; antibodies available from Santa Cruz Biotechnology, Inc., Santa Cruz, Calif., with catalog number sc-390715; and antibodies available from Sigma-Aldrich Co. LLC, with product number: WH0000860M1. Examples of monoclonal antibodies that can be used in assays that measure the levels of Alp in a sample include antibodies from LifeSpan Biosciences Inc., Seattle, Wash., with catalog numbers LS-B2877, LS-B1844, LS-C169212; antibodies available from Santa Cruz Biotechnology, Inc., Santa Cruz, Calif., with catalog number: sc-98652; and antibodies available from Sigma-Aldrich Co. LLC, with product number: SAB1405449. Examples of monoclonal antibodies that can be used in assays that measure the levels of Snai1 in a sample include antibodies from LifeSpan Biosciences Inc., Seattle, Wash., with catalog numbers LS-C161335, LS-C198229, and LS-C169298; antibodies available from Santa Cruz Biotechnology, Inc., Santa Cruz, Calif., with catalog number: sc-393172; and antibodies available from Sigma-Aldrich Co. LLC, with product number: SAB1404386 Examples of antibodies that can be used in assays that measure the levels of phosphosmad2 in a sample include antibodies from Santa Cruz Biotechnology, Inc., Santa Cruz, Calif., with catalog number: sc-101801; and antibodies available from Sigma-Aldrich Co. LLC, with product numbers; SAB4200251 and SAB4300252. Examples of antibodies that can be used in assays that measure the levels of phosphosmad3 in a sample include antibodies from Santa Cruz Biotechnology, Inc., Santa Cruz, Calif., with catalog number: sc-130218; and antibodies available from Sigma-Aldrich Co. LLC, with product numbers: SAB4300253 and SAB4504210. Examples of monoclonal antibodies that can be used in assays that measure the levels of Dkk1 in a sample include antibodies from LifeSpan Biosciences Inc., Seattle, Wash., with catalog numbers LS-C108793, LS-C105116, and LS-C105117; antibodies available from Santa Cruz Biotechnology, Inc., Santa Cruz, Calif., with catalog number: sc-374574; and antibodies available from Sigma-Aldrich Co. LLC, with product number: WH0022943M1. Examples of monoclonal antibodies that can be used in assays that measure the levels of col1a1 in a sample include antibodies from LifeSpan Biosciences Inc., Seattle, Wash., with catalog number LS-B5932; antibodies available from Santa Cruz Biotechnology, Inc., Santa Cruz, Calif., with catalog number: sc-8784; and antibodies available from Sigma-Aldrich Co. LLC, with product number: C2456. Examples of monoclonal antibodies that can be used in assays that measure the levels of activin (e.g., free activin) in a sample include antibodies from LifeSpan Biosciences Inc., Seattle, Wash., with catalog number LS-C308491; and antibodies available from Sigma-Aldrich Co. LLC, with product number: A1719. Examples of monoclonal antibodies that can be used in assays that measure the levels of BSAP in a sample include antibodies from LifeSpan Biosciences Inc., Seattle, Wash., with catalog numbers LS-B2877, LS-B1844, LS-C169212; antibodies available from Santa Cruz Biotechnology, Inc., Santa Cruz, Calif., with catalog number: sc-98652; and antibodies available from Sigma-Aldrich Co. LLC, with product number: SAB1405449. Examples of monoclonal antibodies that can be used in assays that measure the levels of CTX in a sample include ABIN1173415 (Antibodies Online). Examples of monoclonal antibodies that can be used in assays that measure the levels of Osterix in a sample include antibodies from LifeSpan Biosciences Inc., Seattle, Wash., with catalog numbers LS-C139215, LS-C132610, LS-B6531; antibodies available from Santa Cruz Biotechnology, Inc., Santa Cruz, Calif., with catalog number: sc-133871; and antibodies available from Sigma-Aldrich Co. LLC, with product number: WH0121340M1. Examples of monoclonal antibodies that can be used in assays that measure the levels of Klotho in a sample include antibodies from LifeSpan Biosciences Inc., Seattle, Wash., with catalog numbers LS-C165587, LS-C145689, LS-C8376; antibodies available from Santa Cruz Biotechnology, Inc., Santa Cruz, Calif., with catalog number: sc-22218; and antibodies available from Sigma-Aldrich Co. LLC, with product number: SAB1306662. Examples of antibodies that can be used in assays that measure the levels of alpha-SMA in a sample include antibodies from LifeSpan Biosciences Inc., Seattle, Wash., with catalog numbers LS-B6000, LS-B5966, LS-B2161; antibodies available from Santa Cruz Biotechnology, Inc., Santa Cruz, Calif., with catalog number: SC-21561; and antibodies available from Sigma-Aldrich Co. LLC, with product number: A5228. Examples of antibodies that can be used in assays that measure the levels of MYOCD in a sample include antibodies from LifeSpan Biosciences Inc., Seattle, Wash., with catalog numbers LS-C37407, LS-C153495, LS-C137255; antibodies available from Santa Cruz Biotechnology, Inc., Santa Cruz, Calif., with catalog number: SC-53142; and antibodies available from Sigma-Aldrich Co. LLC, with product number: M8948. Examples of monoclonal antibodies that can be used in assays that measure the levels of Sm22-alpha in a sample include antibodies from LifeSpan Biosciences Inc., Seattle, Wash., with catalog numbers LS-B2563, LS-C139114, LS-C210979; antibodies available from Santa Cruz Biotechnology, Inc., Santa Cruz, Calif., with catalog number: sc-271719; and antibodies available from Sigma-Aldrich Co. LLC, with product number: SAB2501014. Examples of monoclonal antibodies that can be used in assays that measure the levels of ActRIIA in a sample include antibodies from Abcam with product code: ab135634.

The activity of Snail, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha can be measured by any assay known in the art including, without limitation, a reporter gene assay (e.g., containing Snail-, phosphosmad2-, phosphosmad3-, urinary protein-, Dkk1-, col1a1-, activin-, Runx2-, Alp-, BSAP-, CTX-, Osterix-, Klotho-, alpha-SMA-, MYOCD-, ActRIIA-, Axin2-, or Sm22-alpha-responsive reporter gene construct, respectively) or any other bioactivity assay.

The level and/or activity of Snail, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha can be assessed in any tissue sample obtained from a subject treated in accordance with the methods described herein. In certain embodiments, Snail, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha level and/or activity is assessed in a sample obtained from aorta, serum, liver, spleen or bone marrow of a subject treated in accordance with the methods described herein. In one embodiment, Snail, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA. Axin2, and/or Sm22-alpha level and/or activity is assessed in a sample obtained from serum of a subject treated in accordance with the methods described herein. In another embodiment, Snail, phosphosmad2, phosphosmad3, urinary protein, Dkk1, col1a1, activin (e.g., free activin). Runx2, Alp, BSAP, CTX, Osterix, Klotho, alpha-SMA, MYOCD, ActRIIA, Axin2, and/or Sm22-alpha level and/or activity is assessed in a sample obtained from aorta, spleen of a subject treated in accordance with the methods described herein. In yet another embodiment, Snail, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha level and/or activity is assessed in a sample obtained from bone marrow of a subject treated in accordance with the methods described herein.

It will be recognized by one skilled in the art that the activity of one or more of Runx2, Alp, Snail, phosphosmad2, Dkk1, col1a1, activin, BSAP, CTX, osterix, Klotho, alpha-SMA, MYOCD, ActRIIA, Axin2, Sm22-alpha, phosphosmad3, and urinary protein determined using assays known in the art and described herein, can be compared respectively to the level and/or activity in a corresponding reference population, such as described above in Section 8.3.1.

In some embodiments, the level and/or activity of Snail, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha in a tissue sample of a subject is compared to the level and/or activity of Snail, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha, respectively, in tissue samples (e.g., in samples from the same tissue) of a reference population as described in Section 8.6. In some embodiments, the level and/or activity of Snail, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha in a tissue sample of a subject is compared to the level and/or activity of Snail, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha, respectively, in a tissue sample (e.g., in a sample from the same tissue) of the subject at an earlier time point (e.g., before the onset of disease, before the onset of treatment, or during treatment). In some embodiments, the level and/or activity of Snail, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha in a tissue sample (e.g., aorta, serum, spleen, liver, or blood marrow) of a subject is compared to the level and/or activity of Snail, phosphosmad2, phosphosmad3, urinary protein, Dkk1, col1a1, activin (e.g., free activin), Runx2, Alp, BSAP, CTX, Osterix, Klotho, and/or Sm22-alpha, respectively, in another tissue sample of the subject. In some embodiments, the level and/or activity of Snail, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha in a tissue sample of a subject is compared to the level and/or activity of another gene product in the tissue sample of the subject (e.g., b-actin, Activin A, Activin B).

In some embodiments, the level and/or activity of Snail, phosphosmad2, phosphosmad3, urinary protein, Dkk1, col1a1, activin (e.g., free activin), Runx2, Alp. BSAP, CTX, Osterix, Klotho, alpha-SMA, MYOCD, ActRIIA, Axin2, and/or Sm22-alpha in a tissue sample of a subject is compared to the level and/or activity of Snail, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha, respectively, in the tissue sample in a reference population. In some embodiments, detection of the elevated level and/or activity of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha in comparison to the level and/or activity of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha, respectively, in a reference population, is followed by administration of an activin receptor signaling inhibitor (such as one or more activin receptor signaling inhibitors described herein). In some embodiments, administration of an activin receptor signaling inhibitor (such as one or more activin receptor signaling inhibitors described herein) is followed by monitoring of the level and/or activity of Snai1, phosphosmad2, phosphosmad3, urinary protein, Dkk1, col1a1, activin (e.g., free activin), Runx2, Alp, CTX, Osterix, Klotho, alpha-SMA, MYOCD, ActRIIA, Axin2, and/or Sm22-alpha and, optionally, comparing the level and/or activity of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha to the level and/or activity of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha, respectively, in a reference population. In some embodiments, administration of a first dose of ActRII signaling inhibitor (e.g., ActRIIA-hFc such as SEQ ID NO:7) is followed by determining the level and/or activity of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha, and if the level and/or activity of Snai1, phosphosmad2, phosphosmad3, urinary protein, Dkk1, col1a1, activin (e.g., free activin), Runx2, Alp, BSAP, CTX, and/or Osterix is elevated as compared to the level and/or activity of Snai1, phosphosmad2, phosphosmad3, urinary protein, Dkk1, col1a1, activin (e.g., free activin), Runx2, Alp, BSAP, CTX, and/or Osterix, respectively, in a reference population, and/or if the level and/or activity of Klotho, alpha-SMA, MYOCD, ActRIIA, Axin2, and/or Sm22-alpha is decreased as compared to the level and/or activity of Klotho, alpha-SMA, MYOCD, ActRIIA, Axin2, and/or Sm22-alpha, respectively, in a reference population, administering a second dose of the ActRII signaling inhibitor which is higher (e.g., 1.25, 1.5, 1.75, 2, 2.5, 3, 4, 5, 6, 7, 8, 9, or 10 times higher) than the first dose, and if the level and/or activity of Snai1, phosphosmad2, phosphosmad3, urinary protein, Dkk1, col1a1, activin (e.g., free activin), Runx2, Alp, BSAP, CTX, and/or Osterix is decreased as compared to the level and/or activity of Snai1, phosphosmad2, phosphosmad3, urinary protein, Dkk1, col1a1, activin (e.g., free activin), Runx2, Alp, BSAP, CTX, and/or Osterix, respectively, in a reference population, and/or if the level and/or activity of Klotho, alpha-SMA, MYOCD, ActRIIA, Axin2, and/or Sm22-alpha is elevated as compared to the level and/or activity of Klotho, alpha-SMA, MYOCD, ActRIIA, Axin2, and/or Sm22-alpha, respectively, in a reference population, administering a second dose of the ActRII signaling inhibitor which is lower (e.g., 1.25, 1.5, 1.75, 2, 2.5, 3, 4, 5, 6, 7, 8, 9, or 10 times lower) than the first dose. In certain embodiments, the reference population is a population as described in Section 8.6.

In some embodiments, the level and/or activity of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha in a tissue sample of the treated subject is compared to the level and/or activity of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha, respectively, in a sample from the same tissue of one or more healthy subjects. In some embodiments, the tissue in which the level and/or activity of Snai1, phosphosmad2, phosphosmad3, urinary protein, Dkk1, col1a1, activin (e.g., free activin), Runx2, Alp. BSAP, CTX, Osterix, Klotho, alpha-SMA, MYOCD, ActRIIA, Axin2, and/or Sm22-alpha is assessed is aorta, blood serum, bone marrow, liver, or spleen. In one embodiment, the tissue in which the level and/or activity of Snai1, phosphosmad2, phosphosmad3, urinary protein, Dkk1, col1a1, activin (e.g., free activin), Runx2, Alp. BSAP, CTX, Osterix, Klotho, alpha-SMA, MYOCD, ActRIIA, Axin2, and/or Sm22-alpha is assessed is serum.

In certain embodiments, the elevated level and/or activity of Snai1, phosphosmad2, phosphosmad3, urinary protein, Dkk1, col1a1, activin (e.g., free activin), Runx2, Alp, BSAP, CTX, and/or Osterix is about 10%, 20%, 25%, 30%, 40%, 50%, 60%, 70%, 75%, 80% 90%, 100%, 200%, or 500% greater than the level and/or activity of Snai1, phosphosmad2, phosphosmad3, urinary protein, Dkk1, col1a1, activin (e.g., free activin), Runx2, Alp. BSAP, CTX, and/or Osterix, respectively, in a reference population; and/or the decreased levels of Klotho, alpha-SMA, MYOCD, ActRIIA, Axin2, and/or Sm22-alpha is about 10%, 20%, 25%, 30%, 40%, 50%, 60%, 70%, 75%, 80% 90%, or 100% less than the level and/or activity of Klotho, alpha-SMA, MYOCD, ActRIIA, Axin2, and/or Sm22-alpha, respectively, in a reference population. In certain embodiments, the elevated level and/or activity of Snai1, phosphosmad2, phosphosmad3, urinary protein, Dkk1, col1a1, activin (e.g., free activin), Runx2, Alp, BSAP, CTX, and/or Osterix is equal to or about 10%, 20%, 25%, 30%, 40%, 50%, 60%, 70%, 75%, 80%, 90%, 100%, 200%, or 500% greater than the level and/or activity of Snai1, phosphosmad2, phosphosmad3, urinary protein, Dkk1, col1a1, activin (e.g., free activin), Runx2, Alp, BSAP, CTX, and/or Osterix, respectively, in the top 10%, top 5%, top 4%, top 3%, top 2%, or top 1% in the reference population; and/or the decreased levels of Klotho, alpha-SMA, MYOCD, ActRIIA, Axin2, and/or Sm22-alpha is equal to or about 10%, 20%, 25%, 30%, 40%, 50%, 60%, 70%, 75%, 80%, 90%, or 100% less than the level and/or activity of Klotho, alpha-SMA, MYOCD, ActRIIA, Axin2, and/or Sm22-alpha, respectively, in the bottom 10%, bottom 5%, bottom 4%, bottom 3%, bottom 2%, or bottom 1% in the reference population. In certain embodiments, the reference population is as described in Section 8.6.

In certain embodiments, the elevated level and/or activity of Klotho, alpha-SMA, MYOCD, ActRIIA, Axin2, and/or Sm22-alpha is about 10%, 20%, 25%, 30%, 40%, 50%, 60%, 70%, 75%, 80% 90%, 100%, 200%, or 500% greater than the level and/or activity of Klotho, alpha-SMA, MYOCD, ActRIIA, Axin2, and/or Sm22-alpha, respectively, in the reference population; and/or the decreased level and/or activity of Snai1, phosphosmad2, phosphosmad3, urinary protein, Dkk1, col1a1, activin (e.g., free activin), Runx2, Alp. BSAP, CTX, and/or Osterix is about 10%, 20%, 25%, 30%, 40%, 50%, 60%, 70%, 75%, 80% 90%, or 100% less than the level and/or activity of Snai1, phosphosmad2, phosphosmad3, urinary protein, Dkk1, col1a1, activin (e.g., free activin), Runx2, Alp, BSAP, CTX, and/or Osterix, respectively, in a reference population. In certain embodiments, the elevated level and/or activity of Klotho, alpha-SMA, MYOCD, ActRIIA, Axin2, and/or Sm22-alpha is equal to or about 10%, 20%, 25%, 30%, 40%, 50%, 60%, 70%, 75%, 80%, 90%, 100%, 200%, or 500% greater than the level and/or activity of Klotho, alpha-SMA, MYOCD, ActRIIA, Axin2, and/or Sm22-alpha in the top 10%, top 5%, top 4%, top 3%, top 2%, or top 1% in the reference population; and/or the decreased level and/or activity of Snai1, phosphosmad2, phosphosmad3, urinary protein, Dkk1, col1a1, activin (e.g., free activin), Runx2, Alp, BSAP, CTX, and/or Osterix is equal to or about 10%, 20%, 25%, 30%, 40%, 50%, 60%, 70%, 75%, 80%, 90%, or 100% less than the level and/or activity of Snai1, phosphosmad2, phosphosmad3, urinary protein, Dkk1, col1a1, activin (e.g., free activin), Runx2, Alp, BSAP, CTX, and/or Osterix in the bottom 10%, bottom 5%, bottom 4%, bottom 3%, bottom 2%, or bottom 1% in the reference population. In certain embodiments, the reference population is as described in Section 8.6.

In certain embodiments, the levels of activin are the levels of free activin, such as, for example, activin not in association with, for example, follistatin, follistatin-like 3, or inhibin. The level of free activin can be determined by, for example, (i) quantifying the concentration of activin in a sample, e.g., in the plasma; (ii) quantifying the concentration of proteins that associate with activin, such as, e.g., follistatin, follistatin-like 3, and inhibin in the sample; and (iii) calculating the stoichiometric ratio of the activin concentration to the concentration of the activin-associated proteins.

The assays described herein can also be utilized to determine the level and/or activity of other proteins and/or transcripts, such as, for example, FGF23, follistatin, follistatin-like 3, inhibin, proteins and/or transcripts involved in endothelial to mesenchymal transition.

In certain embodiments, the level and/or activity of Snai1, phosphosmad2, phosphosmad3, urinary protein, Dkk1, col1a1, activin (e.g., free activin), Runx2, Alp, BSAP, CTX, Osterix, Klotho, alpha-SMA, MYOCD, ActRIIA, Axin2, and/or Sm22-alpha is in a tissue (e.g., tissue sample). In certain embodiments, the tissue is aorta. In certain embodiments, the tissue is kidney. In certain embodiments, the tissue is bone. In certain embodiments, the tissue is serum. In a preferred embodiment, the Runx2, Dkk1, Alp, osterix, sm22-alpha, Klotho, alpha-SMA, ActRIIA, Axin2, and MYOCD levels and/or activity are in aorta. In a preferred embodiment, the phosphosmad2, phosphosmad3, urinary protein, ActRIIA, Axin2, and col1a1 levels and/or activity are in kidney. In a preferred embodiment, the activin levels and/or activity are in serum. In certain embodiments, the elevated activin levels are in peritubular myofibroblasts. In certain embodiments, the elevated activin levels are not in the renal epithelium. In certain embodiments, the elevated activin levels are in the peritubular myofibroblasts, and the elevated activin levels are not in the renal epithelium.

It will be recognized by one skilled in the art that the levels and/or activity of one or more of Runx2, Alp, Snai1, phosphosmad2, Dkk1, col1a1, activin, BSAP, CTX, osterix, Klotho, alpha-SMA, MYOCD. ActRIIA, Axin2, Sm22-alpha, phosphosmad3, and urinary protein can be compared independently and respectively to the level and/or activity in a corresponding reference population, such as described above in Section 8.3.1.

Reference Population

In certain embodiments, data (e.g., biomarker levels or clinical symptoms) obtained from a reference population described herein is utilized to determine whether analogous data obtained from a subject treated or to be treated in accordance with the methods provided herein is pathologically high (e.g., increased) or low (e.g., decreased).

In certain embodiments, the size of the reference population can be 1, 5, 10, 25, 50, 75, 100, 200, 250, 300, 400, 500, or 1000 individuals. In certain embodiments, the reference population consists of random volunteers. In certain embodiments, the reference population consists of healthy people. In certain embodiments, the reference population consists of people of the same age, weight, and/or gender as the patient population as described in Section 8.4. In certain embodiments, the reference population consists of people without cardiovascular disease. In certain embodiments, the reference population consists of people without vascular calcification. In certain embodiments, the reference population consists of people without cardiovascular disease. In certain embodiments, the reference population consists of people without cardiovascular disease associated with and/or resulting from vascular calcification. In certain embodiments, the reference population consists of people without renal disease. In certain embodiments, the reference population consists of people without chronic kidney disease. In certain embodiments, the reference population consists of people without pathologically elevated levels of arterial stiffness. In certain embodiments, the reference population consists of people without cardiovascular disease associated with and/or resulting from elevated levels of arterial stiffness. In certain embodiments, the reference population consists of people without LVH. In certain embodiments, the reference population consists of people without cardiovascular disease associated with and/or resulting from LVH.

In certain embodiments, the reference population refers to a subject treated in accordance with the methods provided herein prior to the onset of one or more symptoms of cardiovascular disease. In certain embodiments, the reference population refers to a subject treated in accordance with the methods provided herein prior to the onset of one or more symptoms of vascular calcification. In certain embodiments, the reference population refers to a subject treated in accordance with the methods provided herein prior to the onset of one or more symptoms of chronic kidney disease. In certain embodiments, the reference population refers to a subject treated in accordance with the methods provided herein prior to the onset of one or more symptoms of elevated levels of arterial stiffness. In certain embodiments, the reference population refers to a subject treated in accordance with the methods provided herein prior to the onset of one or more symptoms of LVH. In certain embodiments, the reference population refers to a subject treated in accordance with the methods provided herein prior to diagnosis of cardiovascular disease in the subject. In certain embodiments, the reference population refers to a subject treated in accordance with the methods provided herein prior to diagnosis of vascular calcification in the subject. In certain embodiments, the reference population refers to a subject treated in accordance with the methods provided herein prior to diagnosis of chronic kidney disease in the subject. In certain embodiments, the reference population refers to a subject treated in accordance with the methods provided herein prior to diagnosis of stage 1 chronic kidney disease. In certain embodiments, the reference population refers to a subject treated in accordance with the methods provided herein prior to diagnosis of stage 2 chronic kidney disease. In certain embodiments, the reference population refers to a subject treated in accordance with the methods provided herein prior to diagnosis of stage 3 chronic kidney disease. In certain embodiments, the reference population refers to a subject treated in accordance with the methods provided herein prior to diagnosis of stage 4 chronic kidney disease. In certain embodiments, the reference population refers to a subject treated in accordance with the methods provided herein prior to diagnosis of stage 5 chronic kidney disease. In certain embodiments, the reference population refers to a subject treated in accordance with the methods provided herein prior to diagnosis of elevated levels of arterial stiffness in the subject. In certain embodiments, the reference population refers to a subject treated in accordance with the methods provided herein prior to diagnosis of LVH in the subject. In certain embodiments, the reference population consists of people who display an increase in arterial stiffness prior to being treated according to the methods provided herein or being diagnosed with a disease described herein. In certain embodiments, the reference population consists of people who display an upward trend of one of the markers recited in the Summary (see Section 6) prior to treatment according to the methods provided herein or being diagnosed with a disease described herein. In certain embodiments, the reference population consists of people who display an increased level of Runx2, Alp, Snail, phosphosmad2, Dkk1, col1a1, activin, BSAP, CTX, Osterix, phosphosmad3, and/or urinary protein prior to treatment according to the methods provided herein or being diagnosed with a disease described herein. In certain embodiments, the reference population consists of people who display a downward trend of one of the markers recited in the Summary (see Section 6) prior to treatment according to the methods provided herein or being diagnosed with a disease described herein. In certain embodiments, the reference population consists of people who display a decreased level of alpha-SMA, MYOCD, Sm22-alpha, or ActRIIA prior to treatment according to the methods provided herein or being diagnosed with a disease described herein.

Endothelial-Mesenchymal Transition

In certain embodiments, EnMT in a subject treated according to the methods provided herein can be monitored through a lineage tracing assay to determine the fate of a cell population. In certain embodiments, EnMT in a subject treated according to the methods provided herein can be monitored by quantifying the level and/or activity of one or more proteins or transcripts associated with EnMT, such as, for example, Snail.

Bone Turnover

Various circulating markers of bone turnover can be used to diagnose bone disorders, such as low bone turnover. Circulating markers of bone turnover are markers of bone formation such as bone specific alkaline phosphatase (bAP), osteocalcin, procollagen type I C-terminal propeptide (PICP) and insulin-like growth factor-1 (IGF-1), some being markers of bone resorption such as pyridinoline, deoxypyridinoline, tartrate-resistant acid phosphatase (TRAP), TRAP type 5b, pyridinoline, deoxypyridinoline and procollagen type I C-terminal telopeptide (ICTP), serum or urine collagen cross-links (N-telopeptide or C-telopeptide), and 25 hydroxyvitamin D. Assays to measure the entire parathyroid hormone (PTH) molecule can also be used. The skilled artisan is aware of imaging methods allowing the assessment of bone mineral density (BMD), bone volume, trabecular bone volume, and trabecular thickness. See, e.g., Tilman B. Drucke and Sharon M. Moc, Disturbances of bone and mineral metabolism in chronic kidney disease: an international initiative to improve diagnosis and treatment, Nephrol Dial Transplant (2004) 19: 534-536; Okuno S, Inaba M., Biochemical markers of bone turnover. New aspect. Dialysis and bone metabolic marker, Clin Calcium. 2009 August; 19(8): 1084-91 Herberth J, Monier-Faugere M C, Mawad H W, Branscum A J, Herberth Z, Wang G, Cantor T, Malluche H H, The five most commonly used intact parathyroid hormone assays are useful for screening but not for diagnosing bone turnover abnormalities in CKD-5 subjects, Clin Nephrol. 2009 July; 72(1):5-14; Lehmann 3, Ott U, Kaemmerer D, Schuetze J, Wolf G., Bone histomorphometry and biochemical markers of bone turnover in subjects with chronic kidney disease Stages 3-5, Clin Nephrol. 2008 October; 70(4):296-305; Drüeke T B., Is parathyroid hormone measurement useful for the diagnosis of renal bone disease?, Kidney Int. 2008 March; 73(6):674-6; Yamada S, Inaba M, Kurajoh M, Shidara K, Imanishi Y, Ishimura E, Nishizawa Y., Utility of serum tartrate-resistant acid phosphatase (TRACP5b) as a bone resorption marker in subjects with chronic kidney disease: independence from renal dysfunction, Clin Endocrinol (Oxf). 2008 August; 69(2): 189-96. Epub 2008 Jan. 23. See also, Paul D. Miller, Diagnosis and Treatment of Osteoporosis in Chronic Renal Disease, 2009.

Another marker for monitoring bone resorption in CKD subjects with mild renal dysfunction is serum concentration of type I collagen N-telopeptide (S-NTX). See, e.g., Hamano T, Fujii N, Nagasawa Y, Isaka Y, Moriyama T, Okada N, Imai E, Horio M, Ito T., Serum NTX is a practical marker for assessing antiresorptive therapy for glucocorticoid treated subjects with chronic kidney disease, Bone. 2006 November; 39(5):1067-72. Epub 2006 Jun. 16.

Quantitative computed tomography (QCT) can also be used to determine bone turnover.

Markers, such as, for example, Runx2 and Alp can be evaluated to monitor the osteoblastic transition in a subject. Markers, such as, for example, Sm22-alpha can be evaluated to monitor vascular smooth muscle function and the levels of differentiated vascular smooth muscle cells.

Calcium Levels

Calcium levels can be assayed by methods known to one skilled in the art, such as, e.g., calcium ion selective electrode. In certain embodiments, total calcium levels are measured in serum, blood, aorta, or urine.

Vascular Calcification

Non-contrast computed tomography (CT) for imaging the extent of coronary artery calcification (CAC) and contrast CT for noninvasive coronary angiography (CTA) are developments generally used to diagnose obstructive coronary disease. Radionuclide stress testing, coronary artery calcium scanning, and noninvasive coronary angiography for diagnostic and prognostic cardiac assessment can also be used. See: Berman D S, Shaw L J, Hachamoviteh R, Friedman J D, Polk D M, Hayes S W, Thomson L E, Germano G, Wong N D, Kang X, Rozanski A., Comparative use of radionuclide stress testing, coronary artery calcium scanning, and noninvasive coronary angiography for diagnostic and prognostic cardiac assessment, Semin Nucl Med. 2007 January; 37(1): 2-16.

Coronary calcium screening results from asymptomatic subjects can be used as a comparison. For example, calcium screening results obtained prior to the onset of kidney disease can be used as a comparison when vascular calcification is related to the kidney disease.

Possible methods of detecting and quantifying coronary artery calcification (CAC) include, but are not limited to, x-ray computed tomography and myocardial perfusion single photon emission computed tomography (SPECT). Moser K W, O'Keefe J H Jr, Bateman, McGhie I A., Coronary calcium screening in asymptomatic subjects as a guide to risk factor modification and stress myocardial perfusion imaging, J Nucl Cardiol. 2003 November-December; 10(6):590-8. Multi-detector computed tomography (MDCT) also can be used to detect vascular calcification (see, e.g., Burrill et al., 2007, Postgrad. Med. J. 83(985): 69%-704).

Another diagnostic method for vascular calcification is fluorine 18 fluorodeoxyglucose (FDG) uptake in the thoracic aortic wall at combined positron emission tomography (PET)/computed tomography (CT). See: Tatsumi M, Cohade C, Nakamoto Y, Wahl R L., Fluorodeoxyglucose uptake in the aortic wall at PET/CT: possible finding for active atherosclerosis, Radiology. 2003 December; 229(3):831-7. Epub 2003 Oct. 30.

In even another embodiment, ultrafast CT can be used to detect the presence of atherosclerotic coronary disease. See, e.g., Breen J F, Sheedy P F 2nd, Schwartz R S, Stanson A W, Kaufmann R B, Moll P P, Rumberger J A, Coronary artery calcification detected with ultrafast CT as an indication of coronary artery disease, Radiology. 1992 November: 185 (2):435-9.

Electron-beam computed tomography scanning can also be used to diagnose coronary artery disease. See: Schmermund A, Baumgart D, Sack S, Möhlenkamp S. Grönemeyer D, Seibel R, Erbel R., Assessment of coronary calcification by electron-beam computed tomography in symptomatic subjects with normal, abnormal or equivocal exercise stress test, Eur Heart J. 2000 October; 21(20):1674-82.

Another test for vascular calcification regards the plaque composition in plexogenic and thromboembolic pulmonary hypertension. Chronic thromboembolic pulmonary hypertension is associated with atherosclerotic plaques with glycophorin-rich pultaceous cores, and plexogenic pulmonary hypertension with fibrous plaques. Thromboembolic material plays a critical role in the formation of pultaceous cores, of which erythrocyte membrane derived glycophorin is a major component. Thereby, chronic thromboembolic and plexogenic pulmonary hypertension (primary and secondary (Eisenmenger syndrome)) are investigated. See: Arbustini E, Morbini P, D'Armini A M, Repetto A, Minzioni G, Piovella F, Viganó M, Tavazzi L, Plaque composition in plexogenic and thromboembolic pulmonary hypertension: the critical role of thrombotic material in pultaceous core formation, Heart. 2002 August; 88(2): 177-82.

Agatston scoring, a calcium scoring system based on density measurements of deposited calcium plaques, can be used to quantify vascular calcification. In this system, levels of vascular calcification can be measured by multi-detector computed tomography (MDCT) and attenuations in the rate of progression in the Agatston score can be assessed (see, e.g., Sharma et al., 2010, Vasc. Health Risk Manag. 6:603-611).

Further, vascular calcification can be assessed using the methods described in Adragao et al., 2004, Nephrol. Dial. Transplant 19:1480-1488.

Another assay for use in quantifying vascular calcification in a subject is the lesion-specific calcium score, which comprises a method of calcium measurement that results from a CT test for coronary artery calcification. This method is described by, e.g., Akram and Voros, 2008, Int. J. cardiovac. Imaging 14:743-749.

Heart Size and Cardiac Hypertrophy

Heart size and cardiac hypertrophy can be determined by any method known to the skilled artisan, such as, for example, magnetic resonance imaging, electrocardiography, echocardiography, and noncontrast-enhanced cardiac computed tomography.

Arterial Stiffness

The levels of arterial stiffness can be determined by any method known to the skilled artisan, such as, for example, ultrasonic Doppler tests, magnetic resonance imaging including magnetic resonance arteriography, computerized tomography (CT) including CT angiography, and other forms of angiography known in the art.

Kidney Disease

Glomerular filtration rate, inulin clearance, hyperphosphatemia, and BUN levels can be determined by any method known to the skilled artisan to determine kidney disease. Renal fibrosis and/or glomerulosclerosis can be diagnosed and/or monitored by any method known to the skilled artisan, such as, for example, biopsy of kidney tissue and examination of the tissue for scarring. Renal fibrosis and/or glomerulosclerosis can also be diagnosed and/or monitored by, for example, measuring the glomerular filtration rate and/or performing ultrasound of the kidney. See website of the National Kidney Foundation.

Animal Models

Atherosclerotic low density lipoprotein receptor-deficient (ldr−/−) males (C57Bl/6J background) can be purchased from Jackson Laboratories and fed high fat diet (42% calories from fat) (Teklad #) beginning at 12 weeks of age. The mice are obese, insulin resistant at 22 weeks of age, diabetic at 28 weeks of age and hypercholesteroleinic.

A two-step procedure can be utilized to create chronic kidney disease as described previously (Davies, M. R., et al., 2003. J Am Soc Nephrol 14:1559-1567; Davies, M. R., et al., 2005. J Am Soc Nephrol 16:917-928.). Electrocautery can be applied to the right kidney through a 2 cm flank incision at 12 weeks post natal, followed by left total nephrectomy at 14 weeks of age. The intensity of the cautery is varied to produce moderate (CKD-3) renal injury that is confirmed by inulin clearances at age 20 weeks. A control group of mice, wild type C57Bl/6J mice, are fed a regular chow diet, which is a normal renal function and diet group used for normative control values. A second group is ldlr−/− mice that are fed a high fat diet and sham operated, which have normal renal function, and serve as the control group to determine the effect of kidney disease. A third group is ldlr−/− mice with GFR reduced equivalent to human CKD stage 3 fed high fat diet (CKD-3) with euthanasia at 22 weeks, the baseline vascular calcification group (CKD-3). The fourth group is ldlr−/− mice with CKD-3 receiving subcutaneous injections of vehicle twice a week beginning at 22 weeks until euthanasia at 28 weeks (CKD-3 V). The fifth group is ldlr−/− mice with CKD-3 receiving subcutaneous injections of mActRIIA-Fc (Celgene, Summit, N.J.), 10 mg/kg twice a week beginning at 22 weeks until euthanasia at 28 weeks (CKD-3 mActRIIA-Fc). The dose used was previously shown in PK/PD studies to be an efficacious dose for stimulation of bone formation (Lotinun, S., et al., 2010. Bone 46:1082-1088.).

A second model of CKD used is the murine homolog of X-linked Alport's syndrome, which is a deficiency in the gene for the a5 chain of type IV collagen, COL4A5 (Rheault, M. N., et al., 2004. Journal of the American Society of Nephrology 15:1466-1474.). This is a model of spontaneous kidney disease. Breeding pairs can be purchased from Jackson Laboratories and bred for experiments. Hemizygote males spontaneously develop kidney disease comparable with human CKD stage 3-4 at 200 days after birth.

A third model of CKD is renal ablation, similar to the ldlr−/− protocol, in a transgenic mouse line used for cellular lineage tracing, the GNZ mouse. GNZ reporter female mice (Stoller, J. Z., et al., 2008. Genesis (New York, N.Y. 2000) 46:200-204) and Tek-Cre transgenic male mouse (Koni, P. A., et al., 2001. The Journal of Experimental Medicine 193:741-754) can be purchased from Jackson Laboratories and bred to produce GNZ/Tek-Cre+mice for experiments. GNZ/Tek-Cre− littermates serve as negative controls. Mouse genotyping can be performed by using specific primers recommended for GNZ and Tek-Cre mouse strains by manufacturer.

Transcriptional Response Assay

In certain embodiments, a transcription response assay can be used to test an ActRII signaling inhibitor or activity of Snai1, phosphosmad2, phosphosmad3, urinary protein, Dkk1, col1a1, activin (e.g., free activin), Runx2, Alp, BSAP, CTX, Osterix, Klotho, ActRIIA, Axin2, and/or Sm22-alpha. Upon ActRII, Snai1, phosphosmad2, phosphosmad3, urinary protein, Dkk1, col1a1, activin (e.g., free activin), Runx2, Osterix, Alp, BSAP, CTX, Klotho, ActRIIA, Axin2, and/or Sm22-alpha signaling, transcription of certain genes is up- or downregulated. A cell culture system used and the transcriptional response can be measured (e.g., by RT-PCR). The effect of an agent on the transcriptional response is a measure of its effectiveness or activity. In certain embodiments, the promoter region that is known to be responsive to ActRII, Snai1, phosphosmad2, phosphosmad3, urinary protein, Dkk1, col1a1, activin (e.g., free activin), Runx2, Osterix, Alp, BSAP, CTX, Klotho, ActRIIA, Axin2, and/or Sm22-alpha signaling can be cloned upstream of a reporter gene. In this way, the assay can be simplified such that only the activity of the reporter gene needs to be assayed.

Screening Assays

Various ActRII polypeptide variants, or soluble ActRII polypeptide variants, may be tested for their ability to inhibit ActRII. In addition, compounds can be tested for their ability to inhibit ActRII. Once inhibitors of ActRII signaling activity are confirmed, these compounds can be used with the methods provided herein. ActRII can be ActRIIA or ActRIIB. The assays below are described for ActRIIA but can be performed analogously for ActRIIB.

For example, the effect of an ActRIIA polypeptide variant on the expression of genes involved in bone production or bone destruction may be assessed. This may, as needed, be performed in the presence of one or more recombinant ActRIIA ligand proteins (e.g., activin), and cells may be transfected so as to produce an ActRIIA polypeptide and/or variants thereof, and optionally, an ActRIIA ligand. Likewise, an ActRIIA polypeptide may be administered to a mouse or other animal, and one or more bone properties, such as density or volume may be assessed. The healing rate for bone fractures may also be evaluated. Dual-energy x-ray absorptiometry (DEXA) is a well-established, non-invasive, quantitative technique for assessing bone density in an animal. In humans central DEXA systems may be used to evaluate bone density in the spine and pelvis. These are the best predictors of overall bone density. Peripheral DEXA systems may be used to evaluate bone density in peripheral bones, including, for example, the bones of the hand, wrist, ankle and foot. Traditional x-ray imaging systems, including CAT scans, may be used to evaluate bone growth and fracture healing. In addition, bone density can be measured using quantitative computed tomography (qCT). The mechanical strength of bone may also be evaluated.

In certain aspects, provided herein is the use of ActRIIA polypeptides (e.g., soluble ActRIIA polypeptides) and activin polypeptides to identify compounds (agents) which are agonist or antagonists of the activin-ActRIIA signaling pathway. Compounds identified through this screening can be tested to assess their ability to modulate bone growth or mineralization in vitro. Optionally, these compounds can further be tested in animal models to assess their ability to modulate tissue growth in vivo.

There are numerous approaches to screening for therapeutic agents for modulating tissue growth by targeting activin and ActRIIA polypeptides. In certain embodiments, high-throughput screening of compounds can be carried out to identify agents that perturb activin or ActRIIA-mediated effects on bone. In certain embodiments, the assay is carried out to screen and identify compounds that specifically inhibit or reduce binding of an ActRIIA polypeptide to activin. Alternatively, the assay can be used to identify compounds that enhance binding of an ActRIIA polypeptide to activin. In a further embodiment, the compounds can be identified by their ability to interact with an activin or ActRIIA polypeptide.

A variety of assay formats will suffice and, in light of the present disclosure, those not expressly described herein will nevertheless be comprehended by one of ordinary skill in the art. As described herein, the test compounds (agents) used herein may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated herein include non-peptidyl organic molecules, peptides, polypeptides, peptidomimetics, sugars, hormones, and nucleic acid molecules. In a specific embodiment, the test agent is a small organic molecule having a molecular weight of less than about 2,000 daltons.

The test compounds can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatable crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between an ActRIIA polypeptide and activin.

Merely to illustrate, in an exemplary screening assay, the compound of interest is contacted with an isolated and purified ActRIIA polypeptide which is ordinarily capable of binding to activin. To the mixture of the compound and ActRIIA polypeptide is then added a composition containing an ActRIIA ligand. Detection and quantification of ActRIIA/activin complexes provides a means for determining the compound's efficacy at inhibiting (or potentiating) complex formation between the ActRIIA polypeptide and activin. The efficacy of the compound can be assessed by generating dose response curves from data obtained using various concentrations of the test compound. Moreover, a control assay can also be performed to provide a baseline for comparison. For example, in a control assay, isolated and purified activin is added to a composition containing the ActRIIA polypeptide, and the formation of ActRIIA/activin complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between the ActRIIA polypeptide and activin may be detected by a variety of techniques. For instance, modulation of the formation of complexes can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled ActRIIA polypeptide or activin, by immunoassay, or by chromatographic detection.

In certain embodiments, contemplated herein is the use of fluorescence polarization assays and fluorescence resonance energy transfer (FRET) assays in measuring, either directly or indirectly, the degree of interaction between an ActRIIA polypeptide and its binding protein. Further, other modes of detection, such as those based on optical waveguides (PCT Publication WO 96/26432 and U.S. Pat. No. 5,677,196), surface plasmon resonance (SPR), surface charge sensors, and surface force sensors, are compatible with many embodiments described herein.

Moreover, an interaction trap assay, also known as the "two hybrid assay," can be used for identifying agents that disrupt or potentiate interaction between an ActRIIA polypeptide and its binding protein. See for example, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In a specific embodiment, contemplated herein is the use of reverse two hybrid systems to identify compounds (e.g., small molecules or peptides) that dissociate interactions between an ActRIIA polypeptide and its binding protein. See for example, Vidal and Legrain, (1999) Nucleic Acids Res 27:919-29; Vidal and Legrain. (1999) Trends Biotechnol 17:374-81; and U.S. Pat. Nos. 5,525,490; 5,955,280; and 5,965,368.

In certain embodiments, the subject compounds are identified by their ability to interact with an ActRIIA or activin polypeptide. The interaction between the compound and the ActRIIA or activin polypeptide may be covalent or non-covalent. For example, such interaction can be identified at the protein level using in vitro biochemical methods, including photo-crosslinking, radiolabeled ligand binding, and affinity chromatography (Jakoby W B et al., 1974, Methods in Enzymology 46: 1). In certain cases, the compounds may be screened in a mechanism based assay, such as an assay to detect compounds which bind to an activin or ActRIIA polypeptide. This may include a solid phase or fluid phase binding event. Alternatively, the gene encoding an activin or ActRIIA polypeptide can be transfected with a reporter system (e.g., β-galactosidase, luciferase, or green fluorescent protein) into a cell and screened against the library preferably by a high throughput screening or with individual members of the library. Other mechanism based binding assays may be used, for example, binding assays which detect changes in free energy. Binding assays can be performed with the target fixed to a well, bead or chip or captured by an immobilized antibody or resolved by capillary electrophoresis. The bound compounds may be detected usually using colorimetric or fluorescence or surface plasmon resonance.

In certain aspects, provided herein are methods and agents for modulating (stimulating or inhibiting) bone formation and increasing bone mass. Therefore, any compound identified can be tested in whole cells or tissues, in vitro or in vivo, to confirm their ability to modulate bone growth or mineralization. Various methods known in the art can be utilized for this purpose. In particular, the compounds can be tested for their ability to increase bone turnover.

For example, the effect of the ActRIIA or activin polypeptides or test compounds on bone or cartilage growth can be determined by measuring induction of Msx2 or differentiation of osteoprogenitor cells into osteoblasts in cell based assays (see. e.g., Daluiski et al., Nat Genet. 2001, 27(1):84-8; Hino et al., Front Biosci. 2004, 9:1520-9). Another example of cell-based assays includes analyzing the osteogenic activity of the subject ActRIIA or activin polypeptides and test compounds in mesenchymal progenitor and osteoblastic cells. To illustrate, recombinant adenoviruses expressing an activin or ActRIIA polypeptide can be constructed to infect pluripotent mesenchymal progenitor C3H10T1/2 cells, preosteoblastic C2Cl2 cells, and osteoblastic TE-85 cells. Osteogenic activity is then determined by measuring the induction of alkaline phosphatase, osteocalcin, and matrix mineralization (see, e.g., Cheng et al., J bone Joint Surg Am. 2003, 85-A(8): 1544-52).

Also provided herein are in vivo assays to measure bone or cartilage growth. For example, Namkung-Matthai et al., Bone, 28:80-86 (2001) discloses a rat osteoporotic model in which bone repair during the early period after fracture is studied. Kubo et al., Steroid Biochemistry & Molecular Biology, 68:197-202 (1999) also discloses a rat osteoporotic model in which bone repair during the late period after fracture is studied. Andersson et al., J. Endocrinol. 170:529-537 describe a mouse osteoporosis model in which mice are ovariectomized, which causes the mice to lose substantial bone mineral content and bone mineral density, with the trabecular bone losing roughly 50% of bone mineral density. Bone density could be increased in the ovariectomized mice by administration of factors such as parathyroid hormone. In certain aspects, fracture healing assays that are known in the art can be used. These assays include fracture technique, histological analysis, and biomechanical analysis, which are described in, for example, U.S. Pat. No. 6,521,750, which is incorporated by reference in its entirety for its disclosure of experimental protocols for causing as well as measuring the extent of fractures, and the repair process.

Dose of Activin Receptor Type 11 Signaling Inhibitor

In certain embodiments, an ActRII signaling inhibitor is an inhibitor of ActRIIA signaling as set forth in Section 8.5.1. In other embodiments, an ActRII inhibitor is an inhibitor of ActRIIB signaling as set forth in Section 8.5.2. In certain embodiments, an ActRII signaling inhibitor is a combination of an ActRIIA signaling inhibitor and an ActRIIB signaling inhibitor.

In certain embodiments, the ActRII signaling inhibitor is dosed at intervals and amounts sufficient to achieve serum concentrations of 0.2 microgram/kg or greater, and serum levels of 1 microgram/kg or 2 microgram/kg or greater are desirable for achieving significant effects on bone density and strength. Dosing regimens may be designed to reach serum concentrations of between 0.2 and 15 microgram/kg, and optionally between 1 and 5 microgram/kg. In humans, serum levels of 0.2 microgram/kg may be achieved with a single dose of 0.1 mg/kg or greater and serum levels of 1 microgram/kg may be achieved with a single dose of 0.3 mg/kg or greater. The observed serum half-life of the molecule is between about 20 and 30 days, substantially longer than most Fc fusion proteins, and thus a sustained effective serum level may be achieved, for example, by dosing with 0.2-0.4 mg/kg on a weekly or biweekly basis, or higher doses may be used with longer intervals between dosings. For example, doses of 1-3 mg/kg might be used on a monthly or bimonthly basis, and the effect on bone may be sufficiently durable that dosing is necessary only once every 3, 4, 5, 6, 9, 12 or more months. Serum levels of the ActRII signaling inhibitor can be measured by any means known to the skilled artisan. For example, antibodies against the ActRII signaling inhibitor can be used to determine the serum levels of the ActRII signaling inhibitor using, e.g., an ELISA.

In certain embodiments, the dose of the ActRII signaling inhibitor ranges from 0.01 to 3.0 mg/kg intravenously or from 0.03 to 0.1 mg/kg subcutaneously. In certain embodiments, the dose of ActRII signaling inhibitor is about 0.01 mg/kg, about 0.1 mg/kg, about 0.13 mg/kg, about 0.2 mg/kg, about 0.26 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, or about 5.0 mg/kg. In certain embodiments, the dose of ActRII signaling inhibitor is about 10.0 mg/kg, about 15.0 mg/kg, about 20.0 mg/kg, about 25.0 mg/kg, or about 30.0 mg/kg. In certain embodiments, the dose of ActRII signaling inhibitor is between 0.01 mg/kg and 0.1 mg/kg, between 0.1 mg/kg and 0.3 mg/kg, between 0.3 mg/kg and 0.5 mg/kg, between 0.3 mg/kg and 0.8 mg/kg, between 0.5 mg/kg and 1.0 mg/kg, between 1.0 mg/kg and 2.0 mg/kg, between 1.0 mg/kg and 3.0 mg/kg, between 2.0 mg/kg and 3.0 mg/kg, between 2.0 mg/kg and 4.0 mg/kg, between 3.0 mg/kg and 5.0 mg/kg, between 5.0 mg/kg and 10.0 mg/kg, between 10.0 mg/kg and 15.0 mg/kg, between 10.0 mg/kg and 20.0 mg/kg, between 15.0 mg/kg and 20.0 mg/kg, or between 20.0 mg/kg and 30.0 mg/kg. In certain embodiments, the dose is about 15 mg, about 30 mg, about 45 mg, about 60 mg, about 75 mg, about 90 mg, or about 1 g. In certain embodiments, the dose is about 0.1 mg/kg. In certain embodiments, the dose is about 0.3 mg/kg. In certain embodiments, the dose is about 0.5 mg/kg. In certain embodiments, the dose is about 0.7 mg/kg.

In certain embodiments, the dose is a pharmaceutically effective dose. In certain embodiments, the pharmaceutically effective dose is about 15 mg, about 30 mg, about 45 mg, about 60 mg, about 75 mg, about 90 mg, or about 1 g, or about 0.1 mg/kg, about 0.13 mg/kg, about 0.2 mg/kg, about 0.26 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, or about 1.5 mg/kg. In certain embodiments, the pharmaceutically effective dose is about 0.1 mg/kg. In certain embodiments, the pharmaceutically effective dose is about 0.3 mg/kg. In certain embodiments, the pharmaceutically effective dose is about 0.5 mg/kg. In certain embodiments, the pharmaceutically effective dose is about 0.7 mg/kg.

In certain embodiments, the dose is an initial dose. In certain embodiments, the initial dose is about 15 mg, about 30 mg, about 45 mg, about 60 mg, about 75 mg, about 90 mg, or about 1 g, or about 0.1 mg/kg, about 0.13 mg/kg, about 0.2 mg/kg, about 0.26 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, or about 1.5 mg/kg. In certain embodiments, the pharmaceutically effective dose is about 0.1 mg/kg. In certain embodiments, the initial dose is about 0.3 mg/kg. In certain embodiments, the initial dose is about 0.5 mg/kg. In certain embodiments, the initial dose is about 0.7 mg/kg. In certain embodiments, the initial dose is administered (i) once every 28 days; or (ii) once every 42 days. In certain embodiments, the initial dose is administered once every 14 days. In certain embodiments, the initial dose is administered once every 21 days.

In certain embodiments the initial dose is administered once every 1, 2, 3, 4, 5, 6, 7, 8, 9 10, 11, 12, 13, 14, 15, 16, 17, 18, 19, 20, 21, 22, 23, 24, 25, 26, 27, or 28 days. In certain embodiments the initial dose is administered once every 1, 2, 3, 4, 5, or 6 weeks. In certain embodiments, the initial dose is administered once every 2 weeks. In certain embodiments, the initial dose is about 0.1 mg/kg, about 0.13 mg/kg, about 0.2 mg/kg, about 0.26 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, or about 1.5 mg/kg and is administered once every 1, 2, 3, 4, 5, or 6 weeks. In certain embodiments, the initial dose is between about 0.3 to about 0.8 mg/kg and is administered once every 2 weeks. In certain embodiments, the initial dose is about 0.1 mg/kg, about 0.13 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, or about 1.5 mg/kg and is administered once every 1, 2, 3, 4, 5, or 6 weeks. In certain embodiments, the initial dose is about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, or about 1.5 mg/kg and is administered once every 2 weeks. In certain embodiments, the initial dose is about 0.3 mg/kg and is administered once every 2 weeks. In certain embodiments, the initial dose is about 0.5 mg/kg and is administered once every 2 weeks. In certain embodiments, the initial dose is about 0.7 mg/kg and is administered once every 2 weeks. In certain embodiments, the initial dose is about 0.8 mg/kg and is administered once every 2 weeks.

In certain embodiments, the dose is an adjusted dose. In certain embodiments, the adjusted dose is greater than the initial dose. In certain embodiments, the adjusted dose is about 2.5 mg, about 5 mg, about 10 mg, about 15 mg, about 20 mg, or about 35 mg greater than the initial dose, or about 0.05 mg/kg, about 0.1 mg/kg, about 0.15 mg/kg, about 0.25 mg/kg, about 0.3 mg/kg, about 0.35 mg/kg, about 0.4 mg/kg, or about 0.5 mg/kg greater than the initial dose. In certain embodiments, the adjusted dose is administered more frequently than the initial dose. In certain embodiments, the adjusted dose is administered every 5, 10, 15, 20, 25, 28, 30, 35, or 40 days.

In certain embodiments, the adjusted dose is less than the initial dose. In certain embodiments, the adjusted dose is about 2.5 mg, about 5 mg, about 10 mg, about 15 mg, about 20 mg, or about 35 mg less than the initial dose, or about 0.05 mg/kg, about 0.1 mg/kg, about 0.15 mg/kg, about 0.25 mg/kg, about 0.3 mg/kg, about 0.35 mg/kg, about 0.4 mg/kg, or about 0.5 mg/kg less than the initial dose. In certain embodiments, the adjusted dose is administered less frequently than the initial dose. In certain embodiments, the adjusted dose is administered every 30, 35, 40, 42, 50, 60, 70, 80, or 90 days.

In certain embodiments, the dose is administered via injection. In certain embodiments, the dose is administered once every 28 days or once every 42 days. In certain embodiments, the dose is administered continuously and/or indefinitely.

In certain embodiments, the dose of an ActRII signaling inhibitor administered to a subject according to the methods provided herein is sufficient to decrease activin levels and/or activity in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80%, 85%, 90%, 95%, or at most 100% as compared to activin levels and/or activity in a reference population (e.g., a reference population as described in Section 8.6). In certain embodiments, the activin is free activin, e.g., activin not associated with follistatin, follistatin-like 3, or inhibin. In certain embodiments, the activin is activin A. In certain embodiments, activin levels and/or activity are determined by an assay as described in Section 8.6.

In certain embodiments, the dose of an ActRII signaling inhibitor administered to a subject according to the methods provided herein is sufficient to decrease Smad-dependent signaling in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80%, 85%, 90%, 95%, or at most 100% as compared to Smad-dependent signaling in a reference population (e.g., a reference population as described in Section 8.6). In certain embodiments, Smad-dependent signaling is determined by an assay as described in Section 8.6.

In certain embodiments, the dose of an ActRII signaling inhibitor administered to a subject according to the methods provided herein is sufficient to decrease Runx2 levels and/or activity in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80%, 85%, 90%, 95%, or at most 100% as compared to Runx2 levels and/or activity of in a reference population (e.g., a reference population as described in Section 8.6). In certain embodiments, Runx2 levels and/or activity are determined by an assay as described in Section 8.6.

In certain embodiments, the dose of an ActRII signaling inhibitor administered to a subject according to the methods provided herein is sufficient to decrease Alp levels and/or activity in the subject by at least 5%, 10%, 15%, 20%, 25%, 30%, 35%, 40%, 45%, 500%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80%, 85%, 90%, 95%, or at most 100% as compared to Alp levels and/or activity in a reference population (e.g., a reference population as described in Section 8.6). In certain embodiments, Alp levels and/or activity are determined by an assay as described in Section 8.6.

In certain embodiments, the dose of an ActRII signaling inhibitor administered to a subject according to the methods provided herein is sufficient to decrease Snai1 levels and/or activity in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 600%, 65%, 70%, 75%, 80%, 85% 90% 95%, or at most 100% as compared to Snai1 levels and/or activity in a reference population (e.g., a reference population as described in Section 8.6). In certain embodiments, Snai1 levels and/or activity is determined by an assay as described in Section 8.6.

In certain embodiments, the dose of an ActRII signaling inhibitor administered to a subject according to the methods provided herein is sufficient to decrease phosphosmad2 levels and/or activity in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80%, 85%, 90%, 95%, or at most 100% as compared to phosphosmad2 levels and/or activity in a reference population (e.g., a reference population as described in Section 8.6). In certain embodiments, phosphosmad2 levels and/or activity are determined by an assay as described in Section 8.6.

In certain embodiments, the dose of an ActRII signaling inhibitor administered to a subject according to the methods provided herein is sufficient to decrease phosphosmad3 levels and/or activity in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80%, 85%, 90%, 95%, or at most 100% as compared to phosphosmad3 levels and/or activity in a reference population (e.g., a reference population as described in Section 8.6). In certain embodiments, phosphosmad3 levels and/or activity are determined by an assay as described in Section 8.6.

In certain embodiments, the dose of an ActRII signaling inhibitor administered to a subject according to the methods provided herein is sufficient to decrease urinary protein levels and/or activity in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80%, 85%, 90%, 95%, or at most 100% as compared to urinary protein levels and/or activity in a reference population (e.g., a reference population as described in Section 8.6). In certain embodiments, urinary protein levels and/or activity are determined by an assay as described in Section 8.6.

In certain embodiments, the dose of an ActRII signaling inhibitor administered to a subject according to the methods provided herein is sufficient to decrease Dkk1 levels and/or activity in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80%, 85%, 90%, 95%, or at most 100% as compared to Dkk1 levels and/or activity in a reference population (e.g., a reference population as described in Section 8.6). In certain embodiments, Dkk1 levels and/or activity are determined by an assay as described in Section 8.6.

In certain embodiments, the dose of an ActRII signaling inhibitor administered to a subject according to the methods provided herein is sufficient to decrease col1a1 levels and/or activity in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80%, 85%, 90%, 95%, or at most 100% as compared to col1a1 levels and/or activity in a reference population (e.g., a reference population as described in Section 8.6). In certain embodiments, col1a1 levels and/or activity are determined by an assay as described in Section 8.6.

In certain embodiments, the dose of an ActRII signaling inhibitor administered to a subject according to the methods provided herein is sufficient to decrease BSAP levels and/or activity in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80%, 85%, 90%, 95%, or at most 100% as compared to BSAP levels and/or activity in a reference population (e.g., a reference population as described in Section 8.6). In certain embodiments, BSAP levels and/or activity are determined by an assay as described in Section 8.6.

In certain embodiments, the dose of an ActRII signaling inhibitor administered to a subject according to the methods provided herein is sufficient to decrease CTX levels and/or activity in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80, 85%, 90%, 95%, or at most 100% as compared to CTX levels and/or activity in a reference population (e.g., a reference population as described in Section 8.6). In certain embodiments, CTX levels and/or activity are determined by an assay as described in Section 8.6.

In certain embodiments, the dose of an ActRII signaling inhibitor administered to a subject according to the methods provided herein is sufficient to decrease Osterix levels and/or activity in the subject by at least 5%, 10%, 15%, 20%, 25%, 30%, 35%, 40%, 45%, 500%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80%, 85%, 90%, 95%, or at most 100% as compared to Osterix levels and/or activity in a reference population (e.g., a reference population as described in Section 8.6). In certain embodiments, Osterix levels and/or activity are determined by an assay as described in Section 8.6.

In certain embodiments, the dose of an ActRII signaling inhibitor administered to a subject according to the methods provided herein is sufficient to decrease ActRIIA levels and/or activity in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 5035%, %, 60%, 65%, 70%, 75%, 80%, 85%, 90%, 95%, or at most 100% as compared to ActRIIA levels and/or activity in a reference population (e.g., a reference population as described in Section 8.6). In certain embodiments, ActRIIA levels and/or activity are determined by an assay as described in Section 8.6.

In certain embodiments, the dose of an ActRII signaling inhibitor administered to a subject according to the methods provided herein is sufficient to increase Klotho levels and/or activity in the subject by at least 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, or by at least 500%, or by at most 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, or by at most 500% as compared to Klotho levels and/or activity in a reference population (e.g., a reference population as described in Section 8.6). In certain embodiments, Klotho levels and/or activity are determined by an assay as described in Section 8.6.

In certain embodiments, the dose of an ActRII signaling inhibitor administered to a subject according to the methods provided herein is sufficient to increase alpha-SMA levels and/or activity in the subject by at least 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, or by at least 500%, or by at most 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, or by at most 500% as compared to alpha-SMA levels and/or activity in a reference population (e.g., a reference population as described in Section 8.6). In certain embodiments, alpha-SMA levels and/or activity are determined by an assay as described in Section 8.6.

In certain embodiments, the dose of an ActRII signaling inhibitor administered to a subject according to the methods provided herein is sufficient to increase MYOCD levels and/or activity in the subject by at least 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, or by at least 500%, or by at most 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, or by at most 500% as compared to MYOCD levels and/or activity in a reference population (e.g., a reference population as described in Section 8.6). In certain embodiments, MYOCD levels and/or activity are determined by an assay as described in Section 8.6.

In certain embodiments, the dose of an ActRII signaling inhibitor administered to a subject according to the methods provided herein is sufficient to increase Axin2 levels and/or activity in the subject by at least 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, or by at least 500%, or by at most 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, or by at most 500% as compared to Axin2 levels and/or activity in a reference population (e.g., a reference population as described in Section 8.6). In certain embodiments, Axin2 levels and/or activity are determined by an assay as described in Section 8.6.

In certain embodiments, the dose of an ActRII signaling inhibitor administered to a subject according to the methods provided herein is sufficient to increase vascular smooth muscle protein levels, such as, for example, Sm22-alpha, in the subject as compared to vascular smooth muscle protein levels reference population (e.g., a reference population as described in Section 8.6). In certain embodiments, vascular smooth muscle protein levels and/or activity are determined by an assay as described in Section 8.6. In certain embodiments, the dose of an ActRII signaling inhibitor administered to a subject according to the methods provided herein is sufficient to increase Sm22-alpha levels and/or activity in the subject by at least 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, or by at least 500%, or by at most 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, or by at most 500% compared to Sm22-alpha levels and/or activity in a reference population (e.g., a reference population as described in Section 8.6). In certain embodiments, Sm22-alpha levels and/or activity are determined by an assay as described in Section 8.6.

In certain embodiments, the dose of an ActRII signaling inhibitor administered to a subject according to the methods provided herein is sufficient to increase bone volume in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 400%, 45%, 50%, 55%, 60%, 65%, 70%, 75%, 80%, 85%, 90%, 95%, or at most 100% as compared to bone volume in a reference population (e.g., a reference population as described in Section 8.6). In certain embodiments, bone volume is determined by an assay as described in Section 8.6.

In certain embodiments, the dose of an ActRII signaling inhibitor administered to a subject according to the methods provided herein is sufficient to decrease osteoclast pit surface in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80%, 85%, 90%, 95%, or at most 100% as compared to osteoclast pit surface in a reference population (e.g., a reference population as described in Section 8.6). In certain embodiments, osteoclast pit surface is determined by an assay as described in Section 8.6.

In certain embodiments, the dose of an ActRII signaling inhibitor administered to a subject according to the methods provided herein is sufficient to maintain bone formation rates in the subject, or minimally increase or decrease bone formation rates in the subject, such as, by at most 1%, 2.5%, 5%, 10%, or 15% as compared to bone formation rates in a reference population (e.g., a reference population as described in Section 8.6). In certain embodiments, bone formation rate is determined by an assay as described in Section 8.6.

In certain embodiments, the dose of an ActRII signaling inhibitor administered to a subject according to the methods provided herein is sufficient to maintain the osteoblast surface in the subject, or minimally increase or decrease the osteoblast surface in the subject, such as, by at most 1%, 2.5%, 5%, 10%, or 15 as compared to osteoblast surface in a reference population (e.g., a reference population as described in Section 8.6). In certain embodiments, osteoblast surface is determined by an assay as described in Section 8.6.

In certain embodiments, the dose of an ActRII signaling inhibitor administered to a subject according to the methods provided herein is sufficient to decrease aortic osteoblastic transition in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80%, 85%, 90%, 95%, or at most 100% as compared to aortic osteoblastic transition in a reference population (e.g., a reference population as described in Section 8.6). In certain embodiments, aortic osteoblast transition is determined by an assay as described in Section 8.6.

In certain embodiments, the dose of an ActRII signaling inhibitor administered to a subject according to the methods provided herein is sufficient to decrease osteoblast number in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80%, 85%, 90%, 95%, or at most 100% as compared osteoblast number in a reference population (e.g., a reference population as described in Section 8.6). In certain embodiments, osteoblast number is determined by an assay as described in Section 8.6.

In certain embodiments, the dose of an ActRII signaling inhibitor administered to a subject according to the methods provided herein is sufficient to decrease osteoblast surface to bone surface ratio in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80%, 85%, 90%, 95%, or at most 100% as compared osteoblast surface to bone surface ratio in a reference population (e.g., a reference population as described in Section 8.6). In certain embodiments, osteoblast surface to bone surface ratio is determined by an assay as described in Section 8.6.

In certain embodiments, the dose of an ActRII signaling inhibitor administered to a subject according to the methods provided herein is sufficient to decrease osteoclast number in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80%, 85%, 90%, 95%, or at most 100% as compared osteoclast number in a reference population (e.g., a reference population as described in Section 8.6). In certain embodiments, osteoclast number is determined by an assay as described in Section 8.6.

In certain embodiments, the dose of an ActRII signaling inhibitor administered to a subject according to the methods provided herein is sufficient to decrease osteoclast surface to bone surface ratio in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 100/0, 15%, 20%, 25%, 30%, 35%, 40%, 45%, 50%, 55%, 60%, 65%, 70%, 75%, 80%, 85%, 90%, 95%, or at most 100% as compared osteoclast surface to bone surface ratio in a reference population (e.g., a reference population as described in Section 8.6). In certain embodiments, osteoclast surface to bone surface ratio is determined by an assay as described in Section 8.6.

In certain embodiments, the dose of an ActRII signaling inhibitor administered to a subject according to the methods provided herein is sufficient to increase trabecular bone volume in the subject by at least 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, or by at least 500%, or by at most 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, or by at most 500% as compared to trabecular bone volume in a reference population (e.g., a reference population as described in Section 8.6). In certain embodiments, trabecular bone volume is determined by an assay as described in Section 8.6.

In certain embodiments, the dose of an ActRII signaling inhibitor administered to a subject according to the methods provided herein is sufficient to increase trabecular thickness in the subject by at least 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, or by at least 500%, or by at most 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, or by at most 500% as compared to trabecular thickness in a reference population (e.g., a reference population as described in Section 8.6). In certain embodiments, trabecular thickness is determined by an assay as described in Section 8.6.

In certain embodiments, the dose of an ActRII signaling inhibitor administered to a subject according to the methods provided herein is sufficient to increase vascular smooth muscle function in the subject by at least 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, or by at least 500%, or by at most 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, or by at most 500% as compared to vascular smooth muscle function in a reference population (e.g., a reference population as described in Section 8.6). In certain embodiments, vascular smooth muscle function is determined by an assay as described in Section 8.6.

In certain embodiments, the dose of an ActRII signaling inhibitor administered to a subject according to the methods provided herein is sufficient to decrease vascular calcification in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80%, 85%, 90%, 95%, or at most 100% as compared to vascular calcification in a reference population (e.g., a reference population as described in Section 8.6). In certain embodiments, vascular calcification is determined by an assay as described in Section 8.6. In certain embodiments, the dose of an ActRII signaling inhibitor administered according to the methods provided herein is sufficient to decrease vascular calcium levels by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80%, 85%, 90%, 95%, or at most 100% as compared to vascular calcium levels in a reference population (e.g., a reference population as described in Section 8.6). In certain embodiments, vascular calcium levels are determined by an assay as described in Section 8.6.

In certain embodiments, the dose of an ActRII signaling inhibitor administered to a subject according to the methods provided herein is sufficient to decrease aortic calcium levels in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80%, 85%, 90%, 95%, or at most 100% as compared to aortic calcium levels in a reference population (e.g., a reference population as described in Section 8.6). In certain embodiments, aortic calcium levels are determined by an assay as described in Section 8.6. In certain embodiments, the dose of an ActRII signaling inhibitor administered to a subject according to the methods provided herein is sufficient to decrease calcium deposits in aortic atheromas in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80%, 85%, 90%, 95%, or at most 100% as compared to calcium deposits in aortic atheromas in a reference population (e.g., a reference population as described in Section 8.6). In certain embodiments, calcium deposits in aortic atheromas are determined by an assay as described in Section 8.6.

In certain embodiments, the dose of an ActRII signaling inhibitor administered to a subject according to the methods provided herein is sufficient to decrease CKD-induced endothelial to mesenchymal transition (EnMT) in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80%, 85%, 90%, 95%, or at most 100% as compared to EnMT in a reference population (e.g., a reference population as described in Section 8.6). In certain embodiments, EnMT is determined by an assay as described in Section 8.6.

In certain embodiments, the dose of an ActRII signaling inhibitor administered to a subject according to the methods provided herein is sufficient to decrease heart size (e.g., heart weight) in the subject by at least 1%, 2%, 3%, 4%, 5%, 6%, 7%, 8%, 9%, or by at least 10%, or by at most 1%, 2%, 3%, 4%, 5%, 6%, 7%, 8%, 9%, or by at least 10% as compared to heart size (e.g., heart weight) in a reference population (e.g., a reference population as described in Section 8.6). In certain embodiments, heart size is determined by an assay as described in Section 8.6.

In certain embodiments, the dose of an ActRII signaling inhibitor administered to a subject according to the methods provided herein is sufficient to increase the levels of differentiated vascular smooth muscle cells in the subject by at least 5%, 10%, 15%, 200%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, or by at least 500%, or by at most 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, or by at most 500% as compared to differentiated vascular smooth muscle cell levels in a reference population (e.g., a reference population as described in Section 8.6). In certain embodiments, levels of differentiated vascular smooth muscle cells are determined by an assay as described in Section 8.6.

In certain embodiments, the dose of an ActRII signaling inhibitor administered to a subject according to the methods provided herein is sufficient to decrease elevated levels of arterial stiffness in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80%, 85%, 90%, 95%, or at most 100% as compared to arterial stiffness in a reference population (e.g., a reference population as described in Section 8.6). In certain embodiments, arterial stiffness is determined by an assay as described in Section 8.6. In certain embodiments, the dose of an ActRII signaling inhibitor administered according to the methods provided herein is sufficient to decrease elevated levels of arterial stiffness in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80%, 85%, 90%, 95%, or at most 100% as compared to arterial stiffness in a reference population (e.g., a reference population as described in Section 8.6). In certain embodiments, arterial stiffness is determined by an assay as described in Section 8.6.

In certain embodiments, the dose of an ActRII signaling inhibitor administered to a subject according to the methods provided herein is sufficient to maintain mineral apposition rate in the subject, or minimally increase or decrease minimal apposition rate in the subject, such as, by at most 1%, 2.5%, 5%, 10%, or 15% as compared to mineral apposition rate in a reference population (e.g., a reference population as described in Section 8.6). In certain embodiments, mineral apposition rate is determined by an assay as described in Section 8.6.

In certain embodiments, the dose of an ActRII signaling inhibitor administered to a subject according to the methods provided herein is sufficient to maintain hyperphosphatemia in the subject, or minimally increase or decrease hyperphosphatemia in the subject, such as, by at most 1%, 2.5%, 5%, 10%, or 15% as compared to hyperphosphatemia in a reference population (e.g., a reference population as described in Section 8.6). In certain embodiments, hyperphosphatemia is determined by an assay as described in Section 8.6.

In certain embodiments, the dose of an ActRII signaling inhibitor administered to a subject according to the methods provided herein is sufficient to maintain the levels of FGF23 in the subject, or minimally increase or decrease the levels of FGF23 in the subject, such as, by at most 1%, 2.5%, 5%, 10%, or 15% as compared to FGF23 levels in a reference population (e.g., a reference population as described in Section 8.6). In certain embodiments, FGF levels are determined by an assay as described in Section 8.6.

In certain embodiments, the dose of an ActRII signaling inhibitor administered to a subject according to the methods provided herein is sufficient to reduce renal fibrosis in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80%, 85%, 90%, 95%, or at most 100% as compared to renal fibrosis in a reference population (e.g., a reference population as described in Section 8.6). In certain embodiments, renal fibrosis is determined by an assay as described in Section 8.6. In certain embodiments, the dose of an ActRII signaling inhibitor administered to a subject according to the methods provided herein is sufficient to reduce glomerulosclerosis in the subject by at least 5%, 10%, 15%, 20%, 25%, 30%, 35%, 40%, 45%, 50%, 55%, 60%, 65%, 70%, 75%, 80%, 85%, 90%, 95%, or at least 100%, or by at most 5%, 10%, 15%, 20%, 25%, 30%, 35%, 40%, 45%, 50%, 55%, 60%, 65%, 70%, 75%, 80%, 85%, 90%, 95%, or at most 100% as compared to glomerulosclerosis in a reference population (e.g., a reference population as described in Section 8.6). In certain embodiments, glomerulosclerosis is determined by an assay as described in Section 8.6.

In certain embodiments, the dose of an ActRII signaling inhibitor administered to a subject according to the methods provided herein is sufficient to normalize the levels of one or more of the biomarkers provided herein (e.g., Runx2, Alp, Snai1, phosphosmad2, Dkk1, col1a1, activin, BSAP, CTX, Osterix, Klotho, alpha-SMA, MYOCD, Sm22-alpha, phosphosmad3, urinary protein, and/or ActRIIA). For example, in certain embodiments, the dose of an ActRII signaling inhibitor administered to a subject according to the methods provided herein is sufficient to increase or decrease the levels of one or more of the biomarkers provided herein (e.g., Runx2, Alp, Snai1, phosphosmad2, Dkk1, col1a1, activin, BSAP, CTX, Osterix, Klotho, alpha-SMA, MYOCD, Sm22-alpha, phosphosmad3, urinary protein, and/or ActRIIA) to the levels of the respective biomarkers in a reference population (e.g., a reference population as described in Section 8.6).

In certain embodiments, the dose of an ActRII signaling inhibitor administered to a subject according to the methods provided herein is sufficient to treat and/or prevent cardiac hypertrophy in the subject. In certain embodiments, cardiac hypertrophy is determined by an assay as described in Section 8.6. In certain embodiments, the dose of an ActRII signaling inhibitor administered to a subject according to the methods provided herein is sufficient to treat and/or prevent LVH in the subject.

When used in conjunction with a dose provided herein (e.g., a dose of an ActRII signaling inhibitor or a dose of a second active agent), the word "about" refers to any number within 1, 5 or 10% of the referenced number.

In certain embodiments, an ActRII signaling inhibitor as described herein is administered to a subject according to the methods provided herein subcutaneously or intravenously.

In certain embodiments, 0.13 mg/kg of ActRIIA-hFc (SEQ ID NO:7) is administered subcutaneously to a subject treated in accordance with the methods provided at an interval of once every 14 days. In certain embodiments, 0.26 mg/kg of ActRIIA-hFc (SEQ ID NO:7) is administered subcutaneously to a subject treated in accordance with the methods provided at an interval of once every 14 days. In certain embodiments, 0.1 mg/kg of ActRIIA-hFc (SEQ ID NO:7) is administered intravenously to a subject treated in accordance with the methods provided at an interval of once every 14 days. In certain embodiments, 0.2 mg/kg of ActRIIA-hFc (SEQ ID NO:7) is administered intravenously to a subject treated in accordance with the methods provided at an interval of once every 14 days. In certain embodiments, 0.3 mg/kg of ActRIIA-hFc (SEQ ID NO:7) is administered subcutaneously to a subject treated in accordance with the methods provided at an interval of once every 28 days. In certain embodiments, 0.5 mg/kg of ActRIIA-hFc (SEQ ID NO:7) is administered subcutaneously to a subject treated in accordance with the methods provided at an interval of once every 28 days. In certain embodiments, 0.7 mg/kg of ActRIIA-hFc (SEQ ID NO:7) is administered subcutaneously to a subject treated in accordance with the methods provided at an interval of once every 28 days.

Combination Therapy

In certain embodiments, the methods provided herein are performed in combination with a second pharmaceutically active agent. Such combination therapy may be achieved by way of the simultaneous, sequential, or separate dosing of the individual components of the treatment. Additionally, when administered as a component of such combination therapy, the ActRII signaling inhibitor and the second pharmaceutically active agent may be synergistic, such that the daily dose of either or both of the components may be reduced as compared to the dose of either component that would normally be given as a monotherapy. Alternatively, when administered as a component of such combination therapy, the ActRII signaling inhibitor provided herein and the second pharmaceutically active agent may be additive, such that the daily dose of each of the components is similar or the same as the dose of either component that would normally be given as a monotherapy.

In certain embodiments, the ActRII signaling inhibitor provided herein is administered on the same day as a second pharmaceutically active agent. In certain embodiments, the ActRII signaling inhibitor is administered one, two, three, or more days before a second pharmaceutically active agent. In certain embodiments, the ActRII signaling inhibitor is administered one, two, three or more days after a second pharmaceutically active agent. In certain embodiments, the ActRII signaling inhibitor is administered within one, two, three or more weeks of a second pharmaceutically active agent.

In certain embodiments, the second pharmaceutically active agent is an antagonist of Snail, phosphosmad2, phosphosmad3, urinary protein, Dkk1, col1a1, activin (e.g., free activin), Runx2, Alp, BSAP, CTX, and/or Osterix, such as an antibody or fragment thereof, a small molecule signaling inhibitor, an antisense nucleic acid, a small interfering nucleic acid, a dominant negative protein or fragment thereof. In certain embodiments, the second pharmaceutically active agent is an agonist of Klotho, alpha-SMA, MYOCD, Axin2 and/or Sm22-alpha, such as an antibody or fragment thereof or a small molecule.

In certain embodiments, the second pharmaceutically active agent is an active agent used to treat cardiovascular disease, vascular calcification, cardiovascular disease associated with and/or resulting from vascular calcification, and/or cardiovascular disease associated with and/or resulting from renal disease, such as, for example, an aldosterone signaling inhibitor, an angiotensin II receptor blocker, a beta-blocker, a calcium channel blocker, a cholesterol-lowering drug, digoxin, a diuretic, an inotropic therapy, potassium or magnesium, a vasodilator, and/or warfarin.

In certain embodiments, the second pharmaceutically active agent is an active agent used to treat chronic kidney disease, such as, for example, an angiotensin II receptor blocker, a beta-blocker, a calcium channel blocker, direct rennin signaling inhibitor, a diuretic, a vasodilator, erythropoietin therapy, iron replacement therapy, and/or vitamin D.

In certain embodiments, the methods provided herein are performed in combination with a method for treating or ameliorating cardiovascular disease, vascular calcification, cardiovascular disease associated with and/or resulting from vascular calcification, and/or cardiovascular disease associated with and/or resulting from renal disease, and/or chronic kidney disease.

Pharmaceutical Compositions

In certain embodiments, activin-ActRII antagonists (e.g., ActRII polypeptides) are formulated with a pharmaceutically acceptable carrier for use with the methods described herein. For example, an ActRII polypeptide can be administered alone or as a component of a pharmaceutical formulation (therapeutic composition). The subject compounds may be formulated for administration in any convenient way for use in human or veterinary medicine. ActRII can be ActRIIA or ActRIIB.

In certain embodiments, the therapeutic methods provided herein include administering the composition (comprising an ActRII signaling inhibitor) systemically, or locally as an implant or device. When administered, the therapeutic composition for uses provided herein is in a pyrogen-free, physiologically acceptable form. Therapeutically useful agents other than the ActRII antagonists which may also optionally be included in the composition as described above, may be administered simultaneously or sequentially with the subject compounds (e.g., ActRII polypeptides, such as ActRIIA and/or ActRIIB polypeptides (see, Section 8.5)).

Typically, ActRII antagonists will be administered parenterally. Pharmaceutical compositions suitable for parenteral administration may comprise one or more ActRII polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions for use in the methods described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Further, the composition may be encapsulated or injected in a form for delivery to a target tissue site (e.g., bone). In certain embodiments, compositions for use in the methods described herein may include a matrix capable of delivering one or more therapeutic compounds (e.g., ActRIIA polypeptides) to a target tissue site (e.g., bone), providing a structure for the developing tissue and optimally capable of being resorbed into the body. For example, the matrix may provide slow release of the ActRIIA polypeptides. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

In certain embodiments, the compositions for use in the methods described herein (comprising ActRII signaling inhibitor) can be administered orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds described herein may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

The compositions described herein may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the compounds described herein (e.g., ActRII polypeptides, such as ActRIIA and/or ActRIIB polypeptides (see, Section 8.5)). The various factors include, but are not limited to, amount of bone weight desired to be formed, the degree of bone density loss, the site of bone damage, the condition of the damaged bone, the subject's age, sex, and diet, the severity of any disease that may be contributing to bone loss, time of administration, and other clinical factors. Optionally, the dosage may vary with the type of matrix used in the reconstitution and the types of compounds in the composition. The addition of other known growth factors to the final composition, may also affect the dosage. Progress can be monitored by periodic assessment of bone growth and/or repair, for example, X-rays (including DEXA), histomorphometric determinations, and tetracycline labeling.

In certain embodiments, provided herein is gene therapy for the in vivo production of ActRII polypeptides. Such therapy would achieve its therapeutic effect by introduction of the ActRII polynucleotide sequences into cells or tissues having the disorders as listed above. Delivery of ActRII polynucleotide sequences can be achieved using a recombinant expression vector such as a chimeric virus or a colloidal dispersion system. Preferred for therapeutic delivery of ActRII polynucleotide sequences is the use of targeted liposomes. The ActRII polypeptides can be ActRIIA and/or ActRIIB polypeptides (see, Section 8.5)).

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the ActRII polynucleotide. In a preferred embodiment, the vector is targeted to bone or cartilage.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for ActRII polynucleotides is a colloidal dispersion system. Colloidal dispersion systems include macromolecule complexes, nanocapsules, microspheres, beads, and lipid-based systems including oilin-water emulsions, micelles, mixed micelles, and liposomes. The preferred colloidal system for use in the methods described herein is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolanine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

In certain embodiments, the ActRII signaling inhibitor is substantially pure in a pharmaceutical composition. Specifically, at most 20%, 10%, 5%, 2.5%, 1%, 0.1%, or at most 0.05% of the compounds in the pharmaceutical composition are compounds other than the ActRII signaling inhibitor and the pharmaceutical acceptable carrier.

Kits

Provided herein is a kit comprising one or more containers filled with one or more reagent to determine the level of one or more biomarkers described herein (e.g., Runx2, Alp, Snai1, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein) in a sample obtained from a subject described herein. In certain embodiments, the kit comprises one or more reagent to determine the level of one biomarker described herein (e.g., Runx2, Alp, Snai1, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein) in a sample obtained from a subject described herein. In certain embodiments, the kit comprises one or more reagent to determine the level of Runx2 in a sample obtained from a subject described herein. In certain embodiments, the kit comprises one or more reagent to determine the level of Alp in a sample obtained from a subject described herein. In certain embodiments, the kit comprises one or more reagent to determine the level of Snai1 in a sample obtained from a subject described herein. In certain embodiments, the kit comprises one or more reagent to determine the level of phosphosmad2 in a sample obtained from a subject described herein. In certain embodiments, the kit comprises one or more reagent to determine the level of Dkk1 in a sample obtained from a subject described herein. In certain embodiments, the kit comprises one or more reagent to determine the level of col1a1 in a sample obtained from a subject described herein. In certain embodiments, the kit comprises one or more reagent to determine the level of activin in a sample obtained from a subject described herein. In certain embodiments, the kit comprises one or more reagent to determine the level of BSAP in a sample obtained from a subject described herein. In certain embodiments, the kit comprises one or more reagent to determine the level of CTX in a sample obtained from a subject described herein. In certain embodiments, the kit comprises one or more reagent to determine the level of osterix in a sample obtained from a subject described herein. In certain embodiments, the kit comprises one or more reagent to determine the level of Klotho in a sample obtained from a subject described herein. In certain embodiments, the kit comprises one or more reagent to determine the level of alpha-SMA in a sample obtained from a subject described herein. In certain embodiments, the kit comprises one or more reagent to determine the level of MYOCD in a sample obtained from a subject described herein. In certain embodiments, the kit comprises one or more reagent to determine the level of Sm22-alpha in a sample obtained from a subject described herein. In certain embodiments, the kit comprises one or more reagent to determine the level of phosphosmad3 in a sample obtained from a subject described herein. In certain embodiments, the kit comprises one or more reagent to determine the level of urinary protein in a sample obtained from a subject described herein. In certain embodiments, the kit comprises one or more reagent to determine the level of ActRIIA in a sample obtained from a subject described herein. In certain embodiments, the kit comprises one or more reagent to determine the level of Axin2 in a sample obtained from a subject described herein.

In certain embodiments, the kit comprises one or more reagent to determine the level of two biomarkers described herein (e.g., two biomarkers selected from the group consisting of Runx2. Alp, Snai1, phosphosmad2, Dkk1, col1a1, activin. BSAP, CTX, osterix. Klotho, alpha-SMA, MYOCD, Sm22-alpha, phosphosmad3, ActRIIA, Axin2, and urinary protein) in a sample obtained from a subject described herein. In certain embodiments, the kit comprises one or more reagent to determine the level of three biomarkers described herein (e.g., three biomarkers selected from the group consisting of Runx2, Alp, Snai1, phosphosmad2, Dkk1, col1a1, activin, BSAP, CTX, osterix. Klotho, alpha-SMA, MYOCD, Sm22-alpha, phosphosmad3, ActRIIA, Axin2, and urinary protein) in a sample obtained from a subject described herein. In certain embodiments, the kit comprises one or more reagent to determine the level of four biomarkers described herein (e.g., four biomarkers selected from the group consisting of Runx2, Alp, Snai1, phosphosmad2, Dkk1, col1a1, activin, BSAP, CTX, osterix, Klotho, alpha-SMA, MYOCD. Sm22-alpha, phosphosmad3, ActRIIA. Axin2, and urinary protein) in a sample obtained from a subject described herein. In certain embodiments, the kit comprises one or more reagent to determine the level of five biomarkers described herein (e.g., five biomarkers selected from the group consisting of Runx2, Alp, Snai1, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein) in a sample obtained from a subject described herein. In certain embodiments, the kit comprises one or more reagent to determine the level of six biomarkers described herein (e.g., six biomarkers selected from the group consisting of Runx2, Alp, Snai1, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein) in a sample obtained from a subject described herein. In certain embodiments, the kit comprises one or more reagent to determine the level of seven biomarkers described herein (e.g., seven biomarkers selected from the group consisting of Runx2, Alp, Snai1, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein) in a sample obtained from a subject described herein. In certain embodiments, the kit comprises one or more reagent to determine the level of eight biomarkers described herein (e.g., eight biomarkers selected from the group consisting of Runx2, Alp, Snail, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein) in a sample obtained from a subject described herein. In certain embodiments, the kit comprises one or more reagent to determine the level of nine biomarkers described herein (e.g., nine biomarkers selected from the group consisting of Runx2, Alp, Snail, phosphosmad2, Dkk1, col1a1, activin. BSAP, CTX, osterix, Klotho, alpha-SMA, MYOCD, Sm22-alpha, phosphosmad3. ActRIIA, Axin2, and urinary protein) in a sample obtained from a subject described herein. In certain embodiments, the kit comprises one or more reagent to determine the level of ten biomarkers described herein (e.g., ten biomarkers selected from the group consisting of Runx2. Alp, Snail, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein) in a sample obtained from a subject described herein. In certain embodiments, the kit comprises one or more reagent to determine the level of eleven biomarkers described herein (e.g., eleven biomarkers selected from the group consisting of Runx2, Alp, Snail, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein) in a sample obtained from a subject described herein. In certain embodiments, the kit comprises one or more reagent to determine the level of twelve biomarkers described herein (e.g., twelve biomarkers selected from the group consisting of Runx2, Alp, Snail, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein) in a sample obtained from a subject described herein. In certain embodiments, the kit comprises one or more reagent to determine the level of thirteen biomarkers described herein (e.g., thirteen biomarkers selected from the group consisting of Runx2, Alp, Snail, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein) in a sample obtained from a subject described herein. In certain embodiments, the kit comprises one or more reagent to determine the level of fourteen biomarkers described herein (e.g., fourteen biomarkers selected from the group consisting of Runx2, Alp, Snail, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein) in a sample obtained from a subject described herein. In certain embodiments, the kit comprises one or more reagent to determine the level of fifteen biomarkers described herein (e.g., fifteen biomarkers selected from the group consisting of Runx2, Alp, Snail, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein) in a sample obtained from a subject described herein. In certain embodiments, the kit comprises one or more reagent to determine the level of sixteen biomarkers described herein (e.g., sixteen biomarkers selected from the group consisting of Runx2, Alp, Snail, phosphosmad2, Dkk1, col1a1, activin, BSAP, CTX, osterix. Klotho, alpha-SMA, MYOCD, Sm22-alpha, phosphosmad3, ActRIIA. Axin2, and urinary protein) in a sample obtained from a subject described herein. In certain embodiments, the kit comprises one or more reagent to determine the level of seventeen biomarkers described herein (e.g., seventeen biomarkers selected from the group consisting of Runx2, Alp, Snail, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein) in a sample obtained from a subject described herein. In certain embodiments, the kit comprises one or more reagent to determine the level of eighteen biomarkers described herein (e.g., eighteen biomarkers selected from the group consisting of Runx2, Alp, Snail, phosphosmad2, Dkk1, col1a1, activin, BSAP, CTX, osterix, Klotho, alpha-SMA, MYOCD, Sm22-alpha, phosphosmad3, ActRIIA, Axin2, and urinary protein) in a sample obtained from a subject described herein. In certain embodiments, the one or more reagent to determine the level of the biomarker is as described in Section 8.6.1. In certain embodiments, the kit further comprises ActRIIA-hFc (SEQ ID NO:7). In certain embodiments, the kit further comprises a second container comprising ActRIIA-hFc (SEQ ID NO:7).

EXAMPLES

The examples presented herein demonstrate that Runx2, Alp, BSAP, CTX, and Osterix mRNA levels are elevated and Klotho, alpha-SMA, MYOCD, ActRIIA, Axin2, and Sm22-alpha mRNA levels can be decreased in certain forms of chronic kidney disease. These examples further demonstrate that treatment with an activin ligand trap decreases Runx2, Alp, CTX, ActRIIA, and/or Osterix mRNA levels and increases Klotho, alpha-SMA, MYOCD, Axin2, and/or Sm22-alpha mRNA levels, which is associated with a decrease in vascular calcification. Accordingly, the examples provided herein demonstrate that Runx2, Alp, CTX, Osterix, Klotho, alpha-SMA, MYOCD, ActRIIA, Axin2, and/or Sm22-alpha can be used as a biomarker(s) for treating cardiovascular disease, vascular calcification, cardiovascular disease associated with and/or resulting from vascular calcification, cardiovascular disease associated with and/or resulting from renal disease, elevated levels of arterial stiffness, cardiovascular disease associated with and/or resulting from elevated levels of arterial stiffness, LVH, and/or cardiovascular disease associated with and/or resulting from LVH.

Example 1. Treatment of the CKD-MBD with a Ligand Trap for the Activin Receptor Type 2A CKD-MBD can comprise vascular calcification, an osteodystrophy, and stimulation of skeletal osteocyte FGF23 secretion at its inception, and hyperphosphatemia, develops later in the course to further stimulate vascular calcification. This example demonstrates that inhibition of ActRIIA signaling, a member of the TGFβ superfamily signaling through the activin type IIA receptor (ActRIIA), induced by CKD inhibits vascular calcification and prevents cardiac hypertrophy.
Methods
CKD with hyperphosphatemia and 60% reduction in GFR (CKD-3) was induced at 14 weeks of age in a type 2 diabetes ldlr-/- mice, high fat fed model of vascular calcification. Some CKD mice were treated with an activin receptor type 2A (mActRIIA) ligand trap mActRIIA-Fc, injected IP weekly beginning at 22 weeks of age, and studied at 28 weeks. Aortic $Ca^{2+}$ levels, expression of osteoblastic and vascular smooth muscle proteins, skeletal histomorphometry and microCT imaging, serum chemistries and FGF23 and PTH levels were measured. Activin, Follistatin and Inhibin levels were measured by ELISA, RT-PCR and Western blots.

Results

Figure 1B:
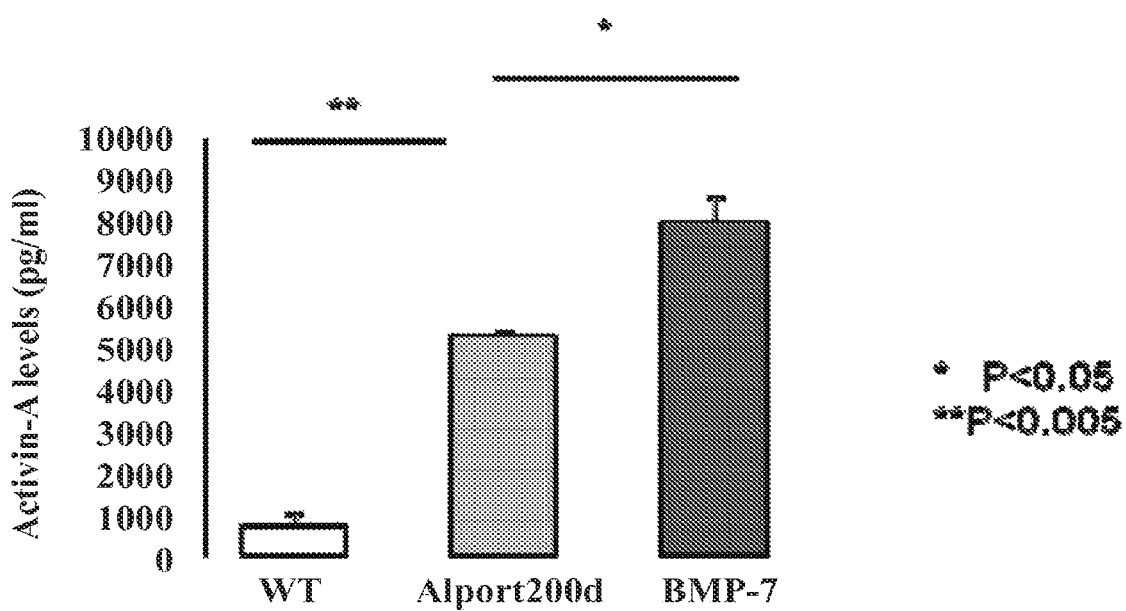
FIG. 1B depicts increased Activin-A levels (pg/ml) in the Alports model of kidney disease (Alport200d) as compared to wildtype (WT) and increased Activin-A levels upon treatment with BMP-7.
Figure 2:
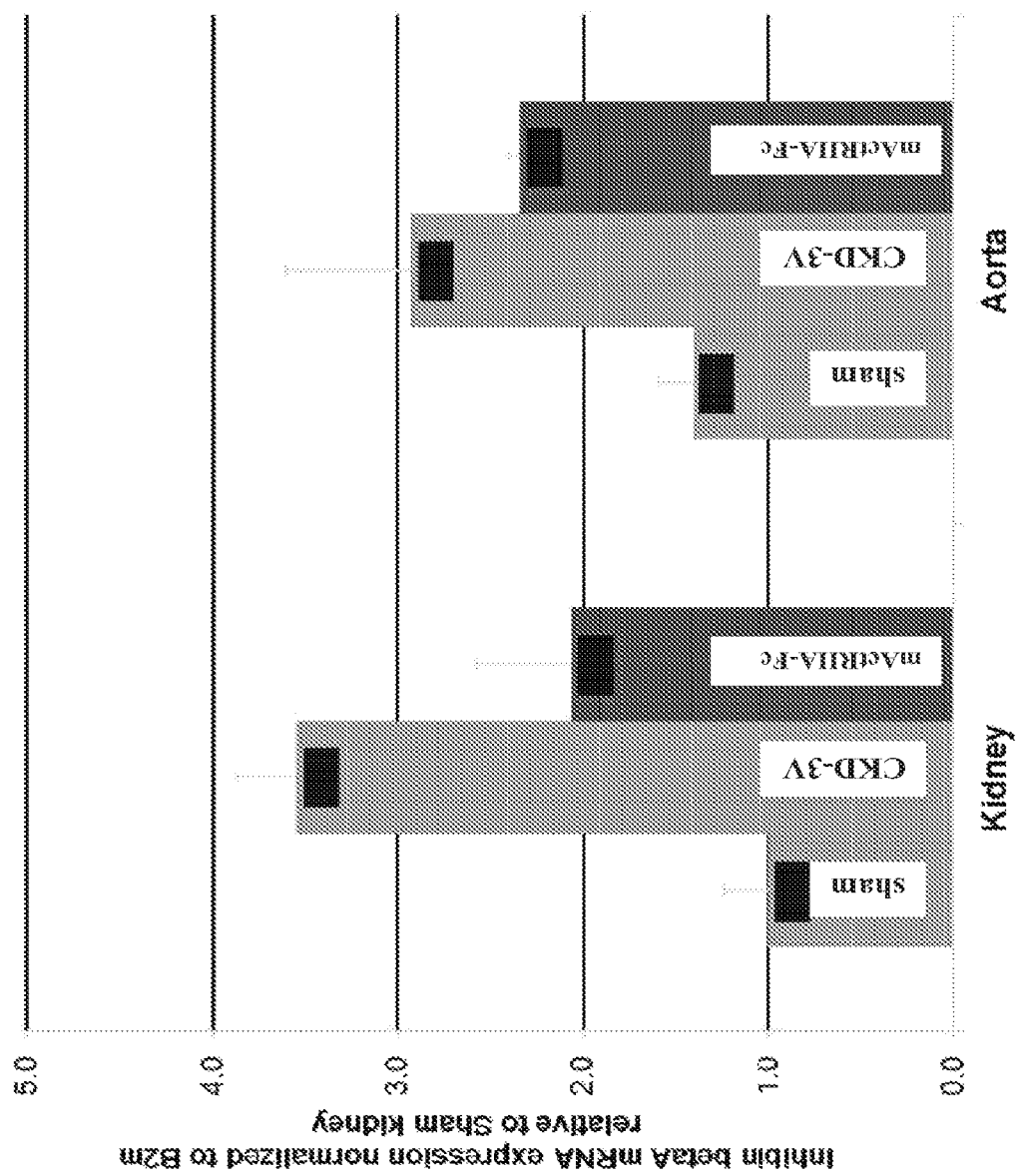
FIG. 2 depicts the increased levels of Activin A (inhibin beta) mRNA in the kidney and aorta of a CKD-3 model (CKD-3 V) as compared to sham. Treatment with mActRIIA-Fc decreases Activin A mRNA in a CKD-3 model (mActRIIA-Fc).
Figure 4F:
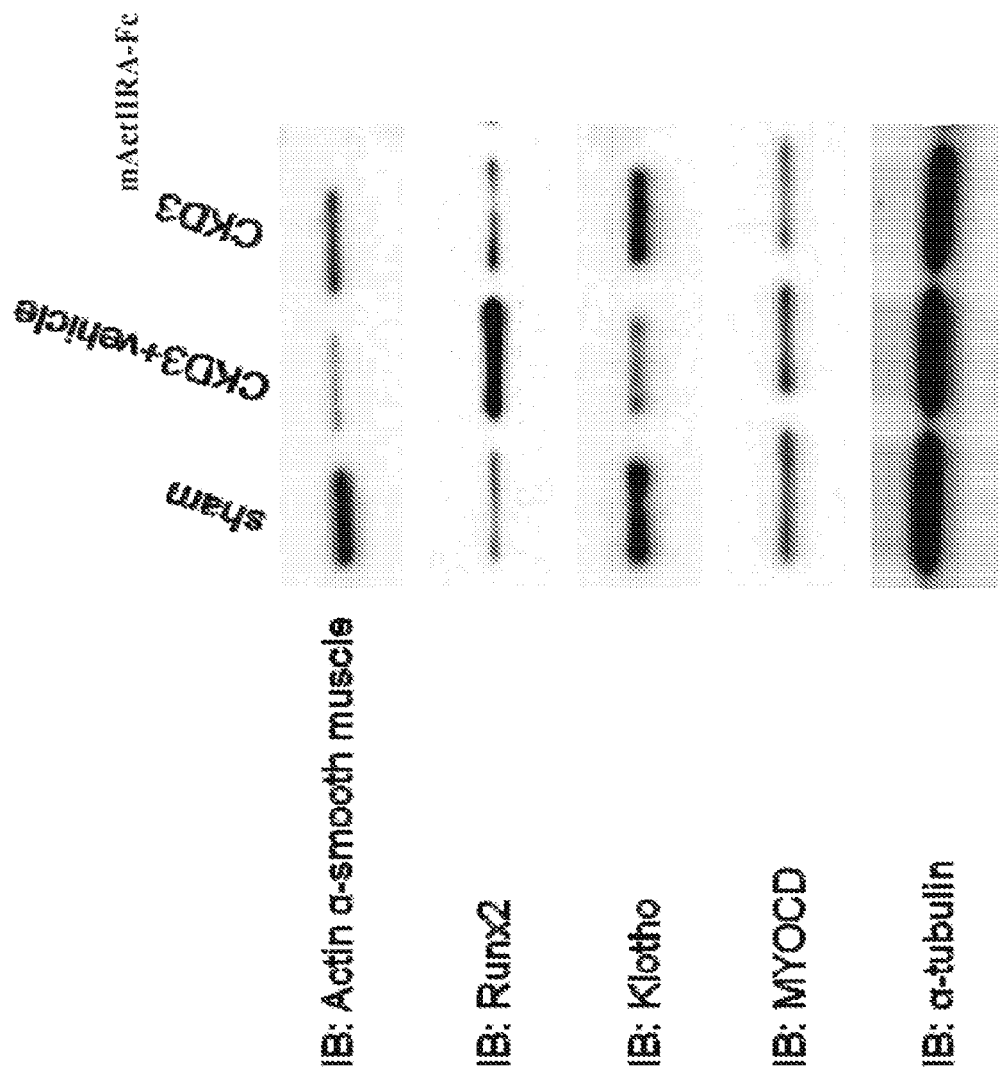
FIG. 4F depicts the protein levels of actin alpha-smooth muscle, Runx2, Klotho, MYOCD, and alpha-tubulin in a model of CKD-3 treated with an inhibitor of ActRII signaling (CKD3+ActRII-Fc) as compared to CKD3 treated with vehicle alone (CKD3+vehicle) or sham.
Figure 5B:
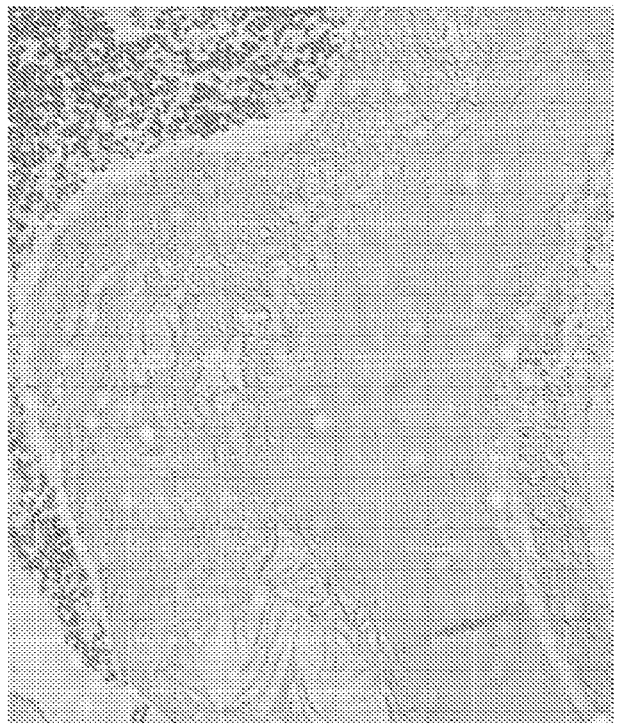
FIG. 5B depicts decreased CKD-3-induced vascular calcification upon treatment with an inhibitor of ActRII signaling (mActRIIA-Fc Rx).
Figure 5A:
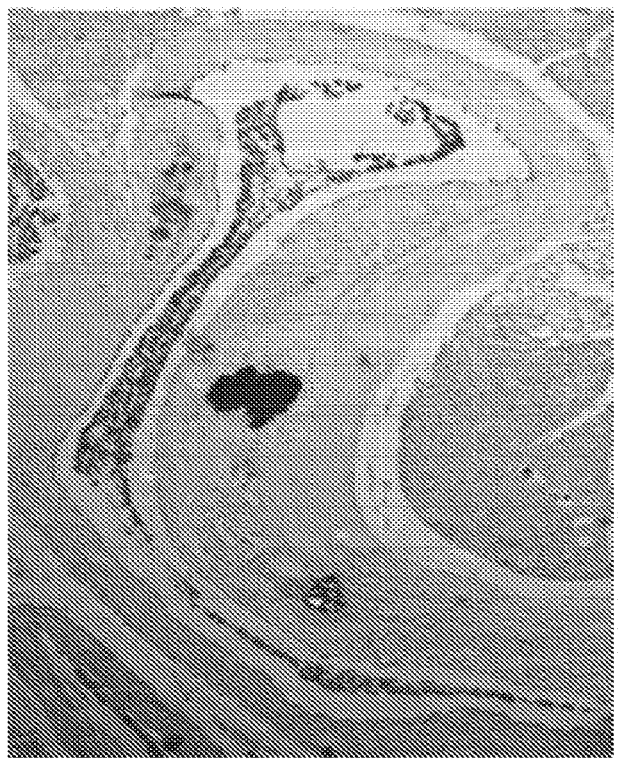
FIG. 5A depicts the CKD-3-induced vascular calcification upon treatment with a vehicle (veh. Rx).
Figure 6A:
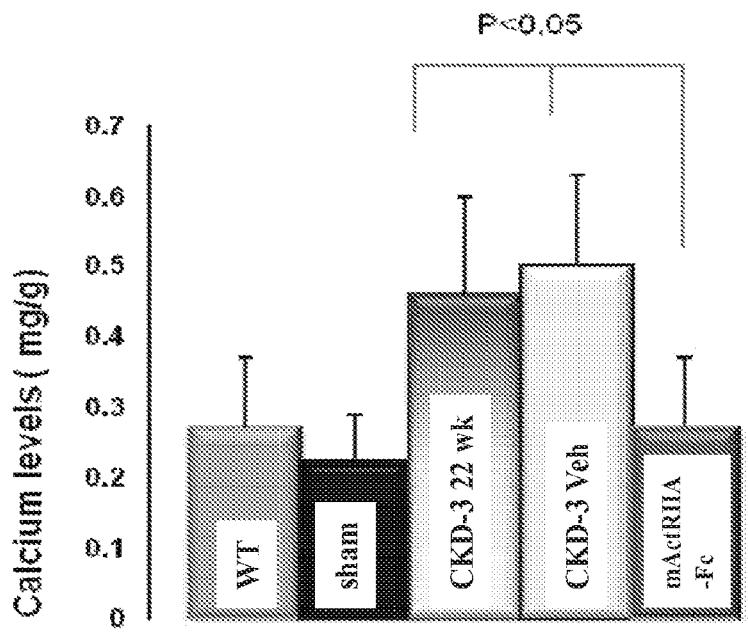
FIG. 6A depicts the CKD-3-induced increase in calcium levels (CKD-3 22 wk) as compared to wildtype (wt), sham, CKD-3 model treated with a vehicle (CKD-3 Veh). Treatment with mActRIIA-Fc decreases CKD-3-induced accumulation of calcium (mActRIIA-Fc).
Figure 6B:
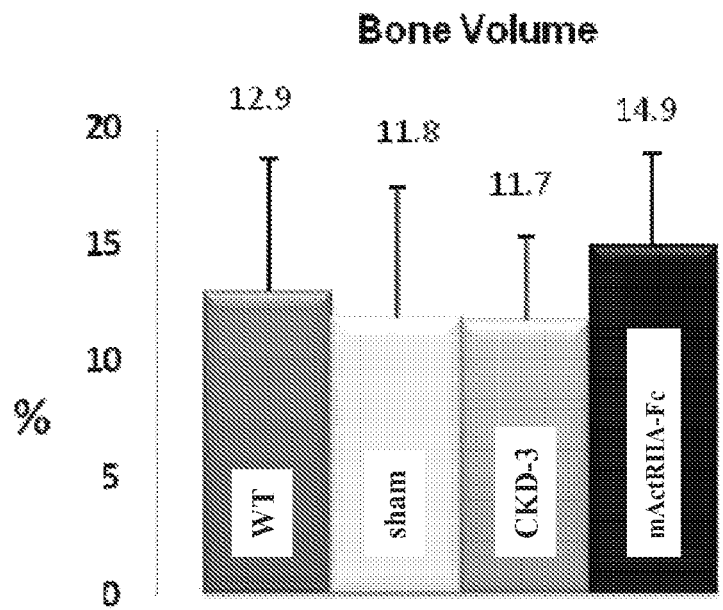
FIG. 6B depicts the bone volume of wildtype mice (wt), sham-treated mice (sham), a mouse model of CKD-3 (CKD-3), or a mouse model CKD-3 treated with an inhibitor of ActRII signaling (mActRIIA-Fc).
Figure 6C:
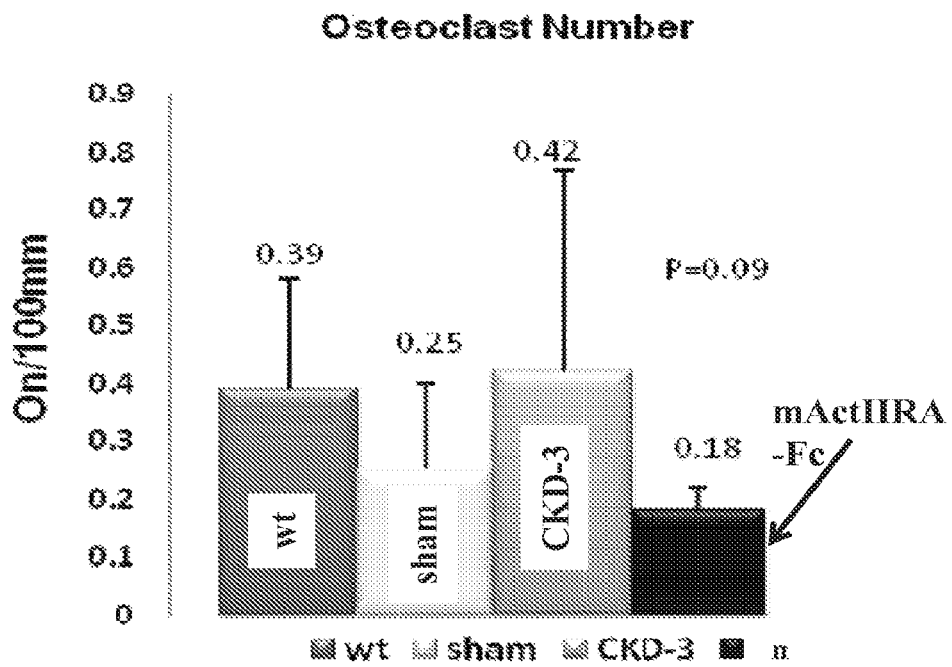
FIG. 6C depicts the osteoclast number of wildtype mice (wt), sham-treated mice (sham), a mouse model of CKD-3 (CKD-3), or a mouse model of CKD-3 treated with an inhibitor of ActRII signaling (mActRIIA-Fc).
Figure 6D:
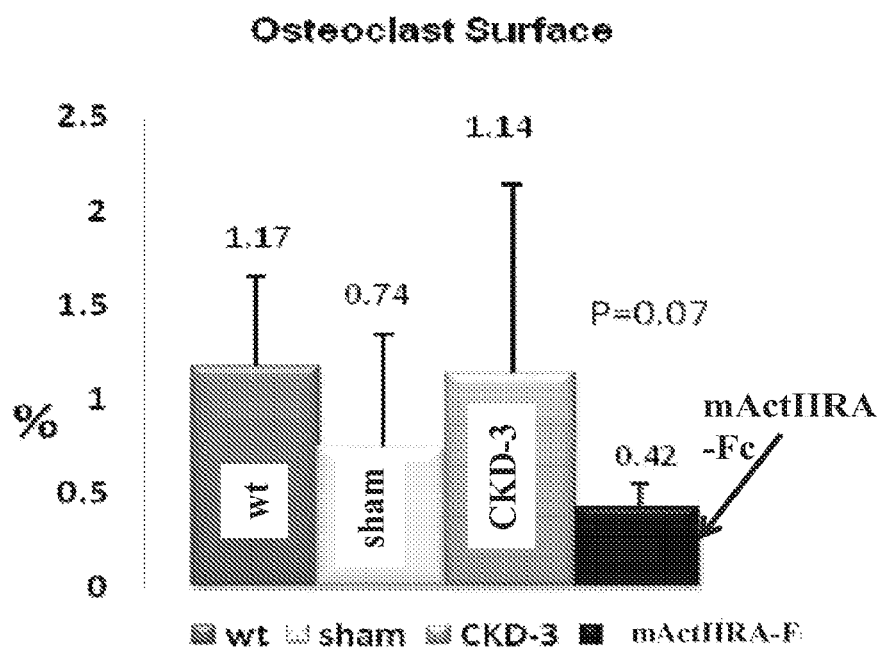
FIG. 6D depicts the osteoclast surface of wildtype mice (wt), sham-treated mice (sham), a mouse model of CKD-3 (CKD-3), or a mouse model of CKD-3 treated with an inhibitor of ActRII signaling (mActRIIA-Fc).
Figure 7A:
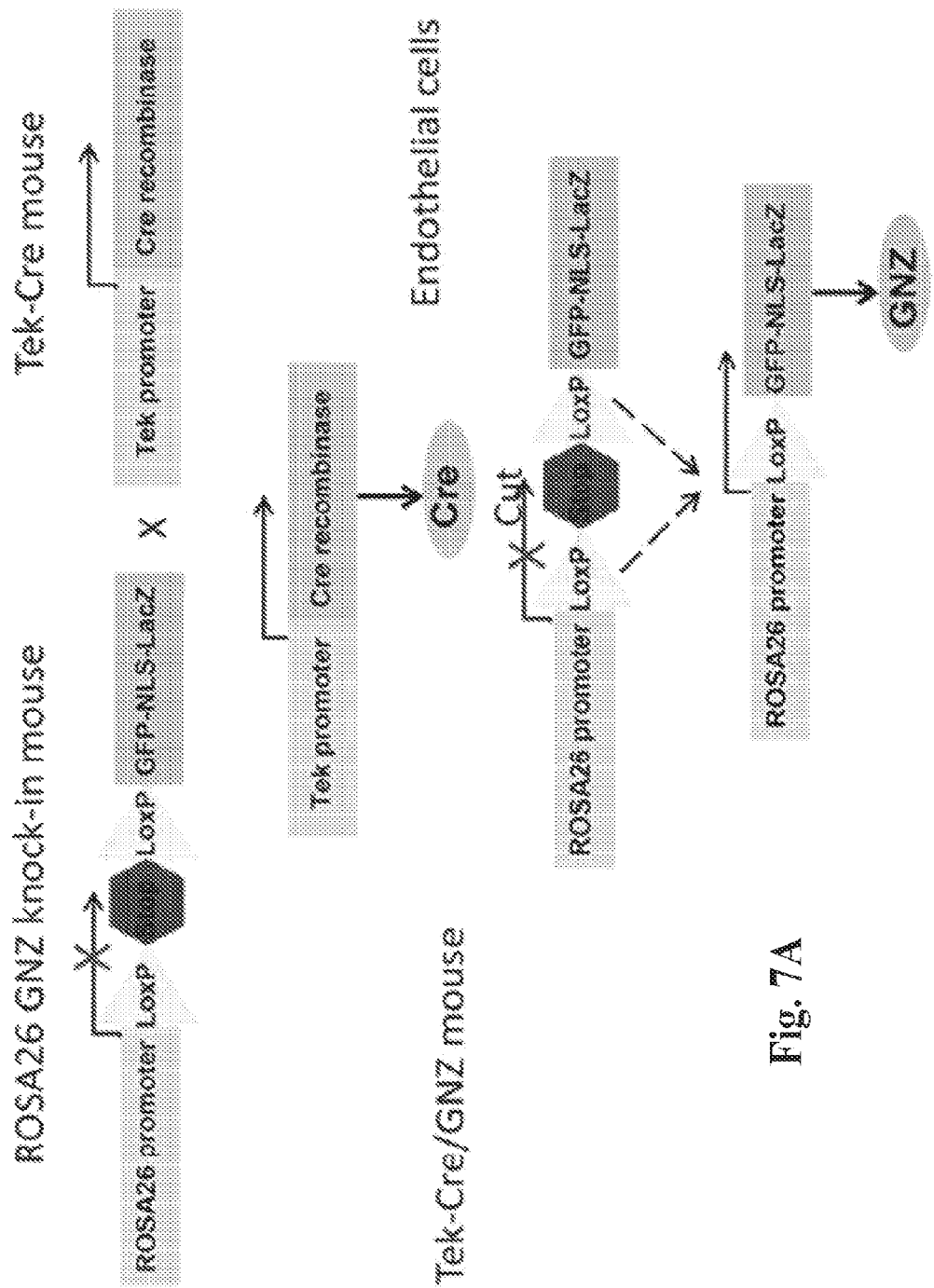
FIG. 7A depicts the strategy for cell lineage tracing as performed in GNZ mice (Stoller et al, Genesis, 2008) bred to endothelial specific Tie2-Cre (also referred to as "Tek-Cre") mice.
Figure 7B:
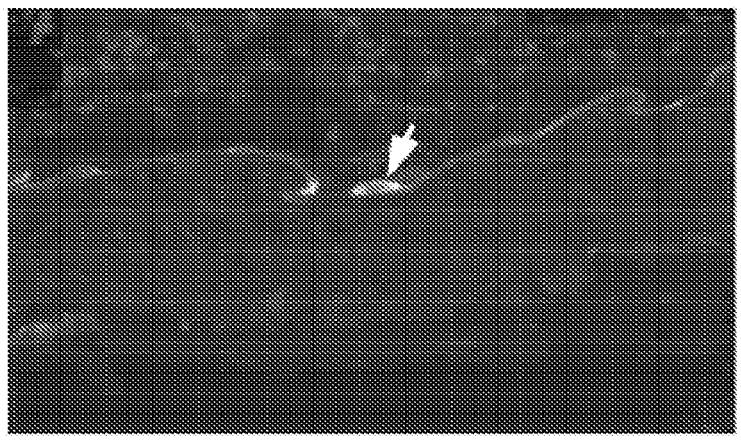
FIG. 7B depicts endothelial cell lineage tracing in sham mice.
Figure 7C:
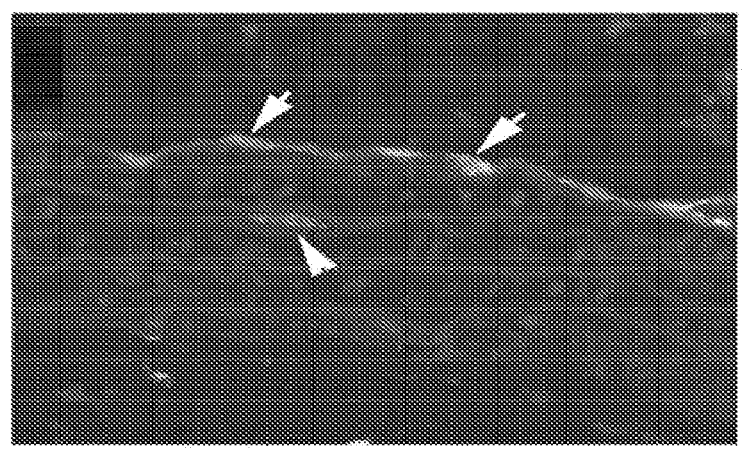
FIG. 7C depicts endothelial cell lineage tracing in CKD mice.
Figure 7D:
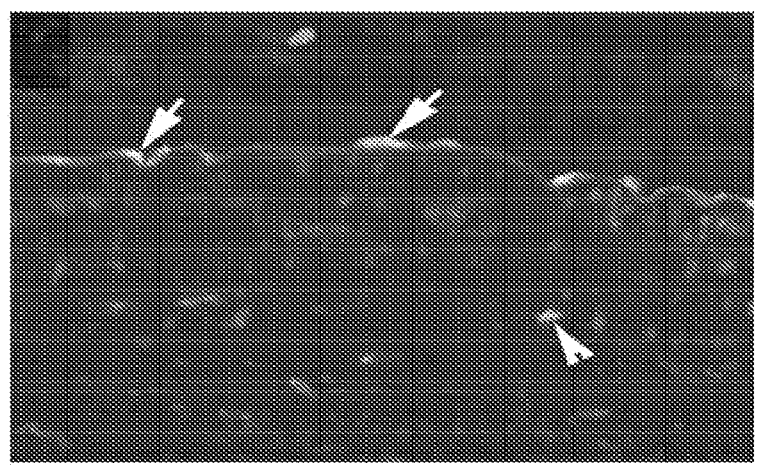
FIG. 7D depicts endothelial cell lineage tracing in CKD mice.

Circulating Activin levels were increased in two different kidney disease models: interstitial fibrosis and X-linked Alports (FIG. 1A and FIG. 1B). Moreover, Activin A mRNA levels were increased in the aorta and kidney of a CKD model (FIG. 2). Activin levels were increased in the vasculature and the circulation without changes in follistatin (FIG. 2A, FIG. 2B, and FIG. 2C). CKD stimulated vascular calcification which was reduced below 22 week levels by treatment with an activin receptor type 2A (mActRIIA) ligand trap (mActRIIA-Fc; see, e.g., U.S. Pat. No. 8,173,601, the disclosure of which is hereby incorporated by reference in its entirety) (FIG. 3A, FIG. 3B, FIG. 3C, FIG. 3D, FIG. 5A, and FIG. 5B), and cardiac hypertrophy was prevented. CKD induced expression of aortic Runx2, osterix, and Alp message and protein, and these were reversed by treatment with an activin receptor type 2A (mActRIIA) ligand trap mActRIIA-Fc (FIG. 4A and FIG. 4B for Runx2 and Alp mRNA, respectively; FIG. 4F for Runx2 protein). FIG. 4B reduced Klotho and Sm22-alpha message and protein, and treatment with an activin receptor type 2A (mActRIIA) ligand trap mActRIIA-Fc normalized Klotho and Sm22-alpha expression (FIG. 4C and FIG. 4E for Klotho and Sm22-alpha mRNA, respectively; FIG. 4F for protein). Moreover, CKD reduced MYOCD message (FIG. 4D). In addition, CKD reduced alpha-smooth muscle actin (actin alpha-smooth muscle) protein (FIG. 4F). Further, CKD stimulated increased levels of calcium which were reduced by treatment with mActRIIA-Fc (FIG. 6A). Bone volume was increased by treatment with an activin receptor type 2A (mActRIIA) ligand trap mActRIIA-Fc, and osteoclast pit surface was decreased, but bone formation rates and osteoblast surfaces were not affected (FIG. 6B, FIG. 6C, and FIG. 6D). Hyperphosphatemia and FGF23 levels were not changed by treatment with an activin receptor type 2A (mActRIIA) ligand trap mActRIIA-Fc.

Treatment with an activin receptor type 2A (mActRIIA) ligand trap mActRIIA-Fc inhibited bone resorption and increased bone volume. Treatment with an activin receptor type 2A (mActRIIA) ligand trap mActRIIA-Fc inhibited Smad dependent signaling, blocked aortic osteoblastic transition, increased vascular smooth muscle protein levels and decreased CKD stimulated vascular calcification and cardiac hypertrophy.

Example 2. Chronic Kidney Disease (CKD) Stimulates Aortic Endothelial to Mesenchymal Transition (EnMT) which Causes Vascular Calcification and is Inhibited by an Activin Ligand Trap The molecular mechanism underlying vascular calcification in chronic kidney disease is incompletely understood. However, activin levels are increased in CKD-stimulated vascular calcification. To assess the role of activins in CKD-stimulated vascular calcification, a recombinant fusion protein that binds a number of TGF-beta superfamily ligands was used in a mouse model of chronic kidney disease in a model of atherosclerosis and type-2 diabetes. The ActRIIA-Fc fusion protein consists of the extracellular domain of Activin Receptor IIA (ActRIIA) linked to an immunoglobulin 1 (IgG1) Fc domain and the protein acts as a ligand trap for TGF-beta family members like activin A, activin B, growth differentiation factor-11 (GDF11) and bone morphogenetic protein-10 (BMP-10).

It has previously been shown that kidney diseases causes vascular calcification by producing systemic Wnt inhibition during kidney repair. This example demonstrates that the vascular effects of CKD stimulated Wnt inhibition are stimulation of vascular activin as well as induction of Smad dependent EnMT, and that an activin receptor ligand trap, inhibits EnMT and vascular calcification.

Methods

CKD with elevated Wnt inhibitors was induced in the mouse models for lineage tracing and vascular calcification. Activin, Follistatin and Inhibin levels were measured by ELISA, RT PCR and Western blots. Cell lineage tracing was performed in GNZ mice (Stoller et al, Genesis, 2008) bred to endothelial specific Tie2-Cre mice. Mice harboring knock in of GNZ express nuclear GFP and lacZ following Cre-mediated recombination.

Results

Activin levels were increased in the vasculature and the circulation without changes in follistatin levels in mouse models of kidney disease and CKD stimulated vascular calcification. CKD induced expression of GFP and lacZ in cells of the adventia and media of GNZ; Tie2-Cre CKD mice compared to GNZ; Tie2-Cre mice with normal kidney function wherein the GFP and lacZ were limited to the aortic endothelium. Tie2 is an endothelial lineage specific receptor, and this demonstrates that CKD induces aortic EnMT (FIG. 7A, FIG. 7B, FIG. 7C, and FIG. 7D). CKD stimulated aortic EnMT produced decreased vascular smooth muscle function, osteoblastic transition and calcification. Treatment with an activin receptor type 2A (mActRIIA) ligand trap (mActRIIA-Fc; see, e.g., U.S. Pat. No. 8,173,601, the disclosure of which is hereby incorporated by reference in its entirety), inhibited Smad dependent signaling, blocked aortic osteoblastic transition, increased vascular smooth muscle function and decreased CKD stimulated vascular calcification. Thus, CKD induced vascular activin and EnMT, and treatment with an activin receptor type 2A (mActRIIA) ligand trap decreased activin signaling inhibiting vascular dedifferentiation, osteoblastic transition and vascular calcification.

Example 3. Initial Signal-Seeking Quantitative Computed Tomography Results for Bone Mass and Vascular Calcification in Hemodialysis Subjects Treated with Escalating Doses High turnover renal osteodystrophy (ROD) is marked by increased cortical porosity, higher trabecular bone mass, and increased risk of fracture. ActRIIA-Fc, an activin A RIIA-IgG1 fusion protein ligand trap under study for the correction of anemia in hemodialysis (HD) subjects, blocks activin A signaling and may reduce osteoclastogenesis and promote osteoblast maturation in bone. The current analysis in HD subjects evaluated the effect of ActRIIA-Fc on bone mineral density (BMD) and vascular calcification using quantitative computed-tomography (QCT).

Methods

Hemodialysis subjects treated with an ActRIIA signaling inhibitor who were erythropoietin-stimulating agent (ESA)-responsive were washed out of ESA effect until hemoglobin (Hb) was <10 g/dL, then randomized to treatment with an ActRIIA signaling inhibitor at the following doses: 0.3 mg/kg (n=9), 0.5 mg/kg (n=8), 0.7 mg/kg (n=6), or placebo (PBO; n=7) subcutaneously every 28 days for up to 8 dose cycles. Subjects were assessed for effects on Hb, bone mineral density (BMD), and biomarkers of bone turnover. Treatment failures (Hb<9 g/dL) were rescued with ESA and/or red blood cell transfusion. Quantitative computed tomography (QCT) of the hip and lumbar spine, was obtained at baseline and after the 225-day treatment phase. Biomarkers, BSAP and CTX, are measured at baseline and after dose cycles 3, 5, and 7.

QCT of the hip, lumbar spine, and abdominal aorta were obtained at baseline and after the 225-day treatment phase. Subjects were positioned supine on a Mindways calibration phantom (Model 3; Mindways Software, Inc., Austin, Tex.). The slice thickness of 2.5 mm and 512×512 matrix is reconstructed using a standard soft-tissue kernel. Mindways analysis software (version 5.0.3) was used to assess volumetric BMD (vBMD). Trabecular vBMD (mg/cm3) was determined for 2 vertebrae within L1-4 (typically L1-2). The left proximal femurs were analyzed for vBMD of the cortical, trabecular, and integral bone compartments of the total hip, femoral neck, and trochanteric regions.

Vascular calcification of the abdominal aorta was assessed using software that semi-automatically segments the area and volume of calcifications within the region adjacent to the top of L1 through the bottom of L4. The number and location of slices was maintained across visits per subject. Agatston and square root transformed volumetric scores were determined as described in Agatston et al., *J Am Col Cardiol*. 1990; 15:827-832 and Hokanson et al., *AJR AM J Roentgenol*. 2004; 182:1327-1332. Lower total Agatston and square root transformed total volume scores (mm3) indicate lower levels of vascular calcification (VC).

All image quality control and blinded analyses are performed centrally by PAREXEL imaging (PAREXEL International Corp. Waltham, Mass.).

Biomarkers, including bone-specific alkaline phosphatase (BSAP), pro-collagen type 1 N-terminal propeptide (P1NP), and C-terminal type 1 collagen telopeptide (CTX), were measured at baseline and after dose cycles 1, 3, 5, and 7.

Results

A total of 31 subjects were randomized and receive more than one dose of study medication.

TABLE 2

Randomized Subjects and QCT Analysis Subset

|  |  | ActRIIA-Fc | | |
| --- | --- | --- | --- | --- |
| Subjects, n | Placebo | 0.3 mg/kg | 0.5 mg/kg | 0.7 mg/kg |
| Randomized and received ≥1 dose of study medication | 8 | 9 | 8 | 6 |
| QCT measures at baseline and Day 225 | 3 | 6 | 5 | 2 |

Figure 8:
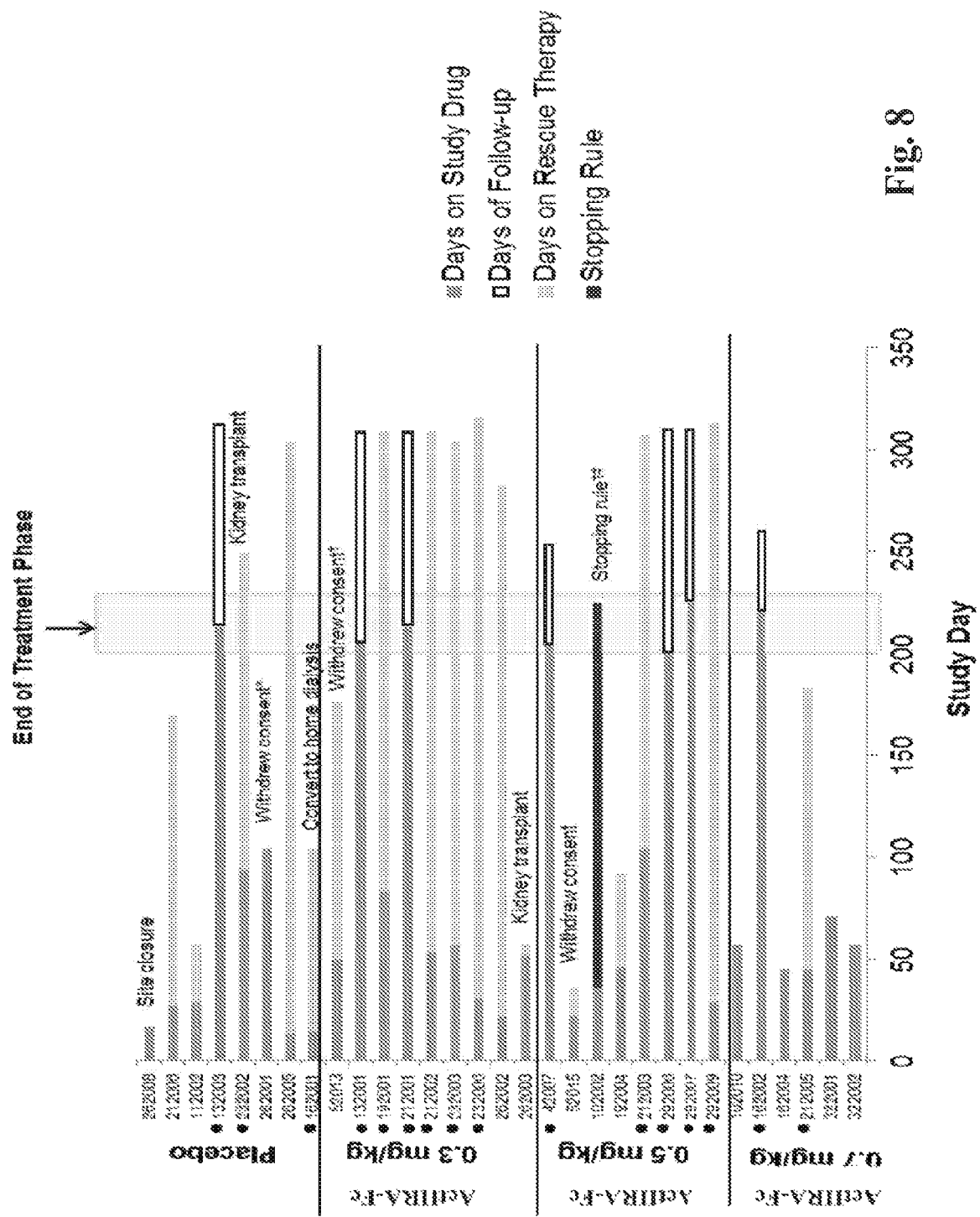
FIG. 8 depicts the subject disposition. Note: "^" indicates the subjects with paired QCT measurements at baseline and Day 225. "*" indicates that the subject receiving placebo has elevated serum erythropoietin levels, suggesting off-protocol erythropoietin administration. "†" indicates a protocol violation. "‡" indicates the subject met stopping rule criteria for elevated blood pressure on Day 29; study treatment was discontinued, and rescue therapy was administered on Day 36, with continued follow-up. Subject was randomized in error with non-qualifying blood pressure, based on incomplete evaluation, at baseline.

The subject disposition is described in FIG. 8, including the subjects with paired QCT measurements at baseline and Day 225.

Most subjects were discontinued from study treatment after treatment failure requiring rescue (generally because of Hb<9 g/dL); no subject discontinues treatment because of an adverse event (AE).

Of the 16 subjects with paired QCT measurements, 9 required rescue therapy during the treatment phase, 8 of whom required rescue within the first 3 dose cycles.

Among subjects with paired QCT measurements, baseline demographic and clinical characteristics were generally similar across treatment groups (Table 3); however, there was a substantially longer time on dialysis in the placebo group, which was also the youngest group. There were also differences between groups in baseline biomarker and Agatston scores (Table 4).

TABLE 3

Baseline Demographic and Clinical Characteristics of Subjects With Paired QCT Measurements

|  |  | ActRIIA-Fc | | |
| --- | --- | --- | --- | --- |
|  | Placebo n = 3 | 0.3 mg/kg n = 6 | 0.5 mg/kg n = 5 | 0.7 mg/kg n = 2 |
| Age, mean, years | 54.0 | 57.3 | 60.8 | 69.0 |
| Female, n (%) | 0 (0.0) | 4 (66.7) | 0 (0.0) | 1 (50.0) |
| Race, n (%) |  |  |  |  |
| White | 1 (33.0) | 3 (50.0) | 3 (60.0) | 1 (50.0) |
| Black | 1 (33.0) | 3 (50.0) | 2 (40.0) | 1 (50.0) |
| Asian | 1 (33.0) | 0 (0.0) | 0 (0.0) | 0 (0.0) |
| Ethnicity, n (%) |  |  |  |  |
| Hispanic | 0 (0.0) | 2 (33.0) | 3 (60.0) | 1 (50.0) |
| Non-Hispanic | 3 (100.0) | 4 (66.7) | 2 (40.0) | 1 (50.0) |
| Postdialysis weight, mean, kg | 70.4 | 80.3 | 79.4 | 84.4 |
| Body mass index, mean, kg/m² | 25.4 | 27.7 | 26.9 | 29.2 |
| Diabetes, n (%) | 2 (66.7) | 5 (83.3) | 5 (100.0) | 2 (100.0) |
| Parathyroidectomy, n (%) | 0 (0.0) | 0 (0.0) | 0 (0.0) | 0 (0.0) |
| Time on dialysis, mean, months | 101.2 | 43.3 | 22.4 | 11.3 |
| Non-calcium phosphate binder, n (%)* | 3 (100) | 3 (50.0) | 3 (60.0) | 0 (0.0) |
| Calcium-based phosphate binder, n (%)* | 1 (33.3) | 4 (66.7) | 4 (80.0) | 2 (100.0) |
| Calcimimetic, n (%)* | 1 (33.3) | 9 (33.3) | 0 (0.0) | 0 (0.0) |
| 1,25-OH vitamin D analog, n (%) | 2 (66.7) | 5 (83.3) | 2 (40.0) | 2 (100.0) |

TABLE 4

Mean Baseline Biomarker, Areal BMD, and Agatston Scores of Subjects With Paired QCT Measurements

|  |  | ActRIIA-Fc | | |
| --- | --- | --- | --- | --- |
|  | Placebo n = 3 | 0.3 mg/kg n = 6 | 0.5 mg/kg n = 5 | 0.7 mg/kg n = 2 |
| Baseline whole PTH, pg/mL | 261.4 | 104.8 | 135.5 | 100.4 |
| BSAP, µg/L | 28.3 | 18.0 | 13.2 | 7.5 |
| P1NP, ng/mL | 623.7 | 376.2 | 468.4 | 308.0 |
| CTX, pg/mL | 3,417.7 | 2,062.5 | 2,266.8 | 1,377.0 |
| Total hip Integral BMD, mg/cm³ | 279.4 | 306.2 | 268.9 | 285.4 |
| Femoral neck cortical BMD, mg/cm³ | 653.1 | 666.9 | 593.1 | 566.5 |
| Mean spine (L1, L2) BMD, mg/cm³ | 123.1 | 125.6 | 149.1 | 150.6 |
| VC total Agatston score* | 8,665.0 | 9,472.7 | 3,618.5 | 823.2 |

PTH = paraythroid hormone.
*Lower Agatston scores indicate lower levels of vascular calcification.

Table 5 provides the percent change from baseline in hip integral, femoral neck cortical, hip cortical, and lumbar spine areal BMD measurements.

TABLE 5

Baseline and Percent Change From Baseline in Hip integral, Femoral Neck Cortical, and Lumbar Spine Areal BMD

|  | Placebo n = 3 | ActRIIA-Fc | | |
|---|---|---|---|---|
|  |  | 0.3 mg/kg n = 6 | 0.5 mg/kg n = 5 | 0.7 mg/kg n = 2 |
| Total hip integral |  |  |  |  |
| Baseline BMD, mg/cm$^3$ | 279.4 | 306.2 | 268.9 | 285.4 |
| % Change from baseline BMD (n) | −0.2 (3) | 2.5 (5) | 4.0 (5) | −1.8 (1) |
| Femoral neck cortical |  |  |  |  |
| Baseline BMD (mg/cm$^3$) | 653.1 | 666.9 | 593.1 | 565.5 |
| % Change from baseline BMD (n) | −0.9 (3) | −1.4 (5) | 1.6 (5) | 3.0 (1) |
| Total hip, cortical |  |  |  |  |
| Baseline BMD (mg/cm$^3$) | 708.6 | 668.4 | 647.3 | 635.6 |
| % Change from baseline BMD (n) | −0.1 (3) | −1.1 (5) | 0.5 (5) | 2.7 (1) |
| Mean lumbar spine (L1, L2) |  |  |  |  |
| Baseline BMD (mg/cm$^3$) | 123.1 | 125.6 | 149.1 | 150.6 |
| % Change from baseline BMD (n) | 12.6 (3) | 8.0 (6) | 0.5 (5) | −2.7 (2) |

Figure 9A:
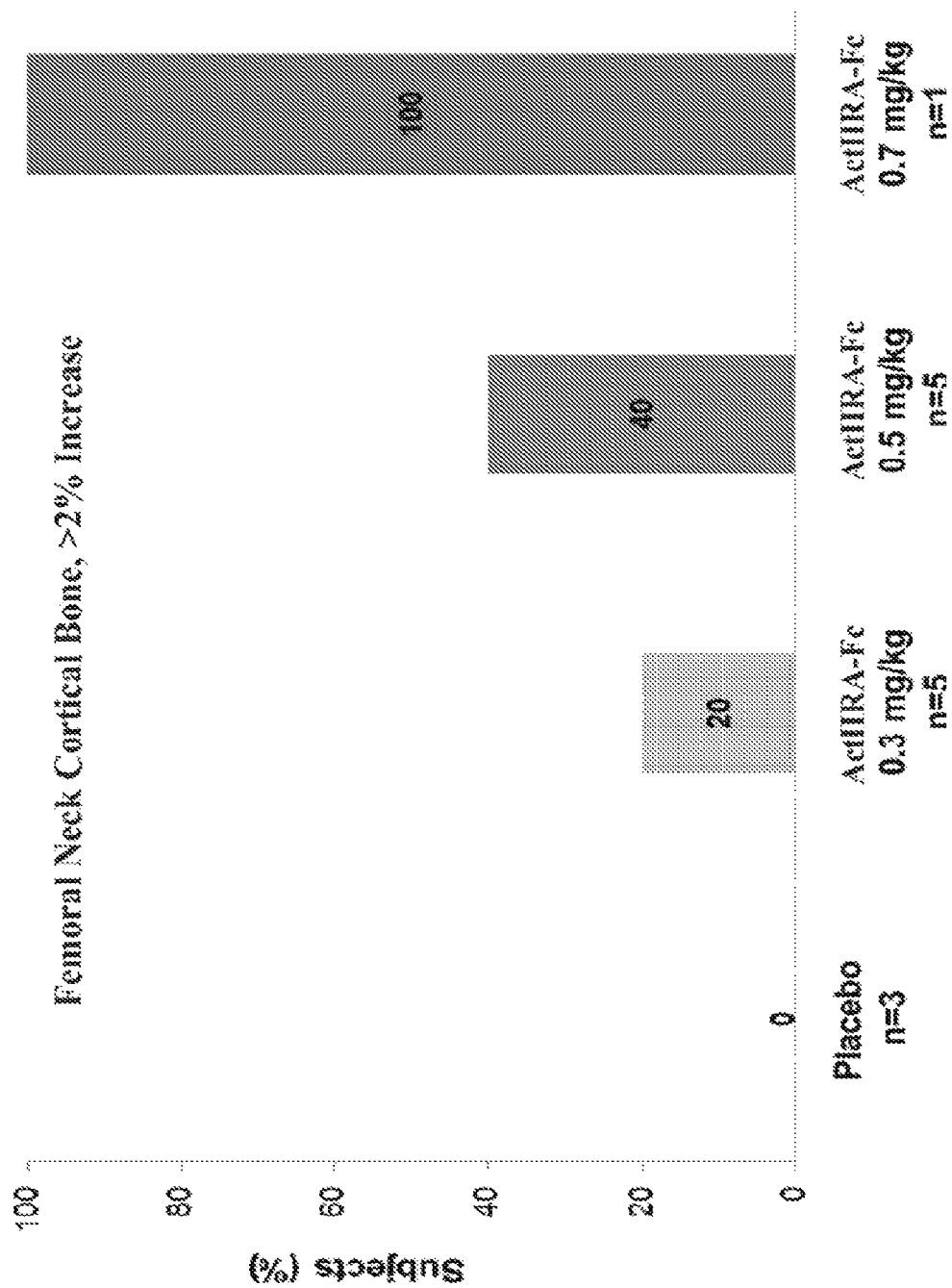
FIG. 9A depicts the percentage of subjects in each treatment category with a greater than 2% femoral neck cortical bone increase.

A 2% increase in cortical bone may reduce fracture risk. ACTRIIA signaling inhibitor treatment was associated with a dose-dependent increase in the proportion of subjects with a greater than or equal to 2% increase in femoral neck cortical bone (Table 5 and FIG. 9A.

Figure 9B:
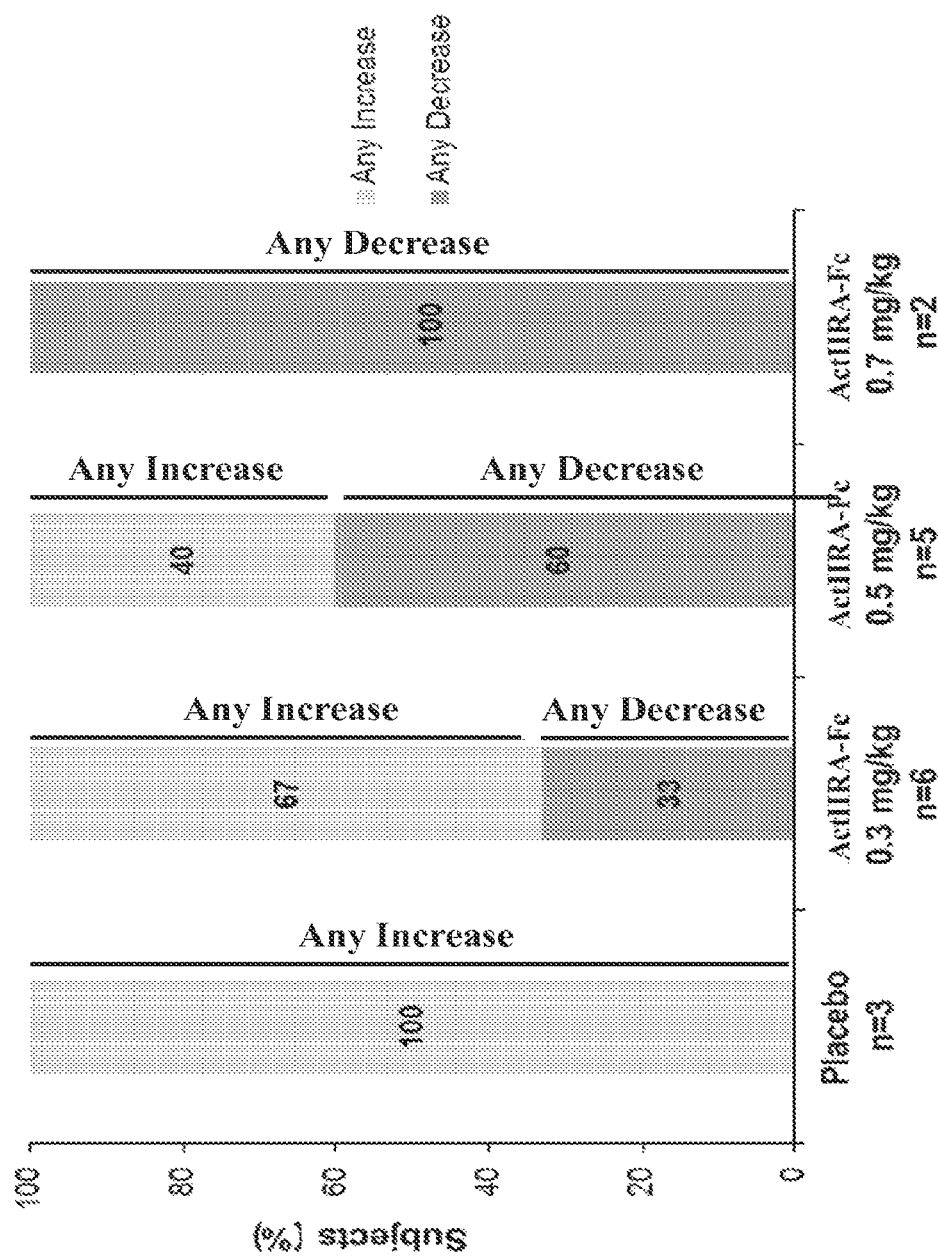
FIG. 9B depicts the percentage of subjects in each treatment group with any increase or decrease in trabecular bone mass in the lumbar spine.

In high-turnover ROD, trabecular bone mass increases (i.e., poorer quality bone), was measured by lumbar spine BMD, without a reduction in vertebral fracture rates in ESKD compared with the general population. Treatment with ACTRIIA prevented the increase in trabecular bone mass in the lumbar spine (Table 5 and FIG. 9B).

The changes from baseline in abdominal aorta total Agatston scores are provided in Table 6. Categories of change in the total Agatston score and square root transformed total volume score are shown in FIG. 9 and Table 7.

TABLE 6

Baseline and Change From Baseline in Abdominal Aorta Total Agatston Score and Square Root Transformed Total Volume Score

|  | Placebo n = 3 | ActRIIA-Fc | | |
|---|---|---|---|---|
|  |  | 0.3 mg/kg n = 6 | 0.5 mg/kg n = 5 | 0.7 mg/kg n = 2 |
| Abdominal aorta total Agatston score |  |  |  |  |
| Baseline total Agatston score | 8,665 | 9,473 | 3,619 | 823 |
| Change from baseline total Agatston score | 1,050.4 | 8,578.9 | 225.7 | 43.4 |
| % Change from baseline total Agatston score | 58.4 | 24.9 | 17.3 | 3.4 |

TABLE 6-continued

Baseline and Change From Baseline in Abdominal Aorta Total Agatston Score and Square Root Transformed Total Volume Score

|  | Placebo n = 3 | ActRIIA-Fc | | |
|---|---|---|---|---|
|  |  | 0.3 mg/kg n = 6 | 0.5 mg/kg n = 5 | 0.7 mg/kg n = 2 |
| Square root transformed total volume score |  |  |  |  |
| Baseline square root of total volume, mm$^3$ | 52.0 | 46.2 | 33.1 | 16.9 |
| Change from baseline square root of total volume, mm$^3$ | 4.5 | 11.1 | 1.2 | 0.4 |

*Lower total Agatston and square root transformed total volume scores indicate lower levels of vascular calcification.

Eleven subjects had baseline Agatston scores that were distributed between 10 and 10,000. Five subjects may be considered outliers at baseline (low outliers: 0.0, 1.1, and 1.4 Agatston scores; high outliers: 21,033 and 44,356 Agatston scores). Therefore, the Agatston scores were analyzed without the outliers (Table 7 and FIG. 10).

TABLE 7

Baseline and Change in Total Agatston Score Excluding 5 Outliers

|  | Placebo n = 1 | ActRIIA-Fc | | |
|---|---|---|---|---|
|  |  | 0.3 mg/kg n = 4 | 0.5 mg/kg n = 4 | 0.7 mg/kg n = 2 |
| Re-baseline total Agatston score, excluding 5 outliers | 4,960 | 3,120 | 4,523 | 823 |
| Change from baseline total Agatston score, excluding 5 outliers | 2,711.3 | 287.7 | 282.0 | 43.4 |
| % Change from baseline, excluding 5 outliers | 54.7 | 9.0 | 5.0 | 3.4 |

*Lower total Agatston and square root transformed total volume scores indicate lower levels of vascular calcification.

Subjects were analyzed by duration of exposure to the ActRIIA signaling inhibitor. Subjects were analyzed by exposure status: ActRIIA-Fc subjects receiving up to 3 doses, regardless of dose level (n=6), and ActRIIA-Fc subjects receiving >3 doses, regardless of dose level (n=7). The placebo group (n=3) was unchanged. Other than gender and Agatston score, key baseline characteristics were generally similar between those receiving ≤3 doses of ActRIIA-Fc and those receiving >3 doses (Table 8). An exposure effect on VC remained intact in all ActRIIA-Fc subjects (Table 9), as well as when excluding outliers (Table 10).

TABLE 8

Baseline Demographic and Clinical Characteristics of Subjects, by ActRIIA-Fc Exposure

|  | ActRIIA-Fc | |
| --- | --- | --- |
|  | ≤3 Doses n = 6 | >3 Doses n = 7 |
| Age, mean, years | 59.0 | 61.7 |
| Female, n (%) | 4 (66.7) | 1 (14.3) |
| Race, n (%) |  |  |
| White | 3 (50.0) | 4 (57.1) |
| Black | 3 (50.0) | 3 (42.9) |
| Asian | 0 (0.0) | 0 (0.0) |
| Body mass index, mean, kg/m$^2$ | 25.7 | 29.3 |
| Diabetes, n (%) | 5 (83.3) | 7 (100.0) |
| Time on dialysis, months | 31.3 | 24.0 |
| Calcium-based phosphate binder, n (%) | 4 (66.7) | 6 (85.7) |
| Calcimimetic, n (%) | 1 (16.7) | 1 (14.3) |
| 1,25-OH vitamin D analog, n (%) | 4 (66.7) | 5 (71.4) |
| Baseline whole PTH, mean, pg/mL | 104.5 | 125.7 |
| BSAP, mean, µg/L | 19.8 | 10.0 |
| P1NP, mean, ng/mL | 432.2 | 374.6 |
| CTX, mean, pg/mL | 2,410.3 | 1,714.4 |
| VC total Agatston score, mean | 8,350 | 3,782 |
| Square root of volume, mm$^3$ | 38.2 | 35.3 |

TABLE 9

Baseline and Change From Baseline in Total Agatston Score and Square Root Transformed Total Volume Score, by ActRIIA-Fc Exposure*

|  | ActRIIA-Fc | |
| --- | --- | --- |
|  | ≤3 Doses n = 6 | >3 Doses n = 7 |
| Baseline total Agatston score | 8,350 | 3,782 |
| Change from baseline total Agatston score | 8,461.4 | 274.3 |
| % Change from baseline total Agatston score | 33.7 | 5.8 |
| Baseline square root of total volume, mm$^3$ | 38.2 | 35.3 |
| Change from baseline square root of total volume, mm$^3$ | 10.6 | 1.4 |

*Lower total Agatston scores and square root transformed total volume scores indicate lower levels of vascular calcification.

TABLE 10

Baseline and Change From Baseline in Total Agatston Score, Excluding 5 Outliers, by ActRIIA-Fc Exposure*

|  | ActRIIA-Fc | |
| --- | --- | --- |
|  | ≤3 Doses n = 3 | >3 Doses n = 7 |
| Re-baseline total Agatston score, excluding 5 outliers | 1,914 | 3,782 |
| Change from baseline total Agatston score, excluding 5 outliers | 148.4 | 274.3 |
| % Change from baseline, excluding 5 outliers | 7.5 | 5.8 |

*Lower total Agatston scores and square root transformed total volume scores indicate lower levels of vascular calcification.

Figure 11:
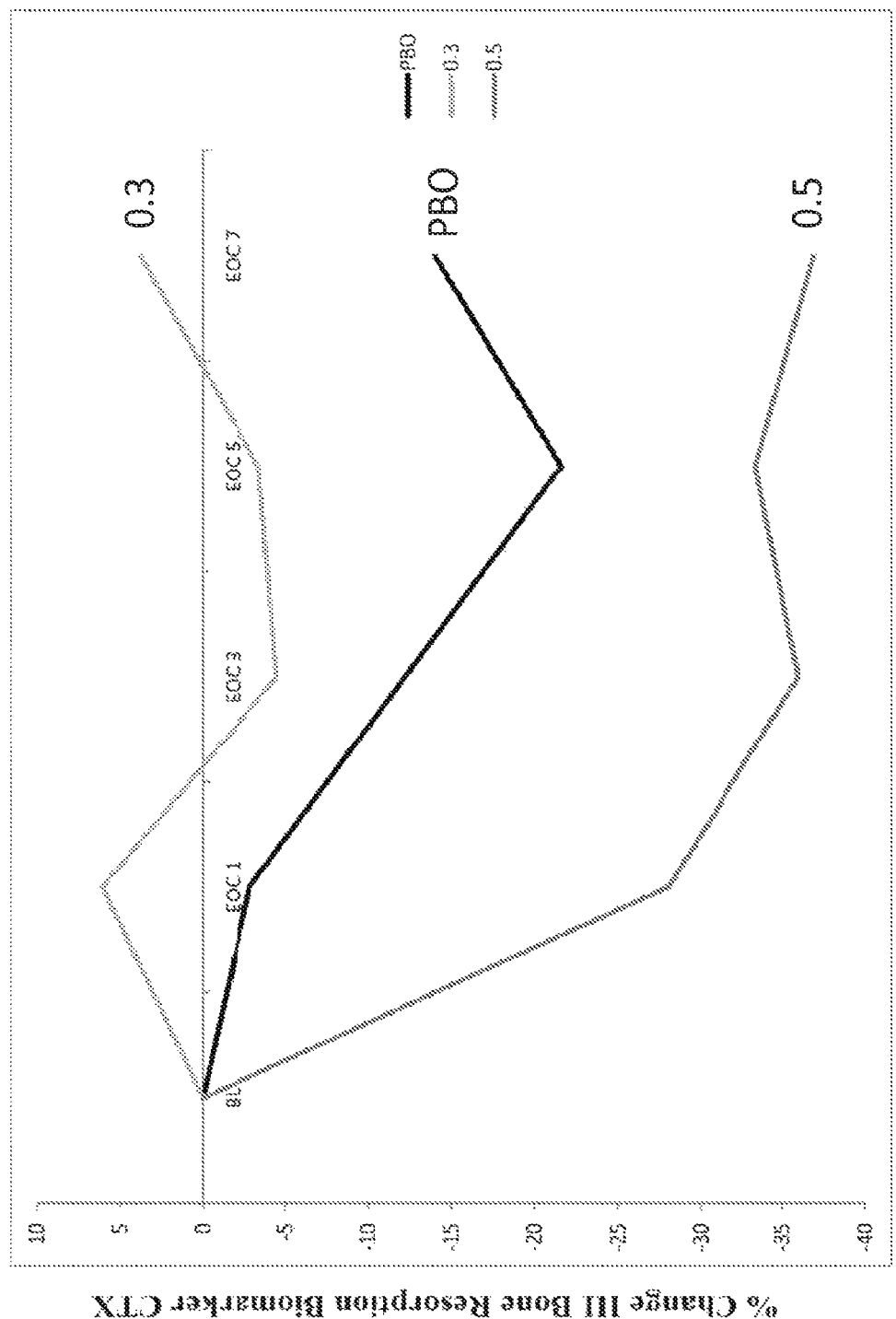
FIG. 11 depicts the percent change in the bone resorption biomarker CTX for subjects treated with placebo (PBO), or with an inhibitor of ActRII signaling at a dose of 0.3 mg/kg (0.3) or 0.5 mg/kg (0.5).

Bone turnover biomarkers were evaluated. The placebo group had the highest PTH, BSAP, P1NP, and CTX levels at baseline (Table 4). No consistent changes from baseline in phosphorous, PTH, FGF-23, or sclerostin levels were observed, except that PTH was lower at all time points than at baseline in the placebo group (−15.2 to −100.7 ng/L). For bone biomarkers, no clear changes were seen in percent change in the formation markers BSAP and P1NP; percent change in the resorption marker CTX is shown in FIG. 11. More subjects receiving 0.5 mg/kg of the ACTRIIA signaling inhibitor had meaningful, persistent decreases in the resorption marker CTX.

Conclusions

Of the 30 randomized subjects, 13 had paired QCT assessments (n=3, 6, and 4 for PBO, 0.3 mg/kg, and 0.5 mg/kg, respectively). Relative BMD changes from baseline for PBO, 0.3 mg/kg, and 0.5 mg/kg were −0.9%, −1.4%, and +1.9% of the femoral neck cortical, and +12.6%, +8.0%, and −1.9% of the lumbar spine, respectively. Biomarker changes with 0.5 mg/kg suggest a beneficial antiresorptive effect.

These data demonstrate an emerging dose effect with ActRIIA-Fc 0.5 mg/kg, which appears to reverse the effects of high turnover ROD on cortical and cancellous bone. PBO results are as expected.

Example 4. Kidney Disease Produced Circulating Renal Repair Factors Cause Cardiovascular Disease Kidney diseases are associated with an extremely high mortality, which is related to their production of cardiovascular disease (Sarnak. M. J. et al., 2003. Circulation 108: 2154-2169.). An ancillary study of the ongoing REGARDS project, demonstrated that in patients having sustained a coronary artery event (cardiac ischemia or non-fatal myocardial infarction) the incidence of second cardiovascular events over a median follow-up of 4 years was 35% in patients with kidney disease, compared to 19% in a high risk group (smokers, diabetes, hypercholesterolemia), and that the incidence of all-cause mortality in the high risk group was half that of the chronic kidney disease (CKD) group (Baber, U., et al., 2013. Am Heart J 166:373-380.). The causes of the increased cardiovascular risk associated with kidney diseases reside in a syndrome named in 2006—the chronic kidney disease—mineral bone disorder (CKD-MBD) (Moe, S., et al., 2006. Kidney Int 69:1945-1953.). In the CKD-MBD, three novel cardiovascular risk factors have been discovered (Block, G. A., et al., 1998. Am J Kidney Dis 31:607-617; Blacher, J., et al., 2001. Hypertension 38:938-942; Gutierrez, O. M., et al., 2008. New Engl J Med 359:584-592.), and their risk factor status confirmed in the general population (Dhingra, R., et al., 2007. Arch Intern Med 167:879-885; Matsushita, K., et al., 2014. Journal of the American Society of Nephrology; Dalal, M., et al., 2011. European Journal of Endocrinology 165:797-803.). These are hyperphosphatemia, vascular calcification, and elevated fibroblast growth factor 23 (FGF23) levels. The CKD-MBD begins in the early stages of CKD (stage 2) (Fang, Y., et al., 2014. Kidney Int 85:142-150; Pereira, R. C., et al., 2009. Bone 45:1161-1168; Fang, Y., et al., 2009. J Am Soc Nephrol 20:36A; Hu. M. C., et al., 2011. J Am Soc Nephrol 22:124-136) consisting of vascular dedifferentiation/calcification, an osteodystrophy, loss of Klotho and increased FGF23 secretion (Fang, Y., et al., 2014. Kidney Int 85:142-150.), but while progress into the causes of the CKD-MBD in early kidney failure have been made (Hu, M. C., et al., 2011. J Am Soc Nephrol 22:124-136; Fang, Y., et al., 2014. J Am Soc Nephrol 25:1760-1763; de Oliveira, R. B., et al., 2013. Nephrology Dialysis Transplantation 28:2510-2517; Sabbagh, Y. 2012. J. Bone Miner. Res. 27:1757-1772.), they are mostly unknown.

It has been demonstrated that kidney diseases reactivate developmental programs involved in nephrogenesis during disease stimulated renal repair (Surendran, K., et al., 2002. Am J Physiol Renal Physiol 282:F431-F441; Surendran, K., et al., 2005. J Am Soc Nephrol 16:2373-2384; Macshima, A., et al., 2001. Cytokine & Growth Factor Reviews 12:289-298; Terada, Y., et al., 2003. Journal of the American Society of Nephrology 14:1223-1233; Kawakami, T., et al., 2013. J Pathol 229:221-231.). Among the nephrogenic factors reactivated in renal repair, the Wnt (portmanteau of Wingless and Integrated) family is critical for tubular epithelial reconstitution (Terada, Y., et al., 2003. Journal of the American Society of Nephrology 14:1223-1233; Kawakami, T., et al., 2013. J Pathol 229:221-231; Rinkevich, Y., et al., 2014. Cell Reports 7:1270-1283.). In the control of Wnt function, canonical signaling transcriptionally induces the expression of a family of Wnt inhibitory proteins which are secreted proteins that serve to restrict the distances of Wnt stimulation to autocrine or paracrine factors (Niida, A., et al., 2004. Oncogene 23:8520-8526; Niehrs, C. 2006. Oncogene 25:7469-7481; Reya, T., et al., 2003. Nature 423:409-414; Chamorro, M. N., et al., 2004. The EMBO Journal 24:73-84; Gonzalez-Sancho, J. M., 2004. Oncogene 24:1098-1103.). The Wnt inhibitors are circulating factors, and the Wnt inhibitor family includes the Dickkopfs (Dkk), the secreted frizzled related proteins (Sfrps), sclerostin, sostDoc 1, crescent, Wnt inhibitor factor 1 (Wif1) and Icat (Niehrs, C. 2006. Oncogene 25:7469-7481). Various forms of kidney disease increase renal expression of Wnt inhibitors and increase their levels in the circulation (Fang, Y., et al., 2014. J Am Soc Nephrol 25:1760-1763; Surendran, K., et al., 2005. J Am Soc Nephrol 16:2373-2384.).

Neutralization of a key Wnt inhibitor elevated in the circulation in CKD, Dkk1, inhibits CKD induced vascular dedifferentiation, vascular calcification, and renal osteodystrophy (Fang, Y., et al., 2014. J Am Soc Nephrol 25:1760-1763.). This effect is surprising since Wnt signaling in the vascular smooth muscle is implicated in stimulating osteoblastic transition and vascular calcification (Al-Aly, Z., et al., 2007. Arteriosclerosis, Thrombosis, and Vascular Biology 27:2589-2596; Shao, J. S., et al., 2005. Journal of Clinical Investigation 115:1210-1220.). However, recent studies demonstrate that Dkk1 mediated inhibition of aortic Wnt7b stimulates smad-mediated aortic endothelial-mesenchymal transition (EnMT) and vascular calcification (Cheng. S.-L., et al., 2013. Arteriosclerosis, Thrombosis, and Vascular Biology 33:1679-1689.). EnMT is a developmental physiologic process involved in the development of the cardiac valves, the cardiac septum and the aortic root (Eisenberg, L. M., and Markwald, R. R. 1995. Circulation Research 77:1-6; Camenisch, T. D., et al., 2002. Developmental Biology 248:170-181.), and it may (Zeisberg, E. M., et al., 2007. Nat Med 13:952-961) or may not (Moore-Morris, T., et al., 2014. The Journal of Clinical Investigation 124:2921-2934) contribute to cardiac fibrosis in various adult disease states. This factor investigates whether other factors involved in attempted renal repair during kidney disease derive from the TGFβ superfamily and are increased in the circulation during CKD.

Methods

Production of Animal Models

The atherosclerotic low density lipoprotein receptor-deficient (ldlr−/−) males (C57Bl/6J background) were purchased from Jackson Laboratories and fed high fat diet (42% calories from fat) (Teklad #) beginning at 12 weeks of age. The mice are obese, insulin resistant at 22 weeks of age, diabetic at 28 weeks of age and hypercholesterolemic.

Figure 12A:
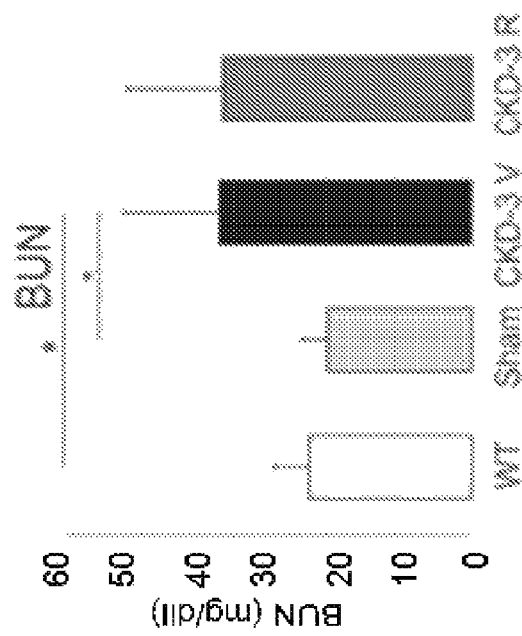
FIG. 12A demonstrates that CKD-3 mice treated with mActRIIA-Fc (CKD-3 R) at 10 mg/kg twice a week subcutaneously had no effect on inulin clearance.
Figure 15A:
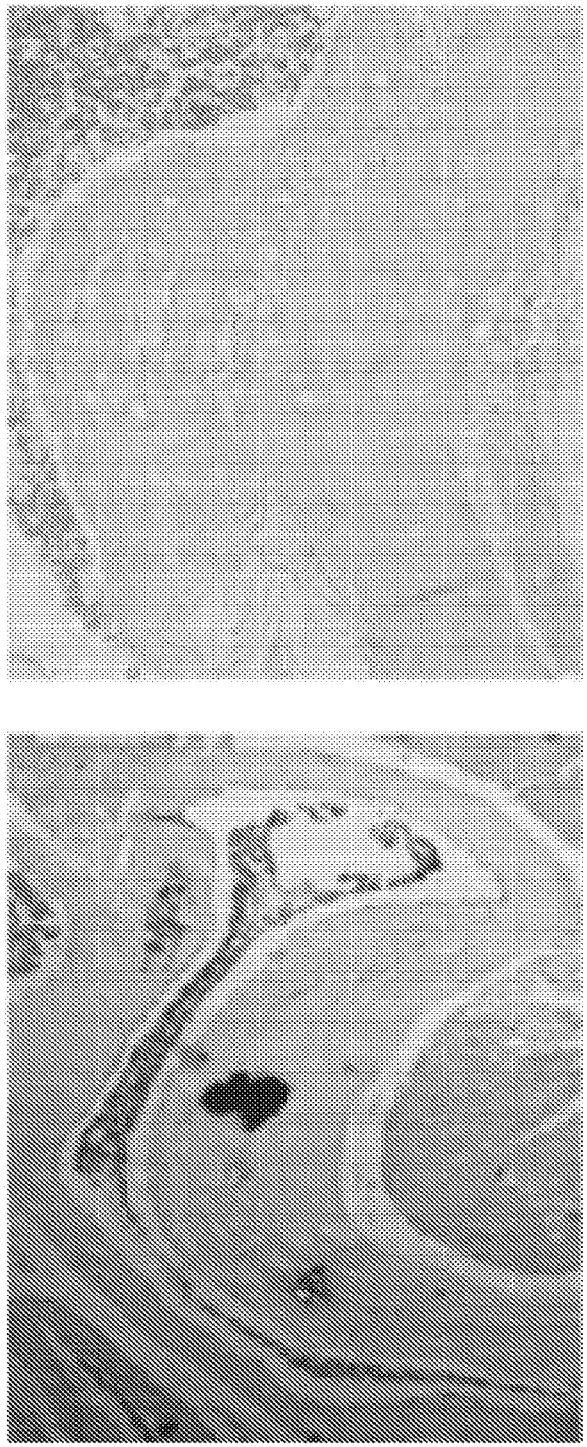
FIG. 15A depicts Alizarin Red stained sections of proximal aortic atherosclerotic plaques from vehicle-(CKD-3 V) and mActRIIA-Fc-treated (CKD-3 mActRIIA-Fc) CKD-3 mice.
Figure 15B:
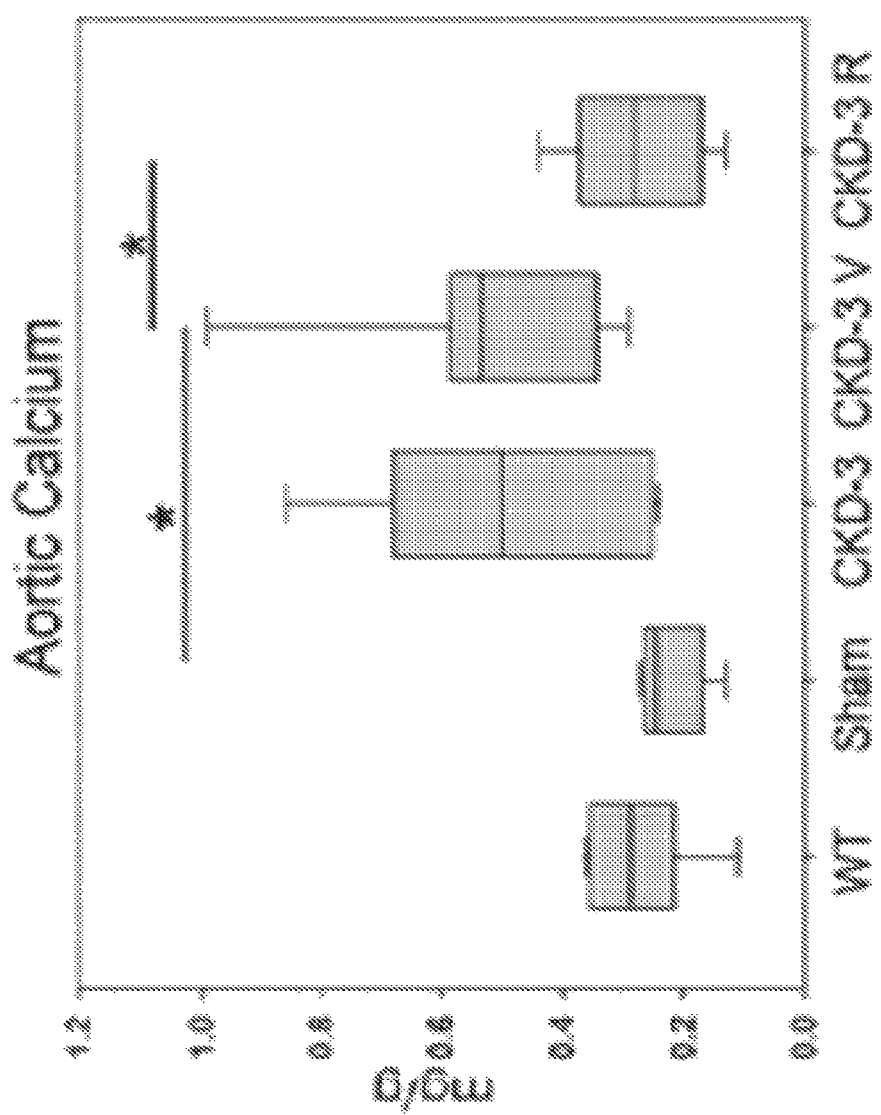
FIG. 15B depicts aortic calcium levels in the groups of mice: wild type (wt); sham operated ldlr−/− high fat fed (sham); CKD-3 euthanasia at 22 weeks, the time of institution of treatment (CKD-3)); CKD-3 treated with vehicle from 22 to 28 weeks (CKD-3 V); CKD-3 treated with mActRIIA-Fc, 10 mg/kg subcutaneous twice weekly from 22 to 28 weeks (CKD-3 R). The boxes represent median (line in box) and interquartile ranges from $25^{th}$ to $75^{th}$ percentile. The error bars represent 1.5 fold of the interquartile range. Groups were compared using ANOVA Holm-Sidak method for multiple comparisons with $p<0.05$ as level for significant difference. * $p<0.02$, n for each group 8-12.

A two-step procedure was utilized to create chronic kidney disease as described previously (Davies, M. R., et al., 2003. J Am Soc Nephrol 14:1559-1567; Davies, M. R., et al., 2005. J Am Soc Nephrol 16:917-928.). Electrocautery was applied to the right kidney through a 2 m flank incision at 12 weeks post natal, followed by left total nephrectomy at 14 weeks of age. The intensity of the cautery was varied to produce moderate (CKD-3) renal injury that was confirmed by inulin clearances at age 20 weeks (FIG. 12A). Control animals received sham operations in which the appropriate kidney was exposed and mobilized but not treated in any other way. Five groups of mice were used in this study (FIG. 15B). The first group was wild type C57Bl/6J mice fed a regular chow diet (WT). This was the normal renal function and diet group used for normative control values. The second group was ldlr−/− mice that were fed a high fat diet and sham operated (Sham). This group had normal renal function, and it served as the control group to determine the effect of kidney disease. The third group was ldlr−/− mice with GFR reduced equivalent to human CKD stage 3 fed high fat diet (CKD-3) with euthanasia at 22 weeks, the baseline vascular calcification group (CKD-3). The fourth group was ldlr−/− mice with CKD-3 receiving subcutaneous injections of vehicle twice a week beginning at 22 weeks until euthanasia at 28 weeks (CKD-3 V). The fifth group was ldlr−/− mice with CKD-3 receiving subcutaneous injections of mActRIIA-Fc (Celgene, Summit, N.J.), 10 mg/kg twice a week beginning at 22 weeks until euthanasia at 28 weeks (CKD-3 mActRIIA-Fc).

The second model of CKD used was the murine homolog of X-linked Alport's syndrome, which is a deficiency in the gene for the a5 chain of type IV collagen, COL4A5 (Rheault, M. N., et al., 2004. Journal of the American Society of Nephrology 15:1466-1474.). This is a model of spontaneous kidney disease, and it was used throughout the results to confirm the effects of renal ablation induced CKD. Breeding pairs were purchased from Jackson Laboratories and were bred for experiments. Hemizygote males spontaneously developed kidney disease comparable with human CKD stage 3-4 at 200 days after birth.

The third model of CKD used was renal ablation, similar to the ldlr−/− protocol, in a transgenic mouse line used for cellular lineage tracing, the GNZ mouse (FIG. 14). GNZ reporter female mice (Stoller, J. Z., et al., 2008. Genesis (New York, N.Y. 2000) 46:200-204) and Tek-Cre transgenic male mouse (Koni, P. A., et al., 2001. The Journal of Experimental Medicine 193:741-754) were purchased from Jackson Laboratories and were bred to produce GNZ/Tek-Cre+mice for experiments. GNZ/Tek-Cre− littermates served as negative controls. Mouse genotyping was performed by using specific primers recommended for GNZ and Tck-Cre mouse strains by manufacturer. In all cases, euthanasia was performed under anesthesia. Intraperitoneal anesthesia (xylazine 13 mg/kg and ketamine 87 mg/kg) was used for all procedures. Saphenous vein blood samples were taken 1 week following the second surgery to assess baseline post-surgical renal function. At the time of sacrifice, blood was taken by intracardiac stab, and the heart and aorta dissected en bloc.

Inulin Clearances

Inulin clearances at 20 weeks or 26 weeks, if euthanasia was at 28 weeks, were performed according to manufacturer instructions (BioPal Inc., Worcester, Mass.).

Chemical Calcification Quantitation

Aorta and hearts were dissected at sacrifice, and all extraneous tissue removed by blunt dissection under a dissecting microscope. Tissues were desiccated for 20-24 hours at 60° C., weighed and crushed to a powder with a pestle and mortar. Calcium was eluted in 1N HCL for 24 hours at 4° C. Calcium content of eluate was assayed using a cresolphthalein complexone method (Sigma, St Louis), according to manufacturer's instructions, and results were corrected for dry tissue weight.

Blood Tests

Serum was analyzed on the day of blood draw for blood urea nitrogen (BUN), calcium, and phosphate by standard autoanalyzer laboratory methods. Plasma activin (Fitzgerald Industries, Acton, Mass.), follistatin (MYBIOSOURCE Inc., San Diego, Calif.) and follistatin-like 3 (MYBIOSOURCE Inc.) levels were determined in ELISA assays. Serum Dkk1 levels were analyzed with an ELISA (R&D Systems, Minn., Minn.). For the ELISA assays, blood was drawn by saphenous vein or cardiac puncture at the time of euthanasia. All blood samples were placed on ice at collection. Platelet poor EDTA plasma samples were made by a 2-step centrifugation at 6000 rpm for 5 minutes and 14000 rpm for 2 minutes both at 4° C. Samples were stored frozen at −20° C. or below until being used.

Histology and Immunohistochemistry

Aortic, kidney and cardiac tissues were fixed in 10% neutral buffered formalin overnight, then transferred to 70% ethanol at 4° C., embedded in paraffin and 5 micron sections were prepared. Slides were deparaffinized in xylene and dehydrated in a graded ethanol series and then rehydrated. Mason Trichome staining was used to detect kidney and heart fibrosis and Alizarin red staining was used to detect calcification, according to a standard protocol (Gregory, C. A., et al., 2004. *Analytical Biochemistry* 329:77-84.). For immunohistochemical staining, endogenous peroxidase was blocked with 3% H O in methanol for 15 min. Non-specific binding was blocked with avidin and biotin blocking agents (Vector laboratories, Burlingame, Calif., USA) for 30 min, then with 3% normal donkey serum for 20 min. After washing with PBS, the slides were incubated with primary antibody at 4° C. overnight, and followed by incubation with biotinylated secondary antibody (Vector laboratories) at room temperature for one hour, then the strepatividin-conjugated peroxidase staining was performed using DAB kit (SK-4100, Vector laboratories). For double immunofluorescent staining, sections were blocked in 20% goat serum and sequentially stained with first primary and secondary antibodies and second primary and secondary antibodies using goat-anti rabbit Alexa 488 and Alexa 568 secondary antibodies 1:400 (Life Technologies, A11008 and A11011) or TSA kit (Life Technologies, T 20932) for signal amplification according manufacture instructions. When primary antibodies from same species were used for double staining, slides were heated 5 min in citrate buffer in microwave before second staining (Toth and Mezey, 2007). Primary antibodies were used in this study for immunostaining: rabbit polyclonal anti-ActRIIA antibody 1:250 (Abcam, ab 135634), rabbit polyclonal anti-Inhibin beta A antibody 1:100 (Santa Cruz, sc-50288), rabbit polyclonal anti-CD31 antibody 1:50 (Abcam, ab28364) and rabbit polyclonal anti-GFP antibodies 1:1000 (Abcam, ab6556).

RT-PCR

RNA was extracted from aortas and cell cultures using RNeasy Mini Kits (Qiagen, Valencia, Calif.). 1 pg of total RNA was DNase treated reverse transcribed using iScript cDNA synthesis kit from Bio-Rad (Hercules, Ca) according to manufacturer's instructions. Primers were designed using Vector NTI (Invitrogen, Grand Island, N.Y.) or Primer Express software. A Perkin-Elmer DNA Thermal Cycler was used to perform the reaction. Following reverse transcription performed as above, real time was performed using the StepOne Plus real time PCR instrument (AB), SYBR Green from Sigma (St. Louis) and the PCR kit from Invitrogen. Each reaction was performed in triplicate at 95° C., 45 sec, and 60° C., 30 sec, and 60 sec at 72° C. for 40 cycles. This was followed by a melt cycle, which consisted of stepwise increase in temperature from 60° C. to 95° C. A single predominant peak was observed in the dissociation curve of each gene, supporting the specificity of the PCR product. Ct numbers (threshold values) were set within the exponential phase of PCR and were used to calculate the expression levels of the genes of interest. B2m was used as an internal standard and used to normalize the values. A standard curve consisting of the $Ct^{versus}$ log cDNA dilutions (corresponding to the log copy numbers) was generated by amplifying serial dilutions of cDNA corresponding to an unknown amount of amplicon. Negative controls were performed by inactivating the reverse transcriptase by boiling for 5 min prior to RT-PCR to insure that genomic DNA was not amplified.

Immunoblotting (Western Analyses)

Whole-cell lysate protein were prepared from kidney and aorta of the mice by RIPA Lysis Buffer (Thermo Scientific) containing a protease inhibitor cocktail (Santa Cruz). Lysates (20 pg) were loaded in 8-12% SDS-PAGE gels and immunoblotted with antibodies to inhibin β-A (Santa Cruz), α-tubulin (Santa Cruz), snai 1 (Cell Signaling), alpha-SMA (Sigma), Runx2 (Cell Signaling), MYOCD (Santa Cruz), ACVRL1 (Origene), ACVR1 (Cell Signaling), Erk1/2 (Cell Signaling), phospho-Erk1/2 (Cell Signaling), ACVR1B (Origene), Col1a1 (Santa Cruz), Smad2/3 (Cell Signaling), or phospho-Smad2/3 (Cell Signaling). In immunoprecipitation (IP) assay, the same whole-cell lysate protein was used. To reduce nonspecific binding, the samples were pre-cleared using pre-washed protein A agarose beads (Cell Signaling). Pre-cleared samples were incubated overnight with the phospho-serine antibody (Abcam). IP-antibody complexes were then captured on protein A agarose beads, and proteins were detected by immunoblotting analysis.

Human Studies

Subjects were enrolled after giving informed consent in accordance with guidelines from the Declaration of Helsinki. Subjects were eligible if they were greater than 18 years of age and had stage 3 CKD (estimated GFR 30-59 ml/min/1.73 m² using the Modification of Diet in Renal Disease study equation (Levey, A. S., et al., 1999. Ann Intern Med 130:461-470.). Exclusion criteria included pregnancy, bone disease, myocardial infarction, congestive heart failure, diastolic dysfunction or severe hypertension. Members of the research team identified their clinic patients that satisfied the inclusion criteria and were interested in the study. Medical records were reviewed to determine final eligibility before enrollment. Blood samples were obtained from each subject at the baseline visit and after 12 months of treatment. There was intersubject variation in the time of day that blood samples were obtained. Aliquots of plasma were generated from each sample and used immediately for biochemical testing or frozen at 80° C. Plasma levels of activin were measured in duplicate using commercially available ELISA kits, according to the manufacturer's instructions (R&D Systems, Minneapolis, Minn.).

Statistics

Statistical analysis was performed using ANOVA. All data are expressed as mean±SD, unless other specified in the figure legend. Differences between groups were assessed post hoc using Fisher LSD method and considered significant at p<0.05. Analyses were performed using Sigma Stat statistical software (Point Richmond, Calif.). Data for all groups represent an "n" of 7-15. For real time PCR analysis minimum 3 samples were used in each experimental group. Unpaired t-tests were used to compare CKD-3 mice treated with mActRIIA-Fc versus vehicle-treated CKD-3 V mice or sham-operated mice (Sham). In FIG. 6, the boxes represent median and interquartile ranges (from $25^{th}$ to $75^{th}$ percentile), and error bars present 1.5-fold of the interquartile range below $25^{th}$ and above $75^{th}$ percentile. Means were compared using ANOVA Holm-Sidak method for multiple comparison p<0.05 as critical level for significant difference.

Results

Kidney Function in Models of CKD

Figure 12B:
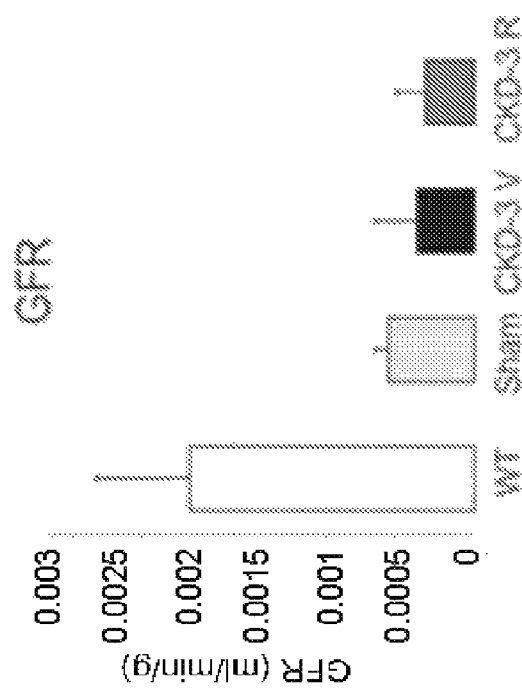
FIG. 12B demonstrates that CKD-3 mice treated with mActRIIA-Fc (CKD-3 R) at 10 mg/kg twice a week subcutaneously had no effect on BUN.
Figure 12D:
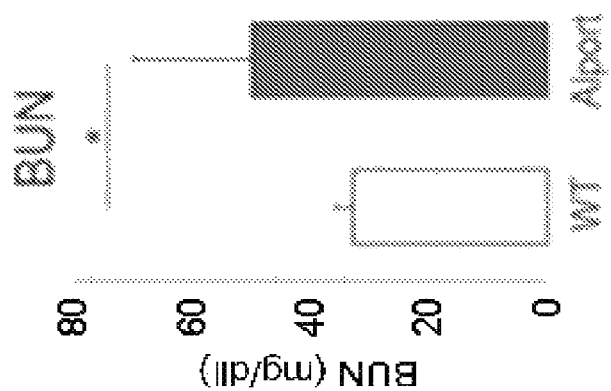
FIG. 12D demonstrates that Col4α5 deficient mice (Alport) at 200 days of age have elevations in BUN equivalent to human stage 3-4 CKD. *$p<0.05$.
Figure 12C:
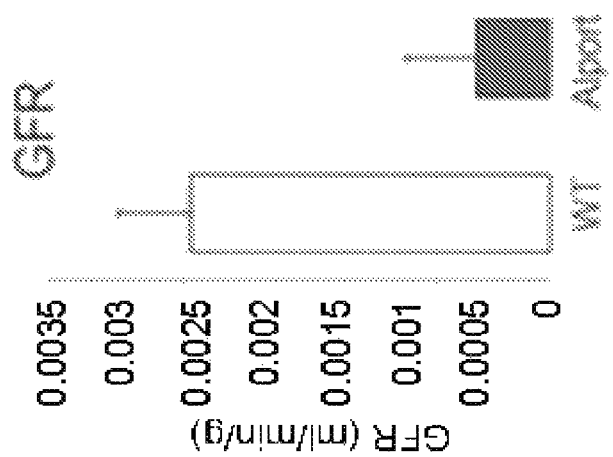
FIG. 12C demonstrates that Col4α5 deficient mice (Alport) at 200 days of age have reductions in inulin clearance equivalent to human stage 3-4 CKD. *$p<0.05$.

CKD analogous to human stage 3 CKD (CKD-3) was induced in three experimental models. The first model was a model of CKD-stimulated atherosclerotic vascular calcification: the ldlr−/− high fat-fed mouse (Fang, Y., et al., 2014. Kidney Int 85:142-150: Fang, Y., et al., 2014. J Am Soc Nephrol 25:1760-1763; Davies, M. R., et al., 2003. J Am Soc Nephrol 14:1559-1567; Davies, M. R., et al., 2005. J Am Soc Nephrol 16:917-928; Lund, R. J., et al., 2004. J Am Soc Nephrol 15:359-369; Mathew, S., et al., 2008. J Am Soc Nephrol 19:1092-1105. PMCID:PMC2396927; Mathew, S., et al., 2007. J Am Soc Nephrol 18:122-130; Mathew, S., et al., 2008. J Am Soc Nephrol 19:1509-1519. PMCID:PMC2488263.). Kidney function measured by inulin clearance and by BUN levels was reduced to the level of human stage 3 CKD in ldlr−/− high fat-fed mice, as described in Section 9.4.1.1, and these mice are hereafter referred to as CKD-3 (FIG. 12A and FIG. 12B). Furthermore, the CKD-3 mice were hyperphosphatemic (Table 11) which is consistent with human stage 3b-4 CKD. A second model of CKD was the spontaneous CKD that develops in mice and humans deficient in the a5 chain of type IV collagen (Col4α5) (Alport's syndrome) (Rheault, M. N., et al., 2004. Journal of the American Society of Nephrology 15:1466-1474.). Col4α5-deficient mice at 200 days of age have reductions in inulin clearance and BUN elevations equivalent to human stage 3-4 CKD (FIG. 12C and FIG. 12D). A third model, CKD-3 in the GNZ mouse is described in Section 9.4.1.1 and below.

TABLE 11

Serum biochemical parameters in the various groups of animals.

| Parameter | Group 1 Wild type | Group 2 Sham | Group 3 CKD-3 | Group 4 CKD-3 | Group 5 CKD-3 |
|---|---|---|---|---|---|
| Strain | C57/BJ6 | Ldlr−/− | Ldlr−/− | Ldlr−/− | Ldlr−/− |
| Diet | Chow | High fat | High fat | High fat | High fat |
| Surgery | None | Sham | CKD | CKD | CKD |
| Weeks postnatal | 28 | 28 | 28 | 28 | 28 |
| Treatment | None | None | Vehicle | mActRIIA-Fc | LaC03 |
| N | 12 | 15 | 14 | 15 | 12 |
| BUN (mg/dL) | 24.0 ± 4.6 | 20.6 ± 3.7 | 37.7 ± 7.6 | 36.5 ± 5.8 | 35.6 ± 9.1 |
| Ca (mg/di) | 8.3 ± 1.8 | 8.9 ± 0.9 | 9.4 ± 0.8 | 8.8 ± 0.3 | 8.8 ± 1.4 |
| Phosphorous (mg/di) | 8.9 ± 0.2 | 7.9 ± 2.3 | 11.0 ± 1.6 | 11.8 ± 1.2 | 10.5 ± 2.1 |

Activin Levels and Aortic Activin Receptor Type IIA (ActRIIA)

Figure 13B:
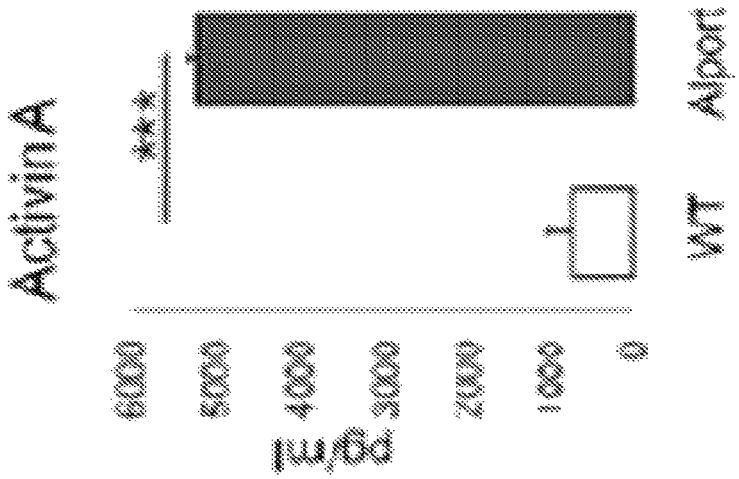
FIG. 13B depicts the induction of circulating activin-A by CKD in Alport's syndrome mice as described in as described in Section 9.4.1.1.
Figure 13A:
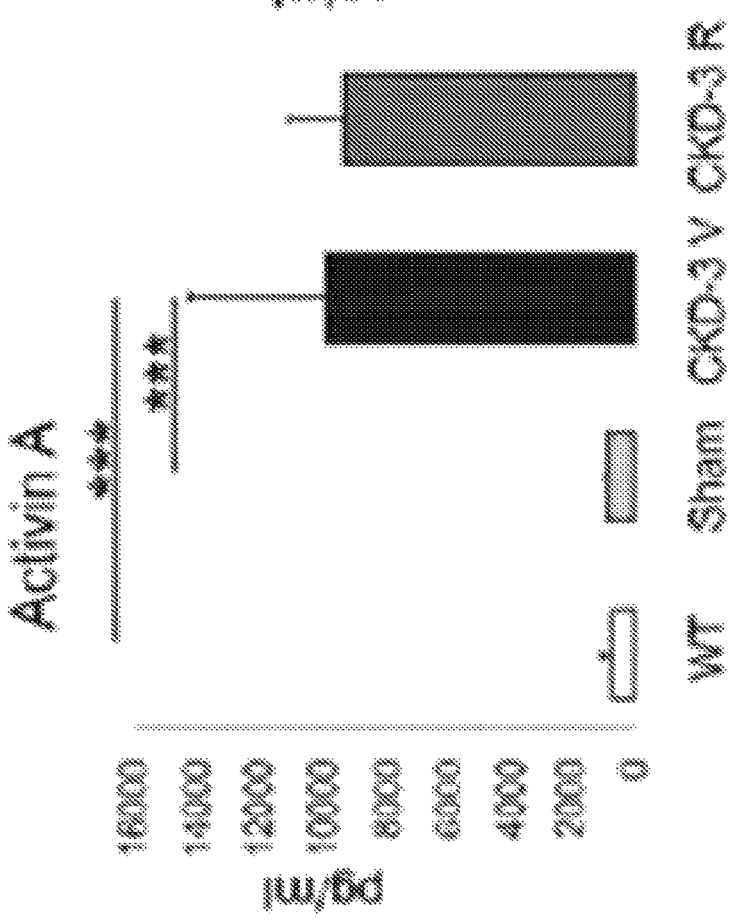
FIG. 13A depicts the induction of circulating activin-A by CKD in a ldldr−/− high fat fed CKD-3 mouse model as described in Section 9.4.1.1.
Figure 13G:
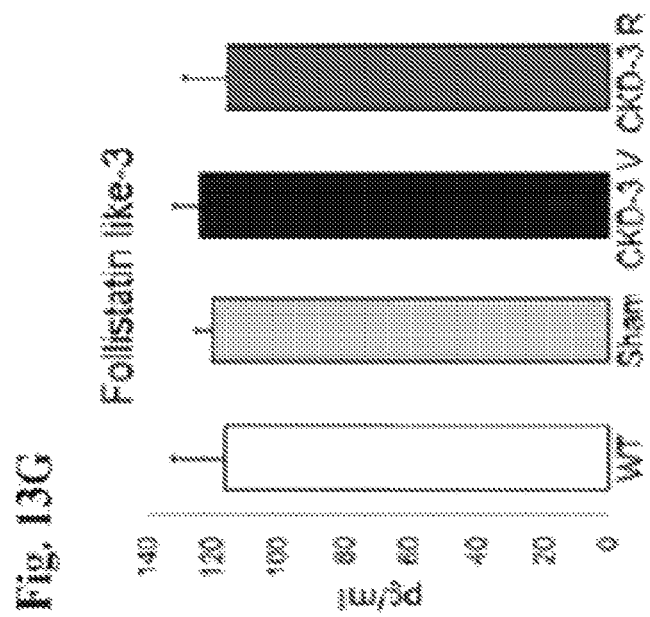
FIG. 13G demonstrates that there is no change in circulating follistatin like 3 (Fstl3) levels in CKD-3 mice (treated with vehicle, CKD-3 V, or with mActRIIA-Fc, CKD-3 R) compared to WT and sham mice. *$p<0.05$, ***$p<0.005$.
Figure 13F:
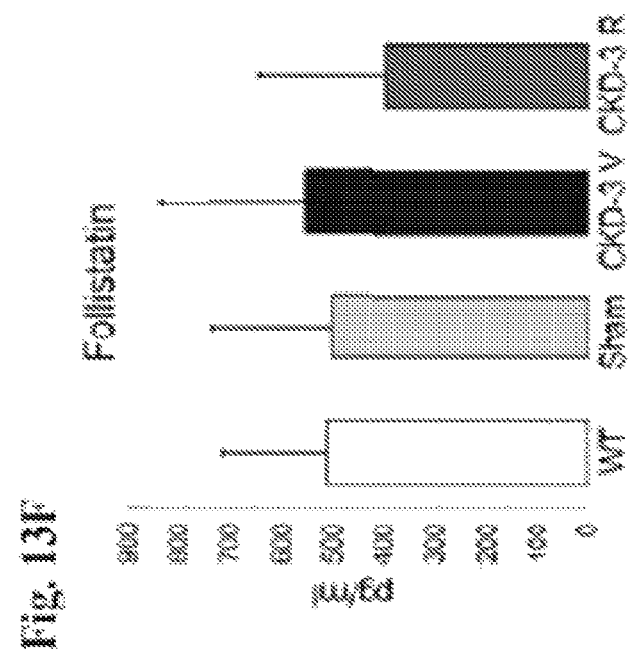
FIG. 13F demonstrates that there is no change in circulating follistatin levels in CKD-3 mice (treated with vehicle, CKD-3 V, or with mActRIIA-Fc, CKD-3 R) compared to WT and sham mice. *$p<0.05$, ***$p<0.005$.

The ability of renal repair in CKD to stimulate circulating levels of a TGFβ superfamily member was investigated. Circulating activin levels were increased in models of CKD (FIG. 13A and FIG. 13B). Kidney and aortic tissues were analyzed for the mRNA for activin A (a homodimer of Inhibin betaA (Inhba)). Inhba mRNA was induced by CKD in the kidney and aorta (FIG. 13C), and protein levels were increased in the kidney (FIG. 13D). Aortas were analyzed from mice with CKD-3 for induction of TGFβ superfamily type II receptors, which are the ligand binding component of the superfamily receptor heteromultimers composed of type II and type I (ALK) receptors. CKD-3 produced in the ldlr−/− high fat-fed mouse induced up regulation of the Activin type II receptor A (ActRIIA) in the aortic vascular smooth muscle (FIG. 13E). Activins associate with regulated inhibitory factors, follistatin and follistatin like 3 (fstL3) (Welt, C., et al., 2002. Experimental Biology and Medicine 227:724-752.), whose circulating levels (FIG. 13F and FIG. 13G) and tissue levels were not affected by CKD-3. The stoichiometry of follistatin, fstL3, and inhibin (sum of 620 pg/ml plus 400 pg/ml of unmeasured inhibin (Sharpe, R. M., et al., 1999. Journal of Andrology 20:94-101.)) to Activin A levels (>5000 pg/ml) in the circulation suggests that CKD produces significant free activin levels, a pathologic event making activin A a circulating factor in CKD.

Aortic Endothelial-Mesenchymal Transition in CKD

Figure 14A:
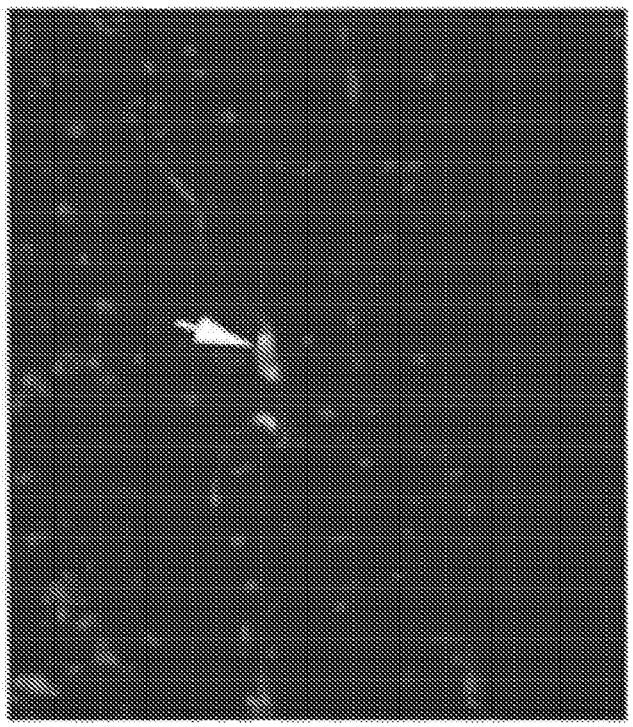
FIG. 14A depicts a diagram of mouse breeding strategy. ROSA26GNZ knock-in mouse (GNZ mouse) have sequences with stop codons, which prevent expression of nuclear localized GFP-LacZ reporter (GNZ). When breed with Tek-Cre mouse, which express Cre recombinase (Cre) in endothelial cells, Cre recombinase (Cre) deletes sequence flanked by loxP and all cells of endothelial origin produce GNZ reporter protein.
Figure 14B:
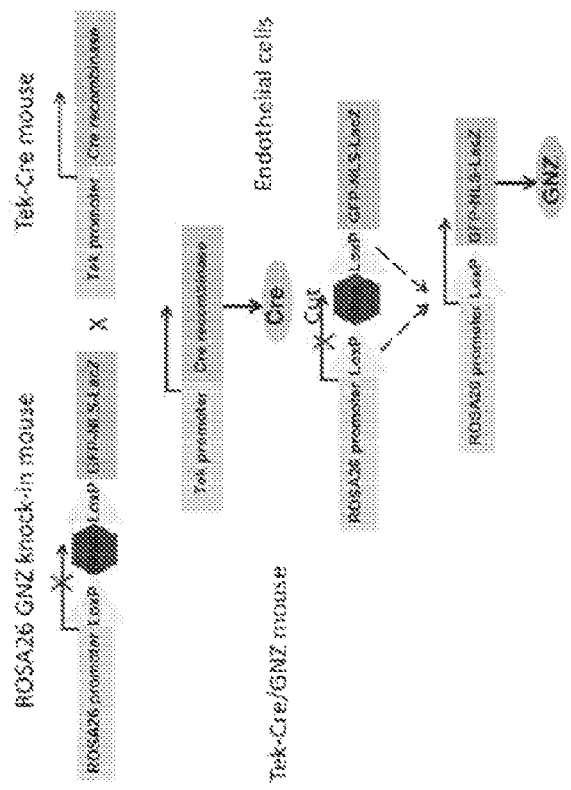
FIG. 14B to FIG. 14D demonstrates double immunostaining of Tek-Cre/GNZ mouse aorta for endothelial cell marker CD31 and GFP with DAPI nuclear staining. Arrows point to double stained endothelial cells. In a Sham operated mouse (FIG. 14B) only endothelial cells demonstrate nuclear and cytoplasmic GFP staining. In CKD3 mice, (FIG. 14C and FIG. 14D) in addition to endothelial cells, cells in the aortic media and adventitia demonstrate GFP staining (arrowheads). Scale bar is 20 µm.
Figure 14C:
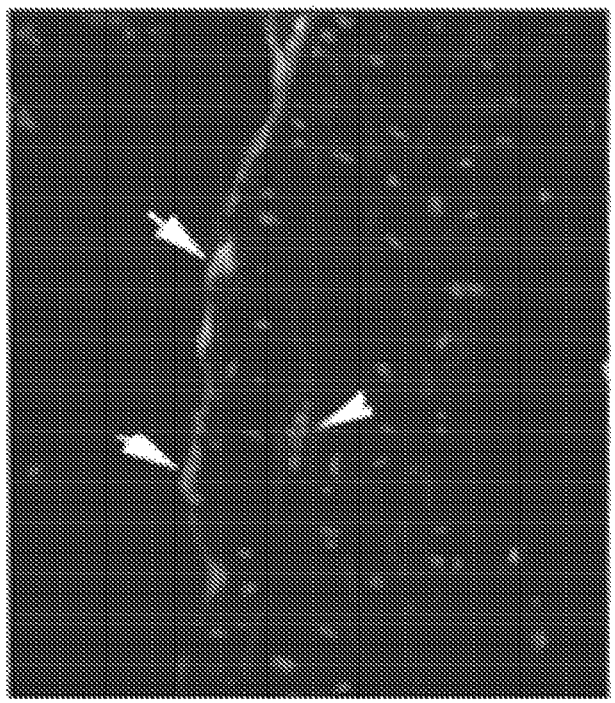
Figure 14D:
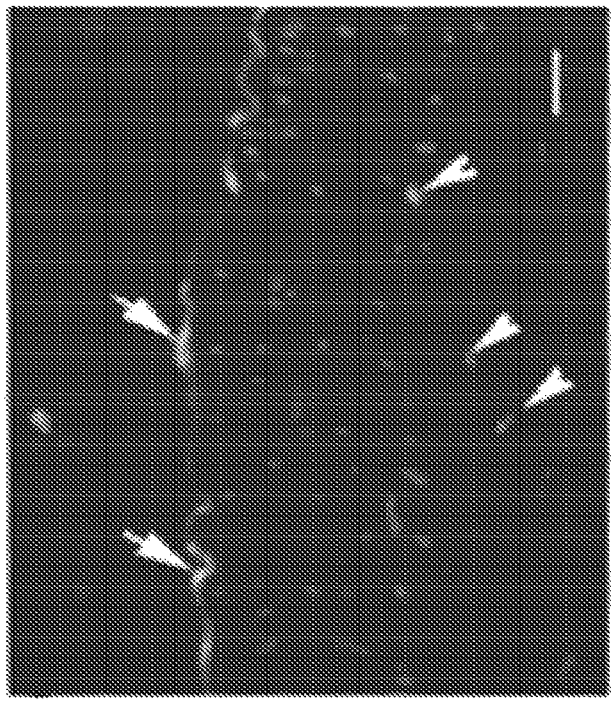
Figure 14E:
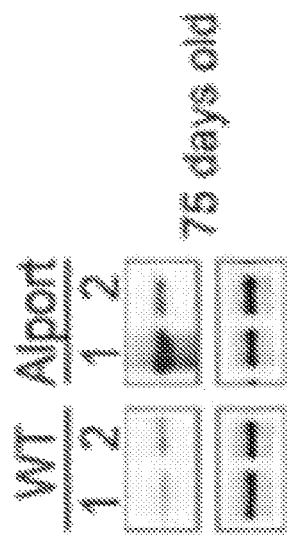
FIG. 14E depicts the aortic mRNA levels of Snail, a transcription factor associated with EnMT (Medici, D., et al., 2008. Molecular Biology of the Cell 19:4875-4887.), are increased in 75 day old Alport's mice compared to wild type (WT) mice. Alpha tubulin served as the loading control. 1 and 2 refer to individual samples.

A third experimental model of CKD was utilized for these studies. The GNZ mouse is used for cellular lineage tracing (Stoller, J. Z., et al., 2008. Genesis (New York, N.Y.: 2000) 46:200-204.), and GNZ mice express nuclear-localized Green Fluorescent Protein and beta galactosidase (GFP/LacZ) once an upstream loxP flanked STOP sequence is removed (FIG. 14A). To remove the loxP sites in the GNZ mice, they were bred with Tek-Cre mice expressing Cre recombinase under the direction of the tyrosine kinase Tek (Tie2) promoter/enhancer. Since Tie2 is an endothelial lineage specific angiopoietin receptor, the GNZ/Tek-Cre+mice express nuclear and cytoplasmic GFP in endothelial lineage cells (FIG. 14A) (Moore-Morris, T., et al., 2014. The Journal of Clinical Investigation 124:2921-2934.). In GNZ/Tek-Cre+mice, aortic GFP co-localized with the nuclear DAPI stain is limited to endothelial cells marked with the CD31 biomarker (FIG. 14B, see arrows). When CKD-3 was produced in GNZ/Tek-Cre+mice, in addition to endothelial cells, cells in the aortic media and adventia demonstrated GFP staining, showing that these cells derived from an endothelial lineage through endothelial-mesenchymal transition (EnMT) (FIG. 14C, 14D, see arrows). To further analyze whether CKD stimulates EnMT, the expression of a transcription factor involved in EnMT, Snai1, was examined in a model of spontaneous CKD, the Alports's syndrome mouse. Snai1 was upregulated early (at 75 doa) in the course of CKD (FIG. 14E), consistent with the timing of peak Activin levels (see below).

Vascular Effects of Inhibiting ActRIIA Signaling in CKD

Figure 23A:
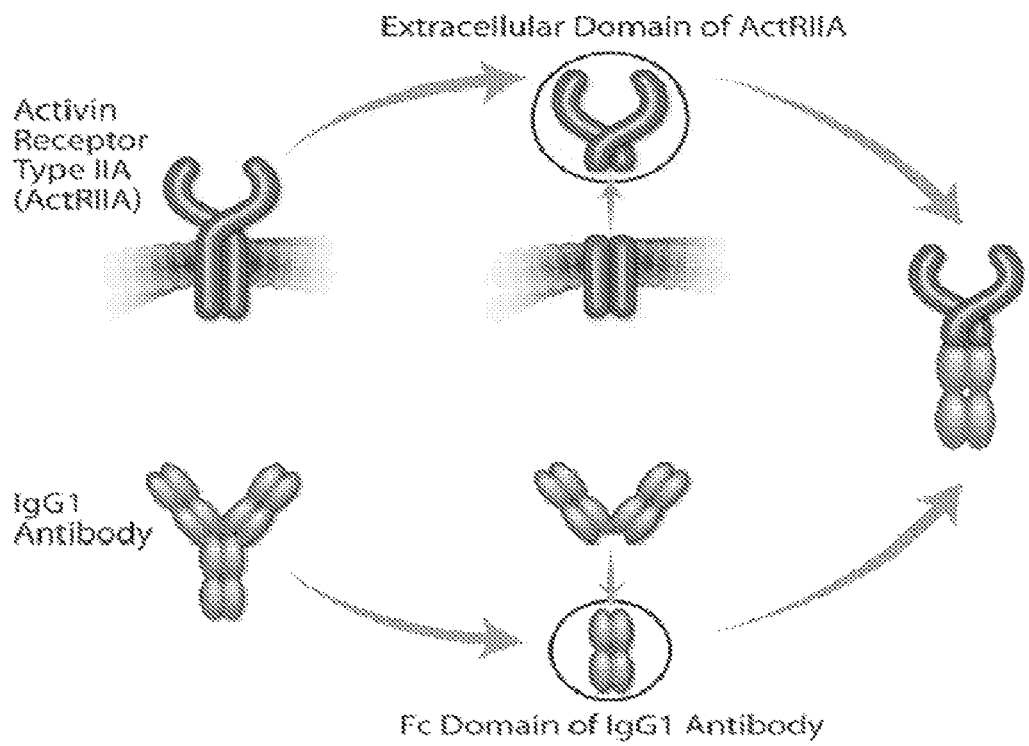
FIG. 23A depicts a schematic diagram of the mouse fusion protein of the extracellular domain of ActRIIA and the Fc domain of IgG1 (mActRIIA-Fc).
Figure 23B:
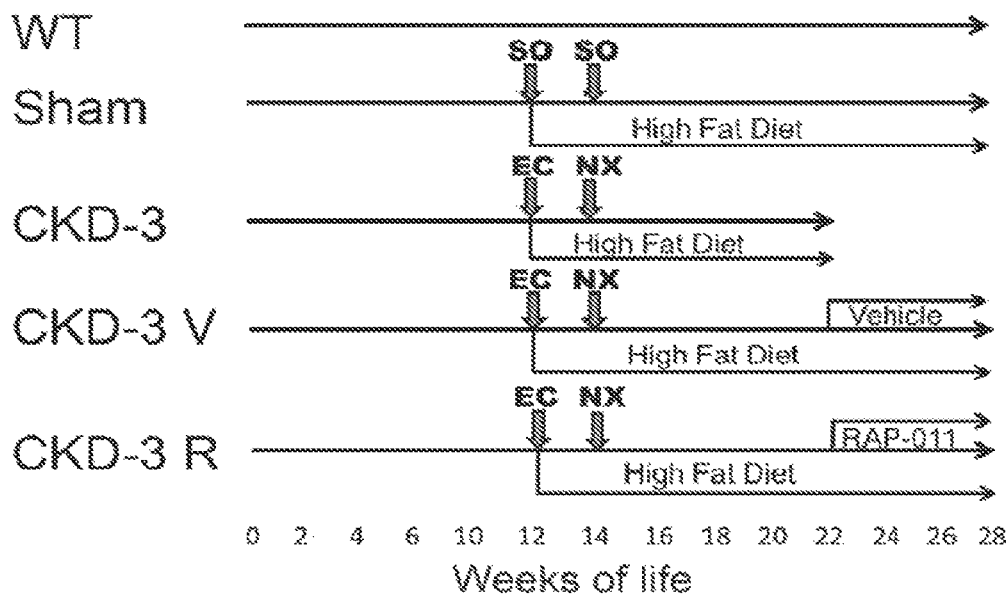
FIG. 23B depicts an experimental design of mActRIIA-Fc effects on the CKD-MBD in ldlr−/− high fat fed mice. Mice in four groups were fed the high fat diet beginning at 12 weeks (wks) of age. At 12 wks either sham operation (SO) or electrocautery cortical injury (EC) was performed. At 14 wks either SO or contralateral nephrectomy (NX) was performed. At 22 wks of life, vehicle treatment or mActRIIA-Fc, 10 mg/kg subcutaneous twice weekly, was instituted. WT, wild type mice on chow diet for normal reference levels. Sham, sham operated ldlr−/− high fat fed mice; CKD-3, CKD-3 ldlr−/− high fat fed mice studied at 22 wks to establish levels of vascular calcium at the start of therapy; CKD-3 V, CKD-3 ldlr−/− high fat fed mice vehicle treated; CKD-3 R, CKD-3 ldlr−/− high fat fed mice mActRIIA-Fc treated; WT, Sham, CKD-3 V and CKD-3 R mice were euthanized at 28 weeks of age.
Figure 25A:
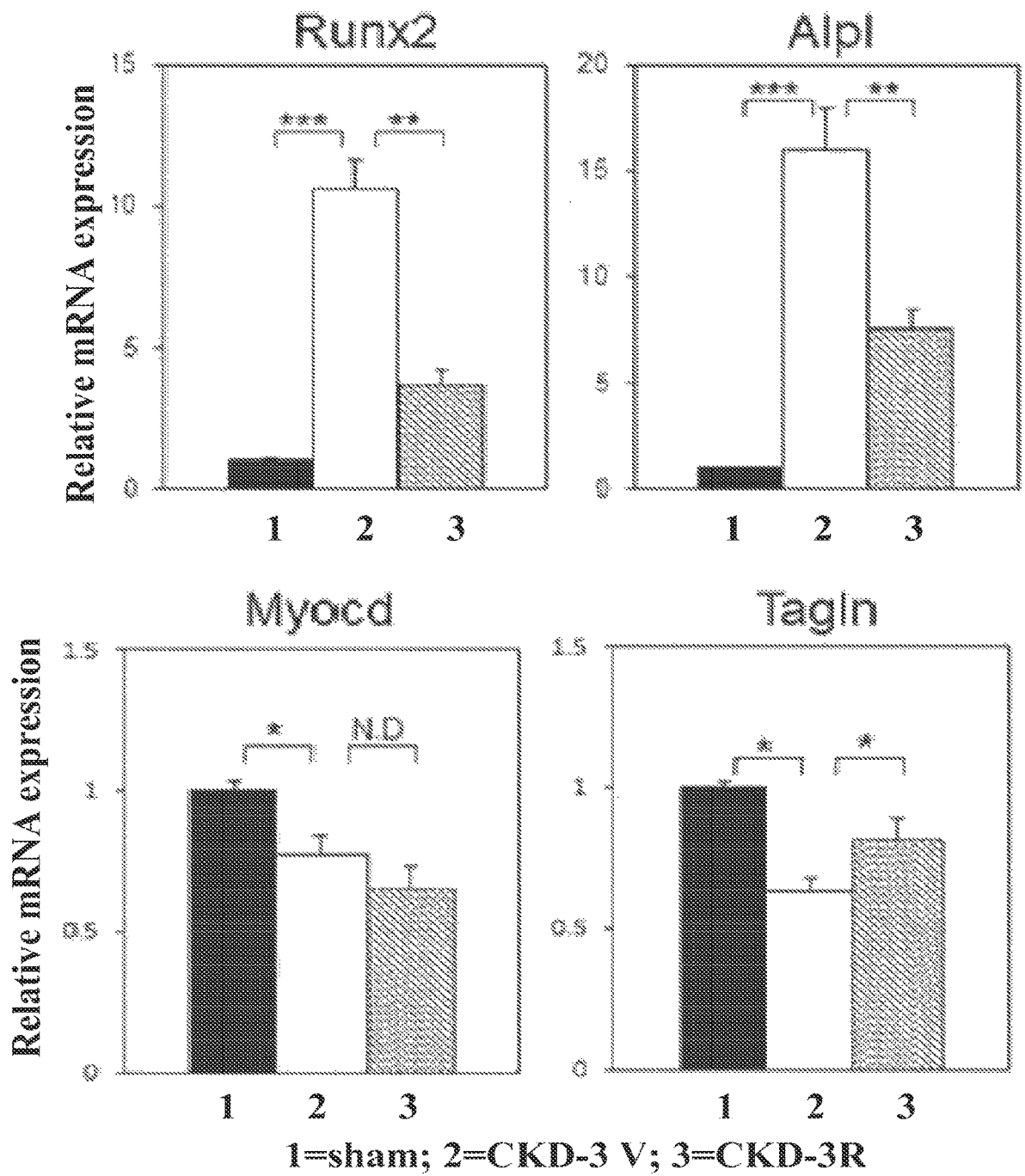
FIG. 25A shows that CKD-3 causes increased mRNA expression of osteoblastic proteins (Runx2 and alkaline phosphatase (Alp1)), and decreased levels of aortic smooth muscle cell 22α (Tagln) which were all reversed by treatment with the mActRIIA-Fc. Aortic myocardin (Myocd) levels were decreased by CKD, but not affected by mActRIIA-Fc.
Figure 25B:
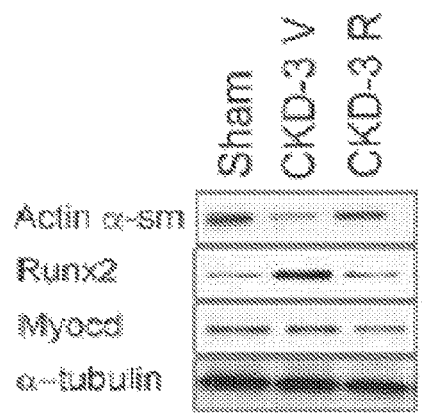
FIG. 25B depicts westerns for proteins in aortic homogenates.
Figure 25C:
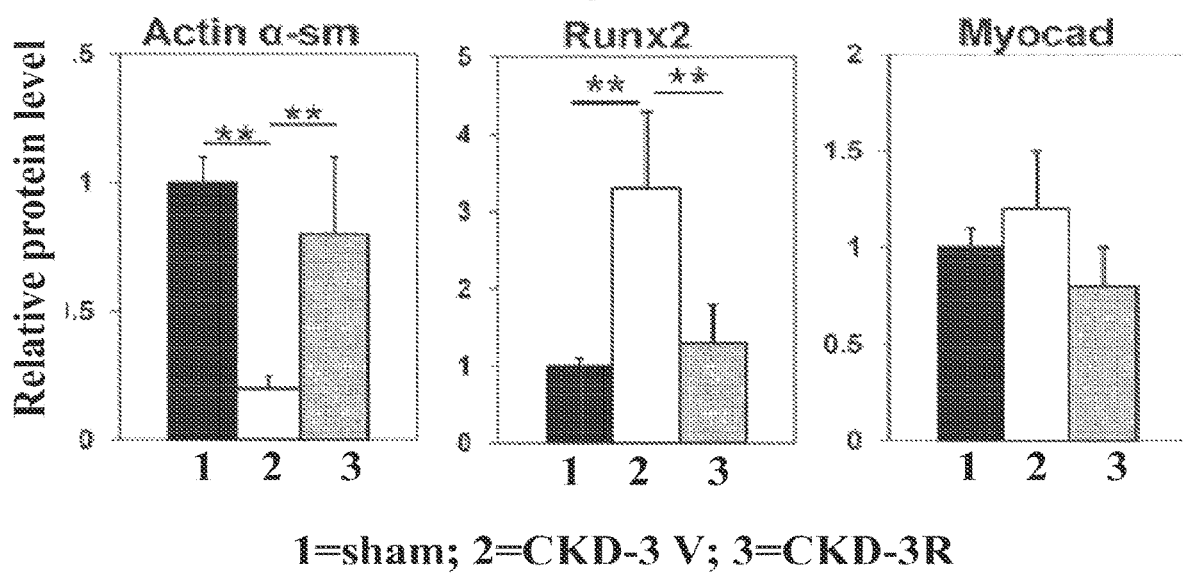
FIG. 25C depicts immunoblot quantitation of the westerns of FIG. 25B. CKD causes decreased levels of aortic α-smooth muscle cell actin protein and increased levels of osteoblastic Runx2, which were reversed by treatment with mActRIIA-Fc, but myocardin levels were not changed. For the quantitation, n=4, **p<0.01.

A ligand trap (FIG. 23A) comprised of the extracellular domain of ActRIIA fused to the Fc domain of IgG1, (herein referred to as mActRIIA-Fc) was utilized. FIG. 23B depicts the experimental design for utilization of mActRIIA-Fc in a vascular calcification model using a treatment protocol which allowed vascular calcification stimulated by CKD-3 to develop for eight weeks prior to instituting mActRIIA-Fc. Using this protocol, treatment of CKD-3 mice with the ActRIIA ligand trap decreased CKD-3 stimulated aortic Runx2 expression and aortic alkaline phosphatase (ALP) expression in the ldlr−/− high fat fed CKD-3 mice (FIG. 25A). Both Runx2 and ALP expression represent potential downstream effects of ActRIIA signaling and biomarkers of osteoblastic transition in the aorta that was reversed by mActRIIA-Fc-treatment. Aortic smooth muscle 22α (Sm22-alpha), a biomarker of differentiated vascular smooth muscle cells was decreased by CKD-3 and stimulated by mActRIIA-Fc. CKD-3 caused decreased aortic myocardin (MYOCD) expression, the vascular smooth muscle cell specific transcription factor, but myocardin was not affected by mActRIIA-Fc-treatment. Aortic Klotho expression, which has been linked to vascular calcification (Lim, K., et al., 2012. Circulation 125:2243-2255.), was very low compared to kidney (data not shown). In terms of the effects of CKD-3 and mActRIIA-Fc-treatment on aortic protein levels of the mRNAs in FIG. 25A, CKD increased aortic Runx2 levels and mActRIIA-Fc normalized aortic Runx2 levels (FIG. 25B). CKD decreased the aortic levels of alpha smooth muscle actin (αSMA), another biomarker of differentiated vascular smooth muscle cells, and mActRIIA-Fc treatment increased aortic levels of αSMA (FIG. 25B). Myocardin levels were not changed by CKD- or mActRIIA-Fc-treatment.

Effects of Decreased ActRIIA Signaling on Vascular Calcification

CKD stimulation of vascular calcification was studied in a model of atherosclerosis and type 2 diabetes (Al-Aly, Z., et al., 2007. Arteriosclerosis, Thrombosis, and Vascular Biology 27:2589-2596; Towler, D. A., et al., 1998. Journal of Biological Chemistry 273:30427-30434.), the ldlr−/− high fat-fed mouse with ablative CKD, as described above. CKD-3 caused accumulation of calcium deposits in the aortic atheromas in CKD-3 vehicle treated mice (CKD-3 V) (FIG. 15A), which were not present in CKD-3 mice treated with mActRIIA-Fc (CKD-3 R), and the aortic tissue calcium content was reduced to levels observed in wild type mice, significantly below those present at the time of institution of mActRIIA-Fc treatment, CKD-3 (FIG. 15B).

Effects of Decreased ActRIIA Signaling on CKD Stimulated Cardiac Disease

Figure 16A:
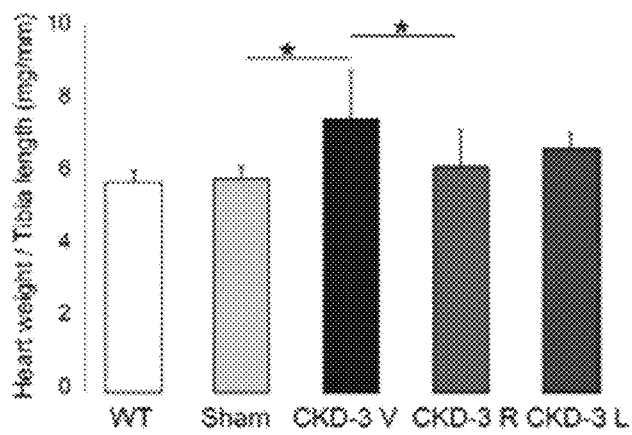
FIG. 16A demonstrates that CKD-3 in the ldlr−/− high fat fed mice increased heart weight, which was reversed in the mActRIIA-Fc treatment group, as compared to sham treated mice. CKD-3-L refers to CKD-3 mice treated with lanthanum carbonate.
Figure 16B:
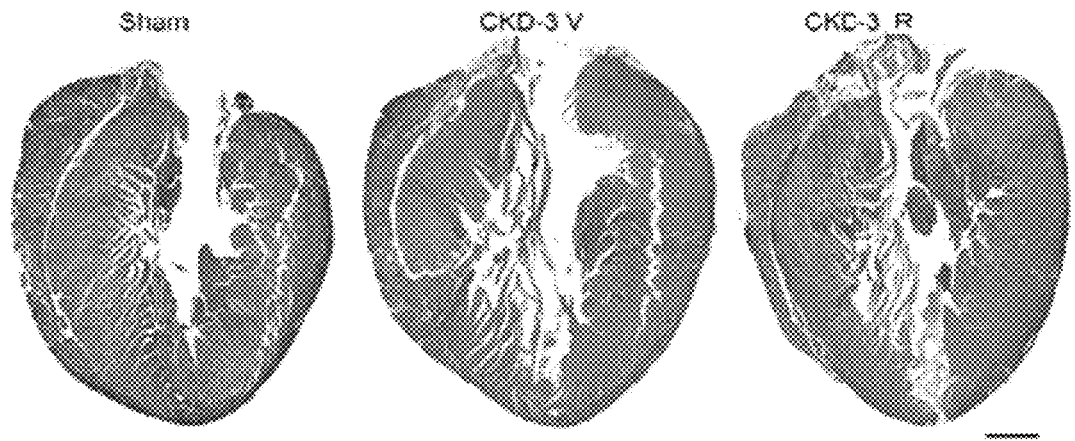
FIG. 16B demonstrates that CKD-3 produced cardiac hypertrophy mainly left ventricular (middle), which was prevented in the mActRIIA-Fc treatment group (right), as compared to sham mice (left). Trichrome staining, scale bar 1 mm.
Figure 16C:
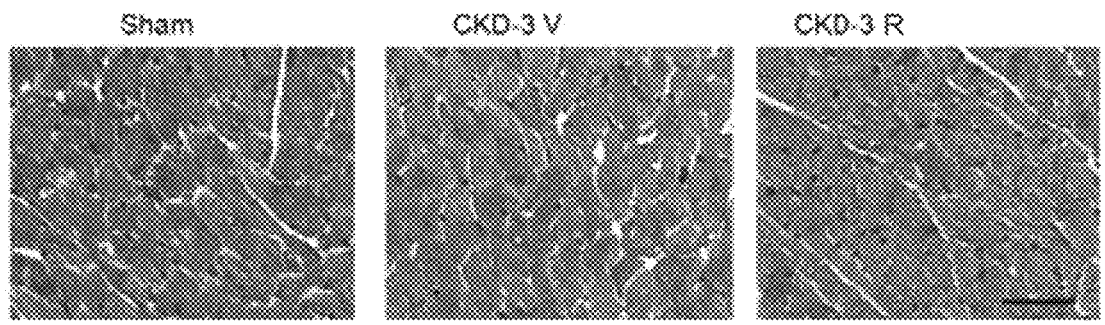
FIG. 16C depicts trichrome staining of left ventricular myocytes at higher magnification, demonstrating no evidence of cardiac fibrosis. Scale bar 20 µm.
Figure 17A:
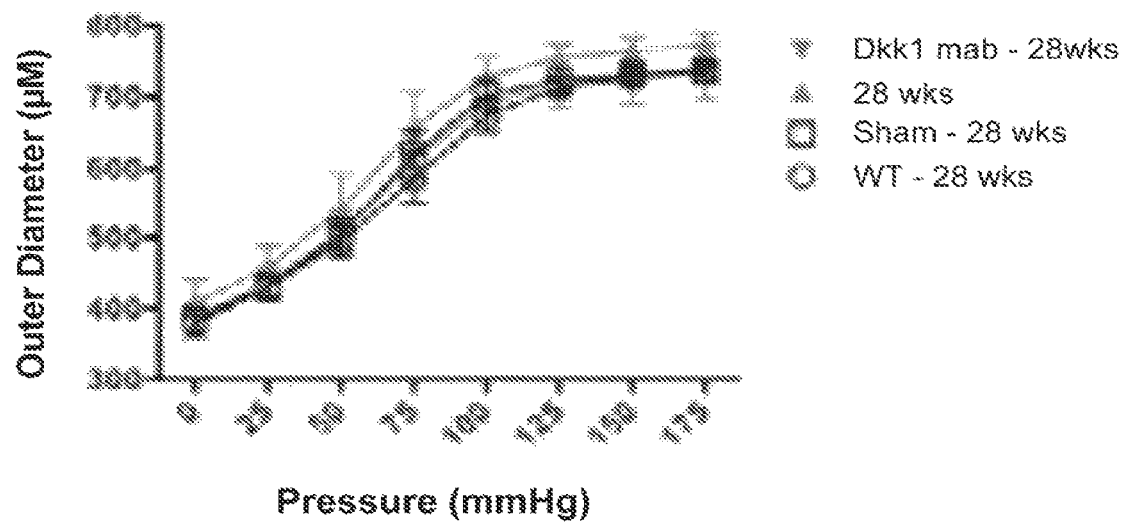
FIG. 17A depicts the pressure-diameter relationships performed as previously reported (Wagenseil, J. E., et al., 2009. *Circulation Research* 104: 1217-1224; Wagenseil, J. E., et al., 2005. *AJP—Heart and Circulatory Physiology* 289: 1209-H1217) of left common carotid arteries.
Figure 17B:
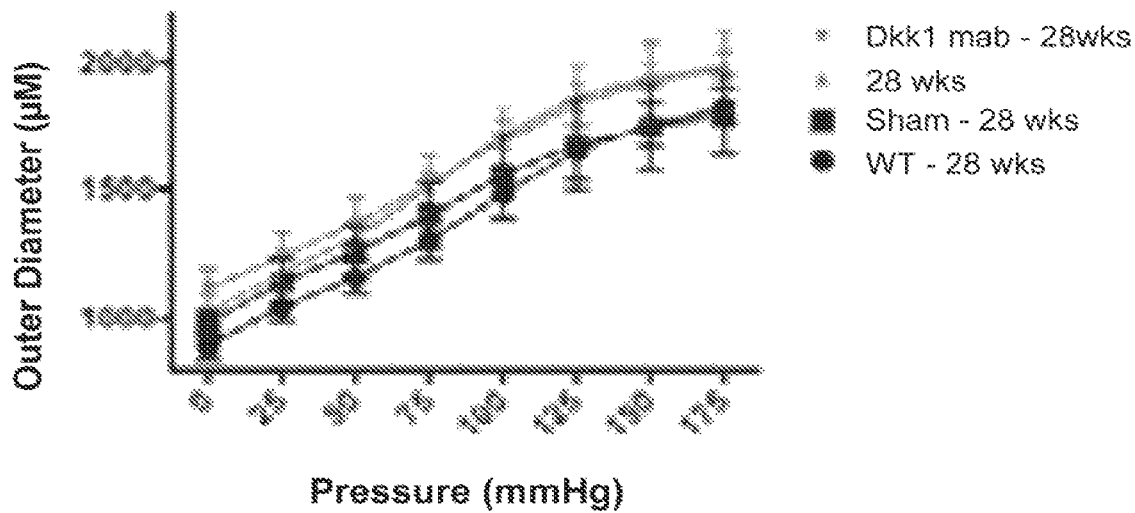
FIG. 17 demonstrates the CKD-3 effects on vascular stiffness in ldlr−/− high fat fed CKD-3 mice, and the absence of a Dkk1 neutralization effect.

CKD stimulation of cardiac disease was studied in the vascular calcification model. CKD-3 V mice had increased heart weight which was reversed by mActRIIA-Fc-treatment (FIG. 16A), but not by lanthanum carbonate treatment (CKD-3 L (Fang, Y., et al., 2014. J Am Soc Nephrol 25:1760-1763)), and CKD-3 V induced mild cardiac hypertrophy (FIG. 16B). However, while there was no evidence of cardiac fibrosis (FIG. 16C), there was evidence of myocyte hypertrophy, which was reversed by mActRIIA-Fc-treatment.

Since one mechanism of vascular calcification and cardiac hypertrophy association in CKD is through large artery stiffness, vascular stiffness and blood pressures were measured using previously reported methods (Wagenseil, J. E., et al., 2009. Circulation Research 104:1217-1224; Wagenseil, J. E., et al., 2005. AJP—Heart and Circulatory Physiology 289:H1209-H1217.). CKD-3 in the ldlr−/− high fat-fed atherosclerotic mouse did not produce vascular stiffness of carotid arteries or of the aorta (FIGS. 19A and 19B) or blood pressure elevations (Table 12). Furthermore, Dkk1 neutralization in CKD-3 mice treated with neutralizing antibody to Dkk1 (Fang, Y., et al., 2014. J Am Soc Nephrol 25:1760-1763) had no effect on aortic stiffness in the absence of increased stiffness.

TABLE 12

Physiologic cardiovascular parameters of 28 weeks old mice.

|  | WT | Sham | CKD-3 V | CKD-3 Dkk1 mAb |
|---|---|---|---|---|
| SBP | 108.9 ± 1.1 | 111.9 ± 4.7 | 100.4 ± 4.6 | 110.7 ± 4.8 |
| DBP | 77.27 ± 1.0 | 78.56 ± 2.2 | 69.14 ± 3.1 | 77.55 ± 3.6 |
| Pulse Pressure | 31.63 ± 0.3 | 33.32 ± 2.5 | 31.27 ± 2.1 | 33.1 ± 1.9 |
| Heart Rate | 547.1 ± 4.7 | 501.2 ± 17.4 | 505.6 ± 14.3 | 558.6 ± 11.2 |

SBP = systolic blood pressure, DBP = diastolic blood pressure.
Values are presented as mean ± standard error of the mean.
N = 4-6 mice per group.

ActRIIA Signaling in Aorta and Kidney and Kidney Fibrosis

Figure 20:
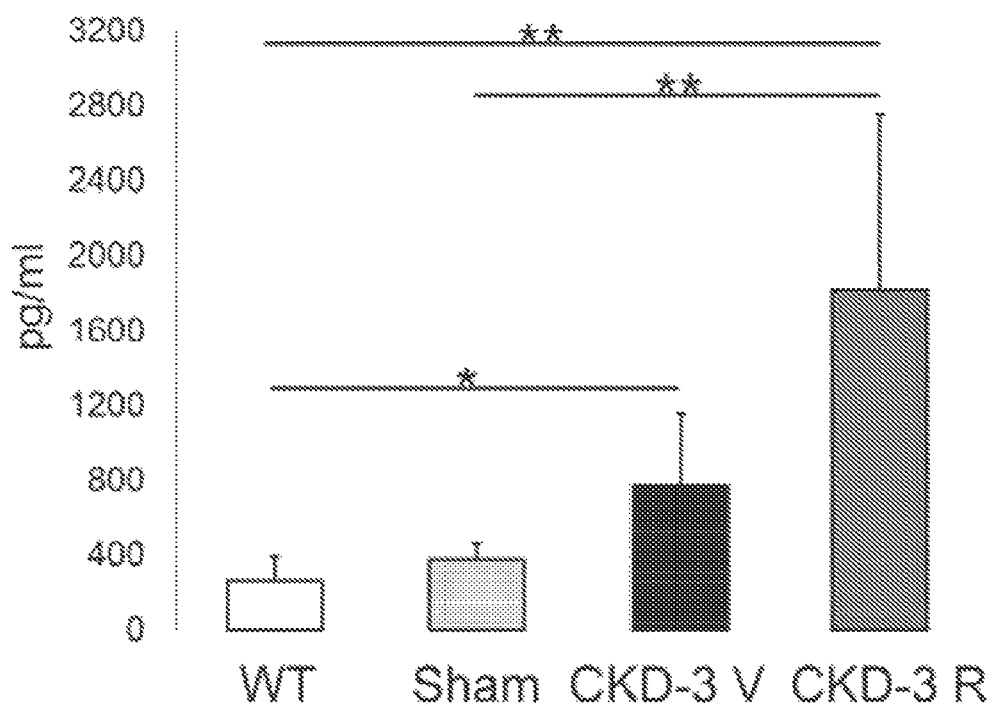
FIG. 20 depicts the levels of FGF-23 in wild type mice (WT), sham-treated mice (sham), CKD-3 mice (CKD-3 V), or CKD-3 mice treated with mActRIIA-Fc (CKD-3 R).

Canonical signal transduction by the TGFβ superfamily involves ligand binding to type II receptors activating their serine/threonine kinase activity and stimulating association and phosphorylation of type I receptors, the Alk kinases (see diagrammatic representation in FIG. 20). There are seven Alk kinases utilized by the TGFβ superfamily, and Alk4 (ActRIIB) is the type I receptor most often associated with activin/ActRIIA signaling (Abe Y, et al., 2004. Growth Factors (Chur, Switzerland) 22:105-110.). In kidney homogenates from the CKD-3 mouse model, Alk4 phosphorlyation was not increased, in agreement with previous studies (Antsiferova, M., and Werner, S. 2012. Journal of Cell Science 125:3929-3937) (FIG. 18A). In contrast, phosphosmad 2 was increased by CKD-3 and was decreased by mActRIIA-Fc (FIG. 18A), indicating a role of another Alk receptor in renal activin signaling in CKD. In the diseased CKD-3 kidney with interstitial nephritis, Col1A1 was upregulated and mActRIIA-Fc decreased Col1a1 levels (FIG. 18A), consistent with the decrease in phosphosmad 2 induced by mActRIIA-Fc. Furthermore, there was a major decrease in renal Klotho expression induced in the CKD-3 V mice that was corrected by mActRIIA-Fc (FIG. 18B). As a result, the renal compartments where Activin was expressed in CKD-3 V were analyzed and heavy expression in peritubular myofibroblasts, but not in the epithelium, was identified.

Figure 18C:
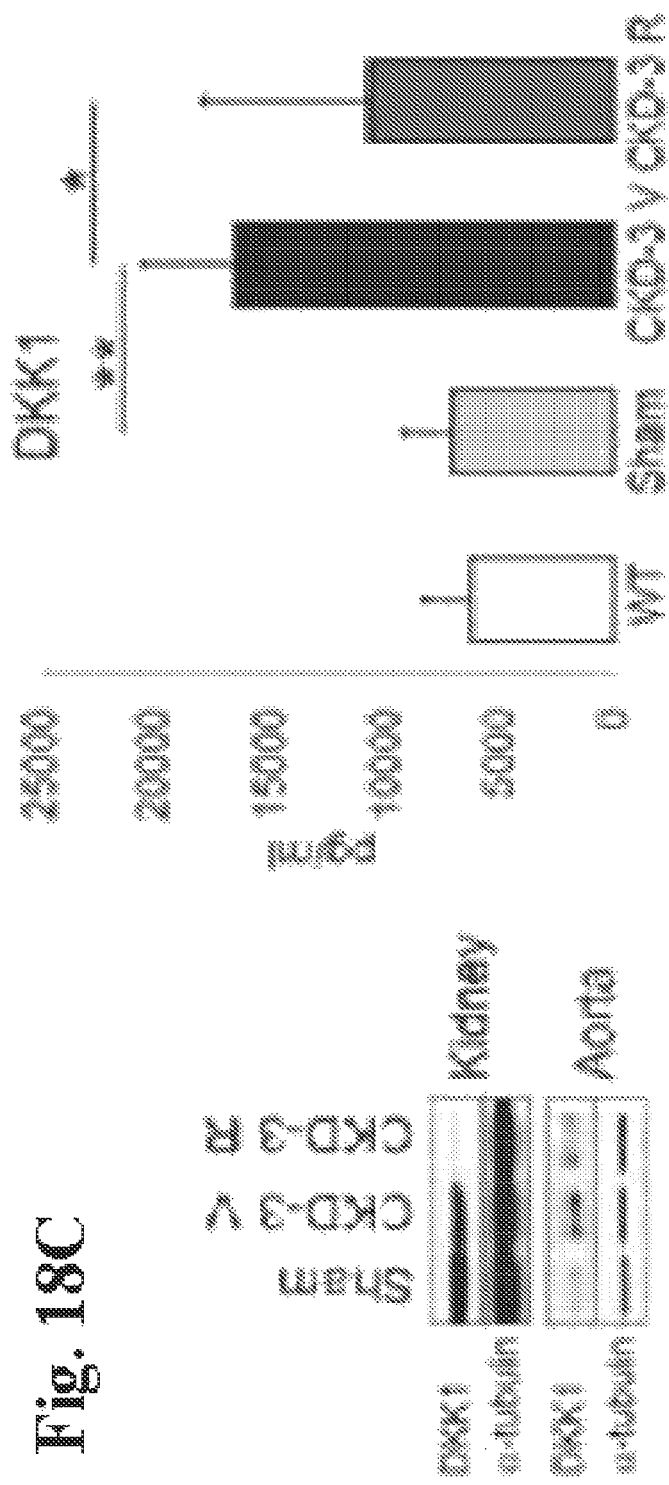
FIG. 18C depicts Wnt signaling as marked by Dkk1 protein expression in westerns of kidney and aortic homogenates from sham, CKD-3 vehicle and mActRIIA-Fc treated mice (left), and the effect of CKD-3 and mActRIIA-Fc on plasma Dkk1 levels (right).

In the aortic smooth muscle, Alk4 and Alk1 (FIG. 18A), but not Alk5 or Alk2, were detected. The levels of Alk4 and Alk1 were not affected by CKD-3. However, CKD-3 did not increase aortic phosphosmad 2/3 levels, nor did mActRIIA-Fc decrease them (FIG. 18A). However, analysis of noncanonical ActRIIA signaling (FIG. 20) indicated that map kinase (phosphoErk1/2) was not activated by CKD nor inhibited by mActRIIA-Fc and that vascular smooth muscle levels of p38 and JNK were very low. Aortic Actin2 levels were also very low, and were not CKD-3-stimulated. Axin2 levels are a standard biomarker of canonical Wnt signaling. However, since Dkk1 is a transcriptional target of canonical Wnt signaling, Dkk1 levels in the kidney and aorta were analyzed as a biomarker of Wnt activity, demonstrating that mActRIIA-Fc-treatment decreased renal Dkk1 levels in the CKD-3 mice (FIG. 18C), producing significant reductions in plasma Dkk1 levels (FIG. 18C). Furthermore, aortic Dkk1 levels were increased by CKD-3 and inhibited by mActRIIA-Fc (FIG. 18C). This indicated that renal and vascular smooth muscle Wnt signaling and systemic release of Dkk1 were inhibited by activin suppression. Accordingly, elevated circulating activin in CKD signals through increased vascular ActRIIA activating Wnt signaling and stimulating atherosclerotic calcification.

Translation of Preclinical Studies to Human Pathophysiology and the Clinic

Figure 19:
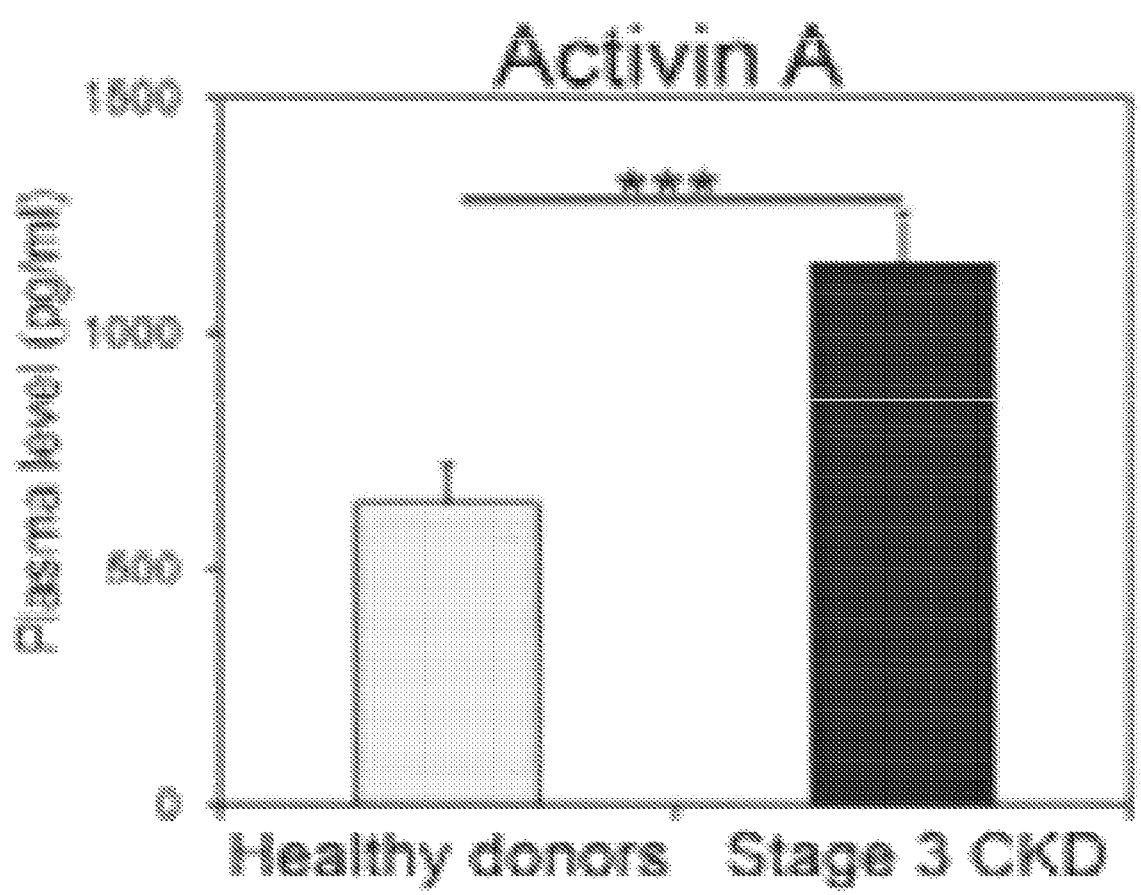
FIG. 19 depicts plasma activin-A levels in patients with stage 3 CKD (n=30) versus healthy donors (n=10). Data were generated by measuring samples in duplicate using a commercial ELISA kit (R&D systems, Minneapolis, Minn.). The coefficient of variation was 2.7% for the assay. *** p<0.002 Student t test.

As shown in FIG. 19, serum activin levels were increased in a cohort of patients with CKD stage 3, as compared to healthy controls.

Conclusions

This example demonstrates that activin is a second factor involved in renal repair that is increased in the circulation during CKD. Without being bound by theory, the results demonstrate that Activin expression is increased in diseased kidneys, is released into the circulation and stimulates aortic vascular smooth muscle dedifferentiation and osteoblastic transition, which is contributed to by endothelial to mesenchymal transition and these effects culminate in CKD-stimulated atherosclerotic calcification and cardiac hypertrophy. CKD upregulates renal Activin expression in myofibroblasts and stimulates progression of kidney disease through increasing renal fibrosis. Inhibition of ActRIIA signaling inhibits osteoblastic transition and atherosclerotic calcification in the aorta. Inhibition of ActRIIA signaling inhibits cardiac hypertrophy and renal fibrosis. The effects of the ActRIIA ligand trap, mActRIIA-Fc, on the early CKD-MBD syndrome resemble those of a monoclonal antibody to Dkk1 in CKD-stimulated vascular calcification (Fang, Y., et al., 2014. J Am Soc Nephrol 25:1760-1763.). These data demonstrate that inhibition of ActRIIA signaling in the diseased kidney decreased Wnt activation and circulating Wnt inhibitors. Furthermore, in the vascular smooth muscle, activin stimulates Wnt activity, which is inhibited by mActRIIA-Fc. Thus, reactivation of two kidney development factors, Wnts and Activin, produce circulating Wnt inhibitors and activin in CKD, causing vascular and cardiac disease. This is the demonstration that kidney diseases directly cause cardiovascular disease and that consideration of the kidney disease process cannot be separated from renal repair and the consequent stimulation of cardiovascular disease.

Further, this example demonstrates that renal activin expression is increased in three models of chronic kidney disease, producing increased circulating activin that exceeds the levels of activin inhibitors in the circulation. Circulating Activin stimulated signal transduction through the ActRIIA receptor producing aortic vascular smooth muscle dedifferentiation, osteoblastic transition, and calcification of atherosclerotic plaques. These effects were due to circulating activin, as supported by the absence of increased activin protein levels in the aorta even though CKD induced increased aortic activin mRNA (FIG. 13B). Without being bound by theory, these data demonstrate that vascular activin signaling is stimulated by CKD through the production of endocrine activin by the kidney.

Since EnMT is a Smad-mediated process (Cooley, B. C., et al., 2014. Science Translational Medicine 6:227ra234.), activated by members of the TGFβ superfamily that includes TGFβs, bone morphogenetic proteins (BMPs), activins/inhibins, and growth and differentiation factors (GDFs) (Piek, E., et al., 1999. The FASEB Journal 13:2105-2124.), the aortas of the vascular calcification model with CKD-3 were analyzed for changes in the levels of type II receptors of the TGFβ superfamily, which are the ligand binding components of the receptors. The activin receptor type IIA (ActRIIA) was upregulated in aortic vascular smooth muscle. Administration of the extracellular domain of ActRIIA in a fusion protein with the Fc domain of IgG1 as a ligand trap (mActRIIA-Fc) demonstrated that inhibition of ActRIIA signaling produced inhibition of osteoblastic transition in the aortic smooth muscle cells, stimulation of vascular smooth muscle cell gene expression and reversal of aortic calcification in a CKD stimulated atherosclerotic model. In addition, CKD stimulated EnMT in a lineage tracing mouse model. However, the major site of activin function appeared to be in the vascular smooth muscle, where ActRIIA expression was increased.

Cardiac hypertrophy, especially left ventricular, is highly prevalent in CKD (Moran, A., et al., 2008. American Journal of Kidney Diseases 52:839-848; Park, M., et al., 2012. Journal of the American Society of Nephrology 23:1725-1734.). In addition, the atherosclerotic vascular calcification model was characterized by cardiac hypertrophy (FIG. 16). However, production of cardiac hypertrophy in the model differs mechanistically from the common paradigm of CKD-stimulated vascular stiffness (Townsend, R. R. 2015. Current Opinion in Nephrology and Hypertension 24:47-53 10.1097/MNH.0000000000000086; Merx, M. W., et al., 2005. Journal of the American Society of Nephrology 16:3357-3364.), hypertension, and cardiac remodeling, because the atherosclerotic CKD-3 mice (ldlr−/− high fat-fed diabetic mice) did not exhibit vascular stiffness nor hypertension. Since mActRIIA-Fc corrected the cardiac hypertrophy in the absence of changes in FGF23 levels (FIG. 19), it is unlikely that the cardiac hypertrophy in the CKD-3 mice was due to FGF23 (Faul, C., et al., 2011. J Clin Invest 121:4393-4408.).

In conclusion, without being bound by theory, this example demonstrates that a second factor involved in renal repair that is increased in the circulation during CKD and causes cardiovascular disease. Without being bound by theory, the example demonstrates that Activin expression is increased in diseased kidneys, is released into the circulation and stimulates aortic vascular smooth muscle dedifferentiation and osteoblastic transition, which is contributed to by endothelial to mesenchymal transition and these effects culminate in CKD-stimulated atherosclerotic calcification, and cardiac hypertrophy. CKD upregulates renal Activin expression in myofibroblasts and stimulates progression of kidney disease through increasing renal fibrosis. Inhibition of ActRIIA signaling inhibits osteoblastic transition and atherosclerotic calcification in the aorta. Inhibition of ActRIIA signaling inhibits cardiac hypertrophy and renal fibrosis. The effects of the ActRIIA ligand trap, mActRIIA-Fc, on the early CKD-MBD syndrome show that inhibition of ActRIIA signaling in the diseased kidney decreased Wnt activation and circulating Wnt inhibitors. Thus, without being bound by theory, reactivation of two kidney development factors, Wnts and Activin, produce circulating Wnt inhibitors and activin in CKD, causing vascular and cardiac disease; thus, kidney disease causes cardiovascular disease.

Example 5: Kidney Injury/Repair Stimulates Vascular Disease Through Systemic Wnt Inhibition and Activin Background The results presented in this example relate to the results presented in Example 4 (Section 9.4).

Kidney diseases cause atherosclerotic vascular calcification by producing systemic Wnt inhibition and activin secretion during kidney repair. Vascular effects of chronic kidney disease (CKD) are an interplay of Wnt inhibition and activin-induced modulation of activin receptor function.

Methods

CKD with elevated Wnt inhibitors, especially Dkk1, and activin was induced in mouse models for lineage tracing and vascular calcification and allowed to develop spontaneously in Alport's mice. Activin. Dkk1, activin receptor type 2A (ActRIIA), phosphosmad 2/3, and collagen levels were measured by ELISA, RT-PCR, and western blots. Vascular smooth muscle function was measured by pressure-induced arterial dilatation. Cell lineage tracing was performed in Rosa-tdT mice bred to endothelial-specific Tie2-Cre mice. Mice harboring Rosa-tdT express tomato red in cells harboring Cre recombinase. mActRIIA-Fc refers to an activin A ligand trap (see, for example, U.S. Pat. No. 8,173,601 and Carrancio et al., 2014, British Journal of Haematology, 165:870-882).

Results

CKD increased circulating Dkk1 and activin levels. In diseased kidneys, activin was expressed in myofibroblasts, and ActRIIA signaling through phosphosmad 3 was increased. In diseased kidneys, mActRIIA-Fc, an ActRIIA ligand trap, inhibited renal psmad 3, Col1A1 expression, urinary protein levels, and Dkk1 levels and increased Klotho levels. In vasculature, ActRIIA levels and signaling were impaired by CKD along with decreased vascular smooth muscle differentiation and function. In CKD mice vasculature, mActRIIA-Fc increased vascular smooth muscle cell differentiation and inhibited osteoblastic transition and vascular calcification. In circulation, mActRIIA-Fc decreased Dkk1 levels. CKD induced expression of tomato red in cells of the adventia of injured femoral arteries of Tek-Cre/Rosa-tdT CKD mice versus Tek-Cre/Rosa-tdT mice with normal kidney function, wherein the tomato red was limited to femoral artery endothelium, demonstrating that CKD induces Tie2-positive cells during vascular injury.

Conclusions

CKD decreased vascular smooth muscle function and stimulated osteoblastic transition and vascular calcification. Decreasing effects of elevated activin in CKD with mActRIIA-Fc inhibited Smad-dependent renal fibrosis, blocked aortic osteoblastic transition, increased vascular smooth muscle differentiation, and decreased vascular calcification.

Figure 21A:
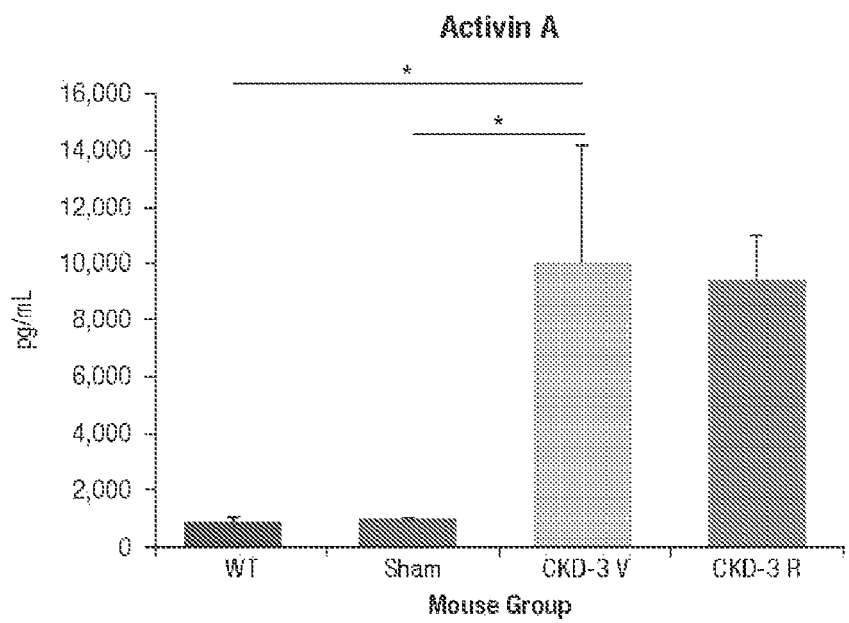
FIG. 21A depicts the level of circulating activin A in wild type mice (WT), sham-operated mice (Sham), CKD-3 mice treated with Vehicle (CKD-3 V), or CKD-3 mice treated mActRIIA-Fc (CKD-3 R). * indicates p<0.005.

Example 6: The Role of Activin Signaling in the Pathogenesis of Renal Osteodystrophy of the CKD-MBD Introduction Chronic kidney disease-mineral/bone disorder (CKD-MBD) includes vascular calcification and osteodystrophy. CKD increases circulating activin (a ligand of the TGFβ superfamily) and activin signaling (FIG. 21A). Inhibition of ActRIIA signaling with an activin type IIA receptor (ActRIIA) ligand trap (mActRIIA-Fc) inhibits vascular calcification and prevents cardiac hypertrophy. This example demonstrates the role of activin signaling in the pathogenesis of renal osteodystrophy.

Methods

Sham operated ldlr−/− high-fat fed mice (SHAM; n=12) manifest diabetes and hypercholesterolemia. CKD with hyperphosphatemia, elevated FGF-23, and 60% reduction in glomerular filtration rate (CKD-3) was induced by 5/6 nephrectomy at 14 weeks of age in the ldlr−/− high-fat-fed mice, and is a model of atherosclerotic vascular calcification. CKD-3 mice were treated with mActRIIA-Fc 10 mg/kg (mActRIIA-Fc; n=15) or vehicle (VEH; n=13), injected intraperitoneally weekly beginning at 22 weeks of age and studied at 28 weeks by skeletal histomorphometry and micro-computed tomography. Results of CKD-3 were compared with wild type (WT; n=5) mice and SHAM.

Results

Figure 21B:
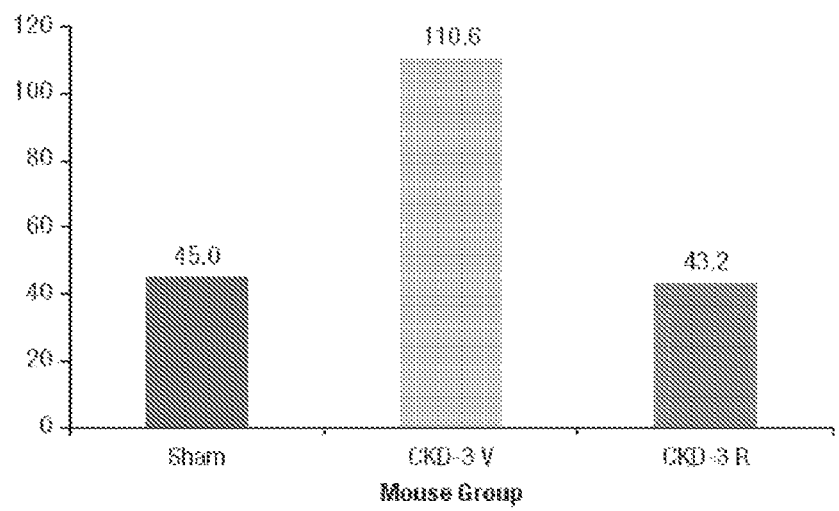
FIG. 21B depicts the osteoblast number/bone perimeter number/100 mm for sham-operated mice (Sham), CKD-3 mice treated with vehicle (CKD-3 V), or CKD-3 mice treated with mActRIIA-Fc (CKD-3 R). p<0.05 for CKD-3 V vs. CKD-3.
Figure 21C:
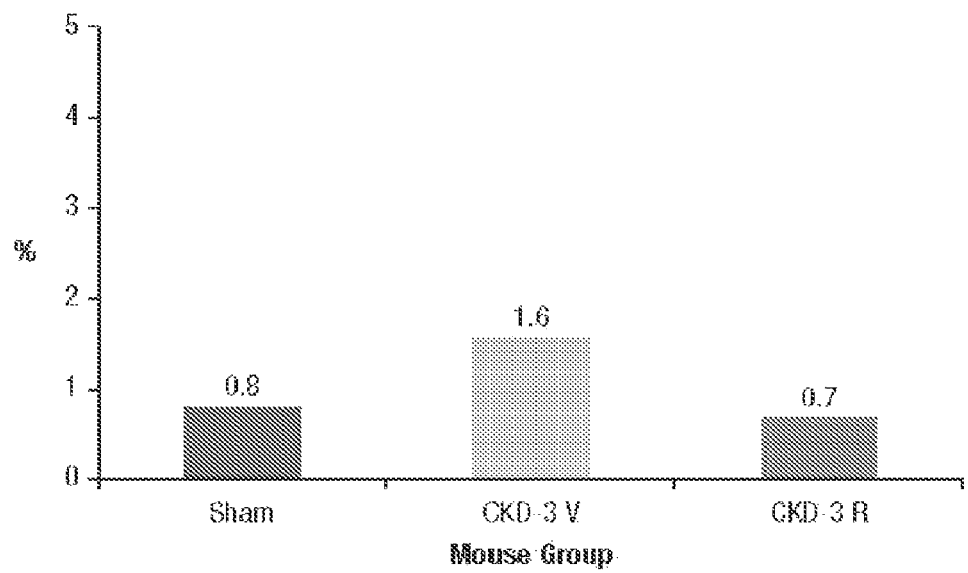
FIG. 21C depicts the percentage of osteoblast surface/bone surface for sham-operated mice (Sham), CKD-3 mice treated with vehicle (CKD-3 V), or CKD-3 mice treated with mActRIIA-Fc (CKD-3 R). p<0.05 for CKD-3 V vs. CKD-3.
Figure 21D:
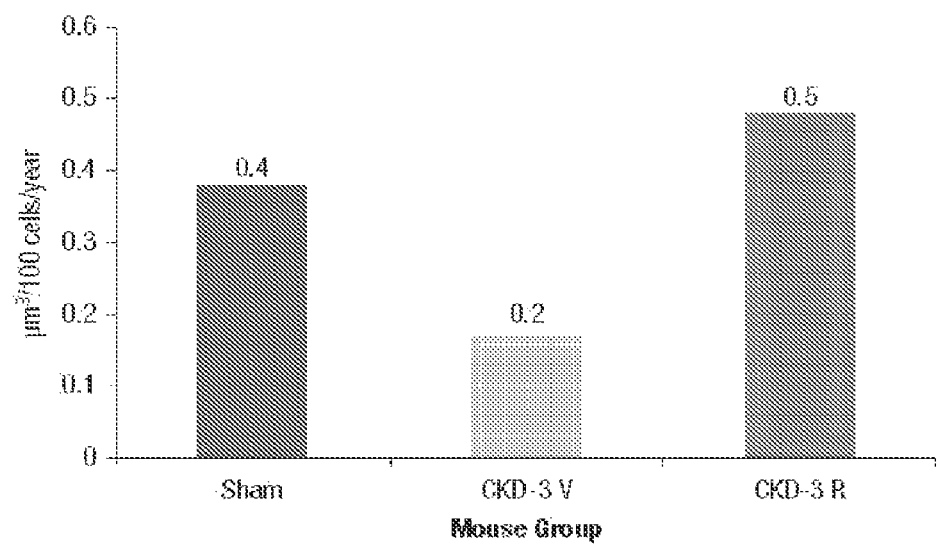
FIG. 21D depicts the bone formation rate/osteoblast for sham-operated mice (Sham), CKD-3 mice treated with vehicle (CKD-3 V), or CKD-3 mice treated with mActRIIA-Fc (CKD-3 R). p<0.05 for CKD-3 V vs. CKD-3.

Relative to WT (cancellous bone volume/tissue volume (BV/TV); 12.90%), SHAM mice demonstrated reduced BV/TV (10.92%) associated with adynamic bone disease. Induction of CKD-3 caused high turnover bone disease in VEH mice, and a lower BV/TV (11.22%); this was reversed by 6 weeks of mActRIIA-Fc-treatment (13.28%). Induction of CKD-3 caused a reduction in trabecular thickness, which was reversed by 6 weeks of mActRIIA-Fc-treatment. CKD-3 VEH-treated mice demonstrated higher erosion surface/bone surface and higher osteoclast number/100 mm bone length (1.83% and 62.32/100 mm, respectively) compared with SHAM (1.05% and 33.40/100 mm), which were mitigated by mActRIIA-Fc (1.23% and 38.37/100 mm). CKD-3 VEH-treated mice also caused demonstrated higher osteoblast surface/bone surface and higher osteoblast number/100 mm bone length (1.58% and 110.63/100 mm respectively; $P<0.05$) when compared with WT or SHAM (FIG. 21B and FIG. 21C, respectively). mActRIIA-Fc significantly reduced both osteoblast surface/bone surface and osteoblast number/100 mm bone length (0.68% and 43.18/100 mm; $P<0.05$) compared with VEH. Despite the significant reduction in the osteoblast number relative to VEH, the mineral apposition rate with mActRIIA-Fc treatment was maintained (0.42 and 0.40 µm3/day, respectively), with a significantly higher bone formation rate/osteoblast (0.17 vs. 0.48 µm3/100 cells/year, respectively; $P<0.05$ vs. VEH), which was similar to WT (0.42 µm3/100 cells/year) (FIG. 21D).

TABLE 13

Histomorphometric Results (mean ± SEM)

|  | Sham | CKD-3 + Vehicle | CKD-3 + mActRIIA-Fc |
|---|---|---|---|
| BV, % | 10.9 ± 1.3 | 11.2 ± 0.8 | 13.3 ± 1.2 |
| Trabecular thickness (plate), µm | 30.9 ± 2.1 | 31.8 ± 1.7 | 33.2 ± 1.9 |
| Trabecular separation (plate) µm | 269.4 ± 17.3 | 261.9 ± 16.6 | 238.1 ± 24.9 |
| Osteoid volume/BV, % | 0.3 ± 0.1 | 0.4 ± 0.1 | 0.2 ± 0.1 |
| Osteoid surface/bone surface, % | 2.5 ± 0.6 | 2.9 ± 0.7 | 1.7 ± 0.4 |
| Osteoid thickness, µm | 2.1 ± 0.4 | 1.9 ± 0.3 | 1.9 ± 0.2 |
| Erosion surface/bone surface, % | 1.1 ± 0.2 | 1.8 ± 0.5 | 1.2 ± 0.5 |
| Osteoclast number/bone perimeter, #/100 mm | 33.4 ± 5.1 | 62.3 ± 19.5 | 38.4 ± 15.4 |
| Osteoclast surface/bone surface, % | 1.0 ± 0.2 | 1.7 ± 0.5 | 1.1 ± 0.5 |
| Mineral apposition rate/day, µm/daty | 0.4 ± 0.0 | 0.4 ± 0.1 | 0.4 ± 0.0 |
| Double labels/bone surface, % | 3.0 ± 0.9 | 3.7 ± 1.0 | 1.6 ± 0.3 |
| Single labels/bone surface, % | 8.0 ± 0.9 | 10.1 ± 1.1 | 10.3 ± 1.9 |
| Mineralizing surface/bone surface, % | 7.0 ± 0.9 | 8.8 ± 1.1 | 6.8 ± 1.1 |
| Bone formation rate/bone surface, mm$^3$/cm$^2$/year | 10.8 ± 2.3 | 13.9 ± 2.5 | 9.5 ± 1.2 |
| Mineralization lag time, days | 1.9 ± 0.4 | 1.9 ± 0.5 | 1.3 ± 0.3 |
| Osteoid maturation time, days | 6.3 ± 1.4 | 5.4 ± 0.9 | 4.9 ± 0.5 |

SEM = standard error of the mean mActRIIA-Fc did not affect hyperphosphatemia and FGF-23 levels.

Conclusions

Increased circulating activin contributes to the high turnover osteodystrophy associated with CKD-3. Activin signaling inhibition with mActRIIA-Fc, an ActRIIA ligand trap, increased bone volume in CKD-3 by inhibiting bone resorption and normalizing the mineral apposition rate and bone formation rate/osteoblast, counteracting the negative effects of CKD.

Example 7: Quantitative Computed Tomography Results for Bone Mass and Abdominal Aortic Vascular Calcification in Hemodialysis Subjects Treated with Escalating Dose Levels of hActRIIA-Fc Introduction High turnover renal osteodystrophy is marked by decreased cortical and increased trabecular bone mass, resulting in an increased risk of fracture. hActRIIA-Fc, an activin type II receptor-IgG1 fusion protein, blocks activin A signaling and may reduce osteoclastogenesis and promote osteoblast maturation in bone, based on in vitro data. The current analysis in subjects on hemodialysis (HD) evaluated the effect of hActRIIA-Fc on bone mineral density (BMD) and abdominal aortic vascular calcification using quantitative computed tomography (QCT).

Methods

In a study of hActRIIA-Fc in subjects on HD for the correction of anemia, subjects who were erythropoietin-stimulating agent (ESA) responsive were washed out of their ESA effect until hemoglobin (Hb) was <10 g/dL, then randomized to hActRIIA-Fc 0.3 mg/kg (n=9), 0.5 mg/kg (n=8), 0.7 mg/kg (n=9; 7 completed, 2 ongoing), or placebo (PBO; n=9) administered subcutaneously every 28 days for up to 8 dose cycles. A dose group utilizing a 14-day dose cycle is currently enrolling. Subjects were assessed for effects on Hb, safety parameters, BMD, vascular calcification, and biomarkers of bone turnover. Treatment failures (Hb<9 g/dL) were rescued with ESA/transfusion. QCT scans of the hip, lumbar spine, and abdominal aorta were obtained at baseline and after the 225-day treatment phase.

Results

Of the 35 subjects who were randomized in the study, 20 had paired QCT assessments (PBO: n=3; 0.3 mg/kg; n=6; 0.5 mg/kg; n=5; and 0.7 mg/kg; n=6). Some subjects with paired QCT had limited exposure to hActRIIA-Fc due to treatment failure. Table 14 displays the BMD and vascular calcification results for PBO and each hActRIIA-Fc dose group. hActRIIA-Fc appeared to mitigate the effects of high turnover renal osteodystrophy on conical and trabecular BMD and slow the progression of vascular calcification, compared with PBO.

TABLE 14

|  |  |  | hActRIIA-Fc | | | | | |
|---|---|---|---|---|---|---|---|---|
|  | PBO | n | 0.3 mg/kg | n | 0.5 mg/kg | n | 0.7 mg/kg | n |
| Days on study drug | 107.3 | 3 | 107.2 | 6 | 152.6 | 5 | 151.8 | 6 |
| Femoral neck cortical BMD, mean % CFB | −0.91% | 3 | −1.38 | 5 | 1.56% | 5 | 0.90% | 4 |
| Subjects with >2% increase in femoral neck cortical BMD, % | 0.00% | 3 | 20.00% | 5 | 40.00% | 5 | 75.00% | 4 |
| Lumbar BMD (trabecular), mean % CFB | 12.59% | 3 | 7.95% | 6 | 0.54% | 5 | 1.93% | 6 |
| Total Agatston score, mean % CFB | 58.42% | 3 | 24.89% | 6 | 17.26% | 5 | 7.42% | 5 |
| Subjects with <15% increase in Agatston score, % | 33.33% | 3 | 83.33% | 6 | 80.00% | 5 | 100.00% | 5 |
| Square root of volumetric score (mm$^3$), mean CFB | 4.54 | 3 | 11.07 | 6 | 1.23 | 5 | 1.26 | 5 |

CFB = change from baseline.

Conclusions

These data demonstrate that hActRIIA-Fc, in a dose-dependent manner, reverses the effects of high turnover renal osteodystrophy on cortical and trabecular bone, and slows the progression of vascular calcification.

Example 8. Quantitative Computed Tomography Results for Bone Mass and Abdominal Aortic Vascular Calcification in Hemodialysis Subjects Treated with Escalating Dose Levels of ActRIIA-hFc (Seq Id No:7; "Sotatercept")

Introduction

See the Introduction (Section 9.7.1) and Methods (Section 9.7.2) for Example 6 (Section 9.7). This example presents additional data from the study performed in Example 6 (Section 9.7), obtained at a later date in the study.

Results

A total of 35 subjects were randomized and received at least one dose of placebo or ActRIIA-hFc (SEQ ID NO:7; "Sotatercept") as indicated in Table 15.

TABLE 15

Randomized Subjects and QCT Analysis Subset

| Subjects | Placebo | Sotatercept 0.3 mg/kg | Sotatercept 0.5 mg/kg | Sotatercept 0.7 mg/kg |
|---|---|---|---|---|
| Randomized and received ≥1 dose of placebo or Sotatercept | 9 | 9 | 8 | 9 |
| QCT measures at baseline and Day 225 | 4 | 6 | 5 | 6 |

Figure 22A:
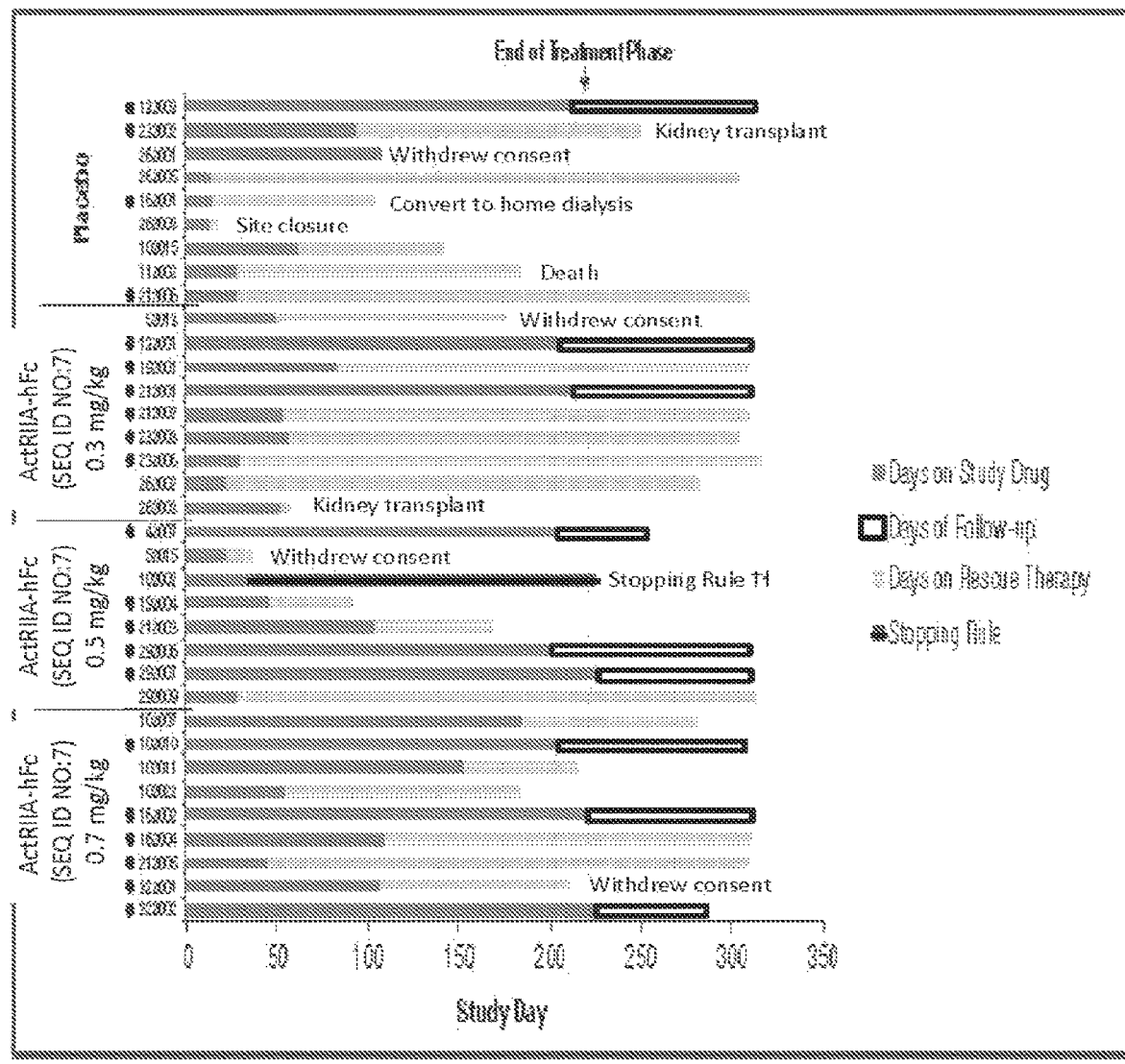
FIG. 22A depicts the subject disposition throughout the course of the study upon treatment with placebo or mActRIIA-Fc at the indicated doses. Each number on the y-axis represents an individual subject.

The subject disposition is depicted in FIG. 22A, including the subjects with paired QCT measurements at baseline and day 225. Most subjects who were discontinued from study treatment had treatment failure requiring rescue, generally because hemoglobin concentration was below 9 g/dL. Most subjects who were discontinued from study treatment received placebo or 0.3 mg/kg of sotatercept. None of the subjects discontinued treatment because of an adverse event. Further, of the 21 subjects with paired QCT measurements, 12 required rescue therapy due to hemoglobin treatment failure during the treatment phase, 9 of whom required rescue within the first 3 dose cycles.

Among subjects with paired QCT measurements, baseline demographic and clinical characteristics were generally similar across treatment groups (Table 16). However, there was a substantially longer time on dialysis in the placebo group, which was also the youngest group. There were also differences between groups in baseline biomarker and Agatston scores (Table 17).

TABLE 16

Baseline demographic and clinical characteristics of subjects with paired QCT measurements

| | Placebo (n = 4) | Sotatercept 0.3 mg/kg (n = 6) | Sotatercept 0.5 mg/kg (n = 5) | Sotatercept 0.7 mg/kg (n = 6) |
|---|---|---|---|---|
| Age, mean, years | 51.3 | 57.3 | 60.8 | 63.0 |
| Female, n (%) | 1 (25.0) | 6 (66.7) | 0 (0.0) | 4 (66.7) |
| Race, n (%) | | | | |
| White | 1 (25.0) | 3 (50.0) | 3 (60.0) | 5 (83.3) |
| Black | 2 (50.0) | 3 (50.0) | 2 (40.0) | 1 (16.7) |
| Asian | 1 (25.0) | 0 (0.0) | 0 (0.0) | 0 (0.0) |

TABLE 16-continued

Baseline demographic and clinical characteristics of subjects with paired QCT measurements

| | Placebo (n = 4) | Sotatercept 0.3 mg/kg (n = 6) | Sotatercept 0.5 mg/kg (n = 5) | Sotatercept 0.7 mg/kg (n = 6) |
|---|---|---|---|---|
| Ethnicity, n (%) | | | | |
| Hispanic | 0 (0.0) | 2 (33.3) | 3 (60.0) | 2 (33.3) |
| Non-Hispanic | 4 (100.0) | 4 (66.7) | 2 (40.0) | 4 (66.7) |
| Postdialysis weight, mean, kg | 65.5 | 80.3 | 79.4 | 84.5 |
| Body mass index, mean, kg/m² | 24.2 | 27.7 | 26.9 | 29.9 |
| Diabetes, n (%) | 9 (50.0) | 5 (83.3) | 5 (100.0) | 5 (83.3) |
| Parathyroidectomy, n (%) | 0 (0.0) | 0 (0.0) | 0 (0.0) | 0 (0.0) |
| Time on dialysis, mean, months | 165.8 | 43.3 | 22.4 | 68.1 |
| Non-calcium phosphate binder, n (%)* | 4 (100.0) | 3 (50.0) | 3 (60.0) | 3 (50.0) |
| Calcium-based phosphate binder, n (%)* | 1 (25.0) | 4 (66.7) | 4 (80.0) | 4 (66.7) |
| Calcimimetic, n (%)* | 1 (25.0) | 2 (33.3) | 0 (0.0) | 2 (33.3) |
| 1,25-OH vitamin D analog, n (%) | 3 (75.0) | 5 (83.3) | 2 (40.0) | 4 (66.7) |

*subjects could be receiving multiple types of binders

TABLE 17

Mean baseline biomarker, volumetric BMD, and Agatston scores of subjects with paired QCT measurements

| | Placebo (n = 4) | Sotatercept 0.3 mg/kg (n = 6) | Sotatercept 0.5 mg/kg (n = 5) | Sotatercept 0.7 mg/kg (n = 6) |
|---|---|---|---|---|
| Baseline whole PTH, pg/mL | 209.2 | 104.8 | 135.5 | 100.4 |
| BSAP$^a$, μg/L | 24.0 | 18.0 | 13.2 | 15.5 |
| P1NP$^b$, ng/mL | 548.3 | 376.2 | 468.4 | 437.5 |
| CTX$^c$, pg/mL | 3,152.3 | 2,062.5 | 2,266.8 | 2,246.5 |
| Total hip integral BMD, mg/cm³ | 276.8 | 286.6 | 280.0 | 281.0 |
| Femoral neck cortical BMD, mg/cm³ | 640.5 | 667.0 | 593.1 | 594.8 |
| Mean spine (L1, L2) BMD, mg/cm³ | 140.1 | 125.6 | 149.1 | 118.7 |
| VC total Agatston score$^d$ | 6,498.8 | 9,472.7 | 3,618.5 | 1,862.1 |

Note:
The n reflects the number of randomized subjects with paired QCT assessments; the actual number of subjects available for each parameter may vary.
PTH = parathyroid hormone.
$^a$Bone = specific alkaline phosphatase (BSAP) reference range: males, 6-30; females (premenopausal), 3-19; females (postmenopausal), 6-26.
$^b$Procollagen type 1 N-propeptide (P1NP) reference range: males, 30-110; females 20-108
$^c$C-terminal telopeptide (CTX) reference range: males, 0-854; females (premenopausal), 26-573; females (postmenopausal), 104-1,008
$^d$Lower Agatston scores indicate lower levels of vascular calcification.

Serious adverse events were generally considered unrelated to sotatercept, did not lead to discontinuation, and resolved with continued therapy. No deaths were reported in the sotatercept treatment groups. Adverse events were mostly mild or moderate in severity, unrelated to the study drug, relatively similar between treatment groups, and generally consistent with the subjects' medical histories. In the first 28-day dose cycle and during the 225-day treatment phase, home blood pressure measurements showed no consistent or dose-dependent changes from baseline among subjects in any of the treatment groups.

Figure 22B:
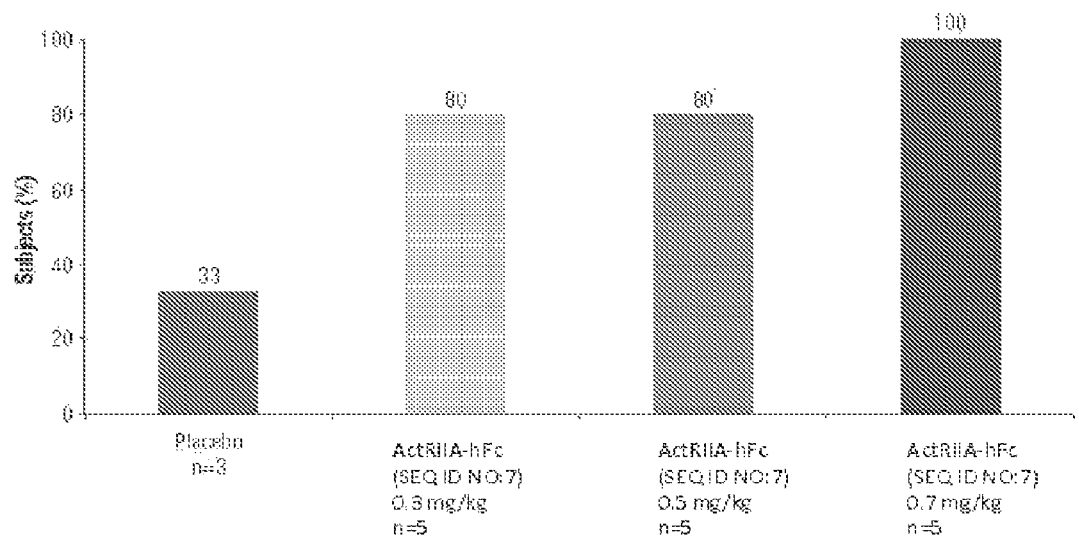
FIG. 22B depicts the proportions of subjects with <15% progression in their abdominal aortal total Agatston score upon treatment with placebo or mActRIIA-Fc at the indicated doses.

The changes from baseline in abdominal aorta total Agatston scores are provided in Table 18. The proportion of subjects with <15% progression in abdominal aorta total Agatston scores is shown in FIG. 22B.

TABLE 18

Baseline and change from baseline in abdominal aorta total Agatston score and square root transformed total volume score*

|  | Placebo (n = 4) | Sotatercept 0.3 mg/kg (n = 6) | Sotatercept 0.5 mg/kg (n = 5) | Sotatercept 0.7 mg/kg (n = 6) |
|---|---|---|---|---|
| Abdominal aorta total Agatston score | | | | |
| Baseline total Agatston score | 6,498.8 | 9,472.7 | 3,618.5 | 1,862.1 |
| Change from baseline total Agatston score | 787.8 | 8,578.9 | 225.7 | 171.0 |
| % change from baseline total Agatston score | 58.4 | 29.9 | 17.3 | 7.4 |
| Square root transformed total volume score | | | | |
| Baseline square root of total volume, mm³ | 39.0 | 46.2 | 33.1 | 27.4 |
| Change from baseline square root of total volume, mm³ | 3.4 | 11.1 | 1.2 | 1.3 |

Note:
The n reflects the number of randomized subjects with paired QCT assessments; actual number of subjects available for each parameter may vary.
*Lower total Agatston and square root transformed total volume scores indicate lower levels of vascular calcification.

Figure 22C:
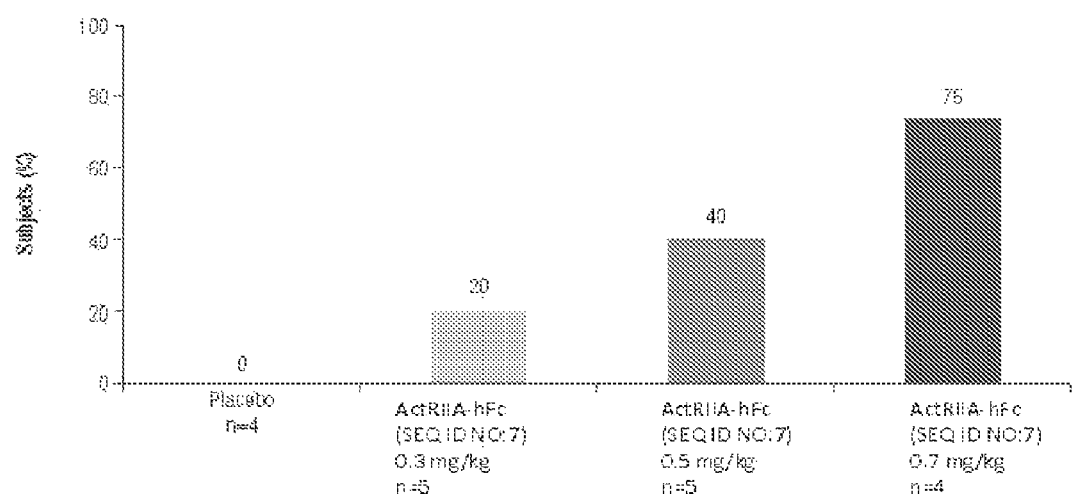
FIG. 22C depicts the proportions of subjects with >2% increase in femoral neck cortical BMD upon treatment with placebo or mActRIIA-Fc at the indicated doses.

Further, Table 19 provides the percent change from baseline in femoral neck cortical and mean lumbar spine trabecular volumetric BMD measurements. The proportions of subjects with >2% gain in femoral neck cortical BMD were analyzed and it was determined that treatment with sotatercept is associated with increases in the proportion of subjects with 22% increase in femoral neck cortical bone (see Table 19 and FIG. 22C). See, also, Malluche et al., 2014, Clin. J. Am. Soc. Nephrol., 9: 1254-1262. Moreover, in high-turnover ROD, trabecular bone mass increases, as measured by lumbar spine trabecular BMD, without a reduction in vertebral fracture rates in ESKD as compared with the general population (see, Leonard M B, 2009, Semin. Nephrol., 29:133-143, and Duan et al., 1999, J. Clin. Endocrinol. Metab. 84:718-722). In this setting, the increased trabecular bone mass is of poor quality (see Malluche et al, 2012, J. Am. Soc. Nephrol. 23:525-532. Treatment with sotatercept slows the increase in trabecular bone mass in the lumbar spine (Table 19).

TABLE 19

Baseline and percent change from baseline in femoral neck cortical and mean lumbar spine (L1, L2) trabecular BMD

|  | Placebo (n = 4) | Sotatercept 0.3 mg/kg (n = 6) | Sotatercept 0.5 mg/kg (n = 5) | Sotatercept 0.7 mg/kg (n = 6) |
|---|---|---|---|---|
| Femoral neck cortical | | | | |
| Baseline BMD, mg/cm³ | 640.5 | 667.0 | 593.1 | 594.8 |
| % change from baseline BMD (n) | −1.4 (4) | −1.4 (5) | 1.6 (5) | −0.1 (4) |
| Mean lumbar spine (L1, L2) trabecular | | | | |
| Baseline BMD, mg/cm³ | 140.1 | 125.6 | 149.1 | 118.7 |
| % change from baseline BMD (n) | 10.9 (4) | 8.0 (6) | 0.5 (5) | 4.5 (6) |

Note:
The n reflects the number of randomized, subjects with paired QCT assessments; actual number of subjects available for each parameter may vary.

Conclusions

Based on the baseline biomarker data, subjects in this example tended to have high-turnover ROD. The placebo group had decreased cortical bone mass, increased trabecular bone mass, and increased vascular calcification that occurred at a rate similar to other large studies in ESKD (Raggi et al., 2011, Nephrol. Dial. Transplant. 26:1327-1339), as expected for high-turnover ROD.

QCT data measured at baseline and day 225 (which is after up to eight 28-day dose cycles), indicated that treatment of high-turnover ROD with sotatercept resulted in an effect on multiple parameters of CKD-MBD, including slowed progression of vascular calcification, increased femoral neck cortical bone mass, and a slowed increase in lumbar spine bone mass. The decrease in vascular calcification and the increase in bone mass are consistent with the histological findings in the mouse model of ldlr−/− high-fat fed, 5/6 nephrectomy for vascular calcification (Fang et al., 2014, Abstract, ASN Kidney Week 2014, Nov. 11-16, 2014, Philadelphia, Pa.).

Example 9: ActRIIA-hFc (Seq Id No:7, "Sotatercept") Affects Multiple Manifestations of End-Stage Kidney Disease Background This example presents data from a clinical study. Examples 7 and 8 (Section Section 9.7 and Section 9.8) also present data from this study.

This ongoing, randomized, single-blind, placebo-controlled study evaluated the pharmacokinetics, safety, and hemoglobin effect of ActRIIA-hFc (SEQ ID NO:7; "sotatercept"), an ActRIIA-IgG1 fusion protein ligand trap for the correction of anemia in hemodialysis subjects, and explored its effects on vascular calcification and bone mineral density using quantitative computed tomography. This example provides interim results for the 0.3, 0.5, and 0.7 mg/kg dose groups.

Methods

Erythropoietin-stimulating agent (ESA)-responsive subjects were washed out of ESA effects until hemoglobin was <10 g/dL and randomized to placebo or sotatercept administered subcutaneously every 28 days for <8 dose cycles. Treatment failures (hemoglobin <9 g/dL) were rescued with ESA or transfusion; intrasubject dose escalation was not permitted. Quantitative computed tomography scans of hip, lumbar spine, and abdominal aorta were obtained at baseline and after the 225-day treatment phase. Reported are interim results for pharmacokinetics, safety, home blood pressure, hemoglobin, vascular calcification, and bone mineral density effects.

Results

Among subjects treated with placebo (n=9) or sotatercept 0.3 mg/kg (n=9), 0.5 mg/kg (n=8), and 0.7 mg/kg (n=9), adverse events were mostly mild/moderate, unrelated to study drug, relatively similar in type/severity between groups, and generally consistent with subject medical histories. Two deaths occurred in the placebo group. There were no dose-dependent changes in home blood pressure. In the 225-day treatment phase, hemoglobin was >10 g/dL in 33%, 33%, 63%, and 78% of subjects treated with placebo or sotatercept 0.3, 0.5, or 0.7 mg/kg, respectively. Paired quantitative computed tomographics obtained in 4, 6, 5, and 6 subjects treated with placebo or sotatercept 0.3, 0.5, or 0.7 mg/kg, respectively, showed <15% progression of vascular calcification in 33%, 80%, 80%, and 100%, and >2% increase in femoral neck cortical bone mineral density in 0%, 20%, 40%, and 75%, respectively.

Conclusions

Sotatercept was tolerated with an acceptable safety profile in hemodialysis, without increases in home blood pressure. There were dose-dependent responses to sotatercept in hemoglobin, vascular calcification, and bone mineral density.

Example 10: Disordered ActRIIA Signaling in CKD Contributes to Atherosclerotic Calcification and Renal Fibrosis This example relates to the experiments described and performed in other examples described herein, including, Example 4.

Methods

Production of Animal Models

The atherosclerotic low density lipoprotein receptor deficient (ldlr−/−) males (C57Bl/6J background) were purchased from Jackson Laboratories, and fed high fat diet (42% calories from fat) beginning at 12 weeks of age. The mice are obese, insulin resistant at 22 weeks of age, diabetic at 28 weeks of age and hypercholesterolemic.

Figure 33A:
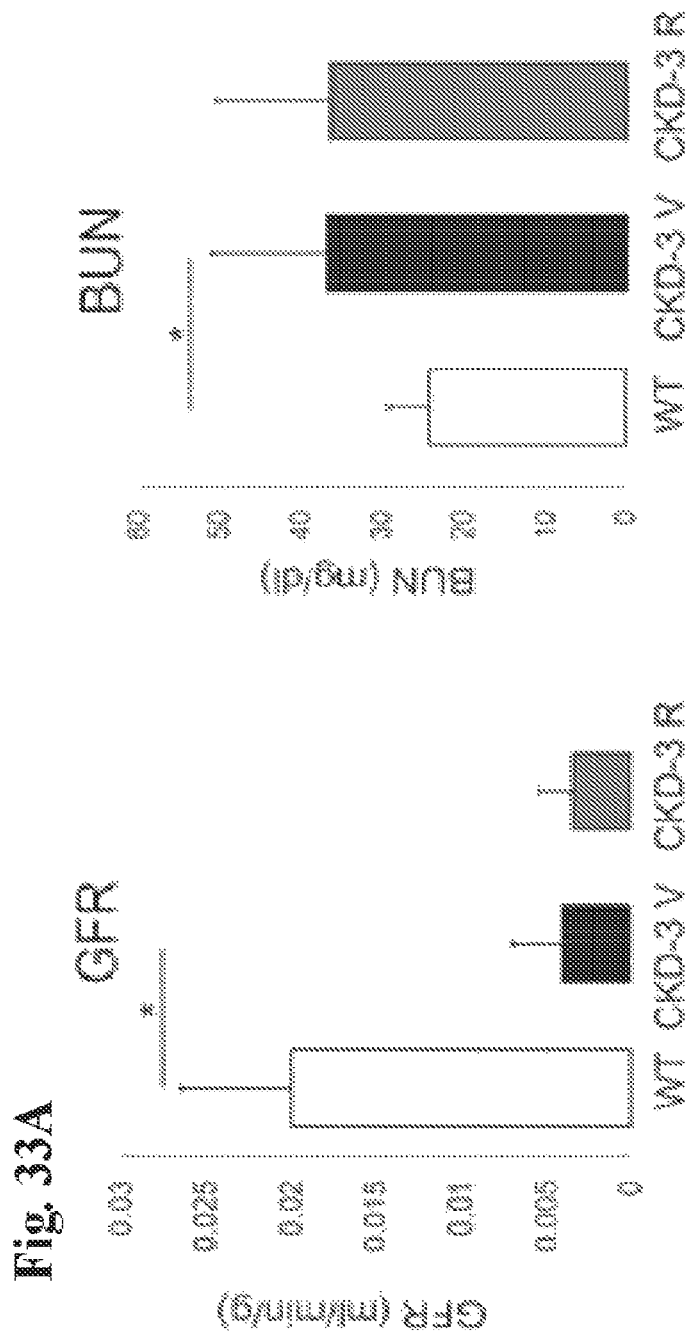

A two-step procedure was utilized to create chronic kidney disease as described previously. (Davies M R, et al. J Am Soc Nephrol 2003; 14: 1559-1567; Davies M R, et al. J Am Soc Nephrol 2005; 16: 917-928). Electrocautery was applied to the right kidney through a 2 cm flank incision at 12 weeks post-natal, followed by left total nephrectomy at 14 weeks of age. The intensity of the cautery was varied to produce moderate (CKD-3) renal injury that was confirmed by inulin clearances at age 20 weeks (FIG. 33A, B). Control animals received sham operations in which the appropriate kidney was exposed and mobilized but not treated in any other way. Five groups of mice were used in this study (FIG. 23B). The first group was wild type C57Bl/6J mice fed a regular chow diet (WT). This was the normal renal function and diet group used for normative control values. The second group was ldlr−/− mice that were fed a high fat diet and sham operated (Sham). This group served as the control group to determine the effect of kidney disease. The third group was ldlr−/− mice with GFR reduced equivalent to human CKD stage 3 fed high fat diet (CKD-3) with euthanasia at 22 weeks, the baseline vascular calcification group (CKD-3) used in FIG. 25A, B, C. The fourth group was ldlr−/− mice with CKD-3 receiving subcutaneous injections of vehicle (phosphate buffered saline) twice a week beginning at 22 weeks until euthanasia at 28 weeks (CKD-3 V). The fifth group was ldlr−/− mice with CKD-3 receiving subcutaneous injections of mActRIIA-Fc (Celgene, Summit, N.J.), 10 mg/kg twice a week beginning at 22 weeks until euthanasia at 28 weeks (CKD-3 R). The dose used was previously shown in PK/PD studies to be an efficacious dose for stimulation of bone formation.

The second model of CKD used was the murine homolog of X-linked Alport's syndrome, which is a deficiency in the gene for the a5 chain of type IV collagen, COL4A5. (Rheault M N, et al. J. the Am. Soc. Neph. 2004; 15: 1466-1474). This is a model of spontaneous kidney disease, and was used throughout the results to confirm the effects of renal ablation induced CKD. Breeding pairs were purchased from Jackson Laboratories and were bred for experiments. Hemizygote males spontaneously developed kidney disease comparable with human CKD stage 3-4 at 150 days after birth and developed hematuria by day 75 of life.

In all cases, euthanasia was performed under anesthesia. Intraperitoneal anesthesia (xylazine 13 mg/kg and ketamine 87 mg/kg) was used for all procedures. Saphenous vein blood samples were taken 1 week following the second surgery to assess baseline post-surgical renal function. At the time of sacrifice, blood was taken by intracardiac stab, and the heart and aorta dissected en bloc.

Inulin Clearances

Inulin clearances were performed at 20 wks or 26 wks if euthanasia was at 28 wks, according to manufacturer instructions (BioPal Inc., Worcester, Mass.).

Chemical Calcification Quantitation

Aortas were dissected at sacrifice, and all extraneous tissue removed by blunt dissection under a dissecting microscope. Tissues were desiccated for 20-24 hours at 60° C., weighed and crushed to a powder with a pestle and mortar. Calcium was eluted in 1N HCL for 24 hours at 4° C. Calcium content of eluate was assayed using a cresolphthalein complexone method (Sigma, St Louis, Mo.), according to manufacturer's instructions, and results were corrected for dry tissue weight.

Blood Tests

Serum was analyzed on the day of blood draw for blood urea nitrogen (BUN), calcium, and phosphate by standard autoanalyzer laboratory methods performed by an animal facility. Plasma activin (Fitzgerald Industries, Acton, Mass.), follistatin (MYBIOSOURCE Inc., San Diego, Calif.) and follistatin-like 3 (MYBIOSOURCE Inc.) levels were determined in ELISA assays. Serum Dkk1 levels were analyzed with an ELISA (R&D Systems, Minn., Minn.). For the Elisa assays blood was drawn by saphenous vein or cardiac puncture at the time of euthanasia. All blood samples were placed on ice at collection. Platelet poor EDTA plasma samples were made by a 2-step centrifugation at 6000 rpm for 5 minutes and 14000 rpm for 2 minutes both at 4° C. Samples were stored frozen at −20° C. or below until being used.

Histology and Immunohistochemistry

Aortic and kidney tissues were fixed in 10% neutral buffered formalin overnight, then transferred to 70% ethanol at 4° C., embedded in paraffin and 5 micron sections were prepared. Slides were deparaffinized in xylene and dehydrated in a graded ethanol series and then rehydrated. Mason Trichome staining was used to detect kidney and heart fibrosis and Alizarin red staining was used to detect calcification, according to a standard protocols. (Gregory C A, et al. Analytical Biochem. 2004; 329: 77-84). For immunostaining, slides were blocked in 20% normal goat serum for 20 min and incubated with primary antibody at 4° C. overnight. Slides were washed in PBS and blocked in 20% normal goat serum for 20 min before incubation with goat-anti rabbit Alexa 488 secondary antibody 1:400 (Life Technologies, A11008) at room temperature for 30 min, or using TSA kit for signal amplification according manufacture instructions (Life Technologies, T 20932). For double immunofluorescent staining sections were blocked in 20% goat serum and sequentially stained with first primary and secondary antibodies and second primary and secondary antibodies using goat-anti rabbit Alexa 488 and Alexa 568 secondary antibodies 1:400 (Life Technologies, A11008 and A11011) or TSA kit for signal amplification according manufacture instructions (Life Technologies, T20932 and T20934). When primary antibodies from same species were used for double staining slides were heated 5 min in citrate buffer in microwave before second staining. (Tóth Z E, J. HistoChem. & CytoChem. 2007; 55: 545-554). Primary antibodies used in this study for immunostaining: rabbit polyclonal anti-ActRIIA antibody 1:250 (Abcam, ab 135634), rabbit polyclonal anti-Inhibin beta A antibody 1:100 (Santa Cruz, sc-50288), rabbit polyclonal anti-CD31 antibody 1:50 (Abcam, ab28364) and rabbit polyclonal anti-beta-catenin antibodies 1:500 (Abcam, ab32572).

RT-PCR

RNA was extracted from aortas and kidneys using RNeasy Mini Kits (Qiagen, Valencia, Calif.). 1 pg of total RNA was DNase treated and reverse transcribed using iScript cDNA synthesis kit from Bio-Rad (Hercules, Ca) according to manufacturer's instructions on Veriti Termal Cycler (Applied Biosystems). Primers were designed using Vector NTI (Invitrogen, Grand Island, N.Y.) or Primer Express (Life Technologies, Grand Island, N.Y.) software. Following reverse transcription real time was performed using the StepOne Plus real time PCR instrument (Applied Biosystems), SYBR Green from Sigma (St. Louis) and the PCR kit from Invitrogen. Each reaction was performed in triplicate at 95'C, 45 sec, and 60'C, 30 sec, and 60 sec at 72° C. for 40 cycles. This was followed by a melt cycle, which consisted of stepwise increase in temperature from 60'C to 95° C. A single predominant peak was observed in the dissociation curve of each gene, supporting the specificity of the PCR product. Ct numbers (threshold values) were set within the exponential phase of PCR and were used to calculate the expression levels of the genes of interest. B2m was used as an internal standard and normalize the values. A standard curve consisting of the $c_T$ versus log cDNA dilutions (corresponding to the log copy numbers) was generated by amplifying serial dilutions of cDNA corresponding to an unknown amount of amplicon. Negative controls were performed by inactivating the reverse transcriptase by boiling for 5 min prior to RT-PCR to insure that genomic DNA was not amplified.

Immunoblotting (Western Analyses)

Whole-cell lysate protein were prepared from kidney and aorta of the mice by RIPA Lysis Buffer (Thermo Scientific) containing a protease inhibitor cocktail (Santa Cruz). Lysates (20 gig) were loaded in 8-12% SDS-PAGE gels and immunoblotted with antibodies to inhibin β-A (Santa Cruz), α-tubulin (Santa Cruz), actin-α smooth muscle (Sigma), Runx2 (Cell Signaling), Myocd (Santa Cruz), ACVRL1 (Origene), ACVR1 (Cell Signaling), Erk1/2 (Cell Signaling), phospho-Erk1/2 (Cell Signaling), ACVR1B (Origene), Col1a1 (Santa Cruz), Smad2/3 (Cell Signaling), or phospho-Smad2/3 (Cell Signaling). Immunoprecipitation (IP) assays used the same whole-cell lysate protein. To reduce nonspecific binding, the samples were pre-cleaned using pre-washed protein A agarose beads (Cell Signaling). Pre-cleaned samples were incubated overnight with the phospho-serine antibody (Abcam). IP-antibody complexes were then captured on protein A agarose beads and proteins were detected by immunoblotting analysis.

Statistical analysis was performed using ANOVA. All data are expressed as mean±SD, unless other specified in the figure legend. Differences between groups were assessed post hoc using Fisher LSD method and considered significant at p<0.05. Data for all groups represent an "n" of 7-15. For real time PCR analysis, a minimum of 3 samples were used in each experimental group. For the vascular calcification data in FIG. 26C, the boxes represent median and interquartile ranges (from $25^{th}$ to $75^{th}$ percentile), and error bars present 1.5-fold of the interquartile range below $25^{th}$ and above $75^{th}$ percentile. Medians were compared using ANOVA Holm-Sidak method for multiple comparisons, p<0.05, as critical level for significant difference.

Results

Experimental Design, and Kidney Function in a Model of CKD

The high fat fed ldlr−/− mouse is a model of atherosclerotic vascular calcification requiring both the diet and the genotype to produce atherosclerotic vascular calcification. (Davies M R, et al. J Am Soc Nephrol 2003; 14: 1559-1567; Towler D A, et al. J. Biological Chem. 1998; 273: 30427-30434). Kidney function was reduced analogous to human stage 3 CKD (CKD-3) in ldlr−/− high fat fed mice by renal cortical injury and contralateral nephrectomy (FIG. 33A, B). The CKD-3 mice were hyperphosphatemic (Table 20) consistent with the onset of hyperphosphatemia in human stage 3b-4 CKD. (Isakova T, et al. Kidney Int 2011; 79: 1370-1378).

TABLE 20

Serum Biochemical Parameters in the Animals Tested

| Parameter | Group 1 Wild Type | Group 2 Sham | Group 3 CKD-3 V | Group 4 CKD-3 R |
|---|---|---|---|---|
| Mouse Strain | C57/BJ6 | ldlr−/− | ldlr−/− | ldlr−/− |
| Diet | Chow | High fat | High fat | High fat |
| Surgery | None | Sham | CKD | CKD |
| Weeks postnatal | 28 | 28 | 28 | 28 |
| Treatment | None | None | Vehicle | mActRIIA-Fc |
| N | 12 | 15 | 14 | 15 |
| BUN (mg/dl) | 24.0 ± 4.6 | 20.6 ± 3.7 | 37.7 ± 7.6* | 36.5 ± 5.8* |
| Ca (mg/di) | 8.3 ± 1.8 | 8.9 ± 0.9 | 9.4 ± 0.8 | 8.8 ± 0.3 |
| Phosphorus (mg/di) | 8.9 ± 0.2 | 7.9 ± 2.3 | 11.0 ± 1.6* | 11.8 ± 1.2* |

*<0.05, groups 3 and 4 compared to group 2.

Activin Receptor Type HA (ActRIIA) Levels in CKD

Figure 24A:
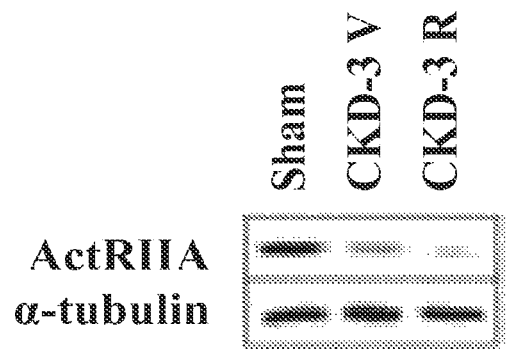
FIG. 24A depicts expression of ActRIIA in mouse aortas as determined by westerns for ActRIIA in aortic homogenates.
Figure 24B:
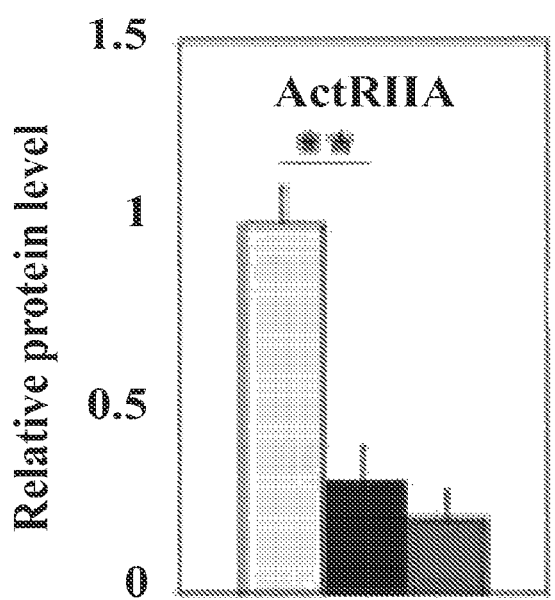
FIG. 24B depicts immunoblot quantitation of FIG. 24A. For the quantitation, n=4. **p<0.01.
Figure 24C:
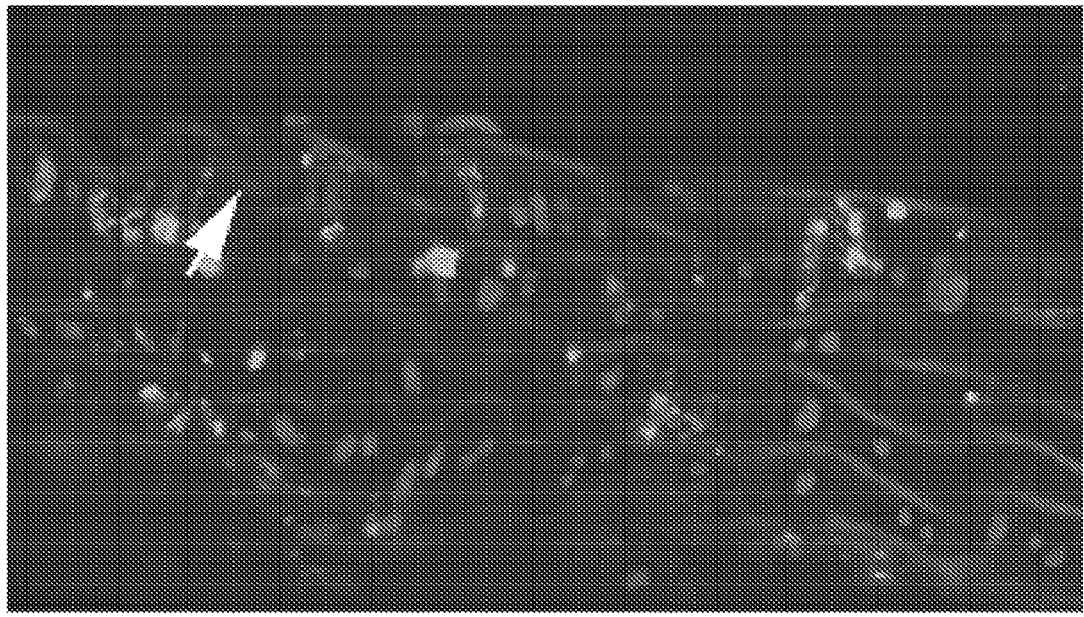
FIG. 24C depicts immunofluorescent detection of ActRIIA in the aortas of sham mice.
Figure 24D:
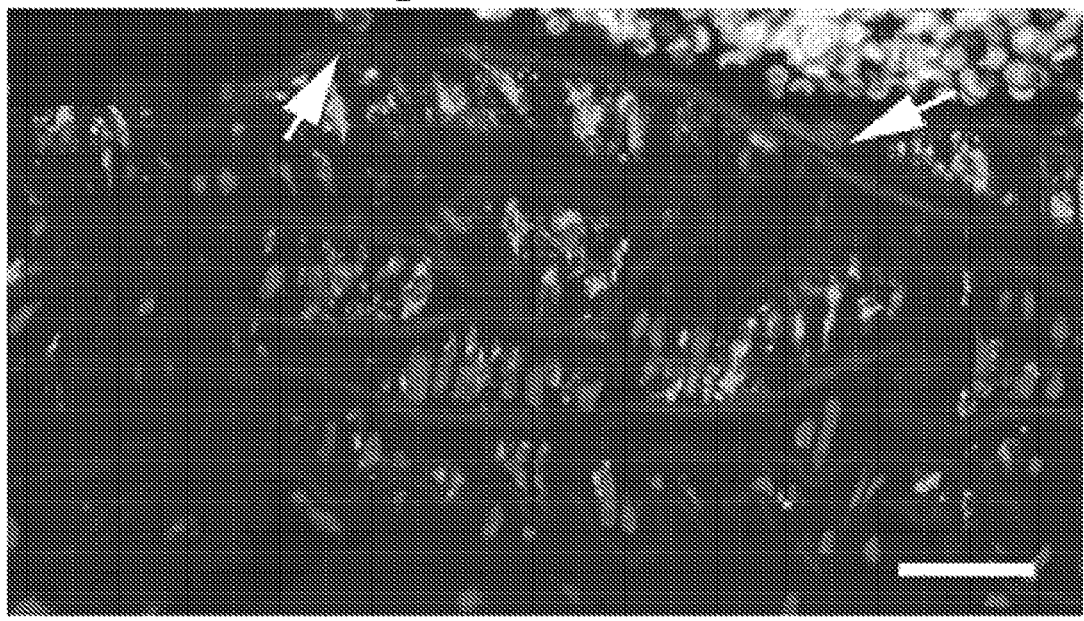
FIG. 24D depicts immunofluorescent detection of ActRIIA in the aortas of CKD-3 mice. ActRIIA was expressed in aortic VSMC, but was not detected in endothelial cells. VSMC ActRIIA levels remained detectable in CKD compared to sham. CD31 (arrows) was used as an endothelial cell marker. Nuclei were stained by DAPI. Scale bar 20 µm.

Aortas from the high fat fed ldlr−/− mice with CKD-3 were analyzed for TGFβ superfamily type II receptors which are one ligand binding component of the superfamily receptor heteromultimers composed of type II and type I (ALK) receptors. The Activin type II receptor A (ActRIIA) was expressed in aortic vascular smooth muscle cells (VSMC) (FIG. 24A, B). CKD-3 produced in the ldlr−/− high fat fed mice induced ActRIIA down regulation in the aorta (FIG. 24A). Without being bound by any particular theory, this is consistent with internalization and degradation of ActRIIA produced by high circulating ligand levels reported in other tissues. (Simone N D, et al. Endocrinology 1998; 139: 1147-1155; Liu Z H, et al. J. Endocrinology 2006; 189: 409-421). Endothelial cell ActRIIA was not detected by immunochemical and immunofluorescent detection. (FIG. 24B).

Vascular Effects of the ActRIIA Ligand Trap in CKD

The effects of CKD-induced suppression of ActRIIA levels were analyzed in aortic homogenates from CKD-3 mice treated with vehicle or the ActRIIA ligand trap (mActRIIA-Fc) (FIG. 25A, B). CKD-3 stimulated osteoblastic transition was assessed by expression of mRNA for Runx2 and alkaline phosphatase (Alp1) in the aortas of ldlr−/− high fat fed mice. CKD-3 stimulated their expression and mActRIIA-Fc treatment reversed the effects of CKD (FIG. 25A). Both Runx2 and Alp1 expression represent biomarkers of osteoblastic transition in the aorta that were reversed by mActRIIA-Fc treatment. Aortic mRNA of smooth muscle 22a or transgelin (Tagln), a biomarker of differentiated vascular smooth muscle cells, (Li L, Miano, et al. *Circulation Res.* 1996; 78: 188-195) was decreased by CKD-3 and stimulated by mActRIIA-Fc. CKD-3 also caused decreased aortic myocardin (Myocd) mRNA expression, the vascular smooth muscle cell specific transcription factor, but myocardin was not affected by mActRIIA-Fc treatment. In terms of the effects of CKD-3 and mActRIIA-Fc treatment on aortic protein levels of the respective mRNAs studied in FIG. 25A, CKD increased aortic Runx2 and Alp1 levels and mActRIIA-Fc normalized them (FIG. 25B, data for Alp1 not shown). CKD decreased the aortic levels of Tagln and alpha smooth muscle actin ($\alpha$SMA), another biomarker of differentiated vascular smooth muscle cells, and mActRIIA-Fc treatment increased them (FIG. 25B, data for Tagln not shown). Myocardin levels were not changed by CKD or mActRIIA-Fc treatment.

Figure 26:
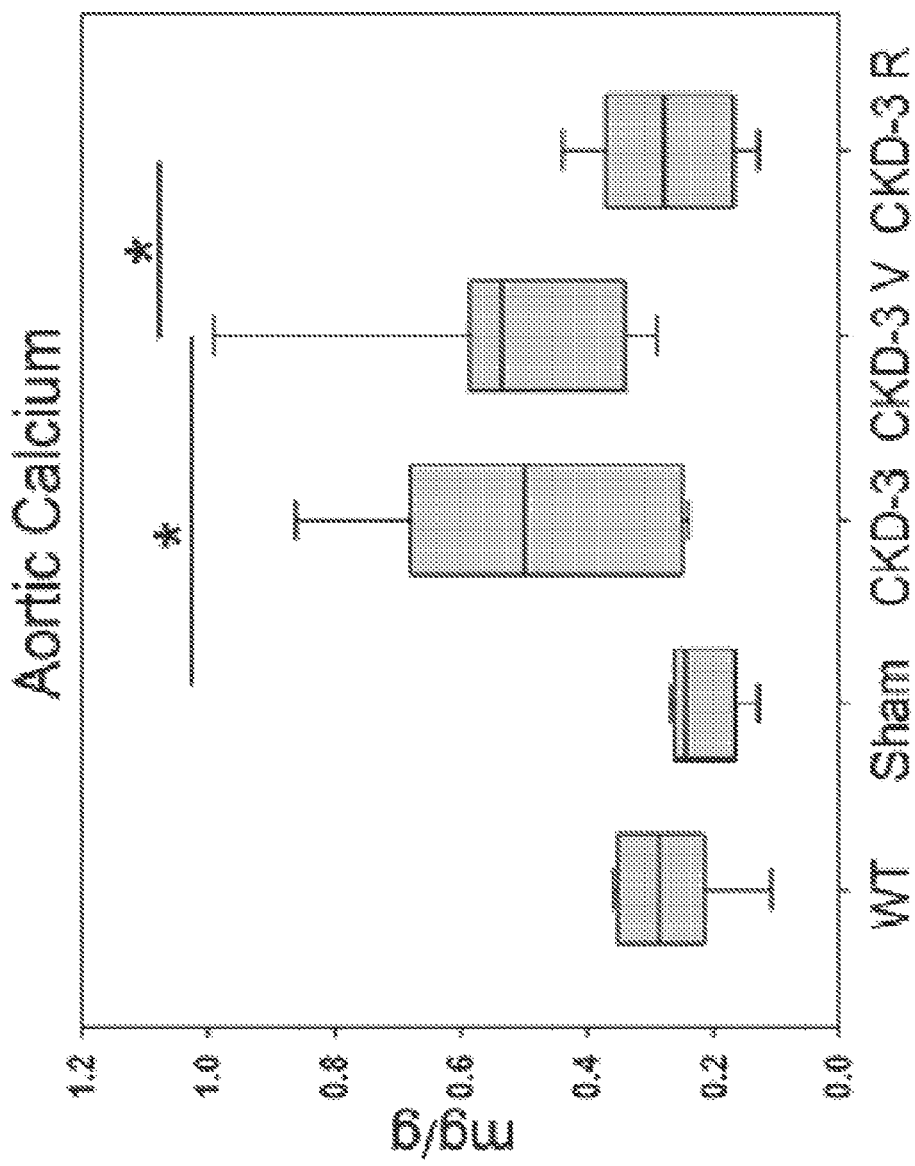
FIG. 26A depicts the effects of CKD and the ActRIIA ligand trap on aortic calcification in ldlr−/− high fat fed mice with CKD-3 showing stained sections of proximal aortic atherosclerotic plaques with Alizarin Red from vehicle.
FIG. 26B depicts the effects of CKD and the ActRIIA ligand trap on aortic calcification in ldlr−/− high fat fed mice with CKD-3 and treated with mActRIIA-Fc as shown by proximal aortic atherosclerotic plaques stained with Alizarin Red. Arrow head indicates calcium deposition in intima (i); m—media. Scale bar 100 µm.
FIG. 26C depicts aortic calcium levels in the groups of mice: wild type (WT); sham operated ldlr−/− high fat fed (Sham); CKD-3 euthanasia at 22 weeks, the time of institution of treatment (CKD-3); CKD-3 treated with vehicle from 22 to 28 weeks (CKD-3 V); CKD-3 treated with mActRIIA-Fc, 10 mg/kg subcutaneous twice weekly from 22 to 28 weeks (CKD-3 R). The boxes represent median (line in box) and interquartile ranges from 25th to 75th percentile. The error bars represent 1.5 fold of the interquartile range. Groups were compared using ANOVA Holm-Sidak method for multiple comparisons with p<0.05 as level for significant difference. *p<0.02; n for each group 8-12.

The ldlr−/− high fat fed mouse is a model of atherosclerosis, atherosclerotic calcification and type 2 diabetes, (Al-Aly Z, et al. Arteriosclerosis, Thrombosis, and Vascular Biol. 2007; 27: 2589-2596; Towler D A, et al. J. Biological Chem. 1998; 273: 30427-30434). Identified, inter alia, CKD-3 caused accumulation of calcium deposits in the aortic atheromas in CKD-3 vehicle treated mice (CKD-3 V) (FIG. 26A) and increased total tissue calcium levels (FIG. 26B). Visible calcium deposits were not present in CKD-3 mice treated with mActRIIA-Fc (CKD-3 mActRIIA-Fc). Moreover, mActRIIA-Fc decreased aortic tissue calcium content to levels like those observed in wild type and sham mice, and levels that were significantly below those present at the time of institution of mActRIIA-Fc treatment in the CKD-3 group (FIG. 26B).

ActRIIA Signaling in the Aorta

Figure 27B:
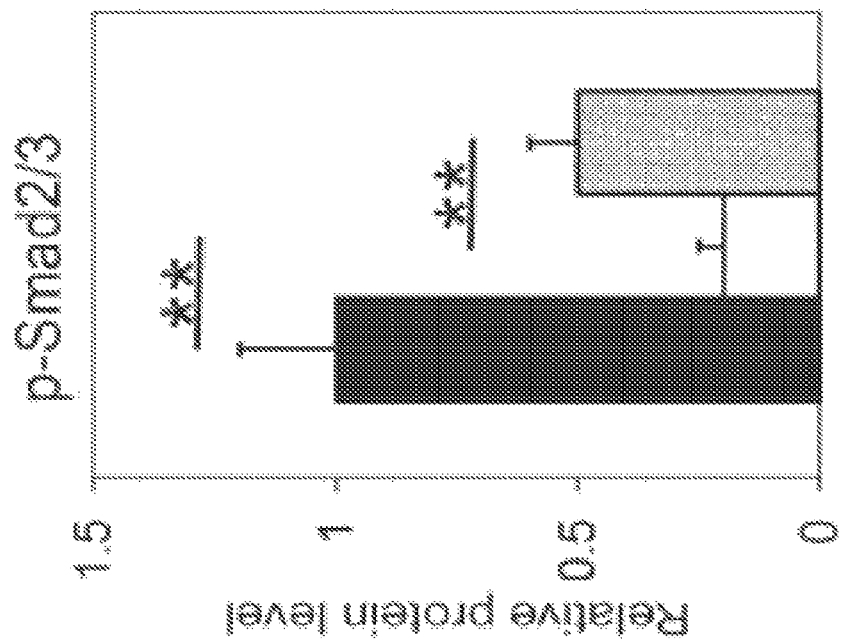
FIG. 27B depicts p-Smad2/3 immunoblot quantitation, n=4, **p<0.01.
Figure 27A:
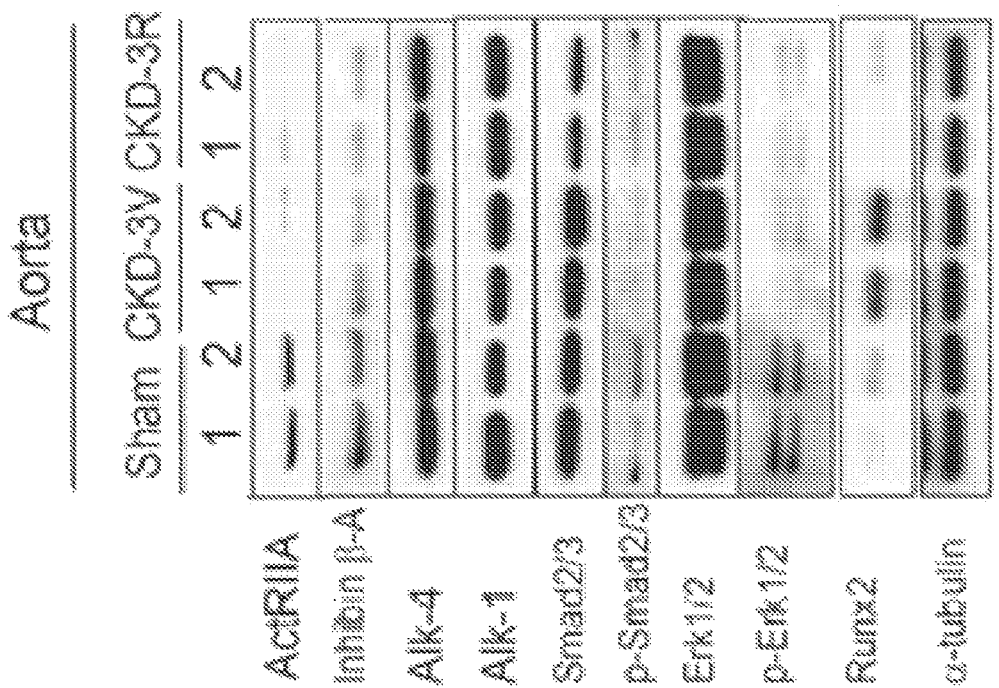
FIG. 27A depicts the analysis of ActRIIA signaling by westerns of aortic homogenates from sham, CKD-3 vehicle and CKD-3 mActRIIA-Fc treated mice. Immunoblots of homogenates from two aortas of animals in each group. ActRIIA and Activin (inhibin β-A) levels were decreased in aortic homogenates from CKD-3 mice. The Alk4 (AcvR1B) and Alk1 (AcvRL1) type 1 receptors were present in aortic homogenates. CKD-3 decreased smad2/3 phosphorylation in aortas which was increased by mActRIIA-Fc treatment. CKD-3 decreased phospho-Erk 1/2 levels. Runx2 levels were increased by CKD-3 and normalized by mActRIIA-Fc treatment.
Figure 34:
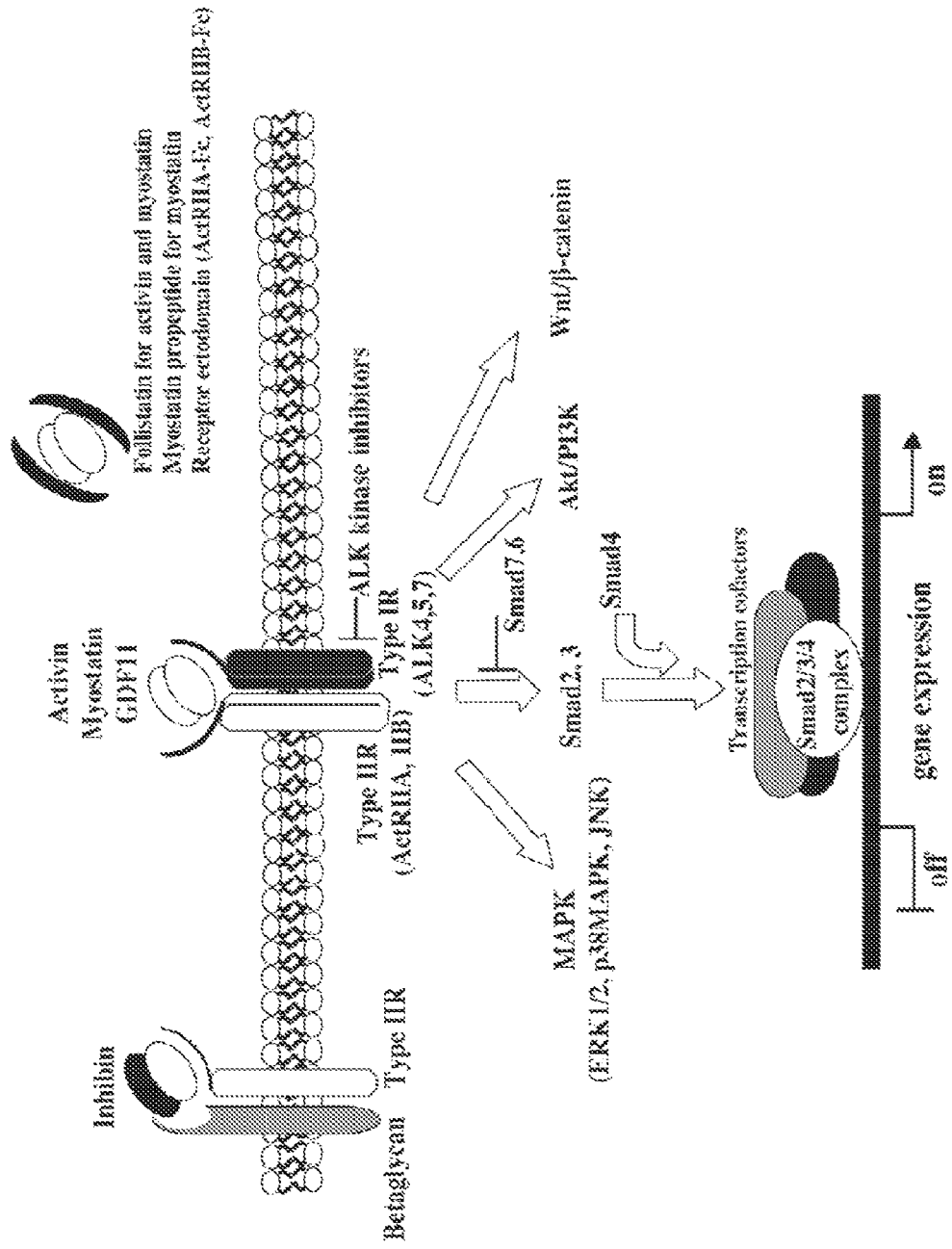
FIG. 34 depicts a diagrammatic representation of ActRIIA signaling from Tsuchida et al (Cell Comm, and Signaling, 2009). Activin, Myostatin, and GDF11 binding to the type II receptors, ActRIIA (primary for activin) and ActRIIB (primary for myostatin and GDF11) activate signal transduction pathways including the canonical pathway through smad 2,3.
Figure 35A:
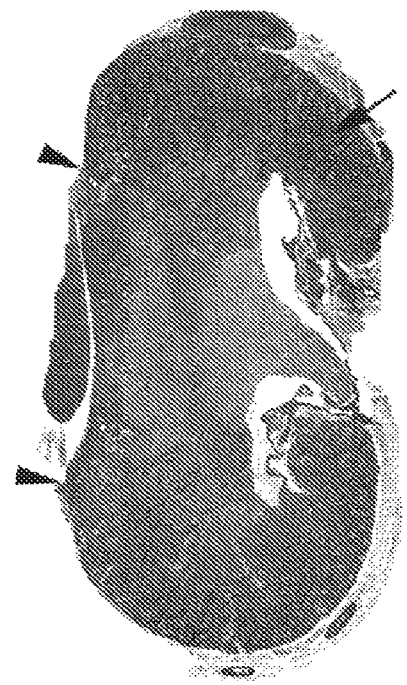
FIG. 35A and FIG. 35B show kidneys (kidney trichrome staining) of CKD-3 vehicle treated mice.
Figure 35B:
Figure 35C:
FIG. 35C and FIG. 35D show kidneys (kidney trichrome staining) of CKD-3 mActRIIA-Fc treated mice. Scale bar 1 mm. The cortical surface scars from the electrocautery injury are marked by arrowheads. The arrows designate the point from which the high power photomicrographs in FIG. 36 were taken. Scale bar 1 mm.
Figure 35D:

Canonical signal transduction by the TGF$\beta$ superfamily involves ligand binding to type II receptors activating their serine/threonine kinase activity and stimulating association and phosphorylation of type I receptors, the Alk kinases (see diagrammatic representation in FIG. 34). There are seven Alk kinases utilized by the TGF$\beta$ superfamily, and Alk4 (ActRIIB) is the type I receptor most often associated with ActRIIA signaling. (Abe Y M T, et al. Growth Factors (Chur, Switzerland) 2004; 22: 105-110). ActRIIA levels were not decreased in aortic homogenates isolated from CKD-3 mice as evidenced in FIG. 24, and were not associated with decreased tissue levels of Alk4 and Alk1 (FIG. 27A). Alk5 and Alk2, other type 1 receptors associated with ActRIIA signaling, were not detectable. ActRIIA activity was assessed by measuring the effect of receptor heteromultimerization (e.g., phosphorylation of regulatory Smads). CKD-3 decreased aortic phosphosmad 2/3 levels (activated smad 2/3), and mActRIIA-Fc increased them compared to CKD-3V (FIG. 27A, B). Noncanonical ActRIIA signaling (FIG. 34) was also analyzed: (1) map kinase (phospho-Erk1/2) was decreased by CKD and not further affected by mActRIIA-Fc (FIG. 27A), and (2) vascular smooth muscle levels of p38 and JNK were very low. Also, mActRIIA-Fc p-AKT levels remained unaffected indicating that aortic AKT/PI3 kinase was not affected by ActRIIA signaling. Aortic ActRIIA signaling (phosphosmad 3) was decreased by CKD and stimulated by the ActRIIA ligand trap associated with suppression of osteoblastic transition in the atherosclerotic aortas by the ActRIIA ligand trap (FIG. 25A, B, C).

Figure 28D:
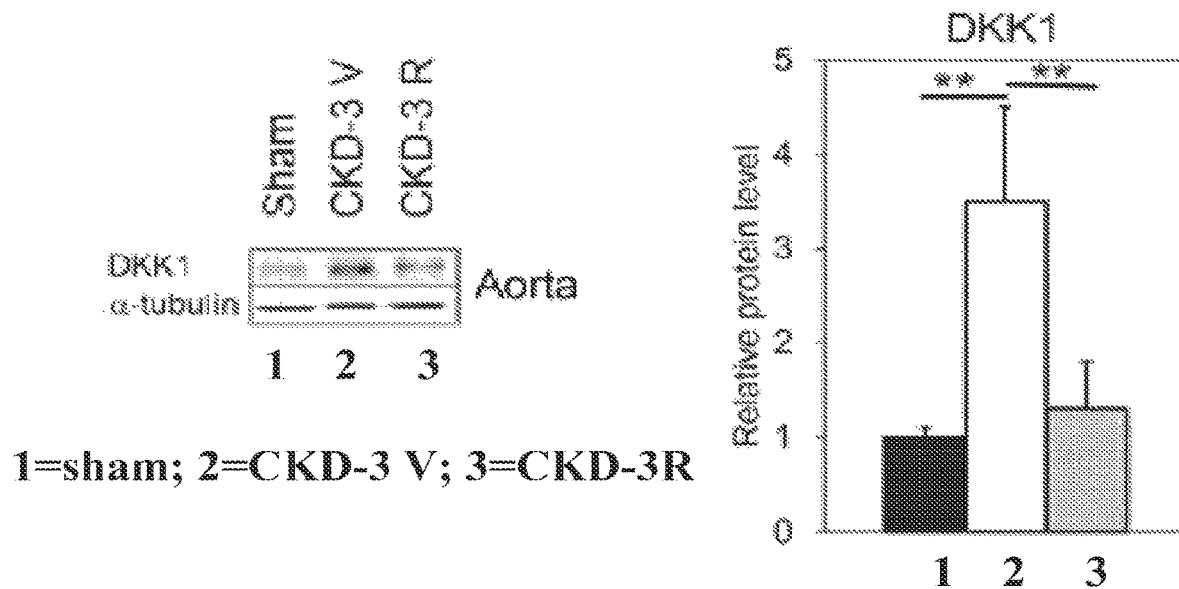
FIG. 28D depicts the analysis of Wnt signaling as marked by Dkk1 protein expression in westerns of aortic homogenates from sham, CKD-3 V and CKD-3 R treated mice and by immunoblot quantitation, n=4.
Figure 28E:
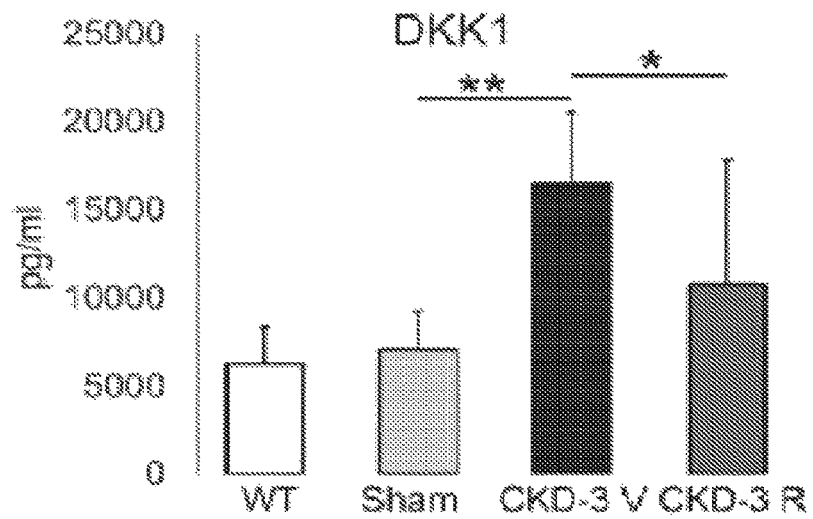
FIG. 28E depicts the effect of CKD-3V and mActRIIA-Fc on plasma Dkk1 levels. *p<0.05, **p<0.01.

Another non-canonical ActRIIA signaling pathway was examined, the Wnt pathway (FIG. 34). Wnt signaling appeared differentially regulated between aortic endothelium and VSMC. Aortic $\beta$-catenin, a major canonical Wnt induced transcription factor, was localized by immunofluorescence to endothelial cells, and was not detectable in VSMC (FIG. 28A, B). Dkk1 levels were analyzed in the VSMC as a biomarker of Wnt activity. CKD increased VSMC Dkk1 levels and mActRIIA-Fc treatment decreased Dkk1 levels in the CKD-3 mice (FIG. 28D). The decrease in aortic Dkk1 levels by mActRIIA-Fc indicates that vascular smooth muscle Wnt signaling was inhibited by the ActRIIA ligand trap. In addition, the effects of the ActRIIA ligand trap to decrease renal Wnt activity as shown below lead to a major decrease in circulating Dkk1 levels (FIG. 28E). The decrease in systemic Dkk1 was most likely to affect the endothelium. This resulted in increased Wnt signaling in the endothelium where beta-catenin is expressed as shown by the increase in aortic Axin2 levels (FIG. 28C). Axin2 is an immediate early gene stimulated by beta-catenin and often used for the assessment of Wnt signaling. (Mao J, Wang J, Liu B, et al. Mol. Cell 2001; 7: 801-809).

Effects of the ActRIIA Ligand Trap on $\alpha$klotho and Renal ActRIIA Signaling Renal $\alpha$klotho levels and the effects of CKD-3 and mActRIIA-Fc treatment were examined. As shown in FIG. 29A, a significant increase in renal $\alpha$klotho levels induced by mActRIIA-Fc treatment. Renal ActRIIA levels and ActRIIA signaling were examined. Renal ActRIIA levels were not affected by CKD-3 (FIG. 29B). A primary ActRIIA ligand, activin A, was strongly induced in the CKD-3 mice and suppressed by mActRIIA-Fc treatment (FIG. 31A-D). The lack of available phospho-Alk antibodies impaired detection of type I receptor activation, requiring instead a phosphoserine antibody to immunoprecipitate. Immunoblots of the precipitate were performed with anti-Alk antibodies. Alk4 phosphorylation was not significantly altered in the diseased kidneys of the CKD-3 model or by mActRIIA-Fc treatment (FIG. 29B). Renal phosphosmad 2/3, however, was increased by CKD-3 and decreased by mActRIIA-Fc indicating that the component of renal Smad 2/3 activation in CKD mediated through ActRIIA involved an Alk different from Alk4 (FIG. 29C).

Figure 30A:
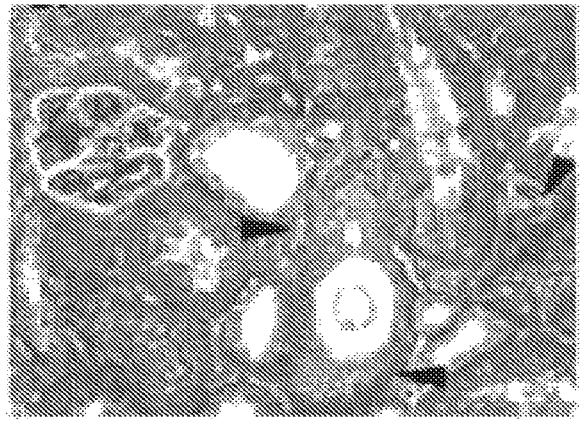
FIG. 30A depicts trichrome staining of kidney sections from CKD-3V mActRIIA-Fc treated mice.
Figure 30B:
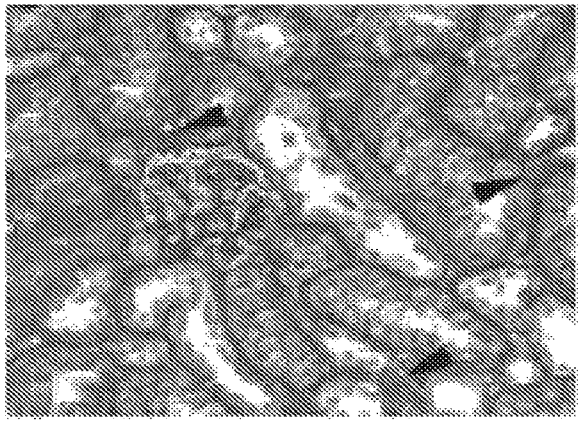
FIG. 30B depicts trichrome staining of kidney sections from CKD-3V mActRIIA-Fc treated mice.
Figure 30C:
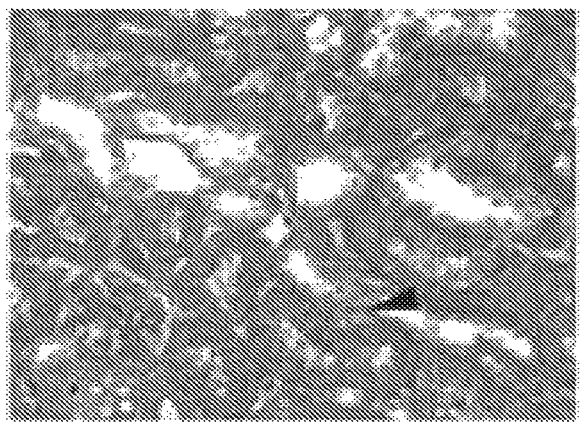
FIG. 30C depicts trichrome staining of kidney sections from CKD-3V mActRIIA-Fc treated mice.
Figure 30D:
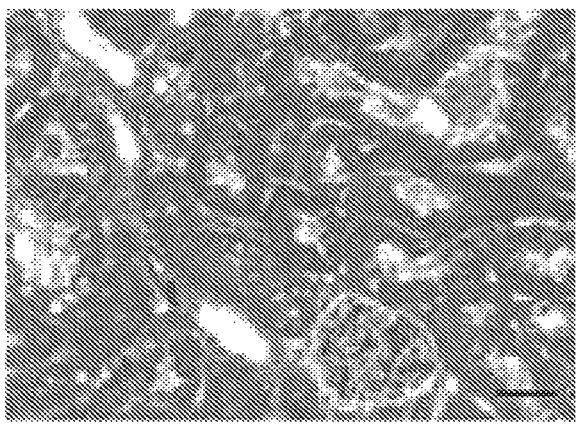
FIG. 30D depicts trichrome staining of kidney sections from CKD-3 mActRIIA-Fc treated mice. Areas of interstitial fibrosis marked by arrowheads. Kidneys of CKD-3 mActRIIA-Fc treated mice had decreased interstitial fibrosis. Scale bar 50 run. See FIG. 35 for marking of whole kidney coronal sections as to where the photomicrograph sections were taken.
Figure 30E:
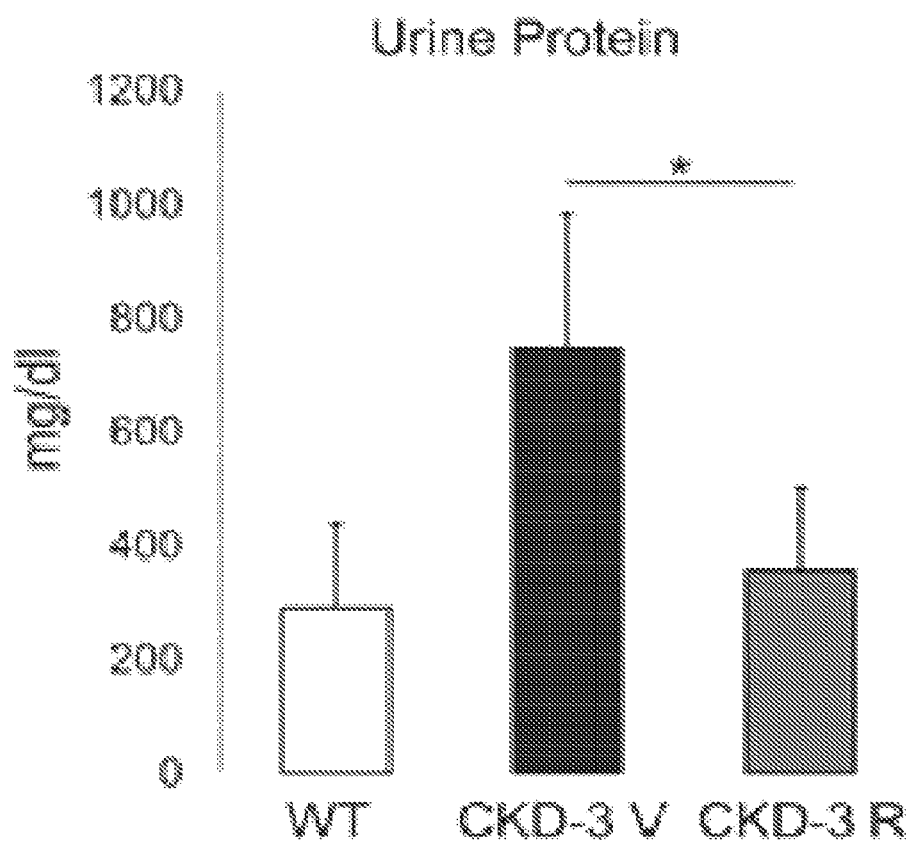
FIG. 30E depicts the effects of mActRIIA-Fc on urinary protein. There was significant proteinuria in the CKD-3V mice, which was decreased by mActRIIA-Fc treatment, *p<0.05.

The effects of the ActRIIA ligand trap were examined on renal fibrosis. FIG. 30A-D shows decreased renal fibrosis in Trichrome stained kidney cortex sections from CKD-3 mActRIIA-Fc treated mice (FIG. 30C and FIG. 30D) when compared to CKD-3V treated mice (FIG. 30A and FIG. 30B). FIG. 35A-D shows low magnification coronal kidney sections with arrows identifying from where the high power sections in FIG. 30A-D were taken and arrow heads delineating the scar reactions from the electrocautery kidney injury. mActRIIA-Fc decreased the scar reaction consistent with the role of activin in wound healing. Furthermore, mActRIIA-Fc decreased the proteinuria stimulated by CKD-3 (FIG. 30E) consistent with the decrease in renal phosphosmad 2/3 and fibrosis induced by mActRIIA-Fc treatment.

Potential ActRIIA Ligands in CKD

Figures 36A, 36B:
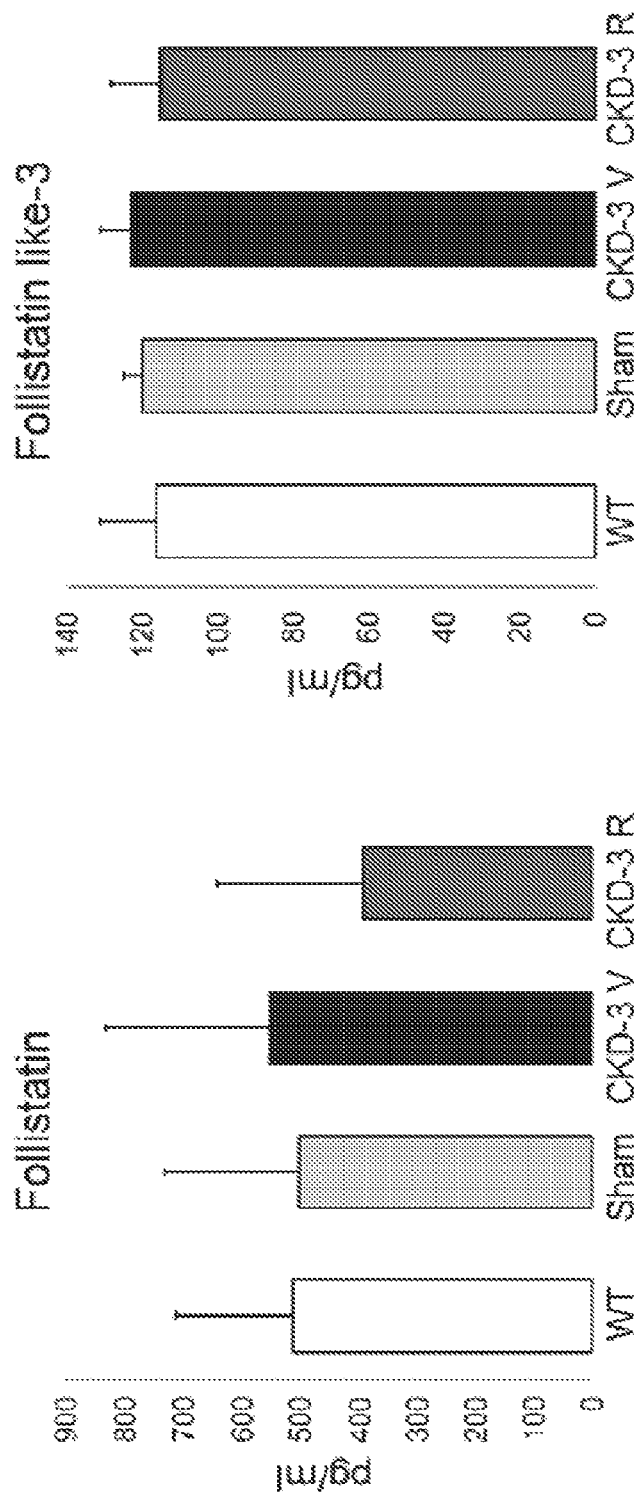
FIG. 36A depicts an absence of change in circulating follistatin levels in CKD-3 mice compared to WT and sham mice.
FIG. 36B depicts an absence of change in circulating follistatin like 3 (Fstl3) levels in CKD-3 mice compared to WT and sham mice.
Figure 37:
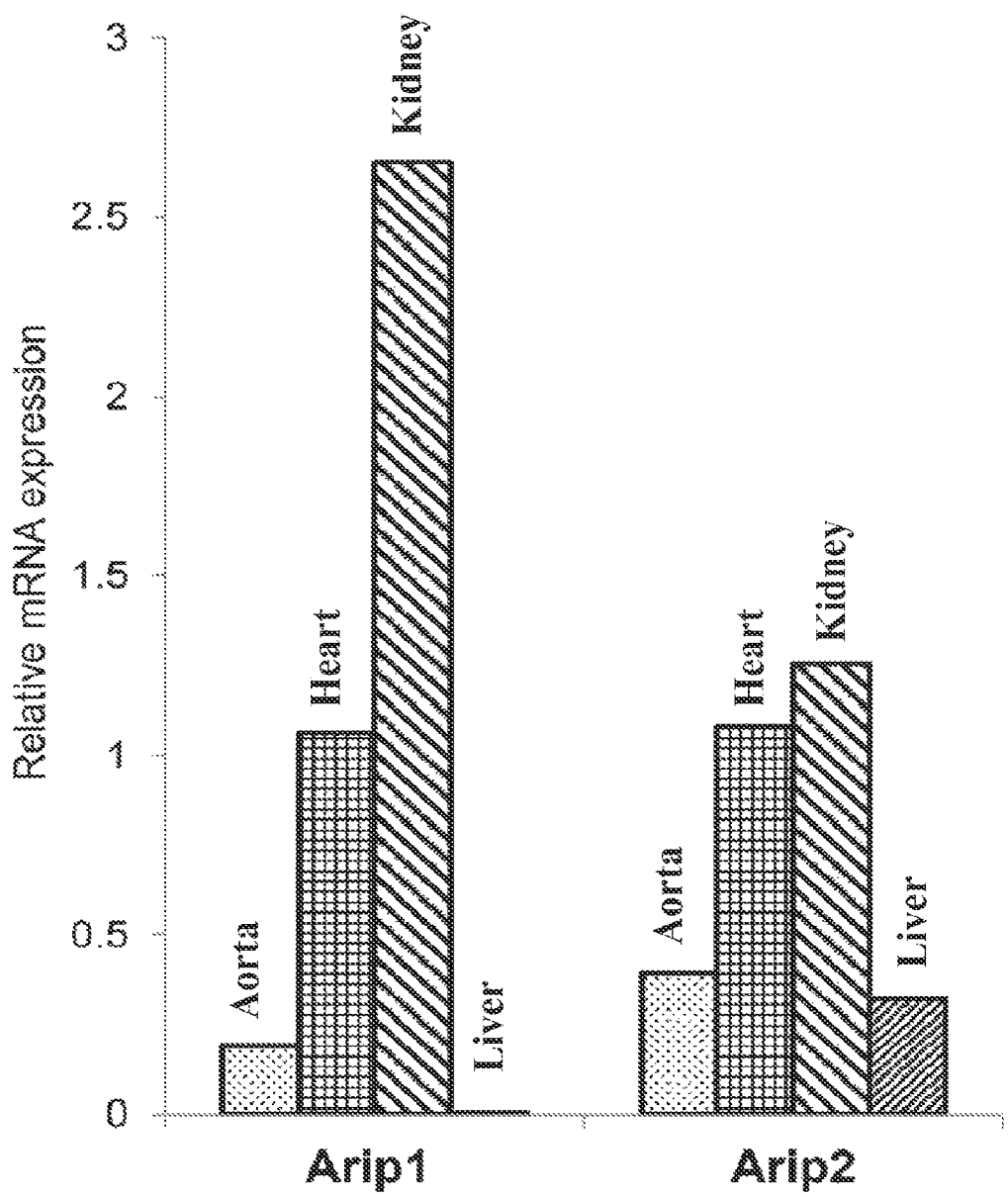
FIG. 37 depicts the levels of Activin Receptor Interacting Proteins (Arip1 and Arip2) in tissues of CKD-3 mice. Arip1 is strongly expressed in the remnant kidney of CKD-3 mice, more that twofold greater than Arip2 expression. Arip1 is expressed at low levels in the aortas of CKD-3 mice, while Arip2 expression in the aorta is twice that of Arip1.

There are multiple potential ActRIIA ligands including activins A and B, growth and differentiation factor 11 (GDF11), bone morphogenetic proteins 9 and 10 (BMP9 and 10), and other BMPs, such as BMP7, which have lower affinity for the receptor. But a primary ActRIIA ligand is activin. Using two models of CKD, it was identified that systemic circulating activin A levels were 10-fold elevated in the ldlr−/− ablative CKD model and 5-fold elevated in the Col4A5 Alport's syndrome mouse model (FIG. 31A, B). Activin B, GDF11, and BMP9 levels were not affected by CKD in these models. Physiologically, there is believed to be a small amount of free activin in the circulation. Without being bound by any particular theory, this may be due to levels of inhibitors stoichiometrically equaling activin levels. Activins associate with circulating inhibitory factors, follistatin and follistatin like 3 (fstL3), (Welt C, et al. Experimental Biol, and Med. 2002; 227: 724-752) and inhibin whose circulating levels (FIG. 36A, B) and tissue levels were not affected or decreased by CKD-3. The stoichiometry of follistatin, fstL3, and inhibin (e.g., the sum of 620 pg/ml, plus 400 pg/ml of unmeasured inhibin (Sharpe R M, et al. *J. Andrology* 1999; 20: 94-101)) to Activin A levels (>5000 pg/ml) in the circulation suggests that CKD produces significant free activin levels—a pathologic event making activin A an active circulating factor in CKD. This data indicates that kidney diseases produce one or more circulating ActRIIA ligands that could downregulate vascular ActRIIA.

Figure 31C:
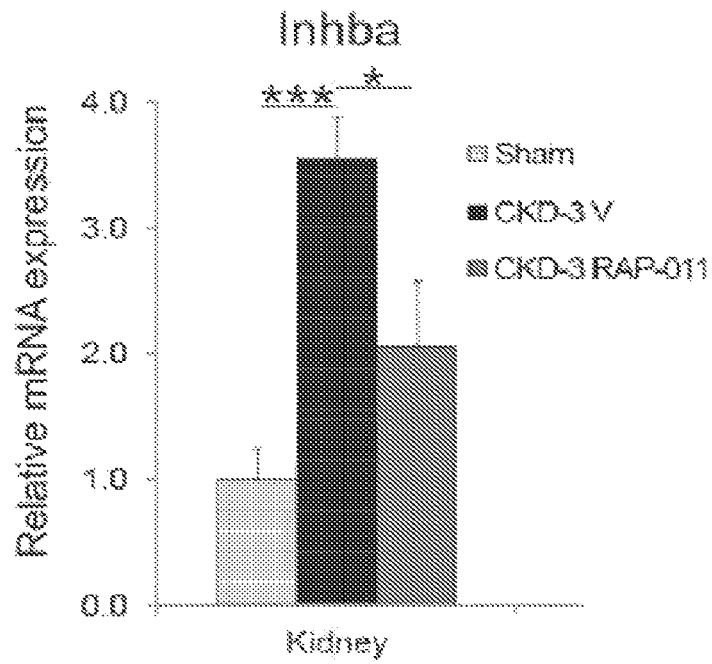
FIG. 31C depicts inhibin betaA (Inhba) mRNA expression in mouse kidney (activin-A is formed of homodimers of inhibin betaA).
Figure 31D:
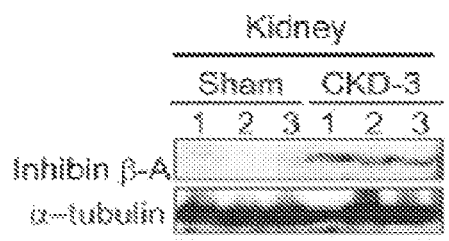
FIG. 31D depicts westerns for inhibin β-A in kidney homogenates.
Figure 31E:
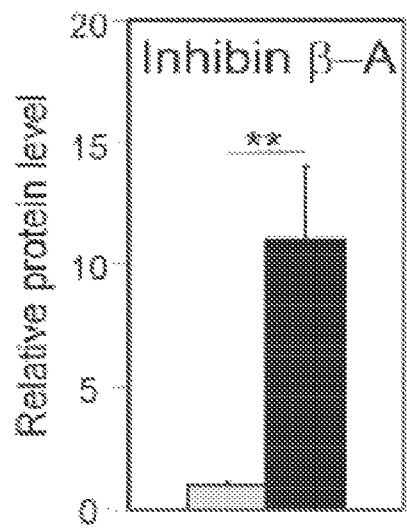
FIG. 31E depicts immunoblot quantitation of FIG. 31D, n=6 for the immunoblot quantitation; *p<0.05, p<0.01, *p<0.005.
Figures 32A, 32B:
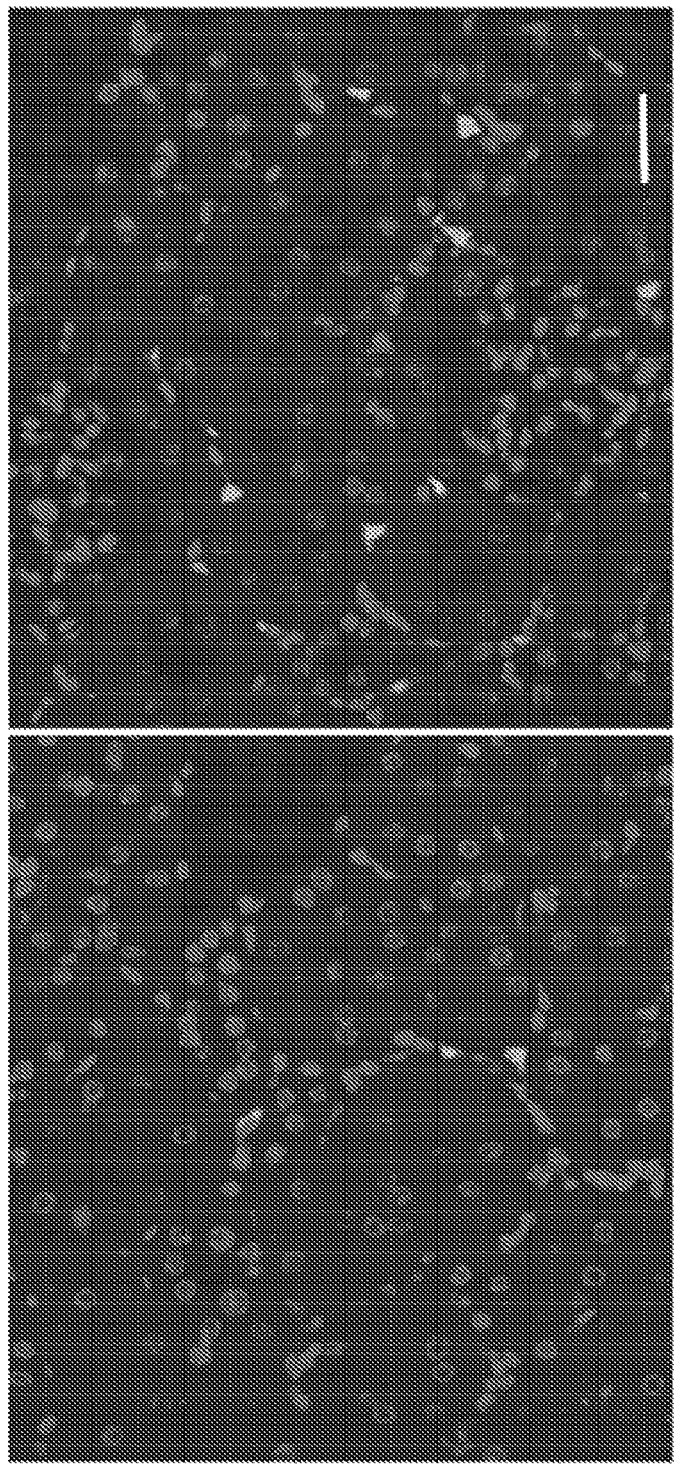
FIG. 32A shows kidney InhbA immunostaining in: sham.
FIG. 32B shows kidney InhbA immunostaining in CKD-3 Vehicle mice. In Sham mice occasional peritubular interstitial cells express activin-A, but in CKD-3 mice many more peritubular interstitial cells are positive for activin-A at varying levels of intensity. Scale bar 50 μm.

Kidney tissues were analyzed from ldlr−/− atherosclerotic calcification model for activin A (a homodimer of Inhibin betaA (Inhba)) to identify the source of increased circulating activin. Inhba mRNA was increased by CKD in the kidney (FIG. 31C) and activin (inhibin (3-A) protein levels were increased (FIG. 31D). Renal activin expression localized in the peritubular myofibroblasts of CKD-3 mice (FIG. 32A, B).

Conclusions

This example demonstrates that mActRIIA-Fc increased aortic ActRIIA signaling assessed by the levels of phosphorylated Smad2/3. Furthermore, mActRIIA-Rc treatment reversed CKD-induced vascular smooth muscle dedifferentiation, osteoblastic transition and neointimal plaque calcification. In the diseased kidneys, mActRIIA-Fc inhibited, rather than stimulated, ActRIIA signaling and decreased renal fibrosis and proteinuria. mActRIIA-Fc treatment decreased renal and circulating Dkk1 levels demonstrating that Wnt activation was downstream of ActRIIA. This example demonstrates that disordered ActRIIA signaling in CKD contributes to the CKD-MBD and renal fibrosis, identifies ActRIIA signaling as a therapeutic target in CKD, and demonstrates that an activin ligand trap (e.g., mActRIIA-Fc) can be utilized in the treatment of CKD.

DESCRIPTION OF THE SEQUENCES

TABLE 21

Sequence Information

| SEQ ID NO: | Description | Sequence |
|---|---|---|
| 1 | human ActRIIA precursor polypeptide | MGAAAKLAFAVFLISCSSGAILGRSETQECLFFNA NWEKDRTNQTGVEPCYGDKDKRRHCFATWKNIS GSIEIVKQGCWLDDINCYDRTDCVEKKDSPEVYF CCCEGNMCNEKFSYFPEMEVTQPTSNPVTPKPPY YNILLYSLVPLMLIAGIVICAFWVYRHHKMAYPP VLVPTQDPGPPPPSPLLGLKPLQLLEVKARGRFGC VWKAQLLNEYVAVKIFPIQDKQSWQNEYEVYSLP GMKHENILQFIGAEKRGTSVDVDLWLITAFHEKG SLSDFLKANVVSWNELCHIAETMARGLAYLHEDI PGLKDGUKPAISHRDIKSKNVLLKNNLTACIADFG LALKFEAGKSAGDTHGQVGTRRYMAPEVLEGAI NFQRDAFLRIDMYAMGLVLWELASRCTAADGPV DEYMLPFEEEIGQHPSLEDMQEVVVHKKKRPVLR DYWQKHAGMAMLCETIEECWDHDAEARLSAGC VGERITQMQRLTNIITTEDIVTVVTMVTNVDFPPK ESSL |
| 2 | human ActRIIA soluble (extracellular), processed polypeptide sequence | ILGRSETQECLFFNANWEKDRTNQTGVEPCYGDK DKRRHCFATWKNISGSIEIVKQGCWLDDINCYDR TDCVEKKDSPEVYFCCCEGNMCNEKFSYFPEMEV TQPTSNPVTPKPP |
| 3 | human ActRIIA soluble (extracellular), processed polypeptide sequence with the C-terminal 15 amino acids deleted | ILGRSETQECLFFNANWEKDRTNQTGVEPCYGDK DKRRHCFATWKNISGSIEIVKQGCWLDDINCYDR TDCVEKKDSPEVYFCCCEGNMCNEKFSYFPEM |
| 4 | nucleic acid sequence encoding human ActRIIA precursor protein | ATGGGAGCTGCTGCAAAGTTGGCGTTTGCCGTC TTTCTTATCTCCTGTTCTTCAGGTGCTATACTTG GTAGATCAGAAACTCAGGAGTGTCTTTTCTTTA ATGCTAATTGGGAAAAAGACAGAACCAATCAA ACTGGTGTTGAACCGTGTTATGGTGACAAAGAT AAACGGCGGCATTGTTTTGCTACCTGGAAGAAT ATTTCTGGTTCCATTGAAATAGTGAAACAAGGT |

TABLE 21-continued

Sequence Information

| SEQ ID NO: | Description | Sequence |
|---|---|---|
| | | TGTTGGCTGGATGATATCAACTGCTATGACAGG<br>ACTGATTGTGTAGAAAAAAAAGACAGCCCTGA<br>AGTATATTTTTGTTGCTGTGAGGGCAATATGTG<br>TAATGAAAAGTTTTCTTATTTTCCAGAGATGGA<br>AGTCACACAGCCCACTTCAAATCCAGTTACACC<br>TAAGCCACCCTATTACAACATCCTGCTCTATTCC<br>TTGGTGCCACTTATGTTAATTGCGGGGATTGTC<br>ATTTGTGCATTTTGGGTGTACAGGCATCACAAG<br>ATGGCCTACCCTCCTGTACTTGTTCCAACTCAA<br>GACCCAGGACCACCCCCACCTTCTCCATTACTA<br>GGGTTGAAACCACTGCAGTTATTAGAAGTGAAA<br>GCAAGGGGAAGATTTGGTTGTGTCTGGAAAGCC<br>CAGTTGCTTAACGAATATGTGGCTGTCAAAATA<br>TTTCCAATACAGGACAAACAGTCATGGCAAAAT<br>GAATACGAAGTCTACAGTTTGCCTGGAATGAAG<br>CATGAGAACATATTACAGTTCATTGGTGCAGAA<br>AAACGAGGCACCAGTGTTGATGTGGATCTTTGG<br>CTGATCACAGCATTTCATGAAAAGGGTTCACTA<br>TCAGACTTTCTTAAGGCTAATGTGGTCTCTTGG<br>AATGAACTGTGTCATATTGCAGAAACCATGGCT<br>AGAGGATTGGCATATTTACATGAGGATATACCT<br>GGCCTAAAAGATGGCCACAAACCTGCCATATCT<br>CACAGGGACATCAAAAGTAAAAATGTGCTGTT<br>GAAAAACAACCTGACAGCTTGCATTGCTGACTT<br>TGGGTTGGCCTTAAAATTTGAGGCTGGCAAGTC<br>TGCAGGCGATACCCATGGACAGGTTGGTACCCG<br>GAGGTACATGGCTCCAGAGGTATTAGAGGGTG<br>CTATAAACTTCGAAAGGGATGCATTTTTGAGGA<br>TAGATATGTATGCCATGGGATTAGTCCTATGGG<br>AACTGGCTTCTCGCTGTACTGCTGCAGATGGAC<br>CTGTAGATGAATACATGTTGCCATTTGAGGAGG<br>AAATrGGCCAGCATCCATCTCTTGAAGACATGC<br>AGGAAGTTGTTGTGCATAAAAAAAAGAGGCCT<br>GTTTTAAGAGATTATTGGCAGAAACATGCTGGA<br>ATGGCAATGCTCTGTGAAACCATTGAAGAATGT<br>TGGGATCACGACGCAGAAGCCAGGTTATCAGCT<br>GGATGTGTAGGTGAAAGAATTACCCAGATGCA<br>GAGACTAACAAATATTATTACCACAGAGGACAT<br>TGTAACAGTGGTCACAATGGTGACAAATGTTGA<br>CTTTCCTCCCAAAGAATCTAGTCTATGA |
| 5 | nucleic acid sequence encoding a human ActRIIA soluble (extracellular) polypeptide | ATACTTGGTAGATCAGAAACTCAGGAGTGTCTT<br>TTCTTTAATGCTAATTGGGAAAAAGACAGAACC<br>AATCAAACTGGTGTTGAACGTGTTATGGTGAC<br>AAAGATAAACGGCGGCATTGTTTTGCTACCTGQ<br>AAGAATATTTCTGGTTCCATTGAAATAGTGAAA<br>CAAGGTTGTTGGCTGGATGATATCAACTGCTAT<br>GACAGGACTGATTGTGTAGAAAAAAAAGACAG<br>CCCTGAAGTATATTTTTGTTGCTGTGAGGGCAA<br>TATGTGTAATGAAAAGTTTTCTTATTTTCCAGAG<br>ATGGAAGTCACACAGCCCACTTCAAATCCAGTT<br>ACACCTAAGCCACCC |
| 6 | fusion protein comprising a soluble extracellular domain of ActRIIA fused to an Fc domain | THTCPPCPAPELLGGPSVFLFPPKPKDTLMISRTPE<br>VTCVVVDX1VSHEDPEVKFNWYVDGVEVHNAKT<br>KPREEQYNSTYRVVSVLTVLHQDWLNGKEYKCK<br>X2VSNKALPVPIEKTISKAKGQPREPQVYTLPPSRE<br>EMTKNQVSLTCLVKGFYPSDIAVEWESNGQPENN<br>YKTTPPVLDSDGPFFLYSKLTVDKSRWQQGNVFS<br>CSVMHEALHNX3HYTQKSLSLSPGK* (wherein X1 is D or A; X2 is K or A and X3 is N or A) |
| 7 | Extracellular domain of human ActRIIA fused to a human Fc domain | ILGRSETQECLFFNANWEKDRTNQTGVEPCYGDK<br>DKRRHCFATWKNISGSIEIVKQGCWLDDINCYDR<br>TDCVEKKDSPEVYFCCCEGNMCNEKFSYFPEMEV<br>TQPTSNPVTPKPPTGGGTHTCPPCPAPELLGGPSV<br>FLFPPKPKDTLMISRTPEVTCVVVDVSHEDPEVKF<br>NWYVDGVEVHNAKTKPREEQYNSTYRVVSVLTV<br>LHQDWLNGKEYKCKVSNKALPVPIEKTISKAKGQ<br>PREPQVYTLPPSREEMTKNQVSLTCLVKGFYPSDI<br>AVEWESNGQPENNYKTTPPVLDSDGSFFLYSKLT<br>VDKSRWQQGNVFSCSVMHEALHNHYTQKSLSLS<br>PGK |

TABLE 21-continued

Sequence Information

| SEQ ID NO: | Description | Sequence |
|---|---|---|
| 8 | Leader sequence of Honey bee mellitin (HBML) | MKFLVNVALVFMVVYISYIYA |
| 9 | Leader sequence of Tissue Plasminogen Activator (TPA) | MDAMKRGLCCVLLLCGAVFVSP |
| 10 | Native ActRIIA leader | MGAAAKLAFAVFLISCSSGA |
| 11 | ActRIIA-hFc and mActRIIA-Fc N-terminal sequence | ILGRSETQE |
| 12 | ActRIIA-Fc Protein with deletion of the C-terminal 15 amino acids of the extracellular domain of ActRIIA | ILGRSETQECLFFNANWEKDRTNQTGVEPCYGDK DKRRHCFATWKNISGSIEIVKQGCWLDDINCYDR TDCVEKKDSPEVYFCCCEGNMCNEKFSYFPEMTG GGTHTCPPCPAPELLGGPSVFLFPPKPKDTLMISRT PEVTCVVVDVSHEDPEVKFNWYVDGVEVHNAKT KPREEQYNSTYRVVSVLTVLHQDWLNGKEYKCK VSNKALPVPIEKTISKAKGQPREPQVYTLPPSREE MTKNQVSLTCLVKGFYPSDIAVEWESNGQPENNY KTTPPVLDSDGSFFLYSKLTVDKSRWQQGNVFSC SVMHEALHNHYTQKSLSLSPGK |
| 13 | Unprocessed ActRIIA-hFc with TPA leader sequence | MDAMKRGLCCVLLLCGAVFVSPGAAILGRSETQE CLFFNANWEKDRTNQTGVEPCYGDKDKRRHCFA TWKNISGSIEIVKQGCWLDDINCYDRTDCVEKKD SPEVYFCCCEGNMCNEKFSYFPEMEVTQPTSNPV TPKPPTGGGTHTCPPCPAPELLGGPSVFLFPPKPKD TLMISRTPEVTCVVVDVSHEDPEVKFNWYVDGVE VHNAKTKPREEQYNSTYRVVSVLTVLHQDWLNG KEYKCKVSNKALPVPIEKTISKAKGQPREPQVYTL PPSREEMTKNQVSLTCLVKGFYPSDIAVEWESNG QPENNYKTTPPVLDSDGSFFLYSKLTVDKSRWQQ GNVFSCSVMHEALHNHYTQKSLSLSPGK |
| 14 | Nucleic acid sequence encoding Unprocessed ActRIIA-hFc with TPA leader sequence | ATGGATGCAATGAAGAGAGGGCTCTGCTGTGTG CTGCTGCTGTGTGGAGCAGTCTTCGTTTCGCCC GGCGCCGCTATACTTGGTAGATCAGAAACTCAG GAGTGTCTTTTTTAATGCTAATTGGGAAAAAG ACAGAACCAATCAAACTGGTGTTGAACCGTGTT ATGGTGACAAAGATAAACGGCGGCATTGTTTTG CTACCTGGAAGAATATTTCTGGTTCCATTGAAT AGTGAAACAAGGTTGTTGGCTGGATGATATCAA CTGCTATGACAGGACTGATTGTGTAGAAAAAAA AGACAGCCCTGAAGTATATTTCTGTTGCTGTGA GGGCAATATGTGTAATGAAAAGTTTTCTTATTT TCCGGAGATGGAAGTCACACAGCCCACTTCAAA TCCAGTTACACCTAAGCCACCCACCGGTGGTGG AACTCACACATGCCCACCGTGCCCAGCACCTGA ACTCCTGGGGGGACCGTCAGTCTTCCTCTTCCC CCCAAAACCCAAGGACACCCTCATGATCTCCCG GACCCCTGAGGTCACATGCGTGGTGGTGGACGT GAGCCACGAAGACCCTGAGGTCAAGTTCAACT GGTACGTGGACGGCGTGGAGGTGCATAATGCC AAGACAAAGCCGCGGGAGGAGCAGTACAACAG CACGTACCGTGTGGTCAGCGTCCTCACCGTCCT GCACCAGGACTGGCTGAATGGCAAGGAGTACA AGTGCAAGGTCTCCAACAAAGCCCTCCCAGTCC CCATCGAGAAAACCATCTCCAAAGCCAAAGGG CAGCCCCGAGAACCACAGGTGTACACCCTGCCC CCATCCCGGGAGGAGATGACCAAGAACCAGGT CAGCCTGACCTGCCTGGTCAAAGGCTTCTATCC CAGCGACATCGCCGTGGAGTGGGAGAGCAATG GGCAGCCGGAGAACAACTACAAGACCACGCCT CCCGTGCTGGACTCCGACGGCTCCTTCTTCCTCT ATAGCAAGCTCACCGTGGACAAGAGCAGGTGG CAGCAGGGGAACGTCTTCTCATGCTCCGTGATG CATGAGGCTCTGCACAACCACTACACGCAGAA GAGCCTCTCCCTGTCTCCGGTAAATGAGAATTC |

TABLE 21-continued

Sequence Information

| SEQ ID NO: | Description | Sequence |
|---|---|---|
| 15 | human ActRIIB soluble (extracellular), processed polypeptide sequence with the N-terminal 6 amino acids of the EC domain deleted and the C-terminal 4 amino acids of the EC domain deleted (amino acids 25-130 of SEQ ID NO: 28) and with an L79D mutation | ETRECIYYNANWELERTNQSGLERCEGEQDKRLH CYASWRNSSGTIELVKKGCWDDDFNCYDRQECV ATEENPQVYFCCCEGNFCNERFTHLPEAGGP EVTYEPPP |
| 16 | human ActRIIB precursor protein sequence (A64) | MTAPWVALALLWGSLWPGSGRGEAETRECIYYN ANWELERTNQSGLERCEGEQDKRLHCYASWANS SGTIELVKKGCWLDDFNCYDRQECVATEENPQV YFCCCEGNFCNERFTHLPEAGGPEVTYEPPPTAPT LLTVLAYSLLPIGGLSLIVLLAFWMYRHRKPPYGH VDIHEDPGPPPPSPLVGLKPLQLLEIKARGRFGCV WKAQLMNDFVAVKIFPLQDKQSWQSEREIFSTPG MKHENLLQFIAAEKRGSNLEVELWLITAFHDKGS LTDYLKGNIITWNELCHVAETMSRGLSYLHEDVP WCRGEGHKPSIAHRDFKSKNVLLKSDLTAVLADF GLAVRFEPGKPPGDTHGQVGTRRYMAPEVLEGAI NFQRDAFLRIDMYAMGLVLWELVSRCKAADGPV DEYMLPFEEEIGQHPSLEELQEVVVHKKMRPTIKD HWLKHPGLAQLCVTIEECWDHDAEARLSAGCVE ERVSLIRRSVNGTTSDCLVSLVTSVTNVDLPPKES SI |
| 17 | human ActRIIB soluble (extracellular), processed polypeptide sequence (amino acids 19-134 of SEQ ID NO: 16) | SGRGEAETRECIYYNANWELERTNQSGLERCEGE QDKRLHCYASWANSSGTIELVKKGCWLDDFNCY DRQECVATEENPQVYFCCCEGNFCNERFTHLPEA GGPEVTYEPPPTAPT |
| 18 | human ActRIIB soluble (extracellular), processed polypeptide sequence with the C-terminal 15 amino acids deleted (amino acids 19-119 of SEQ ID NO: 16) | SGRGEAETRECIYYNANWELERTNQSGLERCEGE QDKRLHCYASWANSSGTIELVKJCGCWLDDFNCY DRQECVATEENPQVYFCCCEGNFCNERFTHLPEA |
| 19 | nucleic acid sequence encoding a human ActRIIB (A64) precursor protein | ATGACGGCGCCCTGGGTGGCCCTCGCCCTCCTC TGGGGATCGCTGTGGCCCGGCTCTGGGCGTGGG GAGGCTGAGACACGGGAGTGCATCTACTACAA CGCCAACTGGGAGCTGGAGCGCACCAACCAGA GCGGCCTGGAGCGCTGCGAAGGCGAGCAGGAC AAGCGGCTGCACTGCTACGCCTCCTGGGCCAAC AGCTCTGGCACCATCGAGCTCGTGAAGAAGGG CTGCTGGCTAGATGACTTCAACTGCTACGATAG GCAGGAGTGTGTGGCCACTGAGGAGAACCCCC AGGTGTACTTCTGCTGCTGTGAAGGCAACTTCT GCAACGAGCGCTTCACTCATTTGCCAGAGGCTG GGGGCCCGGAAGTCACGTACGAGCCACCCCCG ACAGCCCCCACCCTGCTCACGGTGCTGGCCTAC TCACTGCTGCCCATCGGGGGCCTTTCCCTCATC GTCCTGCTGGCCTTTTGGATGTACCGGCATCGC AAGCCCCCCTACGGTCATGTGGACATCCATGAG GACCCTGGGCCTCCACCACCATCCCCTCTGGTG GGCCTGAAGCCACTGCAGCTGCTGGAGATCAA GGCTCGGGGCGCTTTGGCTGTGTCTGGAAGGC CCAGCTCATGAATGACTTTGTAGCTGTCAAGAT CTTCCCACTCCAGGACAAGCAGTCGTGGCAGAG TGAACGGGAGATCTTCAGCACACCTGGCATGAA GCACGAGAACCTGCTACAGTTCATTGCTGCCGA GAAGCGAGGCTCCAACCTCGAAGTAGAGCTGT GGCTCATCACGGCCTTCCATGACAAGGGCTCCC TCACGGATTACCTCAAGGGGAACATCATCACAT GGAACGAACTGTGTCATGTAGCAGAGACGATG TCACGAGGCCTCTCATACCTGCATGAGGATGTG CCCTGGTGCCGTGGCGAGGGCCACAAGCCGTCT ATTGCCCACAGGGACTTTAAAAGTAAGAATGTA TTGCTGAAGAGCGACCTCACAGCCGTGCTGGCT GACTTTGGCTTGGCTGTTCGATTTGAGCCAGGG |

TABLE 21-continued

Sequence Information

| SEQ ID NO: | Description | Sequence |
|---|---|---|
| | | AAACCTCCAGGGGACACCCACGGACAGGTAGG CACGAGACGGTACATGGCTCCTGAGGTGCTCGA GGGAGCCATCAACTTCCAGAGAGATGCCTTCCT GCGCATTGACATGTATGCCATGGGGTTGGTGCT GTGGGAGCTTGTGTCTCGCTGCAAGGCTGCAGA CGGACCCGTGGATGAGTACATGCTGCCCTTTGA GGAAGAGATTGGCCAGCACCCTTCGTTGGAGG AGCTGCAGGAGGTGGTGGTGCACAAGAAGATG AGGCCCACCATTAAAGATCACTGGTTGAAACAC CCGGGGCCTGGCCCAGCTTTGTGTGACCATCGAG GAGTGCTGGGACCATGATGCAGAGGCTCGCTTG TCCGCGGGCTGTGTGGAGGAGCGGGTGTCCCTG ATTCGGAGGTCGGTCAACGGCACTACCTCGGAC TGTCTCGTTTCCCTGGTGACCTCTGTCACCAATG TGGACCTGCCCCCTAAAGAGTCAAGCATCTAA |
| 20 | fusion protein comprising a soluble extracellular domain of ActRIIB (A64; SEQ ID NO: 17) fused to an Fc domain | SGRGEAETRECIYYNANWELERTNQSGLERCEGE QDKRLHCYASWANSSGTIELVKKGCWLDDFNCY DRQECVATEENPQVYFCCCEGNFCNERFTHLPEA GGPEVTYEPPPTAPTGGGTHTCPPCPAPELLGGPS VFLFPPKPKDTLMISRTPEVTCVVVDVSHEDPEVK FNWYVDGVEVHNAKTKPREEQYNSTYRVVSVLT VLHQDWLNGKEYKCKVSNKALPVPIEKTISKAKG QPREPQVYTLPPSREEMTKNQVSLTCLVKGFYPS DIAVEWESNGQPENNYKTTPPVLDSDGSFFLYSKL TVDKSRWQQGNVFSCSVMHEALHNHYTQKSLSL SPGK |
| 21 | fusion protein comprising a soluble extracellular domain of ActRIIB (A64) with the C-terminal 15 amino acids deleted (SEQ ID NO: 18) fused to an Fc domain | SGRGEAETRECIYYNANWELERTNQSGLERCEGE QDKRLHCYASWANSSGTIELVKKGCWLDDFNCY DRQECVATEENPQVYFCCCEGNFCNERFTHLPEA GGGTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPVPIEKTISKAKGQPREPQVYTLPPSR EEMTKNQVSLTCLVKGFYPSDIAVEWESNGQPEN NYKTTPPVLDSDGSFFLYSKLTVDKSRWQQGNVF SCSVMHEALHNHYTQKSLSLSPGK |
| 22 | human ActRIIB soluble (extracellular), processed polypeptide sequence with the N-terminal 6 amino acids of the EC domain deleted and the C-terminal 5 amino acids of the EC domain deleted (amino acids 25-129 of SEQ ID NO: 28) and with an L79D mutation | ETRECIYYNANWELERTNQSGLERCEGEQDKRLH CYASWRNSSGTIELVKKGCWDDDFNCYDRQECV ATEENPQVYFCCCEGNFCNERFTHLPEAGGPEVT YEPP |
| 23 | human ActRIIB soluble (extracellular), processed polypeptide sequence with the N-terminal 6 amino acids of the EC domain deleted and the C-terminal 3 amino acids of the EC domain deleted (amino acids 25-131 of SEQ ID NO: 28) and with an L79D mutation | ETRECIYYNANWELERTNQSGLERCEGEQDKRLH CYASWRNSSGTIELVKKGCWDDDFNCYDRQECV ATEENPQVYFCCCEGNFCNERFTHLPEAGGPEVT YEPPPT |
| 24 | Unprocessed ActRIIB-Fc fusion protein with the N-terminal 6 amino acids of the EC domain deleted and the C-terminal 3 amino acids of the EC domain deleted (amino acids 25-131 of SEQ ID NO: 28) and with an L79D mutation and with TPA leader sequence | MDAMKRGLCCVLLLCGAVFVSPGAAETRECIYY NANWELERTNQSGLERCEGEQDKRLHCYASWRN SSGTIELVKKGCWDDDFNCYDRQECVATEENPQV YFCCCEGNFCNERFTHLPEAGGPEVTYEPPPTGGG THTCPPCPAPELLGGPSVFLFPPKPKDTLMISRTPE VTCVVVDVSHEDPEVKFNWYVDGVEVHNAKTK PREEQYNSTYRVVSVLTVLHQDWLNGKEYKCKV SNKALPAPIEKTISKAKGQPREPQVYTLPPSREEM TKNQVSLTCLVKGFYPSDIAVEWESNGQPENNYK TTPPVLDSDGSFFLYSKLTVDKSRWQQGNVFSCS VMHEALHNHYTQKSLSLSPGK* |

TABLE 21-continued

Sequence Information

| SEQ ID NO: | Description | Sequence |
|---|---|---|
| 25 | Processed ActRIIB-Fc fusion protein with the N-terminal 6 amino acids of the EC domain deleted and the C-terminal 3 amino acids of the EC domain deleted (amino acids 25-131 of SEQ ID NO: 28) and with an L79D mutation | ETRECIYYNANWELERTNQSGLERCEGEQDKRLH CYASWRNSSGTIELVKKGCWDDDFNCYDRQECV ATEENPQVYFCCCEGNFCNERFTHLPEAGGPEVT YEPPPTGGGTHTCPPCPAPELLGGPSVFLFPPKPKD TLMISRTPEVTCVVVDVSHEDPEVKFNWYVDGVE VHNAKTKPREEQYNSTYRVVSVLTVLHQDWLNG KEYKCKVSNKALPAPIEKTISKAKGQPREPQVYTL PPSREEMTKNQVSLTCLVKGFYPSDIAVEWESNG QPENNYKTTPPVLDSDGSFFLYSKLTVDKSRWQQ GNVFSCSVMHEALHNHYTQKSLSLSPGK* |
| 26 | human ActRIIB soluble (extracellular), processed polypeptide sequence (amino acids 20-134 of SEQ ID NO: 16) | GRGEAETRECIYYNANWELERTNQSGLERCEGEQ DKRLHCYASWANSSGTIELVKKGCWLDDFNCYD RQECVATEENPQVYFCCCEGNFCNERFTHLPEAG GPEVTYEPPPTAPT |
| 27 | human ActRIIB soluble (extracellular), processed polypeptide sequence with the C-terminal 15 amino acids deleted (amino acids 20-119 of SEQ ID NO: 16) | GRGEAETRECIYYNANWELERTNQSGLERCEGEQ DKRLHCYASWANSSGTIELVKKGCWLDDFNCYD RQECVATEENPQVYFCCCEGNFCNERFTHLPE A |
| 28 | human ActRIIB precursor protein sequence (R64) | MTAPWVALALLWGSLWPGSGRGEAETRECIYYN ANWELERTNQSGLERCEGEQDKRLHCYASWRNS SGTIELVKKGCWLDDFNCYDRQECVATEENPQV YFCCCEGNFCNERFTHLPEAGGPEVTYEPPPTAPT LLTVLAYSLLPIGGLSLIVLLAFWMYRHRKPPYGH VDIHEDPGPPPPSPLVGLKPLQLLEIKARGRFGCV WKAQLMNDFVAVKIFPLQDKQSWQSEREIFSTPG MKHENLLQFIAAEKRGSNLEVELWLITAPHDKGS LTDYLKGNIITWNELCHVAETMSRGLSYLHEDVP WCRGEGHKPSIAHRDFKSKNVLLKSDLTAVLADF GLAVRFEPGKPPGDTHGQVGTRRYMAPEVLEGAI NFQRDAFLRIDMYAMGLVLWELVSRCKAADGPV DEYMLPFEEEIGQHPSLEELQEVVVHKKMRPTIKD HWLKHPGLAQLCVTIEECWDHDAEARLSAGCVE ERVSLIRRSVNGTTSDCLVSLVTSVTNVDLPPKES SI |
| 29 | human ActRIIB soluble (extracellular), processed polypeptide sequence (amino acids 19-134 of SEQ ID NO: 28) | SGRGEAETRECIYYNANWELERTNQSGLERCEGE QDKRLHCYASWRNSSGTIELVKKGCWLDDFNCY DRQECVATEENPQVYFCCCEGNFCNERFTHLPEA GGPEVTYEPPPTAPT |
| 30 | human ActRIIB soluble (extracellular), processed polypeptide sequence with the C-terminal 15 amino acids deleted (amino acids 19-119 of SEQ ID NO: 28) | SGRGEAETRECIYYNANWELERTNQSGLERCEGE QDKRLHCYASWRNSSGTIELVKKGCWLDDFNCY DRQECVATEENPQVYFCCCEGNFCNERFTHLPEA |
| 31 | human ActRIIB soluble (extracellular), processed polypeptide sequence (amino acids 20-134 of SEQ ID NO: 28) | GRGEAETRECIYYNANWELERTNQSGLERCEGEQ DKRLHCYASWRNSSGTIELVKKGCWLDDFNCYD RQECVATEENPQVYFCCCEGNFCNERFTHLPEAG GPEVTYEPPPTAPT |
| 32 | human ActRIIB soluble (extracellular), processed polypeptide sequence with the C-terminal 15 amino acids deleted (amino acids 20-119 of SEQ ID NO: 28) | GRGEAETRECIYYNANWELERTNQSGLERCEGEQ DKRLHCYASWRNSSGTIELVKKGCWLDDFNCYD RQECVATEENPQVYFCCCEGNFCNERFTHLPE A |

TABLE 21-continued

Sequence Information

| SEQ ID NO: | Description | Sequence |
|---|---|---|
| 33 | human ActRIIB soluble (extracellular), processed polypeptide sequence with the N-terminal 6 amino acids of the EC domain deleted and the C-terminal 3 amino acids of the EC domain deleted (amino acids 25-131 of SEQ ID NO: 16) and with an L79D mutation | ETRECIYYNANWELERTNQSGLERCEGEQDKRLH CYASWANSSGTIELVKKGCWDDDFNCYDRQECV ATEENPQVYFCCCEGNFCNERFTHLPEAGGPEVT YEPPPT |
| 34 | Unprocessed ActRIIB-Fc fusion protein with the N-terminal 6 amino acids of the EC domain deleted and the C-terminal 3 amino acids of the EC domain deleted (amino acids 25-131 of SEQ ID NO: 16) and with an L79D mutation and with TPA leader sequence | MDAMKRGLCCVLLLCGAVFVSPGAAETRECIYY NANWELERTNQSGLERCEGEQDKRLHCYASWAN SSGTIELVKKGCWDDDFNCYDRQECVATEENPQV YFCCCEGNFCNERFTHLPEAGGPEVTYEPPPTGGG THTCPPCPAPELLGGPSVFLFPPKPKDTLMISRTPE VTCVVVDVSHEDPEVKFNWYVDGVEVHNAKTK PREEQYNSTYRVVSVLTVLHQDWLNGKEYKCKV SNKALPAPIEKTISKAKGQPREPQVYTLPPSREEM TKNQVSLTCLVKGFYPSDIAVEWESNGQPENNYK TTPPVLDSDGSFFLYSKLTVDKSRWQQGNVFSCS VMHEALHNHYTQKSLSLSPGK* |
| 35 | Processed ActRIIB-Fc fusion protein with the N-terminal 6 amino acids of the EC domain deleted and the C-terminal 3 amino acids of the EC domain deleted (amino acids 25-131 of SEQ ID NO: 16*) and with an L79D mutation | ETRECIYYNANWELERTTSQSGLERCEGEQDKRLH CYASWANSSGTIELVKKGCWDDDFNCYDRQECV ATEENPQVYFCCCEGNFCNERFTHLPEAGGPEVT YEPPPTGGGTHTCPPCPAPELLGGPSVFLFPPKPKD TLMISRTPEVTCVVVDVSHEDPEVKFNWYVDGVE VHNAKTKPREEQYNSTYRWSVLTVLHQDWLNG KEYKCKVSNKALPAPIEKTISKAKGQPREPQVYTL PPSREEMTKNQVSLTCLVKGFYPSDIAVEWESNG QPENNYKTTPPVLDSDGSFFLYSKLTVDKSRWQQ GNVFSCSVMHEALHNHYTQKSLSLSPGK* |
| 36 | human ActRIIB soluble (extracellular), processed polypeptide sequence (amino acids 20-134 of SEQ ID NO: 28) with L79D mutation | GRGEAETRECIYYNANWELERTNQSGLERCEGEQ DKRLHCYASWRNSSGTIELVKKGCWDDDFNCYD RQECVATEENPQVYFCCCEGNFCNERFTHLPEAG GPEVTYEPPPTAPT |
| 37 | human ActRIIB soluble (extracellular), processed polypeptide sequence (amino acids 20-134 of SEQ ID NO: 16) with L79D mutation | GRGEAETRECIYYNANWELERTNQSGLERCEGEQ DKRLHCYASWANSSGTIELVKKGCWDDDFNCYD RQECVATEENPQVYFCCCEGNFCNERFTHLPEAG GPEVTYEPPPTAPT |
| 38 | human ActRIIB soluble (extracellular), processed polypeptide sequence (amino acids 20-134 of SEQ ID NO: 28) with L79D mutation fused to an Fc domain with a GGG linker | GRGEAETRECIYYNANWELERTNQSGLERCEGEQ DKRLHCYASWRNSSGTIELVKKGCWDDDFNCYD RQECVATEENPQVYFCCCEGNFCNERFTIILPEAG GPEVTYEPPPTAPTGGGTHTCPPCPAPELLGGPSV FLFPPKPKDTLMISRTPEVTCVVVDVSHEDPEVKF NWYVDGVEVHNAKTKPREEQYNSTYRVVSVLTV LHQDWLNGKEYKCKVSNKALPAPIEKTISKAKGQ PREPQVYTLPPSREEMTKNQVSLTCLVKGFYPSDI AVEWESNGQPENNYKTTPPVLDSDGSFFLYSKLT VDKSRWQQGNVFSCSVMFffiALHNHYTQKSLSLS PGK* |
| 39 | human ActRIIB soluble (extracellular), processed polypeptide sequence (amino acids 20-134 of SEQ ID NO: 16) with L79D mutation fused to an Fc domain | GRGEAETRECIYYNANWELERTNQSGLERCEGEQ DKRLHCYASWANSSGTIELVKKGCWDDDFNCYD RQECVATEENPQVYFCCCEGNFCNERFTHLPEAG GPEVTYEPPPTAPTGGGTHTCPPCPAPELLGGPSV FLFPPKPKDTLMISRTPEVTCVVVDVSHEDPEVKF NWYVDGVEVHNAKTKPREEQYNSTYRVVSVLTV LHQDWLNGKEYKCKVSNKALPAPIEKTISKAKGQ PREPQVYTLPPSREEMTKNQVSLTCLVKGFYPSDI AVEWESNGQPENNYKTTPPVLDSDGSFFLYSKLT VDKSRWQQGNVFSCSVMHEALHNHYTQKSLSLS PGK* |

TABLE 21-continued

Sequence Information

| SEQ ID NO: | Description | Sequence |
|---|---|---|
| 40 | human ActRIIB soluble (extracellular), processed polypeptide sequence (amino acids 20-134 of SEQ ID NO: 28) with L79D mutation fused to an Fc domain and with TPA leader sequence | MDAMKRGLCCVLLLCGAVFVSPGASGRGEAETR ECIYYNANWELERTNQSGLERCEGEQDKRLHCY ASWRNSSGTIELVKKGCWDDDFNCYDRQECVAT EENPQVYFCCCEGNFCNERFTHLPEAGGPEVTYEP PPTAFrGGGTHTCPPCPAPELLGGPSVFLFPPKPKD TLMISRTPEVTCVWVDVSHEDPEVKFNWYVDGVE VHNAKTKPREEQYNSTYRVVSVLTVLHQDWLNG KEYKCKVSNKALPAPIEKTISKAKGQPREPQVYTL PPSREEMTKNQVSLTCLVKGFYPSDIAVEWESNG QPENNYKTTPPVLDSDGSFFLYSKLTVDKSRWQQ GNVFSCSVMHEALHNHYTQKSLSLSPGK* |
| 41 | human ActRIIB soluble (extracellular), processed polypeptide sequence (amino acids 20-134 of SEQ ID NO: 16) with L79D mutation fused to an Fc domain and with TPA leader sequence | MDAMKRGLCCVLLLCGAVFVSPGASGRGEAETR ECTYYNANWELERTNQSGLERCEGEQDKRLHCY ASWANSSGTIELVKKGCWDDDFNCYDRQECVAT EENPQVYFCCCEGNFCNERFTHLPEAGGPEVTYEP PPTAPTGGGTHTCPPCPAPELLGGPSVFLFPPKPKD TLMISRTPEVTCVWDVSHEDPEVKFNWYVDGVE VHNAKTKPREEQYNSTYRVVSVLTVLHQDWLNG KEYKCKVSNKALPAPIEKTISKAKGQPREPQVYTL PPSREEMTKNQVSLTCLVKGFYPSDIAVEWESNG QPENNYKTTPPVLDSDGSFFLYSKLTVDKSRWQQ GNVFSCSVMHEALHNHYTQKSLSLSPGK* |
| 42 | human ActRIIB soluble (extracellular), processed polypeptide sequence having a variant C-terminal sequence (disclosed in WO2007/053775) | GRGEAETRECIYYNANWELERTNQSGLERCEGEQ DKRLHCYASWRNSSGTIELVKKGCWLDDFNCYD RQECVATEENPQVYFCCCEGNFCNERFTHLPEAG GPEGPWASTTIPSGGPEATAAAGDQGSGALWLCL EGPAHE |
| 43 | human ActRIIB soluble (extracellular), processed polypeptide sequence having a variant C-terminal sequence (disclosed in WO2007/053775) having an L79D mutation | GRGEAETRECIYYNANWELERTNQSGLERCEGEQ DKRLHCYASWRNSSGTIELVKKGCWDDDFNCYD RQECVATEENPQVYFCCCEGNFCNERFTHLPEAG GPEGPWASTTIPSGGPEATAAAGDQGSGALWLCL EGPAHE |
| 44 | human ActRIIB soluble (extracellular), processed polypeptide sequence having a variant C-terminal sequence (disclosed in WO2007/053775) having an L79D muiation fused to an Fc domain with a TGGG linker | GRGEAETREC1YYNANWELERTNQSGLERCEGEQ DKRLHCYASWRNSSGTIELVKKGCWDDDFNCYD RQECVATEENPQVYFCCCEGNFCNERFTHLPEAG GPEGPWASTTIPSGGPEATAAAGDQGSGALWLCL EGPAHETGGGTHTCPPCPAPELLGGPSVFLFPPKP KDTLMISRTPEVTCVVVDVSHEDPEVKFNWYVD GVEVHNAKTKPREEQYNSTYRWSVLTVLHQDW LNGKEYKCKVSNKALPAPIEKTISKAKGQPREPQV YTLPPSREEMTKNQVSLTCLVKGFYPSDIAVEWES NGQPENNYKTTPPVLDSDGSFFLYSKLTVDKSRW QQONVFSCSVMHEALHNHYTQKSLSLSPGK* |
| 45 | Nucleic Acid Sequence Encoding SEQ ID NO: 24 | ATGGATGCAATGAAGAGAGGGCTCTGCTGTGTG CTGCTGCTGTGTGGAGCAGTCTTCGTTTCGCCC GGCGCCGCCGAAACCCGCGAATGTATTTATTAC AATGCTAATTGGGAACTCGAACGGACGAACCA ATCCGGGCTCGAACGGTGTGAGGGGGAACAGG ATAAACGCCTCCATTGCTATGCGTCGTGGAGGA ACTCCTCCGGGACGATTGAACTGGTCAAGAAAG GGTGCTGGGACGACGATTTCAATTGTTATGACC GCCAGGAATGTGTCGCGACCGAAGAGAATCCG CAGGTCTATTTCTGTTGTTGCGAGGGGAATTTCT GTAATGAACGGTTTACCCACCTCCCCGAAGCCG GCGGGCCCGAGGTGACCTATGAACCCCCGCCC ACCGGTGGTGGAACTCACACATGCCCACCGTGC CCAGCACCTGAACTCCTGGGGGGACCGTCAGTC TTCCTCTTCCCCCCAAAACCCAAGGACACCCTC ATGATCTCCCGGACCCCTGAGGTCACATGCGTG GTGGTGGACGTGAGCCACGAAGACCCTGAGGT CAAGTTCAACTGGTACGTGGACGGCGTGGAGGT GCATAATGCCAAGACAAAGCCGCGGGAGGAGC AGTACAACAGCACGTACCGTGTGGTCAGCGTCC TCACCGTCCTGCACCAGGACTGGCTGAATGGCA AGGAGTACAAGTGCAAGGTCTCCAACAAAGCC CTCCCAGCCCCCATCGAGAAAACCATCTCCAAA GCCAAAGGGCAGCCCCGAGAACCACAGGTGTA CACCCTGCCCCCATCCCGGGAGGAGATGACCA |

TABLE 21-continued

Sequence Information

| SEQ ID NO: | Description | Sequence |
|---|---|---|
| | | AGAACCAGGTCAGCCTGACCTGCCTGGTCAAAG GCTTCTATCCCAGCGACATCGCCGTGGAGTGGG AGAGCAATGGGCAGCCGGAGAACAACTACAAG ACCACGCCTCCCGTGCTGGACTCCGACGGCTCC TTCTTCCTCTATAGCAAGCTCACCGTGGACAAG AGCAGGTGGCAGCAGGGGAACGTCTTCTCATGC TCCGTGATGCATGAGGCTCTGCACAACCACTAC ACGCAGAAGAGCCTCTCCCTGTCCCCGGGTAAA TGA |
| 46 | fusion protein comprising a soluble extracellular domain of ActRIIB (R64; SEQ ID NO: 29) fused to an Fc domain | SGRGEAETRECIYYNANWELERTNQSGLERCEGE QDKRLHCYASWRNSSGTIELVKKGCWLDDFNCY DRQECVATEENPQVYFCCCEGNFCNERFTHLPEA GGPEVTYEPPPTAPTGGGTHTCPPCPAPELLGGPS VFLFPPKPKDTLMISRTPEVTCVVVDVSHEDPEVK FNWYVDGVEVHNAKTKPREEQYNSTYRWSVLT VLHQDWLNGKEYKCKVSNKALPVPIEKTISKAKG QPREPQVYTLPPSREEMTKNQVSLTCLVKGFYPS DIAVEWESNGQPENNYKTTPPVLDSDGSFFLYSKL TVDKSRWQQGNVFSCSVMHEALHNHYTQKSLSL SPGK |
| 47 | fusion protein comprising a soluble extracellular domain of ActRIIB (R64) with the C-terminal 15 amino acids deleted (SEQ ID NO: 30) fused to an Fc domain | SGRGEAETRECIYYNANWELERTNQSGLERCEGE QDKRLHCYASWRNSSGTIELVKKGCWLDDFNCY DRQECVATEENPQVYFCCCEGNFCNERFTHLPEA GGGTHTCPPCPAPELLGGPSVFLFPPKPKDTLMIS RTPEVTCVVVDVSHEDPEVKFNWYVDGVEVHNA KTKPREEQYNSTYRVVSVLTVLHQDWLNGKEYK CKVSNKALPVPIEKTISKAKGQPREPQVYTLPPSR EEMTKNQVSLTCLVKGFYPSDIAVEWESNGQPEN NYKTTPPVLDSDGSFFLYSKLTVDKSRWQQGNVF SCSVMHEALRNHYTQKSLSLSPGK |
| 48 | Runx2 qRT-PCR primer 1 | CCGCACGACAACCGCACCAT |
| 49 | Runx2 qRT-PCR primer 2 | CGCTCCGGCCCACAAATCTC |
| 50 | Alp qRT-PCR primer 1 | ACGTGGCTAAGAATGTCATC |
| 51 | Alp qRT-PCR primer 2 | CTGGTAGGCGATGTCCTTA |
| 52 | osterix qRT-PCR primer 1 | TAGTGGTTTGGGGTTTGTTTACCGC |
| 53 | osterix qRT-PCR primer 2 | AACCAAATAACTCTTATTCCCTAAGT |
| 54 | Klotho qRT-PCR primer 1 | GCTCTCAAAGCCCACATACTG |
| 55 | Klotho qRT-PCR primer 1 | GCAGCATAACGATAGAGGCC |
| 56 | Sm22-alpha qRT-PCR primer 1 | GTTCCAGACTGTTGACCTCTTT |
| 57 | Sm22-alpha qRT-PCR primer 2 | CTGCGCTTTCTTCATAAACC |
| 58 | Human Runx2 mRNA | GTGTGAATGCTTCATTCGCCTCACAAACAACCA CAGAACCACAAGTGCGGTGCAAACTTTCTCCAG GAGGACAGCAAGAAGTCTCTGGTTTTTAAATGG TTAATCTCCGCAGGTCACTACCAGCCACCGAGA CCAACAGAGTCATTTAAGGCTGCAAGCAGTATT TACAACAGAGGGTACAAGTTCTATCTGAAAAA AAAAGGAGGGACTATGGCATCAAACAGCCTCT TCAGCACAGTGACACCATGTCAGCAAAACTTCT TTTGGGATCCGAGCACCAGCCGGCGCTTCAGCC CCCCCTCCAGCAGCCTGCAGCCCGGCAAAATGA GCGACGTGAGCCCGGTGGTGGCTGCGCAACAG CAGCAGCAACAGCAGCAGCAGCAACAGCAGCA GCAGCAGCAGCAACAGCAGCAGCAGCAGCAGG AGGCGGCGGCGGCTGCGGCGGCGGCGGCG GCTGCGGCGGCGGCAGCTGCAGTGCCCCGGTTG CGGCCGCCCCACGACAACCGCACCATGGTGGA GATCATCGCCGACCACCCGGCCGAACTCGTCCG CACCGACAGCCCCAACTTCCTGTGCTCGGTGCT GCCCTCGCACTGGCGCTGCAACAAGACCCTGCC CGTGGCCTTCAAGGTGGTAGCCCTCGGAGAGGT |

TABLE 21-continued

Sequence Information

| SEQ ID NO: | Description | Sequence |
|---|---|---|
| | | ACCAGATGGGACTGTGGTTACTGTCATGGCGGG |
| | | TAACGATGAAAATTATTCTGCTGAGCTCCGGAA |
| | | TGCCTCTGCTGTTATGAAAAACCAAGTAGCAAG |
| | | GTTCAACGATCTGAGATTTGTGGGCCGGAGTGG |
| | | ACGAGGCAAGAGTTTCACCTTGACCATAACCGT |
| | | CTTCACAAATCCTCCCCAAGTAGCTACCTATCA |
| | | CAGAGCAATTAAAGTTACAGTAGATGGACCTCG |
| | | GGAACCCAGAAGGCACAGACAGAAGCTTGATG |
| | | ACTCTAAACCTAGTTTGTTCTCTGACCGCCTCAG |
| | | TGATTTAGGGCGCATTCCTCATCCCAGTATGAG |
| | | AGTAGGTGTCCCGCCTCAGAACCCACGGCCCTC |
| | | CCTGAACTCTGCACCAAGTCCTTTTAATCCACA |
| | | AGGACAGAGTCAGATTACAGACCCCAGGCAGG |
| | | CACAGTCTTCCCCGCCGTGGTCCTATGACCAGT |
| | | CTTACCCCTCCTACCTGAGCCAGATGACGTCCC |
| | | CGTCCATCCACTCTACCACCCCGCTGTCTTCCAC |
| | | ACGGGGCACTGGGCTTCCTGCCATCACCGATGT |
| | | GCCTAGGCGCATTTCAGATGATGACACTGCCAC |
| | | CTCTGACTTCTGCCTCTGGCCTTCCACTCTCAGT |
| | | AAGAAGAGCCAGGCAGGTGCTTCAGAACTGGG |
| | | CCCTTTTTCAGACCCCAGGCAGTTCCCAAGCAT |
| | | TTCATCCCTCACTGAGAGCCGCTTCTCCAACCC |
| | | ACGAATGCACTATCCAGCCACCTTTACTTACAC |
| | | CCCGCCAGTCACCTCAGGCATGTCCCTCGGTAT |
| | | GTCCGCCACCACrCACTACCACACCTACCTGCC |
| | | ACCACCCTACCCCGGCTCTTCCCAAAGCCAGAG |
| | | TGGACCCTTCCAGACCAGCAGCACTCCATATCT |
| | | CTACTATGGCACTTCGTCAGGATCCTATCAGTTT |
| | | CCCATGGTGCCGGGGGAGACCGGTCTCCTTCC |
| | | AGAATGCTTCCGCCATGCACCACCACCTCGAAT |
| | | GGCAGCACGCTATTAAATCCAAATTTGCCTAAC |
| | | CAGAATGATGGTGTTGACGCTGATGGAAGCCAC |
| | | AGCAGTTCCCCAACTGTTTTGAATTCTAGTGGC |
| | | AGAATGGATGAATCTGTTTGGCGACCATATTGA |
| | | AATTCCTCAGCAGTGGCCCAGTGGTATCTGGGG |
| | | GCCACATCCCACACGTATCAATATATACATATA |
| | | TAGAGAGAGTGCATATATATGTATATCGATTAG |
| | | CTATCTACAAAGTGCCTATTTTTTAGAAGATTTT |
| | | TCATTCACTCACTCAGTCATGATCTTGCAGCCAT |
| | | AAGAGGGTAGATATTGAGAAGCAGAAGGCTCA |
| | | AGAGAGACAATTGCAATCGAGCTTCAGATTGTT |
| | | TACTATTTAAGATGTACnTTACAAAGGAACAA |
| | | AGAAGGGAAAAGGTATTTTTGTTTTTGTTGTTT |
| | | GGTCTGTTATCATCAATAACCTGTTCATATGCC |
| | | AATTCAGAGAGGTGGACTCCAGGTTCAGGAGG |
| | | GAGAAGAGCAAAGCCGCTTCCTCTCTGtGCTTT |
| | | GAAACTTCACACCCTCACGGTGGCAGCTGTGTA |
| | | TGGACCAGTGCCCTCCGCAGACAGCTCACAAAA |
| | | CCAGTTGAGGTGCACTAAAGGGACATGAGGTA |
| | | GAATGGATGCTTCCATCACAGTACCATCATTCA |
| | | GAATAACTCTTCCAATTTCTGCTTTCAGACATGC |
| | | TGCAGGTCCTCATCTGAACTGTTGGGTTCGTTTT |
| | | TTTTTTTITTTTTCCTGCTCCAAGAAAGTGACTT |
| | | CAAAAATAACTGATCAGGATAGATTATTTTATT |
| | | TTACTTTTTAACACTCCTTCTCCCCTTTTCCCACT |
| | | GAACCAAAAAGAAATCCCATCCCTAAAACCTG |
| | | CCTTCTCCTTTTATGCAAAACTGAAAATGGCAA |
| | | TACATTATTATAGCCATAATGGTATAGATAGTG |
| | | ATTGCGTTTGGCTATGTGTTGTTTTCTTTTTTTTT |
| | | AAATTATGAATATGTGTAAAATCTGAGGTAACT |
| | | TGCTAACGTGAATGGTCATATAACTTTAAAGAT |
| | | ATATTTATAATTATTTAATGACATTTGGACCCTT |
| | | GAAACATTTCTTAGTGTATTGATATGTTGACTTC |
| | | GGTCTCTAAAAGTGCTCTTTATTAAATAACAAA |
| | | TTTCTTCAGTGGTCTAGAGCCATATCTGAAATA |
| | | TTGCTAAGCAATTTCAGTTCATCCAGGCACAAT |
| | | GTGATTTTAAAAAATACTTCCATCTCCAAATAT |
| | | TTTAGATATAGATTGTTnTGTGATGTATGAAG |
| | | GAAATGTTATGTTTAGTTCTTTCAGATCTTTGAA |
| | | TGCCTCTAACACAGCTTTGCCTTCTAAAGCGGT |
| | | AATTAGGGATTTAAAAAACAACCTTTAGCCCTT |
| | | TATCAGCATGAAATGCTGGAGTGATGTGGTTTT |
| | | CTAATTTCTTTGGGGTAATTATGACTCTTGTCAT |
| | | ATTAAAAAGACAAGCACAAGTAAATCATTGAA |

TABLE 21-continued

Sequence Information

| SEQ ID NO: | Description | Sequence |
|---|---|---|
| | | CTACAGAAAAATGTTCTGTGGTTTCATAGTTAA |
| | | GCAAAACTCTAAATCGCCAGGCTTCATAGCAAA |
| | | GACATAGTCAGCTAAAAGCCGCACATGTGGAT |
| | | AGAGGGTTCAATTATGAGACACCTAGTACAGG |
| | | AGAGCAAAATTGCACCAGAGATTCTTAACCAAC |
| | | CAGCCTTACCAAACAACACAACAGGGGAACCC |
| | | CAATCTGCCTTACCCAAGGCCCCACTGGCAGCT |
| | | TTCCACAGAATTTGCATTTAGAGGAGCAGAATG |
| | | ACATCACTGTCCTTTGGGAGTAGGTCCTCTGAA |
| | | AAGGCAGCAGGTTCCAGCAGGTAGCTGAGCTG |
| | | AGAGGACATATGGCCCACGGGGACCTACAGAC |
| | | AGCCTTTGACATTTGTATTTCTTACAATGGAGG |
| | | GCCAAGGAGGGCAAGGGGCTGTGGAGTTTGGT |
| | | GTCTACTAGTGTGTATGAATTTGAGCTAGAGTC |
| | | CTTCTGTGGCATGCACTTTGACCACTCCTGGCA |
| | | GTCACATGGCAGATTTCCAAGTGCAAATCCTTA |
| | | ATCCAAACAAGGATCATCTAATGACACCACCAG |
| | | GCCAATCCCTGCTCTCCTCCCCGAAAAGTCAGG |
| | | GTCCCTTCATTGGAATCCTCCACCCACCCAAGC |
| | | AGAATTTAGCAGAGATTTGCCTTCAAACCCTAA |
| | | CGGCCCCCTTGTTCTCTGGTCCTTCTCAAACCCA |
| | | CCTTTGTAGGCCACCCAGCATTGCAGGACAGCG |
| | | TGTGGGCAGCTGGACCTGTGCTTCCTGCCTGG |
| | | GAGTCTCCCTTGGAATTCATCCTGACTCCTTCTA |
| | | ATAAAAATGGATGGGAAAGCAAAACACTTTGC |
| | | CTTCTAAAGGCCGTATACCAAGTATGCTTAGAT |
| | | AAATAAGCCACTTTTCTATTACTTAAGTAAGAA |
| | | GGAAGTAGTAATTGATACTATTTATTGTTTGTGT |
| | | GTGGTAGCTTGAAGCACACCACTGTCCATTTAT |
| | | TTGTAAGTGTAAAATATGTGTGTTTGTTTCAGC |
| | | AGCACTTAAAAAAGCCAGTGTCTGGTTACACAT |
| | | TTCAATTTTAATTAATTGACATAAAAATGCTAC |
| | | CGCCAGTGCCAGCTGCATCCTATTTAATTAAAA |
| | | AGGTACTATATTTGTACATTATTTTTTAATGTTA |
| | | AAAGGGCTTTTTTAAGTTTACAGTACACATACC |
| | | GAGTGACTTTAGGGATGCTTTTGTGTTGAAATG |
| | | TTACTATAGTGGCTGCAGGCAGCAACCCAGAAA |
| | | CACTTTAGAAGCTTTTTTTCCTTGGGAAAAATTC |
| | | AAGCACTTCTTCCCTCCACCCTCACTCCAACCA |
| | | CCCCAATGGGGTAATTCACATTTCTTAGAACA |
| | | AATTCTGCCCTTTTTGGTCTAGGGATTAAAATT |
| | | TTGTTTTTCTTTCTTTCTTTTTTTTTTTTTTCACT |
| | | GAACCCTTAATTTGCACTGGGTCATGTGTTTGA |
| | | TTTGTGATTTCAAGACCAAAGCAAAGTCTTACT |
| | | ACTACTGTGGAACCATGTACTAOTTCCTGGGAA |
| | | TTAAAATAGCGTGGTTCTCTTTGTAGCACAAAC |
| | | ATTGCTGGAATTTGCAGTCTTTTCAATGCAGCC |
| | | ACATTTTTATCCATTTCAGTTGTCTCACAAATTT |
| | | TAACCCATATCAGAGTTCCAGAACAGGTACCAC |
| | | AGCTTTGGTTTTAGATTAGTGGAATAACATTCA |
| | | GCCCAGAACTGAGAAACTCAACAGATTAACTAT |
| | | CGTTTGCTCTTTAGACGGTCTCACTGCCTCTCAC |
| | | TTGCCAGAGCCCTTTCAAAATGAGCAGAGAAGT |
| | | CCACACCATTAGGGACCATCTGTGATAAATTCA |
| | | GAAGGGAGGAGATGTGTGTACAGCTTTAAGGA |
| | | TTCCCTCAATTCCGAGGAAAGGGACTGGCCCAG |
| | | AATCCAGGTTAATACATGGAAACACGAAGCATT |
| | | AGCAAAAGTAATAATTATACCTATGGTATTTGA |
| | | AAGAACAATAATAAAAGACACTTCTTCCAAACC |
| | | TTGAATTTGTTGTTTTTAGAAAACGAATGCATTr |
| | | AAAAATATTTTCTATGTGAGAATTTTTTAGATGT |
| | | GTGTTTACTTCATGTTTACAAATAACTGTTTGCT |
| | | TTTTAATGCAGTACTTTGAAATATATCAGCCAA |
| | | AACCATAACTTACAATAATTTCTTAGGTATTCT |
| | | GAATAAAATTCCATTTCTTTTGGATATGCTTTAC |
| | | CATTCTTAGGTTTCTGTGGAACAAAAATATTTG |
| | | TAGCATTTTGTGTAAATACAAGCTTTCATTTTTA |
| | | TTTTTTCCAATTGCTATTGCCCAAGAATTGCTTT |
| | | CCATGCACATATTGTAAAAATTCCGCTTTGTGC |
| | | CACAGGTCATGATTGTGGATGAGTTTACTCTTA |
| | | ACTTCAAAGGGACTATTTGTATTGTATGTTGCA |
| | | ACTGTAAATTGAATTATTTGGCATTTTTCTCATG |
| | | ATTGTAATATTAATTTGAAGTTTGAATTTAATTT |
| | | TCAATAAAATGGCTTTTTTGGTTTTGTTA |

TABLE 21-continued

Sequence Information

| SEQ ID NO: | Description | Sequence |
|---|---|---|
| 59 | Human Alp mRNA | CCGGGCCTCACTCGGGCCCCGCGGCCGCCTTTA
TAAGGCGGCGGGGGTGGTGGCCCGGGCCGCGT
TGCGCTCCCGCCACTCCGCGCCCGCTATCCTGG
CTCCGTGCTCCCACGCGCTTGTGCCTGGACGGA
CCCTCGCCAGTGCTCTGCGCAGGATTGGAACAT
CAGTTAACATCTGACCACTGCCAGCCCACCCCC
TCCCACCCACGTCGATTGCATCTCTGGGCTCCA
GGGATAAAGCAGGTCTTGGGGTGCACCATGATT
TCACCATTCTTAGTACTGGCCATTGGCACCTGC
CTTACTAACTCCTTAGTGCCAGAGAAAGAGAAA
GACCCCAAGTACTGGCGAGACCAAGCGCAAGA
GACACTGAAATATGCCCTGGAGCTTCAGAAGCT
CAACACCAACGTGGCTAAGAATGTCATCATGTT
CCTGGGAGATGGGATGGGTGTCTCCACAGTGAC
GGCTGCCCGCATCCTCAAGGGTCAGCTCCACCA
CAACCCTGGGGAGGAGACCAGGCTGGAGATGG
ACAAGTTCCCCTTCGTGGCCCTCTCCAAGACGT
ACAACACCAATGCCCAGGTCCCTGACAGCGCC
GGCACCGCCACCGCCTACCTGTGTGGGGTGAAG
GCCAATGAGGGCACCGTGGGGGTAAGCGCAGC
CACTGAGCGTTCCCGGTGCAACACCACCCAGGG
GAACGAGGTCACCTCCATCCTGCGCTGGGCCAA
GGACGCTGGGAAATCTGTGGGCATTGTGACCAC
CACGAGAGTGAACCATGCCACCCCCAGCGCCG
CCTACGCCCACTCGGCTGACCGGGACTGGTACT
CAGACAACGAGATGCCCCCTGAGGCCTTGAGCC
AGGGCTGTAAGGACATCGCCTACCAGCTCATGC
ATAACATCAGGGACATTGACGTGATCATGGGG
GGTGGCCGGAAATACATGTACCCCAAGAATAA
AACTGATGTGGAGTATGAGAGTGACGAGAAAG
CCAGGGGCACGAGGCTGGACGGGCCTGGACCTC
GTTGACACCTGGAAGAGCTTCAAACCGAGATAC
AAGCACTCCCACTTCATCTGGAACCGCACGGAA
CTCCTGACCCTTGACCCCCACAATGTGGACTAC
CTATTGGGTCTCTTCGAGCCAGGGGACATGCAG
TACGAGCTGAACAGGAACAACGTGACGGACCC
GTCACTCTCCGAGATGGTGGTGGTGGCCATCCA
GATCCTGCGGAAGAACCCCAAAGGCTTCTTCTT
GCTGGTGGAAGGAGGCAGAATTGACCACGGGC
ACCATGAAGGAAAAGCCAAGCAGGCCCTGCAT
GAGGCGGTGGAGATGGACCGGGCCATCGGGCA
GGCAGGCAGCTTGACCTCCTCGGAAGACACTCT
GACCGTGGTCACTGCGGACCATTCCCACGTCTT
CACATTTGGTGGATACACCCCCCGTGGCAACTC
TATCTTTGGTCTGGCCCCCATGCTGAGTGACAC
AGACAAGAAGCCCTTCACTGCCATCCTGTATGG
CAATGGGCCTGGCTACAAGGTGGTGGGCGGTG
AACGAGAGAATGTCTCCATGGTGGACTATGCTC
ACAACAACTACCAGGCGCAGTCTGCTGTGCCCC
TGCGCCACGAGACCCACGGCGGGGAGGACGTG
GCCGTCTTCTCCAAGGGCCCCATGGCGCACCTG
CTGCACGGCGTCCACGAGCAGAACTACGTCCCC
CACGTGATGGCGTATGCAGCCTGCATCGGGGCC
AACCTCGGCCACTGTGCTCCTGCCAGCTCGGCA
GGCAGCCTTGCTGCAGGCCCCCTGCTGCTCGCG
CTGGCCCTCTACCCCCTGAGCGTCCTGTTCTGA
GGGCCCAGGGCCCGGGCACCCACAAGCCCGTG
ACAGATGCCAACTTCCCACACGGCAGCCCCCCC
CTCAAGGGGCAGGGAGGTGGGGGCCTCCTCAG
CCTCTGCAACTGCAAGAAAGGGGACCCAAGAA
ACCAAAGTCTGCCGCCCACCTCGCTCCCCTCTG
GAATCTTCCCCAAGGGCCAAACCCACTTCTGGC
CTCCAGCCTTTGCTCCCTCCCCGCTGCCCTTTGG
CCAACAGGGTAGATTTCTCTTGGGCAGGCAGAG
AGTACAGACTGCAGACATTCTCAAAGCCTCTTA
TTTTTCTAGCGAACGTATTTCTCCAGACCCAGA
GGCCCTGAAGCCTCCGTGGAACATTCTGGATCT
GACCCTCCCAGTCTCATCTCCTGACCCTCCCACT
CCCATCTCCTTACCTCTGGAACCCCCCAGGCCC
TACAATGCTCATGTCCCTGTCCCCAGGCCCAGC
CCTCCTTCAGGGGAGTTGAGGTCTTTCTCCTCA
GGACAAGGCCTTGCTCACTCACTCACTCCAAGA
CCACCAGGGTCCCAGGAAGCCGGTGCCTGGGT
GGCCATCCTACCCAGCGTGGCCCAGGCCGGGA |

TABLE 21-continued

Sequence Information

| SEQ ID NO: | Description | Sequence |
|---|---|---|
| | | AGAGCCACCTGGCAGGGCTCACACTCCTGGGCT
CTGAACACACACGCCAGCTCCTCTCTGAAGCGA
CTCTCCTGTTTGGAACGGCAAAAAAAAATTTTT
TTTTCTCTTTTTGGTGGTGGTTAAAAGGGAACA
CAAAACATTTAAATAAAACTTTCCAAATATTTC
CGAGGACAAAAAAAAAAA |
| 60 | Human Osterix mRNA | CGGCGGGCGGCAGCAGCCTAGGCAGCAGCAGT
AGCAGAAGCAGCAGCCGCCGAGCAGCAGCAAG
GACTCTGGAGTCAGAGTAGGACTGTAGGACCG
GAGCCTGAGTGGAACAGGAGTGGAGCTGGCCT
GGGAGAGAGCGGATCCCTCCCAGCACCCTCAG
GCCACCCGTTGCCTGCACTCTCCCTGCCAGACC
TCCAGAGAGGAGAGACTCGGGACAGCCAGCCC
CAGGTTCCCCCAGCTCTCTCCATCTGCCTGGCTC
CTTGGGACCCGTTCCCCAGCCTCAGGATGGCGT
CCTCCCTGCTTGAGGAGGAAGTTCACTATGGCT
CCAGTCCCCTGGCCATGCTGACGGCAGCGTGCA
GCAAATTTGGTGGCTCTAGCCCTCTGCGGGACT
CAACAACTCTGGGCAAAGCAGGCACAAAGAAG
CCGTACTCTGTGGGCAGTGACCTTTCAGCCTCC
AAAACCATGGGGGATGCTTATCCAGCCCCCTTT
ACAAGCACTAATGGGCTCCTTTCACCTGCAGGC
AGTCCTCCAGCACCCACCTCAGGCTATGCTAAT
GATTACCCTCCCTTTTCCCACTCATTCCCTGGGC
CCACAGGCACCCAGGACCCTGGGCTACTAGTGC
CCAAGGGGCACAGCTCTTCTGACTGTCTGCCCA
GTGTCTACACCTCTCTGGACATGACACACCCCT
ATGGCTCCTGGTACAAGGCAGGCATCCATGCAG
GCATTTCACCAGGCCCAGGCAACACTCCTACTC
CATGGTGGGATATGCACCCTGGAGGCAACTGGC
TAGGTGGTGGGCAGGGCCAGGGTGATGGGCTG
CAAGGGACACTGCCCACAGGTCCAGCTCAGCCT
CCACTGAACCCCCAGCTGCCCACCTACCCATCT
GACTTTGCTCCCCTTAATCCAGCCCCCTACCCA
GCTCCCCACCTCTTGCAACCAGGGCCCCAGCAT
GTCTTGCCCCAAGATGTCTATAAACCCAAGGCA
GTGGGAAATAGTGGGCAGCTAGAAGGGAGTGG
TGGAGCCAAACCCCCACGGGGTGCAAGCACTG
GGGGTAGTGGTGGATATGGGGGCAGTGGGGCA
GGGCGCTCCTCCTGCGACTGCCCTAATTGCCAG
GAGCTAGAGCGGCTGGGAGCAGCAGCGGCTGG
GCTGCGGAAGAAGCCCATCCACAGCTGCCACAT
CCCTGGCTGCGGCAAGGTGTATGGCAAGGCTTC
GCACCTGAAGGCCCACTTGCGCTGGCACACAGG
CGAGAGGCCCTTCGTCTGCAACTGGCTCTTCTG
CGGCAAGAGGTTCACTCGTTCGGATGAGCTGGA
GCGTCATGTGCGCACTCACACCCGGGAGAAGA
AGTTCACCTGCCTGCTCTGCTCCAAGCGCTTTAC
CCGAAGCGACCACCTGAGCAAACACCAGCGCA
CCCATGGAGAACCAGGCCCGGGTCCCCCTCCCA
GTGGCCCCAAGGAGCTGGGGGAGGGCCGCAGC
ACGGGGGAAGAGGAGGCCAGTCAGACGCCCCG
ACCTTCTGCCTCGCCAGCAACCCCAGAGAAAGC
CCCTGGAGGCAGCCCTGAGCAGAGCAACTTGCT
GGAGATCTGAGCCGGGTGGAAGGTCTCCCACCC
CAGGGCTGCCCTGACAGTCTCTCTTGGCTCTCT
AGACCACTGCTTGCCAATCACTCTCTTTACCCC
ATGCATGCCATCCTTCGGGGCTCTCTCCCTCTGT
CTCCCTCCTGGCCATTCTGGGCTTGGGTATCTCC
TTGCATGCCTCCTCAGCTCACCTTCTCTCTTCAC
CATGAGACTGGCTTTCCACAAACTCTCATCTCA
GGCCCTCCCCTTGTGCCTGATACCTGCACTCCG
GCTTCCTAGACTCTGGCCCTGCCACACCAACAC
ACTTTCTATTTGGGCTCCCAACACTATTTCTCCA
TCTCACTCCTTGACATGTACCCCTTTCTGCTTCT
CAAGCTTATTTCCTGCTGTCCCTCAGCCTCCAGG
CTTCAGTCTTCCCAACTTCTTACACCATTGCTTT
CCATTCTCCAGAACTCTTTTTTCCTTTTTACAAA
CACAATGATAATGATAATTTATTGCCCCCTGGT
GGCCTCTTCATCAGGGGTATTGGGGTTAGTGAC
CTGGCCAGAGGGTCCCAAGAGGGGGGCAGACC
AGTGGGGATCTGATCCCAAAGATGGGGTGACC
CCAGGGTCAGGGAGGCTGCCCCCAGGCCTGTAT |

TABLE 21-continued

Sequence Information

| SEQ ID NO: | Description | Sequence |
|---|---|---|
| | | ATTTAACCCCTATGTACCAGGAGTAATGAATAG<br>TAATAATTCTATTTATGTAAGTTATGATGACGG<br>GTCAGGTAGAGTGAGCTGGGGAGGGAAGTGGA<br>TCCATTTCTGCTAAGGAAATTCTAGTCAAATGC<br>ATCTCTGTATAGACAAAATGTTAGTGGAGAAGA<br>TCTTGTTAATAGAATGTCTATCATCAGAATCTC<br>AGTTGATAGGGTTTCTCTTGTAATGAAGTCTCT<br>ACAAATTGGGTTAGCTACATCTCTGCTAAACAG<br>TTGATGGGGTATCTCTTGATTAGGGGGATCCCT<br>AATATCCCCAGCCCCAGCCAGAAGCTGTGAAAC<br>CTCAAGTCCTATGGAGGGGAGAAGGACTGGAA<br>TGTACCCCATCTCCCTTGACTGCAGAGCAGGTT<br>CCTCCACTGCCCCACCCCTTAGACACCATGACC<br>CCATCAGGTTAATCCCTGTTGCCATGGTTATG<br>GAGAGCTTGCAGCTGCCATCTTAGATGTGCTCT<br>TTGGGGAAGCCCATCTAACAGGAGGACATTGGT<br>TTGGGGGTGCACCTCCTGAAGAATGGGTGGGG<br>AAGGCTTTCTCTAGGATCAGATTCAAATAAGTA<br>TGTATTGAGTGCCTACTCTGTGCAAGGCACTAT<br>GCTAGATCTGGTGCCTAGAAGCCCTGAGAAAG<br>AACTTAAAGAGCTAGGAGGACAGAGGCCCCCA<br>AGCTGATCTGGTGGTGCATCCACGCACCCCCAC<br>CCTGGGACTTTGGATGCTCCCATCTCCACCTCC<br>AGTGACTTTTAAAGCCGCTTCGTGCCTTTCCTGT<br>AACGTTGGATCCTCCTTTTCTGTCCCTGCTGTC<br>TCAAGGCCCCAAGTTAAAGGGTTAAAGCCGCTG<br>GAGCTTGGGGAGAGAACATTGTGGAATGGAAG<br>GGATCATGCCCTTTGTGGAGTCTTTTTTTTTAA<br>TTTAATAAATAAAAGTTGGATTTGAAAAAAAAA<br>AAAAAAAAAAAAAA |
| 61 | Human Klotho mRNA | CGCGCAGCATGCCCGCCAGCGCCCCGCCGCGCC<br>GCCCGCGGCCGCCGCCGCCGTCGCTGTCGCTGC<br>TGCTGGTGCTGCTGGGCCTGGGCGGCCGCCGCC<br>TGCGTGCGGAGCCGGGCGACGGCGCGCAGACC<br>TGGGCCCGTGTCTCGCGGCCTCCTGCCCCCGAG<br>GCCGCGGGCCTCTTCCAGGGCACCTTCCCCGAC<br>GGCTTCCTCTGGGCCGTGGGCAGCGCCGCCTAC<br>CAGACCGAGGGCGGCTGGCAGCAGCACGGCAA<br>GGGTGCGTCCATCTGGGACACGTTCACCCACCA<br>CCCCCTGGCACCCCCGGGAGACTCCCGGAACGC<br>CAGTCTGCCGTTGGGCGCCCCGTCGCCGCTGCA<br>GCCCGCCACCGGGGACGTAGCCAGCGACAGCT<br>ACAACAACGTCTTCCGCGACACGGAGGCGCTGC<br>GCGAGCTCGGGGTCACTCACTACCGCTTCTCCA<br>TCTCGTGGGCGCGAGTGCTCCCAATGGCAGCG<br>CGGGCGTCCCCAACCGCGAGGGGCTGCGCTACT<br>ACCGGCGCCTGCTGGAGCGGCTGCGGGAGCTG<br>GGCGTGCAGCCCGTGGTCACCCTGTACCACTGG<br>GACCTGCCCCAGCGCCTGCAGGACGCCTACGGC<br>GGCTGGGCCAACCGCGCCCTGGCCGACCACTTC<br>AGGGATTACGCGGAGCTCTGCTTCCGCCACTTC<br>GGCGGTCAGGTCAAGTACTGGATCACCATCGAC<br>AACCCCTACGTGGTGGCCTGGACGGCTACGCC<br>ACCGGGCGCCTGGCCCCCGGCATCCGGGGCAG<br>CCCGCGGCTCGGGTACCTGGTGGCGCACAACCT<br>CCTCCTGGCTCATGCCAAAGTCTGGCATCTCTA<br>CAATACTTCTTTCCGTCCCACTCAGGGAGGTCA<br>GGTGTCCATTGCCCTAAGCTCTCACTGGATCAA<br>TCCTCGAAGAATGACCGACCACAGCATCAAAG<br>AATGTCAAAAATCTCTGGACTTTGTACTAGGTT<br>GGTTTGCCAAACCCGTATTTATTGATGGTGACT<br>ATCCCGAGAGCATGAAGAATAACCTTTCATCTA<br>TTCTGCCTGATTTTACTGAATCTGAGAAAAAGT<br>TCATCAAAGGAACTGCTGACTTTTTTGCTCTTTG<br>CTTTGGACCCACCTTGAGTTTTCAACTTTTGGAC<br>CCTCACATGAAGTTCCGCAATTGGAATCTCCC<br>AACCTGAGGCAACTGCTTTCCTGGATTGACCTT<br>GAATTTAACCATCCTCAAATATTTATTGTGGAA<br>AATGGCTGGTTTGTCTCAGGGACCACCAAGAGA<br>GATGATGCCAAATATATGTATTACCTCAAAAAG<br>TTCATCATGGAAACCTTAAAAGCCATCAAGCTG<br>GATGGGGTGGATGTCATCGGGTATACCGCATGG<br>TCCCTCATGGATGGTTTCGAGTGGCACAGAGGT |

TABLE 21-continued

| Sequence Information | | |
|---|---|---|
| SEQ ID NO: | Description | Sequence |
| | | TACAGCATCAGGCGTGGACTCTTCTATGTTGAC |
| | | TTTCTAAGCCAGGACAAGATGTTGTTGCCAAAG |
| | | TCTTCAGCCTTGTTCTACCAAAAGCTGATAGAG |
| | | AAAAATGGCTTCCCTCCTTTACCTGAAAATCAG |
| | | CCCCTAGAAGGGACATTTCCCTGTGACTTTGCT |
| | | TGGGGAGTTGTTGACAACTACATTCAAGTAGAT |
| | | ACCACTCTGTCTCAGTTTACCGACCTGAATGTTT |
| | | ACCTGTGGGATGTCCACCACAGTAAAAGGCTTA |
| | | TTAAAGTGGATGGGGTTGTGACCAAGAAGAGG |
| | | AAATCCTACTGTGTTGACTTTGCTGCCATCCAG |
| | | CCCCAGATCGCTTTACTCCAGGAAATGCACGTT |
| | | ACACATTTTCGCTTCrCCCTGGACTGGGCCCTG |
| | | ATTCTCCCTCTGGGTAACCAGTCCCAGGTGAAC |
| | | CACACCATCCTGCAGTACTATCGCTGCATGGCC |
| | | AGCGAGCTTGTCCGTGTCAACATCACCCCAGTG |
| | | GTGGCCCTGTGGCAGCCTATGGCCCCGAACCAA |
| | | GGACTGCCGCGCCTCCTGGCCAGGCAGGGCGC |
| | | CTGGGAGAACCCCTACACTGCCCTGGCCTTTGC |
| | | AGAGTATGCCCGACTGTGCTTTCAAGAGCTCGG |
| | | CCATCACGTCAAGCTTTGGATAACGATGAATGA |
| | | GCCGTATACAAGGAATATGACATACAGTGCTGG |
| | | CCACAACCTTCTGAAGGCCCATGCCCTGGCTTG |
| | | GCATGTGTACAATGAAAAGTTTAGGCATGCTCA |
| | | GAATGGGAAAATATCCATAGCCTTGCAGGCTGA |
| | | TTGGATAGAACCTGCCTGCCCTTTCTCCCAAAA |
| | | GGACAAAGAGGTGGCCGAGAGAGTTTTGGAAT |
| | | TTGACATTGGCTGGCTGGCTGAGCCCATTTTCG |
| | | GCTCTGGAGATTATCCATGGGTGATGAGGGACT |
| | | GGCTGAACCAAAGAAACAATTTTCTTCTTCCTT |
| | | ATTTCACTGAAGATGAAAAAAAGCTAATCCAG |
| | | GGTACCTTTGACTTTTTGGCTTTAAGCCATTATA |
| | | CCACCATCCTTGTAGACTCAGAAAAAGAAGATC |
| | | CAATAAAATACAATGATTACCTAGAAGTGCAA |
| | | GAAATGACCGACATCACGTGGCTCAACTCCCCC |
| | | AGTCAGGTGGCGGTAGTGCCCTGGGGGTTGCGC |
| | | AAAGTGCTGAACTGGCTGAAGTTCAAGTACGG |
| | | AGACCTCCCCATGTACATAATATCCAACGGAAT |
| | | CGATGACGGGCTGCATGCTGAGGACGACCAGC |
| | | TGAGGGTGTATTATATGCAGAATTACATAAACG |
| | | AAGCTCTCAAAGCCCACATACTGGATGGTATCA |
| | | ATCTTTGCGGATACTTTGCTTATTCGTTTAACGA |
| | | CCGCACAGCTCCGAGGTTTGGCCTCTATCGTTA |
| | | TGCTGCAGATCAGTTTGAGCCCAAGGCATCCAT |
| | | GAAACATTACAGGAAAATTATTGACAGCAATG |
| | | GTTTCCCGGGCCCAGAAACTCTGGAAAGATTTT |
| | | GTCCAGAAGAATTCACCGTGTGTACTGAGTGCA |
| | | GTTTTTTTCACACCCGAAAGTCTTTACTGGCTTT |
| | | CATAGCTTTTCTATTTTTTGCTTCTATTATTTCTC |
| | | TCTCCCTTATATTTTACTACTCGAAGAAAGGCA |
| | | GAAGAAGTTACAAATAGTrCTGAACATTTTTCT |
| | | ATTCATTCATTTTGAAATAATTATGCAGACACA |
| | | TCAGCTGTTAACCATTTGCACCTCTAAGTGTTGT |
| | | GAAACTGTAAATTTCATACATTTGACTTCTAGA |
| | | AAACATTTTTGTGGCTTATGACAGAGGTTTTGA |
| | | AATGGGCATAGGTGATCGTAAAATATTGAATAA |
| | | TGCGAATAGTGCCTGAATTTGTTCTC1TTTTGGG |
| | | TGATTAAAAAACTGACAGGCACTATAATTTCTG |
| | | TAACACACTAACAAAAGCATGAAAAATAGGAA |
| | | CCACACCAATGCAACATTTGTGCAGAAATTTGA |
| | | ATGACAAGATTAGGAATATTTTCTTCTGCACCC |
| | | ACTTCTAAATTTAATGTTTTTCTGGAAGTAGTAA |
| | | TTGCAAGAGTTCGAATAGAAAGTTATGTACCAA |
| | | GTAACCATTTCTCAGCTGCCATAATAATGCCTA |
| | | GTGGCTTCCCCTCTGTCAAATCTAGTTTCCTATG |
| | | GAAAAGAAGATGGCAGATACAGGAGAGACGAC |
| | | AGAGGGTCCTAGGCTGGAATGTTCCTTTCGAAA |
| | | GCAATGCTTCTATCAAATACTAGTATTAATTTAT |
| | | GTATCTGGTTAATGACATACTTGGAGAGCAAAT |
| | | TATGGAAATGTGTATTTTATATGATTTTTGAGGT |
| | | CCTGTCTAAACCCTGTGTCCCTGAGGGATCTGT |
| | | CTCACTGGCATCTTGTTGAGGGCCTTGCACATA |
| | | GGAAACTTTTGATAAGTATCTGCGGAAAAACAA |
| | | ACATGAATCCTGTGATATTGGGCTCTTCAGGAA |
| | | GCATAAAGCAATTGTGAAATACAGTATACCGCA |

TABLE 21-continued

Sequence Information

| SEQ ID NO: | Description | Sequence |
|---|---|---|
| | | GTGGCTCTAGGTGGAGGAAAGGAGGAAAAAGT GCTTATTATGTGCAACATTATGATTAATCTGATT ATACACCATTTTTGAGCAGATCTTGGAATGAAT GACATGACCTTTCCCTAGAGAATAAGGATGAAA TAATCACTCATTCTATGAACAGTGACACTACTT TCTATTCTTTAGCTGTACTGTAATTTCTTTGAGT TGATAGTTTTACAAATTCTTAATAGGTTCAAAA GCAATCTGGTCTGAATAACACTGGATTTGTTTC TGTGATCTCTGAGGTCTATTTTATGTTTTTGCTG CTACTTCTGTGGAAGTAGCTTTGAACTAGTTTTA CTTTGAACTTTCACGCTGAAACATGCTAGTGAT ATCTAGAAAGGGCTAATTAGGTCTCATCCTTTA ATGCCCCTTAAATAAGTCTTGCTGATTTTCAGA CAGGGAAGTCTCTCTATTACACTGGAGCTGTTT TATAGATAAGTCAATATTGTATCAGGCAAGATA AACCAATGTCATAACAGGCATTGCCAACCTCAC TGACACAGGGTCATAGTGTATAATAATATACTG TACTATATAATATATCATCTTTAGAGGTATGATT TTTTCATGAAAGATAAGCTTTTGGTAATATTCAT TTTAAAGTGGACTTATTAAAATTGGATGCTAGA GAATCAAGTTTATTTTATGTATATATTTTTCTGA TTATAAGAGTAATATATGTTCATTGTAAAAATT TTTAAAACACAGAAACTATATGCAAAGAAAAA ATAAAAATTATCTATAATCTCAGAACCCAGAAA TAGCCACTATTAACATTTCCTACGTATTTTATTT TACATAGATCATATTGTATATAGTTAGTATCTTT ATTAATTTTTATTATGAAACTTTCCTTTGTCATT ATTAGTCTTCAAAAGCATGATTTTTAATAGTTGT TGAGTATTCCACCACAGGAATGTATCACAACrr AACCGTTCCCGTTTGTTAGACTAGTlTCTTATTA ATGTTGATGAATGTTGTTTAAAAATAATTrTGTT GCTACATTTACTTTAATTTCCTTGACTGTAAAGA GAAGTAATTTTGCTCCTTGATAAAGTATTATATT AATAATAAATCTGCCTGCAACTTTTTGCCTTCTT TCATAATC |
| 62 | Human Sm22-aipha mRNA | TCACCACGGCGGCAGCCCTTTAAACCCCTCACC CAGCCAGCGCCCCATCCTGTCTGTCCGAACCCA GACACAAGTCTTCACTCCTTCCTGCGAGCCCTG AGGAAGCCTTGTGAGTGCATTGGCTGGGGCTTG GAGGGAAGTTGGGCTGGAGCTGGACAGGAGCA GTGGGTGCATTTCAGGCAGGCTCTCCTGAGGTC CCAGGCGCCAGCTCCAGCTCCCTGGCTAGGGAA ACCCACCCTCTCAGTCAGCATGGGGGCCCAAGC TCCAGGCAGGGTGGGCTGGATCACTAGCGTCCT GGATCTCTCTCAGACTGGGCAGCCCCGGGCTCA TTGAAATGCCCCGGATGACTTGGCTAGTGCAGA GGAATTGATGGAAACCACCGGGGTGAGAGGGA GGCTCCCCATCTCAGCCAGCCACATCCACAAGG TGTGTGTAAGGGTGCAGGCGCCGGCCGGTTAGG CCAAGGCTCTACTGTCTGTTGCCCCTCCAGGAG AACTTCCAAGGAGCTTTCCCCAGACATGGCCAA CAAGGGTCCTTCCTATGGCATGAGCCGCGAAGT GCAGTCCAAAATCGAGAAGAAGTATGACGAGG AGCTGGAGGAGCGGCTGGTGGAGTGGATCATA GTGCAGTGTGGCCCTGATGTGGGCCGCCCAGAC CGTGGGCGCTTGGGCTTCCAGGTCTGGCTGAAG AATGGCGTGATTCTGAGCAAGCTGGTGAACAGC CTGTACCCTGATGGCTCCAAGCCGGTGAAGGTG CCCGAGAACCCACCCTCCATGGTCTTCAAGCAG ATGGAGCAGGTGGCTCAGTTCCTGAAGGCGGCT GAGGACTATGGGGTCATCAAGACTGACATGTTC CAGACTGrrGACCTCTTTGAAGGCAAAGACATG GCAGCAGTGCAGAGGACCCTGATGGCTTTGGGC AGCTTGGCAGTGACCAAGAATGATGGGCACTA CCGTGGAGATCCCAACTGGTTTATGAAGAAAGC GCAGGAGCATAAGAGGGAATTCACAGAGAGCC AGCTGCAGGAGGGAAAGCATGTCATTGGCCTTC AGATGGGCAGCAACAGAGGGGCCTCCCAGGCC GGCATGACAGGCTACGGACGACCTCGGCAGAT CATCAGTTAGAGCGGAGAGGGCTAGCCCTGAG CCCGGCCCTCCCCCAGCTCCTTGGCTGCAGCCA TCCCGCTTAGCCTGCCTCACCCACACCCGTGTG GTACCTTCAGCCCTGGCCAAGCTTTGAGGCTCT |

TABLE 21-continued

Sequence Information

| SEQ ID NO: | Description | Sequence |
|---|---|---|
| | | GTCACTGAGCAATGGTAACTGCACCTGGGCAGC<br>TCCTCCCTGTGCCCCCAGCCTCAGCCCAACTTCT<br>TACCCGAAAGCATCACTGCCTTGGCCCCTCCCT<br>CCCGGCTGCCCCCATCACCTCTACTGTCrCCTCC<br>CTGGGCTAAGCAGGGGAGAAGCGGGCTGGGGG<br>TAGCCTGGATGTGGGCCAAGTCCACTGTCCTCC<br>TTGGCGGCAAAAGCCCATTGAAGAAGAACCAG<br>CCCAGCCTGCCCCCTATCTTGTCCTGGAATATTT<br>TTGGGGTTGGAACTCAAAAAAAAAAAAAAAAA<br>ATCAATCTTTCTCAAAAAAAAAAAAAAAAAA |
| 63 | Human Runx2 protein | MASNSLFSTVTPCQQNFFWDPSTSRRFSPPSSSLQP<br>GKMSDVSPVVAAQQQQQQQQQQQQQQQQQQQ<br>QQQQEAAAAAAAAAAAAAAAAAVPRLRPPHDN<br>RTMVEIIADHPAELVRTDSPNFLCSVLPSHWRCNK<br>TLPVAFKVVALGEVPDGTVVTVMAGNDENYSAE<br>LRNASAVMKNQVARFNDLRFVGRSGRGKSFTLTI<br>TVFTNPPQVATYHRAIKVTVDGPREPRRHRQKLD<br>DSKPSLFSDRLSDLGRIPHPSMRVGVPPQNPRPSL<br>NSAPSPFNPQGQSQITDPRQAQSSPPWSYDQSYPS<br>YLSQMTSPSIHSTTPLSSTRGTGLPAITDVPRRISD<br>DDTATSDFCLWPSTLSKKSQAGASELGPFSDPRQF<br>PSISSLTESRFSNPRMHYPATFTYTPPVTSGMSLG<br>MSATTHYHTYLPPPYPGSSQSQSGPFQTSSTPYLY<br>YGTSSGSYQFPMVPGGDRSPSRMLPPCTTTSNGST<br>LLNPNLPNQNDGVDADGSHSSSPTVLNSSGRMDE<br>SVWRPY |
| 64 | Human Alp protein | MISPFLVLAIGTCLTNSLVPEKEKDPKYWRDQAQ<br>ETLKYALELQKLNTNVAKNVIMFLGDGMGVSTV<br>TAARILKGQLHHNPGEETRLEMDKFPFVALSKTY<br>NTNAQVPDSAGTATAYLCGVKANEGTVGVSAAT<br>ERSRCNTTQGNEVTSILRWAKDAGKSVGIVTTTR<br>VNHATPSAAYAHSADRDWYSDNEMPPEALSQGC<br>KDIAYQLMHNIRDIDVIMGGGRKYMYPKNKTDV<br>EYESDEKARGTRLDGLDLVDTWKSFKPRYKHSHF<br>IWNRTELLTLDPHNVDYLLGLFEPGDMQYELNRN<br>NVTDPSLSEMVVVAIQILRKNPKGFFLLVEGGRID<br>HGHHEGKAKQALHEAVEMDRAIGQAGSLTSSED<br>TLTVVTADHSHVFTFGGYTPRGNSIFGLAPMLSDT<br>DKKPFTAILYGNGPGYKVVGGERENVSMVDYAH<br>NNYAQSAVPLRHETHGGEDVAVFSKGPMAHLL<br>HGVHEQNYVPHVMAYAACIGANLGHCAPASSAG<br>SLAAGPLLLALALYPLSVLF |
| 65 | Human Osterix protein | MASSLLEEEVHYGSSPLAMLTAACSKFGGSSPLR<br>DSTTLGKAGTKKPYSVGSDLSASKTMGDAYPAPF<br>TSTNGLLSPAGSPPAPTSGYANDYPPFSHSFPGPTG<br>TQDPGLLVPKGHSSSDCLPSVYTSLDMTHPYGSW<br>YKAGIHAGISPGPGNTPTPWWDMHPGGNWLGGG<br>QGQGDGLQGTLPTGPAQPPLNPQLPTYPSDFAPL<br>NPAPYPAPHLLQPGPQHVLPQDVYKPKAVGNSG<br>QLEGSGGAKPPRGASTGGSGGYGGSGAGRSSCDC<br>PNCQELERLGAAAAGLRKKPIHSCHIPGCGKVYG<br>KASHLKAHLRWHTGERPFVCNWLFCGKRFTRSD<br>ELERHVRTHTREKKFTCLLCSKRFTRSDHLSKHQ<br>RTHGEPGPGPPPSGPKELGEGRSTGEEEASQTPRP<br>SASPATPEKAPGGSPEQSNLLEI |
| 66 | Human Klotho protein | MPASAPPRRPRPPPPSLSLLLVLLGLGGRRLRAEP<br>GDGAQTWARFSRPPAPEAAGLFQGTFPDGFLWA<br>VGSAAYQTEGGWQQHGKGASIWDTFTHHPLAPP<br>GDSRNASLPLGAPSPLQPATGDVASDSYNNVFRD<br>TEALRELGVTHYRFSISWARVLPNGSAGVPNREG<br>LRYYRRLLERLRELGVQPVVTLYHWDLPQRLQD<br>AYGGWANRALADHFRDYAELCFRHFGGQVKYW<br>ITIDNPYVVAWHGYATGRLAPGIRGSPRLGYLVA<br>HNLLLAHAKVWHLYNTSFRPTQGGQVSIALSSH<br>WTNPRRMTDHSIKECQKSLDFVLGWFAKPVFIDG<br>DYPESMKNNLSSILPDFTESEKKFIKGTADFFALCF<br>GPTLSFQLLDPHMKFRQLESPNLRQLLSWIDLEFN<br>HPQIFIVENGWFVSGTTKRDDAKYMYYLKKF1ME<br>TLKAIKLDGVDVIGYTAWSLMDGFEWHRGYSiRR<br>GLFYVDFLSQDKMLLPKSSALFYQKLIEKNGFPPL |

TABLE 21-continued

Sequence Information

| SEQ ID NO: | Description | Sequence |
|---|---|---|
| | | PENQPLEGTFPCDFAWGVVDNYIQVDTTLSQFTD<br>LNVYLWDVHHSKRLIKVDGVVTKKRKSYCVDFA<br>AIQPQIALLQEMHVTHFRFSLDWALILPLGNQSQV<br>NHTILQYYRCMASELVRVNITPVVALWQPMAPN<br>QGLPRLLARQGAWENPYTALAFAEYARLCFQEL<br>GHHVKLWITMNEPYTRNMTYSAGHNLLKAHALA<br>WHVYNEKFRHAQNGKISIALQADWIEPACPFSQK<br>DKEVAERVLEFDIGWLAEPIFGSGDYPWVMRDW<br>LNQRNNFLLPYFTEDEKKLIQGTFDFLALSHYTTIL<br>VDSEKEDPIKYNDYLEVQEMTDITWLNSPSQVAV<br>VPWGLRKVLNWLKFKYGDLPMYIISNGIDDGLHA<br>EDDQLRVYYMQNYINEALKAHILDGINLCGYFAY<br>SFNDRTAPRFGLYRYAADQFEPKASMKHYRKIID<br>SNGFPGPETLERFCPEEFTVCTECSFFHTRKSLLAF<br>IAFLFFASIISLSLIFYYSKKGRRSYK |
| 67 | Human Sm22-alpha protein | MANKGPSYGMSREVQSKIEKKYDEELEERLVEWI<br>IVQCGPDVGRPDRGRLGFQVWLKNGVILSKLVNS<br>LYPDGSKPVKVPENPPSMVFKQMEQVAQFLKAA<br>EDYGVIKTDMFQTVDLFEGKDMAAVQRTLMALG<br>SLAVTKNDGHYRGDPNWFMKKAQEHKREFTESQ<br>LQEGKHVIGLQMGSNRGASQAGMTGYGRPRQIIS |
| 68 | Human alpha-SMA protein | MCEEEDSTALVCDNGSGLCKAGFAGDDAPRAVF<br>PSIVGRPRHQGVMVGMGQKDSYVGDEAQSKRGI<br>LTLKYPIEHGIITNWDDMEKIWHHSFYNELRVAPE<br>EHPTLLTEAPLNPKANREKMTQIMFETFNVPAMY<br>VAIQAVLSLYASGRTTGIVLDSGDGVTHNVPIYEG<br>YALPHAIMRLDLAGRDLTDYLMKILTERGYSFVT<br>TAEREIVRDIKEKLCYVALDFENEMATAASSSSLE<br>KSYELPDGQVITIGNERFRCPETLFQPSFIGMESAG<br>IHETTYNSIMKCDIDIRKDLYANNVLSGGTTMYPG<br>IADRMQKEITALAPSTMKIKIIAPPERKYSVWIGGS<br>ILASLSTFQQMWISKQEYDEAGPSIVHRKCF |
| 69 | Human MYOCD protein | MTLLGSEHSLLIRSKFRSVLQLRLQQRRTQEQLAN<br>QGIIPPLKRPAEFHEQRKHLDSDKAKNSLKRKARN<br>RCNSADLVNMHILQASTAERSIPTAQMKLKRARL<br>ADDLNEKIALRPGPLELVEKNILPVDSAVKEAIKG<br>NQVSFSKSTDAFAFEEDSSSDGLSPDQTRSEDPQN<br>SAGSPPDAKASDTPSTGSLGTNQDLASGSENDRN<br>DSASQPSHQSDAGKQGLGPPSTPIAVHAAVKSKS<br>LGDSKNRHKKPKDPKPKVKKLKYHQYrPPDQKA<br>EKSPPPMDSAYARLLQQQQLFLQLQILSQQQQQQ<br>QHRFSYLGMHQAQLKEPNEQMVRNPNSSSTPLSN<br>TPLSPVKNSFSGQTGVSSFKPGPLPPNLDDLKVSE<br>LRQQLRIRGLPVSGTKTALMDRLRPFQDCSGNPV<br>PNFGDITTVTFPVTPNTLPNYQSSSSTSALSNGFYH<br>FGSTSSSPPISPASSDLSVAGSLPDTFNDASPSFGLH<br>PSPVHVCTEESLMSSLNGGSVPSELDGLDSEKDK<br>MLVEKQKVINELTWKLQQEQRQVEELRMQLQKQ<br>KRNNCSEKKPLPFLAASIKQEEAVSSCPFASQVPV<br>KRQSSSSECHPPACEAAQLQPLGNAHCVESSDQT<br>NVLSSTFLSPQCSPQHSPLGAVKSPQHISLPPSPNN<br>PHFLPSSSGAQGEGHRVSSPISSQVCTAQNSGAHD<br>GHPPSFSPHSSSLHPPFSGAQADSSHGAGGNPCPK<br>SPCVQQKMAGLHSSDKVGPKFSIPSPTFSKSSSAIS<br>EVTQPPSYEDAVKQQMTRSQQMDELLDVLIESGE<br>MPADAREDHSCLQKVPKIPRSSRSPTAVLTKPSAS<br>FEQASSGSQIPFDPYATDSDEHLEVLLNSQSPLGK<br>MSDVTLLKIGSEEPHFDGIMDGFSGKAAEDLFNA<br>HEILPGPLSPMQTQFSPSSVDSNGLQLSFTESPWET<br>MEWLDLTPPNSTPGFSALTTSSPSIFNIDFLDVTDL<br>NLNSSMDLHLQQW |
| 70 | Human alpha-SMA mRNA | CTCTCCCCGCCCCCGCGGGGCGGCGCGCACTCA<br>CCCACCCGCGCCGGAGCGGACCTTTGGCTTGGC<br>TTGTCAGGGCTTGTCCAGGAGTTCCGCTCCTCTC<br>TCCAACCGGGGTCCCCCTCCAGCGACCCTAAAG<br>CTTCCCAGACTTCCGCTTCAATTCCTGTCCGCAC<br>CCCACGCCCACCTCAACGTGGAGCGCAGTGGTC<br>TCCGAGGAGCGCCGGAGCTGCCCCGCCTGCCCA<br>GCGGGGTCAGCACTTCGCATCAAGGCCCAAGA<br>AAAGCAAGTCCTCCAGCGTTCTGAGCACCCGGG |

TABLE 21-continued

Sequence Information

| SEQ ID NO: | Description | Sequence |
|---|---|---|
| | | CCTGAGGGAAGGTCCTAACAGCCCCCGGGAGC<br>CAGTCTCCAACGCCTCCCGCAGCAGCCCGCCGC<br>TCCCAGGTGCCCGCGTGCGCCGCTGCCGCCGCA<br>ATCCCGCACGCGTCCCGCGCCCGCCCCACTTTG<br>CCTATCCCCGGGACTAAGACGGGAATCCTGTGA<br>AGCAGCTCCAGCTATGTGTGAAGAAGAGGACA<br>GCACTGCCTTGGTGTGTGACAATGGCTCTGGGC<br>TCTGTAAGGCCGGCTTTGCTGGGGACGATGCTC<br>CCAGGGCTGTTTTCCCATCCATTGTGGGACGTC<br>CCAGACATCAGGGGGTGATGGTGGGAATGGGA<br>CAAAAAGACAGCTACGTGGGTGACGAAGCACA<br>GAGCAAAAGAGGAATCCTGACCCTGAAGTACC<br>CGATAGAACATGGCATCATCACCAACTGGGAC<br>GACATGGAAAAGATCTGGCACCACTCTTTCTAC<br>AATGAGCTTCGTGTTGCCCCTGAAGAGCATCCC<br>ACCCTGCTCACGGAGGCACCCCTGAACCCCAAG<br>GCCAACCGGGAGAAAATGACTCAAATTATGTTT<br>GAGACTTTCAATGTCCCAGCCATGTATGTGGCT<br>ATCCAGGCGGTGCTGTCTCTCTATGCCTCTGGA<br>CGCACAACTGGCATCGTGCTGGACTCTGGAGAT<br>GGTGTCACCCACAATGTCCCCATCTATGAGGGC<br>TATGCCTTGCCCCATGCCATCATGCGTCTGGAT<br>CTGGCTGGCCGAGATCTCACTGACTACCTCATG<br>AAGATCCTGACTGAGCGTGGCTATTCCTTCGTT<br>ACTACTGCTGAGCGTGAGATTGTCCGGGACATC<br>AAGGAGAAACTGTGTTATGTAGCTCTGGACTTT<br>GAAAATGAGATGGCCACTGCCGCATCCTCATCC<br>TCCCTTGAGAAGAGTTACGAGTTGCCTGATGGG<br>CAAGTGATCACCATCGGAAATGAACGTTTCCGC<br>TGCCCAGAGACCCTGTTCCAGCCATCCTTCATC<br>GGGATGGAGTCTGCTGGCATCCATGAAACCACC<br>TACAACAGCATCATGAAGTGTGATATTGACATC<br>AGGAAGGACCTCTATGCTAACAATGTCCTATCA<br>GGGGGCACCACTATGTACCCTGGCATTGCCGAC<br>CGAATGCAGAAGGAGATCACGGCCCTAGCACC<br>CAGCACCATGAAGATCAAGATCATTGCCCCTCC<br>GGAGCGCAAATACTCTGTCTGGATCGGTGGCTC<br>CATCCTGGCCTCTCTGTCCACCTTCCAGCAGAT<br>GTGGATCAGCAAACAGGAATACGATGAAGCCG<br>GGCCTTCCATTGTCCACCGCAAATGCTTCTAAA<br>ACACTTTCCTGCTCCTCTCTGTCTCTAGCACACA<br>ACTGTGAATGTCCTGTGGAATTATGCCTTCAGT<br>TCTTTTCCAAATCATTCCTAGCCAAAGCTCTGAC<br>TCGTTACCTATGTGTTTTTTAATAAATCTGAAAT<br>AGGCTACTGGTAAAAAAAAAAAAAAAAAAAA<br>AAAAAAAAAAAAAAAAAAA |
| 71 | Human MYOCD mRNA | AATCGCCGGCAGCCTATGACATCAGACAGGAA<br>CGCCTGGGATGCCGCGCTGCTCCTGGCCAACCT<br>CCGAGGAGGAGGAGGGTCCCGCCGGCTAAGAG<br>TTAATTAGCCCCGCACGGCGAGGGGGAGGCG<br>CCAGTTTTCTGGGGACACTGGCTGCCACTGTAC<br>TCCTACCCAGGGGAGCTCACGGAGAGTTGGATG<br>AATTCTGGGTTGTTAGCTGCGGTCAGCTGGGCT<br>CCCGGGAGCCTGTTGCTGGTGGAGAACAGGGG<br>GCGCCTGGCCAAGGGACCAGCGGCTTGCTGAG<br>ACTCAACATGACACTCCTGGGGTCTGAGCATTC<br>CTTGCTGATTAGGAGCAAGTTCAGATCAGTTTT<br>ACAGTTAAGACTTCAACAAAGAAGGACCCAGG<br>AACAACTGGCTAACCAAGGCATAATACCACCA<br>CTGAAACGTCCAGCTGAATTCCATGAGCAAAGA<br>AAACATTTGGATAGTGACAAGGCTAAAAATTCC<br>CTGAAGCGCAAAGCCAGAAACAGGTGCAACAG<br>TGCCGACTTGGTTAATATGCACATACTCCAAGC<br>TTCCACTGCAGAGAGGTCCATTCCAACTGCTCA<br>GATGAAGCTGAAAAGAGCCCGACTCGCCGATG<br>ATCTCAATGAAAAAATTGCTCTACGACCAGGGC<br>CACTGGAGCTGGTGGAAAAAAACATTCTTCCTG<br>TGGATTCTGCTGTGAAAGAGGCCATAAAAGGTA<br>ACCAGGTGAGTTTCTCCAAATCCACGGATGCTT<br>TTGCCTTTGAAGAGGACAGCAGCAGCGATGGG<br>CTTTCTCCGGATCAGACTCGAAGTGAAGACCCC<br>CAAAACTCAGCGGGATCCCCGCCAGACGCTAA<br>AGCCTCAGATACCCCTTCGACAGGTTCTCTGGG |

TABLE 21-continued

Sequence Information

| SEQ ID NO: | Description | Sequence |
|---|---|---|
| | | GACAAACCAGGATCTTGCTTCTGGCTCAGAAAA<br>TGACAGAAATGACTCAGCCTCACAGCCCAGCCA<br>CCAGTCAGATGCGGGAAGCAGGGGCTTGGCC<br>CCCCCAGCACCCCATAGCCGTGCATGCTGCTG<br>TAAAGTCCAAATCCTTGGGTGACAGTAAGAACC<br>GCCACAAAAAGCCCAAGGACCCCAAGCCAAAG<br>GTGAAGAAGCTTAAATATCACCAGTACATTCCC<br>CCAGACCAGAAGGCAGAGAAGTCCCCTCCACC<br>TATGGACTCAGCCTACGCTCGGCTGCTCCAGCA<br>ACAGCAGCTGTTCCTGCAGCTCCAAATCCTCAG<br>CCAGCAGCAGCAGCAGCAGCAACACCGATTCA<br>GCTACCTAGGGATGCACCAAGCTCAGCTTAAGG<br>AACCAAATGAACAGATGGTCAGAAATCCAAAC<br>TCTTCTTCAACGCCACTGAGCAATACCCCCTTGT<br>CTCCTGTCAAAAACAGTTTTTCTGGACAAACTG<br>GTGTCTCTTCTTTCAAACCAGGCCCACTCCCACC<br>TAACCTGGATGATCTGAAGGTCTCTGAATTAAG<br>ACAACAGCTTCGAATTCGGGGCTTGCCTGTGTC<br>AGGCACCAAAACGGCTCTCATGGACCGGCTTCG<br>ACCCTTCCAGGACTGCTCTGGCAACCCAGTGCC<br>GAACTTTGGGGATATAACGACTGTCACTTTTCC<br>TGTCACACCCAACACGCTGCCCAATTACCAGTC<br>TTCCTCTTCTACCAGTGCCCTGTCCAACGGCTTC<br>TACCACTTTGGCAGCACCAGCTCCAGCCCCCCG<br>ATCTCCCCAGCCTCCTCTGACCTGTCAGTCGCTG<br>GGTCCCTGCCGGACACCTTCAATGATGCCTCCC<br>CCTCCTTCGGCCTGCACCCGTCCCCAGTCCACG<br>TGTGCACGGAGGAAAGTCTCATGAGCAGCCTG<br>AATGGGGGCTCTGTTCCTTCTGAGCTGGATGGG<br>CTGGACTCCGAGAAGGACAAGATGCTGGTGGA<br>GAAGCAGAAGGTGATCAATGAACTCACCTGGA<br>AACTCCAGCAAGAGCAGAGGCAGGTGGAGGAG<br>CTGAGGATGCAGCTTCAGAAGCAGAAAAGGAA<br>TAACTGTTCAGAGAAGAAGCCGCTGCCTTTCCT<br>GGCTGCCTCCATCAAGCAGGAAGAGGCTGTCTC<br>CAGCTGTCCTTTTGCATCCCAAGTACCTGTGAA<br>AAGACAAAGCAGCAGCTCAGAGTGTCACCCAC<br>CGGCTTGTGAAGCTGCTCAACTCCAGCCTCTTG<br>GAAATGCTCATTGTGTGGAGTCCTCAGATCAAA<br>CCAATGTACTTTCTTCCACATTTCTCAGCCCCCA<br>GTGTTCCCCTCAGCATTCACCGCTGGGGCTGT<br>GAAAAGCCCACAGCACATCAGTTTGCCCCCATC<br>ACCCAACAACCCTCACTTTCTGCCCTCATCCTCC<br>GGGGCCCAGGGAGAAGGGCACAGGGTCTCCTC<br>GCCCATCAGCAGCCAGGTGTGCACTGCACAGA<br>ACTCAGGAGCACACGATGGCCATCCTCCAAGCT<br>TCTCTCCCCATTCTTCCAGCCTCCACCCGCCCTT<br>CTCTGGAGCCCAAGCAGACAGCAGTCATGGTGC<br>CGGGGGAAACCCTTGTCCCAAAAGCCCATGTGT<br>ACAGCAAAAGATGGCTGGTTTACACTCTTCTGA<br>TAAGGTGGGGCCAAAGTTTTCAATTCCATCCCC<br>AACTTTTTCTAAGTCAAGTTCAGCAATTTCAGA<br>GGTAACACAGCCTCCATCCTATGAAGATGCCGT<br>AAAGCAGCAAATGACCCGGAGTCAGCAGATGG<br>ATGAACTCCTGGACGTGCTTATTGAAAGCGGAG<br>AAATGCCAGCAGACGCTAGAGAGGATCACTCA<br>TGTCTTCAAAAAGTCCCAAAGATACCCAGATCT<br>TCCCGAAGTCCAACTGCTGTCCTCACCAAGCCC<br>TCGGCTTCCTTTGAACAAGCCTCTTCAGGCAGC<br>CAGATCCCCTTTGATCCCTATGCCACCGACAGT<br>GATGAGCATCTTGAAGTCTTATTAAATTCCCAG<br>AGCCCCCTAGGAAAGATGAGTGATGTCACCCTT<br>CTAAAAATTGGGAGCGAAGAGCCTCACTTTGAT<br>GGGATAATGGATGGATTCTCTGGGAAGGCTGCA<br>GAAGACCTTTCAATGCACATGAGATCTTGCCA<br>GGCCCCTCTCTCCAATGCAGACACAGTTTTCA<br>CCCTCTTCTGTGGACAGCAATGGGCTGCAGTTA<br>AGCTTCACTGAATCTCCCTGGGAAACCATGGAG<br>TGGCTGGACCTCACTCCGCCAAATTCCACACCA<br>GGCTTTAGCGCCCTCACCACCAGCAGCCCCAGC<br>ATCTTCAACATCGATTTCCTGGATGTCACTGATC<br>TCAATTTGAATTCTTCCATGGACCTTCACTTGCA<br>GCAGTGGTAGAATGCCCAATGCACCAGTGCTAT<br>GGAAGACCAATGGAGTTCCATGGGGGAAAGCA |

TABLE 21-continued

Sequence Information

| SEQ ID NO: | Description | Sequence |
|---|---|---|
| | | CACAGCCATACATACTTTACTGTCCAAAAACAG |
| | | AAGAAGAAGAAGAGAATTAAAAAGAAGCAATG |
| | | ATTTCTGTGCCAATGAACAAGAACAAAAGTCAT |
| | | TTTTAGAAATACATATACTGTAATATTTACCAA |
| | | CAGTCAGTAACTGTTAATGATTTCAACAATGCA |
| | | TTAAAAGAATGTGCTTTCTCAGATTAAGGATGC |
| | | CAAAAAAGATATTTCACTGCCTTTTCAAAGACC |
| | | AGTATATTTTCTAGCCCATAATTTTTCTCAGGCA |
| | | TTGTTGGGCATAAGCTCACACTGTAAGCTTTT |
| | | CTCATGAATTCACTAGACATAACGTGGAAGGAA |
| | | AACGTAGTCTTTTGGGAGTACAGGGAAGCCAGC |
| | | CCCTCAAAGCTTATGGAAGACATACCTGCAATG |
| | | GAAGCTGTTGCCCAATGTCTCCATTACTATCTTT |
| | | CAAAAGAGAAGCCAGACCCAGCTTCAGATCAA |
| | | AAGTTCTTGAGACAGAGGAACAAAACCAATCG |
| | | ATTTCCAGGGAAGCTAATCAACTCTCTTTTCCCT |
| | | CTACCACAAAACTGCCCTGCTGGAGTGGTTCTG |
| | | AACCTGTACCCAGGACTCGATGTGGTCACTAAT |
| | | AACAATTAACCTGAACTGAGTCCACAGAACTCC |
| | | ACTCGGAACTTTCTTCTTTTTTAACTAGTGGCCC |
| | | AATCATTCCCACCATCTCTGTGCTGATAAGTAC |
| | | GTGTCCTAGATGAGAACCCTGAAGAATGCAGA |
| | | CCTTCTTCCCCCGAAGGAGATGCCACAAGCTCT |
| | | CCAACACAGCCCCCTTTAGTTCCAAAGACTAGA |
| | | GATGACCACATTGGTAGAAGTATATCTCGAGGC |
| | | ACAGGAAGGGAGCCCCACCAGGGATAATTCAG |
| | | ACAGGACTAGAGAATAACATCATTTCACATACC |
| | | CTGGGATAAACACCCTGGGTTCCTATAGAAGGA |
| | | CTATTACTTATGGGAGTCCAACTTCTCCTTTTGT |
| | | TTTGTTATTATCAGTTTATCTTTCTCCCACTCCA |
| | | CTTTTCCTTCAAGGTACCAATCCTTTCCTGTTCC |
| | | TCGTTTGGCCATCTTTCTTTTTCTGCCTCCACAT |
| | | TGGGAGGGGAGGACTTCTCAGTTCTAACAAGCT |
| | | GCCATACTCCTAAGAAAGCCATTTTTGAAAAAT |
| | | TTAACAATCCAGGTTCTTCTGGAGAACTCATTC |
| | | TCCACACGCACAGTTTGCTGCAAAAGGAAGTTG |
| | | CAAGAATTTCTTGAGGAAGAAACTGGTGACTTG |
| | | GTCCATCAGTCACGAAGTTCTTTCTATTCTCGTT |
| | | TAGTTTTCAAGAAATTATTGGTTTGTGTTGCTCT |
| | | GGGGAAATTGGAAATCATTACATTGTAAAGAC |
| | | AAATATGGATGATATTTACAAGAGAGAATTTCA |
| | | GATCTGGGTTTTTGAAAGAAAACAGAATTGCGC |
| | | ATTGAAAACGATGGAAGGAAAAAGACAATGGT |
| | | CTAATGTGCATTCCTCATTACCTCTCGTGGCTTT |
| | | GGCTGGGAGTTGGAAAAAGCTAAAATTTCAGA |
| | | ACAGTCTCTGTAAGGCTCTCTGTGGCTCCAGTT |
| | | CACCATTTTATATTGTTGCATGCTGTAGAAAGG |
| | | AGCTATTGCTGTTGTTTTGTTTTTTTATTTAAAT |
| | | CACTAAGGCACTGTTTTTATCTTTTGTAAAAAA |
| | | AAAAAAAAAGTTGTTCACTGTGCACTTATAGAA |
| | | AAAATAATCAAAAATGTTGGGATTTTAGAAGCT |
| | | CTCTTTTTGATAAACCAAAGATTTAGAAGTCAT |
| | | TCCATTGTTAACTTGTAAAAATGTGTGAACACA |
| | | GAGAGTTTTTGGTGATTGCTACTCTGAAAGCTG |
| | | CCAGATCTTATTCTGGGGGTGGGATGTGGAGGA |
| | | ATACACATACACACACAAACATACATGTATGTA |
| | | TAATAGATATATACATATGTGTATATTATATCT |
| | | GTGTGTGCATGTATCTCCAAAAGCGGCGTTACA |
| | | GAGTTCTACACCAAAAGCCTTTAACCCTTAATC |
| | | TGCTGTGAATGATACCTGGCCTTTCTCACTATG |
| | | AATTTCTGATTAACCAACCAGACTACACGTTGC |
| | | CTCTCTGTGTATGACTAACGGCTCCAACCCGAT |
| | | GACTCACAGCTACTTGCTTATCGTGAACAAGCT |
| | | CATCTTGGCAATGAATATGGATGTGAAAAGACA |
| | | GAACAGCTTCACCATTAGTAGCTGGAAATGGTA |
| | | TCACAGTCTCTTATAGAGGAATATGAAAGGAAC |
| | | AAGAAAATCATTTTACATTCCTTTTATCTGTATT |
| | | GTGCTTTAAAAGATCCACATGGTAAATTTTTTA |
| | | TTTTGCTTTTATGTCAGTCATCAGAACCAAAAA |
| | | AATCCAGAAGAAAAAATTGCCAGTGTTTCCTTT |
| | | GAAGATGAAGCTACTGGGGAAGAAAACCTTAT |
| | | TAATACACTCCACACATTTGTTCATTCCTCAGCT |
| | | GTTGGTGTTTCTTGGGGTCTTGACAAAGCTTGC |
| | | TGGTCAGTGCACTTTTCAGGTGTCACGTTTTGCT |

TABLE 21-continued

Sequence Information

| SEQ ID NO: | Description | Sequence |
|---|---|---|
| | | GTTTGTATGTTTTTTCTTCCCCTTACTTCCTTTGG |
| | | AAAACAAACTCACACAGTGCCCCTACTCTGAGA |
| | | CCTGGGACTGAGTGTTAATTATTTTTTCCTTGGG |
| | | TATTTCTATCTGAGAGACTAGACCTAGTTAGGA |
| | | GGCCTCTGTACTTCTCCAGATTGTACCTTTTTAT |
| | | GGGGATCTTTGAGGCTATGACCCAGGACTGATA |
| | | GATATGCCTTACGGAAGACAAAAGATAAAATG |
| | | GTTCCTATATCCTAATGCAAACCAACACAGTTA |
| | | AAAGAGCAGATCTCTGGATAACTGCTCTCAACC |
| | | TGCTTCTACAGTCTCCACAAACCGCATTCACCC |
| | | TCTCTCTTCATAGCTCAGACATGAAATTTGAGG |
| | | GAGAAAACTGGAGATAATTGGGAGAAAATTGA |
| | | TGAAGTTGGCTGCTTCCAGTAGATCAGATAATC |
| | | CATGAATTTGTCTCCCATTGAGAATTTTATTTTA |
| | | AATTCTTTTAAACTCTTCGTTGTGTCTTTTGTGA |
| | | TGACAAATCAGGCATGACTAAAAGATGTACAG |
| | | AGACTTACGAAGATGGTCACATTCAAGTTCCCT |
| | | AATGCTCTTAGAACCTGAAGATGACCATGTGTA |
| | | GTTTTCTTAAGACCTCTGAACCCCCATGGTGAT |
| | | GAAGACTTGAAGACATTTGCAGCTATCTGCTGC |
| | | AGTCTGGTAGATTCATACTTATCTAAAGAAGTC |
| | | AAAAAATTTATTCGTGCAAGTGCTTGCAGGAAG |
| | | CCAGTGCTTATTAGTAGTGACCCTGCTTCTATCA |
| | | ACGTTATTGAGACAACACATATTCTATTCTAAG |
| | | GGAGAAAGAGGGAGGAAGAGAGGGAGGGAGG |
| | | GAGGAAGAAGAGGGAGGGAGCGAGGAAGGAA |
| | | GATAGGAGATGGGTAGGGGGGTAAAGAGAAAA |
| | | GGAGGGAGAAGGGAAGGAAGGAAAGAAGAGA |
| | | GGAAAGAAAGGAGGGAAGGAAAAAAGGGCCA |
| | | AACTTTCTGATCTATGAACTTCTCAGTTCAGCTG |
| | | TCACATTATGAGAAGTAAATCAGAATTTTTTTA |
| | | AGGAGAAGTCATTCTTAGCACTACAATAATTGT |
| | | ACCAGTAATTGAGGAAACCAAGACAATCTTCAC |
| | | CTGAATAATAGAGGGTCTGAGAACTGTCAGCCT |
| | | TTTGCCATTCAAAAACATTTATGTCCAACCTGA |
| | | AAAAAAAGCATCAATAAAACCTATCCCAAGCA |
| | | TTCAAAATAGTCCTTTCCAAATGTTATTTATTTT |
| | | AAAGTCAATCAGCTCTTTTAGAAACAGATTCTG |
| | | GTCTGGCTGAAAACTCCCACAACAAATrrACTC |
| | | ATCCAGTGGCTAATATTTAATGCCCACCATGGG |
| | | CAGAGCACACAAATCTTCAGATAAACAATACTG |
| | | AATTGATTCAGCACAGATTGTTCAGATTTGAAT |
| | | GACCAGGGAGTTGTATTTGCACATGCAAGAACA |
| | | CTAAGAATCTCCCAGTCCTCAAACTAGAAACCT |
| | | TTCAGCTACGATGAAAAAAAAAAGGGGTCTT |
| | | CATTTTTCCAAGAGGGGGTGGAGGTGGGGATCA |
| | | CTTTTTAGCTAAAAGCTATCTCTCACTTCAAAAT |
| | | TCTTGTCTTTTTCTTTGTGGACAAACACCAGTAG |
| | | TCTATCACTTGGAGATCTTTTAATATCTCCCATC |
| | | ATTTAAAACATCCACGAGAGTTTGAAGATTTGT |
| | | GTTGATTGCCAGATACAGAAGCCCCTTGAAAAT |
| | | AAGGAAAGGGTGGAGGAAGCATTTTTGTGTCCT |
| | | ATCCCTACTTATCGTAGCAGCTCTATAGACAAA |
| | | AGGGACACTTACTGGTGAGCCTCTGGCCCTTAA |
| | | AAGAAAATCATCTAAGAATATGAAGGCAATTT |
| | | GATTTCCCCCCACAGCCCTCAGCTGCCTTCCTC |
| | | ACAGAAGGAAGTTCCCAAAATTGCTGGTACAC |
| | | AGTTTGCAATCAAATATCAGATATGAGAAAACC |
| | | TGTAGTGAAGAGTCTGGGTTCTTGGTTTTCTCAT |
| | | AAATCCAATATAAATTTGTAGGTTGGTTCAGGG |
| | | TCAAAATTGCCAGTGCTTTATTAGACAGATGAT |
| | | ACTGATAGACACACAGAGCCCAGGTCCTGGAA |
| | | CAAGACAATCCTGTAGTGCCAAGATCTGGTCAG |
| | | TTGCGTTAAGGAGCTGGGTTTGATTCTAGAGTC |
| | | CAGGTTTATAGAGAAACCCTGGCTAGATTGAGC |
| | | CTACCCATGGGGAGACGATTTCAAGACAGGAT |
| | | GAGATCTGGGAAGAATTTGTTGTCATCTGCCA |
| | | GGGAAATTATCACAGGACTCATTGAATGCAATA |
| | | ACATGTGAGTAAGTTCCCTTTTGATTCTGGGAA |
| | | TCAGCGATTTTCCCTGTGGATTAAGACAAACCA |
| | | ACGCCAGAAGGTCTCCTGTGCTTATTTTAACCA |
| | | TCTGCTCCCATCGTGAACCCTGGAGCATGCATT |
| | | TCCTAGAAGTGGTTTCATAGCTCCTGTGTGTTCA |
| | | TGGAAAAGGGGAGTATAATGATGGGGATGCTG |

TABLE 21-continued

Sequence Information

| SEQ ID NO: | Description | Sequence |
|---|---|---|
| | | GAAGCTTTTTTAATGTTTTCCAAAGGAAAGGAA<br>CCCACACTGCTCCCCAGAGTTCCTTTCCAATGG<br>CCCTGCAGTAAGAACGGAGGACAATGTATTGCT<br>GGGTGCTTAAAATCCTCCCTCAGTGAAGCACAA<br>AGAGACACTTTGTAAAGAAAAAAAGAGCAAGC<br>ATAGGTTCTCTGTGGGACCTTGTGGAGTGGTGT<br>TTTCACGTTGGTCTCTTTGGCTCAATTGAGCATA<br>ATCAGAAAGAAATGTGGGTTATTGGGAAGAGA<br>CAAAAAGCAGTGGCTAAAATACCAAAGTTGGC<br>ATGTGTTCTTTTTTAAAAAAAAAAAAAAATGCA<br>TATATTTTTAAATAAAATGTTTATTTTAAAAAG<br>AAAAAAAAAAAAAAAAA |
| 72 | Human BSAP protein | MISPFLVLAIGTCLTNSLVPEKEKDPKYWRDQAQ<br>ETLKYALELQKLNTNVAKNVIMFLGDGMGVSTV<br>TAARILKGQLHHNPGEETRLEMDKFPFVALSKTY<br>NTNAQVPDSAGTATAYLCGVKANEGTVGVSAAT<br>ERSRCNTTQGNEVTSILRWAKDAGKSVGIVTTTR<br>VNHATPSAAYAHSADRDWYSDNEMPPEALSQGC<br>KDIAYQLMHNIRDIDVIMGGGRKYMYPKNKTDV<br>EYESDEKARGTRLDGLDLVDTWKSFKPRYKHSHF<br>IWNRTELLTLDPHNYDYLLGLFEPGDMQYELNKN<br>NVTDPSLSEMVVVAIQILRKNPKGFFLLVEGGRJD<br>HGHHEGKAKQALHEAVEMDRAIGQAGSLTSSED<br>TLTVVTADHSHVFTFGGYTPRGNSIFGLAPMLSDT<br>DKKPFTAILYGNGPGYKVVGGERENVSMVDYAH<br>NNYQAQSAVPLRJIETHGGEDVAVFSKGPMAHLL<br>HGVHEQNYVPHVMAYAACIGANLGHCAPASSAG<br>SLAAGPLLLALALYPLSVLF |
| 73 | Human BSAP mRNA | CCGGGCCTCACTCGGGCCCCGCGGCCGCCTTTA<br>TAAGGCGGCGGGGGTGGTGGCCCGGGCCGCGT<br>TGCGCTCCCGCCACTCCGCGCCCGCTATCCTGG<br>CTCCGTGCTCCCACGCGCTTGTGCCTGGACGGA<br>CCCTCGCCAGTGCTCTGCGCAGGATTGGAACAT<br>CAGTTAACATCTGACCACTGCCAGCCCACCCCC<br>TCCCACCCACGTCGATTGCATCTCTGGGCTCCA<br>GGGATAAAGCAGGTCTTGGGGTGCACCATGATT<br>TCACCATTCTTAGTACTGGCCATTGGCACCTGC<br>CTTACTAACTCCTTAGTGCCAGAGAAAGAGAAA<br>GACCCCAAGTACTGGCGAGACCAAGCGCAAGA<br>GACACTGAAATATGCCCTGGAGCTTCAGAAGCT<br>CAACACCAACGTGGCTAAGAATGTCATCATGTT<br>CCTGGGAGATGGGATGGGTGTCTCCACAGTGAC<br>GGCTGCCCGCATCCTCAAGGGTCAGCTCCACCA<br>CAACCCTGGGGAGGAGACCAGGCTGGAGATGG<br>ACAAGTTCCCCTTCGTGGCCCTCTCCAAGACGT<br>ACAACACCAATGCCCAGGTCCCTGACAGCGCC<br>GGCACCGCCACCGCCTACCTGTGTGGGGTGAAG<br>GCCAATGAGGGCACCGTGGGGGTAAGCGCAGC<br>CACTGAGCGTTCCCGGTGCAACACCACCCAGGG<br>GAACGAGGTCACCTCCATCCTGCGCTGGGCCAA<br>GGACGCTGGGAAATCTGTGGGCATTGTGACCAC<br>CACGAGAGTGAACCATGCCACCCCCAGCGCCG<br>CCTACGCCCACTCGGCTGACCGGGACTGGTACT<br>CAGACAACGAGATGCCCCCTGAGGCCTTGAGCC<br>AGGGCTGTAAGGACATCGCCTACCAGCTCATGC<br>ATAACATCAGGGACATTGACGTGATCATGGGG<br>GGTGGCCGGAAATACATGTACCCCAAGAATAA<br>AACTGATGTGGAGTATGAGAGTGACGAGAAAG<br>CCAGGGGCACGAGGCTGGACGGCCTGGACCTC<br>GTTGACACCTGGAAGAGCTTCAAACCGAGATAC<br>AAGCACTCCCACTTCATCTGGAACCGCACGGAA<br>CTCCTGACCCTTGACCCCCACAATGTGGACTAC<br>CTATTGGGTCTCTTCGAGCCAGGGGACATGCAG<br>TACGAGCTGAACAGGAACAACGTGACGGACCC<br>GTCACTCTCCGAGATGGTGGTGGTGGCCATCCA<br>GATCCTGCGGAAGAACCCCAAAGGCTTCTTCTT<br>GCTGGTGGAAGGAGGCAGAATTGACCACGGGC<br>ACCATGAAGGAAAAGCCAAGCAGGCCCTGCAT<br>GAGGCGGTGGAGATGGACCGGGCCATCGGGCA<br>GGCAGGCAGCTTGACCTCCTCGGAAGACACTCT<br>GACCGTGGTCACTGCGGACCATTCCCACGTCTT<br>CACATTTGGTGGATACACCCCCCGTGGCAACTC |

TABLE 21-continued

Sequence Information

| SEQ ID NO: | Description | Sequence |
|---|---|---|
| | | TATCTTTGGTCTGGCCCCCATGCTGAGTGACAC<br>AGACAAGAAGCCCTTCACTGCCATCCTGTATGG<br>CAATGGGCCTGGCTACAAGGTGGTGGGCGGTG<br>AACGAGAGAATGTCTCCATGGTGGACTATGCTC<br>ACAACAACTACCAGGCGCAGTCTGCTGTGCCCC<br>TGCGCCACGAGACCCACGGCGGGGAGGACGTG<br>GCCGTCTTCTCCAAGGGCCCCATGGCGCACCTG<br>CTGCACGGCGTCCACGAGCAGAACTACGTCCCC<br>CACGTGATGGCGTATGCAGCCTGCATCGGGGCC<br>AACCTCGGCCACTGTGCTCCTGCCAGCTCGGCA<br>GGCAGCCTTGCTGCAGGCCCCCTGCTGCTCGCG<br>CTGGCCCTCTACCCCCTGAGCGTCCTGTTCTGA<br>GGGCCCAGGGCCCGGGCACCCACAAGCCCGTG<br>ACAGATGCCAACTTCCCACACGGCAGCCCCCCC<br>CTCAAGGGGCAGGGAGGTGGGGGCCTCCTCAG<br>CCTCTGCAACTGCAAGAAAGGGGACCCAAGAA<br>ACCAAAGTCTGCCGCCCACCTCGCTCCCCTCTG<br>GAATCTTCCCCAAGGGCCAAACCCACTTCTGGC<br>CTCCAGCCTTTGCTCCCTCCCCGCTGCCCTTTGG<br>CCAACAGGGTAGATTTCTCTTGGGCAGGCAGAG<br>AGTACAGACTGCAGACATTCTCAAAGCCTCTTA<br>TTTTTCTAGCGAACGTATTTCTCCAGACCCAGA<br>GGCCCTGAAGCCTCCGTGGAACATTCTGGATCT<br>GACCCTCCCAGTCTCATCTCCTGACCCTCCCACT<br>CCCATCTCCTTACCTCTGGAACCCCCCAGGCCC<br>TACAATGCTCATGTCCCTGTCCCAGGCCCAGC<br>CCTCCTTCAGGGGAGTTGAGGTCTrTCTCCTCA<br>GGACAAGGCCTTGCTCACTCACTCACTCCAAGA<br>CCACCAGGGTCCAGGAAGCCGGTGCCTGGGT<br>GGCCATCCTACCCAGCGTGGCCCAGGCCGGGA<br>AGAGCCACCTGGCAGGGCTCACACTCCTGGGCT<br>CTGAACACACACGCCAGCTCCTCTCTGAAGCGA<br>CTCTCCTGTTTGGAACGGCAAAAAAAAATTTTT<br>TTTTCTCTTTTTGGTGGTGGTTAAAAGGGAACA<br>CAAAACATTTAAATAAAACTTTCCAAATATTTC<br>CGAGGACAAAAAAAAAAA |
| 74 | Snail mRNA | ATTCATTGCGCCGCGGCACGGCCTAGCGAGTGG<br>TTCTTCTGCGCTACTGCTGCGCGAATCGGCGAC<br>CCCAGTGCCTCGACCACTATGCCGCGCTCTTTC<br>CTCGTCAGGAAGCCCTCCGACCCCAATCGGAAG<br>CCTAACTACAGCGAGCTGCAGGACTCTAATCCA<br>GAGTTTACCTTCCAGCAGCCCTACGACCAGGCC<br>CACCTGCTGGCAGCCATCCCACCTCCGGAGATC<br>CTCAACCCCACCGCCTCGCTGCCAATGCTCATC<br>TGGGACTCTGTCCTGGCGCCCCAAGCCCAGCCA<br>ATTGCCTGGGCCTCCCTTCGGCTCCAGGAGAGT<br>CCCAGGGTGGCAGAGCTGACCTCCCTGTCAGAT<br>GAGGACAGTGGGAAAGGCTCCCAGCCCCCCAG<br>CCCACCCTCACCGGCTCCTTCGTCCTTCTCCTCT<br>ACTTCAGTCTCTTCCTTGGAGGCCGAGGCCTAT<br>GCTGCCTTCCCAGGCTTGGGCCAAGTGCCCAAG<br>CAGCTGGCCCAGCTCTCTGAGGCCAAGGATCTC<br>CAGGCTCGAAAGGCCTTCAACTGCAAATACTGC<br>AACAAGGAATACCTCAGCCTGGGTGCCCTCAAG<br>ATGCACATCCGAAGCCACACGCTGCCCTGCGTC<br>TGCGGAACCTGCGGGAAGGCCTTCTCTAGGCCC<br>TGGCTGCTACAAGGCCATGTCCGGACCCACACT<br>GGCGAGAAGCCCTTCTCCTGTCCCACTGCAGC<br>CGTGCCTTCGCTGACCGCTCCAACCTGCGGGCC<br>CACCTCCAGACCCACTCAGATGTCAAGAAGTAC<br>CAGTGCCAGGCGTGTGCTCGGACCTTCTCCCGA<br>ATGTCCCTGCTCCACAAGCACCAAGAGTCCGGC<br>TGCTCAGGATGTCCCCGCTGACCCTCGAGGCTC<br>CCTCTTCCTCTCCATACCTGCCCCTGCCTGACAG<br>CCTTCCCCAGCTCCAGCAGGAAGGACCCCACAT<br>CCTTCTCACTGCCATGGAATTCCCTCCTGAGTGC<br>CCCACTTCTGGCCACATCAGCCCCACAGGACTT<br>TGATGAAGACCATTTTCTGGTTCTGTGTCCTCTG<br>CCTGGGCTCTGGAAGAGGCCTTCCCATGGCCAT<br>TTCTGTGGAGGGAGGGCAGCTGGCCCCCAGCCC<br>TGGGGGATTCCTGAGCTGGCCTGTCTGCGTGGG<br>TTTTTGTATCCAGAGCTGTrTGGATACAGCTGCT<br>TTGAGCTACAGGACAAAGGCTGACAGACTCACT |

TABLE 21-continued

Sequence Information

| SEQ ID NO: | Description | Sequence |
|---|---|---|
| | | GGGAAGCTCCCACCCCACTCAGGGGACCCCACT CCCCTCACACACACCCCCCCACAAGGAACCCTC AGGCCACCCTCCACGAGGTGTGACTAACTATGC AATAATCCACCCCCAGGTGCAGCCCCAGGGCCT GCGGAGGCGGTGGCAGACTAGAGTCTGAGATG CCCCGAGCCCAGGCAGCTATTTCAGCCTCCTGT TTGGTGGGGTGGCACCTGTTTCCCGGGCAATTT AACAATGTCTGAAAAGGGACTGTGAGTAATGG CTGTCACTTGTCGGGGGCCCAAGTGGGGTGCTC TGGTCTGACCGATGTCTCCCAGAACTATTCT GGGGGCCCGACAGGTGGGCCTGGGAGGAAGAT GTTTACATTTTTAAAGGTACACTGGTATTTATAT TTCAAACATTTTGTATCAAGGAAACGTTTTGTA TAGTTATATGTACAGTTTATTGATATTCAATAA AGCAGTTAATTTATATATTAAAAAAAAAAAAA AAAAA |
| 75 | Dkk1 mRNA | GCAGAGCTCTGTGCTCCCTGCAGTCAGGACTCT GGGACCGCAGGGGGCTCCCGGACCCTGACTCTG CAGCCGAACCGGCACGGTTTCGTGGGGACCCA GGCTTGCAAAGTGACGGTCATTTTCTCTTTCTTT CTCCCTCTTGAGTCCTTCTGAGATGATGGCTCTG GGCGCAGCGGGAGCTACCCGGGTCTTTGTCGCG ATGGTAGCGGCGGCTCTCGGCGGCCACCCTCTG CTGGGAGTGAGCGCCACCTTGAACTCGGTTCTC AATTCCAACGCTATCAAGAACCTGCCCCCACCG CTGGGCGGCGCTGCGGGGCACCCAGGCTCTGCA GTCAGCGCCGCGCCGGGAATCCTGTACCCGGGC GGGAATAAGTACCAGACCATTGACAACTACCA GCCGTACCCGTGCGCAGAGGACGAGGAGTGCG GCACTGATGAGTACTGCGCTAGTCCCACCCGCG GAGGGGACGCAGGCGTGCAAATCTGTCTCGCCT GCAGGAAGCGCCGAAAACGCTGCATGCGTCAC GCTATGTGCTGCCCCGGGAATTACTGCAAAAAT GGAATATGTGTGTCTTCTGATCAAAATCATTTC CGAGGAGAAATTGAGGAAACCATCACTGAAAG CTTTGGTAATGATCATAGCACCTTGGATGGGTA TTCCAGAAGAACCACCTTGTCTTCAAAAATGTA TCACACCAAAGGACAAGAAGGTTCTGTTTGTCT CCGGTCATCAGACTGTGCCTCAGGATTGTGTTG TGCTAGACACTTCTGGTCCAAGATCTGTAAACC TGTCCTGAAAGAAGGTCAAGTGTGTACCAAGCA TAGGAGAAAAGGCTCTCATGGACTAGAAATATT CCAGCGTTGTTACTGTGGAGAAGGTCTGTCTTG CCGGATACAGAAAGATCACCATCAAGCCAGTA ATTCTTCTAGGCTTCACACTTGTCAGAGACACT AAACCAGCTATCCAAATGCAGTGAACTCCTTTT ATATAATAGATGCTATGAAAACCTTTTATGACC TTCATCAACTCAATCCTAAGGATATACAAGTTC TGTGGTTTCAGTTAAGCATTCCAATAACACCTT CCAAAAACCTGGAGTGTAAGAGCTTTGTTTCTT TATGGAACTCCCCTGTGATTGCAGTAAATTACT GTATTGTAAATTCTCAGTGTGGCACTTACCTGT AAATGCAATGAAACTTTTAATTATTTTCTAAA GGTGCTGCACTGCCTATTTTTCCTCTTGTTATGT AAATTTTGTACACATTGATTGTTATCTTGACTG ACAAATATTCTATATTGAACTGAAGTAAATCAT TTCAGCTTATAGTTCTTAAAAGCATAACCCTTTA CCCCATTTAATTCTAGAGTCTAGAACGCAAGGA TCTCTTGGAATGACAAATGATAGGTACCTAAAA TGTAACATGAAAATACTAGCTTATTTTCTGAAA TGTACTATCTTAATGCTTAAATTATATTTCCCTT TAGGCTGTGATAGTTTTTGAAATAAAATTTAAC ATTTAATATCATGAAATGTTATAAGTAGACATA CATTTTGGGATTGTGATCTTAGAGGTTTGTGTGT GTGTACGTATGTGTGTTCTACAAGAACGGAA GTGTGATATGTTTAAAGATGATCAGAGAAAAG ACAGTGTCTAAATATAAGACAATATTGATCAGC TCTAGAATAACTTTAAAGAAAGACGTGTTCTGC ATTGATAAACTCAAATGATCATGGCAGAATGAG AGTGAATCTTACATTACTACTTTCAAAAATAGT TTCCAATAAATTAATAATACCTAAAAAAAAAA |

TABLE 21-continued

Sequence Information

| SEQ ID NO: | Description | Sequence |
|---|---|---|
| 76 | Col1a1 mRNA | TCGTCGGAGCAGACGGGAGTTTCTCCTCGGGGT
CGGAGCAGGAGGCACGCGGAGTGTGAGGCCAC
GCATGAGCGGACGCTAACCCCCTCCCCAGCCAC
AAAGAGTCTACATGTCTAGGGTCTAGACATGTT
CAGCTTTGTGGACCTCCGGCTCCTGCTCCTCTTA
GCGGCCACCGCCCTCCTGACGCACGGCCAAGA
GGAAGGCCAAGTCGAGGGCCAAGACGAAGACA
TCCCACCAATCACCTGCGTACAGAACGGCCTCA
GGTACCATGACCGAGACGTGTGGAAACCCGAG
CCCTGCCGGATCTGCGTCTGCGACAACGGCAAG
GTGTTGTGCGATGACGTGATCTGTGACGAGACC
AAGAACTGCCCCGGCGCCGAAGTCCCCGAGGG
CGAGTGCTGTCCCGTCTGCCCCGACGGCTCAGA
GTCACCCACCGACCAAGAAACCACCGGCGTCG
AGGGACCCAAGGGAGACACTGGCCCCCGAGGC
CCAAGGGGACCCGCAGGCCCCCCTGGCCGAGA
TGGCATCCCTGGACAGCCTGGACTTCCCGGACC
CCCCGGACCCCCCGGACCTCCCGGACCCCCTGG
CCTCGGAGGAAACTTTGCTCCCCAGCTGTCTTA
TGGCTATGATGAGAAATCAACCGGAGGAATTTC
CGTGCCTGGCCCCATGGGTCCCTCTGGTCCTCG
TGGTCTCCCTGGCCCCCTGGTGCACCTGGTCC
CCAAGGCTTCCAAGGTCCCCCTGGTGAGCCTGG
CGAGCCTGGAGCTTCAGGTCCCATGGGTCCCCG
AGGTCCCCCAGGTCCCCCTGGAAAGAATGGAG
ATGATGGGGAAGCTGCAAAACCTGGTCGTCCTG
GTGAGCGTGGGCCTCCTGGGCCTCAGGGTGCTC
GAGGATTGCCCGGAACAGCTGGCCTCCCTGGAA
TGAAGGGACACAGAGGTTTCAGTGGTTTGGATG
GTGCCAAGGGAGATGCTGGTCCTGCTGGTCCTA
AGGGTGAGCCTGGCAGCCCTGGTGAAAATGGA
GCTCCTGGTCAGATGGGCCCCCGTGGCCTGCCT
GGTGAGAGAGGTCGCCCTGGAGCCCCTGGCCCT
GCTGGTGCTCGTGGAAATGATGGTGCTACTGGT
GCTGCCGGGCCCCCTGGTCCCACCGGCCCCGCT
GGTCCTCCTGGCTTCCCTGGTGCTGTTGGTGCTA
AGGGTGAAGCTGGTCCCCAAGGGCCCCGAGGC
TCTGAAGGTCCCCAGGGTGTGCGTGGTGAGCCT
GGCCCCCCTGGCCCTGCTGGTGCTGCTGGCCCT
GCTGGAAACCCTGGTGCTGATGGACAGCCTGGT
GCTAAAGGTGCCAATGGTGCTCCTGGTATTGCT
GGTGCTCCTGGCTTCCCTGGTGCCCGAGGCCCC
TCTGGACCCCAGGGCCCCGGCGGCCCTCCTGGT
CCCAAGGGTAACAGCGGTGAACCTGGTGCTCCT
GGCAGCAAAGGAGACACTGGTGCTAAGGGAGA
GCCTGGCCCTGTTGGTGTTCAAGGACCCCCTGG
CCCTGCTGGAGAGGAAGGAAAGCGAGGAGCTC
GAGGTGAACCCGGACCCACTGGCCTGCCCGGA
CCCCCTGGCGAGCGTGGTGGACCTGGTAGCCGT
GGTTTCCCTGGCGCAGATGGTGTTGCTGGTCCC
AAGGGTCCCGCTGGTGAACGTGGTTCTCCTGGC
CCTGCTGGCCCCAAAGGATCTCCTGGTGAAGCT
GGTCGTCCCGGTGAAGCTGGTCTGCCTGGTGCC
AAGGGTCTGACTGGAAGCCCTGGCAGCCCTGGT
CCTGATGGCAAAACTGGCCCCCCTGGTCCCGCC
GGTCAAGATGGTCGCCCCGGACCCCCAGGCCC
ACCTGGTGCCCGTGGTCAGGCTGGTGTGATGGG
ATTCCCTGGACCTAAAGGTGCTGCTGGAGAGCC
CGGCAAGGCTGGAGAGCGAGGTGTTCCCGGAC
CCCCTGGCGCTGTCGGTCCTGCTGGCAAAGATG
GAGAGGCTGGAGCTCAGGGACCCCCTGGCCCT
GCTGGTCCCGCTGGCGAGAGAGGTGAACAAGG
CCCTGCTGGCTCCCCCGGATTCCAGGGTCTCCC
TGGTCCTGCTGGTCCTCCAGGTGAAGCAGGCAA
ACCTGGTGAACAGGGTGTTCCTGGAGACCTTGG
CGCCCCTGGCCCCTCTGGAGCAAGAGGCGAGA
GAGGTTTCCCTGGCGAGCGTGGTGTGCAAGGTC
CCCCTGGTCCTGCTGGTCCCCGAGGGGCCAACG
GTGCTCCCGGCAACGATGGTGCTAAGGGTGATG
CTGGTGCCCCTGGAGCTCCCGGTAGCCAGGGCG
CCCCTGGCCTTCAGGGAATGCCTGGTGAACGTG
GTGCAGCTGGTCTTCCAGGGCCTAAGGGTGACA
GAGGTGATGCTGGTCCCAAAGGTGCTGATGGCT
CTCCTGGCAAAGATGGCGTCCGTGGTCTGACTG |

TABLE 21-continued

Sequence Information

| SEQ ID NO: | Description | Sequence |
|---|---|---|
| | | GCCCCATTGGTCCTCCTGGCCCTGCTGGTGCCC |
| | | CTGGTGACAAGGGTGAAAGTGGTCCCAGCGGC |
| | | CCTGCTGGTCCCACTGGAGCTCGTGGTGCCCCC |
| | | GGAGACCGTGGTGAGCCTGGTCCCCCCGGCCCT |
| | | GCTGGCTTTGCTGGCCCCCTGGTGCTGACGGC |
| | | CAACCTGGTGCTAAAGGCGAACCTGGTGATGCT |
| | | GGTGCTAAAGGCGATGCTGGTCCCCCTGGCCCT |
| | | GCCGGACCCGCTGGACCCCCTGGCCCCATTGGT |
| | | AATGTTGGTGCTCCTGGAGCCAAAGGTGCTCGC |
| | | GGCAGCGCTGGTCCCCCTGGTGCTACTGGTTTC |
| | | CCTCGTGCTGCTGGCCGAGTCGGTCCTCCTGGC |
| | | CCCTCTGGAAATGCTGGACCCCCTGGCCCTCCT |
| | | GGTCCTGCTGGCAAAGAAGGCGGCAAAGGTCC |
| | | CCGTGGTGAGACTGGCCCTGCTGGACGTCCTGG |
| | | TGAAGTTGGTCCCCCTGGTCCCCCTGGCCCTGC |
| | | TGGCGAGAAAGGATCCCCTGGTGCTGATGGTCC |
| | | TGCTGGTGCTCCTGGTACTCCCGGGCCTCAAGG |
| | | TATTGCTGGACAGCGTGGTGTGGTCGGCCTGCC |
| | | TGGTCAGAGAGGAGAGAGAGGCTTCCCTGGTCT |
| | | TCCTGGCCCCTCTGGTGAACCTGGCAAACAAGG |
| | | TCCCTCTGGAGCAAGTGGTGAACGTGGTCCCCC |
| | | TGGTCCCATGGGCCCCCCTGGATTCGCTGGACC |
| | | CCCTGGTGAATCTGGACGTGAGGGGGCTCCTGG |
| | | TGCCGAAGGTTCCCCTGGACGAGACGGTTCTCC |
| | | TGGCGCCAAGGGTGACCGTGGTGAGACCGGCC |
| | | CCGCTGGACCCCCTGGTGCTCCTGGTGCTCCTG |
| | | GTGCCCCTGGCCCCGTTGGCCCTGCTGGCAAGA |
| | | GTGGTGATCGTGGTGAGACTGGTCCTGCTGGTC |
| | | CCGCCGGTCCTGTCGGCCCTGTTGGCGCCCGTG |
| | | GCCCCGCCGGACCCCAAGGCCCCCGTGGTGAC |
| | | AAGGGTGAGACAGGCGAACAGGGCGACAGAGG |
| | | CATAAAGGGTCACCGTGGCTTCTCTGGCCTCCA |
| | | GGGTCCCCCTGGCCCTCCTGGCTCTCCTGGTGA |
| | | ACAAGGTCCCTCTGGAGCCTCTGGTCCTGCTGG |
| | | TCCCCGAGGTCCCCCTGGCTCTGCTGGTGCTCCT |
| | | GGCAAAGATGGACTCAACGGTCTCCCTGGCCCC |
| | | ATTGGGCCCCCTGGTCCTCGCGGTCGCACTGGT |
| | | GATGCTGGTCCTGTTGGTCCCCCCGGCCCTCCT |
| | | GGACCTCCTGGTCCCCCTGGTCCTCCCAGCGCT |
| | | GGTTTCGACTTCAGCTTCCTGCCCCAGCCACCTC |
| | | AAGAGAAGGCTCACGATGGTGGCCGCTACTAC |
| | | CGGGCTGATGATGCCAATGTGGTTCGTGACCGT |
| | | GACCTCGAGGTGGACACCACCCTCAAGAGCCTG |
| | | AGCCAGCAGATCGAGAACATCCGGAGCCCAGA |
| | | GGGCAGCCGCAAGAACCCCGCCCGCACCTGCC |
| | | GTGACCTCAAGATGTGCCACTCTGACTGGAAGA |
| | | GTGGAGAGTACTGGATTGACCCCAACCAAGGCT |
| | | GCAACCTGGATGCCATCAAAGTCTTCTGCAACA |
| | | TGGAGACTGGTGAGACCTGCGTGTACCCCACTC |
| | | AGCCCAGTGTGGCCCAGAAGAACTGGTACATC |
| | | AGCAAGAACCCCAAGGACAAGAGGCATGTCTG |
| | | GTTCGGCGAGAGCATGACCGATGGATTCCAGTT |
| | | CGAGTATGGCGGCCAGGGCTCCGACCCTGCCGA |
| | | TGTGGCCATCCAGCTGACCTTCCTGCGCCTGAT |
| | | GTCCACCGAGGCCTCCCAGAACATCACCTACCA |
| | | CTGCAAGAACAGCGTGGCCTACATGGACCAGC |
| | | AGACTGGCAACCTCAAGAAGGCCCTGCTCCTCC |
| | | AGGGCTCCAACGAGATCGAGATCCGCGCCGAG |
| | | GGCAACAGCCGCTTCACCTACAGCGTCACTGTC |
| | | GATGGCTGCACGAGTCACACCGGAGCCTGGGG |
| | | CAAGACAGTGATTGAATACAAAACCACCAAGA |
| | | CCTCCCGCCTGCCCATCATCGATGTGGCCCCCT |
| | | TGGACGTTGGTGCCCCAGACCAGGAATTCGGCT |
| | | TCGACGTTGGCCCTGTCTGCTTCCTGTAAACTCC |
| | | CTCCATCCCAACCTGGCTCCCTCCCACCCAACC |
| | | AACTTTCCCCCCAACCCGGAAACAGACAAGCA |
| | | ACCCAAACTGAACCCCCTCAAAAGCAAAAAA |
| | | TGGGAGACAATTTCACATGGACTTTGGAAAATA |
| | | TTTTTTTCCTTTGCATTCATCTCTCAAACTTAGTT |
| | | TTTATCTTTGACCAACCGAACATGACCAAAAAC |
| | | CAAAAGTGCATTCAACTTACCAAAAAAAAA |
| | | AAAAAAAAAGAATAAATAAATAACTTTTTAAA |
| | | AAAGGAAGCTTGGTCCACTTGCTTGAAGACCCA |
| | | TGCGGGGTAAGTCCCTTTCTGCCCGTTGGGCT |

TABLE 21-continued

Sequence Information

| SEQ ID NO: | Description | Sequence |
|---|---|---|
| | | TATGAAACCCCAATGCTGCCCTTTCTGCTCCTTT<br>CTCCACACCCCCTTGGGGCCTCCCCTCCACTC<br>CTTCCCAAATCTGTCTCCCCAGAAGACACAGGA<br>AACAATGTATTGTCTGCCCAGCAATCAAAGGCA<br>ATGCTCAAACACCCAAGTGGCCCCCACCCTCAG<br>CCCGCTCCTGCCCGCCCAGCACCCCCAGGCCCT<br>GGGGGACCTGGGGTTCTCAGACTGCCAAAGAA<br>GCCTTGCCATCTGGCGCTCCCATGGCTCTTGCA<br>ACATCTCCCCTTCGTTTTTGAGGGGGTCATGCC<br>GGGGGAGCCACCAGCCCCTCACTGGGTTCGGA<br>GGAGAGTCAGGAAGGGCCACGACAAAGCAGAA<br>ACATCGGATTTGGGGAACGCGTGTCAATCCCTT<br>GTGCCGCAGGGCTGGGCGGGAGAGACTGTTCT<br>GTTCCTTGTGTAACTGTGTTGCTGAAAGACTAC<br>CTCGTTCTTGTCTTGATGTGTCACCGGGGCAACT<br>GCCTGGGGCGGGGATGGGGGCAGGGTGGAAG<br>CGGCTCCCCATTTTATACCAAAGGTGCTACATC<br>TATGTGATGGGTGGGGTGGGGAGGGAATCACT<br>GGTGCTATAGAAATTGAGATGCCCCCCCAGGCC<br>AGCAAATGTTCCTTTTTGTTCAAAGTCTATTTTT<br>ATTCCTTGATATTTTTCTTTTTTTTTTTTTTTTTT<br>GTGGATGGGGACTTGTGAATTTTTCTAAAGGTG<br>CTATTTAACATGGGAGGAGAGCGTGTGCGGCTC<br>CAGCCCAGCCCGCTGCTCACTTTCCACCCTCTCT<br>CCACCTGCCTCTGGCTTCTCAGGCCTCTGCTCTC<br>CGACCTCTCTCCTCTGAAACCCTCCTCCACAGC<br>TGCAGCCCATCCTCCCGGCTCCCTCCTAGTCTGT<br>CCTGCGTCCTCTGTCCCCGGGTTTCAGAGACAA<br>CTTCCCAAAGCACAAAGCAGTTTTTCCCCCTAG<br>GGGTGGGAGGAAGCAAAAGACTCTGTACCTAT<br>TTTGTATGTGTATAATAATTTGAGATGTTTTTAA<br>TTATTTTGATTGCTGGAATAAAGCATGTGGAAA<br>TGACCCAAACATAA |
| 77 | AcTivin A mRNA | ATGCCCTTGCTTTGGCTGAGAGGATTCTGTTG<br>GCAAGTTGCTGGATTATAGTGAGGAGTTCCCCC<br>ACCCCAGGATCCGAGGGGCACAGCGCGGCCCC<br>CGACTGTCCGTCCTGTGCGCTGGCCGCCCTCCC<br>AAAGGATGTACCCAACTCTCAGCCAGAGATGGT<br>GGAGGCCGTCAAGAAGCACATTTTAAACATGCT<br>GCACTTGAAGAAGAGACCCGATGTCACCCAGC<br>CGGTACCCAAGGCGGCGCTTCTGAACGCGATCA<br>GAAAGCTTCATGTGGGCAAAGTCGGGGAGAAC<br>GGGTATGTGGAGATAGAGGATGACATTGGAAG<br>GAGGGCAGAAATGAATGAACTTATGGAGCAGA<br>CCTCGGAGATCATCACGTTTGCCGAGTCAGGTT<br>GGTGCTGGCATTGGCAGGGGGTGGGGAGGGGT<br>GGGGGGTGGGAGGGTAAAATATATTTCTTTGAC<br>AGTCCCAGGAGGAACTTCTTTTCCCTTCAGCTG<br>GAAACTGCCTGGGAAGGTTATTAGTTATTAGGT<br>GATGGTAGCGGACTAGCCGACGGAGGGCAGGC<br>AGGGGAGGGGGAGAGGACTTTACAGAAAAGGA<br>ATTCTCGGTCGAGCTCTGCCTGGAGATGACTGG<br>CTTACACTTACTAAACCCAGCGGGTCACACAGA<br>GAGGAAGCTCGGGGCCAATGTTGAGCTGGAAG<br>GCAGACTGTGAGGGGCTGCCTTGCCCTGCCTGT<br>GAAACAGATCTGAGCAGCCGGAGGAAAGCCGC<br>GGCATTTTCGGGTGCTAGGGGAGCAGAGGAGG<br>CTTCCGGACCCCATCCAAGTTTTTATTGAGGGT<br>AGAGGGGTGAATGTACCAGGATTGGAGTGGAA<br>TGGCACAGATGAAGTCACTCTCTTAAAACAAAC<br>CTTCCCCTTTAAAAGTCCAATCTGGGCCACAT<br>TGGAGAAGCAGGGCATATTTATGAGTGACAGTC<br>ATTTTTACCTTTAGAAAATGTCTATAAGTGCAC<br>AGGCACCACATTCAAGACAGGGAAGAGCTACT<br>TTGGGGGACAGTTGTCATTGAACCAGCAGTTAC<br>TTTTGGGACACTGACTTTTGCTCTCTGAAAGAA<br>AAAAAAATAAATAAAACAACCAGTTTTGTTCTT<br>TCTAAAGTTACTAAGAGCTCTCTGCCAAGGAAC<br>GAACCTTGACAAAGTACTCTCAGATACTACGCT<br>GAAGTCACTCAATCTTAAGAGGAAGAAG |

TABLE 21-continued

Sequence Information

| SEQ ID NO: | Description | Sequence |
|---|---|---|
| 78 | Snail primer 1 | TCGGAAGCCTAACTACAGCGA |
| 79 | Snail primer2 | AGATGAGCATTGGCAGCGAG |
| 80 | Dkk1 primer 1 | CCTTGAACTCGGTTCTCAATTCC |
| 81 | Dkk1 primer 2 | CAATGGTCTGGTACTTATTCCCG |
| 82 | Col1a1 primer 1 | GAGGGCCAAGACGAAGACATC |
| 83 | Col1a1 primer 2 | CAGATCACGTCATCGCACAAC |
| 84 | Activin primer 1 | TCATCACGTTTGCCGAGTCA |
| 85 | Activin primer 2 | GCTAGTCCGCTACCATCACC |
| 86 | Human Axin2 mRNA | ACTGCCTCCGCGAGCCTGGCCCGGGGGAGTCG GCTGGAGCCGGCTGCGCTTTGATAAGGTCCTGG CAACTCAGTAACAGCCCGAGAGCCGGGAAATA AAAATAACCCCTCAGAGCGATGGATTTCGGGGC CGCCCGGCGGCCGAGGCGCCCGCCGAAGGCCC TGCTGTAAAAGAGAGGAGGTTCAGATGAGCCC CTGCTGACTTGAGAGAGACAGAGAGAGACCACGC CGATTGCTGAGAGGAACTGGAAGAAGAAAAAT TCCCAGACTCAGTGGGAAGAGCTCCCTCACCAT GAGTAGCGCTATGTTGGTGACTTGCCTCCCGGA CCCCAGCAGCAGCTTCCGTGAGGATGCCCCGCG GCCCCCAGTGCCAGGGGAAGAAGGGGAGACCC CACCGTGTCAGCCAGGGGTGGGCAAGGGCCAG GTCACCAAACCCATGCCTGTCTCTTCCAACACC AGGCGGAACGAAGATGGGTTGGGGGAGCCGGA GGGGCGGGCATCTCCGGATTCCCCTCTGACCCG GTGGACCAAGTCCTTACACTCCTTATTGGGCGA TCAAGACGGTGCTTACCTGTTCCGAACTTTCCT GGAGAGGGAGAAATGCGTGGATACCTTAGACT TCTGGTTTGCCTGCAATGGATTCAGGCAGATGA ACCTGAAGGATACCAAAACTTTACGAGTAGCCA AAGCGATCTACAAAAGGTACATTGAGAACAAC AGCATTGTCTCCAAGCAGCTGAAGCCTGCCACC AAGACCTACATAAGAGATGGCATCAAGAAGCA GCAGATTGATTCCATCATGTTTGACCAGGCGCA GACCGAGATCCAGTCGGTGATGGAGGAAAATG CCTACCAGATGTTTTTGACTTCTGATATATACCT CGAATATGTGAGGAGTGGGGGAGAAAACACAG CTTACATGAGTAATGGGGGACTCGGGAGCCTAA AGGTCGTGTGTGGCTATCTCCCCACCTTGAATG AAGAAGAGGAGTGGACTTGTGCCGACTTCAAG TGCAAACTTTCGCCAACCGTGGTTGGCTTGTCC AGCAAAACTCTGAGGGCCACGGCGAGTGTGAG GTCCACGGAAACTGTTGACAGTGGATACAGGTC CTTCAAGAGGAGCGATCCTGTTAATCCTTATCA CATAGGTTCTGGCTATGTCTTTGCACCAGCCAC CAGCGCCAACGACAGTGAGATATCCAGTGATG CGCTGACGGATGATTCCATGTCCATGACGGACA GCAGTGTAGATGGAATTCCTCCTTATCGTGTGG GCACTAAGAAACAGCTCCAGAGAGAAATGCAT CGCAGTGTGAAGGCCAATGGCCAAGTGTCTCTA CCTCATTTCCCGAGAACCCACCGCCTGCCCAAG GAGATGACCCCCGTGGAACCCGCCACCTTTGCA GCTGAGCTGATCTCGAGGCTGGAAAAGCTGAA GCTGGAGTTGGAGAGCCGCCACAGCCTGGAGG AGCGCCTGCAGCAGATCCGAGAGGATGAAGAG AGAGAGGGCTCCGAGCTCACACTCAATTCGCGG GAGGGGGCGCCCACGCAGCACCCCCTCTCCCTA CTGCCCTCCGGCAGCTACGAGGAAGACCCCGCA GACGATACTGGACGATCACCTGTCCAGGGTCCT CAAGACCCCTGGCTGCCAGTCTCCAGGCGTAGG CCGCTATAGCCCCGCTCCCGCTCCCCGGACCA CCACCACCACCACCATTCGCAGTACCACTCCCT GCTCCCGCCCGGTGGCAAGCTGCCTCCCGCGGC CGCCTCGCCGGGCGCCTGCCCCCTCCTCGGGGG CAAAGGCTTTGTGACCAAGCAGACGACGAAGC ATGTCCACCACCACTACATCCACCACCATGCCG TCCCCAAGACCAAGGAGGAGATCGAGGCGGAG |

TABLE 21-continued

Sequence Information

| SEQ ID NO: | Description | Sequence |
|---|---|---|
| | | GCCACGCAGCGGGTGCACTGCTTCTGCCCTGGG GGCAGCGAGTATTACTGCTACTCGAAATGCAAA AGCCACTCCAAGGCTCCGGAAACCATGCCCAG CGAGCAGTTTGGCGGCAGCAGAGGCAGTACCTT GCCCAAACGCAATGGGAAAGGCACGGAGCCGG GCCTGGCCCTGCCCGCCAGGGAAGGAGGGGCC CCCGGCGGAGCTGGGGCCCTGCAGCTTCCCCGG GAGGAAGGAGACAGGTCGCAGGATGTCTGGCA GTGGATGCTGGAGAGTGAGCGGCAGAGCAAGC CCAAGCCCCATAGTGCCCAAAGCACAAAAAAG GCCTACCCCTTGGAGTCTGCCCGCTCGTCTCCA GGCGAACGAGCCAGCCGGCACCATCTGTGGGG GGGCAACAGCGGGCACCCCCGCACCACCCCCC GTGCCCACCTGTTCACCCAGGACCCTGCGATGC CTCCCCTGACCCCACCCAACACGCTGGCTCAGC TGGAGGAGGCCTGTCGCAGGCTAGCTGAGGTGT CGAAGCCCCCAAAGCAGCGGTGCTGTGTGGCC AGTCAGCAGAGGGACAGGAATCATTCGGCCAC TGTTCAGACGGGAGCCACACCCTTCTCCAATCC AAGCCTGGCTCCAGAAGATCACAAAGAGCCAA AGAAACTGGCAGGTGTCCACGCGCTCCAGGCC AGTGAGTTGGTTGTCACTTACTTTTTCTGTGGGG AAGAAATTCCATACCGGAGGATGCTGAAGGCT CAGAGCTTGACCCTGGGCCACTTTAAAGAGCAG CTCAGCAAAAAGGGAAATTATAGGTATTACTTC AAAAAAGCAAGCGATGAGTTTGCCTGTGGAGC GGTGTTTGAGGAGATCTGGGAGGATGAGACGG TGCTCCCGATGTATGAAGGCCGGATTCTGGGCA AAGTGGAGCGGATCGATTGAGCCCTGGGGTCTG GCTTTGGTGAACTGTTGGAGCCCGAAGCTCTTG TGAACTGTCTTGGCTGTGAGCAACTGCGACAAA ACATTTTGAAGGAAAATTAAACCAATGAAGAA GACAAAGTCTAAGGAAGAATCGGCCAGTGGGC CTTCGGGAGGGCGGGGGAGGTTGATTTTCATG ATTCATGAGCTGGGTACTGACTGAGATAAGAAA AGCCTGAACTATTTATTAAAAACATGACCACTC TTGGCTATTGAAGATGCTGCCTGTATTTGAGAG ACTGCCATACATAATATATGACTTCCTAGGGAT CTGAAATCCATAAACTAAGAGAAACTGTGTATA GCTTACCTGAACAGGAATCCTTACTGATATTTA TAGAACAGTTGATTTCCCCCATCCCCAGTTTAT GGATATGCTGCTTTAAACTTGGAAGGGGGAGAC AGGAAGTTTTAATTGTTCTGACTAAACTTAGGA GTTGAGCTAGGAGTGCGTTCATGGTTTCTTCAC TAACAGAGGAATTATGCTTTGCACTACGTCCCT CCAAGTGAAGACAGACTGTTTTAGACAGACTTT TTAAAATGGTGCCCTACCATTGACACATGCAGA AATTGGTGCGTTTTGTTTTTTTTTTCCTATGCTG CTCTGTTTTGTCTTAAAGGTCTTGAGGGTTGACC ATGTTGCGTCATCATCAACATTITGGGGTTGT GTTGGATGGGATGATCTGTTGCAGAGGGAGAG GCAGGGAACCCTGCTCCTTCGGGCCCCAGGTTG ATCCTGTGACTGAGGCTCCCCCTCATGTAGCCT CCCCAGGCCCAGGGCCCTGAGGCCTGCTAGAAT CACTGCCGCTGTGCTTTCGTGGAAATGACAGTT CCTTGTTTTTTTGTTTCTGTTTTTTTTTACATT AGTCATTGGACCACAGCCATTCAGGAACTACCC CCTGCCCCACAAAGAAATGAACAGTTGTAGGG AGACCCAGCAGCACCTTTCCTCCACACACCTTC ATTTTGATGTTCGGGTTTTTGTGTTAAGTTAATC TGTACATTCTGTTTGCCATTGTTACTTGTACTAT ACATCTGTATATAGTGTACGGCAAAAGAGTATT AATCCACTATCTCTAGTGCTTGACTTTAAATCA GTACAGTACCTGTACCTGCACGGTCACCCGCTC CGTGTGTCGCCCTATATTGAGGGCTCAAGCTTT CCCTTGTTTTTTGAAAGGGGTTTATGTATAAATA TATTTTATGCCTTTTTATTACAAGTCTTGTACTC AATGACTTTTGTCATGACATTTTGTTCTACTTAT ACTGTAAATTATGCATTATAAAGAGTTCATTTA AGGAAAATTACTTGGTACAATAATTATTGTAAT TAAGAGATGTAGCCTTTATTAAAATTTTATATTT TTCAAAAAAAAAA |

TABLE 21-continued

Sequence Information

| SEQ ID NO: | Description | Sequence |
|---|---|---|
| 87 | Human Axin2 amino acid sequence | MSSAMLVTCLPDPSSSFREDAPRPPVPGEEGETPP CQPGVGKGQVTKPMPVSSNTRRNEDGLGEPEGR ASPDSPLTRWTKSLHSLLGDQDGAYLFRTFLERE KCVDTLDFWFACNGFRQMNLKDTKTLRVAKAIY KRYIENNSIVSKQLKPATKTYIRDGIKKQQIDSIMF DQAQTEIQSVMEENAYQMFLTSDIYLEYVRSGGE NTAYMSNGGLGSLKVVCGYLPTLNEEEEWTCAD FKCKLSPTWGLSSKTLRATASVRSTETVDSGYRS FKRSDPVNPYHIGSGYVFAPATSANDSEISSDALT DDSMSMTDSSVDGIPPYRVGSKKQLQREMHRSV KANGQVSLPHFPRTHRLPKEMTPVEPATFAAELIS RLEKLKLELESRHSLEERLQQIREDEEREGSELTLN SREGAPTQHPLSLLPSGSYEEDPQTILDDHLSRVL KTPGCQSPGVGRYSPRSRSPDHHHHHHSQYHSLL PPGGKLPPAAASPGACPLLGGKGFVTKQTTKHVH HHYIHHHAVPKTKEEIEAEATQRVHCFCPGGSEY YCYSKCKSHSKAPETMPSEQFGGSRGSTLPKRNG KGTEPGLALPAREGGAPGGAGALQLPREEGDRSQ DVWQWMLESERQSKPKPHSAQSTKKAYPLESAR SSPGERASRHHLWGGNSGHPRTTPRAHLFTQDPA MPPLTPPNTLAQLEEACRRLAEVSKPPKQRCCVA SQQRDRNHSATVQTGATPFSNPSLAPEDHKEPKK LAGVHALQASELVVTYFFCGEEIPYRRMLKAQSL TLGHFKEQLSKKGNYRYYFKKASDEFACGAVFEE IWEDETVLPMYEGRILGKVERID |

EQUIVALENTS

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims. Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference in their entireties.

SEQUENCE LISTING

```
<160> NUMBER OF SEQ ID NOS: 87

<210> SEQ ID NO 1
<211> LENGTH: 513
<212> TYPE: PRT
<213> ORGANISM: Homo sapiens
<220> FEATURE:
<223> OTHER INFORMATION: human ActRIIA precursor polypeptide

<400> SEQUENCE: 1

Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
                20                  25                  30

Phe Asn Ala Asn Trp Glu Lys Asp Arg Thr Asn Gln Thr Gly Val Glu
            35                  40                  45

Pro Cys Tyr Gly Asp Lys Asp Lys Arg Arg His Cys Phe Ala Thr Trp
        50                  55                  60

Lys Asn Ile Ser Gly Ser Ile Glu Ile Val Lys Gln Gly Cys Trp Leu
65                  70                  75                  80
```

```
Asp Asp Ile Asn Cys Tyr Asp Arg Thr Asp Cys Val Glu Lys Lys Asp
                85                  90                  95

Ser Pro Glu Val Tyr Phe Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125

Pro Val Thr Pro Lys Pro Pro Tyr Tyr Asn Ile Leu Leu Tyr Ser Leu
    130                 135                 140

Val Pro Leu Met Leu Ile Ala Gly Ile Val Ile Cys Ala Phe Trp Val
145                 150                 155                 160

Tyr Arg His His Lys Met Ala Tyr Pro Pro Val Leu Val Pro Thr Gln
                165                 170                 175

Asp Pro Gly Pro Pro Pro Pro Ser Pro Leu Leu Gly Leu Lys Pro Leu
            180                 185                 190

Gln Leu Leu Glu Val Lys Ala Arg Gly Arg Phe Gly Cys Val Trp Lys
        195                 200                 205

Ala Gln Leu Leu Asn Glu Tyr Val Ala Val Lys Ile Phe Pro Ile Gln
    210                 215                 220

Asp Lys Gln Ser Trp Gln Asn Glu Tyr Glu Val Tyr Ser Leu Pro Gly
225                 230                 235                 240

Met Lys His Glu Asn Ile Leu Gln Phe Ile Gly Ala Glu Lys Arg Gly
                245                 250                 255

Thr Ser Val Asp Val Asp Leu Trp Leu Ile Thr Ala Phe His Glu Lys
            260                 265                 270

Gly Ser Leu Ser Asp Phe Leu Lys Ala Asn Val Val Ser Trp Asn Glu
        275                 280                 285

Leu Cys His Ile Ala Glu Thr Met Ala Arg Gly Leu Ala Tyr Leu His
    290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
                325                 330                 335

Cys Ile Ala Asp Phe Gly Leu Ala Leu Lys Phe Glu Ala Gly Lys Ser
            340                 345                 350

Ala Gly Asp Thr His Gly Gln Val Gly Thr Arg Arg Tyr Met Ala Pro
        355                 360                 365

Glu Val Leu Glu Gly Ala Ile Asn Phe Gln Arg Asp Ala Phe Leu Arg
    370                 375                 380

Ile Asp Met Tyr Ala Met Gly Leu Val Leu Trp Glu Leu Ala Ser Arg
385                 390                 395                 400

Cys Thr Ala Ala Asp Gly Pro Val Asp Glu Tyr Met Leu Pro Phe Glu
                405                 410                 415

Glu Glu Ile Gly Gln His Pro Ser Leu Glu Asp Met Gln Glu Val Val
            420                 425                 430

Val His Lys Lys Lys Arg Pro Val Leu Arg Asp Tyr Trp Gln Lys His
        435                 440                 445

Ala Gly Met Ala Met Leu Cys Glu Thr Ile Glu Glu Cys Trp Asp His
    450                 455                 460

Asp Ala Glu Ala Arg Leu Ser Ala Gly Cys Val Gly Glu Arg Ile Thr
465                 470                 475                 480

Gln Met Gln Arg Leu Thr Asn Ile Ile Thr Thr Glu Asp Ile Val Thr
                485                 490                 495

Val Val Thr Met Val Thr Asn Val Asp Phe Pro Pro Lys Glu Ser Ser
```

```
                    500                 505                 510

Leu

<210> SEQ ID NO 2
<211> LENGTH: 115
<212> TYPE: PRT
<213> ORGANISM: Homo sapiens
<220> FEATURE:
<223> OTHER INFORMATION: human ActRIIA soluble (extracellular),
      processed polypeptide sequence

<400> SEQUENCE: 2

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
                20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
                100                 105                 110

Lys Pro Pro
        115

<210> SEQ ID NO 3
<211> LENGTH: 100
<212> TYPE: PRT
<213> ORGANISM: Artificial Sequence
<220> FEATURE:
<223> OTHER INFORMATION: human ActRIIA soluble (extracellular),
      processed polypeptide sequence with the C-terminal 15 amino acids
      deleted

<400> SEQUENCE: 3

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
                20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met
        100

<210> SEQ ID NO 4
<211> LENGTH: 1542
<212> TYPE: DNA
<213> ORGANISM: Homo sapiens
<220> FEATURE:
<223> OTHER INFORMATION: nucleic acid sequence encoding human ActRIIA
``` precursor protein

<400> SEQUENCE: 4

```
atgggagctg ctgcaaagtt ggcgtttgcc gtctttctta tctcctgttc ttcaggtgct    60
atacttggta gatcagaaac tcaggagtgt cttttcttta atgctaattg ggaaaaagac   120
agaaccaatc aaactggtgt tgaaccgtgt tatggtgaca agataaacg gcggcattgt    180
tttgctacct ggaagaatat ttctggttcc attgaaatag tgaaacaagg ttgttggctg   240
gatgatatca actgctatga caggactgat tgtgtagaaa aaaagacag ccctgaagta    300
tattttgtt gctgtgaggg caatatgtgt aatgaaaagt tttcttattt tccagagatg    360
gaagtcacac agcccacttc aaatccagtt acacctaagc caccctatta caacatcctg   420
ctctattcct tggtgccact tatgttaatt gcggggattg tcatttgtgc attttgggtg   480
tacaggcatc acaagatggc ctaccctcct gtacttgttc caactcaaga cccaggacca   540
ccccacctt ctccattact agggttgaaa ccactgcagt tattagaagt gaaagcaagg   600
ggaagatttg gttgtgtctg gaaagcccag ttgcttaacg aatatgtggc tgtcaaaata   660
ttccaatac aggacaaaca gtcatggcaa aatgaatacg aagtctacag tttgcctgga   720
atgaagcatg agaacatatt acagttcatt ggtgcagaaa acgaggcac cagtgttgat    780
gtggatcttt ggctgatcac agcatttcat gaaaagggtt cactatcaga ctttcttaag   840
gctaatgtgg tctcttggaa tgaactgtgt catattgcag aaaccatggc tagaggattg   900
gcatatttac atgaggatat acctggccta aagatggcc acaaacctgc catatctcac   960
agggacatca aaagtaaaaa tgtgctgttg aaaacaacc tgacagcttg cattgctgac   1020
tttgggttgg ccttaaaatt tgaggctggc aagtctgcag gcgatacca tggacaggtt   1080
ggtacccgga ggtacatggc tccagaggta ttagagggtg ctataaactt cgaaagggat   1140
gcattttga ggatagatat gtatgccatg ggattagtcc tatgggaact ggcttctcgc   1200
tgtactgctg cagatggacc tgtagatgaa tacatgttgc catttgagga ggaaattggc   1260
cagcatccat ctcttgaaga catgcaggaa gttgttgtgc ataaaaaaaa gaggcctgtt   1320
ttaagagatt attggcagaa acatgctgga atggcaatgc tctgtgaaac cattgaagaa   1380
tgttgggatc acgacgcaga agccaggtta tcagctggat gtgtaggtga agaattacc   1440
cagatgcaga gactaacaaa tattattacc acagaggaca ttgtaacagt ggtcacaatg   1500
gtgacaaatg ttgactttcc tcccaaagaa tctagtctat ga                     1542
```

<210> SEQ ID NO 5
<211> LENGTH: 345
<212> TYPE: DNA
<213> ORGANISM: Homo sapiens
<220> FEATURE:
<223> OTHER INFORMATION: nucleic acid sequence encoding a human ActRIIA soluble (extracellular) polypeptide

<400> SEQUENCE: 5

```
atacttggta gatcagaaac tcaggagtgt cttttcttta atgctaattg ggaaaaagac    60
agaaccaatc aaactggtgt tgaaccgtgt tatggtgaca agataaacg gcggcattgt    120
tttgctacct ggaagaatat ttctggttcc attgaaatag tgaaacaagg ttgttggctg   180
gatgatatca actgctatga caggactgat tgtgtagaaa aaaagacag ccctgaagta    240
tattttgtt gctgtgaggg caatatgtgt aatgaaaagt tttcttattt tccagagatg    300
gaagtcacac agcccacttc aaatccagtt acacctaagc caccc                   345
```

```
<210> SEQ ID NO 6
<211> LENGTH: 228
<212> TYPE: PRT
<213> ORGANISM: Artificial Sequence
<220> FEATURE:
<223> OTHER INFORMATION: fusion protein comprising a soluble
      extracellular domain of ActRIIA fused to an Fc domain
<220> FEATURE:
<221> NAME/KEY: misc_feature
<222> LOCATION: (44)..(44)
<223> OTHER INFORMATION: Xaa = Asp or Ala
<220> FEATURE:
<221> NAME/KEY: misc_feature
<222> LOCATION: (102)..(102)
<223> OTHER INFORMATION: Xaa = Lys or Ala
<220> FEATURE:
<221> NAME/KEY: misc_feature
<222> LOCATION: (215)..(215)
<223> OTHER INFORMATION: Xaa = Asn or Ala

<400> SEQUENCE: 6

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Asp Xaa Val Ser His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
            85                  90                  95

Glu Tyr Lys Cys Lys Xaa Val Ser Asn Lys Ala Leu Pro Val Pro Ile
        100                 105                 110

Glu Lys Thr Ile Ser Lys Ala Lys Gly Gln Pro Arg Glu Pro Gln Val
    115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Pro Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Xaa His Tyr Thr Gln Lys Ser Leu Ser Leu
    210                 215                 220

Ser Pro Gly Lys
225

<210> SEQ ID NO 7
<211> LENGTH: 344
<212> TYPE: PRT
<213> ORGANISM: Artificial Sequence
<220> FEATURE:
<223> OTHER INFORMATION: Extracellular domain of human ActRIIA fused to
      a human Fc domain

<400> SEQUENCE: 7
```

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
                100                 105                 110

Lys Pro Pro Thr Gly Gly Thr His Thr Cys Pro Pro Cys Pro Ala
                115                 120                 125

Pro Glu Leu Leu Gly Gly Pro Ser Val Phe Leu Phe Pro Pro Lys Pro
        130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
                180                 185                 190

Tyr Asn Ser Thr Tyr Arg Val Val Ser Val Leu Thr Val Leu His Gln
            195                 200                 205

Asp Trp Leu Asn Gly Lys Glu Tyr Lys Cys Lys Val Ser Asn Lys Ala
        210                 215                 220

Leu Pro Val Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
                260                 265                 270

Asp Ile Ala Val Glu Trp Glu Ser Asn Gly Gln Pro Glu Asn Asn Tyr
            275                 280                 285

Lys Thr Thr Pro Pro Val Leu Asp Ser Asp Gly Ser Phe Phe Leu Tyr
        290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
                340

<210> SEQ ID NO 8
<211> LENGTH: 21
<212> TYPE: PRT
<213> ORGANISM: Artificial Sequence
<220> FEATURE:
<223> OTHER INFORMATION: Leader sequence of Honey bee mellitin (HBML)

<400> SEQUENCE: 8

Met Lys Phe Leu Val Asn Val Ala Leu Val Phe Met Val Val Tyr Ile
1               5                   10                  15

Ser Tyr Ile Tyr Ala
            20

<210> SEQ ID NO 9
<211> LENGTH: 22
<212> TYPE: PRT
<213> ORGANISM: Artificial Sequence
<220> FEATURE:
<223> OTHER INFORMATION: Leader sequence of Tissue Plasminogen Activator
      (TPA)

<400> SEQUENCE: 9

Met Asp Ala Met Lys Arg Gly Leu Cys Cys Val Leu Leu Cys Gly
1               5                   10                  15

Ala Val Phe Val Ser Pro
            20

<210> SEQ ID NO 10
<211> LENGTH: 20
<212> TYPE: PRT
<213> ORGANISM: Unknown
<220> FEATURE:
<223> OTHER INFORMATION: Native ActRIIA leader

<400> SEQUENCE: 10

Met Gly Ala Ala Ala Lys Leu Ala Phe Ala Val Phe Leu Ile Ser Cys
1               5                   10                  15

Ser Ser Gly Ala
            20

<210> SEQ ID NO 11
<211> LENGTH: 9
<212> TYPE: PRT
<213> ORGANISM: Artificial Sequence
<220> FEATURE:
<223> OTHER INFORMATION: ActRIIA-hFc and mActRIIA-Fc N-terminal sequence

<400> SEQUENCE: 11

Ile Leu Gly Arg Ser Glu Thr Gln Glu
1               5

<210> SEQ ID NO 12
<211> LENGTH: 329
<212> TYPE: PRT
<213> ORGANISM: Artificial Sequence
<220> FEATURE:
<223> OTHER INFORMATION: ActRIIA-Fc Protein with deletion of the
      C-terminal 15 amino acids of the extracellular domain of ActRIIA

<400> SEQUENCE: 12

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
                20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
        50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Thr Gly Gly Gly Thr His Thr Cys Pro Pro Cys Pro

```
            100                 105                 110
Ala Pro Glu Leu Leu Gly Gly Pro Ser Val Phe Leu Phe Pro Pro Lys
            115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Val Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 13
<211> LENGTH: 369
<212> TYPE: PRT
<213> ORGANISM: Artificial Sequence
<220> FEATURE:
<223> OTHER INFORMATION: Unprocessed ActRIIA-hFc with TPA leader
      sequence

<400> SEQUENCE: 13

Met Asp Ala Met Lys Arg Gly Leu Cys Cys Val Leu Leu Leu Cys Gly
1               5                   10                  15

Ala Val Phe Val Ser Pro Gly Ala Ala Ile Leu Gly Arg Ser Glu Thr
            20                  25                  30

Gln Glu Cys Leu Phe Phe Asn Ala Asn Trp Glu Lys Asp Arg Thr Asn
        35                  40                  45

Gln Thr Gly Val Glu Pro Cys Tyr Gly Asp Lys Asp Lys Arg Arg His
    50                  55                  60

Cys Phe Ala Thr Trp Lys Asn Ile Ser Gly Ser Ile Glu Ile Val Lys
65                  70                  75                  80

Gln Gly Cys Trp Leu Asp Asp Ile Asn Cys Tyr Asp Arg Thr Asp Cys
                85                  90                  95

Val Glu Lys Lys Asp Ser Pro Glu Val Tyr Phe Cys Cys Cys Glu Gly
            100                 105                 110

Asn Met Cys Asn Glu Lys Phe Ser Tyr Phe Pro Glu Met Glu Val Thr
        115                 120                 125
```

-continued

```
Gln Pro Thr Ser Asn Pro Val Thr Lys Pro Pro Thr Gly Gly Gly
    130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
        195                 200                 205

Ala Lys Thr Lys Pro Arg Glu Glu Gln Tyr Asn Ser Thr Tyr Arg Val
    210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Val Pro Ile Glu Lys
                245                 250                 255

Thr Ile Ser Lys Ala Lys Gly Gln Pro Arg Glu Pro Gln Val Tyr Thr
            260                 265                 270

Leu Pro Pro Ser Arg Glu Glu Met Thr Lys Asn Gln Val Ser Leu Thr
        275                 280                 285

Cys Leu Val Lys Gly Phe Tyr Pro Ser Asp Ile Ala Val Glu Trp Glu
    290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
        355                 360                 365

Lys
```

<210> SEQ ID NO 14
<211> LENGTH: 1113
<212> TYPE: DNA
<213> ORGANISM: Artificial Sequence
<220> FEATURE:
<223> OTHER INFORMATION: Nucleic acid sequence encoding Unprocessed
    ActRIIA-hFc with TPA leader sequence

<400> SEQUENCE: 14

```
atggatgcaa tgaagagagg ctctgctgtg tgctgctgc tgtgtggagc agtcttcgtt     60
tcgcccggcg ccgctatact tggtagatca gaaactcagg agtgtctttt tttaatgcta   120
attgggaaaa agacagaacc aatcaaactg gtgttgaacc gtgttatggt gacaaagata   180
aacggcggca ttgttttgct acctggaaga atatttctgg ttccattgaa tagtgaaaca   240
aggttgttgg ctggatgata tcaactgcta tgacaggact gattgtgtag aaaaaaaga    300 cagccctgaa gtatatttct gttgctgtga gggcaatatg tgtaatgaaa gttttctta    360 ttttccggag atggaagtca cacagcccac ttcaaatcca gttacaccta agccacccac   420
cggtggtgga actcacacat gcccaccgtg cccagcacct gaactcctgg ggggaccgtc   480
agtcttcctc ttccccccaa aacccaagga caccctcatg atctcccgga cccctgaggt   540
cacatgcgtg gtggtggacg tgagccacga agaccctgag gtcaagttca actggtacgt   600
ggacggcgtg gaggtgcata atgccaagac aaagccgcgg gaggagcagt acaacagcac   660
```

```
gtaccgtgtg gtcagcgtcc tcaccgtcct gcaccaggac tggctgaatg gcaaggagta    720
caagtgcaag gtctccaaca aagccctccc agtccccatc gagaaaacca tctccaaagc    780
caaagggcag ccccgagaac cacaggtgta caccctgccc ccatcccggg aggagatgac    840
caagaaccag gtcagcctga cctgcctggt caaaggcttc tatcccagcg acatcgccgt    900
ggagtgggag agcaatgggc agccggagaa caactacaag accacgcctc ccgtgctgga    960
ctccgacggc tccttcttcc tctatagcaa gctcaccgtg gacaagagca ggtggcagca   1020
ggggaacgtc ttctcatgct ccgtgatgca tgaggctctg cacaaccact acacgcagaa   1080
gagcctctcc ctgtctccgg taaatgagaa ttc                                1113
```

<210> SEQ ID NO 15
<211> LENGTH: 106
<212> TYPE: PRT
<213> ORGANISM: Artificial Sequence
<220> FEATURE:
<223> OTHER INFORMATION: human ActRIIB soluble (extracellular),
      processed polypeptide sequence with the N-terminal 6 amino acids
      of the EC domain deleted and the C-terminal 4 amino acids of the
      EC domain deleted (amino acids 25-130 of SEQ ID NO:28) and with an
      L79D mutation

<400> SEQUENCE: 15

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro
            100                 105
```

<210> SEQ ID NO 16
<211> LENGTH: 512
<212> TYPE: PRT
<213> ORGANISM: Homo sapiens
<220> FEATURE:
<223> OTHER INFORMATION: human ActRIIB precursor protein sequence (A64)

<400> SEQUENCE: 16

```
Met Thr Ala Pro Trp Val Ala Leu Ala Leu Leu Trp Gly Ser Leu Trp
1               5                   10                  15

Pro Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Ala
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95
```

```
Pro Gln Val Tyr Phe Cys Cys Glu Gly Asn Phe Cys Asn Glu Arg
            100                 105                 110

Phe Thr His Leu Pro Glu Ala Gly Pro Glu Val Thr Tyr Glu Pro
            115                 120                 125

Pro Pro Thr Ala Pro Thr Leu Leu Thr Val Leu Ala Tyr Ser Leu Leu
130             135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
            195                 200                 205

Leu Met Asn Asp Phe Val Ala Val Lys Ile Phe Pro Leu Gln Asp Lys
    210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
            245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
            290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
            355                 360                 365

Val Leu Glu Gly Ala Ile Asn Phe Gln Arg Asp Ala Phe Leu Arg Ile
    370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
    435                 440                 445

Gly Leu Ala Gln Leu Cys Val Thr Ile Glu Glu Cys Trp Asp His Asp
            450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
            500                 505                 510
```

<210> SEQ ID NO 17
<211> LENGTH: 116
<212> TYPE: PRT
<213> ORGANISM: Artificial Sequence
<220> FEATURE:
<223> OTHER INFORMATION: human ActRIIB soluble (extracellular),
      processed polypeptide sequence (amino acids 19-134 of SEQ ID NO:
      16)

<400> SEQUENCE: 17

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Ala Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro
            100                 105                 110

Thr Ala Pro Thr
        115

<210> SEQ ID NO 18
<211> LENGTH: 101
<212> TYPE: PRT
<213> ORGANISM: Artificial Sequence
<220> FEATURE:
<223> OTHER INFORMATION: human ActRIIB soluble (extracellular),
      processed polypeptide sequence with the C-terminal 15 amino acids
      deleted (amino acids 19-119 of SEQ ID NO:16)

<400> SEQUENCE: 18

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Ala Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala
            100

<210> SEQ ID NO 19
<211> LENGTH: 1539
<212> TYPE: DNA
<213> ORGANISM: Homo sapiens
<220> FEATURE:
<223> OTHER INFORMATION: nucleic acid sequence encoding a human ActRIIB
      (A64) precursor protein

<400> SEQUENCE: 19

```
atgacggcgc cctgggtggc cctcgccctc ctctggggat cgctgtggcc cggctctggg    60
cgtggggagg ctgagacacg ggagtgcatc tactacaacg ccaactggga gctggagcgc   120
accaaccaga gcggcctgga gcgctgcgaa ggcgagcagg acaagcggct gcactgctac   180
gcctcctggg ccaacagctc tggcaccatc gagctcgtga agaagggctg ctggctagat   240
gacttcaact gctacgatag gcaggagtgt gtggccactg aggagaaccc ccaggtgtac   300
ttctgctgct gtgaaggcaa cttctgcaac gagcgcttca ctcatttgcc agaggctggg   360
ggcccggaag tcacgtacga gccaccccg acagccccca ccctgctcac ggtgctggcc   420
tactcactgc tgcccatcgg gggccttttcc ctcatcgtcc tgctggcctt ttggatgtac   480
cggcatcgca agcccccta cggtcatgtg acatccatg aggaccctgg gcctccacca   540
ccatcccctc tggtgggcct gaagccactg cagctgctgg agatcaaggc tcggggcgc   600
tttggctgtg tctggaaggc ccagctcatg aatgactttg tagctgtcaa gatcttccca   660
ctccaggaca gcagtcgtg gcagagtgaa cgggagatct tcagcacacc tggcatgaag   720
cacgagaacc tgctacagtt cattgctgcc gagaagcgag gctccaacct cgaagtagag   780
ctgtggctca tcacggcctt ccatgacaag ggctccctca cggattacct caaggggaac   840
atcatcacat ggaacgaact gtgtcatgta gcagagacga tgtcacgagg cctctcatac   900
ctgcatgagg atgtgccctg gtgccgtggc gagggccaca gccgtctat tgcccacagg   960
gactttaaaa gtaagaatgt attgctgaag agcgacctca cagccgtgct ggctgacttt  1020
ggcttggctg ttcgatttga ccagggaaa cctccagggg acacccacgg acaggtaggc  1080
acgagacggt acatggctcc tgaggtgctc gagggagcca tcaacttcca gagagatgcc  1140
ttcctgcgca ttgacatgta tgccatgggg ttggtgctgt gggagcttgt gtctcgctgc  1200
aaggctgcag acggacccgt ggatgagtac atgctgccct tgaggaaga gattggccag  1260
caccccttcgt tggaggagct gcaggaggtg gtggtgcaca agaagatgag gcccaccatt  1320
aaagatcact ggttgaaaca cccgggcctg gcccagcttt gtgtgaccat cgaggagtgc  1380
tgggaccatg atgcagaggc tcgcttgtcc gcgggctgtg tggaggagcg ggtgtccctg  1440
attcggaggt cggtcaacgg cactacctcg gactgtctcg tttccctggt gacctctgtc  1500
accaatgtgg acctgccccc taaagagtca agcatctaa                          1539
```

<210> SEQ ID NO 20
<211> LENGTH: 344
<212> TYPE: PRT
<213> ORGANISM: Artificial Sequence
<220> FEATURE:
<223> OTHER INFORMATION: fusion protein comprising a soluble
      extracellular domain of ActRIIB (A64; SEQ ID NO:17) fused to an Fc
      domain

<400> SEQUENCE: 20

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Ala Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

```
Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro
            100                 105                 110

Thr Ala Pro Thr Gly Gly Gly Thr His Thr Cys Pro Pro Cys Pro Ala
        115                 120                 125

Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Val Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
    290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 21
<211> LENGTH: 329
<212> TYPE: PRT
<213> ORGANISM: Artificial Sequence
<220> FEATURE:
<223> OTHER INFORMATION: fusion protein comprising a soluble
      extracellular domain of ActRIIB (A64) with the C-terminal 15 amino
      acids deleted (SEQ ID NO:18) fused to an Fc domain

<400> SEQUENCE: 21

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Ala Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80
```

```
Val Tyr Phe Cys Cys Cys Glu Gly Asn Phe Cys Asn Glu Arg Phe Thr
                85                  90                  95

His Leu Pro Glu Ala Gly Gly Thr His Thr Cys Pro Pro Cys Pro
        100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Val Pro Ile Glu Lys Thr Ile Ser Lys Ala Lys Gly Gln
210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325
```

<210> SEQ ID NO 22
<211> LENGTH: 105
<212> TYPE: PRT
<213> ORGANISM: Artificial Sequence
<220> FEATURE:
<223> OTHER INFORMATION: human ActRIIB soluble (extracellular),
      processed polypeptide sequence with the N-terminal 6 amino acids
      of the EC domain deleted and the C-terminal 5 amino acids of the
      EC domain deleted (amino acids 25-129 of SEQ ID NO:28) and with an
      L79D mutation

<400> SEQUENCE: 22

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
                20                  25                  30

Leu His Cys Tyr Ala Ser Trp Arg Asn Ser Ser Gly Thr Ile Glu Leu
        35                  40                  45

Val Lys Lys Gly Cys Trp Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95
```

```
Gly Pro Glu Val Thr Tyr Glu Pro Pro
            100                 105
```

<210> SEQ ID NO 23
<211> LENGTH: 107
<212> TYPE: PRT
<213> ORGANISM: Artificial Sequence
<220> FEATURE:
<223> OTHER INFORMATION: human ActRIIB soluble (extracellular),
      processed polypeptide sequence with the N-terminal 6 amino acids
      of the EC domain deleted and the C-terminal 3 amino acids of the
      EC domain deleted (amino acids 25-131 of SEQ ID NO:28) and with an
      L79D mutation

<400> SEQUENCE: 23

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Asp Asp Asp Phe Asn Cys Tyr Asp Arg Gln
50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr
            100                 105
```

<210> SEQ ID NO 24
<211> LENGTH: 360
<212> TYPE: PRT
<213> ORGANISM: Artificial Sequence
<220> FEATURE:
<223> OTHER INFORMATION: Unprocessed ActRIIB-Fc fusion protein with the
      N-terminal 6 amino acids of the EC domain deleted and the C-
      terminal 3 amino acids of the EC domain deleted (amino acids 25-
      131 of SEQ ID NO:28) and with an L79D mutation and with TPA leader
      sequence

<400> SEQUENCE: 24

```
Met Asp Ala Met Lys Arg Gly Leu Cys Cys Val Leu Leu Leu Cys Gly
1               5                   10                  15

Ala Val Phe Val Ser Pro Gly Ala Ala Glu Thr Arg Glu Cys Ile Tyr
            20                  25                  30

Tyr Asn Ala Asn Trp Glu Leu Glu Arg Thr Asn Gln Ser Gly Leu Glu
        35                  40                  45

Arg Cys Glu Gly Glu Gln Asp Lys Arg Leu His Cys Tyr Ala Ser Trp
    50                  55                  60

Arg Asn Ser Ser Gly Thr Ile Glu Leu Val Lys Lys Gly Cys Trp Asp
65                  70                  75                  80

Asp Asp Phe Asn Cys Tyr Asp Arg Gln Glu Cys Val Ala Thr Glu Glu
                85                  90                  95

Asn Pro Gln Val Tyr Phe Cys Cys Cys Glu Gly Asn Phe Cys Asn Glu
            100                 105                 110

Arg Phe Thr His Leu Pro Glu Ala Gly Gly Pro Glu Val Thr Tyr Glu
        115                 120                 125

Pro Pro Pro Thr Gly Gly Gly Thr His Thr Cys Pro Pro Cys Pro Ala
    130                 135                 140
```

Pro Glu Leu Leu Gly Gly Pro Ser Val Phe Leu Phe Pro Lys Pro
145                 150                 155                 160

Lys Asp Thr Leu Met Ile Ser Arg Thr Pro Glu Val Thr Cys Val Val
            165                 170                 175

Val Asp Val Ser His Glu Asp Pro Glu Val Lys Phe Asn Trp Tyr Val
        180                 185                 190

Asp Gly Val Glu Val His Asn Ala Lys Thr Lys Pro Arg Glu Glu Gln
            195                 200                 205

Tyr Asn Ser Thr Tyr Arg Val Val Ser Val Leu Thr Val Leu His Gln
        210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Glu Glu Met Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 25
<211> LENGTH: 335
<212> TYPE: PRT
<213> ORGANISM: Artificial Sequence
<220> FEATURE:
<223> OTHER INFORMATION: Processed ActRIIB-Fc fusion protein with the N-
      terminal 6 amino acids of the EC domain deleted and the C-terminal
      3 amino acids of the EC domain deleted (amino acids 25-131 of SEQ
      ID NO:28) and with an L79D mutation

<400> SEQUENCE: 25

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Asp Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
            85                  90                  95

Gly Pro Glu Val Thr Tyr Glu Pro Pro Thr Gly Gly Thr His
        100                 105                 110

Thr Cys Pro Pro Cys Pro Ala Pro Glu Leu Leu Gly Gly Pro Ser Val
    115                 120                 125

```
Phe Leu Phe Pro Pro Lys Pro Lys Asp Thr Leu Met Ile Ser Arg Thr
        130                 135                 140

Pro Glu Val Thr Cys Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
                180                 185                 190

Val Leu Thr Val Leu His Gln Asp Trp Leu Asn Gly Lys Glu Tyr Lys
            195                 200                 205

Cys Lys Val Ser Asn Lys Ala Leu Pro Ala Pro Ile Glu Lys Thr Ile
210                 215                 220

Ser Lys Ala Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
                260                 265                 270

Gly Gln Pro Glu Asn Asn Tyr Lys Thr Thr Pro Pro Val Leu Asp Ser
                275                 280                 285

Asp Gly Ser Phe Phe Leu Tyr Ser Lys Leu Thr Val Asp Lys Ser Arg
290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 26
<211> LENGTH: 115
<212> TYPE: PRT
<213> ORGANISM: Artificial Sequence
<220> FEATURE:
<223> OTHER INFORMATION: human ActRIIB soluble (extracellular),
      processed polypeptide sequence (amino acids 20-134 of SEQ ID NO:
      16)

<400> SEQUENCE: 26

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Leu Asp Asp Phe Asn
50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 27
<211> LENGTH: 100
```

```
<212> TYPE: PRT
<213> ORGANISM: Artificial Sequence
<220> FEATURE:
<223> OTHER INFORMATION: human ActRIIB soluble (extracellular),
      processed polypeptide sequence with the C-terminal 15 amino acids
      deleted (amino acids 20-119 of SEQ ID NO:16)

<400> SEQUENCE: 27

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala
            100

<210> SEQ ID NO 28
<211> LENGTH: 512
<212> TYPE: PRT
<213> ORGANISM: Homo sapiens
<220> FEATURE:
<223> OTHER INFORMATION: human ActRIIB precursor protein sequence (R64)

<400> SEQUENCE: 28

Met Thr Ala Pro Trp Val Ala Leu Ala Leu Leu Trp Gly Ser Leu Trp
1               5                   10                  15

Pro Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205
```

Leu Met Asn Asp Phe Val Ala Val Lys Ile Phe Pro Leu Gln Asp Lys
210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
        355                 360                 365

Val Leu Glu Gly Ala Ile Asn Phe Gln Arg Asp Ala Phe Leu Arg Ile
370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
        435                 440                 445

Gly Leu Ala Gln Leu Cys Val Thr Ile Glu Glu Cys Trp Asp His Asp
450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
            500                 505                 510

<210> SEQ ID NO 29
<211> LENGTH: 116
<212> TYPE: PRT
<213> ORGANISM: Artificial Sequence
<220> FEATURE:
<223> OTHER INFORMATION: human ActRIIB soluble (extracellular),
      processed polypeptide sequence (amino acids 19-134 of SEQ ID NO:
      28)

<400> SEQUENCE: 29

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Arg Asn Ser
        35                  40                  45

Ser Gly Thr Ile Glu Leu Val Lys Lys Gly Cys Trp Leu Asp Asp Phe

```
                 50                  55                  60

Asn Cys Tyr Asp Arg Gln Glu Cys Val Ala Thr Glu Glu Asn Pro Gln
 65                  70                  75                  80

Val Tyr Phe Cys Cys Cys Glu Gly Asn Phe Cys Asn Glu Arg Phe Thr
                 85                  90                  95

His Leu Pro Glu Ala Gly Gly Pro Glu Val Thr Tyr Glu Pro Pro Pro
            100                 105                 110

Thr Ala Pro Thr
        115

<210> SEQ ID NO 30
<211> LENGTH: 101
<212> TYPE: PRT
<213> ORGANISM: Artificial Sequence
<220> FEATURE:
<223> OTHER INFORMATION: human ActRIIB soluble (extracellular),
      processed polypeptide sequence with the C-terminal 15 amino acids
      deleted (amino acids 19-119 of SEQ ID NO:28)

<400> SEQUENCE: 30

Ser Gly Arg Gly Glu Ala Glu Thr Arg Glu Cys Ile Tyr Tyr Asn Ala
  1               5                  10                  15

Asn Trp Glu Leu Glu Arg Thr Asn Gln Ser Gly Leu Glu Arg Cys Glu
                 20                  25                  30

Gly Glu Gln Asp Lys Arg Leu His Cys Tyr Ala Ser Trp Arg Asn Ser
             35                  40                  45

Ser Gly Thr Ile Glu Leu Val Lys Lys Gly Cys Trp Leu Asp Asp Phe
     50                  55                  60

Asn Cys Tyr Asp Arg Gln Glu Cys Val Ala Thr Glu Glu Asn Pro Gln
 65                  70                  75                  80

Val Tyr Phe Cys Cys Cys Glu Gly Asn Phe Cys Asn Glu Arg Phe Thr
                 85                  90                  95

His Leu Pro Glu Ala
            100

<210> SEQ ID NO 31
<211> LENGTH: 115
<212> TYPE: PRT
<213> ORGANISM: Artificial Sequence
<220> FEATURE:
<223> OTHER INFORMATION: human ActRIIB soluble (extracellular),
      processed polypeptide sequence (amino acids 20-134 of SEQ ID NO:
      28)

<400> SEQUENCE: 31

Gly Arg Gly Glu Ala Glu Thr Arg Glu Cys Ile Tyr Tyr Asn Ala Asn
  1               5                  10                  15

Trp Glu Leu Glu Arg Thr Asn Gln Ser Gly Leu Glu Arg Cys Glu Gly
                 20                  25                  30

Glu Gln Asp Lys Arg Leu His Cys Tyr Ala Ser Trp Arg Asn Ser Ser
             35                  40                  45

Gly Thr Ile Glu Leu Val Lys Lys Gly Cys Trp Leu Asp Asp Phe Asn
     50                  55                  60

Cys Tyr Asp Arg Gln Glu Cys Val Ala Thr Glu Glu Asn Pro Gln Val
 65                  70                  75                  80

Tyr Phe Cys Cys Cys Glu Gly Asn Phe Cys Asn Glu Arg Phe Thr His
                 85                  90                  95

Leu Pro Glu Ala Gly Gly Pro Glu Val Thr Tyr Glu Pro Pro Pro Thr
            100                 105                 110
```

```
Ala Pro Thr
        115

<210> SEQ ID NO 32
<211> LENGTH: 100
<212> TYPE: PRT
<213> ORGANISM: Artificial Sequence
<220> FEATURE:
<223> OTHER INFORMATION: human ActRIIB soluble (extracellular),
      processed polypeptide sequence with the C-terminal 15 amino acids
      deleted (amino acids 20-119 of SEQ ID NO:28)

<400> SEQUENCE: 32

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala
            100

<210> SEQ ID NO 33
<211> LENGTH: 107
<212> TYPE: PRT
<213> ORGANISM: Artificial Sequence
<220> FEATURE:
<223> OTHER INFORMATION: human ActRIIB soluble (extracellular),
      processed polypeptide sequence with the N-terminal 6 amino acids
      of the EC domain deleted and the C-terminal 3 amino acids of the
      EC domain deleted (amino acids 25-131 of SEQ ID NO:16) and with an
      L79D mutation

<400> SEQUENCE: 33

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Ala Asn Ser Ser Gly Thr Ile Glu Leu
        35                  40                  45

Val Lys Lys Gly Cys Trp Asp Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Pro Thr
            100                 105

<210> SEQ ID NO 34
<211> LENGTH: 360
<212> TYPE: PRT
<213> ORGANISM: Artificial Sequence
<220> FEATURE:
<223> OTHER INFORMATION: Unprocessed ActRIIB-Fc fusion protein with the
```

N-terminal 6 amino acids of the EC domain deleted and the C-terminal 3 amino acids of the EC domain deleted (amino acids 25-131 of SEQ ID NO:16) and with an L79D mutation and with TPA leader sequence

<400> SEQUENCE: 34

```
Met Asp Ala Met Lys Arg Gly Leu Cys Cys Val Leu Leu Leu Cys Gly
1               5                   10                  15

Ala Val Phe Val Ser Pro Gly Ala Ala Glu Thr Arg Glu Cys Ile Tyr
            20                  25                  30

Tyr Asn Ala Asn Trp Glu Leu Glu Arg Thr Asn Gln Ser Gly Leu Glu
        35                  40                  45

Arg Cys Glu Gly Glu Gln Asp Lys Arg Leu His Cys Tyr Ala Ser Trp
50                  55                  60

Ala Asn Ser Ser Gly Thr Ile Glu Leu Val Lys Lys Gly Cys Trp Asp
65                  70                  75                  80

Asp Asp Phe Asn Cys Tyr Asp Arg Gln Glu Cys Val Ala Thr Glu Glu
                85                  90                  95

Asn Pro Gln Val Tyr Phe Cys Cys Cys Glu Gly Asn Phe Cys Asn Glu
            100                 105                 110

Arg Phe Thr His Leu Pro Glu Ala Gly Gly Pro Glu Val Thr Tyr Glu
        115                 120                 125

Pro Pro Pro Thr Gly Gly Thr His Thr Cys Pro Pro Cys Pro Ala
130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Glu Glu Met Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360
```

<210> SEQ ID NO 35
<211> LENGTH: 335

<212> TYPE: PRT
<213> ORGANISM: Artificial Sequence
<220> FEATURE:
<223> OTHER INFORMATION: Processed ActRIIB-Fc fusion protein with the N-
terminal 6 amino acids of the EC domain deleted and the C-terminal
3 amino acids of the EC domain deleted (amino acids 25-131 of SEQ
ID NO:16) and with an L79D mutation

<400> SEQUENCE: 35

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Ala Asn Ser Ser Gly Thr Ile Glu Leu
        35                  40                  45

Val Lys Lys Gly Cys Trp Asp Asp Phe Asn Cys Tyr Asp Arg Gln
50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Gly Gly Thr His
            100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
210                 215                 220

Ser Lys Ala Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Phe Leu Tyr Ser Lys Leu Thr Val Asp Lys Ser Arg
290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335
```

<210> SEQ ID NO 36
<211> LENGTH: 115
<212> TYPE: PRT
<213> ORGANISM: Artificial Sequence
<220> FEATURE:

<223> OTHER INFORMATION: human ActRIIB soluble (extracellular),
processed polypeptide sequence (amino acids 20-134 of SEQ ID NO:
28) with L79D mutation

<400> SEQUENCE: 36

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 37
<211> LENGTH: 115
<212> TYPE: PRT
<213> ORGANISM: Artificial Sequence
<220> FEATURE:
<223> OTHER INFORMATION: human ActRIIB soluble (extracellular),
processed polypeptide sequence (amino acids 20-134 of SEQ ID NO:
16) with L79D mutation

<400> SEQUENCE: 37

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 38
<211> LENGTH: 343
<212> TYPE: PRT
<213> ORGANISM: Artificial Sequence
<220> FEATURE:
<223> OTHER INFORMATION: human ActRIIB soluble (extracellular),
processed polypeptide sequence (amino acids 20-134 of SEQ ID NO:
28) with L79D mutation fused to an Fc domain with a GGG linker

<400> SEQUENCE: 38

Gly Arg Gly Glu Ala Glu Thr Arg Glu Cys Ile Tyr Tyr Asn Ala Asn

```
            1               5                  10                 15
Trp Glu Leu Glu Arg Thr Asn Gln Ser Gly Leu Glu Arg Cys Glu Gly
                    20                  25                 30

Glu Gln Asp Lys Arg Leu His Cys Tyr Ala Ser Trp Arg Asn Ser Ser
                35                  40                  45

Gly Thr Ile Glu Leu Val Lys Lys Gly Cys Trp Asp Asp Phe Asn
        50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                    85                  90                  95

Leu Pro Glu Ala Gly Gly Pro Glu Val Thr Tyr Glu Pro Pro Pro Thr
                100                 105                 110

Ala Pro Thr Gly Gly Gly Thr His Thr Cys Pro Pro Cys Pro Ala Pro
            115                 120                 125

Glu Leu Leu Gly Gly Pro Ser Val Phe Leu Phe Pro Pro Lys Pro Lys
            130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                    165                 170                 175

Gly Val Glu Val His Asn Ala Lys Thr Lys Pro Arg Glu Glu Gln Tyr
                180                 185                 190

Asn Ser Thr Tyr Arg Val Val Ser Val Leu Thr Val Leu His Gln Asp
                195                 200                 205

Trp Leu Asn Gly Lys Glu Tyr Lys Cys Lys Val Ser Asn Lys Ala Leu
            210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                    245                 250                 255

Asn Gln Val Ser Leu Thr Cys Leu Val Lys Gly Phe Tyr Pro Ser Asp
                260                 265                 270

Ile Ala Val Glu Trp Glu Ser Asn Gly Gln Pro Glu Asn Asn Tyr Lys
                275                 280                 285

Thr Thr Pro Pro Val Leu Asp Ser Asp Gly Ser Phe Phe Leu Tyr Ser
            290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                    325                 330                 335

Leu Ser Leu Ser Pro Gly Lys
            340

<210> SEQ ID NO 39
<211> LENGTH: 343
<212> TYPE: PRT
<213> ORGANISM: Artificial Sequence
<220> FEATURE:
<223> OTHER INFORMATION: human ActRIIB soluble (extracellular),
      processed polypeptide sequence (amino acids 20-134 of SEQ ID NO:
      16) with L79D mutation fused to an Fc domain

<400> SEQUENCE: 39

Gly Arg Gly Glu Ala Glu Thr Arg Glu Cys Ile Tyr Tyr Asn Ala Asn
1               5                   10                  15
```

```
Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Asp Asp Phe Asn
50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 40
<211> LENGTH: 368
<212> TYPE: PRT
<213> ORGANISM: Artificial Sequence
<220> FEATURE:
<223> OTHER INFORMATION: human ActRIIB soluble (extracellular),
      processed polypeptide sequence (amino acids 20-134 of SEQ ID NO:
      28) with L79D mutation fused to an Fc domain and with TPA leader
      sequence

<400> SEQUENCE: 40

Met Asp Ala Met Lys Arg Gly Leu Cys Cys Val Leu Leu Leu Cys Gly
1               5                   10                  15
```

Ala Val Phe Val Ser Pro Gly Ala Ser Gly Arg Gly Glu Ala Glu Thr
                20                  25                  30

Arg Glu Cys Ile Tyr Tyr Asn Ala Asn Trp Glu Leu Glu Arg Thr Asn
            35                  40                  45

Gln Ser Gly Leu Glu Arg Cys Glu Gly Glu Gln Asp Lys Arg Leu His
        50                  55                  60

Cys Tyr Ala Ser Trp Arg Asn Ser Ser Gly Thr Ile Glu Leu Val Lys
65                  70                  75                  80

Lys Gly Cys Trp Asp Asp Phe Asn Cys Tyr Asp Arg Gln Glu Cys
                85                  90                  95

Val Ala Thr Glu Glu Asn Pro Gln Val Tyr Phe Cys Cys Glu Gly
                100                 105                 110

Asn Phe Cys Asn Glu Arg Phe Thr His Leu Pro Glu Ala Gly Gly Pro
            115                 120                 125

Glu Val Thr Tyr Glu Pro Pro Thr Ala Pro Thr Gly Gly Gly Thr
        130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365

<210> SEQ ID NO 41
<211> LENGTH: 368
<212> TYPE: PRT
<213> ORGANISM: Artificial Sequence
<220> FEATURE:
<223> OTHER INFORMATION: human ActRIIB soluble (extracellular),
      processed polypeptide sequence (amino acids 20-134 of SEQ ID NO:
      16) with L79D mutation fused to an Fc domain and with TPA leader
      sequence

<400> SEQUENCE: 41

```
Met Asp Ala Met Lys Arg Gly Leu Cys Cys Val Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
            35                  40                  45

Gln Ser Gly Leu Glu Arg Cys Glu Gly Glu Gln Asp Lys Arg Leu His
50                  55                  60

Cys Tyr Ala Ser Trp Ala Asn Ser Ser Gly Thr Ile Glu Leu Val Lys
65                  70                  75                  80

Lys Gly Cys Trp Asp Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Pro Thr Ala Pro Thr Gly Gly Gly Thr
        130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
        290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365

<210> SEQ ID NO 42
<211> LENGTH: 141
<212> TYPE: PRT
<213> ORGANISM: Artificial Sequence
<220> FEATURE:
<223> OTHER INFORMATION: human ActRIIB soluble (extracellular),
      processed polypeptide sequence having a variant C-terminal
      sequence (disclosed in WO2007/053775)
```

<400> SEQUENCE: 42

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
                20                  25                  30

Glu Gln Asp Lys Arg Leu His Cys Tyr Ala Ser Trp Arg Asn Ser Ser
            35                  40                  45

Gly Thr Ile Glu Leu Val Lys Lys Gly Cys Trp Leu Asp Asp Phe Asn
        50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Gly Pro Trp Ala Ser Thr Thr Ile
            100                 105                 110

Pro Ser Gly Gly Pro Glu Ala Thr Ala Ala Ala Gly Asp Gln Gly Ser
        115                 120                 125

Gly Ala Leu Trp Leu Cys Leu Glu Gly Pro Ala His Glu
    130                 135                 140

<210> SEQ ID NO 43
<211> LENGTH: 141
<212> TYPE: PRT
<213> ORGANISM: Artificial Sequence
<220> FEATURE:
<223> OTHER INFORMATION: human ActRIIB soluble (extracellular),
      processed polypeptide sequence having a variant C-terminal
      sequence (disclosed in WO2007/053775) having an L79D mutation

<400> SEQUENCE: 43

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
                20                  25                  30

Glu Gln Asp Lys Arg Leu His Cys Tyr Ala Ser Trp Arg Asn Ser Ser
            35                  40                  45

Gly Thr Ile Glu Leu Val Lys Lys Gly Cys Trp Asp Asp Asp Phe Asn
        50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Gly Pro Trp Ala Ser Thr Thr Ile
            100                 105                 110

Pro Ser Gly Gly Pro Glu Ala Thr Ala Ala Ala Gly Asp Gln Gly Ser
        115                 120                 125

Gly Ala Leu Trp Leu Cys Leu Glu Gly Pro Ala His Glu
    130                 135                 140

<210> SEQ ID NO 44
<211> LENGTH: 370
<212> TYPE: PRT
<213> ORGANISM: Artificial Sequence
<220> FEATURE:
<223> OTHER INFORMATION: human ActRIIB soluble (extracellular),
      processed polypeptide sequence having a variant C-terminal
      sequence (disclosed in WO2007/053775) having an L79D mutation
      fused to an Fc domain with a TGGG linker

<400> SEQUENCE: 44

```
Gly Arg Gly Glu Ala Glu Thr Arg Glu Cys Ile Tyr Tyr Asn Ala Asn
1               5                   10                  15
Trp Glu Leu Glu Arg Thr Asn Gln Ser Gly Leu Glu Arg Cys Glu Gly
            20                  25                  30
Glu Gln Asp Lys Arg Leu His Cys Tyr Ala Ser Trp Arg Asn Ser Ser
        35                  40                  45
Gly Thr Ile Glu Leu Val Lys Lys Gly Cys Trp Asp Asp Phe Asn
    50                  55                  60
Cys Tyr Asp Arg Gln Glu Cys Val Ala Thr Glu Glu Asn Pro Gln Val
65                  70                  75                  80
Tyr Phe Cys Cys Cys Glu Gly Asn Phe Cys Asn Glu Arg Phe Thr His
                85                  90                  95
Leu Pro Glu Ala Gly Gly Pro Glu Gly Pro Trp Ala Ser Thr Thr Ile
            100                 105                 110
Pro Ser Gly Gly Pro Glu Ala Thr Ala Ala Gly Asp Gln Gly Ser
        115                 120                 125
Gly Ala Leu Trp Leu Cys Leu Glu Gly Pro Ala His Glu Thr Gly Gly
    130                 135                 140
Gly Thr His Thr Cys Pro Pro Cys Pro Ala Pro Glu Leu Leu Gly Gly
145                 150                 155                 160
Pro Ser Val Phe Leu Phe Pro Pro Lys Pro Lys Asp Thr Leu Met Ile
                165                 170                 175
Ser Arg Thr Pro Glu Val Thr Cys Val Val Val Asp Val Ser His Glu
            180                 185                 190
Asp Pro Glu Val Lys Phe Asn Trp Tyr Val Asp Gly Val Glu Val His
        195                 200                 205
Asn Ala Lys Thr Lys Pro Arg Glu Glu Gln Tyr Asn Ser Thr Tyr Arg
    210                 215                 220
Val Val Ser Val Leu Thr Val Leu His Gln Asp Trp Leu Asn Gly Lys
225                 230                 235                 240
Glu Tyr Lys Cys Lys Val Ser Asn Lys Ala Leu Pro Ala Pro Ile Glu
                245                 250                 255
Lys Thr Ile Ser Lys Ala Lys Gly Gln Pro Arg Glu Pro Gln Val Tyr
            260                 265                 270
Thr Leu Pro Pro Ser Arg Glu Glu Met Thr Lys Asn Gln Val Ser Leu
        275                 280                 285
Thr Cys Leu Val Lys Gly Phe Tyr Pro Ser Asp Ile Ala Val Glu Trp
    290                 295                 300
Glu Ser Asn Gly Gln Pro Glu Asn Asn Tyr Lys Thr Thr Pro Pro Val
305                 310                 315                 320
Leu Asp Ser Asp Gly Ser Phe Phe Leu Tyr Ser Lys Leu Thr Val Asp
                325                 330                 335
Lys Ser Arg Trp Gln Gln Gly Asn Val Phe Ser Cys Ser Val Met His
            340                 345                 350
Glu Ala Leu His Asn His Tyr Thr Gln Lys Ser Leu Ser Leu Ser Pro
        355                 360                 365
Gly Lys
    370
```

<210> SEQ ID NO 45
<211> LENGTH: 1083
<212> TYPE: DNA

<213> ORGANISM: Artificial Sequence
<220> FEATURE:
<223> OTHER INFORMATION: Nucleic Acid Sequence Encoding SEQ ID NO:24

<400> SEQUENCE: 45

```
atggatgcaa tgaagagagg gctctgctgt gtgctgctgc tgtgtggagc agtcttcgtt      60
tcgcccggcg ccgccgaaac ccgcgaatgt atttattaca atgctaattg ggaactcgaa     120
cggacgaacc aatccgggct cgaacggtgt gaggggggaac aggataaacg cctccattgc    180
tatgcgtcgt ggaggaactc ctccgggacg attgaactgg tcaagaaagg gtgctgggac    240
gacgatttca attgttatga ccgccaggaa tgtgtcgcga ccgaagagaa tccgcaggtc    300
tatttctgtt gttgcgaggg gaatttctgt aatgaacggt ttacccacct ccccgaagcc    360
ggcgggcccg aggtgaccta taacccccg cccaccggtg gtggaactca cacatgccca    420
ccgtgcccag cacctgaact cctgggggga ccgtcagtct tcctcttccc cccaaaaccc    480
aaggacaccc tcatgatctc ccggacccct gaggtcacat gcgtggtggt ggacgtgagc    540
cacgaagacc ctgaggtcaa gttcaactgg tacgtggacg gcgtggaggt gcataatgcc    600
aagacaaagc cgcgggagga gcagtacaac agcacgtacc gtgtggtcag cgtcctcacc    660
gtcctgcacc aggactggct gaatggcaag gagtacaagt gcaaggtctc caacaaagcc    720
ctcccagccc ccatcgagaa aaccatctcc aaagccaaag gcagccccg agaaccacag    780
gtgtacaccc tgcccccatc ccgggaggag atgaccaaga accaggtcag cctgacctgc    840
ctggtcaaag gcttctatcc cagcgacatc gccgtggagt gggagagcaa tgggcagccg    900
gagaacaact acaagaccac gcctcccgtg ctggactccg acggctcctt cttcctctat    960
agcaagctca ccgtggacaa gagcaggtgg cagcagggga acgtcttctc atgctccgtg   1020
atgcatgagg ctctgcacaa ccactacacg cagaagagcc tctccctgtc cccgggtaaa   1080
tga                                                                 1083
```

<210> SEQ ID NO 46
<211> LENGTH: 344
<212> TYPE: PRT
<213> ORGANISM: Artificial Sequence
<220> FEATURE:
<223> OTHER INFORMATION: fusion protein comprising a soluble
      extracellular domain of ActRIIB (R64; SEQ ID NO:29) fused to an Fc
      domain

<400> SEQUENCE: 46

```
Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Arg Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro
            100                 105                 110

Thr Ala Pro Thr Gly Gly Gly Thr His Thr Cys Pro Pro Cys Pro Ala
        115                 120                 125
```

Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Val Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
    290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 47
<211> LENGTH: 329
<212> TYPE: PRT
<213> ORGANISM: Artificial Sequence
<220> FEATURE:
<223> OTHER INFORMATION: fusion protein comprising a soluble
    extracellular domain of ActRIIB (R64) with the C-terminal 15 amino
    acids deleted (SEQ ID NO:30) fused to an Fc domain

<400> SEQUENCE: 47

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Arg Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Thr His Thr Cys Pro Pro Cys Pro
            100                 105                 110

Ala Pro Glu Leu Leu Gly Gly Pro Ser Val Phe Leu Phe Pro Pro Lys
        115                 120                 125

```
Pro Lys Asp Thr Leu Met Ile Ser Arg Thr Pro Glu Val Thr Cys Val
    130                 135                 140
Val Val Asp Val Ser His Glu Asp Pro Glu Val Lys Phe Asn Trp Tyr
145                 150                 155                 160
Val Asp Gly Val Glu Val His Asn Ala Lys Thr Lys Pro Arg Glu Glu
                165                 170                 175
Gln Tyr Asn Ser Thr Tyr Arg Val Val Ser Val Leu Thr Val Leu His
            180                 185                 190
Gln Asp Trp Leu Asn Gly Lys Glu Tyr Lys Cys Lys Val Ser Asn Lys
        195                 200                 205
Ala Leu Pro Val Pro Ile Glu Lys Thr Ile Ser Lys Ala Lys Gly Gln
    210                 215                 220
Pro Arg Glu Pro Gln Val Tyr Thr Leu Pro Pro Ser Arg Glu Glu Met
225                 230                 235                 240
Thr Lys Asn Gln Val Ser Leu Thr Cys Leu Val Lys Gly Phe Tyr Pro
                245                 250                 255
Ser Asp Ile Ala Val Glu Trp Glu Ser Asn Gly Gln Pro Glu Asn Asn
            260                 265                 270
Tyr Lys Thr Thr Pro Pro Val Leu Asp Ser Asp Gly Ser Phe Phe Leu
        275                 280                 285
Tyr Ser Lys Leu Thr Val Asp Lys Ser Arg Trp Gln Gln Gly Asn Val
    290                 295                 300
Phe Ser Cys Ser Val Met His Glu Ala Leu His Asn His Tyr Thr Gln
305                 310                 315                 320
Lys Ser Leu Ser Leu Ser Pro Gly Lys
                325

<210> SEQ ID NO 48
<211> LENGTH: 20
<212> TYPE: DNA
<213> ORGANISM: Artificial Sequence
<220> FEATURE:
<223> OTHER INFORMATION: Runx2 qRT-PCR primer 1

<400> SEQUENCE: 48
ccgcacgaca accgcaccat                                                 20

<210> SEQ ID NO 49
<211> LENGTH: 20
<212> TYPE: DNA
<213> ORGANISM: Artificial Sequence
<220> FEATURE:
<223> OTHER INFORMATION: Runx2 qRT-PCR primer 2

<400> SEQUENCE: 49
cgctccggcc cacaaatctc                                                 20

<210> SEQ ID NO 50
<211> LENGTH: 20
<212> TYPE: DNA
<213> ORGANISM: Artificial Sequence
<220> FEATURE:
<223> OTHER INFORMATION: Alp qRT-PCR primer 1

<400> SEQUENCE: 50
acgtggctaa gaatgtcatc                                                 20

<210> SEQ ID NO 51
<211> LENGTH: 19
<212> TYPE: DNA
```

```
<213> ORGANISM: Artificial Sequence
<220> FEATURE:
<223> OTHER INFORMATION: Alp qRT-PCR primer 2

<400> SEQUENCE: 51
ctggtaggcg atgtcctta                                                  19

<210> SEQ ID NO 52
<211> LENGTH: 25
<212> TYPE: DNA
<213> ORGANISM: Artificial Sequence
<220> FEATURE:
<223> OTHER INFORMATION: osterix qRT-PCR primer 1

<400> SEQUENCE: 52
tagtggtttg gggtttgttt accgc                                           25

<210> SEQ ID NO 53
<211> LENGTH: 26
<212> TYPE: DNA
<213> ORGANISM: Artificial Sequence
<220> FEATURE:
<223> OTHER INFORMATION: osterix qRT-PCR primer 2

<400> SEQUENCE: 53
aaccaaataa ctcttattcc ctaagt                                          26

<210> SEQ ID NO 54
<211> LENGTH: 21
<212> TYPE: DNA
<213> ORGANISM: Artificial Sequence
<220> FEATURE:
<223> OTHER INFORMATION: Klotho qRT-PCR primer 1

<400> SEQUENCE: 54
gctctcaaag cccacatact g                                               21

<210> SEQ ID NO 55
<211> LENGTH: 20
<212> TYPE: DNA
<213> ORGANISM: Artificial Sequence
<220> FEATURE:
<223> OTHER INFORMATION: Klotho qRT-PCR primer 1

<400> SEQUENCE: 55
gcagcataac gatagaggcc                                                 20

<210> SEQ ID NO 56
<211> LENGTH: 22
<212> TYPE: DNA
<213> ORGANISM: Artificial Sequence
<220> FEATURE:
<223> OTHER INFORMATION: Sm22-alpha qRT-PCR primer 1

<400> SEQUENCE: 56
gttccagact gttgacctct tt                                              22

<210> SEQ ID NO 57
<211> LENGTH: 20
<212> TYPE: DNA
<213> ORGANISM: Artificial Sequence
<220> FEATURE:
<223> OTHER INFORMATION: Sm22-alpha qRT-PCR primer 2

<400> SEQUENCE: 57
ctgcgctttc ttcataaacc                                                 20
```

<210> SEQ ID NO 58
<211> LENGTH: 5553
<212> TYPE: DNA
<213> ORGANISM: Homo sapiens
<220> FEATURE:
<223> OTHER INFORMATION: Human Runx2 mRNA

<400> SEQUENCE: 58

```
gtgtgaatgc ttcattcgcc tcacaaacaa ccacagaacc acaagtgcgg tgcaaacttt      60
ctccaggagg acagcaagaa gtctctggtt tttaaatggt taatctccgc aggtcactac     120
cagccaccga gaccaacaga gtcatttaag gctgcaagca gtatttacaa cagagggtac     180
aagttctatc tgaaaaaaaa aggagggact atggcatcaa acagcctctt cagcacagtg     240
acaccatgtc agcaaaactt cttttgggat ccgagcacca gccggcgctt cagcccccc      300
tccagcagcc tgcagcccgg caaaatgagc gacgtgagcc cggtggtggc tgcgcaacag     360
cagcagcaac agcagcagca gcaacagcag cagcagcagc agcaacagca gcagcagcag     420
caggaggcgg cggcggcggc tgcggcggcg gcggcggctg cggcggcggc agctgcagtg     480
ccccggttgc ggccgcccca cgacaaccgc accatggtgg agatcatcgc cgaccacccg     540
gccgaactcg tccgcaccga cagccccaac ttcctgtgct cggtgctgcc ctcgcactgg     600
cgctgcaaca gaccctgcc cgtggccttc aaggtggtag ccctcggaga ggtaccagat     660
gggactgtgg ttactgtcat ggcgggtaac gatgaaaatt attctgctga gctccggaat     720
gcctctgctg ttatgaaaaa ccaagtagca aggttcaacg atctgagatt tgtgggccgg     780
agtggacgag gcaagagttt caccttgacc ataaccgtct tcacaaatcc tccccaagta     840
gctacctatc acagagcaat taagttacag tagatggac tcgggaacc cagaaggcac      900
agacagaagc ttgatgactc taaacctagt ttgttctctg accgcctcag tgatttaggg     960
cgcattcctc atcccagtat gagagtaggt gtcccgcctc agaacccacg gccctccctg    1020
aactctgcac caagtccttt taatccacaa ggacagagtc agattacaga ccccaggcag    1080
gcacagtctt ccccgccgtg gtcctatgac cagtcttacc cctcctacct gagccagatg    1140
acgtccccgt ccatccactc taccacccg ctgtcttcca cacggggcac tgggcttcct    1200
gccatcaccg atgtgcctag cgcatttca gatgatgaca ctgccaccct tgacttctgc    1260
ctctggcctt ccactctcag taagaagagc caggcaggtg cttcagaact gggccctttt    1320
tcagacccca ggcagttccc aagcatttca tccctcactg agagccgctt ctccaaccca    1380
cgaatgcact atccagccac ctttacttac accccgccag tcacctcagg catgtccctc    1440
ggtatgtccg ccaccactca ctaccacacc tacctgccac caccctaccc cggctcttcc    1500
caaagccaga gtgacccctt ccagaccagc agcactccat atctctacta tggcacttcg    1560
tcaggatcct atcagtttcc catggtgccg ggggagacc ggtctccttc cagaatgctt    1620
ccgccatgca ccaccactc gaatggcagc acgctattaa atccaaattt gcctaaccag    1680
aatgatggtg ttgacgctga tggaagccac agcagttccc caactgtttt gaattctagt    1740
ggcagaatgg atgaatctgt ttggcgacca tattgaaatt cctcagcagt ggcccagtgg    1800
tatctggggg ccacatccca cacgtatcaa tatatacata tatagagaga gtgcatatat    1860
atgtatatcg attagctatc tacaaagtgc ctattttta gaagattttt cattcactca    1920
ctcagtcatg atcttgcagc cataagaggg tagatattga gaagcagaag gctcaagaga    1980
gacaattgca atcgagcttc agattgttta ctatttaaga tgtacttta caaaggaaca    2040
```

```
aagaagggaa aaggtatttt tgttttgtt gtttggtctg ttatcatcaa taacctgttc    2100
atatgccaat tcagagaggt ggactccagg ttcaggaggg agaagagcaa agccgcttcc    2160
tctctgtgct ttgaaacttc acaccctcac ggtggcagct gtgtatggac cagtgccctc    2220
cgcagacagc tcacaaaacc agttgaggtg cactaaaggg acatgaggta gaatggatgc    2280
ttccatcaca gtaccatcat tcagaataac tcttccaatt tctgctttca gacatgctgc    2340
aggtcctcat ctgaactgtt gggttcgttt ttttttttt ttttcctgct ccaagaaagt    2400
gacttcaaaa ataactgatc aggatagatt atttattt acttttaac actccttctc    2460 ccctttccc actgaaccaa aaagaaatcc catccctaaa acctgccttc tcctttatg    2520 caaaactgaa aatggcaata cattattata gccataatgg tatagatagt gattgcgttt    2580
ggctatgtgt tgttttcttt ttttttaaat tatgaatatg tgtaaaatct gaggtaactt    2640
gctaacgtga atggtcatat aactttaaag atatatttat aattatttaa tgacatttgg    2700
acccttgaaa catttcttag tgtattgata tgttgacttc ggtctctaaa agtgctcttt    2760
attaaataac aaatttcttc agtggtctag agccatatct gaaatattgc taagcaattt    2820
cagttcatcc aggcacaatg tgattttaaa aaatacttcc atctccaaat attttagata    2880
tagattgttt ttgtgatgta tgaaggaaat gttatgttta gttctttcag atctttgaat    2940
gcctctaaca cagctttgcc ttctaaagcg gtaattaggg atttaaaaaa caacctttag    3000 cccctttatca gcatgaaatg ctggagtgat gtggttttct aatttctttg gggtaattat    3060
gactcttgtc atattaaaaa gacaagcaca agtaaatcat tgaactacag aaaaatgttc    3120
tgtggtttca tagttaagca aaactctaaa tcgccaggct tcatagcaaa gacatagtca    3180
gctaaaagcc gcacatgtgg atagagggtt caattatgag acacctagta caggagagca    3240
aaattgcacc agagattctt aaccaaccag ccttaccaaa caacacaaca ggggaacccc    3300
aatctgcctt acccaaggcc ccactggcag cttccacag aatttgcatt tagaggagca    3360
gaatgacatc actgtccttt gggagtaggt cctctgaaaa ggcagcaggt tccagcaggt    3420
agctgagctg agaggacata tggcccacgg ggacctacag acagcctttg acatttgtat    3480
ttcttacaat ggagggccaa ggagggcaag gggctgtgga gtttggtgtc tactagtgtg    3540
tatgaatttg agctagagtc cttctgtggc atgcactttg accactcctg gcagtcacat    3600
ggcagatttc caagtgcaaa tccttaatcc aaacaaggat catctaatga caccaccagg    3660
ccaatccctg ctctcctccc cgaaaagtca gggtcccttc attggaatcc tccacccacc    3720
caagcagaat ttagcagaga tttgccttca aaccctaacg gccccttgt tctctggtcc    3780 ttctcaaacc caccttgta ggccacccag cattgcagga cagcgtgtgg ggcagctgga    3840
cctgtgcttc ctgcctggga gtctcccttg gaattcatcc tgactccttc taataaaaat    3900
ggatgggaaa gcaaaacact tgccttcta aaggccgtat accaagtatg cttagataaa    3960
taagccactt ttctattact taagtaagaa ggaagtagta attgatacta tttattgttt    4020
gtgtgtggta gcttgaagca caccactgtc catttatttg taagtgtaaa atatgtgtgt    4080
ttgtttcagc agcacttaaa aaagccagtg tctggttaca catttcaatt ttaattaatt    4140
gacataaaaa tgctaccgcc agtgccagct gcatcctatt taattaaaaa ggtactatat    4200
ttgtacatta tttttaatg ttaaaagggc tttttaagt ttacagtaca cataccgagt    4260
gactttaggg atgcttttgt gttgaaatgt tactatagtg gctgcaggca gcaacccaga    4320
aacactttag aagctttttt tccttgggaa aaattcaagc acttcttccc tccaccctca    4380
ctccaaccac cccaatgggg gtaattcaca tttcttagaa caaattctgc cctttttgg    4440
```

```
tctagggatt aaaattttgt ttttctttct ttctttttt tttttttca ctgaacccttt    4500 aatttgcact gggtcatgtg tttgatttgt gatttcaaga ccaaagcaaa gtcttactac    4560
tactgtggaa ccatgtacta gttcctggga attaaaatag cgtggttctc tttgtagcac    4620
aaacattgct ggaatttgca gtcttttcaa tgcagccaca ttttatcca tttcagttgt    4680 ctcacaaatt ttaacccata tcagagttcc agaacaggta ccacagcttt ggttttagat    4740
tagtggaata acattcagcc cagaactgag aaactcaaca gattaactat cgtttgctct    4800
ttagacggtc tcactgcctc tcacttgcca gagccctttc aaaatgagca gagaagtcca    4860
caccattagg gaccatctgt gataaattca gaagggagga gatgtgtgta cagctttaag    4920
gattccctca attccgagga aagggactgg cccagaatcc aggttaatac atggaaacac    4980
gaagcattag caaaagtaat aattatacct atggtatttg aaagaacaat aataaaagac    5040
acttcttcca aaccttgaat ttgttgtttt tagaaaacga atgcatttaa aaatatttc    5100 tatgtgagaa tttttagat gtgtgtttac ttcatgttta caaataactg tttgcttttt    5160
aatgcagtac tttgaaatat atcagccaaa accataactt acaataattt cttaggtatt    5220
ctgaataaaa ttccatttct tttggatatg ctttaccatt cttaggtttc tgtggaacaa    5280
aaatatttgt agcattttgt gtaaatacaa gctttcattt ttatttttc caattgctat    5340 tgcccaagaa ttgctttcca tgcacatatt gtaaaaattc cgctttgtgc cacaggtcat    5400
gattgtggat gagtttactc ttaacttcaa agggactatt tgtattgtat gttgcaactg    5460
taaattgaat tatttggcat ttttctcatg attgtaatat taatttgaag tttgaattta    5520
attttcaata aaatggcttt tttggttttg tta                                 5553
```

<210> SEQ ID NO 59
<211> LENGTH: 2606
<212> TYPE: DNA
<213> ORGANISM: Homo sapiens
<220> FEATURE:
<223> OTHER INFORMATION: Human Alp mRNA

<400> SEQUENCE: 59

```
ccgggcctca ctcgggcccc gcggccgcct ttataaggcg gcggggggtgg tggcccgggc     60 cgcgttgcgc tcccgccact ccgcgcccgc tatcctggct ccgtgctccc acgcgcttgt    120
gcctggacgg accctcgcca gtgctctgcg caggattgga acatcagtta acatctgacc    180
actgccagcc cacccctcc cacccacgtc gattgcatct ctgggctcca gggataaagc    240
aggtcttggg gtgcaccatg atttcaccat tcttagtact ggccattggc acctgcctta    300
ctaactcctt agtgccagag aaagagaaag accccaagta ctggcgagac caagcgcaag    360
agacactgaa atatgccctg agcttcaga agctcaacac caacgtggct aagaatgtca    420
tcatgttcct gggagatggg atgggtgtct ccacagtgac ggctgcccgc atcctcaagg    480
gtcagctcca ccacaaccct ggggaggaga ccaggctgga gatggacaag ttccccttcg    540
tggccctctc caagacgtac aacaccaatg cccaggtccc tgacagcgcc ggcaccgcca    600
ccgcctacct gtgtgggtg aaggccaatg agggcaccgt gggggtaagc gcagccactg    660
agcgttcccg gtgcaacacc acccagggga acgaggtcac ctccatcctg cgctgggcca    720
aggacgctgg gaaatctgtg ggcattgtga ccaccacgag agtgaaccat gccacccca    780 gcgccgccta cgcccactcg gctgaccggg actggtactc agacaacgag atgcccctg    840 aggccttgag ccagggctgt aaggacatcg cctaccagct catgcataac atcagggaca    900
```

-continued

| | |
|---|---|
| ttgacgtgat catgggggt ggccggaaat acatgtaccc caagaataaa actgatgtgg | 960 |
| agtatgagag tgacgagaaa gccaggggca cgaggctgga cggcctggac ctcgttgaca | 1020 |
| cctggaagag cttcaaaccg agatacaagc actcccactt catctggaac cgcacggaac | 1080 |
| tcctgaccct tgaccccac aatgtggact acctattggg tctcttcgag ccaggggaca | 1140 |
| tgcagtacga gctgaacagg aacaacgtga cggacccgtc actctccgag atggtggtgg | 1200 |
| tggccatcca gatcctgcgg aagaacccca aaggcttctt cttgctggtg aaggaggca | 1260 |
| gaattgacca cgggcaccat gaaggaaaag ccaagcaggc cctgcatgag gcggtggaga | 1320 |
| tggaccgggc catcgggcag gcaggcagct tgacctcctc ggaagacact ctgaccgtgg | 1380 |
| tcactgcgga ccattcccac gtcttcacat ttggtggata cacccccgt ggcaactcta | 1440 |
| tctttggtct ggccccatg ctgagtgaca cagacaagaa gccccttcact gccatcctgt | 1500 |
| atggcaatgg gcctggctac aaggtggtgg gcggtgaacg agagaatgtc tccatggtgg | 1560 |
| actatgctca caacaactac caggcgcagt ctgctgtgcc cctgcgccac gagacccacg | 1620 |
| gcggggagga cgtggccgtc ttctccaagg gccccatggc gcacctgctg cacggcgtcc | 1680 |
| acgagcagaa ctacgtcccc cacgtgatgg cgtatgcagc ctgcatcggg gccaacctcg | 1740 |
| gccactgtgc cctgccagc tcggcaggca gccttgctgc aggcccctg ctgctcgcgc | 1800 |
| tggccctcta cccctgagc gtcctgttct gagggcccag ggcccgggca cccacaagcc | 1860 |
| cgtgacagat gccaacttcc cacacggcag cccccccctc aaggggcagg gaggtggggg | 1920 |
| cctcctcagc ctctgcaact gcaagaaagg ggacccaaga aaccaaagtc tgccgcccac | 1980 |
| ctcgctcccc tctggaatct tccccaaggg ccaaacccac ttctggcctc cagcctttgc | 2040 |
| tccctcccg ctgccctttg gccaacaggg tagatttctc ttgggcaggc agagagtaca | 2100 |
| gactgcagac attctcaaag cctcttattt ttctagcgaa cgtatttctc cagacccaga | 2160 |
| ggccctgaag cctccgtgga acattctgga tctgaccctc ccagtctcat ctcctgaccc | 2220 |
| tcccactccc atctccttac ctctggaacc ccccaggccc tacaatgctc atgtccctgt | 2280 |
| ccccaggccc agccctcctt caggggagtt gaggtctttc tcctcaggac aaggccttgc | 2340 |
| tcactcactc actccaagac caccagggtc ccaggaagcc ggtgcctggg tggccatcct | 2400 |
| acccagcgtg gcccaggccg ggaagagcca cctggcaggg ctcacactcc tgggctctga | 2460 |
| acacacacgc cagctcctct ctgaagcgac tctcctgttt ggaacggcaa aaaaaaattt | 2520 |
| ttttttctct ttttggtggt ggttaaaagg gaacacaaaa catttaaata aaactttcca | 2580 |
| aatatttccg aggacaaaaa aaaaaa | 2606 |

<210> SEQ ID NO 60
<211> LENGTH: 3173
<212> TYPE: DNA
<213> ORGANISM: Homo sapiens
<220> FEATURE:
<223> OTHER INFORMATION: Human Osterix mRNA

<400> SEQUENCE: 60

| | |
|---|---|
| cggcgggcgg cagcagccta ggcagcagca gtagcagaag cagcagccgc cgagcagcag | 60 |
| caaggactct ggagtcagag taggactgta ggaccggagc ctgagtggaa caggagtgga | 120 |
| gctggcctgg gagagagcgg atccctccca gcaccctcag gccacccgtt gcctgcactc | 180 |
| tccctgccag acctcagag aggagagact cgggacagcc agcccaggt tcccccagct | 240 |
| ctctccatct gcctggctcc ttgggacccg ttccccagcc tcaggatggc gtcctccctg | 300 |
| cttgaggagg aagttcacta tggctccagt cccctggcca tgctgacggc agcgtgcagc | 360 |

-continued

```
aaatttggtg gctctagccc tctgcgggac tcaacaactc tgggcaaagc aggcacaaag    420
aagccgtact ctgtgggcag tgacctttca gcctccaaaa ccatggggga tgcttatcca    480
gccccttta caagcactaa tgggctcctt tcacctgcag gcagtcctcc agcacccacc    540
tcaggctatg ctaatgatta ccctccctt tcccactcat tccctgggcc acaggcacc    600
caggaccctg ggctactagt gcccaagggg cacagctctt ctgactgtct gcccagtgtc    660
tacacctctc tggacatgac acaccctat ggctcctggt acaaggcagg catccatgca    720
ggcatttcac caggcccagg caacactcct actccatggt gggatatgca ccctggaggc    780
aactggctag gtggtgggca gggccagggt gatgggctgc aagggacact gcccacaggt    840
ccagctcagc ctccactgaa ccccagctg cccacctacc catctgactt tgctcccctt    900
aatccagccc cctacccagc tccccacctc ttgcaaccag gccccagca tgtcttgccc    960
caagatgtct ataaacccaa ggcagtggga atagtgggc agctagaagg gagtggtgga   1020
gccaaacccc cacggggtgc aagcactggg ggtagtggtg gatatggggg cagtggggca   1080
gggcgctcct cctgcgactg ccctaattgc caggagctag agcggctggg agcagcagcg   1140
gctgggctgc ggaagaagcc catccacagc tgccacatcc ctggctgcgg caaggtgtat   1200
ggcaaggctt cgcacctgaa ggcccacttg cgctggcaca caggcgagag gcccttcgtc   1260
tgcaactggc tcttctgcgg caagaggttc actcgttcgg atgagctgga gcgtcatgtg   1320
cgcactcaca cccgggagaa gaagttcacc tgcctgctct gctccaagcg ctttacccga   1380
agcgaccacc tgagcaaaca ccagcgcacc catggagaac caggcccggg tccccctccc   1440
agtggcccca aggagctggg ggagggccgc agcacggggg aagaggaggc cagtcagacg   1500
ccccgacctt ctgcctcgcc agcaacccca gagaaagccc ctggaggcag ccctgagcag   1560
agcaacttgc tggagatctg agccgggtgg aaggtctccc accccagggc tgccctgaca   1620
gtctctcttg gctctctaga ccactgcttg ccaatcactc tctttacccc atgcatgcca   1680
tccttcgggg ctctctccct ctgtctccct cctggccatt ctgggcttgg gtatctcctt   1740
gcatgcctcc tcagctcacc ttctctcttc accatgagac tggctttcca caaactctca   1800
tctcaggccc tccccttgtg cctgatacct gcactccggc ttcctagact ctggccctgc   1860
cacaccaaca cactttctat ttgggctccc aacactattt ctccatctca ctccttgaca   1920
tgtacccctt tctgcttctc aagcttattt cctgctgtcc ctcagcctcc aggcttcagt   1980
cttcccaact tcttacacca ttgctttcca ttctccagaa ctctttttc cttttacaa   2040
acacaatgat aatgataatt tattgccccc tggtggcctc ttcatcaggg gtattggggt   2100
tagtgacctg gccagagggt gccaagaggg gggcagacca gtgggatct gatcccaaag   2160
atggggtgac cccagggtca ggaggctgc cccaggcct gtatatttaa ccctatgta     2220
ccaggagtaa tgaatagtaa taattctatt tatgtaagtt atgatgacgg gtcaggtaga   2280
gtgagctggg gagggaagtg gatccatttc tgctaaggaa attctagtca aatgcatctc   2340
tgtatagaca aaatgttagt ggagaagatc ttgttaatag aatgtctatc atcagaatct   2400
cagttgatag ggtttctctt gtaatgaagt ctctacaaat tgggttagct acatctctgc   2460
taaacagttg atggggtatc tcttgattag ggggatccct aatatcccca gccccagcca   2520
gaagctgtga aacctcaagt cctatggagg ggagaaggac tggaatgtac cccatctccc   2580
ttgactgcag agcaggttcc tccactgccc caccccttag acaccatgac cccatcaggt   2640
taatcccctg ttgccatggt tatggagagc ttgcagctgc catcttagat gtgctctttg   2700
```

| | |
|---|---|
| gggaagccca tctaacagga ggacattggt ttggggtgc acctcctgaa gaatgggtgg | 2760 |
| ggaaggcttt ctctaggatc agattcaaat aagtatgtat tgagtgccta ctctgtgcaa | 2820 |
| ggcactatgc tagatctggt gcctagaagc cctgagaaag aacttaaaga gctaggagga | 2880 |
| cagaggcccc caagctgatc tggtggtgca tccacgcacc cccaccctgg gactttggat | 2940 |
| gctcccatct ccacctccag tgacttttaa agccgcttcg tgcctttcct gtaacgttgg | 3000 |
| atcctccttt tctgtcccct gctgtctcaa ggccccaagt taaagggtta aagccgctgg | 3060 |
| agcttgggga gagaacattg tggaatggaa gggatcatgc cctttgtgga gtctttttt | 3120 |
| tttaatttaa taaataaaag ttggatttga aaaaaaaaaa aaaaaaaaaa aaa | 3173 |

<210> SEQ ID NO 61
<211> LENGTH: 5003
<212> TYPE: DNA
<213> ORGANISM: Homo sapiens
<220> FEATURE:
<223> OTHER INFORMATION: Human Klotho mRNA

<400> SEQUENCE: 61

| | |
|---|---|
| cgcgcagcat gcccgccagc gccccgccgc gccgcccgcg gccgccgccg ccgtcgctgt | 60 |
| cgctgctgct ggtgctgctg ggcctgggcg ccgccgcct cgtgcggag ccgggcgacg | 120 |
| gcgcgcagac ctgggcccgt gtctcgcggc ctcctgcccc cgaggccgcg ggcctcttcc | 180 |
| agggcaccttc ccccgacggc ttcctctggg ccgtgggcag cgccgcctac cagaccgagg | 240 |
| gcggctggca gcagcacggc aagggtgcgt ccatctggga cacgttcacc caccaccccc | 300 |
| tggcaccccc gggagactcc cggaacgcca gtctgccgtt gggcgccccg tcgccgctgc | 360 |
| agcccgccac cggggacgta gccagcgaca gctacaacaa cgtcttccgc gacacggagg | 420 |
| cgctgcgcga gctcggggtc actcactacc gcttctccat ctcgtgggcg cgagtgctcc | 480 |
| ccaatggcag cgcgggcgtc cccaaccgcg aggggctgcg ctactaccgg cgcctgctgg | 540 |
| agcggctgcg ggagctgggc gtgcagcccg tggtcaccct gtaccactgg gacctgcccc | 600 |
| agcgcctgca ggacgcctac ggcggctggg ccaaccgcgc cctggccgac cacttcaggg | 660 |
| attacgcgga gctctgcttc cgccacttcg gcggtcaggt caagtactgg atcaccatcg | 720 |
| acaaccccta cgtggtggcc tggcacggct acgccaccgg gcgcctggcc ccggcatcc | 780 |
| ggggcagccc cgcggctcggg tacctggtgg cgcacaacct cctcctggct catgccaaag | 840 |
| tctggcatct ctacaatact tcttttcgtc ccactcaggg aggtcaggtg tccattgccc | 900 |
| taagctctca ctggatcaat cctcgaagaa tgaccgacca cagcatcaaa gaatgtcaaa | 960 |
| aatctctgga ctttgtacta ggttggtttg ccaaacccgt atttattgat ggtgactatc | 1020 |
| ccgagagcat gaagaataac ctttcatcta ttctgcctga ttttactgaa tctgagaaaa | 1080 |
| agttcatcaa aggaactgct gacttttttg ctctttgctt tggacccacc ttgagttttc | 1140 |
| aacttttgga ccctcacatg aagttccgcc aattggaatc tcccaacctg aggcaactgc | 1200 |
| tttcctggat tgaccttgaa tttaaccatc tcaaatatt tattgtggaa atggctggt | 1260 |
| ttgtctcagg gaccaccaag agagatgatg ccaaatatat gtattacctc aaaaagttca | 1320 |
| tcatggaaac cttaaaagcc atcaagctgg atggggtgga tgtcatcggg tataccgcat | 1380 |
| ggtccctcat ggatggtttc gagtggcaca gaggttacag catcaggcgt ggactcttct | 1440 |
| atgttgactt tctaagccag gacaagatgt tgttgccaaa gtcttcagcc ttgttctacc | 1500 |
| aaaagctgat agaaaaaat ggcttccctc ctttacctga aaatcagccc ctagaaggga | 1560 |
| catttccctg tgactttgct tggggagttg ttgacaacta cattcaagta gataccactc | 1620 |

```
tgtctcagtt taccgacctg aatgtttacc tgtgggatgt ccaccacagt aaaaggctta    1680
ttaaagtgga tggggttgtg accaagaaga ggaaatccta ctgtgttgac tttgctgcca    1740
tccagcccca gatcgcttta ctccaggaaa tgcacgttac acattttcgc ttctccctgg    1800
actgggccct gattctccct ctgggtaacc agtcccaggt gaaccacacc atcctgcagt    1860
actatcgctg catggccagc gagcttgtcc gtgtcaacat caccccagtg gtggccctgt    1920
ggcagcctat ggccccgaac caaggactgc cgcgcctcct ggccaggcag ggcgcctggg    1980 agaacccta cactgccctg cctttgcag agtatgcccg actgtgcttt caagagctcg       2040
gccatcacgt caagctttgg ataacgatga atgagccgta taaggaat atgacataca      2100 gtgctggcca aaccttctg aaggcccatg ccctggcttg gcatgtgtac aatgaaaagt    2160
ttaggcatgc tcagaatggg aaaatatcca tagccttgca ggctgattgg atagaacctg    2220
cctgcccttt ctcccaaaag gacaaagagg tggccgagag agttttggaa tttgacattg    2280
gctggctggc tgagcccatt tcggctctg gagattatcc atgggtgatg agggactggc      2340
tgaaccaaag aaacaatttt cttcttcctt atttcactga agatgaaaaa aagctaatcc    2400
agggtacctt tgacttttg gctttaagcc attataccac catccttgta gactcagaaa     2460
aagaagatcc aataaaatac aatgattacc tagaagtgca agaaatgacc gacatcacgt    2520
ggctcaactc ccccagtcag gtggcggtag tgccctgggg gttgcgcaaa gtgctgaact    2580
ggctgaagtt caagtacgga gacctcccca tgtacataat atccaacgga atcgatgacg    2640
ggctgcatgc tgaggacgac cagctgaggg tgtattatat gcagaattac ataaacgaag    2700
ctctcaaagc ccacatactg gatggtatca atctttgcgg atactttgct tattcgttta    2760
acgaccgcac agctccgagg tttggcctct atcgttatgc tgcagatcag tttgagccca    2820
aggcatccat gaaacattac aggaaaatta ttgacagcaa tggtttcccg ggcccagaaa    2880
ctctggaaag atttttgtcca gaagaattca ccgtgtgtac tgagtgcagt ttttttcaca    2940
cccgaaagtc tttactggct ttcatagctt ttctatttt tgcttctatt atttctctct      3000
cccttatatt ttactactcg aagaaaggca gaagaagtta caaatagttc tgaacatttt    3060
tctattcatt cattttgaaa taattatgca gacacatcag ctgttaacca tttgcacctc    3120
taagtgttgt gaaactgtaa atttcataca tttgacttct agaaaacatt tttgtggctt    3180
atgacagagg ttttgaaatg ggcataggtg atcgtaaaat attgaataat gcgaatagtg    3240
cctgaatttg ttctcttttt gggtgattaa aaaactgaca ggcactataa tttctgtaac    3300
acactaacaa aagcatgaaa aataggaacc acaccaatgc aacatttgtg cagaaatttg    3360
aatgacaaga ttaggaatat tttcttctgc acccacttct aaatttaatg ttttttctgga    3420 agtagtaatt gcaagagttc gaatagaaag ttatgtacca agtaaccatt tctcagctgc    3480
cataataatg cctagtggct tcccctctgt caaatctagt ttcctatgga aagaagatg      3540 gcagatacag gagagacgac agagggtcct aggctggaat gttcctttcg aaagcaatgc    3600
ttctatcaaa tactagtatt aatttatgta tctggttaat gacatacttg gagagcaaat    3660
tatgaaatgt gtattttat atgatttttg aggtcctgtc taaaccctgt gtccctgagg      3720
gatctgtctc actggcatct tgttgagggc cttgcacata ggaaactttt gataagtatc     3780
tgcggaaaaa caaacatgaa tcctgtgata ttgggctctt caggaagcat aaagcaattg    3840
tgaaatacag tataccgcag tggctctagg tggaggaaag gaggaaaaag tgcttattat    3900
gtgcaacatt atgattaatc tgattataca ccatttttga gcagatcttg gaatgaatga    3960
```

| | |
|---|---|
| catgaccttt ccctagagaa taaggatgaa ataatcactc attctatgaa cagtgacact | 4020 |
| actttctatt ctttagctgt actgtaattt ctttgagttg atagttttac aaattcttaa | 4080 |
| taggttcaaa agcaatctgg tctgaataac actggatttg tttctgtgat ctctgaggtc | 4140 |
| tattttatgt ttttgctgct acttctgtgg aagtagcttt gaactagttt tacttttgaac | 4200 |
| tttcacgctg aaacatgcta gtgatatcta gaaagggcta attaggtctc atcctttaat | 4260 |
| gcccctaaaa taagtcttgc tgattttcag acagggaagt ctctctatta cactggagct | 4320 |
| gttttataga taagtcaata ttgtatcagg caagataaac caatgtcata acaggcattg | 4380 |
| ccaacctcac tgacacaggg tcatagtgta taataatata ctgtactata taatatatca | 4440 |
| tctttagagg tatgattttt tcatgaaaga taagcttttg gtaatattca ttttaaagtg | 4500 |
| gacttattaa aattggatgc tagagaatca agtttatttt atgtatatat ttttctgatt | 4560 |
| ataagagtaa tatatgttca ttgtaaaaat ttttaaaaca cagaaactat atgcaaagaa | 4620 |
| aaaataaaaa ttatctataa tctcagaacc cagaaatagc cactattaac atttcctacg | 4680 |
| tattttattt tacatagatc atattgtata tagttagtat cttttattaat ttttattatg | 4740 |
| aaactttcct ttgtcattat tagtcttcaa aagcatgatt tttaatagtt gttgagtatt | 4800 |
| ccaccacagg aatgtatcac aacttaaccg ttcccgtttg ttagactagt ttcttattaa | 4860 |
| tgttgatgaa tgttgtttaa aaataatttt gttgctacat ttactttaat ttccttgact | 4920 |
| gtaaagagaa gtaattttgc tccttgataa agtattatat taataataaa tctgcctgca | 4980 |
| acttttttgcc ttctttcata atc | 5003 |

<210> SEQ ID NO 62
<211> LENGTH: 1574
<212> TYPE: DNA
<213> ORGANISM: Homo sapiens
<220> FEATURE:
<223> OTHER INFORMATION: Human Sm22-alpha mRNA

<400> SEQUENCE: 62

| | |
|---|---|
| tcaccacggc ggcagccctt taaaccctc acccagccag cgccccatcc tgtctgtccg | 60 |
| aacccagaca caagtcttca ctccttcctg cgagccctga ggaagccttg tgagtgcatt | 120 |
| ggctggggct tggagggaag ttgggctgga gctggacagg agcagtgggt gcatttcagg | 180 |
| caggctctcc tgaggtccca ggcgccagct ccagctccct ggctagggaa acccaccctc | 240 |
| tcagtcagca tgggggccca agctccaggc agggtgggct ggatcactag cgtcctggat | 300 |
| ctctctcaga ctgggcagcc ccgggctcat tgaaatgccc cggatgactt ggctagtgca | 360 |
| gaggaattga tggaaaccac cggggtgaga gggaggctcc ccatctcagc cagccacatc | 420 |
| cacaaggtgt gtgtaagggt gcaggcgccg gccggttagg ccaaggctct actgtctgtt | 480 |
| gcccctccag gagaacttcc aaggagcttt ccccagacat ggccaacaag ggtccttcct | 540 |
| atggcatgag ccgcgaagtg cagtccaaaa tcgagaagaa gtatgacgag gagctggagg | 600 |
| agcggctggt ggagtggatc atagtgcagt gtggcccctga tgtgggccgc ccagaccgtg | 660 |
| ggcgcttggg cttccaggtc tggctgaaga atggcgtgat tctgagcaag ctggtgaaca | 720 |
| gcctgtaccc tgatggctcc aagcggtga aggtgcccga gaaccccacc tccatggtct | 780 |
| tcaagcagat ggagcaggtg gctcagttcc tgaaggcggc tgaggactat ggggtcatca | 840 |
| agactgacat gttccagact gttgacctct ttgaaggcaa agacatggca gcagtgcaga | 900 |
| ggaccctgat ggctttgggc agcttggcag tgaccaagaa tgatgggcac taccgtggag | 960 |
| atcccaactg gtttatgaag aaagcgcagg agcataagag ggaattcaca gagagccagc | 1020 |

-continued

```
tgcaggaggg aaagcatgtc attggccttc agatgggcag caacagaggg gcctcccagg      1080
ccggcatgac aggctacgga cgacctcggc agatcatcag ttagagcgga gagggctagc      1140
cctgagcccg gccctccccc agctccttgg ctgcagccat cccgcttagc ctgcctcacc      1200
cacacccgtg tggtaccttc agccctggcc aagctttgag gctctgtcac tgagcaatgg      1260
taactgcacc tgggcagctc ctccctgtgc ccccagcctc agcccaactt cttacccgaa      1320
agcatcactg ccttggcccc tccctccccgg ctgcccccat cacctctact gtctcctccc      1380
tgggctaagc aggggagaag cgggctgggg gtagcctgga tgtgggccaa gtccactgtc      1440
ctccttggcg gcaaaagccc attgaagaag aaccagccca gcctgccccc tatcttgtcc      1500
tggaatattt ttggggttgg aactcaaaaa aaaaaaaaaa aaatcaatct tttctcaaaa      1560
aaaaaaaaaa aaaa                                                        1574
```

<210> SEQ ID NO 63
<211> LENGTH: 521
<212> TYPE: PRT
<213> ORGANISM: Homo sapiens
<220> FEATURE:
<223> OTHER INFORMATION: Human Runx2 protein

<400> SEQUENCE: 63

```
Met Ala Ser Asn Ser Leu Phe Ser Thr Val Thr Pro Cys Gln Gln Asn
1               5                   10                  15

Phe Phe Trp Asp Pro Ser Thr Ser Arg Arg Phe Ser Pro Pro Ser Ser
            20                  25                  30

Ser Leu Gln Pro Gly Lys Met Ser Asp Val Ser Pro Val Val Ala Ala
        35                  40                  45

Gln Gln Gln Gln Gln Gln Gln Gln Gln Gln Gln Gln Gln Gln
    50                  55                  60

Gln Gln Gln Gln Gln Gln Glu Ala Ala Ala Ala Ala Ala Ala
65                  70                  75                  80

Ala Ala Ala Ala Ala Ala Ala Ala Val Pro Arg Leu Arg Pro Pro
                85                  90                  95

His Asp Asn Arg Thr Met Val Glu Ile Ile Ala Asp His Pro Ala Glu
            100                 105                 110

Leu Val Arg Thr Asp Ser Pro Asn Phe Leu Cys Ser Val Leu Pro Ser
        115                 120                 125

His Trp Arg Cys Asn Lys Thr Leu Pro Val Ala Phe Lys Val Val Ala
    130                 135                 140

Leu Gly Glu Val Pro Asp Gly Thr Val Val Thr Val Met Ala Gly Asn
145                 150                 155                 160

Asp Glu Asn Tyr Ser Ala Glu Leu Arg Asn Ala Ser Ala Val Met Lys
                165                 170                 175

Asn Gln Val Ala Arg Phe Asn Asp Leu Arg Phe Val Gly Arg Ser Gly
            180                 185                 190

Arg Gly Lys Ser Phe Thr Leu Thr Ile Thr Val Phe Thr Asn Pro Pro
        195                 200                 205

Gln Val Ala Thr Tyr His Arg Ala Ile Lys Val Thr Val Asp Gly Pro
    210                 215                 220

Arg Glu Pro Arg Arg His Arg Gln Lys Leu Asp Asp Ser Lys Pro Ser
225                 230                 235                 240

Leu Phe Ser Asp Arg Leu Ser Asp Leu Gly Arg Ile Pro His Pro Ser
                245                 250                 255
```

```
Met Arg Val Gly Val Pro Pro Gln Asn Pro Arg Pro Ser Leu Asn Ser
                260                 265                 270

Ala Pro Ser Pro Phe Asn Pro Gln Gly Gln Ser Gln Ile Thr Asp Pro
            275                 280                 285

Arg Gln Ala Gln Ser Ser Pro Pro Trp Ser Tyr Asp Gln Ser Tyr Pro
        290                 295                 300

Ser Tyr Leu Ser Gln Met Thr Ser Pro Ser Ile His Ser Thr Thr Pro
305                 310                 315                 320

Leu Ser Ser Thr Arg Gly Thr Gly Leu Pro Ala Ile Thr Asp Val Pro
                325                 330                 335

Arg Arg Ile Ser Asp Asp Thr Ala Thr Ser Asp Phe Cys Leu Trp
            340                 345                 350

Pro Ser Thr Leu Ser Lys Lys Ser Gln Ala Gly Ala Ser Glu Leu Gly
                355                 360                 365

Pro Phe Ser Asp Pro Arg Gln Phe Pro Ser Ile Ser Ser Leu Thr Glu
        370                 375                 380

Ser Arg Phe Ser Asn Pro Arg Met His Tyr Pro Ala Thr Phe Thr Tyr
385                 390                 395                 400

Thr Pro Pro Val Thr Ser Gly Met Ser Leu Gly Met Ser Ala Thr Thr
                405                 410                 415

His Tyr His Thr Tyr Leu Pro Pro Pro Tyr Pro Gly Ser Ser Gln Ser
            420                 425                 430

Gln Ser Gly Pro Phe Gln Thr Ser Ser Thr Pro Tyr Leu Tyr Tyr Gly
        435                 440                 445

Thr Ser Ser Gly Ser Tyr Gln Phe Pro Met Val Pro Gly Gly Asp Arg
450                 455                 460

Ser Pro Ser Arg Met Leu Pro Pro Cys Thr Thr Thr Ser Asn Gly Ser
465                 470                 475                 480

Thr Leu Leu Asn Pro Asn Leu Pro Asn Gln Asn Asp Gly Val Asp Ala
                485                 490                 495

Asp Gly Ser His Ser Ser Ser Pro Thr Val Leu Asn Ser Ser Gly Arg
            500                 505                 510

Met Asp Glu Ser Val Trp Arg Pro Tyr
        515                 520

<210> SEQ ID NO 64
<211> LENGTH: 524
<212> TYPE: PRT
<213> ORGANISM: Homo sapiens
<220> FEATURE:
<223> OTHER INFORMATION: Human Alp protein

<400> SEQUENCE: 64

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
                20                  25                  30

Ala Gln Glu Thr Leu Lys Tyr Ala Leu Glu Leu Gln Lys Leu Asn Thr
            35                  40                  45

Asn Val Ala Lys Asn Val Ile Met Phe Leu Gly Asp Gly Met Gly Val
        50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95
```

```
Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270

Thr Glu Leu Leu Thr Leu Asp Pro His Asn Val Asp Tyr Leu Leu Gly
        275                 280                 285

Leu Phe Glu Pro Gly Asp Met Gln Tyr Glu Leu Asn Arg Asn Asn Val
    290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
        355                 360                 365

Glu Asp Thr Leu Thr Val Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ser Lys
    450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
            500                 505                 510

Leu Ala Leu Ala Leu Tyr Pro Leu Ser Val Leu Phe
```

-continued

```
            515                 520
```

<210> SEQ ID NO 65
<211> LENGTH: 431
<212> TYPE: PRT
<213> ORGANISM: Homo sapiens
<220> FEATURE:
<223> OTHER INFORMATION: Human Osterix protein

<400> SEQUENCE: 65

```
Met Ala Ser Ser Leu Leu Glu Glu Val His Tyr Gly Ser Ser Pro
1               5                   10                  15

Leu Ala Met Leu Thr Ala Ala Cys Ser Lys Phe Gly Gly Ser Ser Pro
            20                  25                  30

Leu Arg Asp Ser Thr Thr Leu Gly Lys Ala Gly Thr Lys Lys Pro Tyr
            35                  40                  45

Ser Val Gly Ser Asp Leu Ser Ala Ser Lys Thr Met Gly Asp Ala Tyr
        50                  55                  60

Pro Ala Pro Phe Thr Ser Thr Asn Gly Leu Leu Ser Pro Ala Gly Ser
65                  70                  75                  80

Pro Pro Ala Pro Thr Ser Gly Tyr Ala Asn Asp Tyr Pro Pro Phe Ser
                    85                  90                  95

His Ser Phe Pro Gly Pro Thr Gly Thr Gln Asp Pro Gly Leu Leu Val
                100                 105                 110

Pro Lys Gly His Ser Ser Ser Asp Cys Leu Pro Ser Val Tyr Thr Ser
                115                 120                 125

Leu Asp Met Thr His Pro Tyr Gly Ser Trp Tyr Lys Ala Gly Ile His
        130                 135                 140

Ala Gly Ile Ser Pro Gly Pro Gly Asn Thr Pro Thr Pro Trp Trp Asp
145                 150                 155                 160

Met His Pro Gly Gly Asn Trp Leu Gly Gly Gln Gly Gln Gly Asp
                    165                 170                 175

Gly Leu Gln Gly Thr Leu Pro Thr Gly Pro Ala Gln Pro Pro Leu Asn
                180                 185                 190

Pro Gln Leu Pro Thr Tyr Pro Ser Asp Phe Ala Pro Leu Asn Pro Ala
                195                 200                 205

Pro Tyr Pro Ala Pro His Leu Leu Gln Pro Gly Pro Gln His Val Leu
        210                 215                 220

Pro Gln Asp Val Tyr Lys Pro Lys Ala Val Gly Asn Ser Gly Gln Leu
225                 230                 235                 240

Glu Gly Ser Gly Gly Ala Lys Pro Pro Arg Gly Ala Ser Thr Gly Gly
                    245                 250                 255

Ser Gly Gly Tyr Gly Gly Ser Gly Ala Gly Arg Ser Ser Cys Asp Cys
                260                 265                 270

Pro Asn Cys Gln Glu Leu Glu Arg Leu Gly Ala Ala Ala Gly Leu
                275                 280                 285

Arg Lys Lys Pro Ile His Ser Cys His Ile Pro Gly Cys Gly Lys Val
        290                 295                 300

Tyr Gly Lys Ala Ser His Leu Lys Ala His Leu Arg Trp His Thr Gly
305                 310                 315                 320

Glu Arg Pro Phe Val Cys Asn Trp Leu Phe Cys Gly Lys Arg Phe Thr
                    325                 330                 335

Arg Ser Asp Glu Leu Glu Arg His Val Arg Thr His Thr Arg Glu Lys
                340                 345                 350

Lys Phe Thr Cys Leu Leu Cys Ser Lys Arg Phe Thr Arg Ser Asp His
```

```
                355                 360                 365
Leu Ser Lys His Gln Arg Thr His Gly Glu Pro Gly Pro Pro
    370                 375                 380

Pro Ser Gly Pro Lys Glu Leu Gly Glu Gly Arg Ser Thr Gly Glu Glu
385                 390                 395                 400

Glu Ala Ser Gln Thr Pro Arg Pro Ser Ala Ser Pro Ala Thr Pro Glu
                405                 410                 415

Lys Ala Pro Gly Gly Ser Pro Glu Gln Ser Asn Leu Leu Glu Ile
                420                 425                 430

<210> SEQ ID NO 66
<211> LENGTH: 1012
<212> TYPE: PRT
<213> ORGANISM: Homo sapiens
<220> FEATURE:
<223> OTHER INFORMATION: Human Klotho protein

<400> SEQUENCE: 66

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65              70                  75                  80

Gln Gln His Gly Lys Gly Ala Ser Ile Trp Asp Thr Phe Thr His His
            85                  90                  95

Pro Leu Ala Pro Pro Gly Asp Ser Arg Asn Ala Ser Leu Pro Leu Gly
        100                 105                 110

Ala Pro Ser Pro Leu Gln Pro Ala Thr Gly Asp Val Ala Ser Asp Ser
    115                 120                 125

Tyr Asn Asn Val Phe Arg Asp Thr Glu Ala Leu Arg Glu Leu Gly Val
130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
```

-continued

```
            290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                    325                 330                 335

Tyr Pro Glu Ser Met Lys Asn Asn Leu Ser Ser Ile Leu Pro Asp Phe
                340                 345                 350

Thr Glu Ser Glu Lys Lys Phe Ile Lys Gly Thr Ala Asp Phe Phe Ala
            355                 360                 365

Leu Cys Phe Gly Pro Thr Leu Ser Phe Gln Leu Leu Asp Pro His Met
        370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                    405                 410                 415

Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
        450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ala Leu Phe
                    485                 490                 495

Tyr Gln Lys Leu Ile Glu Lys Asn Gly Phe Pro Pro Leu Pro Glu Asn
                500                 505                 510

Gln Pro Leu Glu Gly Thr Phe Pro Cys Asp Phe Ala Trp Gly Val Val
            515                 520                 525

Asp Asn Tyr Ile Gln Val Asp Thr Thr Leu Ser Gln Phe Thr Asp Leu
        530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                    565                 570                 575

Ala Ile Gln Pro Gln Ile Ala Leu Leu Gln Glu Met His Val Thr His
                580                 585                 590

Phe Arg Phe Ser Leu Asp Trp Ala Leu Ile Leu Pro Leu Gly Asn Gln
            595                 600                 605

Ser Gln Val Asn His Thr Ile Leu Gln Tyr Tyr Arg Cys Met Ala Ser
        610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                    645                 650                 655

Trp Glu Asn Pro Tyr Thr Ala Leu Ala Phe Ala Glu Tyr Ala Arg Leu
                660                 665                 670

Cys Phe Gln Glu Leu Gly His His Val Lys Leu Trp Ile Thr Met Asn
            675                 680                 685

Glu Pro Tyr Thr Arg Asn Met Thr Tyr Ser Ala Gly His Asn Leu Leu
        690                 695                 700

Lys Ala His Ala Leu Ala Trp His Val Tyr Asn Glu Lys Phe Arg His
705                 710                 715                 720
```

-continued

```
Ala Gln Asn Gly Lys Ile Ser Ile Ala Leu Gln Ala Asp Trp Ile Glu
            725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
            755                 760                 765

Asp Tyr Pro Trp Val Met Arg Asp Trp Leu Asn Gln Arg Asn Asn Phe
            770                 775                 780

Leu Leu Pro Tyr Phe Thr Glu Asp Lys Lys Leu Ile Gln Gly Thr
785                 790                 795                 800

Phe Asp Phe Leu Ala Leu Ser His Tyr Thr Thr Ile Leu Val Asp Ser
            805                 810                 815

Glu Lys Glu Asp Pro Ile Lys Tyr Asn Asp Tyr Leu Gly Val Gln Glu
            820                 825                 830

Met Thr Asp Ile Thr Trp Leu Asn Ser Pro Ser Gln Val Ala Val Val
            835                 840                 845

Pro Trp Gly Leu Arg Lys Val Leu Asn Trp Leu Lys Phe Lys Tyr Gly
            850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
            885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
            915                 920                 925

Arg Tyr Ala Ala Asp Gln Phe Glu Pro Lys Ala Ser Met Lys His Tyr
            930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
            965                 970                 975

His Thr Arg Lys Ser Leu Leu Ala Phe Ile Ala Phe Leu Phe Phe Ala
            980                 985                 990

Ser Ile Ile Ser Leu Ser Leu Ile Phe Tyr Tyr Ser Lys Lys Gly Arg
            995                 1000                1005

Arg Ser Tyr Lys
    1010

<210> SEQ ID NO 67
<211> LENGTH: 201
<212> TYPE: PRT
<213> ORGANISM: Homo sapiens
<220> FEATURE:
<223> OTHER INFORMATION: Human Sm22-alpha protein

<400> SEQUENCE: 67

Met Ala Asn Lys Gly Pro Ser Tyr Gly Met Ser Arg Glu Val Gln Ser
1               5                   10                  15

Lys Ile Glu Lys Lys Tyr Asp Glu Glu Leu Glu Glu Arg Leu Val Glu
            20                  25                  30

Trp Ile Ile Val Gln Cys Gly Pro Asp Val Gly Arg Pro Asp Arg Gly
        35                  40                  45

Arg Leu Gly Phe Gln Val Trp Leu Lys Asn Gly Val Ile Leu Ser Lys
    50                  55                  60
```

```
Leu Val Asn Ser Leu Tyr Pro Asp Gly Ser Lys Pro Val Lys Val Pro
 65                  70                  75                  80

Glu Asn Pro Pro Ser Met Val Phe Lys Gln Met Glu Gln Val Ala Gln
                 85                  90                  95

Phe Leu Lys Ala Ala Glu Asp Tyr Gly Val Ile Lys Thr Asp Met Phe
            100                 105                 110

Gln Thr Val Asp Leu Phe Glu Gly Lys Asp Met Ala Ala Val Gln Arg
        115                 120                 125

Thr Leu Met Ala Leu Gly Ser Leu Ala Val Thr Lys Asn Asp Gly His
    130                 135                 140

Tyr Arg Gly Asp Pro Asn Trp Phe Met Lys Lys Ala Gln Glu His Lys
145                 150                 155                 160

Arg Glu Phe Thr Glu Ser Gln Leu Gln Glu Gly Lys His Val Ile Gly
                165                 170                 175

Leu Gln Met Gly Ser Asn Arg Gly Ala Ser Gln Ala Gly Met Thr Gly
            180                 185                 190

Tyr Gly Arg Pro Arg Gln Ile Ile Ser
            195                 200

<210> SEQ ID NO 68
<211> LENGTH: 377
<212> TYPE: PRT
<213> ORGANISM: Homo sapiens
<220> FEATURE:
<223> OTHER INFORMATION: Human alpha-SMA protein

<400> SEQUENCE: 68

Met Cys Glu Glu Glu Asp Ser Thr Ala Leu Val Cys Asp Asn Gly Ser
  1               5                  10                  15

Gly Leu Cys Lys Ala Gly Phe Ala Gly Asp Asp Ala Pro Arg Ala Val
             20                  25                  30

Phe Pro Ser Ile Val Gly Arg Pro Arg His Gln Gly Val Met Val Gly
         35                  40                  45

Met Gly Gln Lys Asp Ser Tyr Val Gly Asp Glu Ala Gln Ser Lys Arg
     50                  55                  60

Gly Ile Leu Thr Leu Lys Tyr Pro Ile Glu His Gly Ile Ile Thr Asn
 65                  70                  75                  80

Trp Asp Asp Met Glu Lys Ile Trp His His Ser Phe Tyr Asn Glu Leu
                 85                  90                  95

Arg Val Ala Pro Glu Glu His Pro Thr Leu Leu Thr Glu Ala Pro Leu
            100                 105                 110

Asn Pro Lys Ala Asn Arg Glu Lys Met Thr Gln Ile Met Phe Glu Thr
        115                 120                 125

Phe Asn Val Pro Ala Met Tyr Val Ala Ile Gln Ala Val Leu Ser Leu
    130                 135                 140

Tyr Ala Ser Gly Arg Thr Thr Gly Ile Val Leu Asp Ser Gly Asp Gly
145                 150                 155                 160

Val Thr His Asn Val Pro Ile Tyr Glu Gly Tyr Ala Leu Pro His Ala
                165                 170                 175

Ile Met Arg Leu Asp Leu Ala Gly Arg Asp Leu Thr Asp Tyr Leu Met
            180                 185                 190

Lys Ile Leu Thr Glu Arg Gly Tyr Ser Phe Val Thr Thr Ala Glu Arg
        195                 200                 205

Glu Ile Val Arg Asp Ile Lys Glu Lys Leu Cys Tyr Val Ala Leu Asp
    210                 215                 220
```

-continued

```
Phe Glu Asn Glu Met Ala Thr Ala Ser Ser Ser Leu Glu Lys
225                 230                 235                 240

Ser Tyr Glu Leu Pro Asp Gly Gln Val Ile Thr Ile Gly Asn Glu Arg
            245                 250                 255

Phe Arg Cys Pro Glu Thr Leu Phe Gln Pro Ser Phe Ile Gly Met Glu
            260                 265                 270

Ser Ala Gly Ile His Glu Thr Thr Tyr Asn Ser Ile Met Lys Cys Asp
            275                 280                 285

Ile Asp Ile Arg Lys Asp Leu Tyr Ala Asn Asn Val Leu Ser Gly Gly
290                 295                 300

Thr Thr Met Tyr Pro Gly Ile Ala Asp Arg Met Gln Lys Glu Ile Thr
305                 310                 315                 320

Ala Leu Ala Pro Ser Thr Met Lys Ile Lys Ile Ile Ala Pro Pro Glu
            325                 330                 335

Arg Lys Tyr Ser Val Trp Ile Gly Gly Ser Ile Leu Ala Ser Leu Ser
            340                 345                 350

Thr Phe Gln Gln Met Trp Ile Ser Lys Gln Glu Tyr Asp Glu Ala Gly
            355                 360                 365

Pro Ser Ile Val His Arg Lys Cys Phe
370                 375

<210> SEQ ID NO 69
<211> LENGTH: 986
<212> TYPE: PRT
<213> ORGANISM: Homo sapiens
<220> FEATURE:
<223> OTHER INFORMATION: Human MYOCD protein

<400> SEQUENCE: 69

Met Thr Leu Leu Gly Ser Glu His Ser Leu Leu Ile Arg Ser Lys Phe
1               5                   10                  15

Arg Ser Val Leu Gln Leu Arg Leu Gln Gln Arg Arg Thr Gln Glu Gln
            20                  25                  30

Leu Ala Asn Gln Gly Ile Ile Pro Pro Leu Lys Arg Pro Ala Glu Phe
            35                  40                  45

His Glu Gln Arg Lys His Leu Asp Ser Asp Lys Ala Lys Asn Ser Leu
        50                  55                  60

Lys Arg Lys Ala Arg Asn Arg Cys Asn Ser Ala Asp Leu Val Asn Met
65                  70                  75                  80

His Ile Leu Gln Ala Ser Thr Ala Glu Arg Ser Ile Pro Thr Ala Gln
            85                  90                  95

Met Lys Leu Lys Arg Ala Arg Leu Ala Asp Asp Leu Asn Glu Lys Ile
            100                 105                 110

Ala Leu Arg Pro Gly Pro Leu Glu Leu Val Glu Lys Asn Ile Leu Pro
            115                 120                 125

Val Asp Ser Ala Val Lys Glu Ala Ile Lys Gly Asn Gln Val Ser Phe
130                 135                 140

Ser Lys Ser Thr Asp Ala Phe Ala Phe Glu Glu Asp Ser Ser Ser Asp
145                 150                 155                 160

Gly Leu Ser Pro Asp Gln Thr Arg Ser Glu Asp Pro Gln Asn Ser Ala
            165                 170                 175

Gly Ser Pro Pro Asp Ala Lys Ala Ser Asp Thr Pro Ser Thr Gly Ser
            180                 185                 190

Leu Gly Thr Asn Gln Asp Leu Ala Ser Gly Ser Glu Asn Asp Arg Asn
            195                 200                 205
```

```
Asp Ser Ala Ser Gln Pro Ser His Gln Ser Asp Ala Gly Lys Gln Gly
    210                 215                 220
Leu Gly Pro Pro Ser Thr Pro Ile Ala Val His Ala Ala Val Lys Ser
225                 230                 235                 240
Lys Ser Leu Gly Asp Ser Lys Asn Arg His Lys Lys Pro Lys Asp Pro
                245                 250                 255
Lys Pro Lys Val Lys Lys Leu Lys Tyr His Gln Tyr Ile Pro Pro Asp
            260                 265                 270
Gln Lys Ala Glu Lys Ser Pro Pro Met Asp Ser Ala Tyr Ala Arg
        275                 280                 285
Leu Leu Gln Gln Gln Leu Phe Leu Gln Leu Gln Ile Leu Ser Gln
    290                 295                 300
Gln Gln Gln Gln Gln Gln His Arg Phe Ser Tyr Leu Gly Met His Gln
305                 310                 315                 320
Ala Gln Leu Lys Glu Pro Asn Glu Gln Met Val Arg Asn Pro Asn Ser
                325                 330                 335
Ser Ser Thr Pro Leu Ser Asn Thr Pro Leu Ser Pro Val Lys Asn Ser
                340                 345                 350
Phe Ser Gly Gln Thr Gly Val Ser Ser Phe Lys Pro Gly Pro Leu Pro
            355                 360                 365
Pro Asn Leu Asp Asp Leu Lys Val Ser Glu Leu Arg Gln Gln Leu Arg
    370                 375                 380
Ile Arg Gly Leu Pro Val Ser Gly Thr Lys Thr Ala Leu Met Asp Arg
385                 390                 395                 400
Leu Arg Pro Phe Gln Asp Cys Ser Gly Asn Pro Val Pro Asn Phe Gly
                405                 410                 415
Asp Ile Thr Thr Val Thr Phe Pro Val Thr Pro Asn Thr Leu Pro Asn
                420                 425                 430
Tyr Gln Ser Ser Ser Ser Thr Ser Ala Leu Ser Asn Gly Phe Tyr His
            435                 440                 445
Phe Gly Ser Thr Ser Ser Ser Pro Pro Ile Ser Pro Ala Ser Ser Asp
    450                 455                 460
Leu Ser Val Ala Gly Ser Leu Pro Asp Thr Phe Asn Asp Ala Ser Pro
465                 470                 475                 480
Ser Phe Gly Leu His Pro Ser Pro Val His Val Cys Thr Glu Glu Ser
                485                 490                 495
Leu Met Ser Ser Leu Asn Gly Gly Ser Val Pro Ser Glu Leu Asp Gly
                500                 505                 510
Leu Asp Ser Glu Lys Asp Lys Met Leu Val Glu Lys Gln Lys Val Ile
            515                 520                 525
Asn Glu Leu Thr Trp Lys Leu Gln Gln Glu Gln Arg Gln Val Glu Glu
    530                 535                 540
Leu Arg Met Gln Leu Gln Lys Gln Lys Arg Asn Asn Cys Ser Glu Lys
545                 550                 555                 560
Lys Pro Leu Pro Phe Leu Ala Ala Ser Ile Lys Gln Glu Glu Ala Val
                565                 570                 575
Ser Ser Cys Pro Phe Ala Ser Gln Val Pro Val Lys Arg Gln Ser Ser
                580                 585                 590
Ser Ser Glu Cys His Pro Pro Ala Cys Glu Ala Ala Gln Leu Gln Pro
            595                 600                 605
Leu Gly Asn Ala His Cys Val Glu Ser Ser Asp Gln Thr Asn Val Leu
    610                 615                 620
```

-continued

Ser Ser Thr Phe Leu Ser Pro Gln Cys Ser Pro Gln His Ser Pro Leu
625                 630                 635                 640

Gly Ala Val Lys Ser Pro Gln His Ile Ser Leu Pro Pro Ser Pro Asn
            645                 650                 655

Asn Pro His Phe Leu Pro Ser Ser Ser Gly Ala Gln Gly Glu Gly His
        660                 665                 670

Arg Val Ser Ser Pro Ile Ser Ser Gln Val Cys Thr Ala Gln Asn Ser
    675                 680                 685

Gly Ala His Asp Gly His Pro Pro Ser Phe Ser Pro His Ser Ser Ser
690                 695                 700

Leu His Pro Pro Phe Ser Gly Ala Gln Ala Asp Ser Ser His Gly Ala
705                 710                 715                 720

Gly Gly Asn Pro Cys Pro Lys Ser Pro Cys Val Gln Gln Lys Met Ala
            725                 730                 735

Gly Leu His Ser Ser Asp Lys Val Gly Pro Lys Phe Ser Ile Pro Ser
        740                 745                 750

Pro Thr Phe Ser Lys Ser Ser Ala Ile Ser Glu Val Thr Gln Pro
    755                 760                 765

Pro Ser Tyr Glu Asp Ala Val Lys Gln Gln Met Thr Arg Ser Gln Gln
770                 775                 780

Met Asp Glu Leu Leu Asp Val Leu Ile Glu Ser Gly Glu Met Pro Ala
785                 790                 795                 800

Asp Ala Arg Glu Asp His Ser Cys Leu Gln Lys Val Pro Lys Ile Pro
            805                 810                 815

Arg Ser Ser Arg Ser Pro Thr Ala Val Leu Thr Lys Pro Ser Ala Ser
        820                 825                 830

Phe Glu Gln Ala Ser Ser Gly Ser Gln Ile Pro Phe Asp Pro Tyr Ala
    835                 840                 845

Thr Asp Ser Asp Glu His Leu Glu Val Leu Leu Asn Ser Gln Ser Pro
850                 855                 860

Leu Gly Lys Met Ser Asp Val Thr Leu Leu Lys Ile Gly Ser Glu Glu
865                 870                 875                 880

Pro His Phe Asp Gly Ile Met Asp Gly Phe Ser Gly Lys Ala Ala Glu
            885                 890                 895

Asp Leu Phe Asn Ala His Glu Ile Leu Pro Gly Pro Leu Ser Pro Met
        900                 905                 910

Gln Thr Gln Phe Ser Pro Ser Ser Val Asp Ser Asn Gly Leu Gln Leu
    915                 920                 925

Ser Phe Thr Glu Ser Pro Trp Glu Thr Met Glu Trp Leu Asp Leu Thr
930                 935                 940

Pro Pro Asn Ser Thr Pro Gly Phe Ser Ala Leu Thr Thr Ser Ser Pro
945                 950                 955                 960

Ser Ile Phe Asn Ile Asp Phe Leu Asp Val Thr Asp Leu Asn Leu Asn
            965                 970                 975

Ser Ser Met Asp Leu His Leu Gln Gln Trp
        980                 985

<210> SEQ ID NO 70
<211> LENGTH: 1798
<212> TYPE: DNA
<213> ORGANISM: Homo sapiens
<220> FEATURE:
<223> OTHER INFORMATION: Human alpha-SMA mRNA

<400> SEQUENCE: 70

| | |
|---|---|
| ctctccccgc ccccgcgggg cggcgcgcac tcacccaccc gcgccggagc ggacctttgg | 60 |
| cttggcttgt cagggcttgt ccaggagttc cgctcctctc tccaaccggg gtcccctcc | 120 |
| agcgacccta aagcttccca gacttccgct tcaattcctg tccgcacccc acgcccacct | 180 |
| caacgtggag cgcagtggtc tccgaggagc gccggagctg ccccgcctgc ccagcggggt | 240 |
| cagcacttcg catcaaggcc caagaaaagc aagtcctcca gcgttctgag cacccgggcc | 300 |
| tgagggaagg tcctaacagc cccggggagc cagtctccaa cgcctcccgc agcagcccgc | 360 |
| cgctcccagg tgcccgcgtg cgccgctgcc gccgcaatcc cgcacgcgtc ccgcgcccgc | 420 |
| cccactttgc ctatccccgg gactaagacg ggaatcctgt gaagcagctc cagctatgtg | 480 |
| tgaagaagag gacagcactg ccttggtgtg tgacaatggc tctgggctct gtaaggccgg | 540 |
| ctttgctggg gacgatgctc ccagggctgt tttcccatcc attgtgggac gtcccagaca | 600 |
| tcaggggtg atggtgggaa tgggacaaaa agacagctac gtgggtgacg aagcacagag | 660 |
| caaaagagga atcctgaccc tgaagtaccc gatagaacat ggcatcatca ccaactggga | 720 |
| cgacatggaa aagatctggc accactcttt ctacaatgag cttcgtgttg cccctgaaga | 780 |
| gcatcccacc ctgctcacgg aggcacccct gaaccccaag gccaaccggg agaaaatgac | 840 |
| tcaaattatg tttgagactt tcaatgtccc agccatgtat gtggctatcc aggcggtgct | 900 |
| gtctctctat gcctctggac gcacaactgg catcgtgctg gactctggag atggtgtcac | 960 |
| ccacaatgtc cccatctatg agggctatgc cttgccccat gccatcatgc gtctggatct | 1020 |
| ggctggccga gatctcactg actacctcat gaagatcctg actgagcgtg gctattcctt | 1080 |
| cgttactact gctgagcgtg agattgtccg ggacatcaag gagaaactgt gttatgtagc | 1140 |
| tctggacttt gaaaatgaga tggccactgc cgcatcctca tcctcccttg agaagagtta | 1200 |
| cgagttgcct gatgggcaag tgatcaccat cggaaatgaa cgtttccgct gcccagagac | 1260 |
| cctgttccag ccatccttca tcgggatgga gtctgctggc atccatgaaa ccacctacaa | 1320 |
| cagcatcatg aagtgtgata ttgacatcag gaaggacctc tatgctaaca atgtcctatc | 1380 |
| aggggggcacc actatgtacc ctggcattgc cgaccgaatg cagaaggaga tcacggccct | 1440 |
| agcacccagc accatgaaga tcaagatcat tgccccctcg gagcgcaaat actctgtctg | 1500 |
| gatcggtggc tccatcctgg cctctctgtc caccttccag cagatgtgga tcagcaaaca | 1560 |
| ggaatacgat gaagccgggc cttccattgt ccaccgcaaa tgcttctaaa acactttcct | 1620 |
| gctcctctct gtctctagca cacaactgtg aatgtcctgt ggaattatgc cttcagttct | 1680 |
| tttccaaatc attcctagcc aaagctctga ctcgttacct atgtgttttt taataaatct | 1740 |
| gaaataggct actggtaaaa aaaaaaaaaa aaaaaaaaa aaaaaaaaa aaaaaaaa | 1798 |

<210> SEQ ID NO 71
<211> LENGTH: 8580
<212> TYPE: DNA
<213> ORGANISM: Homo sapiens
<220> FEATURE:
<223> OTHER INFORMATION: Human MYOCD mRNA

<400> SEQUENCE: 71

| | |
|---|---|
| aatcgccggc agcctatgac atcagacagg aacgcctggg atgccgcgct gctcctggcc | 60 |
| aacctccgag gaggaggagg gtcccgccgg ctaagagtta attagccccg cacggcgagg | 120 |
| gggaggcgc cagttttctg gggacactgg ctgccactgt actcctaccc aggggagctc | 180 |
| acggagagtt ggatgaattc tgggttgtta gctgcggtca gctgggctcc cgggagcctg | 240 |
| ttgctggtgg agaacagggg gcgcctggcc aagggaccag cggcttgctg agactcaaca | 300 |

```
tgacactcct ggggtctgag cattccttgc tgattaggag caagttcaga tcagttttac      360
agttaagact tcaacaaaga aggacccagg aacaactggc taaccaaggc ataataccac      420
cactgaaacg tccagctgaa ttccatgagc aaagaaaaca tttggatagt gacaaggcta      480
aaaattccct gaagcgcaaa gccagaaaca ggtgcaacag tgccgacttg gttaatatgc      540
acatactcca agcttccact gcagagaggt ccattccaac tgctcagatg aagctgaaaa      600
gagcccgact cgccgatgat ctcaatgaaa aaattgctct acgaccaggg ccactggagc      660
tggtggaaaa aaacattctt cctgtggatt ctgctgtgaa agaggccata aaaggtaacc      720
aggtgagttt ctccaaatcc acggatgctt ttgcctttga agaggacagc agcagcgatg      780
ggctttctcc ggatcagact cgaagtgaag accccaaaa ctcagcggga tccccgccag      840
acgctaaagc ctcagatacc ccttcgacag gttctctggg gacaaaccag gatcttgctt      900
ctggctcaga aaatgacaga atgactcag cctcacagcc cagccaccag tcagatgcgg      960
ggaagcaggg gcttggcccc ccagcaccc ccatagccgt gcatgctgct gtaaagtcca     1020
aatccttggg tgacagtaag aaccgccaca aaaagcccaa ggaccccaag ccaaaggtga     1080
agaagcttaa atatcaccag tacattcccc cagaccagaa ggcagagaag tcccctccac     1140
ctatggactc agcctacgct cggctgctcc agcaacagca gctgttcctg cagctccaaa     1200
tcctcagcca gcagcagcag cagcagcaac accgattcag ctacctaggg atgcaccaag     1260
ctcagcttaa ggaaccaaat gaacagatgg tcagaaatcc aaactcttct tcaacgccac     1320
tgagcaatac ccccttgtct cctgtcaaaa acagttttc tggacaaact ggtgtctctt     1380 cttcaaacc aggcccactc ccacctaacc tggatgatct gaaggtctct gaattaagac     1440
aacagcttcg aattcggggc ttgcctgtgt caggcaccaa aacggctctc atggaccggc     1500
ttcgacccct ccaggactgc tctggcaacc cagtgccgaa ctttggggat ataacgactg     1560
tcacttttcc tgtcacaccc aacacgctgc ccaattacca gtcttcctct tctaccagtg     1620
ccctgtccaa cggcttctac cactttggca gcaccagctc cagcccccg atctccccag     1680 cctcctctga cctgtcagtc gctgggtccc tgccggacac cttcaatgat gcctccccct     1740
ccttcggcct gcacccgtcc ccagtccacg tgtgcacgga ggaaagtctc atgagcagcc     1800
tgaatggggg ctctgttcct tctgagctga tgggctgga ctccgagaag gacaagatgc     1860
tggtggagaa gcagaaggtg atcaatgaac tcacctggaa actccagcaa gagcagaggc     1920
aggtggagga gctgaggatg cagcttcaga agcagaaaag gaataactgt tcagagaaga     1980
agccgctgcc tttcctggct gcctccatca agcaggaaga ggctgtctcc agctgtcctt     2040
ttgcatccca agtacctgtg aaaagacaaa gcagcagctc agagtgtcac ccaccggctt     2100
gtgaagctgc tcaactccag cctcttggaa atgctcattg tgtggagtcc tcagatcaaa     2160
ccaatgtact ttcttccaca tttctcagcc cccagtgttc ccctcagcat tcaccgctgg     2220
gggctgtgaa aagcccacag cacatcagtt tgccccatc acccaacaac cctcactttc     2280
tgccctcatc ctccggggcc cagggagaag ggcacagggt ctcctcgccc atcagcagcc     2340
aggtgtgcac tgcacagaac tcaggagcac acgatggcca tcctccaagc ttctctcccc     2400
attcttccag cctccacccg cccttctctg gagcccaagc agacagcagt catggtgccg     2460
ggggaaaccc ttgtcccaaa agcccatgtg tacagcaaaa gatggctggt ttacactctt     2520
ctgataaggt ggggccaaag ttttcaattc catcccaac ttttttctaag tcaagttcag     2580 caatttcaga ggtaacacag cctccatcct atgaagatgc cgtaaagcag caaatgaccc     2640
```

```
ggagtcagca gatggatgaa ctcctggacg tgcttattga aagcggagaa atgccagcag    2700
acgctagaga ggatcactca tgtcttcaaa aagtcccaaa gatacccaga tcttcccgaa    2760
gtccaactgc tgtcctcacc aagccctcgg cttcctttga acaagcctct tcaggcagcc    2820
agatcccctt tgatccctat gccaccgaca gtgatgagca tcttgaagtc ttattaaatt    2880
cccagagccc cctaggaaag atgagtgatg tcacccttct aaaaattggg agcgaagagc    2940
ctcactttga tgggataatg gatggattct ctgggaaggc tgcagaagac ctcttcaatg    3000
cacatgagat cttgccaggc cccctctctc caatgcagac acagttttca ccctcttctg    3060
tggacagcaa tgggctgcag ttaagcttca ctgaatctcc ctgggaaacc atggagtggc    3120
tggacctcac tccgccaaat tccacaccag gctttagcgc cctcaccacc agcagcccca    3180
gcatcttcaa catcgatttc ctggatgtca ctgatctcaa tttgaattct tccatggacc    3240
ttcacttgca gcagtggtag aatgcccaat gcaccagtgc tatggaagac caatggagtt    3300
ccatggggga aagcacacag ccatacatac tttactgtcc aaaaacagaa gaagaagaag    3360
agaattaaaa agaagcaatg atttctgtgc caatgaacaa gaacaaaagt cattttaga    3420 aatacatata ctgtaatatt taccaacagt cagtaactgt taatgatttc aacaatgcat    3480
taaaagaatg tgctttctca gattaaggat gccaaaaaag atatttcact gccttttcaa    3540
agaccagtat attttctagc ccataatttt tctcaggcat tgttggggca taagctcaca    3600
ctgtaagctt ttctcatgaa ttcactagac ataacgtgga aggaaaacgt agtcttttgg    3660
gagtacaggg aagccagccc ctcaaagctt atggaagaca tacctgcaat ggaagctgtt    3720
gcccaatgtc tccattacta tctttcaaaa gagaagccag acccagcttc agatcaaaag    3780
ttcttgagac agaggaacaa aaccaatcga tttccaggga agctaatcaa ctctcttttc    3840
cctctaccac aaaactgccc tgctggagtg gttctgaacc tgtacccagg actcgatgtg    3900
gtcactaata acaattaacc tgaactgagt ccacagaact ccactcggaa cttcttctt    3960 ttttaactag tggcccaatc attcccacca tctctgtgct gataagtacg tgtcctagat    4020
gagaaccctg aagaatgcag accttcttcc cccgaaggag atgccacaag ctctccaaca    4080
cagccccctt tagttccaaa gactagagat gaccacattg gtagaagtat atctcgaggc    4140
acaggaaggg agccccacca gggataattc agacaggact agagaataac atcatttcac    4200
ataccctggg ataaacaccc tgggttccta tagaaggact attacttatg ggagtccaac    4260
ttctcctttt gttttgttat tatcagttta tctttctccc actccacttt tccttcaagg    4320
taccaatcct ttcctgttcc tcgtttggcc atctttcttt ttctgcctcc acattgggag    4380
gggaggactt ctcagttcta acaagctgcc atactcctaa gaaagccatt tttgaaaaat    4440
ttaacaatcc aggttcttct ggagaactca ttctccacac gcacagtttg ctgcaaaagg    4500
aagttgcaag aatttcttga ggaagaaact ggtgacttgg tccatcagtc acgaagttct    4560
ttctattctc gtttagtttt caagaaatta ttggtttgtg ttgctctggg gaaattggaa    4620
atcattacat tgtaaagaca aatatggatg atatttacaa gagagaattt cagatctggg    4680
tttttgaaag aaaacagaat tgcgcattga aaacgatgga aggaaaaaga caatggtcta    4740
atgtgcattc ctcattacct ctcgtggctt tggctgggag ttggaaaaag ctaaaatttc    4800
agaacagtct ctgtaaggct ctctgtggct ccagttcacc attttatatt gttgcatgct    4860
gtagaaagga gctattgctg ttgttttgtt tttttattta aatcactaag gcactgtttt    4920 tatctttttgt aaaaaaaaaa aaaagttgt tcactgtgca cttatagaaa aataataaa    4980 aaatgttggg attttagaag ctctctttttt gataaaccaa agatttagaa gtcattccat    5040
```

```
tgttaacttg taaaaatgtg tgaacacaga gagttttggg tgattgctac tctgaaagct   5100
gccagatctt attctggggg tgggatgtgg aggaatacac atacacacac aaacatacat   5160
gtatgtataa tagatatata catatgtgta tattatatct gtgtgtgcat gtatctccaa   5220
aagcggcgtt acagagttct acaccaaaag cctttaaccc ttaatctgct gtgaatgata   5280
cctggccttt ctcactatga atttctgatt aaccaaccag actacacgtt gcctctctgt   5340
gtatgactaa cggctccaac ccgatgactc acagctactt gcttatcgtg aacaagctca   5400
tcttggcaat gaatatggat gtgaaaagac agaacagctt caccattagt agctggaaat   5460
ggtatcacag tctcttatag aggaatatga aggaacaag aaaatcattt acattcctt    5520
ttatctgtat tgtgctttaa aagatccaca tggtaaattt tttattttgc ttttatgtca   5580
gtcatcagaa ccaaaaaaat ccagaagaaa aaattgccag tgtttccttt gaagatgaag   5640
ctactgggga agaaaacctt attaatacac tccacacatt tgttcattcc tcagctgttg   5700
gtgtttcttt ggggtcttga caaagcttgc tggtcagtgc acttttcagg tgtcacgttt   5760
tgctgtttgt atgttttttc ttccccttac ttcctttgga aaacaaactc acacagtgcc   5820
cctactctga gacctgggac tgagtgttaa ttatttttc cttgggtatt tctatctgag    5880
agactagacc tagttaggag gcctctgtac ttctccagat tgtaccttt tatggggatc    5940
tttgaggcta tgacccagga ctgatagata tgccttacgg aagacaaaag ataaaatggt   6000
tcctatatcc taatgcaaac caacacagtt aaaagagcag atctctggat aactgctctc   6060
aacctgcttc tacagtctcc acaaaccgca ttcaccctct ctcttcatag ctcagacatg   6120
aaatttgagg gagaaaactg gagataattg ggagaaaatt gatgaagttg gctgcttcca   6180
gtagatcaga taatccatga atttgtctcc cattgagaat tttatttaa attcttttaa    6240
actcttcgtt gtgtcttttg tgatgacaaa tcaggcatga ctaaagatg tacagagact     6300
tacgaagatg gtcacattca agttccctaa tgctcttaga acctgaagat gaccatgtgt   6360
agttttctta agacctctga accccatgg tgatgaagac ttgaagacat ttgcagctat     6420
ctgctgcagt ctggtagatt catacttatc taaagaagtc aaaaaattta ttcgtgcaag   6480
tgcttgcagg aagccagtgc ttattagtag tgaccctgct tctatcaacg ttattgagac   6540
aacacatatt ctattctaag ggagaaagag ggaggaagag agggagggag ggaggaagaa   6600
gagggaggga gcgaggaagg aagataggag atgggtaggg gggtaaagag aaaaggaggg   6660
agaagggaag gaaggaaaga agagaggaaa gaaaggaggg aaggaaaaaa gggccaaact   6720
ttctgatcta tgaacttctc agttcagctg tcacattatg agaagtaaat cagaattttt   6780
ttaaggagaa gtcattctta gcactacaat aattgtacca gtaattgagg aaaccaagac   6840
aatcttcacc tgaataatag agggtctgag aactgtcagc cttttgccat tcaaaaacat   6900
ttatgtccaa cctgaaaaaa aagcatcaat aaaacctatc ccaagcattc aaaatagtcc   6960
tttccaaatg ttatttattt taaagtcaat cagctcttt agaaacagat tctggtctgg     7020
ctgaaaactc ccacaacaaa tttactcatc cagtggctaa tatttaatgc ccaccatggg   7080
cagagcacac aaatcttcag ataaacaata ctgaattgat tcagcacaga ttgttcagat   7140
ttgaatgacc agggagttgt atttgcacat gcaagaacac taagaatctc ccagtcctca   7200
aactagaaac ctttcagcta cgatgaaaaa aaaaagggg tcttcatttt tccaagaggg    7260
ggtggaggtg gggatcactt tttagctaaa agctatctct cacttcaaaa ttcttgtctt   7320
tttctttgtg gacaaacacc agtagtctat cacttggaga tctttaata tctcccatca   7380
```

-continued

```
tttaaaaacat ccacgagagt ttgaagattt tgtgttgattg ccagatacag aagccccttg    7440
aaaataagga aagggtggag gaagcatttt tgtgtcctat ccctacttat cgtagcagct     7500
ctatagacaa aagggacact tactggtgag cctctggccc ttaaaagaaa atcatctaag     7560
aatatgaagg caatttgatt tcccccaca gccctcagct gccttcctca cagaaggaag      7620
ttcccaaaat tgctggtaca cagtttgcaa tcaaatatca gatatgagaa aacctgtagt     7680
gaagagtctg ggttcttggt tttctcataa atccaatata aatttgtagg ttggttcagg     7740
gtcaaaattg ccagtgcttt attagacaga tgatactgat agacacacag agcccaggtc    7800
ctggaacaag acaatcctgt agtgccaaga tctggtcagt tgcgttaagg agctgggttt     7860
gattctagag tccaggttta tagagaaacc ctggctagat tgagcctacc catggggaga    7920
cgatttcaag acaggatgag atctgggaag aattttgttg tcatctgcca gggaaattat    7980
cacaggactc attgaatgca ataacatgtg agtaagttcc cttttgattc tgggaatcag    8040 cgatttccc tgtggattaa gacaaaccaa cgccagaagg tctcctgtgc ttattttaac     8100
catctgctcc catcgtgaac cctggagcat gcatttccta gaagtggttt catagctcct    8160
gtgtgttcat ggaaaagggg agtataatga tggggatgct ggaagctttt ttaatgtttt    8220
ccaaaggaaa ggaacccaca ctgctccccca gagttccttt ccaatggccc tgcagtaaga   8280
acggaggaca atgtattgct gggtgcttaa aatcctccct cagtgaagca caaagagaca    8340 cttttgtaaag aaaaaaagag caagcatagg ttctctgtgg gaccttgtgg agtggtgttt   8400
tcacgttggt ctctttggct caattgagca taatcagaaa gaaatgtggg ttattgggaa    8460
gagacaaaaa gcagtggcta aaataccaaa gttggcatgt gttcttttt aaaaaaaaaa     8520 aaaaatgcat atattttaa ataaaatgtt tattttaaaa agaaaaaaaa aaaaaaaaa      8580
```

<210> SEQ ID NO 72
<211> LENGTH: 524
<212> TYPE: PRT
<213> ORGANISM: Homo sapiens
<220> FEATURE:
<223> OTHER INFORMATION: Human BSAP protein

<400> SEQUENCE: 72

```
Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160
```

Val Gly Ile Val Thr Thr Thr Arg Val Asn His Ala Thr Pro Ser Ala
            165                 170                 175

Ala Tyr Ala His Ser Ala Asp Arg Asp Trp Tyr Ser Asp Asn Glu Met
        180                 185                 190

Pro Pro Glu Ala Leu Ser Gln Gly Cys Lys Asp Ile Ala Tyr Gln Leu
    195                 200                 205

Met His Asn Ile Arg Asp Ile Asp Val Ile Met Gly Gly Gly Arg Lys
210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270

Thr Glu Leu Leu Thr Leu Asp Pro His Asn Val Asp Tyr Leu Leu Gly
        275                 280                 285

Leu Phe Glu Pro Gly Asp Met Gln Tyr Glu Leu Asn Arg Asn Asn Val
    290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
        355                 360                 365

Glu Asp Thr Leu Thr Val Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ser Lys
    450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
            500                 505                 510

Leu Ala Leu Ala Leu Tyr Pro Leu Ser Val Leu Phe
    515                 520

<210> SEQ ID NO 73
<211> LENGTH: 2606
<212> TYPE: DNA
<213> ORGANISM: Homo sapiens
<220> FEATURE:
<223> OTHER INFORMATION: Human BSAP mRNA

<400> SEQUENCE: 73

```
ccgggcctca ctcgggcccc gcggccgcct ttataaggcg gcggggtgg tggcccgggc      60
cgcgttgcgc tcccgccact ccgcgcccgc tatcctggct ccgtgctccc acgcgcttgt     120
gcctggacgg accctcgcca gtgctctgcg caggattgga acatcagtta acatctgacc    180
actgccagcc caccccctcc cacccacgtc gattgcatct ctgggctcca gggataaagc    240
aggtcttggg gtgcaccatg atttcaccat tcttagtact ggccattggc acctgcctta    300
ctaactcctt agtgccagag aaagagaaag accccaagta ctggcgagac caagcgcaag    360
agacactgaa atatgccctg gagcttcaga agctcaacac caacgtggct aagaatgtca    420
tcatgttcct gggagatggg atgggtgtct ccacagtgac ggctgcccgc atcctcaagg    480
gtcagctcca ccacaaccct ggggaggaga ccaggctgga gatggacaag ttccccttcg    540
tggccctctc caagacgtac aacaccaatg cccaggtccc tgacagcgcc ggcaccgcca    600
ccgcctacct gtgtgggggtg aaggccaatg agggcaccgt gggggtaagc gcagccactg    660
agcgttcccg gtgcaacacc acccagggga acgaggtcac ctccatcctg cgctgggcca    720
aggacgctgg gaaatctgtg ggcattgtga ccaccacgag agtgaaccat gccaccccca    780
gcgccgccta cgcccactcg gctgaccggg actggtactc agacaacgag atgcccctg    840
aggccttgag ccagggctgt aaggacatcg cctaccagct catgcataac atcagggaca    900
ttgacgtgat catgggggt ggccggaaat acatgtaccc caagaataaa actgatgtgg    960
agtatgagag tgacgagaaa gccaggggca cgaggctgga cggcctggac ctcgttgaca   1020
cctggaagag cttcaaaccg agatacaagc actcccactt catctggaac cgcacggaac   1080
tcctgacct tgaccccac aatgtggact acctattggg tctcttcgag ccaggggaca   1140
tgcagtacga gctgaacagg aacaacgtga cggacccgtc actctccgag atggtggtgg   1200
tggccatcca gatcctgcgg aagaacccca aaggcttctt cttgctggtg aaggaggca   1260
gaattgacca cgggcaccat gaaggaaaag ccaagcaggc cctgcatgag gcggtggaga   1320
tggaccgggc catcgggcag gcaggcagct tgacctcctc ggaagacact ctgaccgtgg   1380
tcactgcgga ccattcccac gtcttcacat ttggtggata cacccccgt ggcaactcta   1440
tctttggtct ggccccatg ctgagtgaca cagacaagaa gccttcact gccatcctgt   1500
atggcaatgg gcctggctac aaggtggtgg gcggtgaacg agagaatgtc tccatggtgg   1560
actatgctca caacaactac caggcgcagt ctgctgtgcc cctgcgccac gagacccacg   1620
gcggggagga cgtggccgtc ttctccaagg gccccatggc gcacctgctg cacggcgtcc   1680
acgagcagaa ctacgtcccc cacgtgatgg cgtatgcagc ctgcatcggg ccaacctcg   1740
gccactgtgc tcctgccagc tcggcaggca gccttgctgc aggcccctg ctgctcgcgc   1800
tggccctcta ccccctgagc gtcctgttct gagggcccag ggcccgggca ccacaagcc   1860
cgtgacagat gccaacttcc cacacggcag ccccccctc aaggggcagg gaggtggggg   1920
cctcctcagc ctctgcaact gcaagaaagg ggacccaaga aaccaaagtc tgccgcccac   1980
ctcgctcccc tctggaatct tccccaaggg ccaaacccac ttctggcctc cagcctttgc   2040
tccctccccg ctgcccttg gccaacaggg tagatttctc ttgggcaggc agagagtaca   2100
gactgcagac attctcaaag cctcttattt ttctagcgaa cgtatttctc cagacccaga   2160
ggccctgaag cctccgtgga acattctgga tctgacccctc ccagtctcat ctcctgaccc   2220
tcccactccc atctccttac ctctggaacc cccaggccc tacaatgctc atgtccctgt   2280
ccccaggccc agccctcctt caggggagtt gaggtctttc tcctcaggac aaggccttgc   2340
```

| | |
|---|---|
| tcactcactc actccaagac caccagggtc ccaggaagcc ggtgcctggg tggccatcct | 2400 |
| acccagcgtg gcccaggccg ggaagagcca cctggcaggg ctcacactcc tgggctctga | 2460 |
| acacacacgc cagctcctct ctgaagcgac tctcctgttt ggaacggcaa aaaaaaattt | 2520 |
| tttttctct ttttggtggt ggttaaaagg gaacacaaaa catttaaata aaactttcca | 2580 |
| aatatttccg aggacaaaaa aaaaaa | 2606 |

<210> SEQ ID NO 74
<211> LENGTH: 1722
<212> TYPE: DNA
<213> ORGANISM: Artificial Sequence
<220> FEATURE:
<223> OTHER INFORMATION: Snai1 mRNA

<400> SEQUENCE: 74

| | |
|---|---|
| attcattgcg ccgcggcacg gcctagcgag tggttcttct gcgctactgc tgcgcgaatc | 60 |
| ggcgacccca gtgcctcgac cactatgccg cgctctttcc tcgtcaggaa gccctccgac | 120 |
| cccaatcgga agcctaacta cagcgagctg caggactcta atccagagtt taccttccag | 180 |
| cagccctacg accaggccca cctgctggca gccatcccac ctccggagat cctcaacccc | 240 |
| accgcctcgc tgccaatgct catctgggac tctgtcctgg cgcccaagc ccagccaatt | 300 |
| gcctgggcct cccttcggct ccaggagagt cccagggtgg cagagctgac ctccctgtca | 360 |
| gatgaggaca gtgggaaagg ctcccagccc ccagcccac cctcaccggc ccttcgtcc | 420 |
| ttctcctcta cttcagtctc ttccttggag gccgaggcct atgctgcctt cccaggcttg | 480 |
| ggccaagtgc ccaagcagct ggcccagctc tctgaggcca aggatctcca ggctcgaaag | 540 |
| gccttcaact gcaaatactg caacaaggaa tacctcagcc tgggtgccct caagatgcac | 600 |
| atccgaagcc acacgctgcc ctgcgtctgc ggaacctgcg gaaggccttt ctctaggccc | 660 |
| tggctgctac aaggccatgt ccggacccac actggcgaga agcccttctc ctgtccccac | 720 |
| tgcagccgtg cctttcgctga ccgctccaac ctgcgggccc acctccagac ccactcagat | 780 |
| gtcaagaagt accagtgcca ggcgtgtgct cggaccttct cccgaatgtc cctgctccac | 840 |
| aagcaccaag agtccggctg ctcaggatgt ccccgctgac cctcgaggct ccctcttcct | 900 |
| ctccatacct gcccctgcct gacagccttc cccagctcca gcaggaagga ccccacatcc | 960 |
| ttctcactgc catggaattc cctcctgagt gccccacttc tggccacatc agccccacag | 1020 |
| gactttgatg aagaccattt tctggttctg tgtcctctgc ctgggctctg gaagaggcct | 1080 |
| tcccatggcc atttctgtgg agggagggca gctggcccc agccctgggg gattcctgag | 1140 |
| ctggcctgtc tgcgtgggtt tttgtatcca gagctgtttg gatacagctg ctttgagcta | 1200 |
| caggacaaag gctgacagac tcactgggaa gctcccaccc cactcagggg accccactcc | 1260 |
| cctcacacac accccccac aaggaaccct caggccaccc tccacgaggt gtgactaact | 1320 |
| atgcaataat ccaccccag gtgcagcccc agggcctgcg gaggcggtgg cagactagag | 1380 |
| tctgagatgc cccgagccca ggcagctatt tcagcctcct gtttggtggg gtggcacctg | 1440 |
| tttcccgggc aatttaacaa tgtctgaaaa gggactgtga gtaatggctg tcacttgtcg | 1500 |
| ggggcccaag tggggtgctc tggtctgacc gatgtgtctc ccagaactat tctgggggcc | 1560 |
| cgacaggtgg gcctgggagg aagatgttta cattttaaa ggtacactgg tatttatatt | 1620 |
| tcaaacattt tgtatcaagg aaacgttttg tatagttata tgtacagttt attgatattc | 1680 |
| aataaagcag ttaatttata tattaaaaaa aaaaaaaaa aa | 1722 |

<210> SEQ ID NO 75
<211> LENGTH: 1815
<212> TYPE: DNA
<213> ORGANISM: Artificial Sequence
<220> FEATURE:
<223> OTHER INFORMATION: Dkk1 mRNA

<400> SEQUENCE: 75

| | | | | | |
|---|---|---|---|---|---|
| gcagagctct | gtgctccctg | cagtcaggac | tctgggaccg | caggggggctc | ccggaccctg | 60 |
| actctgcagc | cgaaccggca | cggtttcgtg | gggacccagg | cttgcaaagt | gacggtcatt | 120 |
| ttctctttct | ttctccctct | tgagtccttc | tgagatgatg | gctctgggcg | cagcgggagc | 180 |
| tacccgggtc | tttgtcgcga | tggtagcggc | ggctctcggc | ggccaccctc | tgctgggagt | 240 |
| gagcgccacc | ttgaactcgg | ttctcaattc | caacgctatc | aagaacctgc | ccccaccgct | 300 |
| gggcggcgct | gcggggcacc | caggctctgc | agtcagcgcc | gcgccgggaa | tcctgtaccc | 360 |
| gggcgggaat | aagtaccaga | ccattgacaa | ctaccagccg | tacccgtgcg | cagaggacga | 420 |
| ggagtgcggc | actgatgagt | actgcgctag | tcccacccgc | ggaggggacg | caggcgtgca | 480 |
| aatctgtctc | gcctgcagga | agcgccgaaa | acgctgcatg | cgtcacgcta | tgtgctgccc | 540 |
| cgggaattac | tgcaaaaatg | gaatatgtgt | gtcttctgat | caaaatcatt | ccgaggagaa | 600 |
| aattgaggaa | accatcactg | aaagctttgg | taatgatcat | agcaccttgg | atgggtattc | 660 |
| cagaagaacc | accttgtctt | caaaaatgta | tcacaccaaa | ggacaagaag | gttctgtttg | 720 |
| tctccggtca | tcagactgtg | cctcaggatt | gtgttgtgct | agacacttct | ggtccaagat | 780 |
| ctgtaaacct | gtcctgaaag | aaggtcaagt | gtgtaccaag | cataggagaa | aaggctctca | 840 |
| tggactagaa | atattccagc | gttgttactg | tggagaaggt | ctgtcttgcc | ggatacagaa | 900 |
| agatcaccat | caagccagta | attcttctag | gcttcacact | tgtcagagac | actaaaccag | 960 |
| ctatccaaat | gcagtgaact | ccttttatat | aatagatgct | atgaaaacct | tttatgacct | 1020 |
| tcatcaactc | aatcctaagg | atatacaagt | tctgtggttt | cagttaagca | ttccaataac | 1080 |
| accttccaaa | aacctggagt | gtaagagctt | tgtttcttta | tggaactccc | ctgtgattgc | 1140 |
| agtaaattac | tgtattgtaa | attctcagtg | tggcacttac | ctgtaaatgc | aatgaaactt | 1200 |
| ttaattattt | ttctaaaggt | gctgcactgc | ctatttttcc | tcttgttatg | taaatttttg | 1260 |
| tacacattga | ttgttatctt | gactgacaaa | tattctatat | tgaactgaag | taaatcattt | 1320 |
| cagcttatag | ttcttaaaag | cataacccctt | tacccccattt | aattctagag | tctagaacgc | 1380 |
| aaggatctct | tggaatgaca | aatgataggt | acctaaaatg | taacatgaaa | atactagctt | 1440 |
| attttctgaa | atgtactatc | ttaatgctta | aattatattt | cccttaggc | tgtgatagtt | 1500 |
| tttgaaataa | aatttaacat | ttaatatcat | gaaatgttat | aagtagacat | acattttggg | 1560 |
| attgtgatct | tagaggtttg | tgtgtgtgta | cgtatgtgtg | tgttctacaa | gaacggaagt | 1620 |
| gtgatatgtt | taaagatgat | cagagaaaag | acagtgtcta | aatataagac | aatattgatc | 1680 |
| agctctagaa | taactttaaa | gaaagacgtg | ttctgcattg | ataaactcaa | atgatcatgg | 1740 |
| cagaatgaga | gtgaatctta | cattactact | ttcaaaaata | gtttccaata | aattaataat | 1800 |
| acctaaaaaa | aaaaa | | | | | 1815 |

<210> SEQ ID NO 76
<211> LENGTH: 5927
<212> TYPE: DNA
<213> ORGANISM: Artificial Sequence
<220> FEATURE:
<223> OTHER INFORMATION: Col1a1 mRNA

```
<400> SEQUENCE: 76
tcgtcggagc agacgggagt ttctcctcgg ggtcggagca ggaggcacgc ggagtgtgag        60
gccacgcatg agcggacgct aaccccctcc ccagccacaa agagtctaca tgtctagggt       120
ctagacatgt tcagctttgt ggacctccgg ctcctgctcc tcttagcggc caccgccctc       180
ctgacgcacg gccaagagga aggccaagtc gagggccaag acgaagacat cccaccaatc       240
acctgcgtac agaacggcct caggtaccat gaccgacgg tgtggaaacc cgagccctgc        300
cggatctgcg tctgcgacaa cggcaaggtg ttgtgcgatg acgtgatctg tgacgagacc       360
aagaactgcc ccgcgccga agtccccgag ggcgagtgct gtcccgtctg ccccgacggc        420
tcagagtcac ccaccgacca agaaaccacc ggcgtcgagg acccaaggg agacactggc        480
ccccgaggcc caaggggacc cgcaggcccc cctggccgag atggcatccc tggacagcct       540
ggacttcccg acccccgg acccccgga cctcccggac cccctggcct cggaggaaac         600
tttgctcccc agctgtctta tggctatgat gagaaatcaa ccggaggaat ttccgtgcct       660
ggccccatgg gtccctctgg tcctcgtggt ctccctggcc ccctggtgc acctggtccc        720
caaggcttcc aaggtccccc tggtgagcct ggcgagcctg gagcttcagg tcccatgggt      780
ccccgaggtc ccccaggtcc ccctggaaag aatggagatg atggggaagc tggaaaacct     840
ggtcgtcctg gtgagcgtgg gcctcctggg cctcagggtg ctcgaggatt gcccggaaca     900
gctggcctcc ctggaatgaa gggacacaga ggtttcagtg gtttggatgg tgccaaggga    960
gatgctggtc ctgctggtcc taagggtgag cctggcagcc ctggtgaaaa tggagctcct   1020
ggtcagatgg gccccgtgg cctgcctggt gagagaggtc gccctggagc cctggcccct   1080
gctggtgctc gtggaaatga tggtgctact ggtgctgccg ggccccctgg tcccaccggc   1140
cccgctggtc ctcctggctt ccctggtgct gttggtgcta agggtgaagc tggtccccaa    1200
gggccccgag gctctgaagg tccccagggt gtgcgtggtg agcctggccc cctggccct     1260
gctggtgctc ctgccctgc tggaaaccct ggtgctgatg acagcctgg tgctaaaggt      1320
gccaatggtg ctcctggtat tgctggtgct cctggcttcc ctggtgcccg aggcccctct    1380
ggaccccagg gccccggcgg ccctcctggt cccaagggta acagcggtga acctggtgct    1440
cctggcagca aaggagacac tggtgctaag ggagagcctg gccctgttgg tgttcaagga    1500
cccccctggcc ctgctggaga ggaaggaaag cgaggagctc gaggtgaacc cggacccact   1560
ggcctgcccg accccctgg cgagcgtggt ggacctggta gccgtggttt ccctggcgca    1620
gatggtgttg ctggtcccaa gggtcccgct ggtgaacgtg gttctcctgg ccctgctggc    1680
cccaaaggat ctcctggtga agctggtcgt cccggtgaag ctggtctgcc tggtgccaag   1740
ggtctgactg gaagccctgg cagccctggt cctgatggca aaactggccc cctggtcccc   1800
gccggtcaag atggtcgccc cggacccca ggcccacctg gtcccgtgg tcaggctggt     1860
gtgatgggat tccctggacc taaaggtgct gctggagagc ccggcaaggc tggagagcga    1920
ggtgttcccg accccctgg cgctgtcggt cctgctggca agatggaga ggctggagct     1980
cagggacccc ctggccctgc tggtcccgct ggcgagagag gtgaacaagg ccctgctggc    2040
tcccccggat ccagggtct ccctggtcct gctggtcctc caggtgaagc aggcaaacct    2100
ggtgaacagg gtgttcctgg agaccttggc gcccctggcc ctctggagc aagaggcgag    2160
agaggtttcc ctggcgagcg tggtgtgcaa ggtcccccctg gtcctgctgg tcccgaggg    2220
gccaacggtg ctcccggcaa cgatggtgct aaggtgatg ctggtgcccc tggagctccc    2280
ggtagccagg gcgcccctgg ccttcaggga atgcctggtg aacgtggtgc agctggtctt    2340
```

```
ccagggccta agggtgacag aggtgatgct ggtcccaaag gtgctgatgg ctctcctggc    2400
aaagatggcg tccgtggtct gactggcccc attggtcctc ctggccctgc tggtgccct     2460 ggtgacaagg gtgaaagtgg tcccagcggc cctgctggtc ccactggagc tcgtggtgcc    2520
cccggagacc gtggtgagcc tggtcccccc ggccctgctg gctttgctgg ccccctggt     2580 gctgacggcc aacctggtgc taaaggcgaa cctggtgatg ctggtgctaa aggcgatgct    2640 ggtcccctg gccctgccgg acccgctgga cccctggcc ccattggtaa tgttggtgct      2700
cctggagcca aggtgctcg cggcagcgct ggtcccctg gtgctactgg tttccctggt     2760
gctgctggcc gagtcggtcc tcctggcccc tctggaaatg ctggaccccc tggccctcct    2820
ggtcctgctg gcaaagaagg cggcaaaggt ccccgtggtg agactggccc tgctggacgt    2880
cctggtgaag ttggtcccc tggtcccct ggccctgctg gcgagaaagg atcccctggt     2940
gctgatggtc ctgctggtgc tcctggtact cccgggcctc aaggtattgc tggacagcgt    3000
ggtgtggtcg gcctgcctgg tcagagagga gagagaggct tccctggtct tcctggcccc    3060
tctggtgaac ctggcaaaca aggtccctct ggagcaagtg gtgaacgtgg tccccctggt    3120
cccatgggcc cccctggatt ggctggaccc cctggtgaat ctggacgtga ggggctcct    3180 ggtgccgaag gttcccctgg acgagacggt tctcctggcg ccaagggtga ccgtggtgag    3240 accgccccg ctggacccc tggtgctcct ggtgctcctg gtgccctgg cccgttggc       3300 cctgctggca gagtggtga tcgtggtgag actggtcctg ctggtcccgc cggtcctgtc    3360
ggccctgttg gcgcccgtgg ccccgccgga ccccaaggcc ccgtggtga caagggtgag    3420 acaggcgaac agggcgacag aggcataaag gtcaccgtg gcttctctgg cctccagggt     3480 cccctggcc ctcctggctc tcctggtgaa caaggtccct ctggagcctc tggtcctgct    3540
ggtccccgag gtccccctgg ctctgctggt gctcctggca aagatggact caacggtctc    3600
cctggcccca ttgggccccc tggtcctcgc ggtcgcactg gtgatgctgg tcctgttggt    3660
ccccccggcc ctcctggacc tcctggtccc ctggtcctc ccagcgctgg tttcgacttc    3720
agcttcctgc cccagccacc tcaagagaag gctcacgatg gtggccgcta ctaccgggct    3780
gatgatgcca atgtggttcg tgaccgtgac ctcgaggtgg acaccaccct caagagcctg    3840
agccagcaga tcgagaacat ccggagccca gagggcagcc gcaagaaccc cgcccgcacc    3900
tgccgtgacc tcaagatgtg ccactctgac tggaagagtg gagtactg gattgaccc     3960 aaccaaggct gcaacctgga tgccatcaaa gtcttctgca acatggagac tggtgagacc    4020
tgcgtgtacc ccactcagcc cagtgtggcc cagaagaact ggtacatcag caagaacccc    4080
aaggacaaga ggcatgtctg gttcggcgag agcatgaccg atggattcca gttcgagtat    4140
ggcggccagg gctccgaccc tgccgatgtg gccatccagc tgaccttcct gcgcctgatg    4200
tccaccgagg cctcccagaa catcacctac cactgcaaga acagcgtggc ctacatggac    4260
cagcagactg gcaacctcaa gaaggccctg ctcctccagg gctccaacga gatcgagatc    4320
cgcgccgagg gcaacagccg cttcacctac agcgtcactg tcgatggctg cacgagtcac    4380
accggagcct ggggcaagac agtgattgaa tacaaaacca ccaagacctc ccgcctgccc    4440
atcatcgatg tgccccctt ggacgttggt gcccagacc aggaattcgg cttcgacgtt     4500
ggccctgtct gcttcctgta aactccctcc atcccaacct ggctccctcc cacccaacca    4560
actttccccc caacccggaa acagacaagc aacccaaact gaacccccctc aaaagccaaa    4620 aaatgggaga caatttcaca tggactttgg aaaatatttt tttccttgc attcatctct    4680
```

| | | | |
|---|---|---|---|
| caaacttagt | ttttatcttt gaccaaccga acatgaccaa aaaccaaaag tgcattcaac | | 4740 |
| cttaccaaaa | aaaaaaaaaa aaaaagaata aataaataac ttttaaaaa aggaagcttg | | 4800 |
| gtccacttgc | ttgaagaccc atgcgggggt aagtcccttt ctgcccgttg ggcttatgaa | | 4860 |
| accccaatgc | tgccctttct gctcctttct ccacaccccc cttggggcct ccctccact | | 4920 |
| ccttcccaaa | tctgtctccc cagaagacac aggaaacaat gtattgtctg cccagcaatc | | 4980 |
| aaaggcaatg | ctcaaacacc caagtggccc ccaccctcag cccgctcctg cccgcccagc | | 5040 |
| accccaggc | cctgggggac ctggggttct cagactgcca aagaagcctt gccatctggc | | 5100 |
| gctcccatgg | ctcttgcaac atctccccctt cgttttgag gggtcatgc cgggggagcc | | 5160 |
| accagcccct | cactgggttc ggaggagagt caggaagggc cacgacaaag cagaaacatc | | 5220 |
| ggatttgggg | aacgcgtgtc aatcccttgt gccgcagggc tggcgggag agactgttct | | 5280 |
| gttccttgtg | taactgtgtt gctgaaagac tacctcgttc ttgtcttgat gtgtcaccgg | | 5340 |
| ggcaactgcc | tggggggggg gatgggggca gggtggaagc ggctccccat tttataccaa | | 5400 |
| aggtgctaca | tctatgtgat gggtggggtg gggagggaat cactggtgct atagaaattg | | 5460 |
| agatgccccc | ccaggccagc aaatgttcct ttttgttcaa agtctatttt tattccttga | | 5520 |
| tatttttctt | ttttttttt tttttttgtg gatggggact tgtgaatttt tctaaaggtg | | 5580 |
| ctatttaaca | tgggaggaga gcgtgtgcgg ctccagccca gcccgctgct cactttccac | | 5640 |
| cctctctcca | cctgcctctg gcttctcagg cctctgctct ccgacctctc tcctctgaaa | | 5700 |
| ccctcctcca | cagctgcagc ccatcctccc ggctccctcc tagtctgtcc tgcgtcctct | | 5760 |
| gtccccgggt | tcagagaca acttcccaaa gcacaaagca gttttccccc ctaggggtgg | | 5820 |
| gaggaagcaa | aagactctgt acctattttg tatgtgtata ataatttgag atgttttaa | | 5880 |
| ttatttgat | tgctggaata aagcatgtgg aaatgaccca aacataa | | 5927 |

<210> SEQ ID NO 77
<211> LENGTH: 1203
<212> TYPE: DNA
<213> ORGANISM: Artificial Sequence
<220> FEATURE:
<223> OTHER INFORMATION: Activin A mRNA

<400> SEQUENCE: 77

| | | | |
|---|---|---|---|
| atgcccttgc | tttggctgag aggatttctg ttggcaagtt gctggattat agtgaggagt | | 60 |
| tcccccaccc | caggatccga ggggcacagc gcggcccccg actgtccgtc ctgtgcgctg | | 120 |
| ccgcccctcc | caaggatgt acccaactct cagccagaga tggtggaggc cgtcaagaag | | 180 |
| cacatttaa | acatgctgca cttgaagaag agacccgatg tcacccagcc ggtacccaag | | 240 |
| gcggcgcttc | tgaacgcgat cagaaagctt catgtgggca aagtcgggga gaacgggtat | | 300 |
| gtggagatag | aggatgacat tggaaggagg gcagaaatga tgaacttat ggagcagacc | | 360 |
| tcggagatca | tcacgtttgc cgagtcaggt tggtgctggc attggcaggg ggtggggagg | | 420 |
| ggtgggggt | gggagggtaa aatatatttc tttgacagtc ccaggaggaa cttcttttcc | | 480 |
| cttcagctgg | aaactgcctg ggaaggttat tagttattag gtgatggtag cggactagcc | | 540 |
| gacggagggc | aggcaggga gggggagagg actttacaga aaaggaattc tcggtcgagc | | 600 |
| tctgcctgga | gatgactggc ttacacttac taaacccagc gggtcacaca gagaggaagc | | 660 |
| tcggggccaa | tgttgagctg gaaggcagac tgtgaggggc tgccttgccc tgcctgtgaa | | 720 |
| acagatctga | gcagcggag gaaagccgcg gcatttcgg gtgctagggg agcagaggag | | 780 |
| gcttccggac | cccatccaag ttttttattga gggtagaggg gtgaatgtac caggattgga | | 840 |

```
gtggaatggc acagatgaag tcactctctt aaaacaaacc ttccccttta aaagtccaat    900
ctggggccac attggagaag cagggcatat ttatgagtga cagtcatttt tacctttaga    960
aaatgtctat aagtgcacag gcaccacatt caagacaggg aagagctact ttgggggaca   1020
gttgtcattg aaccagcagt tactttggg acactgactt ttgctctctg aaagaaaaaa   1080
aaataaataa aacaaccagt tttgttcttt ctaaagttac taagagctct ctgccaagga   1140
acgaaccttg acaaagtact ctcagatact acgctgaagt cactcaatct taagaggaag   1200
aag                                                                1203
```

<210> SEQ ID NO 78
<211> LENGTH: 21
<212> TYPE: DNA
<213> ORGANISM: Artificial Sequence
<220> FEATURE:
<223> OTHER INFORMATION: Snail primer 1

<400> SEQUENCE: 78
tcggaagcct aactacagcg a                                              21

<210> SEQ ID NO 79
<211> LENGTH: 20
<212> TYPE: DNA
<213> ORGANISM: Artificial Sequence
<220> FEATURE:
<223> OTHER INFORMATION: Snail primer 2

<400> SEQUENCE: 79
agatgagcat tggcagcgag                                                20

<210> SEQ ID NO 80
<211> LENGTH: 23
<212> TYPE: DNA
<213> ORGANISM: Artificial Sequence
<220> FEATURE:
<223> OTHER INFORMATION: Dkk1 primer 1

<400> SEQUENCE: 80
ccttgaactc ggttctcaat tcc                                            23

<210> SEQ ID NO 81
<211> LENGTH: 23
<212> TYPE: DNA
<213> ORGANISM: Artificial Sequence
<220> FEATURE:
<223> OTHER INFORMATION: Dkk1 primer 2

<400> SEQUENCE: 81
caatggtctg gtacttattc ccg                                            23

<210> SEQ ID NO 82
<211> LENGTH: 21
<212> TYPE: DNA
<213> ORGANISM: Artificial Sequence
<220> FEATURE:
<223> OTHER INFORMATION: Col1a1 primer 1

<400> SEQUENCE: 82
gagggccaag acgaagacat c                                              21

<210> SEQ ID NO 83
<211> LENGTH: 21
<212> TYPE: DNA

```
<213> ORGANISM: Artificial Sequence
<220> FEATURE:
<223> OTHER INFORMATION: Col1a1 primer 2

<400> SEQUENCE: 83
cagatcacgt catcgcacaa c                                              21

<210> SEQ ID NO 84
<211> LENGTH: 20
<212> TYPE: DNA
<213> ORGANISM: Artificial Sequence
<220> FEATURE:
<223> OTHER INFORMATION: Activin primer 1

<400> SEQUENCE: 84
tcatcacgtt tgccgagtca                                                20

<210> SEQ ID NO 85
<211> LENGTH: 20
<212> TYPE: DNA
<213> ORGANISM: Artificial Sequence
<220> FEATURE:
<223> OTHER INFORMATION: Activin primer 2

<400> SEQUENCE: 85
gctagtccgc taccatcacc                                                20

<210> SEQ ID NO 86
<211> LENGTH: 4241
<212> TYPE: DNA
<213> ORGANISM: Homo sapiens
<220> FEATURE:
<223> OTHER INFORMATION: Human Axin2 mRNA

<400> SEQUENCE: 86
actggctccg cgagcctggc ccgggggagt cggctggagc cggctgcgct ttgataaggt      60
cctggcaact cagtaacagc ccgagagccg ggaaataaaa ataaccccctc agagcgatgg    120 atttcggggc cgcccggcgg ccgaggcgcc cgccgaaggc cctgctgtaa aagagaggag    180
gttcagatga gccccctgctg acttgagaga gacagagaga ccacgccgat tgctgagagg    240
aactggaaga agaaaaattc ccagactcag tgggaagagc tccctcacca tgagtagcgc    300
tatgttggtg acttgcctcc cggaccccag cagcagcttc cgtgaggatg ccccgcggcc    360
cccagtgcca ggggaagaag gggagacccc accgtgtcag ccaggggtgg gcaagggcca    420
ggtcaccaaa cccatgcctg tctcttccaa caccaggcgg aacgaagatg ggttggggga    480
gccggagggg cgggcatctc cggattcccc tctgacccgg tggaccaagt ccttacactc    540
cttattgggc gatcaagacg gtgcttacct gttccgaact ttcctggaga gggagaaatg    600
cgtggatacc ttagacttct ggtttgcctg caatggattc aggcagatga acctgaagga    660 taccaaaaact ttacgagtag ccaaagcgat ctacaaaagg tacattgaga acaacagcat    720
tgtctccaag cagctgaagc ctgccaccaa gacctacata agagatggca tcaagaagca    780
gcagattgat tccatcatgt ttgaccaggc gcagaccgag atccagtcgg tgatggagga    840
aaatgcctac cagatgttt tgacttctga tatataccctc gaatatgtga ggagtggggg    900
agaaaacaca gcttacatga gtaatggggg actcgggagc ctaaaggtcg tgtgtggcta    960
tctccccacc ttgaatgaag aagaggagtg gacttgtgcc gacttcaagt gcaaactttc   1020
gccaaccgtg gttggcttgt ccagcaaaac tctgagggcc acggcgagtg tgaggtccac   1080
ggaaactgtt gacagtggat acaggtcctt caagaggagc gatcctgtta atccttatca   1140
```

| | |
|---|---|
| cataggttct ggctatgtct ttgcaccagc caccagcgcc aacgacagtg agatatccag | 1200 |
| tgatgcgctg acggatgatt ccatgtccat gacggacagc agtgtagatg gaattcctcc | 1260 |
| ttatcgtgtg ggcagtaaga aacagctcca gagagaaatg catcgcagtg tgaaggccaa | 1320 |
| tggccaagtg tctctacctc atttcccgag aacccaccgc ctgcccaagg agatgacccc | 1380 |
| cgtggaaccc gccacctttg cagctgagct gatctcgagg ctggaaaagc tgaagctgga | 1440 |
| gttggagagc cgccacagcc tggaggagcg cctgcagcag atccgagagg atgaagagag | 1500 |
| agagggctcc gagctcacac tcaattcgcg ggaggggggcg cccacgcagc accccctctc | 1560 |
| cctactgccc tccggcagct acgaggaaga cccgcagacg atactggacg atcacctgtc | 1620 |
| cagggtcctc aagacccctg gctgccagtc tccaggcgta ggccgctata gcccccgctc | 1680 |
| ccgctccccg gaccaccacc accaccacca ttcgcagtac cactccctgc tcccgcccgg | 1740 |
| tggcaagctg cctcccgcgg ccgcctcgcc gggcgcctgc cccctcctcg ggggcaaagg | 1800 |
| ctttgtgacc aagcagacga cgaagcatgt ccaccaccac tacatccacc accatgccgt | 1860 |
| ccccaagacc aaggaggaga tcgaggcgga ggccacgcag cgggtgcact gcttctgccc | 1920 |
| tgggggcagc gagtattact gctactcgaa atgcaaaagc cactccaagg ctccggaaac | 1980 |
| catgcccagc gagcagtttg gcggcagcag aggcagtacc ttgcccaaac gcaatgggaa | 2040 |
| aggcacggag ccgggcctgg ccctgcccgc cagggaagga ggggcccccg gcggagctgg | 2100 |
| ggccctgcag cttccccggg aggaaggaga caggtcgcag gatgtctggc agtggatgct | 2160 |
| ggagagtgag cggcagagca agcccaagcc ccatagtgcc caaagcacaa aaaaggccta | 2220 |
| cccccttggag tctgcccgct cgtctccagg cgaacgagcc agccggcacc atctgtgggg | 2280 |
| gggcaacagc gggcaccccc gcaccacccc ccgtgcccac ctgttcaccc aggaccctgc | 2340 |
| gatgcctccc ctgaccccac ccaacacgct ggctcagctg gaggaggcct gtcgcaggct | 2400 |
| agctgaggtg tcgaagcccc caaagcagcg gtgctgtgtg gccagtcagc agagggacag | 2460 |
| gaatcattcg gccactgttc agacgggagc cacacccttc tccaatccaa gcctggctcc | 2520 |
| agaagatcac aaaagagccaa agaaactggc aggtgtccac gcgctccagg ccagtgagtt | 2580 |
| ggttgtcact tacttttttct gtggggaaga aattccatac cggaggatgc tgaaggctca | 2640 |
| gagcttgacc ctgggccact ttaaagagca gctcagcaaa aagggaaatt ataggtatta | 2700 |
| cttcaaaaaa gcaagcgatg agtttgcctg tggagcggtg tttgaggaga tctgggagga | 2760 |
| tgagacggtg ctcccgatgt atgaaggccg gattctgggc aaagtggagc ggatcgattg | 2820 |
| agccctgggg tctggctttg gtgaactgtt ggagcccgaa gctcttgtga actgtcttgg | 2880 |
| ctgtgagcaa ctgcgacaaa acattttgaa ggaaaattaa accaatgaag aagacaaagt | 2940 |
| ctaaggaaga atcggccagt gggccttcgg gagggcgggg ggaggttgat tttcatgatt | 3000 |
| catgagctgg gtactgactg agataagaaa agcctgaact atttattaaa aacatgacca | 3060 |
| ctcttggcta ttgaagatgc tgcctgtatt tgagagactg ccatacataa tatatgactt | 3120 |
| cctagggatc tgaaatccat aaactaagag aaactgtgta tagcttacct gaacaggaat | 3180 |
| ccttactgat attttatagaa cagttgattt cccccatccc cagtttatgg atatgctgct | 3240 |
| ttaaacttgg aaggggggaga caggaagttt taattgttct gactaaactt aggagttgag | 3300 |
| ctaggagtgc gttcatggtt tcttcactaa cagaggaatt atgctttgca ctacgtccct | 3360 |
| ccaagtgaag acagactgtt ttagacagac ttttttaaaat ggtgccctac cattgacaca | 3420 |
| tgcagaaatt ggtgcgtttt gtttttttttt ttcctatgct gctctgtttt gtcttaaagg | 3480 |

-continued

```
tcttgagggt tgaccatgtt gcgtcatcat caacattttg ggggttgtgt tggatgggat    3540
gatctgttgc agagggagag gcagggaacc ctgctccttc gggccccagg ttgatcctgt    3600
gactgaggct ccccctcatg tagcctcccc aggcccaggg ccctgaggcc tgctagaatc    3660
actgccgctg tgctttcgtg gaaatgacag ttccttgttt tttttgtttc tgttttttgtt   3720 ttacattagt cattggacca cagccattca ggaactaccc cctgccccac aaagaaatga    3780
acagttgtag ggagacccag cagcaccttt cctccacaca ccttcatttt gatgttcggg    3840
tttttgtgtt aagttaatct gtacattctg tttgccattg ttacttgtac tatacatctg    3900
tatatagtgt acggcaaaag agtattaatc cactatctct agtgcttgac tttaaatcag    3960
tacagtacct gtacctgcac ggtcacccgc tccgtgtgtc gccctatatt gagggctcaa    4020
gctttccctt gttttttgaa aggggtttat gtataaatat attttatgcc tttttattac    4080
aagtcttgta ctcaatgact tttgtcatga cattttgttc tacttatact gtaaattatg    4140
cattataaag agttcattta aggaaaatta cttggtacaa taattattgt aattaagaga    4200
tgtagccttt attaaaattt tatatttttc aaaaaaaaa a                          4241
```

<210> SEQ ID NO 87
<211> LENGTH: 843
<212> TYPE: PRT
<213> ORGANISM: Homo sapiens
<220> FEATURE:
<223> OTHER INFORMATION: Human Axin2 amino acid sequence

<400> SEQUENCE: 87

```
Met Ser Ser Ala Met Leu Val Thr Cys Leu Pro Asp Pro Ser Ser
1               5                   10                  15

Phe Arg Glu Asp Ala Pro Arg Pro Val Pro Gly Glu Glu Gly Glu
                20                  25                  30

Thr Pro Pro Cys Gln Pro Gly Val Gly Lys Gly Gln Val Thr Lys Pro
            35                  40                  45

Met Pro Val Ser Ser Asn Thr Arg Arg Asn Glu Asp Gly Leu Gly Glu
        50                  55                  60

Pro Glu Gly Arg Ala Ser Pro Asp Ser Pro Leu Thr Arg Trp Thr Lys
65                  70                  75                  80

Ser Leu His Ser Leu Leu Gly Asp Gln Asp Gly Ala Tyr Leu Phe Arg
                85                  90                  95

Thr Phe Leu Glu Arg Glu Lys Cys Val Asp Thr Leu Asp Phe Trp Phe
                100                 105                 110

Ala Cys Asn Gly Phe Arg Gln Met Asn Leu Lys Asp Thr Lys Thr Leu
            115                 120                 125

Arg Val Ala Lys Ala Ile Tyr Lys Arg Tyr Ile Glu Asn Asn Ser Ile
        130                 135                 140

Val Ser Lys Gln Leu Lys Pro Ala Thr Lys Thr Tyr Ile Arg Asp Gly
145                 150                 155                 160

Ile Lys Lys Gln Gln Ile Asp Ser Ile Met Phe Asp Gln Ala Gln Thr
                165                 170                 175

Glu Ile Gln Ser Val Met Glu Glu Asn Ala Tyr Gln Met Phe Leu Thr
            180                 185                 190

Ser Asp Ile Tyr Leu Glu Tyr Val Arg Ser Gly Gly Glu Asn Thr Ala
        195                 200                 205

Tyr Met Ser Asn Gly Gly Leu Gly Ser Leu Lys Val Val Cys Gly Tyr
    210                 215                 220

Leu Pro Thr Leu Asn Glu Glu Glu Glu Trp Thr Cys Ala Asp Phe Lys
```

```
            225                 230                 235                 240
Cys Lys Leu Ser Pro Thr Val Gly Leu Ser Ser Lys Thr Leu Arg
                245                 250                 255

Ala Thr Ala Ser Val Arg Ser Thr Glu Thr Val Asp Ser Gly Tyr Arg
                260                 265                 270

Ser Phe Lys Arg Ser Asp Pro Val Asn Pro Tyr His Ile Gly Ser Gly
                275                 280                 285

Tyr Val Phe Ala Pro Ala Thr Ser Ala Asn Asp Ser Glu Ile Ser Ser
                290                 295                 300

Asp Ala Leu Thr Asp Asp Ser Met Ser Met Thr Asp Ser Ser Val Asp
305                 310                 315                 320

Gly Ile Pro Pro Tyr Arg Val Gly Ser Lys Lys Gln Leu Gln Arg Glu
                325                 330                 335

Met His Arg Ser Val Lys Ala Asn Gly Gln Val Ser Leu Pro His Phe
                340                 345                 350

Pro Arg Thr His Arg Leu Pro Lys Glu Met Thr Pro Val Glu Pro Ala
                355                 360                 365

Thr Phe Ala Ala Glu Leu Ile Ser Arg Leu Glu Lys Leu Lys Leu Glu
                370                 375                 380

Leu Glu Ser Arg His Ser Leu Glu Glu Arg Leu Gln Gln Ile Arg Glu
385                 390                 395                 400

Asp Glu Glu Arg Glu Gly Ser Glu Leu Thr Leu Asn Ser Arg Glu Gly
                405                 410                 415

Ala Pro Thr Gln His Pro Leu Ser Leu Leu Pro Ser Gly Ser Tyr Glu
                420                 425                 430

Glu Asp Pro Gln Thr Ile Leu Asp Asp His Leu Ser Arg Val Leu Lys
                435                 440                 445

Thr Pro Gly Cys Gln Ser Pro Gly Val Gly Arg Tyr Ser Pro Arg Ser
                450                 455                 460

Arg Ser Pro Asp His His His His His Ser Gln Tyr His Ser Leu
465                 470                 475                 480

Leu Pro Pro Gly Gly Lys Leu Pro Pro Ala Ala Ser Pro Gly Ala
                485                 490                 495

Cys Pro Leu Leu Gly Gly Lys Gly Phe Val Thr Lys Gln Thr Thr Lys
                500                 505                 510

His Val His His His Tyr Ile His His His Ala Val Pro Lys Thr Lys
                515                 520                 525

Glu Glu Ile Glu Ala Glu Ala Thr Gln Arg Val His Cys Phe Cys Pro
530                 535                 540

Gly Gly Ser Glu Tyr Tyr Cys Tyr Ser Lys Cys Lys Ser His Ser Lys
545                 550                 555                 560

Ala Pro Glu Thr Met Pro Ser Glu Gln Phe Gly Gly Ser Arg Gly Ser
                565                 570                 575

Thr Leu Pro Lys Arg Asn Gly Lys Gly Thr Glu Pro Gly Leu Ala Leu
                580                 585                 590

Pro Ala Arg Glu Gly Gly Ala Pro Gly Gly Ala Gly Ala Leu Gln Leu
                595                 600                 605

Pro Arg Glu Glu Gly Asp Arg Ser Gln Asp Val Trp Gln Trp Met Leu
                610                 615                 620

Glu Ser Glu Arg Gln Ser Lys Pro Lys Pro His Ser Ala Gln Ser Thr
625                 630                 635                 640

Lys Lys Ala Tyr Pro Leu Glu Ser Ala Arg Ser Ser Pro Gly Glu Arg
                645                 650                 655
```

```
Ala Ser Arg His His Leu Trp Gly Gly Asn Ser Gly His Pro Arg Thr
            660                 665                 670
Thr Pro Arg Ala His Leu Phe Thr Gln Asp Pro Ala Met Pro Pro Leu
        675                 680                 685
Thr Pro Pro Asn Thr Leu Ala Gln Leu Glu Glu Ala Cys Arg Arg Leu
        690                 695                 700
Ala Glu Val Ser Lys Pro Pro Lys Gln Arg Cys Cys Val Ala Ser Gln
705                 710                 715                 720
Gln Arg Asp Arg Asn His Ser Ala Thr Val Gln Thr Gly Ala Thr Pro
                725                 730                 735
Phe Ser Asn Pro Ser Leu Ala Pro Glu Asp His Lys Glu Pro Lys Lys
                740                 745                 750
Leu Ala Gly Val His Ala Leu Gln Ala Ser Glu Leu Val Val Thr Tyr
                755                 760                 765
Phe Phe Cys Gly Glu Glu Ile Pro Tyr Arg Arg Met Leu Lys Ala Gln
770                 775                 780
Ser Leu Thr Leu Gly His Phe Lys Glu Gln Leu Ser Lys Lys Gly Asn
785                 790                 795                 800
Tyr Arg Tyr Tyr Phe Lys Lys Ala Ser Asp Glu Phe Ala Cys Gly Ala
                805                 810                 815
Val Phe Glu Glu Ile Trp Glu Asp Glu Thr Val Leu Pro Met Tyr Glu
                820                 825                 830
Gly Arg Ile Leu Gly Lys Val Glu Arg Ile Asp
                835                 840
```

What is claimed:

1. A method for treating a disease in a subject, comprising administering to the subject a pharmaceutically effective dose of an activin receptor type II (ActRII) signaling inhibitor, wherein the subject has:
   (a) elevated levels of snail homolog 1 (Snai1) as compared to levels of Snai1 in a reference population;
   (b) decreased levels of alpha smooth muscle actin (alpha-SMA) as compared to levels of alpha-SMA in a reference population;
   (c) elevated levels of urinary protein as compared to levels of urinary protein in a reference population; and/or
   (d) decreased levels of Axin2 as compared to levels of Axin2 in a reference population,
   wherein the disease is:
   (a) cardiovascular disease;
   (b) vascular calcification;
   (c) cardiovascular disease associated with and/or resulting from vascular calcification;
   (d) arterial stiffness;
   (e) cardiovascular disease associated with and/or resulting from arterial stiffness;
   (f) left ventricular hypertrophy (LVH);
   (g) cardiovascular disease associated with and/or resulting from left ventricular hypertrophy;
   (h) cardiovascular disease associated with and/or resulting from renal disease; or
   (i) bone resorption associated with chronic kidney disease-mineral and bone disease (CKD-MBD), and
   wherein said ActRII signaling inhibitor comprises an amino acid sequence that is
   (a) at least 98% identical to SEQ ID NO:2;
   (b) at least 98% identical to SEQ ID NO:3;
   (c) at least 98% identical to SEQ ID NO:6;
   (d) at least 98% identical to SEQ ID NO:7; or
   (e) at least 98% identical to SEQ ID NO:12.

2. The method of claim 1, wherein the pharmaceutically effective dose of the ActRII signaling inhibitor is about 15 mg, about 30 mg, about 45 mg, about 60 mg, about 75 mg, about 90 mg, or about 1 g or about 0.1 mg/kg, about 0.13 mg/kg, about 0.2 mg/kg, about 0.26 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, or about 1.5 mg/kg.

3. The method of claim 1, wherein the elevated levels of Snai1, and/or urinary protein, are about 10%, 20%, 25%, 30%, 40%, 50%, 60%, 70%, 75%, 80% 90%, 100%, 200%, or 500% greater than the levels of Snai1, and/or urinary protein, respectively, in the reference population.

4. The method of claim 1, wherein the decreased levels of alpha-SMA, and/or Axin2 are about 10%, 20%, 25%, 30%, 40%, 50%, 60%, 70%, 75%, 80%, or 90% less than the levels of alpha-SMA, and/or Axin2 respectively, in the reference population.

5. A method for treating a disease in a subject, wherein the method comprises:
   (a) administering to the subject an initial dose of an ActRII signaling inhibitor to the subject;
   (b) taking a first measurement of the level of Snai1, urinary protein, alpha-SMA, and/or Axin2 in the subject;
   (c) after a period of time, taking a second measurement of the level of Snai1, urinary protein, alpha-SMA, and/or Axin2 in the subject; and
   (d) administering to the subject an adjusted dose of the activin receptor type II signaling inhibitor, wherein the adjusted dose is based on the detected change between the first measurement and the second measurement, thereby treating and/or preventing said disease;

wherein said disease is:
(a) cardiovascular disease;
(b) vascular calcification;
(c) cardiovascular disease associated with and/or resulting from vascular calcification;
(d) arterial stiffness;
(e) cardiovascular disease associated with and/or resulting from arterial stiffness;
(f) left ventricular hypertrophy (LVH);
(g) cardiovascular disease associated with and/or resulting from left ventricular hypertrophy;
(h) cardiovascular disease associated with and/or resulting from renal disease; or
(i) bone resorption associated with CKD-MBD; and
wherein said ActRII signaling inhibitor comprises an amino acid sequence that is
(a) at least 98% identical to SEQ ID NO:2;
(b) at least 98% identical to SEQ ID NO:3;
(c) at least 98% identical to SEQ ID NO:6;
(d) at least 98% identical to SEQ ID NO:7; or
(e) at least 98% identical to SEQ ID NO:12.

6. The method of claim 5, wherein the initial dose of the ActRII signaling inhibitor is about 15 mg, about 30 mg, about 45 mg, about 60 mg, about 75 mg, about 90 mg, or about 1 g or about 0.1 mg/kg, about 0.13 mg/kg, about 0.2 mg/kg, about 0.26 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, or about 1.5 mg/kg.

7. The method of claim 5, wherein the adjusted dose of the ActRII signaling inhibitor is greater than the initial dose if:
(a) the level of Snai1 is elevated as compared to the level of Snai1 in a reference population;
(b) the level of alpha-SMA is decreased as compared to the level of alpha-SMA in a reference population;
(c) the level of urinary protein is elevated as compared to the level of urinary protein in a reference population; and/or
(d) the level of Axin2 is decreased compared to the level of Axin2 in a reference population.

8. The method of claim 7, wherein the adjusted dose is about 2.5 mg, about 5 mg, about 10 mg, about 15 mg, about 20 mg, or about 35 mg greater than the initial dose, or about 0.05 mg/kg, about 0.1 mg/kg, about 0.15 mg/kg, about 0.25 mg/kg, about 0.3 mg/kg, about 0.35 mg/kg, about 0.4 mg/kg, or about 0.5 mg/kg greater than the initial dose.

9. The method of claim 5, wherein the adjusted dose of the ActRII signaling inhibitor is less than the initial dose if:
(a) the level of Snai1 is decreased as compared to the level of Snai1 in a reference population;
(b) the level of alpha-SMA is elevated as compared to the level of alpha-SMA in a reference population;
(c) the level of urinary protein is decreased as compared to the level of urinary protein in a reference population; and/or
(d) the level of Axin2 is elevated as compared to the level of Axin2 in a reference population.

10. The method of claim 9, wherein the adjusted dose is about 2.5 mg, about 5 mg, about 10 mg, about 15 mg, about 20 mg, or about 35 mg less than the initial dose, or about 0.05 mg/kg, about 0.1 mg/kg, about 0.15 mg/kg, about 0.25 mg/kg, about 0.3 mg/kg, about 0.35 mg/kg, about 0.4 mg/kg, or about 0.5 mg/kg less than the initial dose.

11. The method of claim 5, wherein
(a) the first measurement is taken prior to the commencement of the treatment;
(b) the first measurement is taken immediately after commencement of the treatment or within at most 1 day, 2 days, 3 days, 4 days, 5 days, 6 days, or 1 week, 2 weeks, 3 weeks, 4 weeks, or 2 months thereof; or
(c) the second measurement is taken immediately after commencement of the treatment or within at most 1 day, 2 days, 3 days, 4 days, 5 days, 6 days, or 1 week, 2 weeks, 1 month, 2 months, 3 months, 4 months, 5 months, 6 months, 7 months, 8 months, 9 months, 10 months, 11 months, or 12 months thereof.

12. The method of claim 7, wherein
(a) the elevated levels of Snai1, and/or urinary protein, are about 10%, 20%, 25%, 30%, 40%, 50%, 60%, 70%, 75%, 80%, 90%, 100%, 200%, or 500% greater than the levels of Snai1, and/or urinary protein, respectively, in the reference population; and/or
(b) the decreased levels of alpha-SMA, and/or Axin2 are about 10%, 20%, 25%, 30%, 40%, 50%, 60%, 70%, 75%, 80%, or 90% less than the levels of alpha-SMA, and/or Axin2 respectively, in a reference population.

13. The method of claim 9, wherein
(a) the elevated levels of alpha-SMA, and/or Axin2 are about 10%, 20%, 25%, 30%, 40%, 50%, 60%, 70%, 75%, 80% 90%, 100%, 200%, or 500% greater than the levels of alpha-SMA, and/or Axin2 respectively, in the reference population; and/or
(b) the decreased levels of Snai1, and/or urinary protein, are about 10%, 20%, 25%, 30%, 40%, 50%, 60%, 70%, 75%, 80%, or 90% less than the levels of Snai1, and/or urinary protein, respectively, in a reference population.

14. The method of claim 1, wherein the ActRII signaling inhibitor is a polypeptide comprising the amino acid sequence of SEQ ID NO:7.

15. The method of claim 1, wherein the ActRII signaling inhibitor is a humanized fusion-protein consisting of the extracellular domain of ActRIIA and the human IgG1 Fc domain.

16. The method of claim 1, wherein the subject is human.

17. The method of claim 1, wherein the reference population consists of:
(a) 1, 5, 10, 25, 50, 75, 100, 200, 250, 300, 400, 500, or 1000 individuals;
(b) people of the same age, weight, and/or gender as the subject;
(c) people without cardiovascular disease;
(d) people without vascular calcification;
(e) people without renal disease;
(f) people without chronic kidney disease;
(g) people without pathologically elevated levels of arterial stiffness; and
(h) people without left ventricular hypertrophy.

18. The method of claim 1, wherein the ActRII signaling inhibitor is a polypeptide comprising the amino acid sequence of SEQ ID NO:2.

19. The method of claim 1, wherein the ActRII signaling inhibitor is a polypeptide comprising the amino acid sequence of SEQ ID NO:3.

20. The method of claim 1, wherein the ActRII signaling inhibitor is a polypeptide comprising the amino acid sequence of SEQ ID NO:6.

21. The method of claim 1, wherein the ActRII signaling inhibitor is a polypeptide comprising the amino acid sequence of SEQ ID NO:12.

22. The method of claim 5, wherein the ActRII signaling inhibitor is a polypeptide comprising the amino acid sequence of SEQ ID NO:2.

23. The method of claim 5, wherein the ActRII signaling inhibitor is a polypeptide comprising the amino acid sequence of SEQ ID NO:3.

24. The method of claim 5, wherein the ActRII signaling inhibitor is a polypeptide comprising the amino acid sequence of SEQ ID NO:6.

25. The method of claim 5, wherein the ActRII signaling inhibitor is a polypeptide comprising the amino acid sequence of SEQ ID NO:7.

26. The method of claim 5, wherein the ActRII signaling inhibitor is a polypeptide comprising the amino acid sequence of SEQ ID NO:12.

* * * * *

UNITED STATES PATENT AND TRADEMARK OFFICE
CERTIFICATE OF CORRECTION

PATENT NO. : 11,813,308 B2
APPLICATION NO. : 15/517782
DATED : November 14, 2023
INVENTOR(S) : Keith Hruska et al.

It is certified that error appears in the above-identified patent and that said Letters Patent is hereby corrected as shown below:

On the Title Page

Under item (73) Assignees, replace:
"Assignees: Celgene Corporation, Missouri (MO); Washington University, St. Louis, MO (US)"
With:
-- Assignees: Celgene Corporation, Summit, NJ (US); Washington University, St. Louis, MO (US) --

In the Claims

In Column 354, Line 48 (Claim 3), replace:
"75%, 80% 90%, 100%"
With:
-- 75%, 80%, 90%, 100% --

In Column 356, Line 28 (Claim 13), replace:
"75%, 80% 90%, 100%"
With:
-- 75%, 80%, 90%, 100% --

Signed and Sealed this
Fourth Day of June, 2024

Katherine Kelly Vidal
*Director of the United States Patent and Trademark Office*